United States Patent
Bacani et al.

(10) Patent No.: US 8,399,465 B2
(45) Date of Patent: Mar. 19, 2013

(54) COMPOUNDS WITH TWO FUSED BICYCLIC HETEROARYL MOIETIES AS MODULATORS OF LEUKOTRIENE $A_4$ HYDROLASE

(75) Inventors: Genesis Bacani, San Diego, CA (US); Christa C. Chrovian, San Diego, CA (US); Wendy Eccles, San Diego, CA (US); Anne M. Fourie, San Diego, CA (US); Laurent Gomez, San Diego, CA (US); Cheryl A. Grice, San Diego, CA (US); Aaron M. Kearney, Lakeside, CA (US); Adrienne M. Landry-Bayle, Carlsbad, CA (US); Alice Lee-Dutra, San Diego, CA (US); Alejandro Santillán, Jr., San Diego, CA (US); Virginia M. Tanis, San Diego, CA (US); John J. M. Wiener, San Diego, CA (US)

(73) Assignee: Janssen Pharmaceutica NV, Beerse (BE)

(*) Notice: Subject to any disclaimer, the term of this patent is extended or adjusted under 35 U.S.C. 154(b) by 422 days.

(21) Appl. No.: 12/778,646

(22) Filed: May 12, 2010

(65) Prior Publication Data
US 2010/0292208 A1 Nov. 18, 2010

Related U.S. Application Data

(60) Provisional application No. 61/178,169, filed on May 14, 2009, provisional application No. 61/252,774, filed on Oct. 19, 2009.

(51) Int. Cl.
*A61K 31/535* (2006.01)
*A61K 31/47* (2006.01)
*A61K 31/445* (2006.01)
*A61K 31/425* (2006.01)
*C07D 417/14* (2006.01)
*C07D 417/12* (2006.01)

(52) U.S. Cl. ............ 514/236.8; 514/307; 514/321; 514/367; 544/135; 546/148; 546/270.1; 548/159

(58) Field of Classification Search ........... 514/367, 514/321, 307, 236.8; 544/135; 546/148, 546/270.1; 548/159
See application file for complete search history.

(56) References Cited

U.S. PATENT DOCUMENTS

| | | | |
|---|---|---|---|
| 4,273,778 A | 6/1981 | Hadley |
| 4,321,378 A | 3/1982 | Dostert |
| 4,329,466 A | 5/1982 | Dostert |
| 4,336,259 A | 6/1982 | Hadley |
| 4,352,802 A | 10/1982 | Blaney |
| 4,410,535 A | 10/1983 | Watts |
| 4,424,358 A | 1/1984 | Dostert |
| 4,471,120 A | 9/1984 | Dostert |
| 4,536,580 A | 8/1985 | Dostert |
| 4,544,660 A | 10/1985 | Hadley |
| 4,599,420 A | 7/1986 | Hadley |
| 4,705,858 A | 11/1987 | Hadley |
| 5,585,492 A | 12/1996 | Chandrakumar et al. |
| 5,700,816 A | 12/1997 | Isakson et al. |
| 5,719,306 A | 2/1998 | Chandrakumar et al. |
| 5,723,492 A | 3/1998 | Chandrakumar et al. |
| 5,990,148 A | 11/1999 | Isakson |
| 6,110,944 A | 8/2000 | Chen et al. |
| 6,316,490 B1 | 11/2001 | Vernier |
| 6,407,140 B1 | 6/2002 | Gregory et al. |
| 6,432,976 B1 | 8/2002 | Thompson |
| 6,506,876 B1 | 1/2003 | Chandrakumar et al. |
| 6,559,140 B2 | 5/2003 | Bennani et al. |
| 6,632,823 B1 | 10/2003 | Vernier |
| 2003/0004191 A1 | 1/2003 | Gregory et al. |
| 2005/0043355 A1 | 2/2005 | Gregory et al. |
| 2005/0043378 A1 | 2/2005 | Axe et al. |
| 2005/0043379 A1 | 2/2005 | Axe et al. |
| 2006/0074121 A1 | 4/2006 | Chen et al. |
| 2006/0223792 A1 | 10/2006 | Butler et al. |
| 2007/0079078 A1 | 4/2007 | Fujita et al. |
| 2007/0155726 A1 | 7/2007 | Arnaiz et al. |
| 2007/0167425 A1 | 7/2007 | Nakade et al. |
| 2008/0057074 A1 | 3/2008 | Takaoka |
| 2008/0194630 A1 | 8/2008 | Barchuk et al. |
| 2009/0111794 A1 | 4/2009 | Bacani et al. |

FOREIGN PATENT DOCUMENTS

| | | |
|---|---|---|
| EP | 0266576 | 5/1988 |
| EP | 416521 | 9/1990 |
| EP | 0468789 | 1/1992 |
| EP | 623621 | 4/1994 |
| FR | 2446823 | 1/1979 |
| JP | 63170356 | 7/1988 |
| WO | WO96/11192 | 4/1996 |
| WO | WO96/41625 | 12/1996 |
| WO | WO97/29774 | 8/1997 |
| WO | WO 01/81347 | 1/2001 |
| WO | WO03/037904 | 5/2003 |
| WO | WO 2004/103959 | 12/2004 |
| WO | WO2006/002133 | 1/2006 |
| WO | WO 2006/004475 | 1/2006 |
| WO | WO2006/133802 | 12/2006 |
| WO | WO 2007/007069 | 1/2007 |
| WO | WO 2007/079078 | 7/2007 |
| WO | WO2008/016811 | 2/2008 |
| WO | WO 2009/058347 | 5/2009 |

OTHER PUBLICATIONS

International Search Report dated Jul. 29, 2010 for International Application No. PCT/US2010/34597.
Ott, V.L. et al. Cell-Dependent Migration of Effector CD8+ T Cells Through Production of Leukotriene B4. Nat. Immunol. 2003, 4(10), 974-981.
Penning, T.D. Inhibitor of Leukotriene A4 (LTA4) Hydrolase as Potential Anti-Inflammatory Agents. Curr. Pharm. Des. 2001, 7(3), 163-179.
Reid, G.K. et al. Correlation Between Expression of 5-Lipoxygenase-Activating Protein, 5-Lipoxygenase, and Cellular Leukotriene Synthesis. J. Biol. Chem. 1990, 265(32), 19818-19823.

(Continued)

*Primary Examiner* — Rebecca Anderson

(57) ABSTRACT

Compounds with two fused bicyclic heteroaryl moieties and their pharmaceutical compositions, and methods of using them as leukotriene $A_4$ hydrolase ($LTA_4H$) modulators and for the treatment of diseases, disorders and conditions mediated by $LTA_4H$.

54 Claims, No Drawings

OTHER PUBLICATIONS

Robinson, R. et al. Discovery of the Hemifumarate and (α-L-Alanyloxy) methyl Ether as Prodrugs of an Antirheumatic Oxindole: Prodrugs for the Enolic OH Group. J. Med. Chem. 1996, 39, 10-18.
Samuelsson, B. et al. Leukotrienes: Mediators of Immediate Hypersensitivity Reactions and Inflammation. Science (Washington, D.C.) 1983, 220 (4597), 568-575.
Samuelsson, B et al. Enzymes Involved in the Biosynthesis of Leukotriene B4. J. Biol. Chem. 1989, 264(33), 19469-19472.
Shan et al. Prodrug strategies based on intramolecular cyclization reactions. Journal of Pharmaceutical Sciences 1997, 86(7), 765-767.
Sharon, P. et al. Enhanced Synthesis of Leukotriene B4 by Colonic Mucosa in Inflammatory Bowel Disease. Gastroenterology 1984, 86(3), 453-460.
Sidbury, R. et al. Old, new, and emerging therapies for atopic dermatitis. Dermatol. Clin. 2000, 18(1), 1-11.
Steinberg, D. Atherogenesis in Perspective: Hypercholesterolemia and Inflammation as Partners in Crime. Nat. Med. 2002, 8(11), 1211-1217.
Su, J.C. et al. Atopic eczema: its impact on the family and financial cost. Arch. Dis. Child 1997, 76, 159-162.
Subbarao, K. et al. Role of Leukotriene B4 Receptors in the Development of Atherosclerosis: Potential Mechanisms. Arterioscler. Thromb. Vasc. Biol. 2004, 24, 369-375.
Tager, A.M. et al. Leukotriene B4 Receptor BLT1 Mediates Early Effector T Cell Recruitment. Nat. Immunol. 2003, 4(10), 982-990.
Takakuwa, T. et al. Relationships between plasma levels of type-II phospholipase A2, PAF-acetylhydrolase, leukotriene B4, complements, endothelin-1 and thrombomodulin in patients with sepsis. Res. Commun. Chem. Pathol. Pharmacol. 1994, 84(3), 271-281.
Terawaki K. et al. Absence of leukotriene $B_4$ receptor 1 confers resistance to airway hyperresponsiveness and Th2-type immune responses. J Immunol. 2005, 17(7), 4217-4225.
Tracey, K.J. The Inflammatory Reflex. Nature (London) 2002, 420(6917), 853-859.
Tsuji F. et al. Involvement of Leukotriene B4 in Arthritis Models. Life Sci. 1998, 64(3), L51-L56.
Wang, S. et al. A Novel Hepatointestinal Leukotriene B4 Receptor. Cloning and Functional Characterization. J. Biol. Chem. 2000, 275(52), 40686-40694.
Weiner, H.L., et al. Inflammation and Therapeutic Vaccination in CNS Diseases. Nature (London) 2002, 420(6917), 879-884.
Willemsen M.A. et al. Clinical and biochemical effects of zileuton in patients with the Sjogren-Larsson syndrome. Eur J Pediatr. 2001,160, 711-717.
Woodmansee D.P. et al. Simon RA. A pilot study examining the role of zileuton in atopic dermatitis. Ann Allergy Asthma Immunol. 1999, 83, 548-552.
Message et al., "The Immunology of Virus Infection in Asthma" 2001, European Respiratory Journal, vol. 18:1013-1025.
Schimmer et al., Adrenocorticotropic Hormone; Adrenocortical Steroids and Their Synthetic Analogs; Inhibitors of the Synthesis and Action of Adrenocortical Hormones 2001; in Hardman JG, Limbird LE; eds. Goodman and Gilman's The Pharmacological Basis of Therapeutics, 10th ed. New York: McGraw-Hill; 1666-1668.
Yokomizo, T. et al. Leukotriene A4 Hydrolase and Leukotriene B4 Metabolism. J. Lipid Mediat. Cell Signal. 1995, 12(2-3), 321-332.
Yokomizo, T. et al. A Second Leukotriene B4 Receptor, BLT2: A New Therapeutic Target in Inflammation and Immunological Disorders. J. Exp. Med. 2000, 192(3), 421-431.
Yokomizo, T. et al. Co-expression of two LTB4 Receptors in Human Mononuclear Cells. Life Sci. 2001, 68(19-20), 2207-2212.
Yokomizo, T. et al. Leukotriene B4: Metabolism and Signal Transduction. Arch. Biochem. Biophys. 2001, 385(2), 231-241.
Zhu, Y.I. et al. Preview of Potential Therapeutic Applications of Leukotriene B4 Inhibitors in Dermatology. Skin Pharmacol. Appl. Skin Physiol. 2000, 13(5), 235-245.
Zhu, L. et al. A convenient synthesis of 2-mercapto and 2-chlorobenzothiazoles. J. Heterocyclic Chem. 2005, 42, 727-730.
Zouboulis, Ch.C. et al. Zileuton, an Oral 5-Lipoxygenase Inhibitor, Directly Reduces Sebum Production. Dermatology 2005, 210(1), 36-38.
Zouboulis, Ch.C. et al. A new concept for acne therapy: a pilot study with zileuton, an oral 5-lipoxygenase inhibitor. Arch. Dermatol. 2003, 139(5), 668-670.
Dostert, P. et al., Studies on the Neuropleptic Benzamides. III—Synthesis and Antidopaminergic Properties of New 3-nortropane Derivatives, Eur. J. Med. Chem. vol. 19, No. 2, 1984, 105-110.
Szefler et al., Am. J. Respir. Crit. Care Med. Feb. 1, 2003; 176(3):290-291.
Vippagunta et al., "Crystalline Solids", Advanced Drug Delivery Reviews, 2001 vol. 48, 3-26.
Gavezzotti, "Are Crystal Structures Predictable?"? Accounts of Chemical Research, 1994 vol. 27, 309-314.
Penning et al., "Pyrrolidine and Piperidine Analogues of SC-57461A as Potent, orally Active Inhibitors of Leukotriene A4 Hydrolase" Bioorganic & Medicinal Chemistry Letters 2002, 12, 3383-3386.
Morisseau et al., "Potent Urea and Carbamate Inhibitors of Soluble Epoxide Hydrolases" Proceedings of the National Academy of Sciences 1999, 96, 8849-8854.
Wolff, M.E. Burger's Medicinal Chemistry $4^{th}$ Ed. Par I, Wiley: New York, 1979 336-337.
West, Anthony R., Solid State Chemistry and its Applications, Wiley, New York, 1988, pp. 358 &35565.
Patani et al.: "Biosoterism: A Rational Approach in Drug Design" 1996; Chem. Rev.; 96:3147-3176.
Agner, T. "Compliance Among Patients with Atopic Eczema", Acta Derm. Venereol. 2005; Suppl. 215; 33-35.
Ahmadzadeh et al., "Relationship Betweetn Leukotriene $B_4$ and Immunological Parameters in Rhematoid Synovial Fluids", 1991, Inflammation, vol. 15:497-503.
Ahluwalia et al., Inhibited Aortic Aneurysm Formation in BLT1-Deficient Mice, 2007, Journal of Immunology vol. 179:691-697.
Allen et al., "Inhaled Corticosteroids: Past Lessons and Future Issues" 2003 Allergy Clin. Immunol. vol. 112,3:S1-S40.
Bellamy et al., "Poor Perceptions and Expectations of Asthma Control: Results of the International Control of Asthma Symptoms (ICAS) Survey of Patients and General Practitioners" 2005, Primary Care Respiratory Journal, vol. 14:252-258.
Biernacki, et al., "Increased Leukotriene $B_4$ and 8-Isoprostane in Exhaled Breath Condensate of Patients with Exacerbations of COPD" 2003, Thorax.
Busse et al., "Advances in Immunology" 2001, New England Journal of Medicine, vol. 344:350-362.
Collin, "Structural Requirements of D-2 Antidopaminergic Genzamides. Comparison with 5HT-3 Antiserotoninergic Orthopramides", 1991, Pharmacie de Belgique, vol. 46 Issue 1:55-66.
Dahlen et al., "Treatment of Asthma with Antileukotrienes: First Line or Last Resort Therapy" 2006, European Journal of Pharmacology, 533:40-56.
Fitzgerald et al., "Asthma Control in Canada Remains Suboptimal: The Reality of Asthma Control (TRAC) Study" 2006, Can Resp. J. vol. 13, No. 5:253.
Frieri et al., "Allergen-Stimulated Leukotriene $B_4$ and Interleukin-8 Levels in Patients with Asthma and Allergic Rhinitis-Modulation by a Lipid Pathway Inhibitor" 1998, Ann. Allergy Asthma Immunol. vol. 81:331.
Koro et al., Chemical Mediators in Atopic Dermatitis: Involvement of Leukotriene $B_4$ Released by a Type I Allergic Reaction in the Pathogenesis of topic Dermatitis, J. Allergy Clin. Immunol. (1999) vol. 103:663-670.
Mathis et al., "Role of Leukotriene $B_4$ Receptors iin Rheumatoid Arthritis" 2007 Autoimmunity Reviews, vol. 7:12-17.
Milgrom et al., "Noncompliance and Treatment Failure in Children with Asthma" 1996, J. Allergy Clin. Immunol. vol. 98:1051-1057.
Moore et al., "Severe Asthma: An Overview" 2006 American Academy of Allergy, Asthma and Immunology, vol. 117:487-494.
Neu et al., "Leukotrienes in Patients with Clinically Active Multiple Sclerosis", 2002 Acta Neurol. Scand, vol. 105:63-66.
Rabier, et al., "Neuropeptides Modulate Leukotriene $B_4$ Mitogenicity Toward Cultured Human Keratinocytes", 1993 J. Invest. Deermatol. vol. 110:132-136.

Ruzicka et al., "Skin Levels of Arachidonic Acid-Derived Inflammatory Mediators and Histamine in Atopic Dermatitis and Psoriasis" 1986, J. Invest. Dermatol. vol. 86:105-108.

Seggev et al., "Serum Leukotriene $B_4$ Levels in Patients with Obstructive Pulmonary Disease" 1991, Chest. vol. 99-289-291.

Turner et al., "In Vitro and in Vivo Effects of Leukotriene $B_4$ Antagonism in a Primate Model of Asthma" 1996, J. Clin. Invest., vol. 97-381-387.

Wedi et al., Pathophysiological Role of Leukotrienes in Dermatological Diseases, 2001, BioDrugs vol. 15(11):729-743.

Wenzel et al., "Bronchoscopic Evaluation of Severe Asthma" 1997, American Journal of Respiratory and Critical Care Medicine, vol. 156:737-743.

Whatling et al., "The Potential Link Between Atherosclerosis and the 5-Lipoxygenase Pathway Investigational Agents with New Implications for the Cardiovascular Field" 2007, Informa Healthcare, vol. 16:1879-1893.

Whittle et al., "Attenuation of Inflammation and Cytokine Production in Rat Colitis by a Novel Selective Inhibitor of Leukotriene $A_4$ Hydrolase" 2008, British Journal of Pharmacology, vol. 153:983-991.

Willemsen et al., "Deffective Metabolism of Leukotriene $B_4$ in the Sjogren-Larsson Syndrome" 2001, Journal of the Neurological Sciences vol. 183:61-67.

Lundeen et al., "Leukotriene $B_4$ Receptors BLT1 and BLT2: Expression and Function in Human and Murine Mast Cells" 2006, The Journal of Immunology, vol. 177:3439-3447.

Rao et al., "Anti-Inflammatory Activity of A potent, Selective Leukotriene $A_4$ Hydrolase Inhibitor in Comparison with the 5-Lipoxygenase Inhibitor Zileuton", 2007, vol. 321, No. 3:1154-1160.

Grice et al., Discovery of Potent and Selective Leukotriene A4 Hydrolase Inhibitors Abstracts of Papers, $234^{th}$ ACS National Meeting, Boston, MA, US Aug. 19, 2007.

Alestas, T. et al. Enzymes involved in the biosynthesis of leukotriene B4 and prostaglandin E2 are active in sebaceous glands. J. Mol. Med. 2006, 84(1), 75-87.

Andoh, T. et al. Intradermal leukotriene B4, but not prostaglandin E2, induces itch-associated responses in mice. Eur. J. Pharmacol. 1998, 353(1), 93-96.

Andoh, T. et al. Involvement of blockade of leukotriene B4 action in anti-pruritic effects of emedastine in mice. Eur. J. Pharmacol. 2000, 406(1), 149-152.

Andoh, T. et al. Involvement of leukotriene B4 in substance P-induced itch-associated response in mice. J. Investigativ. Dermatol. 2001, 117(6), 1621-1626.

Andoh, T. et al. Intradermal nociceptin elicits itch-associated responses through leukotriene B4 in mice. J. Investigativ. Dermatol. 2004, 123(1), 196-201.

Andoh, T. et al. Suppression by bepotastine besilate of substance P-induced itch-associated responses through the inhibition of the leukotriene B4 action in mice. Eur. J. Pharmacol. 2006, 547(1-3), 59-64.

Barnes, P.J. Future Advances in COPD Therapy. Respiration 2001, 68(5), 441-448.

Bagshawe Et Al. Antibody-Directed Enzyme Prodrug Therapy: A Review Drug Dev. Res. 1995, 34, 220-230.

Barone, F.C. et al. Time-related changes in myeloperoxidase activity and leukotriene B4 receptor binding reflect leukocyte influx in cerebral focal stroke. Mol. Chem. Neuropathol. 1995, 24(1), 13-30.

Benoist, C. and D. Mathis. Mast Cells in Autoimmune Disease. Nature 2002, 420(6917), 875-878.

Berge et al. Pharmaceutical Salts Journal of Pharmaceutical Sciences 1977, 66(1), 1-19.

Bertolini et al. A New Rational Hypothesis for the Pharmacophore of the Active Metabolite of Leflunomide, A Potent Immunosuppressive Drug. J Med Chem 1997, 40, 2011-2016.

Bodor et al. Novel Approaches to the Design of Safer Drugs: Soft Drugs and Site-Specific Chemical Delivery Systems Advances in Drug Research 1984, 13, 224-331.

Byrum, R.S. et al. Determination of the Contribution of Cysteinyl Leukotrienes and Leukotriene B4 in Acute Inflammatory Responses Using 5-Lipoxygenase- and Leukotriene $A_4$ Hydrolase-Deficient Mice. J. Immunol. 1999, 163(12), 6810-6819.

Camp, R.D.R. et al. Responses of Human Skin to Intradermal Injection of Leukotrienes $C_4$, $D_4$ and $B_4$. Br. J. Pharmacol. 1983, 80(3), 497-502.

Camp, R. et al. Production of Intraepidermal Microabscesses by Topical Application of Leukotriene $B_4$. J. Invest. Dermatol. 1984, 82(2), 202-204.

Carpagnano, G.E. et al. Increased leukotrien B4 and interleukin-6 in exhaled breath condensate in cystic fibrosis. Am. J. Respir. Crit. Care Med. 2003, 167(8), 1109-1112.

Chen, X. et al. Leukotriene A4 hydrolase in rat and human esophageal adenocarcinomas and inhibitory effects of bestatin. J. Natl. Cancer Inst. 2003, 95(14), 1053-1061.

Chen, X. et al. Leukotriene A4 hydrolase as a target for cancer prevention and therapy. Curr. Cancer Drug Targets 2004, 4(3), 267-283.

Hakonarson, H. et al. Effects of a 5-lipoxygenase-activating protein inhibitor on biomarkers associated with risk of myocardial infarction. A randomized trial. JAMA 2005, 293(18), 2245-2256.

Hanifin, J.M. et al. Guidelines of care for atopic dermatitis, developed in accordance with the American Academy of Dermatology (AAD)/ American Academy of Dermatology Association Administrative Regulations for Evidence-Based Clinical Practice Guidelines. J. Am. Acad. Dermatol. 2004, 50, 391-404.

Helgadottir, A. et al. The Gene Encoding 5-Lipoxygenase Activating Protein Confers Risk of Myocardial Infarction and Stroke. Nat. Genet. 2004, 36(3), 233-239.

Helgadottir A. et al. A variant of the gene encoding leukotriene A4 hydrolase confers ethnicity-specific risk of myocardial infarction. Nat Genet. 2006, 38, 68-74.

Huang L, et al. Molecular and Biological Characterization of the Murine Leukotriene B4 Receptor Expressed on Eosinophils. J. Exp. Med. 1998, 188(6), 1063-1074.

Hwang, S.W. et al. Direct activation of capsaicin receptors by products of lipoxygenases: endogenous capsaicin-like substances. Proc. Natl. Acad. Sci. USA 2000, 97(11), 6155-6160.

Ikai, K. Psoriasis and the Arachidonic Acid Cascade, Jour. Of Derm. Sci., 1999, 21, 135-146.

Jala, V.R. et al. Leukotrienes and Atherosclerosis: New Role for Old Mediators. Trends Immunol. 2004, 25(6), 315-322.

Kachur, J.F. et al. Pharmacological Characterization of SC-57461A (3-[Methyl[3-[4- (phenylmethyl)phenoxy]propyl]amino]propanoic acid HCI), a Potent and Selective Inhibitor of Leukotriene $A_4$ Hydrolase II: In Vivo Studies. J. Pharmacol. Exp. Ther. 2002, 300(2), 583-587.

Klein, A. et al. Stem Cell Factor Plays a Major Role in the Recruitment of Eosinophils in Allergic Pleurisy in Mice via the Production of Leukotriene $B_4$. J. Immunol. 2000, 164(8), 4271-4276.

Laughter, D. et al. The prevalence of atopic dermatitis in Oregon schoolchildren. J. Am. Acad. Dermatol. 2000, 43, 649-655.

Liao, T. et al. Blockade of the interaction of leukotriene B4 with its receptor prevents development of autoimmune uveitis. Invest. Ophthalmol. Vis. Sci. 2006, 47(4), 1543-1549.

Libby, P. Inflammation in Atherosclerosis. Nature (London) 2002, 420(6917), 868-874.

Miyahara N. et al. Role of the LTB4/BLT1 pathway in allergen-induced airway hyperresponsiveness and inflammation. Allergy Intl. 2006, 55(2), 91-97.

Munafo, D.A. et al. Leukotriene A4 Hydrolase in Human Bronchoalveolar Lavage Fluid. J. Clin. Invest. 1994, 93(3), 1042-1050.

Nakae, H. et al. Relationship between cytokines and leukotriene B4 in sepsis. Res. Commun. Chem. Pathol. Pharmacol. 1994, 83(2), 151-156.

Nathan, C. Points of Control in Inflammation. Nature (London) 2002, 420(6917), 846-852.

Cohen, J. The Immunopathogenesis of Sepsis. Nature (London) 2002, 420(6917), 885-891.

Coussens, L.M. et al. Inflammation and Cancer. Nature (London) 2002, 420(6917), 860-867.

Crooks, S.W. and R.A. Stockley. Leukotriene $B_4$. Int. J. Biochem. Cell Biol. 1998, 30(2), 173-178.

Cunha, J.M. et al. The critical role of leukotriene B4 in antigen-induced mechanical hyperalgesia in immunised rats. Br. J. Pharmacol. 2003, 139(6), 1135-1145.

Ellis, C.N. et al. Cost of atopic dermatitis and eczema in the United States. J. Am. Acad. Dermatol. 2002, 46, 361-370.

Emingil, G. et al. Levels of leukotriene B4 in gingival crevicular fluid and gingival tissue in specific periodontal diseases. J. Periodontol. 2001, 72(8), 1025-1031.

Fitzpatrick, F.A. et al. Effects of Leukotriene $A_4$ on Neutrophil Activation. Ann. N.Y. Acad. Sci. 1994, 714, 64-74.

Ford-Hutchinson, A.W. et al. 5-Lipoxygenase. Ann. Rev. Biochem. 1994, 63, 383-417.

Fleisher, D. et al. Improved oral drug delivery: solubility limitations overcome by the use of prodrugs. Advanced Drug Delivery Reviews, 1996, 19, 115-130.

Friedrich E.B. et al. Mechanisms of leukotriene $B_4$-triggered monocyte adhesion. Arterioscler Thromb Vasc Biol 2003, 23, 1761-1767.

Funk et al. Molecular Cloning and Amino Acid Sequence of Leukotriene A4 Hydrolase. PNAS 1987, 84, 6677-6681.

Gelfand, E.W. et al. CD8+ T lymphocytes and leukotriene B4: novel interactions in the persistence and progression of asthma. J. Allergy Clin. Immunol. 2006, 117(3), 577-582.

Gierse et al. High level Experssion and Purification of Human Leukotriene A4 Hydrolase from Insect Cells Infected with a Baculovirus Vector. Protein Expression and Purification, 1993, 4, 358-366.

Gompertz, S. et al. Changes in bronchial inflammation during acute exacerbations of chronic bronchitis. Eur. Respir. J. 2001, 17(6), 1112-1119.

Goodarzi, K. et al. Leukotriene $B_4$ and BLT1 Control Cytotoxic Effector T Cell Recruitment to Inflamed Tissues. Nat. Immunol. 2003) 4(10), 965-973.

Griffiths, R.J. et al. Leukotriene $B_4$ Plays a Critical Role in the Progression of Collagen-Induced Arthritis. PNAS 1995, 92(2), 517-521.

COMPOUNDS WITH TWO FUSED BICYCLIC HETEROARYL MOIETIES AS MODULATORS OF LEUKOTRIENE A$_4$ HYDROLASE

This application claims the benefit of U.S. provisional patent application Ser. Nos. 61/178,169, filed on May 14, 2009, and 61/252,774, filed on Oct. 19, 2009, both of which are incorporated herein by reference in their entirety.

FIELD OF THE INVENTION

The present invention relates to certain compounds comprising two fused bicyclic heteroaryl moieties, pharmaceutical compositions containing them, methods of using such compounds, including leukotriene A$_4$ hydrolase (LTA$_4$H) modulation, and pharmaceutical compositions for the treatment of disease states, disorders, and conditions mediated by leukotriene A$_4$ hydrolase (LTA$_4$H).

BACKGROUND OF THE INVENTION

Inflammation is normally an acute response by the immune system to invasion by microbial pathogens, chemicals or physical injury. In some cases, however, the inflammatory response can progress to a chronic state, and be the cause of inflammatory disease. Therapeutic control of this chronic inflammation in diverse diseases is a medical need.

Leukotrienes (LT) are biologically active metabolites of arachidonic acid (B. Samuelsson, Science 1983, 220(4597): 568-575) that have been implicated in inflammatory diseases, including asthma (D. A. Munafo et al., J. Clin. Invest. 1994, 93(3): 1042-1050; N. Miyahara, et al., Allergol Int., 2006, 55(2): 91-7; E. W. Gelfand, et al., J. Allergy Clin. Immunol. 2006, 117(3): 577-82; K. Terawaki, et al., J. Immunol. 2005, 175(7): 4217-25), inflammatory bowel disease (IBD) (P. Sharon and W. F. Stenson, Gastroenterology 1984, 86(3): 453-460), chronic obstructive pulmonary disease (COPD) (P. J. Barnes, Respiration 2001, 68(5): 441-448), arthritis (R. J. Griffiths et al., Proc. Natl. Acad. Sci. U.S.A. 1995, 92(2): 517-521; F. Tsuji et al., Life Sci. 1998, 64(3): L51-L56), psoriasis (K. Ikai, J. Dermatol. Sci. 1999, 21(3): 135-146; Y. I. Zhu and M. J. Stiller, Skin Pharmacol. Appl. Skin Physiol. 2000, 13(5): 235-245) and atherosclerosis (Friedrich, E. B. et al. Arterioscler Thromb Vasc Biol 23, 1761-7 (2003); Subbarao, K. et al. Arterioscler Thromb Vasc Biol 24, 369-75 (2004); Helgadottir, A. et al. Nat Genet. 36, 233-9 (2004); Jala, V. R. et al Trends in Immun. 25, 315-322 (2004)). The synthesis of leukotrienes is initiated by the conversion of arachidonic acid to an unstable epoxide intermediate, leukotriene A$_4$ (LTA$_4$), by 5-lipoxygenase (5-LO) (A. W. Ford-Hutchinson et al., Annu. Rev. Biochem. 1994, 63: 383-347). This enzyme is expressed predominantly by cells of myeloid origin, particularly neutrophils, eosinophils, monocytes/macrophages and mast cells (G. K. Reid et al., J. Biol. Chem. 1990, 265(32): 19818-19823). LTA$_4$ can either be conjugated with glutathione by leukotriene C$_4$ (LTC$_4$) synthase to produce the cysteinyl leukotriene, LTC$_4$, or hydrolyzed to the diol, leukotriene B$_4$ (LTB$_4$) (B. Samuelsson, Science 1983, 220(4597): 568-575). LTC$_4$ and its metabolites, LTD$_4$ and LTE$_4$, induce smooth muscle contraction, broncho-constriction and vascular permeability, while LTB$_4$ is a potent chemoattractant and activator of neutrophils, eosinophils, monocytes/macrophages, T cells and mast cells.

The stereospecific hydrolysis of LTA$_4$ to LTB$_4$ is catalyzed by leukotriene A$_4$ hydrolase (LTA$_4$H), a zinc-containing cytosolic enzyme. This enzyme is ubiquitously expressed with high levels in small intestinal epithelial cells, lung, and aorta (B. Samuelsson and C. D. Funk, J. Biol. Chem. 1989, 264 (33): 19469-19472). Moderate expression of LTA$_4$H is observed in leukocytes, particularly neutrophils (T. Yokomizo et al., J. Lipid Mediators Cell Signalling 1995, 12(2,3): 321-332).

Leukotriene B4 is a key pro-inflammatory lipid mediator, able to recruit and activate inflammatory cells, such as neutrophils, eosinophils, monocytes/macrophages, T cells and mast cells (F. A. Fitzpatrick et al., Ann. N.Y. Acad. Sci. 1994, 714: 64-74; S. W. Crooks and R. A. Stockley, Int. J. Biochem. Cell Biol. 1998, 30(2): 173-178; A. Klein et al., J. Immunol. 2000, 164: 4271-4276). LTB$_4$ mediates its pro-inflammatory effects by binding to G protein-coupled receptors, leukotriene B$_4$ receptor 1 (BLT1) and leukotriene B$_4$ receptor 2 (BLT2) (T. Yokomizo et al., Arch. Biochem. Biophys. 2001, 385(2): 231-241). The receptor first identified, BLT1, binds LTB$_4$ with high affinity, leading to intracellular signaling and chemotaxis. BLT1 is expressed mainly in peripheral leukocytes, particularly neutrophils, eosinophils, macrophages (Huang, W. W. et al. J Exp Med 188, 1063-74 (1998)) and monocytes (Yokomizo, T., Izumi, T. & Shimizu, T. Life Sci 68, 2207-12 (2001)). The murine receptor is also expressed on effector T cells and was recently shown to mediate LTB$_4$-dependent migration of effector CD8+ T cells (Goodarzi, K., Goodarzi, M., Tager, A. M., Luster, A. D. & von Andrian, U. H. Nat Immunol 4, 965-73 (2003); Ott, V. L., Cambier, J. C., Kappler, J., Marrack, P. & Swanson, B. J. Nat Immunol 4, 974-81 (2003)), early effector CD4+T helper type 1 (TH1) and TH2 chemotaxis and adhesion to endothelial cells, as well as early effector CD4+ and CD8+ T cell recruitment in an asthma animal model (Tager, A. M. et al., Nat Immunol 4, 982-90 (2003)). LTB$_4$ receptor BLT2 (S. Wang et al., J. Biol. Chem. 2000, 275(52): 40686-40694; T. Yokomizo et al., J. Exp. Med. 2000, 192(3): 421-431) shares 42% amino acid homology with BLT1, but is more broadly expressed, including in peripheral tissues such as the spleen, ovary and liver, as well as in leukocytes. BLT2 binds LTB$_4$ with lower affinity than BLT1 does, mediates chemotaxis at higher concentrations of LTB$_4$, and differs from BLT1 in its affinity for certain antagonists. While LTB$_4$ receptor antagonists may differ in their affinity for BLT1 versus BLT2, blocking the production of LTB$_4$ using LTA$_4$H inhibitors would be expected to inhibit the downstream events mediated through both BLT1 and BLT2.

Studies have shown that introduction of exogenous LTB$_4$ into normal tissues can induce inflammatory symptoms (R. D. R. Camp et al., Br. J. Pharmacol. 1983, 80(3): 497-502; R. Camp et al., J. Invest. Dermatol. 1984, 82(2): 202-204). Increased production of LTB$_4$ is considered important for the inflammatory component in a number of diseases, including atopic dermatitis (O. Koro et al. J. Allergy Clin. Immunol. 1999, 103, 663-670), asthma (M. Frieri et al., Ann. Allergy Asthma Immunol. 1998, 81, 331-336), inflammatory bowel disease, chronic obstructive pulmonary disease (W. A. Biernacki et al. Thorax 2003, 58, 294-298; J. S. Seggev et al., Chest 1991, 99, 289-291), atherosclerosis and cardiovascular disease, multiple sclerosis (I. S. Neu et al., Acta Neurol. Scand. 2002, 105, 63-66), psoriasis (D. M. Reilly, Acta Derm. Venereol. 2000, 80, 171-174), cystic fibrosis (J. T. Zakrzewski, et al., Br J Clin Pharmacol 1987, 23:19-27), and rheumatoid arthritis (N. Ahmadzadeh, Inflammation 1991, 15, 497-503). Therefore, inhibitors of LTB$_4$ production should have therapeutic value as anti-inflammatory agents for these conditions. Thus, reduction of LTB$_4$ production by an inhibitor of LTA$_4$H activity would be predicted to have therapeutic potential in a wide range of diseases.

This idea is supported by a study of LTA$_4$H-deficient mice that, while otherwise healthy, exhibited markedly decreased neutrophil influx in arachidonic acid-induced ear inflammation and zymosan-induced peritonitis models (R. S. Byrum et al., J. Immunol. 1999, 163(12): 6810-6819). LTA$_4$H inhibitors have been shown to be effective anti-inflammatory agents in pre-clinical studies. For example, oral administration of LTA$_4$H inhibitor SC57461 caused inhibition of ionophore-induced LTB$_4$ production in mouse blood ex vivo, and in rat peritoneum in vivo (J. K. Kachur et al., J. Pharm. Exp. Ther. 2002, 300(2), 583-587). Eight weeks of treatment with the same inhibitor compound significantly improved colitis symptoms in cotton top tamarins (T. D. Penning, Curr. Pharm. Des. 2001, 7(3): 163-179). The spontaneous colitis that develops in these animals is very similar to human IBD. The results therefore indicate that LTA$_4$H inhibitors would have therapeutic utility in this and other human inflammatory diseases.

Events that elicit the inflammatory response include the formation of the pro-inflammatory mediator leukotriene B$_4$. Hydrolase LTA$_4$H catalyzes the formation of this mediator, and LTA$_4$H inhibitors block the production of the pro-inflammatory mediator LTB$_4$, thus providing the ability to prevent and/or treat leukotriene-mediated conditions, such as inflammation. The inflammatory response is characterized by pain, increased temperature, redness, swelling, or reduced function, or by a combination of two or more of these symptoms. Regarding the onset and evolution of inflammation, inflammatory diseases or inflammation-mediated diseases or conditions include, but are not limited to, acute inflammation, allergic inflammation, and chronic inflammation.

Compounds of the present invention were shown to inhibit LTA$_4$H in in vitro assays. Inhibition was shown in a recombinant enzymatic assay containing the human LTA$_4$ hydrolase and in a cellular assay using murine blood (diluted 1 in 15). Embodiments of the invention were also shown to inhibit murine ex vivo LTB4 production in whole blood (diluted 1:1), as well as arachidonic acid-induced neutrophil influx in murine ear tissue.

Atopic dermatitis (AD) is a chronic inflammatory skin disease that usually occurs in individuals with a personal or family history of atopy. The major features are pruritus and chronic or relapsing eczematous lesions. Complications include bacterial, fungal and viral infections as well as ocular disease. Atopic dermatitis is the most common inflammatory skin disease in children and affects more than 15% of children in the US (Laughter, D., et al., J. Am. Acad. Dermatol. 2000, 43, 649-655). Atopic dermatitis may persist in 60% of adults who were affected as children (Sidbury, R., et al., Dermatol. Clin. 2000, 18(1), 1-11).

Atopic dermatitis has significant societal impact. The family stress related to caring for children with moderate to severe AD may be comparable to the stress seen in families of children with type I diabetes mellitus (Su, J. C., et al., Arch. Dis. Child 1997, 76, 159-162). In the US, the annual cost of medical services and prescription drugs for the treatment of AD/eczema is similar to those for emphysema, psoriasis and epilepsy (Ellis, C. N., et al., J. Am. Acad. Dermatol. 2002, 46, 361-370).

Several lines of evidence support the role of LTB$_4$ in AD. LTB$_4$ levels are elevated in skin lesions (K. Fogh et al., J. Allergy Clin. Immunol. 1989, 83, 450-455; T. Ruzicka et al., J. Invest. Dermatol. 1986, 86, 105-108) and plasma in AD, and contribute to the inflammation through chemotactic effects on inflammatory cells (Wedi and Kapp BioDrugs. 2001; 15, 729-743). Reported in vivo and in vitro studies have shown that leukotrienes, especially LTB$_4$, contribute to the inflammation of the skin in AD through their chemotactic effect on inflammatory cells. LTB$_4$ receptors are expressed on mast cells, T cells, eosinophils, dendritic cells and macrophages, all of which accumulate in AD lesions. LTB$_4$ itself is a pruritic agent, and has also been shown to mediate substance P-induced pruritus (T. Andoh et al., J. Invest. Dermatol. 2001, 117, 1621-1626), a key component of the itching in AD (T. Ohmura et al., Eur. J. Pharmacol. 2004, 491, 191-194). LTB$_4$ induces proliferation of keratinocytes, an effect that is further potentiated by substance P (M. J. Rabier et al., J. Invest. Dermatol. 1993, 110, 132-136). Recent reports indicate a role for LTB$_4$ in development of a Th2 immune response and IgE production. The role of LTB$_4$ in AD is supported by beneficial effects of the 5-lipoxygenase inhibitor, zileuton, in a small, open-label clinical trials of AD (Woodmansee et al., Ann. Allergy Asthma Immunol. 1999, 83, 548-552) and in relieving the pruritus in Sjogren-Larsson syndrome patients who have elevated LTB$_4$ due to an impairment in its degradation (Willemsen et al., Eur. J. Pediatr. 2001, 160, 711-717).

While AD that is mild to moderate in severity generally responds to topical therapy, correct use of these therapies and compliance remain a major issue in the clinic (T. Agner, Acta Derm. Verereol. Suppl. (Stockh) 2005, 213, 33-35). Topical corticosteroids and emollients are the standard of care in the treatment of AD. However, systemic immunomodulatory therapies and potent topical corticosteroids used to treat severe AD are associated with significant cutaneous side effects, such as striae, atrophy and telangeictasia that limit the long-term use of these agents (Hanifin et al., J. Am. Acad. Dermatol. 2004, 50, 391-404).

Emollients have a steroid-sparing effect and are useful for both prevention and maintenance therapy. Crude coal tar and preparations containing coal tar derivatives have also been used for many years in the treatment of AD and have significant cosmetic disadvantages that influence compliance (Hanifin, et al., 2004). Topical doxepin may be a useful short-term adjunctive therapy for the relief of pruritus but sedation and contact dermatitis may complicate its use (Hanifin, et al., 2004).

Tacrolimus (Protopic®) and pimecrolimus (Elidel®) are topical calcineurin inhibitors that have been shown to reduce the extent, severity and symptoms of AD in adults and children and are approved for use as second-line therapy of AD. However, the recent addition of boxed warnings to the product labels regarding rare cases of malignancy reported in patients treated with topical calcineurin inhibitors limits long term use of these agents in the treatment of AD (Food and Drug Administration [FDA]/Center for Drug Evaluation and Research [CDER] resources page).

Antibiotics are used in the treatment of *Staphylococcus aureus* infections in patients with AD but have a minimal effect on the dermatitis (Hanifin, et al., 2004). Although sedating antihistamines may be useful if sleep disruption is present, oral antihistamines are generally not effective in treating AD-associated pruritus (Hanifin, et al., 2004). Ultraviolet (UV) phototherapy, including photochemotherapy with psoralen is well established in the treatment of AD but relapse upon cessation of therapy frequently occurs (Hanifin, et al., 2004).

Systemic immunomodulatory therapy with cyclosporine and corticosteroids is effective but can be associated with severe side effects and is generally reserved for patients with severe disease. Systemic corticosteroids are associated with growth retardation in children, avascular necrosis of bone, osteopenia, increased risk of infection, poor wound healing, cataracts, hyperglycemia and hypertension. Cyclosporine is nephrotoxic in a majority of patients and is associated with tremor, hirsutism, hypertension, hyperlipidemia and gum hyperplasia.

While AD that is mild to moderate in severity generally responds to topical therapy, correct use of these therapies and compliance remain a major issue in the clinic. An oral or topical agent lacking the risks associated with corticosteroids and the calcineurin inhibitors would be a welcome addition to the armamentarium of treatments for AD that is mild to moderate in severity. An effective oral or topical therapy with fewer side effects than systemic immunomodulatory therapies and potent topical corticosteroids would fill an unmet medical need in the treatment of AD.

Sjogren-Larsson syndrome is an autosomal recessive neurocutaneous disorder with severe ichthyosis. It is caused by mutation of the gene encoding microsomal fatty aldehyde dehydrogenase (FALDH) leading to a defect in fatty alcohol metabolism. FALDH catalyzes the oxidation of medium- to long-chain fatty aldehydes to their corresponding carboxylic acids. $LTB_4$, a pro-inflammatory mediator synthesized from arachidonic acid, is inactivated by microsomal omega-oxidation, successively yielding 20-OH-$LTB_4$, 20-CHO-$LTB_4$ and 20-COOH-$LTB_4$. The urine of Sjogren-Larsson syndrome patients contains highly elevated levels of $LTB_4$ and 20-OH-$LTB_4$. Defective LTB4 degradation in Sjogren-Larsson syndrome patients is now considered to be shown with "unambiguous evidence" (Willemsen et al., J. Neurol. Sci. 2001, 183(1), 61-7). Sjogren syndrome is an autoimmune disease that features inflammation in some glands. Sjogren syndrome may feature also extraglandular manifestations. When the gland inflammation is not associated with another connective tissue disease, then the syndrome is referred to as primary Sjogren syndrome. When it is associated with a connective tissue disease, such as rheumatoid arthritis, systemic lupus erythematosus or scleroderma, then it is referred to as secondary Sjogren syndrome. The term "Sjogren syndrome" herein refers to any one of the primary and secondary Sjogren syndromes. No cure is currently known for this syndrome. The current treatments usually focus on the specific area of the body that is affected and also in the treatment of associated complications. Immuno-suppressants such as cortisones, azathioprine and cyclophosphamide are sometimes used to threat some serious complications, and antibiotics are also used to treat associated infections.

Embodiments of this invention have shown dose-dependent inhibition of dermal inflammation in the arachidonic acid-induced murine ear inflammation model. Oral administration of embodiments of this invention dose-dependently inhibited neutrophil influx and edema, and were shown to inhibit the ex vivo ionophore-stimulated $LTB_4$ production at doses between 0.3 and 30 mg/kg.

$LTA_4H$ inhibitors are hypothesized to specifically block the production of $LTB_4$ from $LTA_4$, without affecting the biosynthesis of lipoxins, which are also produced from $LTA_4$. Increasing or maintaining lipoxin $A_4$ ($LXA_4$) production may have beneficial therapeutic effects in dermal inflammation as it has been reported that topical application of a stable lipoxin analogue inhibits edema, granulocyte infiltration and epidermal hyperproliferation in murine skin inflammation models. 5-LO inhibitors block the pathway upstream of $LTA_4$. This would be expected to lead to a block in not only synthesis of $LTA_4$, $LTB_4$ and cysteinyl leukotrienes (CysLT), but also $LXA_4$.

Asthma is a chronic disease characterized by a variable degree of airflow obstruction, bronchial hyperresponsiveness and airway inflammation (Busse & Lemanske, 2001). Immunohistopathologic features include denudation of airway epithelium, collagen deposition beneath basement membrane, edema, mast cell activation, and inflammatory cell infiltration by neutrophils (especially in sudden-onset, fatal asthma exacerbations), eosinophils, and Th2 lymphocytes (Busse et al., N. Engl. J. Med. 2001, 344, 350-362). Airway inflammation contributes to the airway hyperresponsiveness, airflow limitation (acute bronchoconstriction, airway edema, mucus plug formation and airway wall remodeling, leading to bronchial obstruction), respiratory symptoms and disease chronicity (NIH Guidelines for the Diagnosis and Management of Asthma 1997).

Current therapy for asthma is directed at controlling acute bronchoconstrictive symptoms with beta2-adrenergic receptor agonists and managing underlying airway inflammation with inhaled corticosteroids, chromates such as cromolyn sodium and nedocromil, and antileukotriene agents, such as the cysteinyl leukotriene receptor antagonists montelukast and zafirlukast and the 5-lipoxygenase inhibitor zileuton. Systemic steroids are used in severe disease and acute exacerbations of asthma. The humanized monoclonal anti-IgE antibody omalizumab was approved for the treatment of patients with moderate-to-severe persistent asthma who have a positive skin test or in vitro reactivity to a perennial aeroallergen and whose symptoms are inadequately controlled with inhaled corticosteroids (XOLAIR® [omalizumab] July 2007).

The inflammatory component of mild persistent and moderate asthma can generally be controlled with inhaled corticosteroids, but patient compliance remains a major issue in disease management (H. Milgrom et al., J. Allergy Clin. Immunol. 1996, 98, 1051-1057). Despite optimum therapy, including long-acting beta-agonists and inhaled corticosteroids, many patients have poorly controlled asthma (Fitzgerald et al., Can. Respir. J. 2006, 13, 253-259; Bellamy et al., Prim. Care Respir. J. 2005, 14, 252-258). Severe asthma requires treatment with high-dose inhaled steroids or the frequent use of oral corticosteroids (Moore et al., J. Allergy Clin. Immunol. 2006, 117, 487-494), both of which can be associated with negative side effects such as osteopenia and growth retardation in children (Allen et al., Suppl. J. Allergy Clin. Immunol., 2003, 112, 51; Schimmer et al., Adrenocorticotropic Hormone; Adrenocortical Steroids and Their Synthetic Analogs; Inhibitors of the Synthesis and Action of Adrenocortical Hormones in Hardman J G, Limbird L E; eds. Goodman and Gilman's The Pharmacological Basis of Therapeutics, 10th ed. New York: McGraw-Hill; 2001; 1666-1668). An oral therapy that could effectively treat moderate-to-severe asthma and reduce corticosteroid requirements would address unmet medical needs.

Leukotrienes are important mediators in asthma pathogenesis and comprise two classes—the cysteinyl leukotrienes ($LTC_4$, $LTD_4$ and $LTE_4$) and $LTB_4$. Leukotriene receptor antagonists, such as montelukast or zafirlukast, target only the cysteinyl leukotrienes, while 5-lipoxygenase inhibitors, such as zileuton, inhibit the pathway upstream of both classes, and thus decrease formation of both the cysteinyl leukotrienes and $LTB_4$. $LTA_4H$ inhibitors selectively inhibit $LTB_4$ synthesis and do not impact cysteinyl leukotriene (CysLT) synthesis. Both classes of leukotrienes are elevated in asthma, and $LTB_4$ is more significantly increased in severe asthma, which is associated with increased neutrophilic inflammation.

Several preclinical and clinical findings suggest that inhibition of $LTB_4$ synthesis by $LTA_4H$ inhibitors will have therapeutic benefit in asthma. Studies in mice lacking $LTB_4$ receptors have shown that $LTB_4$ plays a role in eosinophil and effector T cell recruitment, IL-13 production, goblet cell hyperplasia and mucus secretion, IgE production and airway hyperreactivity (Miyahara et al., Allergy Intl. 2006, 55, 91-97). The importance of $LTB_4$ in development in airway hyperreactivity is supported by data with the $LTB_4$ receptor antagonist (CP-105,696), which reduced airway hyperresponsiveness induced by multiple antigen challenges in a primate model (Turner et al., J. Clin. Invest. 1996, 97, 381-387). Furthermore, the reduction of bronchial hyperresponsiveness in human asthma by the 5-LO inhibitor, zileuton, has been attributed to its inhibition of $LTB_4$ synthesis (Dahlen et al., Eur. J. Pharmacol. 2006, 533(1-3), 40-56). Inhibition of $LTB_4$ may also be beneficial in severe asthma (Wenzel et al., Am. J. Respir. Grit. Care Med., 1997, 156, 737-743) and viral exacerbations of asthma (S.D. Message, Eur. Respir. J., 2001, 18, 1013-1025), where neutrophilic inflammation is more prominent. CysLT antagonists and steroids have limited efficacy in severe asthmatics, while zileuton has been shown to significantly improve quality of life in these patients (R. Menendez et al., American Thoracic Society Meeting, San Diego, 2006).

An allergy is an abnormal reaction to an allergen (an ordinarily harmless substance) that triggers an abnormal response in a sensitized individual. Allergic rhinitis is an inflammation of the mucus membranes of the nose that occurs in response to an airborne antigen (allergen). Allergic rhinitis, also called allergic rhinoconjunctivitis, is characterized by frequent or repetitive sneezing, runny or congested nose, and pruritus of the nose, eyes and throat. It may also be associated with other symptoms such as headache, impaired smell, postnasal drip, conjunctival symptoms (e.g., itchy watery eyes), sinusitis and other complicating respiratory symptoms. Depending upon the time of exposure, allergic rhinitis can be classified as perennial, seasonal or occupational.

Based upon the well-described leukotriene biosynthesis pathway, $LTA_4H$ inhibitors are hypothesized to specifically block the production of $LTB_4$ from $LTA_4$, without affecting the biosynthesis of lipoxins, which are also produced from $LTA_4$. Lipoxins, such as $LXA_4$, have been the focus of intense study and are known to play a key role as natural anti-inflammatory agents and key mediators of the natural process of resolving an inflammatory response. Furthermore, production of endogenous $LXA_4$ has been described in a variety of inflammatory diseases and lower levels of $LXA_4$ have been found in patients with severe versus moderate asthma. These data are consistent with the proposition that $LXA_4$ plays an important role in resolution of acute inflammation. Unlike $LTA_4H$ inhibitors, 5-LO inhibitors block this pathway upstream of $LTA_4$. This would lead to a block in not only synthesis of $LTA_4$, $LTB_4$ and cysteinyl leukotrienes, but also $LXA_4$. Furthermore, there is a possibility that $LTA_4H$ inhibitors result in a buildup of $LTA_4$, and pathway shunting to pro-inflammatory cysteinyl leukotrienes, although to date there is no known data to support this possibility.

Neutrophil infiltration is a prominent feature of severe asthma. Zileuton (Zyflo®), which targets both $LTB_4$ and cysteinyl leukotrienes, has been suggested to be efficacious in severe asthma patients, while CysLT antagonists (for example, Montelukast/Singulair®), which target only cysteinyl leukotrienes, show limited efficacy. Combination of an $LTA_4H$ inhibitor and at least one of a CysLT receptor antagonist (for example, Montelukast/Singulair®) and $LTC_4$ synthase inhibitor would target both $LTB_4$ and cysteinyl leukotrienes, while leaving production of the anti-inflammatory lipoxins intact. Embodiments of this invention are envisioned to reduce inflammatory responses to airway allergen challenge, leading to dose-dependent decreases in airway recruitment of inflammatory cells.

Embodiments of this invention are expected to find utility in treating inflammatory bowel disease. In trinitrobenzene sulfonic acid (TNBS)-induced colitis in rats, $LTA_4H$ inhibition had significant inhibitory effects on colonic inflammation, including macroscopic colonic injury, inflammatory cell content, and levels of tumor necrosis factor alpha (TNF-$\alpha$), LTB4, and IL-6 (Whittle et al., Br J. Pharmacol., 2008, 153, 983-991). $LTA_4H$ inhibition reportedly also significantly attenuated the joint inflammation and swelling associated with the destruction of collagen in murine models of arthritis. Mice deficient in receptors for $LTB_4$ or lacking $LTA_4H$ do not develop arthritis in murine models (Mathis, S., et al. Role of leukotriene $B_4$ receptors in rheumatoid arthritis, Autoimmun. Rev., 2007 Nov., 7(1):12-7). Embodiments of this invention are thus expected to find utility in treating arthritis, including, but not limited to, rheumatoid arthritis.

Abdominal aortic aneurysm (AAA) is a localized dilatation of the abdominal aorta that exceeds the normal diameter (2 cm) by more than 50%. It is caused by a degenerative process of the aortic wall. An aortic aneurysm may also occur in the thorax. Surgery is eventually required to prevent the progression to AAA rupture, which is most often a fatal event. Thus therapeutics which delay or prevent the need for surgery are an unmet medical need.

Recent genetic studies in humans as well as studies in mice and rabbits have implicated the leukotriene synthesis pathway in cardiovascular disease (reviewed in Whatling et al., Expert Opin Investig Drugs 2007, 16(12), 1879-93). In a well-established murine abdominal aortic aneurysm (AAA) model, mice that lack the receptor for LTB4 exhibit a reduced incidence of AAA formation (Ahluwalia et al., J. Immunol. 2007, 179(1), 691-7). Diminished AAA formation in $LTB_4$-receptor-deficient mice was associated with significant reductions in mononuclear cell chemoattractants and leukocyte accumulation in the vessel wall, as well as striking reductions in the production of matrix metalloproteinases-2 and -9. Thus, it has been shown that signaling by $LTB_4$ through its receptor contributes to the frequency and size of abdominal aortic aneurysms in mice, and prevention of $LTB_4$ signaling by deletion of the gene coding for the $LTB_4$ receptor in turn inhibits proinflammatory circuits and enzymes that modulate vessel wall integrity. Thus $LTB_4$ signaling is a target for intervention in modulating development of aortic aneurysms. Inhibitors of $LTA_4H$ in the context of this invention are expected to have utility in inhibition of aortic aneurysms.

Adiposity-associated inflammation and insulin resistance are associated with the development of type II diabetes and atherosclerosis. Macrophages are recruited into adipose tissue and atherosclerotic plaques, and are activated to release inflammatory cytokines and chemokines. In particular, MCP-1 has been shown to play a role in macrophage infiltration into adipose tissue. Leukotriene $B_4$ is a potent pro-inflammatory lipid mediator which is a chemoattractant for inflammatory leukocytes including monocytes and macrophages. In addition, $LTB_4$ has been shown to induce MCP-1 production by monocytes, thus potentially amplifying accumulation and activation of macrophages in adipose tissue and atherosclerotic plaques. $LTA_4H$ is an enzyme in the 5-lipoxygenase pathway which catalyzes the rate-limiting step in the production of $LTB_4$. This pathway is amplified in atherosclerotic lesions of diabetic patients and is genetically linked to cardiovascular disease. Thus inhibitors of $LTA_4H$ may have beneficial therapeutic effects in metabolic disorders through reduction of inflammation.

$LTB_4$ release in the alveoli has been implicated in emphysema of $\alpha$1-antitrypsin ($\alpha$1AT) deficiency (R. C. Hubbard, et al., J. Clinical Investigation 1991, 88, 891-97). Consequently, LTA$_4$H inhibitors may have beneficial therapeutic effects in the treatment or prevention of emphysema of α1AT deficiency.

The effect of the administration of an LTA$_4$H inhibitor, such as the compound in example 150 in U.S. Patent Appl. Publ. No. US2005/0043378, was tested in the context of this invention in the treatment of insulin resistance in the DIO mouse model. LTA$_4$H inhibitor administration (10 mg/kg PO) significantly reduced fed and fasted glucose levels and improved insulin sensitivity as measured by an insulin tolerance test, and significantly reduced fat content of liver and muscle. In mice treated with the LTA$_4$H inhibitor, a reduction in MCP-1 expression was observed in the liver, as well as reduced F4/80 immunoreactivity as a marker of macrophage infiltration, in adipose tissue. Our data suggest that LTA$_4$H inhibitors may be of use for type II diabetes and related metabolic diseases.

Embodiments of this invention are expected to find utility in treating any one or a combination of atopic dermatitis, contact dermatitis, acne (Alestas, et al., J. Mol. Med. 2006, 84(1): 75-87; Zouboulis, et al., Dermatology, 2005, 210(1): 36-8; Arch. Dermatol. 2003, 139(5): 668-70), myocardial infarction (Helgadottir, et al., Nat. Genet. 2006, 38(1): 68-74; Nat. Genet. 2004, 36(3): 233-9; Hakonarson, et al., JAMA 2005, 293(18): 2245-56), stroke (Helgadottir, et al., Nat. Genet. 2004, 36(3): 233-9; Barone, et al., Mol. Chem. Neuropathol. 1995, 24(1): 13-30), pain (Cunha, et al., Br. J. Pharmacol. 2003, 139(6): 1135-45; Hwang, et al., Proc. Natl. Acad. Sci. USA 2000, 97(11): 6155-60), itch (Andoh, et al., Eur. J. Pharmacol. 2006, 547(1-3): 59-64; Andoh et al., J. Investigativ. Dermatol. 2004, 123(1): 196-201); gingivitis (Emingil, et al., J. Periodontol. 2001, 72(8): 1025-31), uveitis (Liao, et al., Invest. Opthalmol. Vis. Sci. 2006, 47(4): 1543-9), bronchitis (Gompertz, et al., Eur. Respir. J. 2001, 17(6): 1112-9), allergic rhinitis, cystic fibrosis (Carpagnano, et al., Am. J. Respir. Crit. Care Med. 2003, 167(8): 1109-12), upper grastrointestinal cancer (Chen, et al., Curr. Cancer Drug Targets 2004, 4(3): 267-83; J. Natl. Cancer Inst. 2003, 95(14): 1053-61), and sepsis (Nakae, et al., Res. Commun. Chem. Pathol. Pharmacol. 1994, 83(2): 151-6, and 84(3): 271-81), Sjogren Larsson syndrome, Sjogren syndrome, skin burns, such as those due to sunburn or some other agent, and type II diabetes.

Examples of textbooks on the subject of inflammation include: 1) Gallin, J. I.; Snyderman, R., Inflammation: Basic Principles and Clinical Correlates, 3rd ed.; Lippincott Williams & Wilkins: Philadelphia, 1999; 2) Stvrtinova, V., et al., Inflammation and Fever. Pathophysiology Principles of Diseases (Textbook for Medical Students); Academic Press: New York, 1995; 3) Cecil; et al. Textbook Of Medicine, 18th ed.; W.B. Saunders Co., 1988; and 4) Stedman's Medical Dictionary.

Background and review material on inflammation and conditions related with inflammation can be found in articles such as the following: C. Nathan, Points of control in inflammation, Nature 2002, 420: 846-852; K. J. Tracey, The inflammatory reflex, Nature 2002, 420: 853-859; L. M. Coussens and Z. Werb, Inflammation and cancer, Nature 2002, 420: 860-867; P. Libby, Inflammation in atherosclerosis, Nature 2002, 420: 868-874; C. Benoist and D. Mathis, Mast cells in autoimmune disease, Nature 2002, 420: 875-878; H. L. Weiner and D. J. Selkoe, Inflammation and therapeutic vaccination in CNS diseases, Nature 2002, 420: 879-884; J. Cohen, The immunopathogenesis of sepsis, Nature 2002, 420: 885-891; D. Steinberg, Atherogenesis in perspective: Hypercholesterolemia and inflammation as partners in crime, Nature Medicine 2002, 8(11): 1211-1217.

Inflammation is due to or associated with any one of a plurality of conditions, such as asthma, chronic obstructive pulmonary disease (COPD), α1-antitrypsin (α1AT) deficiency, atherosclerosis, rheumatoid arthritis, multiple sclerosis, inflammatory bowel diseases (including Crohn's disease and ulcerative colitis), psoriasis, atopic dermatitis, contact dermatitis, acne, myocardial infarction, stroke, pain, itch (pruritus), gingivitis, uveitis, bronchitis, allergic rhinitis, cystic fibrosis, upper gastrointestinal cancer, sepsis, Sjogren syndrome, Sjogren-Larssen syndrome, and skin burns, which are each characterized by excessive or prolonged inflammation at some stage of the disease.

Organ transplant rejection and autoimmune disease treatment with a cyclooxygenase-2 inhibitor and an LTA$_4$H inhibitor are disclosed in WO1997/29774, U.S. Patent Appl. Publ. Nos. US2003/004191 and US2005/043355, and in U.S. Pat. Nos. 5,700,816, 6,407,140. LTA$_4$H inhibitors are disclosed in U.S. Pat. Nos. 5,719,306, 6,506,876, 5,723,492, 5,585,492, and publication WO1996/11192. Cyclic and bicyclic diamino histamine-3 receptor antagonists are disclosed in U.S. Pat. No. 6,559,140. Certain indole derivative compounds are disclosed in U.S. Pat. No. 5,639,752. Benzothiazole and benzoxazole LTA$_4$H modulators have been described in U.S. Patent Appl. Publ. Nos. US2005/0043378 and US2005/0043379, and by Grice et al. (Abstracts of Papers, 234th ACS National Meeting, Boston, Mass., United States, Aug. 19-23, 2007), Rao et al. (J. Pharmacol. Exp. Ther. 2007, 321(3), 1154-1160) and Whittle et al. (Br J. Pharmacol. 2008, 153, 983-991). In addition, diamine derivatives are described as LTA4H inhibitors in U.S. Patent Appl. Publ. No. 2007/0155726 and Intl. Patent Appl. Publ. No. WO2007/079078. Aryl-substituted bridged diamines are disclosed as LTA4H modulators in U.S. Provisional Pat. Appl. No. 60/984,126. Combinations of a cyclooxygenase-2 inhibitor and an LTA$_4$H inhibitor for the treatment of inflammation and inflammation-related disorders are disclosed in U.S. Pat. No. 5,990,148 and in publication WO1996/41625. Nitrogenous derivatives have been disclosed in patent-related as well as in nonpatent-related publications, such as WO2008/016811; US2008/0057074; WO2006/002133; U.S. Pat. No. 6,316,490; U.S. Pat. No. 6,632,823; U.S. Pat. No. 6,432,976; WO2006/133802; WO2003/037904; EP 623621; EP 416521; S. Collin, J. Pharmacie de Belgique, 1991, 46(1) 55-66; P. Dostert, et al., European. J. Med. Chem., 1984, 19(2) 105-110; FR 2446823; U.S. Pat. No. 4,410,535; U.S. Pat. No. 4,352,802; U.S. Pat. No. 4,471,120; U.S. Pat. No. 4,424,358; U.S. Pat. No. 4,321,378; U.S. Pat. No. 4,329,466; U.S. Pat. No. 4,536,580; U.S. Pat. No. 4,273,778; U.S. Pat. No. 4,336,259; U.S. Pat. No. 4,544,660; U.S. Pat. No. 4,599,420; and U.S. Pat. No. 4,705,858. Certain compounds that contain 1,2,3,4-tetrahydrobenzofuro[3,2-c]pyridine moiety are described in Kennis et al., Bioorg & Med Chem. Lett., 2000, 10, 71-74. The synthesis of 1,2,3,4-tetrahydrothianaphtheno[3,2-c]pyridine is disclosed in Capps et al., J Am Chem. Soc., 1953, 75(3), 697-699. Certain tricyclic delta3-piperidines are described in U.S. Pat. No. 6,495,555. Certain thiazolopyridin-2-yloxy-phenyl and thiazolopyrazin-2-yloxy-phenyl amine compounds are disclosed in U.S. patent application Ser. No. 12/421,406. Synthesis of 4-methanesulfonyl-piperidin-1-ylmethyl is described in Intl. Pat. Appl. No. WO 2000/50391. However, there remains a need for potent LTA$_4$H modulators with desirable pharmaceutical properties.

Certain fused bicyclic heteroaryl derivatives have been found in the context of this invention to have LTA$_4$H-modulating activity. References cited throughout the written description are incorporated herein by reference.

SUMMARY OF THE INVENTION

In one aspect, the invention relates to chemical entities encompassing compounds of Formula (I), pharmaceutically acceptable salts of compounds of Formula (I), pharmaceutically acceptable prodrugs of compounds of Formula (I), and solvates of compounds of Formula (I)

(I)
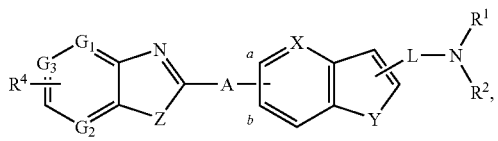

wherein
A is O, bound at site a or at site b;
Z is O or S;
$G_1$, $G_2$ and $G_3$ are each independently $CR^4$ or N;
$R^4$ is H, —$C_{1-4}$alkyl, or halo;
X is CH or N;
Y is O, S, or $NR^3$;
$R^3$ is H or —$C_{1-4}$alkyl;
when Y is O, then L is —$CH_2$—, —$CH_2CH_2$—, or —C(O)—;
when Y is S or $NR^3$, then L is —$CH_2$— or —$CH_2CH_2$—;
$R^1$ and $R^2$ are each independently H, —$C_{1-4}$alkyl, —C(O)$R^i$, —(CH_2)_2C(O)OR^3$, —(CH_2)_2N(CH_2CH_3)_2$, —(CH_2)_3N(CH_3)_2$, —$C_{3-6}$cycloalkyl, —(CH_2)_{1-4}OCH_3$, indan-2-yl,

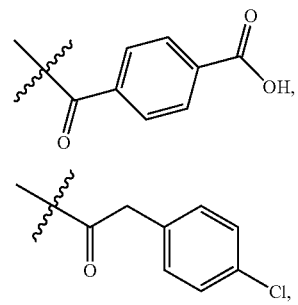

or —(CH_2)_{0-2}$—(O)_{0-1}$-phenyl wherein said phenyl is optionally substituted with halo, —$OCH_3$, or —$SO_2NH_2$; provided that $R^1$ and $R^2$ are not both H simultaneously;
$R^i$ is —$CH_3$, 4-acetyl-piperazin-1-ylmethyl, 3-methyl-isoxazol-5-ylmethyl, 4-hydroxy-cyclohexyl, or

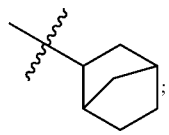 [SMILES: *C1CC2CCC1C2]

or
$R^1$ and $R^2$ are taken together as in one of the following assignments (i) and (ii);
(i) $R^1$ and $R^2$ taken together with the nitrogen member to which they are attached form an unbridged monocyclic moiety, said moiety optionally containing one additional heteroatom member selected from N, O, and S; said moiety being optionally substituted with $R^5$ and $(R^{5'})_m$;
m is 0 or 1;
when m is 1, $R^{5'}$ is —$C_{1-4}$alkyl, halo, or OH;
$R^5$ is selected from H; halo; =O; —OH; —$OR^3$; —$CF_3$; —S(O)(O)CH_3$; —$C_{1-4}$alkyl; —$OC_{1-4}$alkyl; —C(CH_3)_2OH; —(CH_2)_{0-1}C(O)OR^3$; —N(R^3)_2$; —$CH_2OH$; —$CH_2OCH_3$; —(CH_2)_{0-2}NR^9C(O)R^7$; —(CH_2)_{0-2}NHS(O)(O)CH_3$; —C(O)$R^8$; —$C_{3-6}$cycloalkyl; pyrimidin-2-yloxy; 1-piperidinyl; 1-piperidinyl-2-one; 1-pyrrolidinyl; 4-morpholinyl; pyridinyl; pyrimidyl; thiophenylmethyl; 5-oxo-1; 5-dihydro-[1,2,4]triazol-4-yl; —(CH_2)_{0-2}$-phenyl wherein said phenyl is optionally substituted with halo or $OCH_3$; and 1-pyrrolidinyl-2-one optionally substituted with —OH;
Q is $CH_2$ or O;
$R^7$ is —$C_{1-4}$alkyl, —$NH_2$, or —$OC_{1-4}$alkyl;
$R^8$ is —$C_{1-4}$alkyl; —$NH_2$; —$NHCH_3$; —$C_{3-6}$cycloalkyl; —(CH_2)_{0-1}$phenyl wherein said phenyl is optionally substituted with halo or $CO_2H$; 1-pyrrolidinyl; or

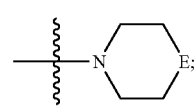

E is $CH_2$, O, or $N(CH_3)$;
$R^9$ is H, —$C_{1-4}$alkyl, or —$C_{3-6}$cycloalkyl;

(ii) R¹ and R² taken together with the nitrogen member to which they are attached form one of the following

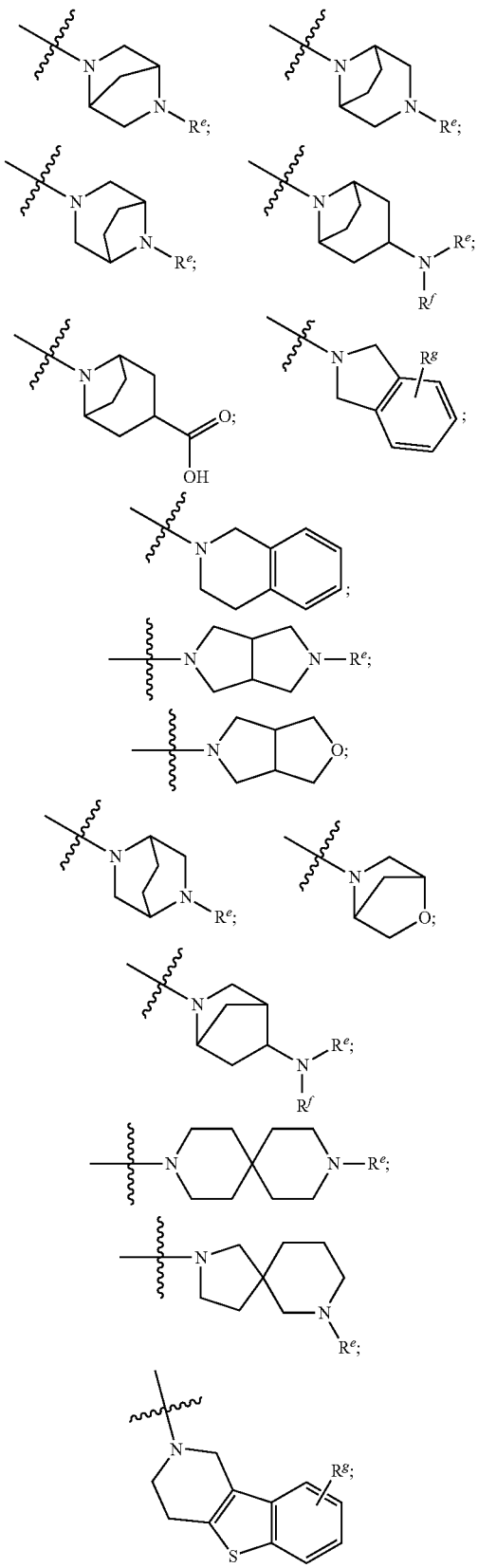

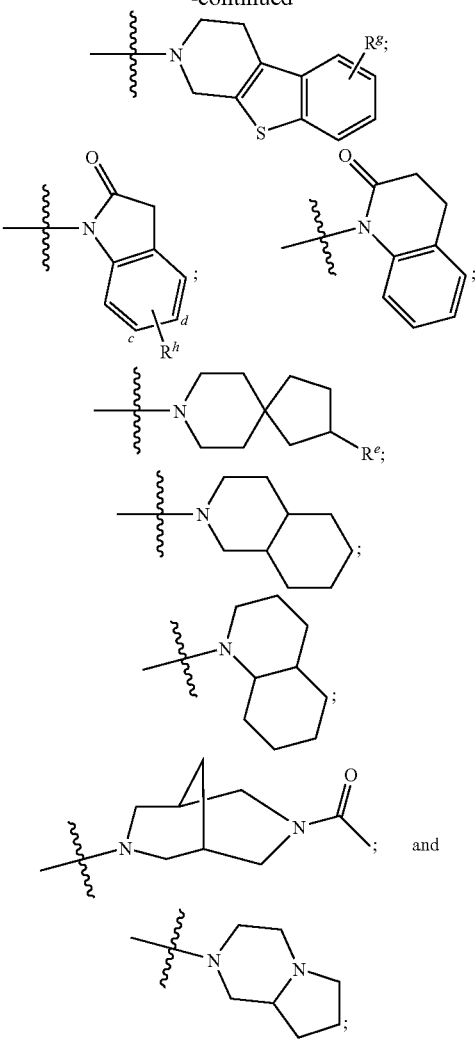

$R^e$ is H, —$C_{1-4}$alkyl, —C(O)$C_{1-4}$alkyl, —C(O)O$C_{1-4}$alkyl, —C(O)NH$_2$, —C(O)-tetrahydrofuranyl, —C(O)CH$_2$OH, —C(O)isoxazol-5-yl, —C(O)furan-3-yl, —C(O)pyrazin-2-yl, —C(O)cyclobutyl, —S(O)(O)CH$_3$, or 4-methoxycarbonyl-benzyl;

$R^f$ is H, —CH$_3$, or —CH$_2$C(O)OR$^3$;

$R^g$ is H or halo; and $R^h$ is bound at site c or d and is selected from H, CF$_3$, and halo.

In certain embodiments, the compound of Formula (I) is a compound selected from those species described or exemplified in the detailed description below.

In a further aspect, the invention relates to pharmaceutical compositions each comprising an effective amount of at least one chemical entity selected from compounds of Formula (I), pharmaceutically acceptable salts of compounds of Formula (I), pharmaceutically acceptable prodrugs of compounds of Formula (I), and solvates of compounds of Formula (I). Pharmaceutical compositions according to the invention may further comprise a pharmaceutically acceptable excipient.

In another aspect, embodiments of the invention are useful as LTA$_4$H modulators. Thus, the invention is directed to methods for modulating LTA$_4$H activity, comprising exposing LTA$_4$H to an effective amount of at least one chemical entity selected from compounds of Formula (I), pharmaceutically acceptable salts of compounds of Formula (I), and pharmaceutically acceptable prodrugs of compounds of Formula (I).

In another aspect, the invention is directed to a method of treating a subject suffering from or diagnosed with a disease, disorder, or medical condition mediated by LTA$_4$H activity, comprising administering to the subject in need of such treatment an effective amount of at least one chemical entity selected from compounds of Formula (I), pharmaceutically acceptable salts of compounds of Formula (I), and pharmaceutically acceptable prodrugs of compounds of Formula (I).

In certain embodiments of the inventive method, the disease, disorder, or medical condition is inflammation, atopic dermatitis, or asthma. An object of the present invention is to overcome or ameliorate at least one of the disadvantages of the conventional methodologies and/or prior art, or to provide a useful alternative thereto.

Additional embodiments, features, and advantages of the invention will be apparent from the following detailed description and through practice of the invention.

DETAILED DESCRIPTION

For the sake of brevity, the disclosures of the publications, including patents, cited in this specification are herein incorporated by reference.

The terms "including", "containing" and "comprising" are used herein in their open, non-limiting sense.

The term "alkyl" refers to a straight- or branched-chain alkyl group having, unless indicated explicitly otherwise, from 1 to 12 carbon atoms in the chain. Examples of alkyl groups include methyl (Me), ethyl (Et), n-propyl, isopropyl, butyl, isobutyl, sec-butyl, tert-butyl (tBu), pentyl, isopentyl, tert-pentyl, hexyl, isohexyl, and groups that in light of the ordinary skill in the art and the teachings provided herein would be considered equivalent to any one of the foregoing examples.

The term "cycloalkyl" refers to a saturated or partially saturated, monocyclic, fused polycyclic, or spiro polycyclic carbocycle having, unless indicated explicitly otherwise, from 3 to 12 ring atoms per carbocycle. Illustrative examples of cycloalkyl groups include the following entities, in the form of properly bonded moieties:

A "heterocycloalkyl" refers to a monocyclic, or fused, bridged, or spiro polycyclic ring structure that is saturated or partially saturated and has, unless indicated explicitly otherwise, from 3 to 12 ring atoms per ring structure selected from carbon atoms and up to three heteroatoms selected from nitrogen, oxygen, and sulfur. The ring structure may optionally contain up to two oxo groups on carbon or sulfur ring members. Illustrative entities, in the form of properly bonded moieties, include:

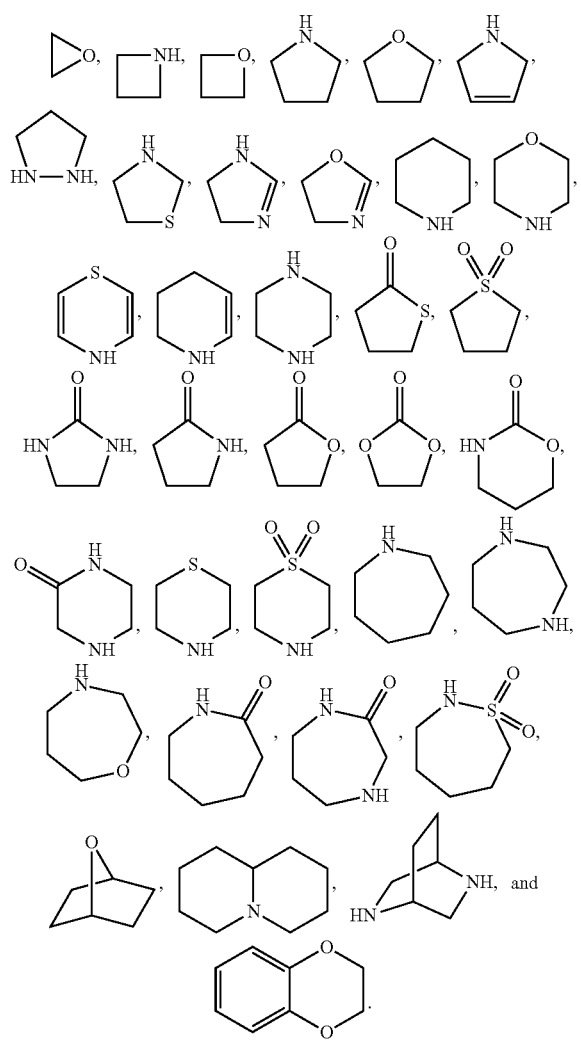

The term "heteroaryl" refers to a monocyclic, fused bicyclic, or fused polycyclic aromatic heterocycle (ring structure having ring atoms selected from carbon atoms and up to four heteroatoms selected from nitrogen, oxygen, and sulfur) having, unless indicated explicitly otherwise, from 3 to 12 ring atoms per heterocycle. Illustrative examples of heteroaryl groups include the following entities, in the form of properly bonded moieties:

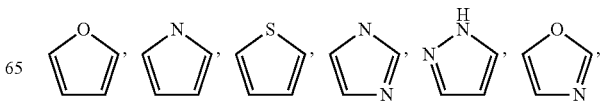

-continued

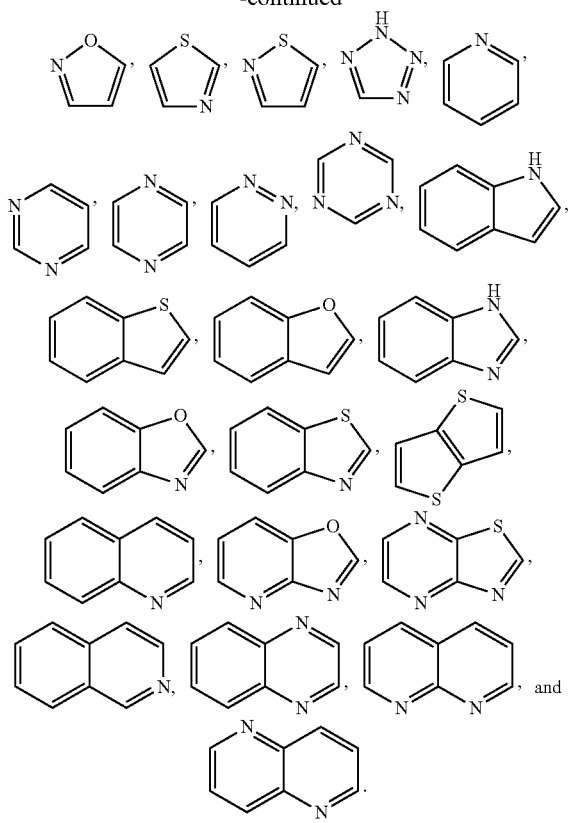

Those skilled in the art will recognize that the species of cycloalkyl, heterocycloalkyl, and heteroaryl groups listed or illustrated above are not exhaustive, and that additional species within the scope of these defined terms may also be selected.

The term "halogen" represents chlorine, fluorine, bromine, or iodine. The term "halo" represents chloro, fluoro, bromo, or iodo.

The term "substituted" means that the specified group or moiety bears one or more substituents. The term "unsubstituted" means that the specified group bears no substituents. The term "optionally substituted" means that the specified group is unsubstituted or substituted by one or more substituents. Where the term "substituted" is used to describe a structural system, unless specified otherwise, the substitution is meant to occur at any valency-allowed position on the system.

Any formula given herein is intended to represent compounds having structures depicted by the structural formula as well as certain variations or forms. In particular, compounds of any formula given herein may have asymmetric centers and therefore exist in different enantiomeric forms. All optical isomers and stereoisomers of the compounds of the general formula, and mixtures thereof, are then considered within the scope of the formula. Thus, any formula given herein is intended to represent in such case a racemate, one or more enantiomeric forms, one or more diastereomeric forms, one or more atropisomeric forms, and mixtures thereof. Furthermore, structures that may exist as geometric isomers (i.e., cis and trans isomers), as tautomers, or as atropisomers, are also in such case envisaged within the scope of the corresponding structural formula or formulae given herein.

Certain formulae given herein may be meso compounds, which are compounds that possess asymmetric centers (in this case, asymmetric carbons), but which are achiral molecules. Such compounds are named herein as meso compounds. In some cases, meso compounds are depicted and named herein with a specific stereochemical configuration. However, one skilled in the art will recognize the meso nature of such compounds. Examples of such compounds are meso-endo-N-{8-[6-(4-fluoro-benzothiazol-2-yloxy)-1H-indol-3-ylmethyl]-8-aza-bicyclo[3.2.1]oct-3-yl}-acetamide and meso-endo-N-{8-[6-(thiazolo[4,5-b]pyridin-2-yloxy)-1H-indol-3-ylmethyl]-8-aza-bicyclo[3.2.1]oct-3-yl}-acetamide.

Compounds that incorporate amines such as ExA, ExB, ExC, and ExD, which are listed below, are described as "endo" or "exo" in their chemical name to denote the orientation of the two-methylene bridge with respect to the functionalized exocyclic amine. One skilled in the art will recognize that ExA and ExB are equivalent and that ExC and ExD are equivalent. Furthermore, stereochemical labels for stereocenters (e.g., R and/or S) in meso compounds have been omitted since such labels are extraneous due to the plane of symmetry.

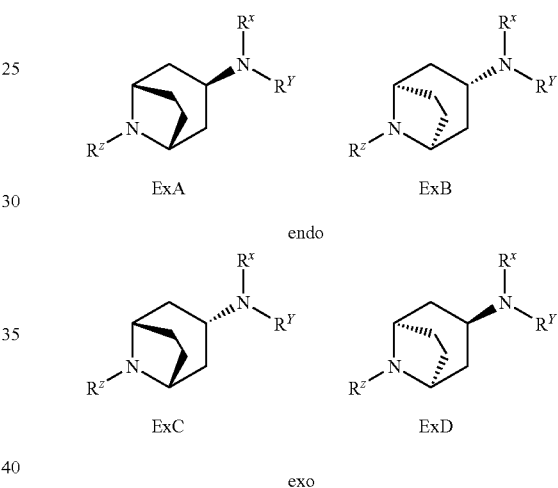

Additionally, any formula given herein is intended to refer also to hydrates, solvates, and polymorphs of such compounds, and mixtures thereof, even if such forms are not listed explicitly. Certain compounds of Formula (I) or pharmaceutically acceptable salts of compounds of Formula (I) may be obtained as solvates.

To provide a more concise description, some of the quantitative expressions given herein are not qualified with the term "about". It is understood that, whether the term "about" is used explicitly or not, every quantity given herein is meant to refer to the actual given value, and it is also meant to refer to the approximation to such given value that would reasonably be inferred based on the ordinary skill in the art, including equivalents and approximations due to the experimental and/or measurement conditions for such given value. Whenever a yield is given as a percentage, such yield refers to a mass of the entity for which the yield is given with respect to the maximum amount of the same entity that could be obtained under the particular stoichiometric conditions. Concentrations that are given as percentages refer to mass ratios, unless indicated differently.

Reference to a chemical entity herein stands for a reference to any one of: (a) the actually recited form of such chemical entity, and (b) any of the forms of such chemical entity in the medium in which the compound is being considered when named. For example, reference herein to a compound such as R—COOH, encompasses reference to any one of, for example, R—COOH$_{(s)}$, R—COOH$_{(sol)}$, and R—COO$^-_{(sol)}$. In this example, R—COOH$_{(s)}$ refers to the solid compound, as it could be for example in a tablet or some other solid pharmaceutical composition or preparation; R—COOH$_{(sol)}$ refers to the undissociated form of the compound in a solvent; and R—COO$^-_{(sol)}$ refers to the dissociated form of the compound in a solvent, such as the dissociated form of the compound in an aqueous environment, whether such dissociated form derives from R—COOH, from a salt thereof, or from any other entity that yields R—COO$^-$ upon dissociation in the medium being considered. In another example, an expression such as "exposing an entity to compound of formula R—COOH" refers to the exposure of such entity to the form, or forms, of the compound R—COOH that exists, or exist, in the medium in which such exposure takes place. In still another example, an expression such as "reacting an entity with a compound of formula R—COOH" refers to the reacting of (a) such entity in the chemically relevant form, or forms, of such entity that exists, or exist, in the medium in which such reacting takes place, with (b) the chemically relevant form, or forms, of the compound R—COOH that exists, or exist, in the medium in which such reacting takes place. In this regard, if such entity is for example in an aqueous environment, it is understood that the compound R—COOH is in such same medium, and therefore the entity is being exposed to species such as R—COOH$_{(aq)}$ and/or R—COO$^-_{(aq)}$, where the subscript "(aq)" stands for "aqueous" according to its conventional meaning in chemistry and biochemistry. A carboxylic acid functional group has been chosen in these nomenclature examples; this choice is not intended, however, as a limitation but it is merely an illustration. It is understood that analogous examples can be provided in terms of other functional groups, including but not limited to hydroxyl, basic nitrogen members, such as those in amines, and any other group that interacts or transforms according to known manners in the medium that contains the compound. Such interactions and transformations include, but are not limited to, dissociation, association, tautomerism, solvolysis, including hydrolysis, solvation, including hydration, protonation, and deprotonation.

In another example, a zwitterionic compound is encompassed herein by referring to a compound that is known to form a zwitterion, even if it is not explicitly named in its zwitterionic form. Terms such as zwitterion, zwitterions, and their synonyms zwitterionic compound(s) are standard IUPAC-endorsed names that are well known and part of standard sets of defined scientific names. In this regard, the name zwitterion is assigned the name identification CHEBI:27369 by the Chemical Entities of Biological Interest (ChEBI) dictionary of molecular entities. As generally well known, a zwitterion or zwitterionic compound is a neutral compound that has formal unit charges of opposite sign. Sometimes these compounds are referred to by the term "inner salts". Other sources refer to these compounds as "dipolar ions", although the latter term is regarded by still other sources as a misnomer. As a specific example, aminoethanoic acid (the amino acid glycine) has the formula $H_2NCH_2COOH$, and it exists in some media (in this case in neutral media) in the form of the zwitterion $^+H_3NCH_2COO^-$. Zwitterions, zwitterionic compounds, inner salts and dipolar ions in the known and well established meanings of these terms are within the scope of this invention, as would in any case be so appreciated by those of ordinary skill in the art. Because there is no need to name each and every embodiment that would be recognized by those of ordinary skill in the art, no structures of the zwitterionic compounds that are associated with the compounds of this invention are given explicitly herein. They are, however, part of the embodiments of this invention. No further examples in this regard are provided herein because the interactions and transformations in a given medium that lead to the various forms of a given compound are known by any one of ordinary skill in the art.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, chlorine, and iodine, such as $^2H$, $^3H$, $^{11}C$, $^{13}C$, $^{14}C$, $^{15}N$, $^{18}O$, $^{17}O$, $^{32}P$, $^{33}P$, $^{35}S$, $^{18}F$, $^{36}Cl$, and $^{125}I$, respectively. Such isotopically labelled compounds are useful in metabolic studies (preferably with $^{14}C$) reaction kinetic studies (with, for example $^2H$ or $^3H$), detection or imaging techniques [such as positron emission tomography (PET) or single-photon emission computed tomography (SPECT)] including drug or substrate tissue distribution assays, or in radioactive treatment of patients. In particular, an $^{18}F$ or $^{11}C$ labeled compound may be particularly preferred for PET or SPECT studies. Further, substitution with heavier isotopes such as deuterium (i.e., $^2H$) may afford certain therapeutic advantages resulting from greater metabolic stability, for example increased in vivo half-life or reduced dosage requirements. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

When referring to any formula given herein, the selection of a particular moiety from a list of possible species for a specified variable is not intended to define the same choice of the species for the variable appearing elsewhere. In other words, where a variable appears more than once, the choice of the species from a specified list is independent of the choice of the species for the same variable elsewhere in the formula, unless stated otherwise.

By way of a first example on substituent terminology, if substituent $S^1_{example}$ is one of $S_1$ and $S_2$, and substituent $S^2_{example}$ is one of $S_3$ and $S_4$, then these assignments refer to embodiments of this invention given according to the choices $S^1$ example is $S_1$ and $S^2_{example}$ is $S_3$; $S^1_{example}$ is $S_1$ and $S^2_{example}$ is $S_4$; $S^1_{example}$ is $S_2$ and $S^2_{example}$ is $S_3$; $S^1_{example}$ is $S_2$ and $S^2_{example}$ is $S_4$; and equivalents of each one of such choices. The shorter terminology "$S^1_{example}$ is one of $S_1$ and $S_2$, and $S^2_{example}$ is one of $S_3$ and $S_4$" is accordingly used herein for the sake of brevity, but not by way of limitation. The foregoing first example on substituent terminology, which is stated in generic terms, is meant to illustrate the various substituent assignments described herein. The foregoing convention given herein for substituents extends, when applicable, to members such as $R^1$, $R^2$, $R^3$, A, Z, $G_1$, $G_2$, X, and E, and any other generic substituent symbol used herein.

Furthermore, when more than one assignment is given for any member or substituent, embodiments of this invention comprise the various groupings that can be made from the listed assignments, taken independently, and equivalents thereof. By way of a second example on substituent terminology, if it is herein described that substituent $S_{example}$ is one of $S_1$, $S_2$, and $S_3$, this listing refers to embodiments of this invention for which $S_{example}$ is $S_1$; $S_{example}$ is $S_2$; $S_{example}$ is $S_3$; $S_{example}$ is one of $S_1$ and $S_2$; $S_{example}$ is one of $S_1$ and $S_3$;

$S_{example}$ is one of $S_2$ and $S_3$; $S_{example}$ is one of $S_1$, $S_2$ and $S_3$; and $S_{example}$ is any equivalent of each one of these choices. The shorter terminology "$S_{example}$ is one of $S_1$, $S_2$, and $S_3$" is accordingly used herein for the sake of brevity, but not by way of limitation. The foregoing second example on substituent terminology, which is stated in generic terms, is meant to illustrate the various substituent assignments described herein. The foregoing convention given herein for substituents extends, when applicable, to members such as $R^1$, $R^2$, $R^3$, A, Z, $G_1$, $G_2$, X, and E, and any other generic substituent symbol used herein.

The nomenclature "$C_{i-j}$" with j>i, when applied herein to a class of substituents, is meant to refer to embodiments of this invention for which each and every one of the number of carbon members, from i to j including i and j, is independently realized. By way of example, the term $C_{1-3}$ refers independently to embodiments that have one carbon member ($C_1$), embodiments that have two carbon members ($C_2$), and embodiments that have three carbon members ($C_3$).

The term $C_{n-m}$alkyl refers to an aliphatic chain, whether straight or branched, with a total number N of carbon members in the chain that satisfies n≦N≦m, with m>n.

Any disubstituent referred to herein is meant to encompass the various attachment possibilities when more than one of such possibilities are allowed. For example, reference to disubstituent -A-B-, where A≠B, refers herein to such disubstituent with A attached to a first substituted member and B attached to a second substituted member, and it also refers to such disubstituent with A attached to the second substituted member and B attached to the first substituted member.

According to the foregoing interpretive considerations on assignments and nomenclature, it is understood that explicit reference herein to a set implies, where chemically meaningful and unless indicated otherwise, independent reference to embodiments of such set, and reference to each and every one of the possible embodiments of subsets of the set referred to explicitly.

In certain embodiments of Formula (I), L is —$CH_2$— or —$CH_2CH_2$—. In certain embodiments of Formula (I), when Y is O, then L is selected from —$CH_2$—, —$CH_2CH_2$—, and —C(O)—. In further embodiments of Formula (I), when Y is S or $NR^3$, then L is selected from —$CH_2$— or —$CH_2CH_2$—.

In certain embodiments of Formula (I), $R^1$ and $R^2$ are each independently H, —$C_{1-4}$alkyl, —$C_{3-6}$cycloalkyl, —$(CH_2)_{1-4}$OCH_3$,

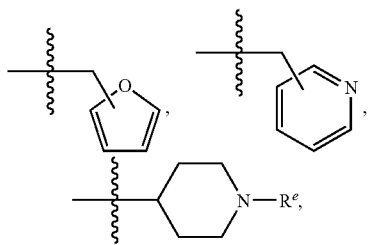

or benzyl, provided that $R^1$ and $R^2$ are not both H simultaneously. In further embodiments of Formula (I), $R^1$ and $R^2$ are each independently H, —$C_{1-4}$alkyl, —C(O)$R^i$, —$(CH_2)_2$C(O)$OR^3$, —$(CH_2)_2$N(CH_2CH_3)_2$, —$(CH_2)_3$N(CH_3)_2$, —$C_{3-6}$cycloalkyl, —$(CH_2)_{1-4}$OCH_3$ or indan-2-yl, provided that $R^1$ and $R^2$ are not both H simultaneously. In further embodiments of Formula (I), $R^1$ and $R^2$ are each independently

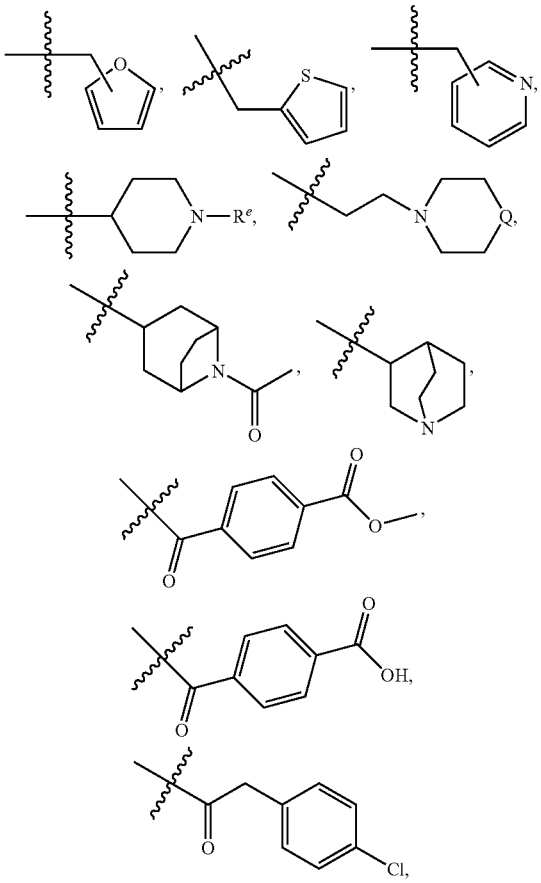

or —$(CH_2)_{0-2}$—$(O)_{0-1}$-phenyl wherein said phenyl is optionally substituted with halo, —$OCH_3$, or —$SO_2NH_2$.

In certain embodiments of Formula (I), $R^i$ is —$CH_3$.

In certain embodiments of Formula (I), $R^i$ is 4-acetyl-piperazin-1-ylmethyl.

In certain embodiments of Formula (I), $R^i$ is 3-methyl-isoxazol-5-ylmethyl.

In certain embodiments of Formula (I), $R^i$ is selected from 4-hydroxy-cyclohexyl, and

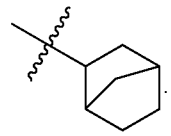

In further embodiments of Formula (I), $R^1$ and $R^2$ are taken together with the nitrogen member to which they are attached to form an unbridged monocyclic moiety, said moiety optionally containing one additional heteroatom member selected from N, O, and S; and said moiety being optionally substituted with $R^5$.

In certain embodiments of Formula (I), $R^5$ is selected from H, halo, —$CF_3$, —S(O)(O)$CH_3$, —$C_{1-4}$alkyl, —C($CH_3$)$_2$OH, —$(CH_2)_{0-1}$C(O)$OR^3$, —$NH_2$, —$CH_2$OH, —$CH_2$OCH_3$, —$(CH_2)_{0-1}$NHC(O)$R^7$, —NHS(O)(O)$CH_3$, —C(O)$R^8$, phenyl, pyridinyl, pyrimidin-2-yloxy, and 1-pyrrolidinyl-2-one optionally substituted with —OH; wherein $R^7$ is —$C_{1-4}$alkyl, —$NH_2$, or —O$C_{1-4}$alkyl; $R^8$ is —$C_{1-4}$alkyl, —$NH_2$, —$NHCH_3$, 1-pyrrolidinyl, or

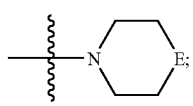

and

E is CH$_2$, O, or N(CH$_3$).

In some embodiments, E is O. In other embodiments, E is N(CH$_3$).

In some embodiments, Q is O. In other embodiments, Q is CH$_2$.

In further embodiments of Formula (I), R$^1$ and R$^2$ taken together with the nitrogen member to which they are attached form one of the following

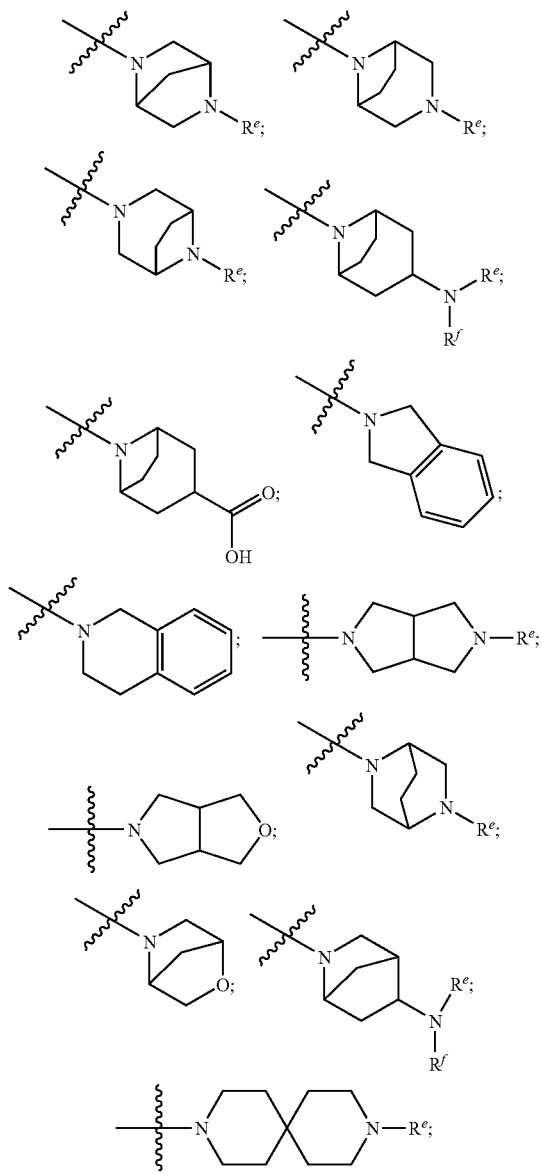

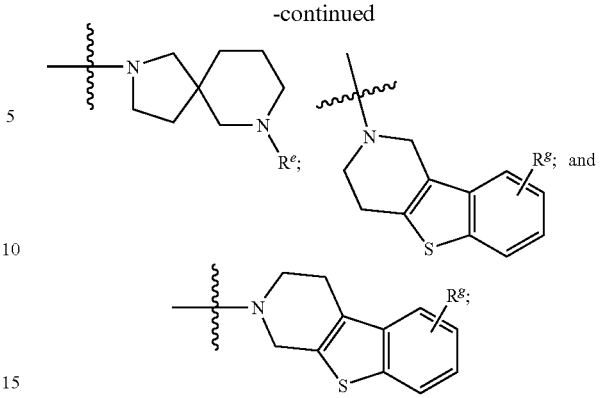

wherein R$^e$ is H, —C(O)C$_{1-4}$alkyl, —C(O)OC$_{1-4}$alkyl, —S(O)(O)CH$_3$, or —C(O)NH$_2$; R$^f$ is H, —CH$_3$, or —CH$_2$C(O)OR$^3$; and R$^g$ is H or halo.

In certain embodiments of Formula (I), R$^1$ and R$^2$ are each independently H, —C$_{1-4}$alkyl, or benzyl, provided that R$^1$ and R$^2$ are not both H simultaneously.

In further embodiments of Formula (I), R$^1$ and R$^2$ are taken together with the nitrogen member to which they are attached to form an unbridged monocyclic moiety, said moiety optionally containing one additional heteroatom that is N; said moiety being optionally substituted with R$^5$.

In further embodiments of Formula (I), R$^1$ and R$^2$ are taken together with the nitrogen member to which they are attached to form an unbridged monocyclic moiety, said moiety optionally containing one additional heteroatom member that is O; said moiety being optionally substituted with R$^5$.

In further embodiments of Formula (I), R$^1$ and R$^2$ are taken together with the nitrogen member to which they are attached to form an unbridged monocyclic moiety, said moiety optionally containing one additional heteroatom member that is S; said moiety being optionally substituted with R$^5$.

In certain embodiments of Formula (I), R$^5$ is selected from H, halo, —S(O)(O)CH$_3$, —C$_{1-4}$alkyl, —(CH$_2$)$_{0-1}$C(O)OR$^3$, —NH$_2$, —CH$_2$OH, —NHC(O)R$^7$, —NHS(O)(O)CH$_3$, —C(O)R$^8$, phenyl, pyrimidin-2-yloxy, and 1-pyrrolidinyl-2-one optionally substituted with —OH; and wherein R$^7$ is —CH$_3$, —NH$_2$, or —OC$_{1-4}$alkyl; R$^8$ is —C$_{1-4}$alkyl, —NH$_2$, —NHCH$_3$, 1-pyrrolidinyl, or

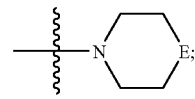

and E is CH$_2$, O, or N(CH$_3$).

In further embodiments of Formula (I), R$^1$ and R$^2$ taken together with the nitrogen member to which they are attached form one of the following

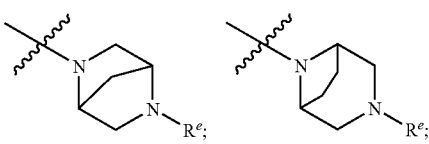

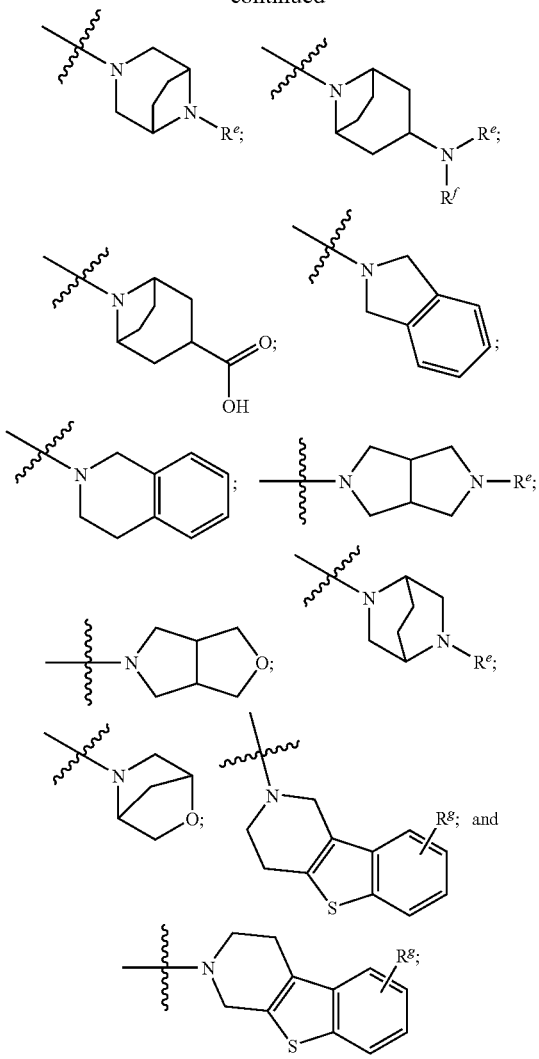

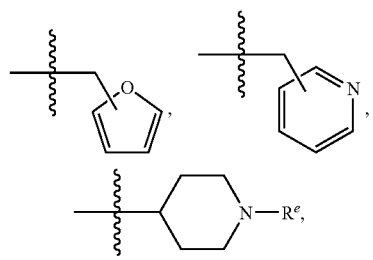

or benzyl, provided that $R^1$ and $R^2$ are not both H simultaneously.

In further embodiments, $R^1$ and $R^2$ taken together with the nitrogen member to which they are attached form one of the following

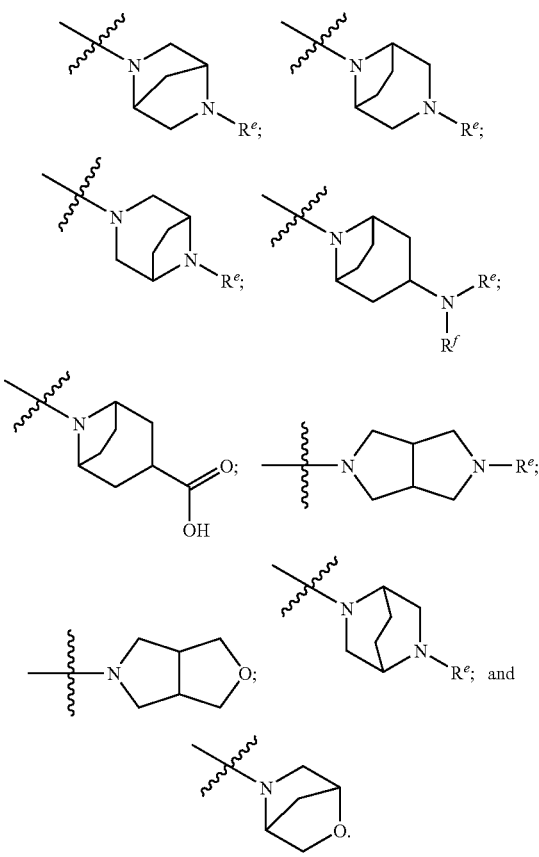

wherein $R^e$ is H, —C(O)C$_{1-4}$alkyl, —C(O)OC$_{1-4}$alkyl, or —C(O)NH$_2$; $R^f$ is H, —CH$_3$, or —CH$_2$C(O)OR$^3$; and $R^g$ is H or halo.

In certain embodiments of Formula (I), Z is O. In other embodiments, Z is S.

In certain embodiments, $G_1$ is N. In further embodiments, $G_1$ is CR$^4$.

In certain embodiments, $G_2$ is N. In further embodiments, $G_2$ is CR$^4$.

In certain embodiments, $G_3$ is N. In further embodiments, $G_3$ is CR$^4$.

In further embodiments, Z is O and $G_1$ is N.

In other embodiments, Y is O. In other embodiments, Y is NR$^3$.

In yet further embodiments, Y is NR$^3$ and R$^3$ is H.

In further embodiments, Y is S.

In certain embodiments, Z is S and $G_1$ is N. In certain embodiments, Z is S, $G_1$ is N, and X is CH. In certain embodiments, Z is S, $G_1$ is N, and A is bound at site b.

In certain embodiments of Formula (I), L is —CH$_2$—. In further embodiments, L is —CH$_2$CH$_2$—. In yet further embodiments, L is —C(O)— and Y is O.

In certain embodiments of Formula (I), $R^1$ and $R^2$ are each independently H, C$_{1-4}$alkyl, —C$_{3-6}$cycloalkyl, —(CH$_2$)$_{1-4}$OCH$_3$, In some embodiments, $R^1$ and $R^2$ taken together with the nitrogen member to which they are attached form one of the following

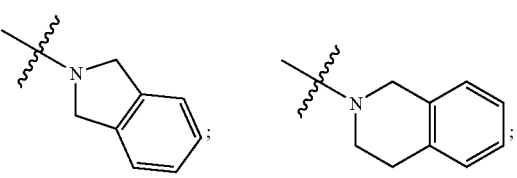

-continued

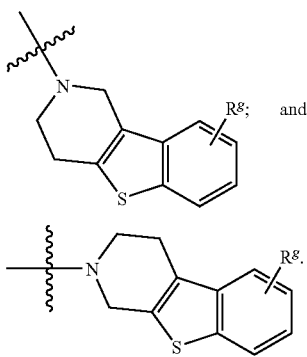

In some embodiments, $R^1$ and $R^2$ taken together with the nitrogen member to which they are attached form one of the following

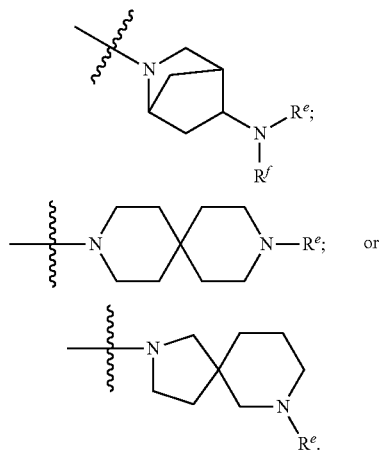

In some embodiments, $R^1$ and $R^2$ taken together with the nitrogen member to which they are attached form one of the following

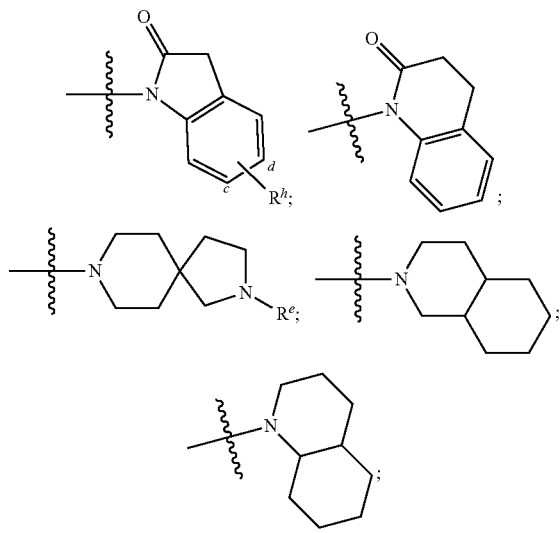

-continued

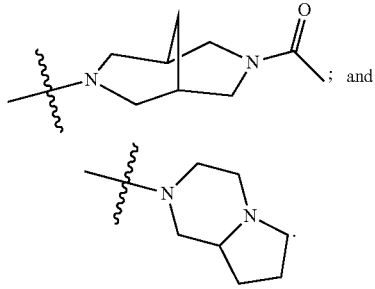

In some embodiments, $R^1$ and $R^2$ are taken together with the nitrogen member to which they are attached to form one of the following moieties; azetidine, pyrrolidine, piperidine, piperazine, or [1,4]-diazepane, wherein each of said moieties is optionally substituted with $R^5$ and $(R^{5'})_m$.

In some embodiments, $R^1$ and $R^2$ are taken together with the nitrogen member to which they are attached to form piperidine, optionally substituted with $R^5$, with $R^5$ being —$(CH_2)_{0-2}NR^9C(O)R^7$.

In some embodiments, $R^7$ is —$C_{1-4}$alkyl.

In other embodiments, $R^7$ is —$NH_2$, or —$OC_{1-4}$alkyl.

In some embodiments, $R^8$ is —$C_{1-4}$alkyl; —$NH_2$; —$NHCH_3$; —$C_{3-6}$cycloalkyl; —$(CH_2)_{0-1}$-phenyl wherein said phenyl is optionally substituted with halo or $CO_2H$; 1-pyrrolidinyl; or

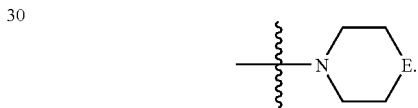

In some embodiments, $R^9$ is H.

In some embodiments, $R^9$ is —$C_{1-4}$alkyl, or —$C_{3-6}$cycloalkyl.

In some embodiments, m is 0.

When m is 1, $R^{5'}$ is in some embodiments —OH.

$R^5$ is selected in some embodiments from H; halo; =O; —OH; —$CF_3$; —$C_{3-6}$cycloalkyl; —$C_{1-4}$alkyl; and —$(CH_2)_{0-2}$-phenyl wherein said phenyl is optionally substituted with halo or $OCH_3$.

$R^5$ is selected in some embodiments from —$S(O)(O)CH_3$; —$(CH_2)_{0-2}NHS(O)(O)CH_3$; and thiophenylmethyl.

$R^5$ is selected in some embodiments from —$OR^3$; —$OC_{1-4}$alkyl; —$C(CH_3)_2OH$; —$(CH_2)_{0-1}C(O)OR^3$; —$CH_2OH$; —$CH_2OCH_3$; —$C(O)R^8$.

$R^5$ is selected in some embodiments from —$N(R^3)_2$; —$(CH_2)_{0-2}NR^9C(O)R^7$; pyrimidin-2-yloxy; 1-piperidinyl; 1-piperidinyl-2-one; 1-pyrrolidinyl; 4-morpholinyl; pyridinyl; pyrimidyl; 5-oxo-1; 5-dihydro-[1,2,4]triazol-4-yl; and 1-pyrrolidinyl-2-one optionally substituted with —OH.

$R^5$ is selected in some embodiments from —$S(O)(O)CH_3$; —$OC_{1-4}$alkyl; —$C(CH_3)_2OH$; —$(CH_2)_{0-1}C(O)OR^3$; —$N(R^3)_2$; —$CH_2OH$; —$CH_2OCH_3$; —$(CH_2)_{0-2}NR^9C(O)R^7$; —$(CH_2)_{0-2}NHS(O)(O)CH_3$; —$C(O)R^8$; —$C_{3-6}$cycloalkyl; pyrimidin-2-yloxy; 1-piperidinyl; 1-piperidinyl-2-one; 1-pyrrolidinyl; 4-morpholinyl; pyridinyl; pyrimidyl; thiophenylmethyl; 5-oxo-1; 5-dihydro-[1,2,4]triazol-4-yl; —$(CH_2)_{0-2}$-phenyl wherein said phenyl is optionally substituted with halo or $OCH_3$; and 1-pyrrolidinyl-2-one optionally substituted with —OH.

In some embodiments, chemical entities of the present invention are selected from the compounds exemplified below and pharmaceutically acceptable salts, prodrugs, and solvates thereof.

The invention includes also pharmaceutically acceptable salts of compounds of Formula (I), including, but not limited to, the specific compounds exemplified herein, and methods using such salts.

A "pharmaceutically acceptable salt" is intended to mean a salt of a free acid or base of a compound represented by Formula (I) that is non-toxic, biologically tolerable, or otherwise biologically suitable for administration to the subject. See, generally, S. M. Berge, et al., "Pharmaceutical Salts", J. Pharm. Sci., 1977, 66:1-19, and *Handbook of Pharmaceutical Salts, Properties, Selection, and Use*, Stahl and Wermuth, Eds., Wiley-VCH and VHCA, Zurich, 2002. Preferred pharmaceutically acceptable salts are those that are pharmacologically effective and suitable for contact with the tissues of patients without undue toxicity, irritation, or allergic response. A compound of Formula (I) may possess a sufficiently acidic group, a sufficiently basic group, or both types of functional groups, and accordingly react with a number of inorganic or organic bases, and inorganic and organic acids, to form a pharmaceutically acceptable salt. Examples of pharmaceutically acceptable salts include sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methyl benzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycolates, tartrates, methane-sulfonates, propanesulfonates, naphthalene-1-sulfonates, naphthalene-2-sulfonates, and mandelates.

If the compound of Formula (I) contains a basic nitrogen, the desired pharmaceutically acceptable salt may be prepared by any suitable method available in the art, for example, treatment of the free base with an inorganic acid, such as hydrochloric acid, hydrobromic acid, sulfuric acid, sulfamic acid, nitric acid, boric acid, phosphoric acid, and the like, or with an organic acid, such as acetic acid, phenylacetic acid, propionic acid, stearic acid, lactic acid, ascorbic acid, maleic acid, hydroxymaleic acid, isethionic acid, succinic acid, valeric acid, fumaric acid, malonic acid, pyruvic acid, oxalic acid, glycolic acid, salicylic acid, oleic acid, palmitic acid, lauric acid, a pyranosidyl acid, such as glucuronic acid or galacturonic acid, an alpha-hydroxy acid, such as mandelic acid, citric acid, or tartaric acid, an amino acid, such as aspartic acid or glutamic acid, an aromatic acid, such as benzoic acid, 2-acetoxybenzoic acid, naphthoic acid, or cinnamic acid, a sulfonic acid, such as laurylsulfonic acid, p-toluenesulfonic acid, methanesulfonic acid, ethanesulfonic acid, any compatible mixture of acids such as those given as examples herein, and any other acid and mixture thereof that are regarded as equivalents or acceptable substitutes in light of the ordinary level of skill in this technology.

If the compound of Formula (I) is an acid, such as a carboxylic acid or sulfonic acid, the desired pharmaceutically acceptable salt may be prepared by any suitable method, for example, treatment of the free acid with an inorganic or organic base, such as an amine (primary, secondary or tertiary), an alkali metal hydroxide, alkaline earth metal hydroxide, any compatible mixture of bases such as those given as examples herein, and any other base and mixture thereof that are regarded as equivalents or acceptable substitutes in light of the ordinary level of skill in this technology. Illustrative examples of suitable salts include organic salts derived from amino acids, such as glycine and arginine, ammonia, carbonates, bicarbonates, primary, secondary, and tertiary amines, and cyclic amines, such as benzylamines, pyrrolidines, piperidine, morpholine, and piperazine, and inorganic salts derived from sodium, calcium, potassium, magnesium, manganese, iron, copper, zinc, aluminum, and lithium.

In further embodiments, compounds of Formula (I) were obtained in free base form, and in salt forms, such as hydrochloride salt and formate salt.

The invention also relates to pharmaceutically acceptable prodrugs of the compounds of Formula (I), and methods employing such pharmaceutically acceptable prodrugs. The term "prodrug" means a precursor of a designated compound that, following administration to a subject, yields the compound in vivo via a chemical or physiological process such as solvolysis or enzymatic cleavage, or under physiological conditions (e.g., a prodrug on being brought to physiological pH is converted to the compound of Formula (I)). A "pharmaceutically acceptable prodrug" is a prodrug that is non-toxic, biologically tolerable, and otherwise biologically suitable for administration to the subject. Illustrative procedures for the selection and preparation of suitable prodrug derivatives are described, for example, in "Design of Prodrugs", ed. H. Bundgaard, Elsevier, 1985.

Examples of prodrugs include compounds having an amino acid residue, or a polypeptide chain of two or more (e.g., two, three or four) amino acid residues, covalently joined through an amide or ester bond to a free amino, hydroxy, or carboxylic acid group of a compound of Formula (I). Examples of amino acid residues include the twenty naturally occurring amino acids, commonly designated by three letter symbols, as well as 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone.

Additional types of prodrugs may be produced, for instance, by derivatizing free carboxyl groups of structures of Formula (I) as amides or alkyl esters. Examples of amides include those derived from ammonia, primary $C_{1-6}$alkyl amines and secondary di($C_{1-6}$alkyl) amines. Secondary amines include 5- or 6-membered heterocycloalkyl or heteroaryl ring moieties. Examples of amides include those that are derived from ammonia, $C_{1-3}$alkyl primary amines, and di($C_{1-2}$alkyl)amines. Examples of esters of the invention include $C_{1-7}$alkyl, $C_{5-7}$cycloalkyl, phenyl, and phenyl($C_{1-6}$alkyl) esters. Preferred esters include methyl esters. Prodrugs may also be prepared by derivatizing free hydroxy groups using groups including hemisuccinates, phosphate esters, dimethylaminoacetates, and phosphoryloxymethyloxycarbonyls, following procedures such as those outlined in *Adv. Drug Delivery Rev.* 1996, 19, 115. Carbamate derivatives of hydroxy and amino groups may also yield prodrugs. Carbonate derivatives, sulfonate esters, and sulfate esters of hydroxy groups may also provide prodrugs. Derivatization of hydroxy groups as (acyloxy)methyl and (acyloxy)ethyl ethers, wherein the acyl group may be an alkyl ester, optionally substituted with one or more ether, amine, or carboxylic acid functionalities, or where the acyl group is an amino acid ester as described above, is also useful to yield prodrugs. Prodrugs of this type may be prepared as described in *J. Med. Chem.* 1996, 39, 10. Free amines can also be derivatized as amides, sulfonamides or phosphonamides. All of these prodrug moieties may incorporate groups including ether, amine, and carboxylic acid functionalities.

Pharmaceutically active metabolites of compounds of Formula (I), and uses of such metabolites in the methods of the invention are considered within the scope of this invention. A "pharmaceutically active metabolite" means a pharmacologically active product of metabolism in the body of a compound of Formula (I) or salt thereof. Prodrugs and active metabolites of a compound may be determined using routine techniques known or available in the art. See, e.g., Bertolini, et al., *J. Med. Chem.* 1997, 40, 2011-2016; Shan, et al., *J. Pharm. Sci.* 1997, 86 (7), 765-767; Bagshawe, *Drug Dev. Res.* 1995, 34, 220-230; Bodor, *Adv. Drug Res.* 1984, 13, 224-331; Bundgaard, Design of Prodrugs (Elsevier Press, 1985); and Larsen, Design and Application of Prodrugs, Drug Design and Development (Krogsgaard-Larsen, et al., eds., Harwood Academic Publishers, 1991).

The compounds of Formula (I) and their pharmaceutically acceptable salts, pharmaceutically acceptable prodrugs, and pharmaceutically active metabolites (collectively, "active agents") of the present invention are useful as $LTA_4H$ modulators in the methods of the invention. Such methods for modulating $LTA_4H$ activity comprise exposing $LTA_4H$ to an effective amount of at least one chemical entity selected from compounds of Formula (I), pharmaceutically acceptable salts of compounds of Formula (I), and pharmaceutically acceptable prodrugs of compounds of Formula (I). Embodiments of this invention inhibit $LTA_4H$ activity.

In some embodiments, the $LTA_4H$ is in a subject with a disease, disorder, or medical condition mediated by $LTA_4H$ activity, such as those described herein. Symptoms or disease states are intended to be included within the scope of "medical conditions, disorders, or diseases."

Accordingly, the invention relates to methods of using the active agents described herein to treat subjects diagnosed with or suffering from a disease, disorder, or condition mediated through $LTA_4H$ activity, such as inflammation. Active agents according to the invention may therefore be used as anti-inflammatory agents.

In some embodiments, an active agent of the present invention is administered to treat inflammation. Inflammation may be associated with various diseases, disorders, or conditions, such as inflammatory disorders, allergic disorders, dermatological disorders, autoimmune disease, lymphatic disorders, and immunodeficiency disorders, including the more specific conditions and diseases given below. Regarding the onset and evolution of inflammation, inflammatory diseases or inflammation-mediated diseases or conditions include, but are not limited to, acute inflammation, allergic inflammation, and chronic inflammation.

Illustrative types of inflammation treatable with an $LTA_4H$ modulating agent include inflammation due to any one of a plurality of conditions such as allergy, abdominal aortic aneurysm, asthma, nasal polyps, allergic rhinitis, nasal itch, ocular inflammation (e.g., post-surgical ocular inflammation), conjunctivitis, uveitis, dry eye, psoriasis, pruritis, itch, itchy skin, atopic dermatitis, urticaria (hives), contact dermatitis, scleroderma, skin burns, acne, inflammatory bowel diseases (including colitis, Crohn's disease and ulcerative colitis), chronic obstructive pulmonary disease (COPD), α1-antitrypsin (α1AT) deficiency, atherosclerosis, arthritis (including rheumatoid arthritis), multiple sclerosis, myocardial infarction, stroke, pain, gingivitis, bronchitis, cystic fibrosis, upper gastrointestinal cancer, sepsis, autoimmune thyroid diseases, and immune-mediated (also known as type 1) diabetes mellitus and lupus, which are characterized by excessive or prolonged inflammation at some stage of the disease. Other autoimmune diseases that lead to inflammation include Myasthenia gravis, autoimmune neuropathies, such as Guillain-Barré, autoimmune uveitis, autoimmune hemolytic anemia, pernicious anemia, autoimmune thrombocytopenia, temporal arteritis, anti-phospholipid syndrome, vasculitides, such as Wegener's granulomatosis, Behcet's disease, dermatitis herpetiformis, pemphigus vulgaris, vitiligio, primary biliary cirrhosis, autoimmune hepatitis, autoimmune oophoritis and orchitis, autoimmune disease of the adrenal gland, polymyositis, dermatomyositis, spondyloarthropathies, such as ankylosing spondylitis, Sjogren syndrome, and Sjogren-Larsson syndrome.

Pruritis treatable with an $LTA_4H$-modulating agent according to the invention includes that which is a symptom of allergic cutaneous diseases (such as atopic dermatitis and hives) and other metabolic disorders (such as chronic renal failure, hepatic cholestasis, and diabetes mellitus).

In other embodiments, an active agent of the present invention is administered to treat allergy, aortic aneurysm, asthma, autoimmune diseases, pruritis, inflammatory bowel disease, ulcerative colitis, type II diabetes, or cardiovascular disease, including atherosclerosis and prevention of myocardial infarction. In further embodiments, an active agent of the present invention, alone or in combination with some other agent, is administered to treat aortic aneurysms, delaying the time to or avoiding the surgical intervention to repair aortic aneurysms, slowing the progression of aortic aneurysms, or avoiding or slowing down the progression towards or the incidence of aortic rupture. In certain embodiments, an active agent, alone or in combination with some other agent, is administered for any of such treatments when the aortic aneurysm is an abdominal aortic aneurysm. Examples of embodiments of such another agent is given by CysLT receptor antagonists and $LTC_4$ synthase inhibitors.

Thus, the active agents may be used to treat subjects diagnosed with or suffering from a disease, disorder, or condition mediated through $LTA_4H$ activity. The term "treat" or "treating" as used herein is intended to refer to administration of an active agent or composition of the invention to a subject for the purpose of effecting a therapeutic or prophylactic benefit through modulation of $LTA_4H$ activity. Treating includes reversing, ameliorating, alleviating, inhibiting the progress of, lessening the severity of, or preventing a disease, disorder, or condition, or one or more symptoms of such disease, disorder or condition mediated through modulation of $LTA_4H$ activity. The term "subject" refers to a mammalian patient in need of such treatment, such as a human. "Modulators" include both inhibitors and activators, where "inhibitors" refer to compounds that decrease, prevent, inactivate, desensitize or down-regulate $LTA_4H$ expression or activity, and "activators" are compounds that increase, activate, facilitate, sensitize, or up-regulate $LTA_4H$ expression or activity. Embodiments of chemical entities according to this invention are $LTA_4H$-modulating chemical entities.

Embodiments of this invention inhibit $LTA_4H$ activity. Thus, the invention is directed to methods for inhibiting $LTA_4H$ activity, comprising exposing $LTA_4H$ to an effective amount of at least one chemical entity selected from compounds of Formula (I), pharmaceutically acceptable salts of compounds of Formula (I), and pharmaceutically acceptable prodrugs of compounds of Formula (I).

In treatment methods according to the invention, an effective amount of at least one active agent according to the invention is administered to a subject suffering from or diagnosed as having such a disease, disorder, or condition. An "effective amount" means an amount or dose sufficient to generally bring about the desired therapeutic or prophylactic benefit in patients in need of such treatment for the designated disease, disorder, or condition. When referring to modulating the target receptor, an "effective amount" means an amount sufficient to at least affect the activity of such receptor. Measuring the activity of the target receptor may be performed by routine analytical methods. Target receptor modulation is useful in a variety of settings, including assays and treating conditions modulated through $LTA_4H$ activity.

In addition, effective amounts or doses of the active agents of the present invention may be ascertained by routine methods such as modeling, dose escalation studies or clinical trials, and by taking into consideration routine factors, e.g., the mode or route of administration or drug delivery, the pharmacokinetics of the agent, the severity and course of the disease, disorder, or condition, the subject's previous or ongoing therapy, the subject's health status and response to drugs, and the judgment of the treating physician. An exemplary dose is in the range of from about 0.001 to about 200 mg of active agent per kg of subject's body weight per day, preferably from about 0.05 to about 100 mg/kg/day, or from about 0.5 to about 35 mg/kg/day, or from about 0.5 to about 20 mg/kg/day, or from about 0.1 to about 10 mg/kg daily in single or divided dosage units (e.g., BID, TID, QID). For a 70-kg human, an illustrative range for a suitable dosage amount is from about 0.02 to about 7 g/day, or from about 0.2 to about 2.5 g/day. Dosages from about 20 mg/day to about 60 mg/day are contemplated. In some embodiments, such dosages would be administered once daily. Examples of embodiments of this invention are given by tablets containing from about 0.005 mol free base per tablet to about 0.5 mol free base per tablet. Other embodiments are given by tablets containing from about 0.005 mol free base per tablet to about 0.01 mol free base per tablet. Additional embodiments are given by tablets containing from about 0.03 mol free base per tablet to about 0.06 mol free base per tablet. Further embodiments are given by tablets containing from about 0.3 mol free base per tablet to about 0.6 mol free base per tablet.

Once improvement of the patient's disease, disorder, or condition has occurred, the dose may be adjusted for preventative or maintenance treatment. For example, the dosage or the frequency of administration, or both, may be reduced as a function of the symptoms, to a level at which the desired therapeutic or prophylactic effect is maintained. Of course, if symptoms have been alleviated to an appropriate level, treatment may cease. Patients may, however, require intermittent treatment on a long-term basis upon any recurrence of symptoms.

In addition, the active agents of the invention may be used in combination with additional active ingredients in the treatment of the above conditions or with other active ingredients. Montelukast salts are examples of such additional active ingredients, such as montelukast sodium. Conditions that are mediated by $LTA_4H$ activity, such as asthma for example, could be treated by embodiments of this invention such as active agents of this invention alone or in combination with others, such as montelukast salts. The additional active ingredients may be coadministered separately with an active agent of Formula (I) or included with such an agent in a pharmaceutical composition according to the invention. In an exemplary embodiment, additional active ingredients are those that are known or discovered to be effective in the treatment of conditions, disorders, or diseases mediated by $LTA_4H$ activity, such as another $LTA_4H$ modulator or a compound active against another target associated with the particular condition, disorder, or disease. The combination may serve to increase efficacy (e.g., by including in the combination a compound potentiating the potency or effectiveness of an agent according to the invention), decrease one or more side effects, or decrease the required dose of the active agent according to the invention.

Other embodiments of this invention further comprise the administration of at least one CysLT receptor antagonist (for example, Montelukast/Singulair®) and/or at least one $LTC_4$ synthase inhibitor. In some embodiments of this invention, such $LTA_4H$ modulator and CysLT receptor antagonist and/or $LTC_4$ synthase inhibitor are coadministered. Examples of CysLT receptor antagonists are CysLT1 and CysLT2 antagonists.

The active agents of the invention are used, alone or in combination with one or more additional active ingredients, to formulate pharmaceutical compositions of the invention. A pharmaceutical composition of the invention comprises an effective amount of at least one active agent in accordance with the invention. Such compositions may further comprise a pharmaceutically acceptable excipient.

A "pharmaceutically acceptable excipient" refers to a substance that is non-toxic, biologically tolerable, and otherwise biologically suitable for administration to a subject, such as an inert substance, added to a pharmacological composition or otherwise used as a vehicle, carrier, or diluent to facilitate administration of a agent and that is compatible therewith. Examples of excipients include calcium carbonate, calcium phosphate, various sugars and types of starch, cellulose derivatives, gelatin, vegetable oils, and polyethylene glycols. Suitable excipients may also include antioxidants. Such antioxidants may be used in a pharmaceutical composition or in a storage medium to prolong the shelf-life of the drug product.

Delivery forms of the pharmaceutical compositions containing one or more dosage units of the active agents may be prepared using suitable pharmaceutical excipients and compounding techniques known or that become available to those skilled in the art. The compositions may be administered in the inventive methods by a suitable route of delivery, e.g., oral, parenteral, rectal, topical, or ocular routes, or by inhalation.

The preparation may be in the form of tablets, capsules, sachets, dragees, powders, granules, lozenges, powders for reconstitution, liquid preparations, or suppositories. Preferably, the compositions are formulated for intravenous infusion, topical administration, or oral administration. In further preferred embodiments, compounds of the present invention are orally active inhibitors of $LTA_4H$.

For oral administration, the active agents of the invention can be provided in the form of tablets or capsules, or as a solution, emulsion, or suspension. To prepare the oral compositions, the active agents may be formulated to yield a dosage of, e.g., from about 0.05 to about 50 mg/kg daily, or from about 0.05 to about 20 mg/kg daily, or from about 0.1 to about 10 mg/kg daily, or from about 0.2 to about 1 mg/kg daily.

Oral tablets may include the active ingredient(s) mixed with compatible pharmaceutically acceptable excipients such as diluents, disintegrating agents, binding agents, lubricating agents, sweetening agents, flavoring agents, coloring agents and preservative agents. Suitable inert fillers include sodium and calcium carbonate, sodium and calcium phosphate, lactose, starch, sugar, glucose, methyl cellulose, magnesium stearate, mannitol, sorbitol, and the like. Examples of liquid oral excipients include ethanol, glycerol, water, and the like. Starch, polyvinyl-pyrrolidone (PVP), sodium starch glycolate, microcrystalline cellulose, and alginic acid are exemplary disintegrating agents. Binding agents may include starch and gelatin. The lubricating agent, if present, may be magnesium stearate, stearic acid or talc. If desired, the tablets may be coated with a material such as glyceryl monostearate or glyceryl distearate to delay absorption in the gastrointestinal tract, or may be coated with an enteric coating. Extragranular excipients that may used in the preparation of embodiments of this invention are illustratively given by lubricants and disintegrants, such as magnesium stearate and polyplasdone XL-10.

Capsules for oral administration include hard and soft gelatin capsules. To prepare hard gelatin capsules, active ingredient(s) may be mixed with a solid, semi-solid, or liquid diluent. Soft gelatin capsules may be prepared by mixing the active ingredient with water, an oil such as peanut oil or olive oil, liquid paraffin, a mixture of mono and di-glycerides of short chain fatty acids, polyethylene glycol 400, or propylene glycol.

Embodiments of this invention are provided by tablet forms with an amount of active compound corresponding to from about 1% to about 30% of free base. Other embodiments contain active compound corresponding to from about 5% to about 25% of free base. Still other embodiments contain active compound corresponding to from about 1% to about 10% of free base. Further embodiments contain active compound corresponding to from about 20% to about 30% of free base. Additional embodiments contain active compound corresponding to from about 10% to about 20% of free base. Embodiments of this invention in the form of tablet doses of about 5 mg per tablet and about 25 mg per tablet may be prepared in the form of compositions with active compound corresponding to about 5% free base. Embodiments of this invention in the form of tablet doses of about 250 mg per tablet may be prepared in the form of compositions with active compound corresponding to about 25% free base. Actual amounts depended on the salt of choice. In some embodiments, lactose can be used as the adjustable excipient for suitable batch correction depending on the specific salt form being used. In other embodiments, avicel can be used as the adjustable excipient for suitable batch correction depending on the specific salt form being used.

Embodiments of this invention in the form of tablets may comprise from about 70% to about 95% of non-active intragranular excipients and from about 0.2% to about 4% of non-active extragranular excipients. Embodiments of this invention in the form of tablets may comprise from about 90% to about 95% of non-active intragranular excipients and from about 0.2% to about 0.3% of non-active extragranular excipients. Embodiments of this invention in the form of tablets may comprise from about 70% to about 75% of non-active intragranular excipients and from about 3% to about 4% of non-active extragranular excipients. Embodiments of this invention in the form of tablets may comprise from about 65% to about 95% of intragranular filler. Embodiments of this invention in the form of tablets may comprise from about 90% to about 95% of intragranular filler. Embodiments of this invention in the form of tablets may comprise from about 65% to about 70% of intragranular filler. Embodiments of this invention in the form of tablets may comprise from about 2.5% to about 3.5% of intragranular disintegrant. Embodiments of this invention in the form of tablets may comprise from about 0.2% to about 0.4% of intragranular pigment. Embodiments of this invention in the form of tablets may comprise from about 0.1% to about 1.0% of intragranular lubricant. Embodiments of this invention in the form of tablets may comprise from about 0.1% to about 1.0% of extragranular lubricant. Embodiments of this invention in the form of tablets may comprise from about 2.5% to about 3.5% of extragranular disintegrant.

Tabletting equipment that can be used in the preparation of some embodiments of this invention may comprise standard technology used to this effect, including 60 mesh sieve and balance for weighing, TFC Labo roller compactor for compaction, TFC Labo granulator for granulating, Bohle bin blender for blending, and Piccola press for tableting with various punch sets depending on the choice of tablet image.

Tabletting processes that can be used in embodiments of this invention comprise low shear blending of excipients, low shear blending with lubricant, milling and tablet formation. Some process embodiments may include geometric blending.

Liquids for oral administration may be in the form of suspensions, solutions, emulsions or syrups or may be lyophilized or presented as a dry product for reconstitution with water or other suitable vehicle before use. Such liquid compositions may optionally contain: pharmaceutically-acceptable excipients such as suspending agents (for example, sorbitol, methyl cellulose, sodium alginate, gelatin, hydroxyethylcellulose, carboxymethylcellulose, aluminum stearate gel and the like); non-aqueous vehicles, e.g., oil (for example, almond oil or fractionated coconut oil), propylene glycol, ethyl alcohol, or water; preservatives (for example, methyl or propyl p-hydroxybenzoate or sorbic acid); wetting agents such as lecithin; and, if desired, flavoring or coloring agents.

The active agents of this invention may also be administered by non-oral routes. For example, compositions may be formulated for rectal administration as a suppository. For parenteral use, including intravenous, intramuscular, intraperitoneal, or subcutaneous routes, the agents of the invention may be provided in sterile aqueous solutions or suspensions, buffered to an appropriate pH and isotonicity or in parenterally acceptable oil. Suitable aqueous vehicles include Ringer's solution and isotonic sodium chloride. Such forms may be presented in unit-dose form such as ampules or disposable injection devices, in multi-dose forms such as vials from which the appropriate dose may be withdrawn, or in a solid form or pre-concentrate that can be used to prepare an injectable formulation. Illustrative infusion doses range from about 1 to 1000 µg/kg/minute of agent admixed with a pharmaceutical carrier over a period ranging from several minutes to several days.

For topical administration, the agents may be mixed with a pharmaceutical carrier at a concentration of about 0.1% to about 10% of drug to vehicle. Another mode of administering the agents of the invention may utilize a patch formulation to affect transdermal delivery.

Active agents may alternatively be administered in methods of this invention by inhalation, via the nasal or oral routes, e.g., in a spray formulation also containing a suitable carrier.

List of abbreviations: Ac=acetyl, AcOH=acetic acid, AIBN=azobisisobutyronitrile, $BBr_3$=boron tribromide, Boc=tert-butylcarbamoyl, m-CPBA=meta-chloroperoxybenzoic acid, DCE=dichloroethane, DCM=dichloromethane, DEAD=diethyldiazodicarboxylate, DIBALH=diisobutyl aluminum hydride, DIEA=N,N-diisopropylethylamine, DMA=N,N-dimethylacetamide, DME=dimethyl ether, DMF=dimethylformamide, DMSO=dimethyl sulfoxide, EDC=1-ethyl-3-(3-dimethylaminopropyl) carbodiimide hydrochloride, $Et_3N$=triethylamine, $Et_2O$=diethyl ether, EtOAc=ethyl acetate, IPA=isopropanol, LAH=lithium aluminum hydride, MeCN=acetonitrile, MeOH=methanol, $Ms_2O$=methane sulfonic anhydride, MsCl=methanesulfonyl chloride, NMP=N-methyl-pyrrolidine, Rochelle's Salt=potassium sodium tartrate, RT=room temperature, TBDMS=tert-butyldimethylsilyl, TEA=triethylamine, TFA=trifluoroacetic acid, TFAA=trifluoroacetic acid anhydride, THF=tetrahydrofuran, TLC=thin layer chromatography, Q-Phos=1,2,3,4,5-pentaphenyl-1'-(di-tert-butylphosphino)ferrocene.

Exemplary chemical entities useful in methods of the invention will now be described by reference to illustrative synthetic schemes for their general preparation below and the specific examples that follow. It is recognized that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Additionally, those of ordinary skill in the art will recognize the synthetic steps shown may be performed in a different order than that depicted in the Schemes below. Unless otherwise specified, the variables are as defined above in reference to Formula (I).

Unless noted otherwise, groups and other substituent and variable designations used in the schemes below have the meanings as defined in the specification and claims appended hereto.

Scheme A

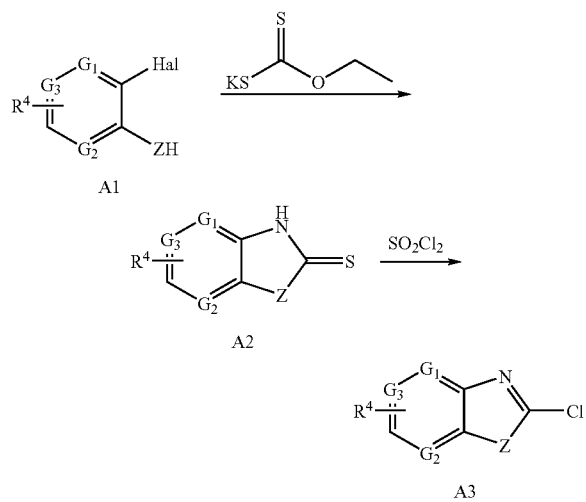

Intermediates of formula A3 are commercially available or are prepared according to Scheme A (See: Intl. Pat. Appl. Nos. WO 2007/146066 and WO 2006/04475; and L. Zhu, et al. *J. Heterocyclic Chem.*, 2005, 42, pp. 727-730). Compounds A1, where Hal is bromo or chloro, are reacted with potassium alkyl xanthate, preferably potassium ethyl xanthate, in a polar solvent such as DMF or NMP at a temperature from about 100° C. to about 150° C., to provide compounds of formula A2. Compounds of formula A2 are treated with $SO_2Cl_2$ in the presence or absence of DCM with or without heating to 70° C. to provide compounds of Formula A3. Compounds of formula A3 may be optionally converted to their corresponding hydrochloride salts for storage.

Scheme B

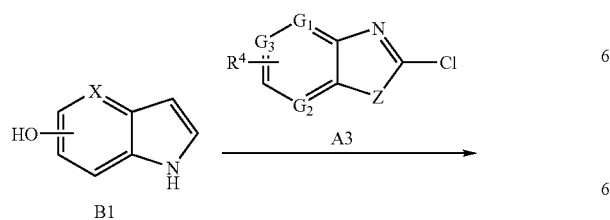

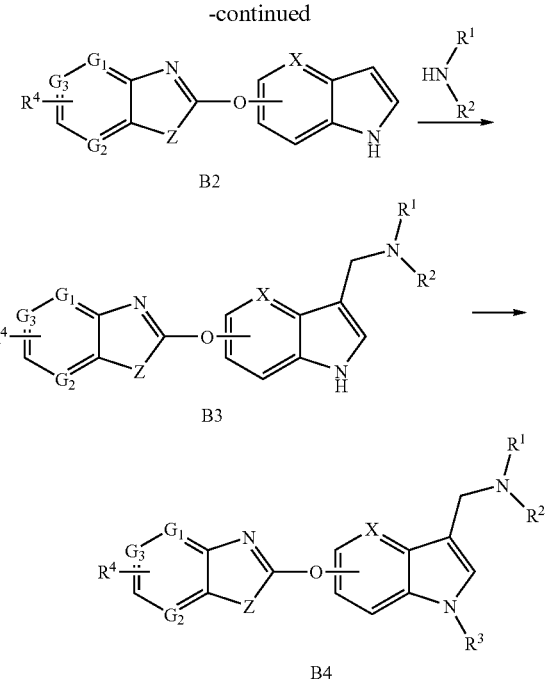

Compounds of formula B4 are prepared according to Scheme B. Commercially available B1 is converted to B2 by the addition of A3 in the presence of a suitable base such as $K_2CO_3$, $Cs_2CO_3$, or $Na_2CO_3$ in a polar solvent such as $CH_3CN$, DMF or DMSO. Further reaction of compounds B2 with amine $NHR^1R^2$ in the presence of formaldehyde in dioxane/AcOH mixture furnishes compounds B3. Alkylation of B3 in the presence of $C_{1-4}$alkylhalide, such as $C_{1-4}$alkyliodide, and NaH in DMF gives B4 where $R^3$ is $C_{1-4}$alkyl.

Scheme C

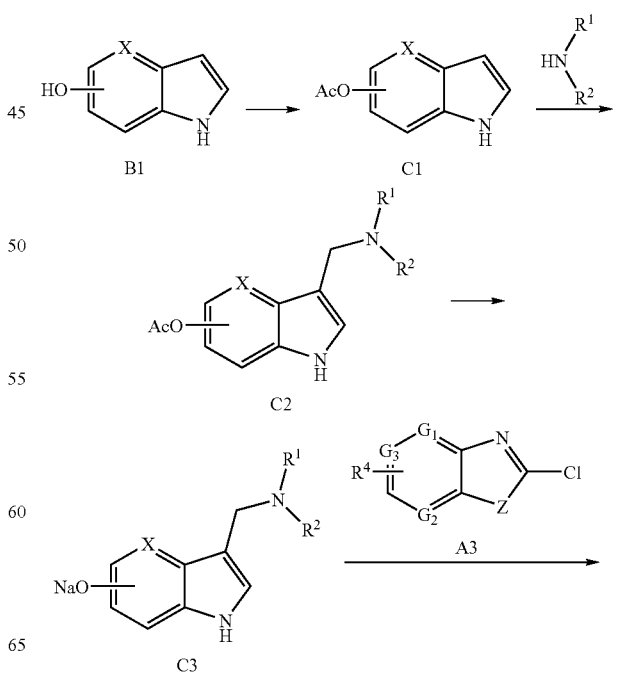

-continued

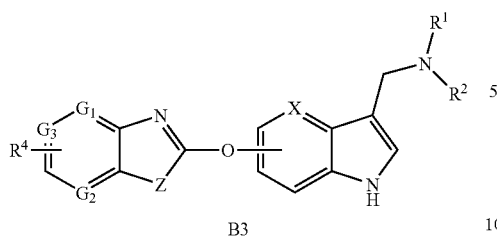

B3

An alternative route to generate compounds B3 is given in Scheme C. Initial acylation of B1 with acetic anhydride in the presence of triethylamine in DCM provides compounds C1. Further reaction of C1 with amine $NHR^1R^2$ in the presence of formaldehyde in dioxane/AcOH mixture furnishes compounds C2. Hydrolysis of C2 with NaOH gives the sodium salt C3. Further treatment of C3 with compounds A3 in the presence of $Cs_2CO_3$ in DMF gives B3.

Scheme D

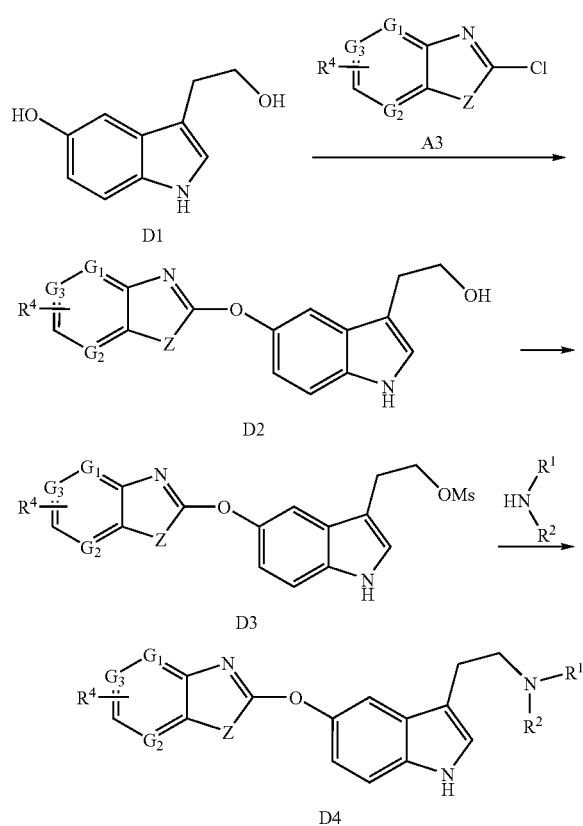

Compounds D4 are prepared according to Scheme D. Commercially available D1 is converted to D2 by the addition of A3 in the presence of $K_2CO_3$ in DMF. Subsequent conversion of D2 to the mesylate D3 is done by treating D2 with methanesulfonyl chloride in the presence of DIEA in MeCN. Further reaction of compounds D3 with amine $NHR^1R^2$ in MeCN gives compounds D4. This reaction of compounds D3 with amine $NHR^1R^2$ is performed in some embodiments in the presence of $K_2CO_3$.

Scheme E

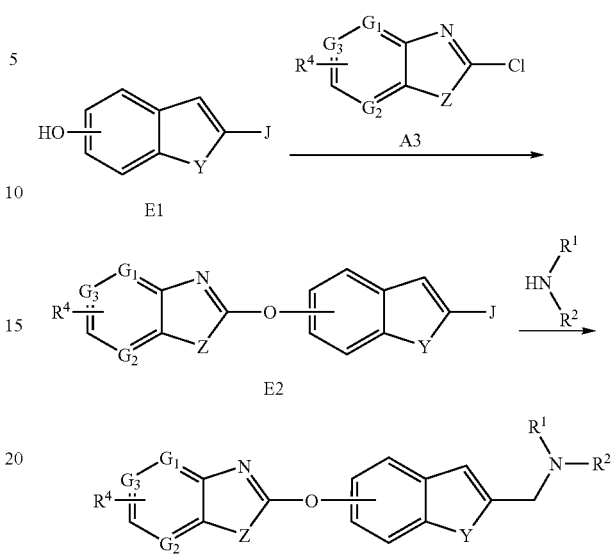

Compounds E3 are prepared according to Scheme E where Y is $NR^3$ or S. Commercially available E1 where Y is NH and J is C(O)OH is converted to E2 by the addition of A3 in the presence of $K_2CO_3$ in DMF. Subsequent treatment of E2 with amine $NHR^1R^2$ in the presence of EDC in DCM provides the corresponding amides E2 where J is —$C(O)NR^1R^2$. Reduction of the amides E2 where J is —$C(O)NR^1R^2$ with LAH or DIBALH in polar aprotic solvents such as THF or DCM provides compounds E3 with Y being NH.

Compounds E3 with Y being NH are also synthesized by forming an E2 ester rather than an E2 amide as described above. For example, treatment of E2 where Y is NH and J is —C(O)OH with MeOH in HCl gives E2 where J is —C(O)OMe, which is reduced with LAH or DIBALH in a polar aprotic solvent, such as THF and DCM, to form the E2 alcohol with J being —$CH_2OH$. Subsequent oxidation of this alcohol with $MnO_2$ in $CHCl_3$ provides the corresponding aldehyde E2 where J is —CHO, which upon treatment with amine $NHR^1R^2$ in the presence of $NaBH(OAc)_3$ in DCE gives E3, where Y is NH.

Compounds E3 with Y being an $NC_{1-4}$alkyl member are prepared as follows. Compounds E2 where Y is NH and J is —C(O)OH are treated with ethylbromide in the presence of $Cs_2CO_3$ in DMF to obtain esters E2 where Y is N-Et and J is —C(O)OEt. These esters are reduced to alcohols E2 where J is —$CH_2OH$ by using LAH or DIBALH in polar aprotic solvents, such as THF and DCM. Subsequent oxidation of these E2 alcohols with $MnO_2$ in $CHCl_3$ provides the corresponding aldehydes E2 where J is —CHO, which upon treatment with amine $NHR^1R^2$ in the presence of $NaBH(OAc)_3$ in DCE give E3, where Y is N-Et.

Compounds E3 with Y being S are prepared as follows. Compounds E1 with J being —C(O)OMe are prepared according to literature procedures, see for example, V. Fedi et al., J Med. Chem., 2007, 50, 4793-4807. Further conversion of such E1 to E2 and subsequently to E3 is achieved by using the methods described above in this Scheme when Y is NH.

Scheme F

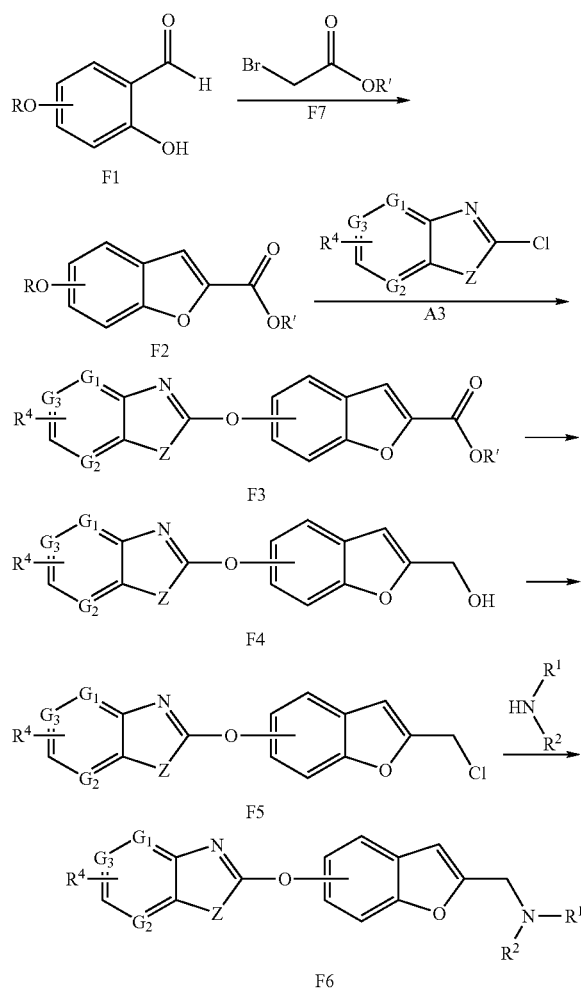

Benzofuran compounds F6 are prepared according to Scheme F. Initial alkylation/cyclization of compounds F1 where R is benzyl or methyl with alkylbromoacetate F7 where R' is methyl or ethyl in the presence of $K_2CO_3$ in DMF gives benzofurans F2. Certain compounds F2 are also obtained from commercially available precursors, such as compounds of formula

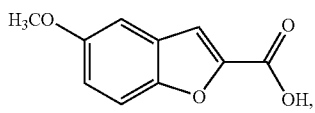

by successively treating such compounds with $BBr_3$ in DCM and MeOH in the presence of sulfuric acid to give embodiments of F2 where R is —H and R' is —$CH_3$. Where compounds of formula F2 contain R that is benzyl, deprotection is achieved with $H_2$ Pd/C.

Treatment of F2 with compounds A3 in the presence of $K_2CO_3$ in DMF furnishes intermediates F3. Reduction of F3 with DIBALH or LAH furnishes F4. Treatment of F4 with $SOCl_2$ gives F5. Subsequent treatment of F5 with amine $NHR^1R^2$ in the presence of a suitable base, such as $K_2CO_3$ or DIEA, in a polar solvent, such as DMF, MeCN and DMSO, provides benzofurans F6.

Scheme G

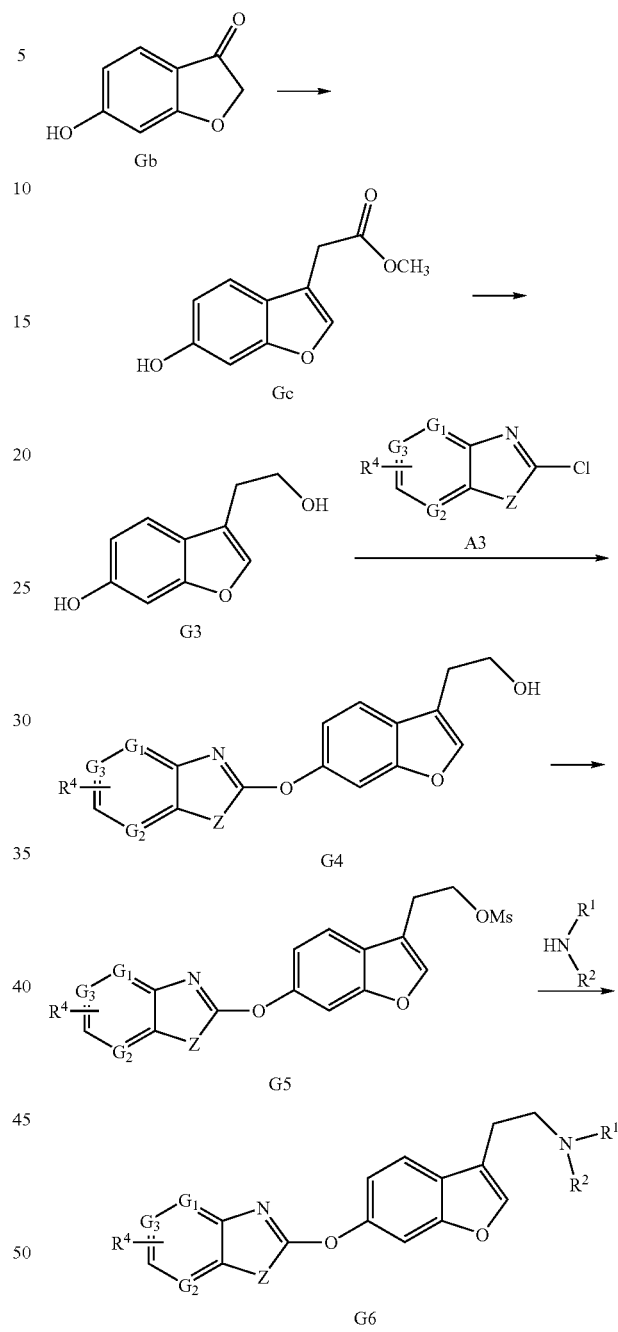

Benzofuran compounds G6 are prepared according to Scheme G. In this scheme, initial Wittig condensation of compound Gb generates ester Gc. Reduction of this ester with LAH furnishes diol G3, which is subsequently treated with compounds A3 in the presence of $K_2CO_3$ or $Cs_2CO_3$ in DMF or MeCN to furnish alcohol intermediates G4. Activation of this alcohol intermediate with $Ms_2O$ in the presence of DIEA in MeCN gives G5. Further treatment of G5 with amine $NHR^1R^2$ in the presence of a suitable base, such as $K_2CO_3$ and DIEA, in a polar solvent, such as DMF, MeCN and DMSO, provides benzofurans G6.

Scheme H

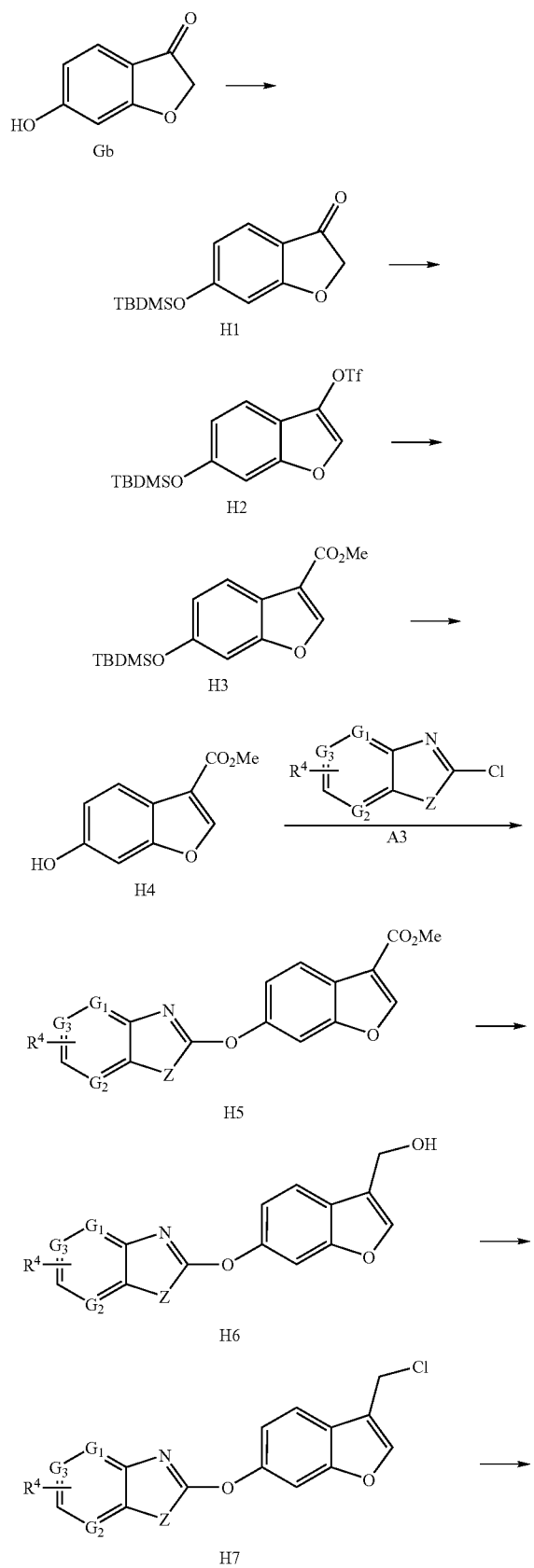

Benzofuran compounds H8 are prepared according to Scheme H. In this scheme, initial protection of the hydroxy group in Gb with tert-butyl-chloro-dimethyl-silane (TBDMS) in the presence of DIEA generates H1 which is converted to the triflate (Tf) H2 using triflate anhydride and DIEA. Palladium catalyzed carbonylation of H2 using $CO_{(g)}$ yields the 3,6-substituted benzofuran intermediate H3. Removal of the TBDMS protecting group using aqueous HCl in MeOH yields phenol H4. Subsequent treatment of H4 with A3 in the presence of a suitable base, such as $K_2CO_3$ or $Cs_2CO_3$, in DMF or MeCN provides the methyl ester intermediate H5. Further reduction of H5 with DIBALH provides the alcohol intermediate H6 which is converted to H7 with $SOCl_2$. Chloride displacement with amine $NHR^1R^2$ in the presence of a suitable base, such as $K_2CO_3$ and DIEA, in a polar solvent, such as DMF, MeCN and DMSO, provides benzofurans H8. In certain alternatives methods, chloride displacement was conducted with amides, pre-treated with sodium hydride, in a polar solvent, such as DMF, to provide benzofurans H8.

Scheme I

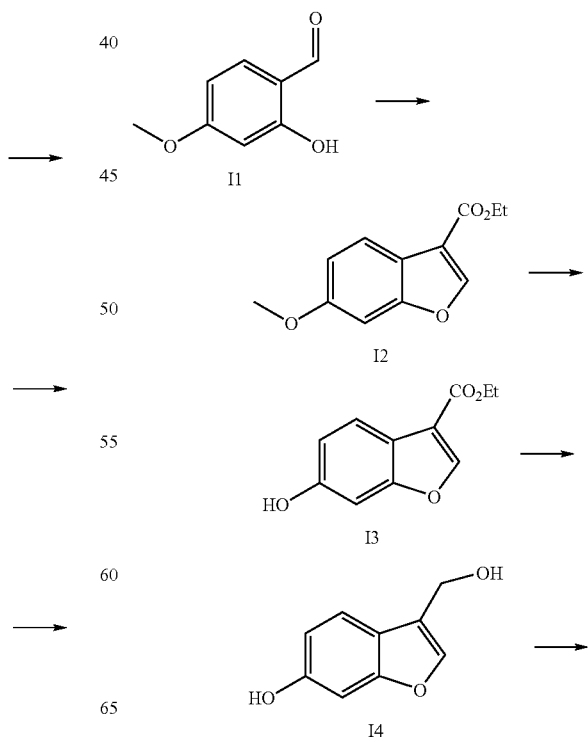

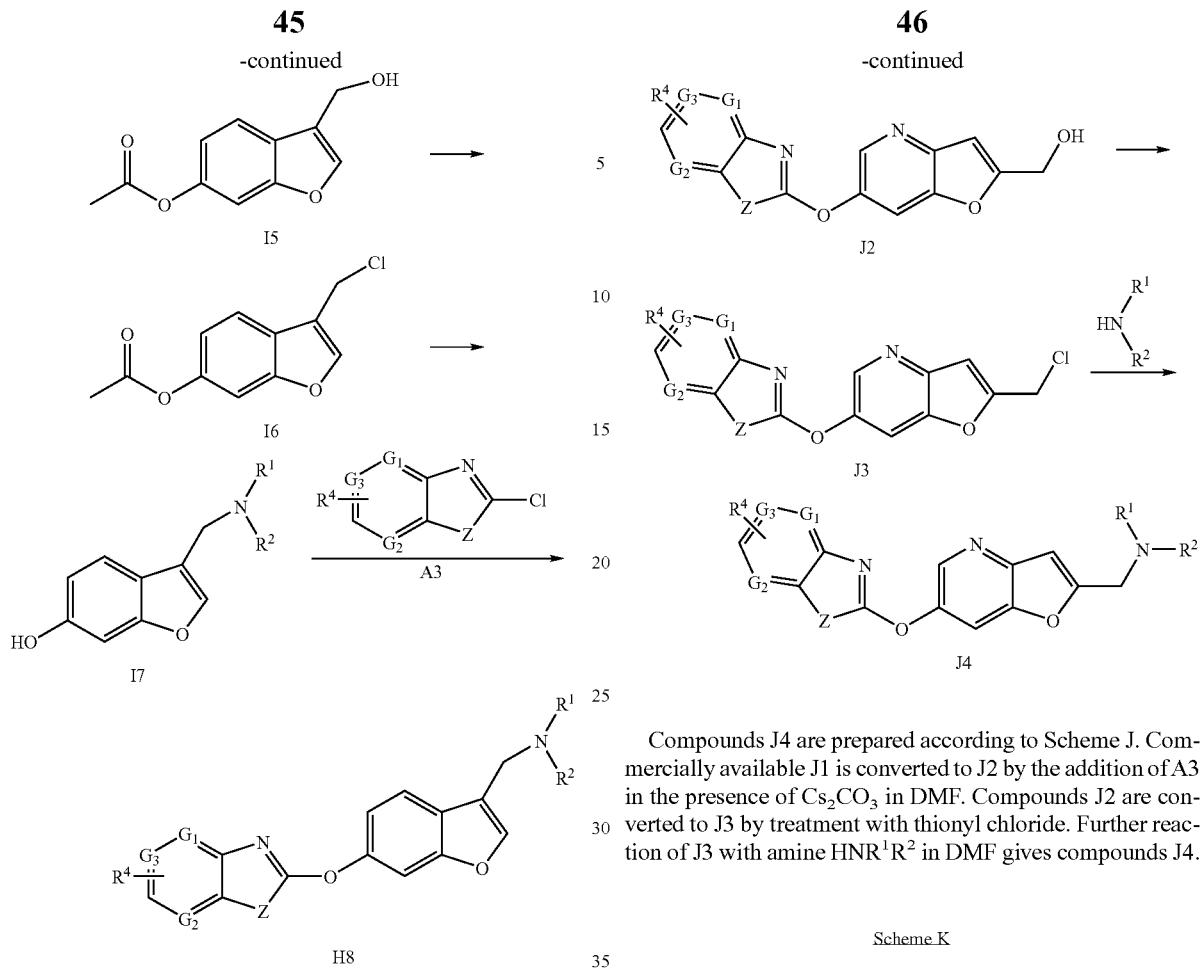

In other embodiments, benzofuran compounds H8 are prepared according to Scheme I. In this sequence, 2-hydroxy-4-methoxybenzaldehyde I1 is treated with ethyl diazoacetate in the presence of $HBF_4$ etherate followed by dehydration by, for example, reflux in toluene, to furnish the 3,6-substituted benzofuran I2. Removal of the methyl protecting group using $BBr_3$ in DCM yields phenol I3. Reduction of I3 with DIBALH provides the diol intermediate I4 which is selectively protected at the phenolic alcohol using acetic anhydride in the presence of NaOH to give I5. Conversion of the alcohol I5 to the chloride I6 is achieved using carbon tetrachloride in the presence of triphenylphosphine. Chloride displacement with amine $NHR^1R^2$ in the presence of a suitable base, such as $K_2CO_3$ and DIEA, in a polar solvent, such as DMF, MeCN and DMSO, followed by acetate hydrolysis with KOH provides the phenol I7. Subsequent treatment of I7 with A3 in the presence of a suitable base, such as $K_2CO_3$ and $Cs_2CO_3$, in DMF or MeCN provides benzofuran H8.

Compounds J4 are prepared according to Scheme J. Commercially available J1 is converted to J2 by the addition of A3 in the presence of $Cs_2CO_3$ in DMF. Compounds J2 are converted to J3 by treatment with thionyl chloride. Further reaction of J3 with amine $HNR^1R^2$ in DMF gives compounds J4.

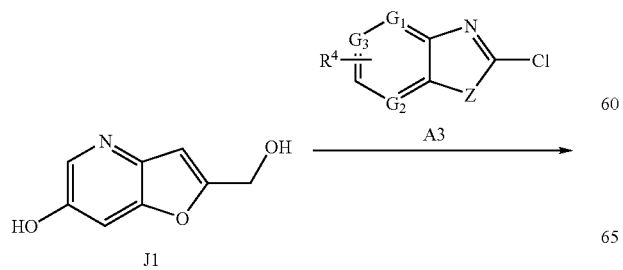

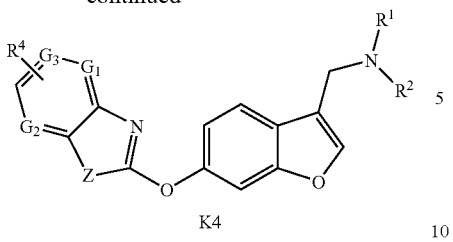

K4

Compounds K4 are prepared according to Scheme K. Treatment of H7 with sodium azide in DMF furnishes K1. Reduction of K1 using triphenylphosphine followed by the addition of di-tert-butyl dicarbonate leads to the isolation of K2. Removal of the protecting group provides K3. Reductive amination with aldehydes or acylation with carboxylic acids or acid chlorides using methods known in the art (Jives compounds K4.

Scheme L

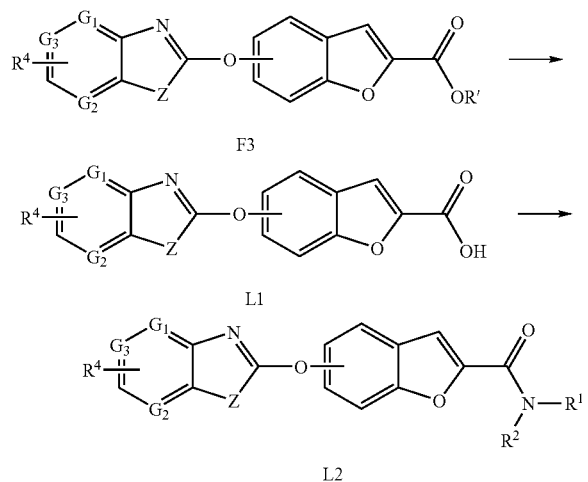

Compounds L2 are prepared according to Scheme L. Treatment of F3 under saponification conditions provides L1. Further reaction of L1 with thionyl chloride provides the acid chloride, which can be reacted with amine $HNR^1R^2$ in DCM to give compounds L2.

Scheme M

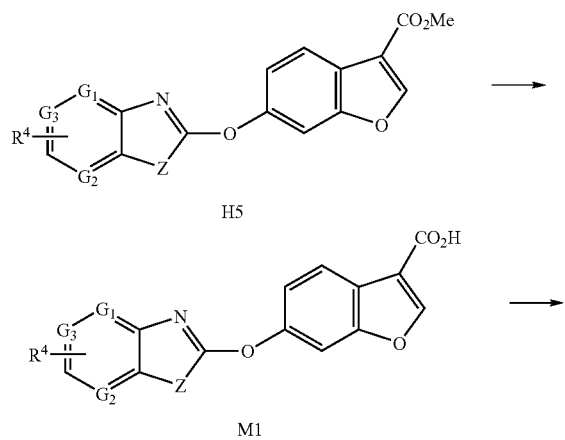

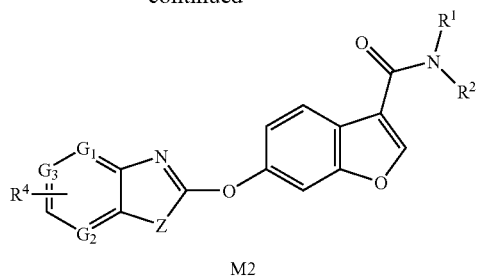

M2

Compounds M2 are prepared according to Scheme M. Treatment of H5 under saponification conditions provides M1. Further reaction of M1 under amide coupling conditions with amine $HNR^1R^2$ using methods known in the art provides compounds M2.

Compounds of Formula (I) that are synthesized in a protected form according to the schemes described herein, such as where an amine is protected with a suitable protecting group (such as Boc group), are converted to compounds of Formula (I) using generally known methods. For example, where the protecting group is a Boc group, deprotection is accomplished with an acid, such as HCl and TFA, in a solvent, such as diethyl ether, dioxane, and DCM.

Synthetic procedures for the —$N(R^1)R^2$ moiety in embodiments according to this invention are described in, for example, Kennis et al., Bioorg & Med Chem. Lett., 2000, 10, 71-74, for 1,2,3,4-tetrahydrobenzofuro[3,2-c]pyridine moieties; Capps et al., J Am Chem. Soc., 1953, 75(3), 697-699, for the synthesis of 1,2,3,4-tetrahydrothianaphtheno[3,2-c]pyridine moieties; Mapes et al., Org. Process Res Dev., 2007, 11, 482-486 for 4R-piperidin-4-yl}-4-(tert-butyl-dimethyl-silanyloxy)-pyrrolidin-2-one; in U.S. Pat. No. 6,495,555 for certain tricyclic delta3-piperidines; and in Intl. Pat. Appl. publication WO 2000/50391 for 4-methanesulfonyl-piperidin-1-ylmethyl moieties, all of which are incorporated herein by reference. Substituents on the —$NR^1R^2$ moiety may be incorporated by, for example, acylation, urea formation, sulfonylation, carbamoylation, or alkylation protocols using methods known in the art.

Compounds of Formula (I) may be converted to their corresponding salts using methods described in the art. For example, an amine of Formula (I) may be treated with TFA, HCl, or citric acid in a solvent such as diethyl ether, DCM, THF, MeOH, or isopropanol to provide the corresponding salt form.

Compounds prepared according to the schemes described above may be obtained as single enantiomers, diastereomers, or regioisomers, by enantio-, diastero-, or regiospecific synthesis, or by resolution. Compounds prepared according to the schemes above may alternately be obtained as racemic (1:1) or non-racemic (not 1:1) mixtures or as mixtures of diastereomers or regioisomers. Where racemic and non-racemic mixtures of enantiomers are obtained, single enantiomers may be isolated using conventional separation methods known to one skilled in the art, such as chiral chromatography, recrystallization, diastereomeric salt formation, derivatization into diastereomeric adducts, biotransformation, or enzymatic transformation. Where regioisomeric or diastereomeric mixtures are obtained, single isomers may be separated using conventional methods such as chromatography or crystallization.

The following specific examples are provided to further illustrate the invention and various preferred embodiments.

EXAMPLES

Chemistry Methods

In obtaining the compounds described in the examples below and the corresponding analytical data, the following experimental and analytical protocols were followed unless otherwise indicated.

Unless otherwise stated, reaction mixtures were magnetically stirred at room temperature (rt). Where solutions were "dried," they were generally dried over a drying agent such as $Na_2SO_4$ or $MgSO_4$. Where mixtures, solutions, and extracts were "concentrated", they were typically concentrated on a rotary evaporator under reduced pressure. Reactions were typically monitored using chromatographic methods such as thin layer chromatography (TLC), high performance liquid chromatography (HPLC), or liquid chromatography mass spectrometry (LCMS). Column chromatography was typically conducted on disposable silica gel columns for flash chromatography (Teledyne Isco, Inc.).

Analytical reversed-phase high performance liquid chromatography (HPLC) was performed on an Agilent 1100 Series instrument using one of the following protocols: 1 to 99% acetonitrile/water (0.05% trifluoroacetic acid) over 5.0 min or 7.0 min with a flow rate of 1 mL/min [Waters XTerra MS C18 (5 µm, 4.6×100 mm) column or Phenomenex Synergi max-RP (4 µm, 4.6×150 mm) column], or 1 to 99% acetonitrile/water (20 mM $NH_4OH$) over 5.0 min or 7.0 min with a flow rate of 1.5 mL/min (Phenomenex Gemini C18 (5 µm, 3.0×150 mm) column). Analytical reversed phase LC/MS was performed either on an Agilent 1100 Series instrument using 5 to 99% acetonitrile/water (0.05% trifluoroacetic acid) over 5.0 min or 7.0 min with a flow rate of 0.6 mL/min (Waters XTerra RP18 (5 µm, 3.0×100 mm) column) or on a Waters 2790 instrument using 5 to 99% acetonitrile/water (0.1% formic acid) over 5.0 min with a flow rate of 0.6 mL/min (Waters XTerra RP18 (5 µm, 3.0×100 mm) column).

Preparative reversed phase HPLC was performed on a Dionex APS2000 LC/MS or HPLC with a Phenomenex Gemini C18 (5 µm, 30×100 mm) column or a Waters XBridge C18 (5 µm, 30×100 mm) column and variable gradients of acetonitrile/water (20 mM $NH_4OH$) at a flow rate of 30 mL/min. Alternatively, the purification was performed with a Phenomenex Gemini C18 (5 µm, 50×100 mm) column or a Waters XBridge C18 (5 µm, 50×100 mm) column and variable gradients of acetonitrile/water (20 mM $NH_4OH$) at a flow rate of 80 mL/min. A formate or trifluoroacetate salt of the desired compound was obtained when purifications for each of these salts were performed using an Inertsil ODS-3 C18 (3 µm, 30×100 mm) column at 46° C. with variable gradients of acetonitrile/water (0.1% formic acid or 0.05% TFA) at a flow rate of 90 mL/min. In certain embodiments, free base compounds were obtained through neutralization of the salt using such reagents as NaOH, $NaHCO_3$, or the like.

Mass spectra (MS) were obtained on an Agilent series 1100 MSD using electrospray ionization (ESI) in positive mode unless otherwise indicated. Calculated (calcd.) mass corresponds to the exact mass.

Nuclear magnetic resonance (NMR) spectra were obtained on Bruker model DRX spectrometers. The format of the $^1H$ NMR data below is: chemical shift in ppm downfield of the tetramethylsilane reference (multiplicity, coupling constant J in Hz, integration). NMR interpretation was performed using MestReC or MestReNova software to assign chemical shift and multiplicity. In cases where two adjacent peaks of equal or unequal height were observed, these two peaks may be labeled either as a multiplet or as a doublet. In the case of a doublet, a coupling constant using this software may be assigned. In certain instances, proton signal peaks may be missing due to overlap with solvent peaks, and are not reported. In certain instances, integration is split due to the presence of rotamer mixtures.

Chemical names were typically generated using ChemDraw Ultra Version 6.0.2 (CambridgeSoft.com, Cambridge, Mass., USA).

Intermediate 1: 2-(1H-Indol-6-yloxy)-benzothiazole

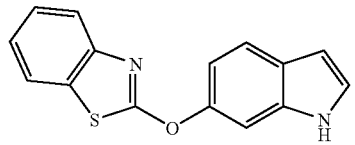

To a suspension of 6-hydroxyindole (5.0 g, 37.6 mmol) and $Cs_2CO_3$ (36.7 g, 112.8 mmol) in MeCN (75 mL) was added 2-chlorobenzthiazole (6.4 g, 4.7 mL, 37.6 mmol) and the resulting suspension was stirred (rt, 2 d). The reaction mixture was partitioned with brine and EtOAc (200 mL each) and the aqueous layer was extracted with EtOAc (200 mL). The organic layers were combined, washed with brine (300 mL), dried, filtered and concentrated in vacuo. The resulting residue was purified by silica gel column chromatography using EtOAc:hexane (0-40%) to afford the title compound as a tan solid (6.1 g, 61%). MS (ESI): mass calcd. for $C_{15}H_{10}N_2OS$, 266.3; m/z found, 267.1 [M+H]$^+$. $^1H$ NMR (400 MHz, $CDCl_3$): 8.57 (s, 1H), 7.72 (dd, J=8.4, 0.6, 1H), 7.65-7.63 (m, 2H), 7.39-7.35 (m, 2H), 7.27-7.22 (m, 1H), 7.19-7.18 (m, 1H), 7.08 (dd, J=8.4, 2.1, 1H), 6.55-6.53 (m, 1H).

Intermediates 2 to 7 were prepared using methods analogous to those described for Intermediate 1.

Intermediate 2: 2-(1H-Indol-5-yloxy)-benzothiazole

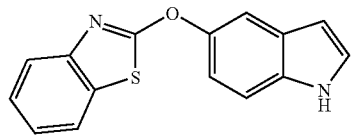 [SMILES: c1ccc2sc(Oc3ccc4[nH]ccc4c3)nc2c1]

MS (ESI): mass calcd. for $C_{15}H_{10}N_2OS$, 266.3; m/z found, 267.1 [M+H]$^+$. $^1H$ NMR (400 MHz, $CDCl_3$): 8.47 (s, 1H), 7.75-7.72 (m, 1H), 7.63-7.63 (m, 1H), 7.59 (d, J=2.4, 1H), 7.41-7.35 (m, 2H), 7.28-7.22 (m, 2H), 7.15 (dd, J=8.7, 2.4, 1H), 6.58-6.57 (m, 1H).

Intermediate 3: 2-(1H-Indol-6-yloxy)-thiazolo[4,5-b]pyridine

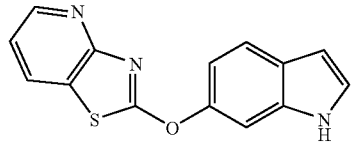 [SMILES: c1cnc2nc(Oc3ccc4cc[nH]c4c3)sc2c1]

MS (ESI): mass calcd. for $C_{14}H_9N_3OS$, 267.0; m/z found, 268.0 [M+H]$^+$. $^1H$ NMR (400 MHz, $CDCl_3$): 8.51 (d, J=4.9, 1H), 8.01 (dd, J=7.9, 1.6, 1H), 7.66 (d, J=8.6, 1H), 7.55 (d, J=1.8, 1H), 7.30 (d, J=3.2, 1H), 7.21 (dd, J=7.9, 4.9, 1H), 7.06 (dd, J=8.5, 2.2, 1H), 6.57 (d, J=2.4, 1H).

Intermediate 4:
2-(1H-Indol-6-yloxy)-thiazolo[5,4-b]pyridine

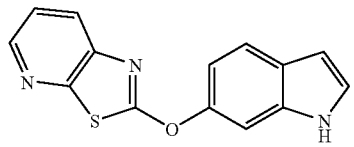

MS (ESI): mass calcd. for $C_{14}H_9N_3OS$, 267.3; m/z found, 268.1 [M+H]$^+$. $^1$H NMR (400 MHz, CDCl$_3$): 8.47 (s, 1H), 8.41 (dd, J=4.8, 1.5, 1H), 7.96 (dd, J=8.2, 1.5, 1H), 7.70 (d, J=8.5, 1H), 7.41-7.40 (m, 1H), 7.35-7.32 (m, 1H), 7.29-7.26 (m, 1H), 7.11 (dd, J=8.5, 2.2, 1H), 6.62 (br s, 1H).

Intermediate 5:
4-Fluoro-2-(1H-indol-6-yloxy)-benzothiazole

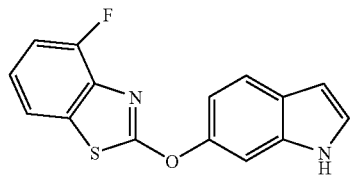 [SMILES: Fc1cccc2sc(Oc3ccc4cc[nH]c4c3)nc12]

MS (ESI): mass calcd. for $C_{15}H_9FN_2OS$, 284.0; m/z found, 285.0 [M+H]$^+$. $^1$H NMR (500 MHz, CDCl$_3$): 8.43 (br s, 1H), 7.68 (d, J=8.4, 1H), 7.46 (d, J=1.6, 1H), 7.41 (d, J=8.0, 1H), 7.28-7.26 (m, 1H), 7.22-7.18 (m, 1H), 7.15-7.11 (m, 2H), 6.61-6.59 (m, 1H).

Intermediate 6: 2-(1H-Indol-6-yloxy)-benzooxazole

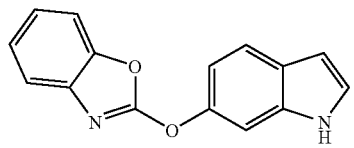 [SMILES: c1ccc2oc(Oc3ccc4cc[nH]c4c3)nc2c1]

MS (ESI): mass calculated for $C_{15}H_{10}N_2O_2$, 250.0; m/z found, 251.0 [M+H]$^+$. $^1$H NMR (400 MHz, CDCl$_3$): 8.40 (s, 1H), 7.66 (d, J=8.6, 1H), 7.55-7.39 (m, 3H), 7.36-7.19 (m, 3H), 7.12 (dd, J=8.6, 2.1, 1H), 6.55 (s, 1H).

Intermediate 7:
2-(1H-Pyrrolo[3,2-b]pyridin-6-yloxy)-benzothiazole

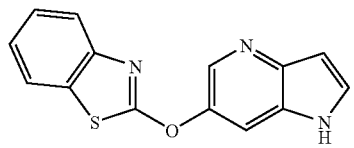 [SMILES: c1ccc2sc(Oc3cnc4cc[nH]c4c3)nc2c1]

MS (ESI): mass calcd. for $C_{14}H_9N_3OS$, 267.0; m/z found, 268.0 [M+H]$^+$. $^1$H NMR (500 MHz, CDCl$_3$): 8.99 (br s, 1H), 5.84 (d, J=2.4, 1H), 7.77 (d, J=2.3, 1H), 7.72-7.69 (m, 2H), 7.42-7.39 (m, 2H), 7.33-7.29 (m, 1H), 6.74 (br s, 1H).

Intermediate 8:
3-Morpholin-4-ylmethyl-1H-indol-6-ol sodium salt

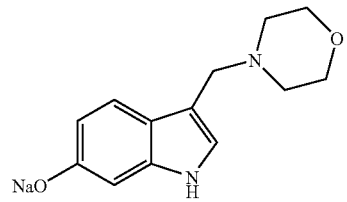

Acetic acid 1H-indol-6-yl ester. To a solution of 1H-indol-6-ol (1.5 g, 11.4 mmol) and acetic anhydride (1.2 mL, 12.6 mmol) in DCM (114 mL) was added Et$_3$N (3.18 mL, 22.8 mmol) and the reaction mixture was stirred (rt, 64 h). The reaction mixture was washed with H$_2$O (4×25 mL) and brine (50 mL). The organic layer was dried, filtered and concentrated in vacuo to provide the title compound (2.0 g, 100%). MS (ESI): mass calculated for $C_{10}H_9NO_2$, 175.1; m/z found, 176.1 [M+H]$^+$. $^1$H NMR (500 MHz, CDCl$_3$): 8.23 (s, 1H), 7.62 (d, J=8.5, 1H), 7.21 (dd, J=3.2, 2.4, 1H), 7.18-7.15 (m, 1H), 6.87 (dd, J=8.5, 2.1, 1H), 6.55 (ddd, J=3.1, 2.0, 0.9, 1H), 2.35 (s, 3H).

Acetic acid 3-morpholin-4-ylmethyl-1H-indol-6-yl ester. To a solution of acetic acid 1H-indol-6-yl ester (2.0 g, 11.4 mmol) in dioxane/acetic acid (1:1, 114 mL) was added formaldehyde (0.85 mL, 0.93 g, 11.4 mmol) and morpholine (1 mL, 1 g, 11.4 mmol) and the resulting mixture was stirred (rt, 16 h). The reaction mixture was concentrated in vacuo, diluted with DCM (200 mL) and washed with 1N NaOH (20 mL), 4 N NaOH (20 mL) and brine (2×10 mL). The organic layer was dried, filtered and concentrated in vacuo to provide the title compound (2.87 g, 92%). MS (ESI): mass calculated for $C_{15}H_{18}N_2O_3$, 274.1; m/z found, 275.1 [M+H]$^+$. $^1$H NMR (600 MHz, CDCl$_3$): 8.09 (s, 1H), 7.73 (d, J=8.5, 1H), 7.11 (dd, J=11.7, 2.1, 2H), 6.85 (dd, J=8.5, 2.0, 1H), 3.71-3.68 (m, 4H), 3.67 (s, 2H), 2.48 (s, 4H), 2.32 (s, 3H).

3-Morpholin-4-ylmethyl-1H-indol-6-ol sodium salt. To a mixture of DCM:MeOH:H$_2$O (3:2:1, 24 mL) was added NaOH (413 mg, 10.32 mmol) followed by acetic acid 3-morpholin-4-ylmethyl-1H-indol-6-yl ester (2.83 g, 10.3 mmol) and the resulting suspension was stirred (rt, 15 min). The solution was concentrated in vacuo to provide the title compound as a black solid (2.62 g, 100%). MS (ESI): mass calculated for $C_{13}H_{16}N_2O_2$ (phenol), 232.1; m/z found, 233.1 [M+H]$^+$. $^1$H NMR (500 MHz, CD$_3$OD): 7.35 (d, J=8.5, 1H), 6.94 (s, 1H), 6.69 (d, J=2.1, 1H), 6.59 (dd, J=8.5, 2.1, 1H), 3.72-3.65 (m, 6H), 2.54 (s, 4H).

Intermediate 9: 2-Chloro-thiazolo[4,5-b]pyrazine

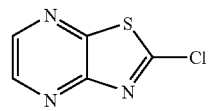

3H-Thiazolo[4,5-b]pyrazine-2-thione. To a mixture of 2-amino-3-chloropyrazine (5 g, 38.6 mmol) and potassium ethyl xanthate (9.28 g, 57.9 mmol) was added 1-methyl-2- pyrrolidinone (68 mL) and the solution was heated (150° C., 16 h). The suspension was cooled (rt) and treated with glacial acetic acid (10 mL) and H$_2$O (1500 mL). The suspension was filtered and the resulting solid was suspended and sonicated in ethanol:H$_2$O (1:1, 500 mL). The suspension was filtered and the solid was washed with H$_2$O, dried (calcium sulfate) in vacuo to yield the title compound as a solid (4.36 g, 67%). MS (ESI): mass calculated for C$_5$H$_3$N$_3$S$_2$, 168.98; m/z found, 170.00 [M+H]$^+$. $^1$H NMR (500 MHz, DMSO-d$_6$): 14.69 (s, 1H), 8.42 (d, J=2.8, 1H), 8.39 (d, J=2.8, 1H).

2-Chloro-thiazolo[4,5-b]pyrazine. A mixture of 3H-thiazolo[4,5-b]pyrazine-2-thione (4.36 g, 25.8 mmol) and DCM (60 mL) was sonicated (5 min). The suspension was treated with sulfuryl chloride (99.9 g, 740 mmol, 60 mL) and heated (40° C., 16 h). The reaction mixture was cooled (0° C.) and slowly treated with H$_2$O (250 mL), followed by 4 N NaOH (550 mL). The aqueous mixture was extracted with EtOAc (2×1800 mL). The organic layer was dried, filtered and concentrated in vacuo to provide the title compound as a solid (2.63 g, 53%). MS (ESI): mass calculated for C$_5$H$_2$ClN$_3$S, 170.9; m/z found, 172.1 [M+H]$^+$. $^1$H NMR (500 MHz, DMSO-d$_6$): 8.84 (d, J=2.5, 1H), 8.75 (d, J=2.5, 1H).

Intermediates 10 to 14 were prepared using methods analogous to those described for Intermediate 9.

Intermediate 10:
2-Chloro-7-methyl-thiazolo[4,5-b]pyridine

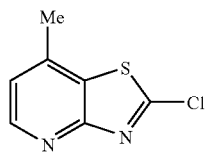 [SMILES: Cc1ccnc2nc(Cl)sc12]

MS (ESI): mass calculated for C$_7$H$_5$ClN$_2$S, 183.9; m/z found, 185.0 [M+H]$^+$. $^1$H NMR (600 MHz, DMSO-d$_6$): 8.61 (d, J=4.9, 1H), 7.41 (dd, J=4.8, 0.6, 1H), 2.58 (s, 3H).

Intermediate 11:
2-Chloro-6-fluoro-thiazolo[4,5-b]pyridine

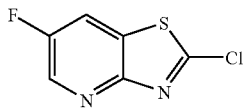

MS (ESI): mass calculated for C$_6$H$_2$ClFN$_2$S, 187.9; m/z found, 189.0 [M+H]$^+$. $^1$H NMR (600 MHz, DMSO-d$_6$): 8.75 (dd, J=2.8, 0.9, 1H), 8.58 (dd, J=8.2, 2.9, 1H).

Intermediate 12:
2,6-Dichloro-thiazolo[4,5-b]pyridine

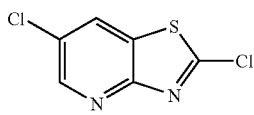 [SMILES: Clc1cnc2nc(Cl)sc2c1]

MS (ESI): mass calculated for C$_6$H$_2$Cl$_2$N$_2$S, 203.9; m/z found, 204.9 [M+H]$^+$. $^1$H NMR (500 MHz, DMSO-d$_6$): 8.78 (s, 1H), 8.75 (s, 1H).

Intermediate 13:
2-Chloro-6-fluoro-thiazolo[5,4-b]pyridine

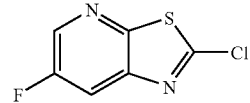

MS (ESI): mass calculated for C$_6$H$_2$ClFN$_2$S, 187.9; m/z found, 189.0 [M+H]$^+$. $^1$H NMR (500 MHz, DMSO-d$_6$): 8.77 (s, 1H), 8.55-8.46 (m, 1H).

Intermediate 14: 2-Chloro-thiazolo[5,4-b]pyridine

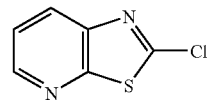

MS (ESI): mass calcd. for C$_6$H$_3$ClN$_2$S, 170.0; m/z found, 171.0 [M+H]$^+$. $^1$H NMR (400 MHz, CDCl$_3$): 8.58 (dd, J=4.7, 1.5, 1H), 8.19 (dd, J=8.2, 1.6, 1H), 7.45 (dd, J=8.2, 4.7, 1H).

Intermediate 15: meso-endo-[Acetyl-(8-aza-bicyclo[3.2.1]oct-3-yl)-amino]-acetic acid ethyl ester

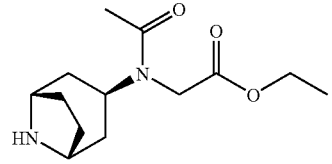 [SMILES: CCOC(=O)CN(C(C)=O)[C@H]1C[C@H]2CC[C@@H](C1)N2]

meso-endo-3-(Ethoxycarbonylmethyl-amino)-8-aza-bicyclo[3.2.1]octane-8-carboxylic acid tert-butyl ester. To a solution of meso-endo-3-amino-8-aza-bicyclo[3.2.1]octane-8-carboxylic acid tert-butyl ester (0.525 g, 2.3 mmol) in DCM (46 mL) was added ethylglyoxylate (50% toluene, 0.46 mL, 0.24 g, 2.3 mmol) and the resulting solution was heated (reflux, 2 h). The reaction mixture was cooled (rt), treated with NaBH(OAc)$_3$ (1.23 g, 5.8 mmol) and stirred (rt, 14 h). The reaction mixture was partitioned with EtOAc and 1 M aqueous NaOH (200 mL each). The organic layer was washed with 1 M NaOH (200 mL) and brine (200 mL). The organic layer was dried, filtered and concentrated in vacuo to provide the title compound as clear oil (0.6 g, 83%). MS (ESI): mass calcd. for C$_{16}$H$_{28}$N$_2$O$_4$, 312.2; m/z found, 313.2 [M+H]$^+$.

meso-endo-[Acetyl-(8-aza-bicyclo[3.2.1]oct-3-yl)amino]-acetic acid ethyl ester. To a solution of meso-endo-3-(ethoxycarbonylmethyl-amino)-8-aza-bicyclo[3.2.1]octane-8-carboxylic acid tert-butyl ester (0.6 g, 1.92 mmol) and Et$_3$N (0.54 mL, 389 mg, 3.84 mmol) in DCM (19 mL) was added acetyl chloride (0.28 mL, 302 mg, 3.84 mmol) and the resulting solution was stirred (rt, 15 h). The reaction mixture was partitioned with EtOAc and brine (75 mL each) and the organic layer was dried, filtered and concentrated in vacuo. The resulting residue was treated with 2 M HCl dioxane (20 mL) and stirred (rt, 4 h). The reaction mixture was concen- Intermediate 16: meso-endo-[(8-Aza-bicyclo[3.2.1]oct-3-yl)-tert-butoxycarbonyl-amino]-acetic acid tert-butyl ester

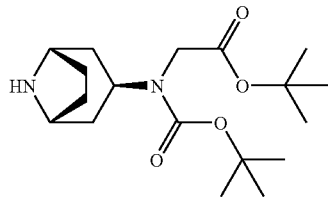 [SMILES: CC(C)(C)OC(=O)CN(C(=O)OC(C)(C)C)[C@H]1C[C@H]2CC[C@@H](C1)N2]

meso-endo-[(8-Benzyl-8-aza-bicyclo[3.2.1]oct-3-yl)-tert-butoxycarbonyl-amino]-acetic acid tert-butyl ester. To a slurry of 8-benzyl-8-aza-bicyclo[3.2.1]oct-3-ylamine (3.0 g, 13.9 mmol) in MeCN (15 mL) was added DIEA (7 mL, 41.6 mmol) and then treated with a solution of tert-butyl bromoacetate (2.0 mL, 13.9 mmol) in MeCN (15 mL) dropwise (5 h) and then stirred (rt, 16 h). The reaction mixture was concentrated in vacuo and the resulting residue was purified by flash column chromatography using MeOH (0.2 M NH$_3$):DCM (0-10%) to provide a yellow oil. To a solution of this oil in DCM (35 mL) was added DIEA (3.6 mL, 20.9 mmol, 1.5 equiv) and di-tert-butyl dicarbonate (3.2 mL, 13.9 mmol) and the reaction mixture was stirred (rt, 16 h). The reaction mixture was treated with di-tert-butyl dicarbonate (1 mL, 4.6 mmol) and stirred (rt, 23 h). The reaction mixture was washed with 1 N NaOH, H$_2$O and brine. The organic layer was dried, filtered and concentrated in vacuo. The resulting residue was purified using flash column chromatography MeOH (0.2 M NH$_3$):DCM (0-10%) to provide the title compound as a colorless oil (5.4 g, 90%). MS (ESI): mass calcd. for $C_{25}H_{38}N_2O_4$, 430.2; m/z found, 431.3 [M+H]$^+$. $^1$H NMR (400 MHz, CDCl$_3$): 7.42-7.34 (m, 2H), 7.32-7.18 (m, 5H), 3.39 (s, 2H), 3.30-3.16 (m, 2H), 2.39-2.24 (m, 2H), 2.16-2.07 (m, 2H), 1.52-1.37 (m, 20H).

meso-endo-[(8-Aza-bicyclo[3.2.1]oct-3-yl)-tert-butoxycarbonyl-amino]-acetic acid tert-butyl ester. To a flask charged with 20% Pd(OH)$_2$ (537 mg, 10% by wt) and ethanol (10 mL) was added a solution of [(8-benzyl-8-aza-bicyclo[3.2.1]oct-3-yl)-tert-butoxycarbonyl-amino]-acetic acid tert-butyl ester (5.4 g, 12.5 mmol) in ethanol (20 mL). The solution was further diluted with ethanol (15 mL) and stirred under hydrogen gas (1 atm, 17 h). The solution was filtered (Celite®) and the solid rinsed with MeOH. The filtrate was concentrated in vacuo to provide the title compound as a brown-black oil (2.8 g, 66%). MS (ESI): mass calcd. for $C_{18}H_{32}N_2O_4$, 340.2; m/z found, 341.3 [M+H]$^+$. $^1$H NMR (400 MHz, CDCl$_3$): 3.74-3.66 (m, 2H), 3.65-3.57 (m, 2H), 2.38-2.18 (m, 3H), 1.89-1.79 (m, 2H), 1.67-1.57 (m, 2H), 1.50-1.40 (m, 18H), 1.39-1.30 (m, 2H).

Intermediate 17: (1S,4S)-2,5-Diaza-bicyclo[2.2.1]heptane-2-carboxylic acid amide hydrochloride

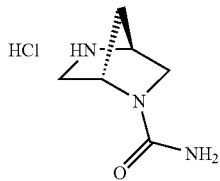

To a solution of (1S,4S)-2,5-Diaza-bicyclo[2.2.1]heptane-2-carboxylic acid tert-butyl ester (35.6 g, 179 mmol) in CH$_2$Cl$_2$ (600 mL) was added trimethylsilylisocyanate (82.5 g, 716 mmol, 4 equiv.). The reaction was stirred at rt for 2 h. After concentration, the resulting white solid was dissolved in CH$_2$Cl$_2$ (500 mL) and treated with a solution of HCl (4 M in dioxane, 135 mL, 3 equiv.). The solution quickly became heterogeneous. The suspension was then stirred at rt overnight. Upon concentration, the desired product was isolated as a white solid (33 g, 104%). [Note: the mass balance was found to be 104%, which arises from additional HCl that could not be removed by standard evaporation under vacuum]. $^1$H NMR (500 MHz, CD$_3$OD): 4.77 (s, 1H), 4.55 (s, 1H), 3.69 and 3.64 (AB, $J_{AB}$=12.1, 2H), 3.47 and 3.40 (AB, $J_{AB}$=11.3, 2H), 2.22 and 2.15 (AB, $J_{AB}$=11.5, 2H).

Intermediates 18 to 23 were prepared using methods analogous to those described for Intermediate 17.

Intermediate 18: (1R,4R)-2,5-Diaza-bicyclo[2.2.1]heptane-2-carboxylic acid amide hydrochloride

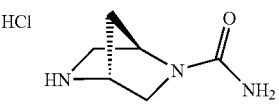

MS (ESI): mass calcd. for $C_6H_{11}N_3O$, 141.1; m/z found, 142.1 [M+H]$^+$. $^1$H NMR (500 MHz, DMSO-d$_6$): 9.82 (s, 1H), 9.21 (s, 1H), 4.50 (s, 1H), 4.34-4.31 (m, 2H), 3.57 (s, 1H), 3.54-3.45 (m, 1H), 3.33-3.25 (m, 1H), 3.18-3.09 (m, 1H), 1.96-1.87 (m, 1H), 1.84-1.77 (m, 1H).

Intermediate 19: meso-endo-(8-Aza-bicyclo[3.2.1]oct-3-yl)-urea hydrochloride

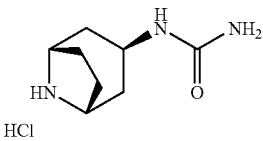 [SMILES: NC(=O)N[C@H]1C[C@H]2CC[C@@H](C1)N2 ; Cl]

$^1$H NMR (400 MHz, CD$_3$OD): 4.16-4.07 (m, 1H), 4.06-3.99 (m, 1H), 3.95-3.88 (m, 0.5H), 3.75-3.60 (m, 0.5H), 2.60 (ddd, J=16.4, 7.3, 4.7, 1H), 2.40-2.23 (m, 3H), 2.23-2.12 (m, 2H), 2.12-1.98 (m, 2H).

Intermediate 20:
meso-3,8-Diaza-bicyclo[3.2.1]octane-3-carboxylic acid amide hydrochloride

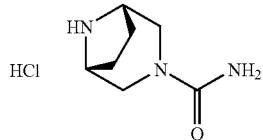 [SMILES: Cl ; NC(=O)N1C[C@H]2CC[C@@H](C1)N2]

MS (ESI): mass calcd. for $C_7H_{13}N_3O$, 155.11; m/z found, 156.1 $[M+H]^+$. $^1$H NMR (400 MHz, $CD_3OD$): 4.41-4.24 (m, 1H), 4.17-4.07 (m, 2H), 4.02-3.87 (m, 2H), 3.71-3.60 (m, 1H), 3.56-3.49 (m, 1H), 3.41-3.33 (m, 3H).

Intermediate 21:
meso-exo-(8-Aza-bicyclo[3.2.1]oct-3-yl)-urea hydrochloride

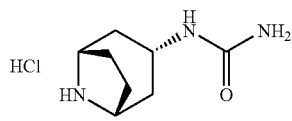

MS (ESI): mass calcd. for $C_8H_{15}N_3O$, 169.12; m/z found, 170.10 $[M+H]^+$. $^1$H NMR (500 MHz, $CD_3OD$): 4.09 (s, 2H), 4.07-3.99 (m, 1H), 2.20-2.06 (m, 6H), 1.81 (t, J=12.3, 2H).

Intermediate 22:
Hexahydro-pyrrolo[3,4-c]pyrrole-2-carboxylic acid amide hydrochloride

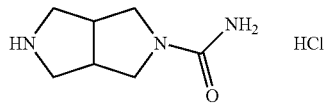 [SMILES: NC(=O)N1CC2CNCC2C1 ; Cl]

$^1$H NMR (400 MHz, DMSO-$d_6$): 9.84 (s, 1H), 3.75 (s, 6H), 3.48-3.17 (m, 4H), 3.04-2.89 (m, 2H).

Intermediate 23: (1S,4S)-2,5-Diaza-bicyclo[2.2.2]octane-2-carboxylic acid amide hydrochloride

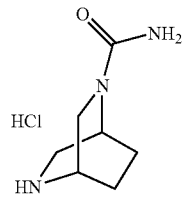

MS (ESI): mass calculated for $C_7H_{13}N_3O$, 155.11; m/z found, 156.15 $[M+H]^+$. $^1$H NMR (500 MHz, $CD_3OD$): 4.36 (s, 1H), 3.89-3.78 (m, 2H), 3.66 (s, 2H), 3.65-3.59 (m, 1H), 3.53-3.39 (m, 2H), 2.24-2.04 (m, 2H), 2.03-1.88 (m, 2H).

Intermediate 24: meso-endo-N-(8-Aza-bicyclo[3.2.1]oct-3-yl)-acetamide hydrochloride

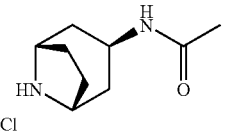

To a solution of meso-endo-3-amino-8-aza-bicyclo[3.2.1] octane-8-carboxylic acid tert-butyl ester (3.4 g, 15 mmol) in $CH_2Cl_2$ (50 mL) was added acetic anhydride (1.2 mL, 16.5 mmol, 1.1 equiv.). The reaction was stirred at rt for 2 h. After concentration, the resulting white solid was dissolved in $CH_2Cl_2$ (50 mL) and treated with HCl (4 M in dioxane, 15 mL, 4 equiv.). The solution quickly became heterogeneous. The suspension was then stirred at rt overnight. Upon concentration, the desired product was isolated as a white solid (3.35 g, 109%). [Note: the mass balance was found to be 109% is attributed to additional HCl that could not be removed by standard evaporation under reduced pressure]. $^1$H NMR (400 MHz, $CD_3OD$): 4.05-3.99 (m, 2H), 3.99-3.94 (m, 1H), 2.40-2.24 (m, 4H), 2.21-2.07 (m, 4H), 2.04 (s, 3H).

Alternative Synthesis of Intermediate 24:

meso-8-Aza-bicyclo[3.2.1]octan-3-one hydrochloride. A solution of meso-8-methyl-8-aza-bicyclo[3.2.1]octan-3-one (1.0 equiv.) in toluene (1.2 M) was treated with 1-chloroethyl chloroformate (1.5 equiv.). The reaction mixture was heated at reflux overnight (18 h) then cooled to rt and concentrated to a brown oil. To this brown oil was slowly added MeOH (1.2 M relative to starting material) over a period of 10 min with vigorous stirring. After heating at reflux for 3 h, the reaction was cooled to rt and then concentrated to a dark colored oil. With vigorous stirring, MeCN (4.8 M relative to starting material) was added to form a precipitate. To this mixture was added EtOAc (1.2 M relative to starting material). The resultant slurry was stirred overnight and filtered to recover the title compound as a brown solid. The filtrate was concentrated down before the addition of MeCN/EtOAc (1:4). The solids were filtered to recover another portion of product for an overall yield of 78%. MS (ESI): mass calcd. for $C_7H_{11}NO$, 125.08; m/z found, 126.1 $[M+H]^+$. $^1$H NMR (500 MHz, $CD_3OD$): 1.96-2.00 (q, J=7.0, 15.5, 2H), 2.24-2.27 (m, 2H), 2.55 (d, J=17.3, 2H), 2.95 (dd, J=4.8, 17.7, 2H), 4.33-4.35 (m, 2H).

meso-8-Benzyl-8-aza-bicyclo[3.2.1]octan-3-one. A mixture of meso-8-aza-bicyclo[3.2.1]octan-3-one hydrochloride (1.0 equiv.), benzyl bromide (1.0 equiv.), and $Na_2CO_3$ (2.5 equiv.) in MeCN (0.8 M) was heated at reflux for 2 h and then concentrated to half the original volume. The mixture was quenched with water (1.2 M relative to starting material) and tert-butyl methyl ether (1.2 M relative to starting material) and then, with vigorous stirring, slowly acidified to pH 1-2 with concentrated HCl. The separated aqueous layer was basified with NaOH pellets until pH 13-14 was obtained and extracted with tert-butyl methyl ether. The combined organic layers were dried, filtered and concentrated to afford the title compound (75%). MS (ESI): mass calcd. for $C_{14}H_{17}NO$, 215.13; m/z found, 216.1 $[M+H]^+$. $^1$H NMR (500 MHz, $CDCl_3$): 1.62-1.64 (d, J=7.9, 2H), 2.11-2.13 (m, 2H), 2.21 (dd, J=1.5, 17.1, 2H), 2.69 (dd, J=4.4, 16.1, 2H), 3.49-3.5 (m, 2H), 3.75 (s, 2H), 7.28 (d, J=7.3, 1H), 7.35 (t, J=7.5, 2H), 7.42 (d, J=7.5, 2H).

meso-8-Benzyl-8-aza-bicyclo[3.2.1]octan-3-one oxime. To a solution of meso-8-benzyl-8-aza-bicyclo[3.2.1]octan-3-one (1.0 equiv.) in EtOH (0.78 M) and water (0.78 M) was added hydroxylamine hydrochloride (2.0 equiv.). This addition caused a mild exothermic reaction. With vigorous stirring, slowly NaHCO$_3$ was added in six portions over a period of 15 min to minimize gas evolution. The reaction mixture was heated to 50° C. for 1 h, becoming cloudy in appearance before precipitation occurred. After stirring for 48 h at rt, the white slurry was filtered and washed with 9:1 water/EtOH (0.25 M relative to starting material). The white solids were dried to recover the title compound (93%). MS (ESI): mass calcd. for $C_{14}H_{18}N_2O$, 230.14; m/z found, 231.1 [M+H]$^+$. $^1$H NMR (500 MHz, CDCl$_3$): 1.47-1.68 (m, 2H), 1.97-2.09 (m, 2H), 2.13 (d, J=14.7, 1H), 2.23 (dd, J=3.9, 15.5, 1H), 2.59 (dd, J=3.5, 14.7, 1H), 2.96-3.0 (d, J=15.5, 1H), 3.33-3.36 (m, 2H), 3.65 (s, 2H). 7.24-7.27 (m, 1H), 7.31-7.35 (m, 2H), 7.39-7.41 (m, 2H), 8.22 (s, 1H).

meso-endo-N-(8-Benzyl-8-aza-bicyclo[3.2.1]oct-3-yl)-acetamide. To a solution of meso-8-benzyl-8-aza-bicyclo[3.2.1]octan-3-one oxime (1.0 equiv.) in EtOAc (1.6 M) was added acetic anhydride (1.05 M), acetic acid (15% wt) and 10% Pt/C (41% wt). The mixture was agitated under 55 psi H$_2$ (g) overnight at rt. After the reaction was complete, the catalyst was filtered and washed with EtOAc. The filtrate was quenched with water then carefully basified to pH 10-11 using excess NaOH pellets under a cold bath. Caution was exercised as a high exotherm could cause partial deacylation and hydrolysis of the amine to give meso-8-benzyl-8-azabicyclo[3.2.1]octan-3-one. The aqueous layer was extracted with EtOAc (6×). The combined organic layers were dried, filtered and concentrated to a crude solid. The crude product was slurried overnight in 1:1 tert-butyl methyl ether/hexanes (0.6 M relative to starting material) and filtered to recover the title compound with a yield of about 75%, of which at least 95% was in endo form. MS (ESI): mass calcd. for $C_{16}H_{22}N_2O$, 258.17; m/z found, 259.1 [M+H]$^+$. $^1$H NMR (500 MHz, CDCl$_3$): 1.58 (d, J=14.8, 2H), 1.73-1.77 (m, 2H), 1.96 (s, 3H), 2.13-2.17 (m, 2H), 2.19-2.24 (m, 2H), 3.19 (s, 2H), 3.52 (s, 2H), 4.11 (q, J=7.1, 14.3, 1H), 5.82 (s, 1H), 7.24 (t, J=7.2, 1H), 7.31 (t, J=7.7, 2H) 7.36 (d, J=6.9, 2H).

In other embodiments, to a solution of meso-8-benzyl-8-aza-bicyclo[3.2.1]octan-3-one oxime (1.0 equiv.) in EtOAc (0.1 M) was added AcOH (0.5 equiv.) and acetic anhydride (10 equiv.) forming an ethyl acetate, acetic anhydride and acetic acid solution approximately 0.1 M. An H-Cube Midi™ continuous flow hydrogenation instrument with 10% Pt/C was utilized to hydrogenate the mixture at flow rate of 3 ml/min, 80 bar and 60° C. After completion, GC/MS analysis showed a 95/5 endo/enamine isomer ratio. The reaction mixture from the continuous flow hydrogenation instrument was concentrated to oil, then washed with 1 N NaOH solution and EtOAc. The organic layer was extracted, dried with Na$_2$SO$_4$, filtered and concentrated to recover title compound (80%).

meso-endo-N-(8-Aza-bicyclo[3.2.1]oct-3-yl)-acetamide. To a solution of meso-endo-N-(8-benzyl-8-aza-bicyclo[3.2.1]oct-3-yl)acetamide (1.0 equiv.) in EtOH (0.5 M) was added 20% Pd(OH)$_2$ (16% wt). The mixture was agitated under 55 psi H$_{2(g)}$ overnight at rt. After the reaction was complete, the catalyst was filtered and washed with EtOH (1.2 M relative to starting material). The filtrate was concentrated to a white solid then dried overnight to afford the title compound (100%). MS (ESI): mass calcd. for $C_9H_{16}N_2O$, 168.13; m/z found, 169.1 [M+H]$^+$. $^1$H NMR (500 MHz, CDCl$_3$): 1.68 (dd, J=1.4, 14.8, 2H), 1.84-1.94 (m, 4H), 1.97 (s, 3H), 2.07-2.12 (m, 2H), 3.54 (s, 2H), 4.11 (q, J=6.9, 14.0, 1H), 5.84 (s, 1H). $^{13}$C NMR (500 MHz, CDCl$_3$): 169.01, 53.31, 41.97, 37.34, 29.08, 23.55.

Intermediates 25 to 30 were prepared using methods analogous to those described for Intermediate 24.

Intermediate 25: meso-1-(3,8-Diaza-bicyclo[3.2.1]oct-3-yl)ethanone hydrochloride

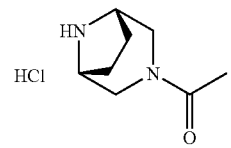

MS (ESI): mass calcd. for $C_8H_{14}N_2O$, 154.14; m/z found, 155.1 [M+H]$^+$. $^1$H NMR (400 MHz, CD$_3$OD): 4.45-4.36 (m, 1H), 4.35-4.29 (m, 2H), 4.15-4.08 (m, 2H), 3.97-3.86 (m, 1H), 3.71-3.58 (m, 2H), 3.57-3.47 (m, 2H), 2.15 (s, 3H).

Intermediate 26: meso-exo-N-(8-Aza-bicyclo[3.2.1]oct-3-yl)-acetamide hydrochloride MS (ESI): mass calcd. for $C_9H_{16}N_2O$, 168.13; m/z found, 169.20 [M+H]$^+$. $^1$H NMR (500 MHz, CD$_3$OD): 4.20 (tt, J=11.6, 5.6, 1H), 4.09 (s, 2H), 2.19-2.03 (m, 6H), 1.96 (d, J=3.0, 3H), 1.85-1.76 (m, 2H).

Intermediate 27: (1S,4S)-1-(2,5-Diaza-bicyclo[2.2.1]hept-2-yl)-ethanone hydrochloride MS (ESI): mass calcd. for $C_7H_{12}N_2O$, 140.09; m/z found, 141.10 [M+H]$^+$. $^1$H NMR (500 MHz, CD$_3$OD): 4.98-4.78 (m, 1H), 4.52 (d, J=17.2, 1H), 3.79-3.66 (m, 1H), 3.63-3.52 (m, 1H), 3.43 (q, J=11.6, 1H), 3.36 (s, 1H), 2.23 (d, J=11.5, 0.6H), 2.20-2.13 (m, 2H), 2.12-2.03 (m, 2H), 2.01 (d, J=11.5, 0.4H).

Intermediate 28: (1R,4R)-1-(2,5-Diaza-bicyclo[2.2.1]hept-2-yl)ethanone hydrochloride MS (ESI): mass calcd. for $C_7H_{12}N_2O$, 140.1; m/z found, 141.1 [M+H]$^+$. $^1$H NMR (500 MHz, DMSO-d$_6$): 9.86-9.62 (m, 1H), 9.48-9.10 (m, 1H), 6.38 (s, 1H), 4.70-4.63 (m, 1H), 4.43-4.34 (m, 1H), 3.81-3.76 (m, 0.5H), 3.55-3.46 (m, 1H), 3.34-3.28 (m, 0.5H), 3.28-3.08 (m, 2H), 2.04-2.01 (m, 1H), 2.01-1.90 (m, 1H), 1.88-1.86 (m, 1H).

Intermediate 29:
1-(Hexahydro-pyrrolo[3,4-c]pyrrol-2-yl)-ethanone hydrochloride

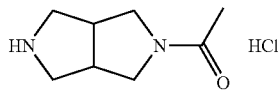

$^1$H NMR (500 MHz, DMSO-d$_6$): 9.59 (s, 1H), 3.86 (s, 8H), 3.50-3.42 (m, 1H), 3.38-3.29 (m, 2H), 3.09-2.90 (m, 2H).

Intermediate 30: (1S,4S)-1-(2,5-Diaza-bicyclo[2.2.2]oct-2-yl)-ethanone hydrochloride

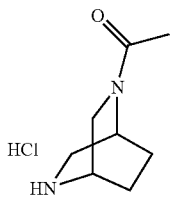

MS (ESI): mass calculated for C$_8$H$_{14}$N$_2$O, 154.11; m/z found, 155.20 [M+H]$^+$. $^1$H NMR (400 MHz, CD$_3$OD): 4.72-4.67 (m, 0.5H), 4.26-4.20 (m, 0.5H), 3.92 (dt, J=12.0, 2.6, 0.5H), 3.87-3.80 (m, 1H), 3.80-3.56 (m, 1.5H), 3.55-3.39 (m, 2H), 2.76 (br s, 1H), 2.22-1.87 (m, 6H).

Intermediate 31: Hexahydro-furo[3,4-c]pyrrole

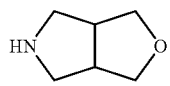

1-Benzyl-pyrrolidine-3,4-dicarboxylic acid dimethyl ester. A cooled (0° C.) solution of benzyl-methoxymethyl-trimethylsilanylmethyl-amine (9.25 g, 39 mmol) and dimethyl maleate (6.19 g, 43 mmol) in DCM (80 mL) was stirred at 0° C. for 15 min. The reaction mixture was treated with TFA (300 µL, 3.9 mmol) and stirred (0° C., 1 h). The reaction mixture was treated with saturated aqueous NaHCO$_3$ (80 mL) and stirred with slow warming (rt, 30 min). The reaction mixture was washed with brine (60 mL) and the aqueous layer was extracted with DCM (2×80 mL). The pH of the aqueous layer was adjusted to pH>12 and extracted with DCM (2×80 mL). The combined organic layers were dried, filtered and concentrated in vacuo. The resulting residue was purified by silica gel column chromatography using EtOAc:hexane (0-40%) to afford a yellow oil (8.66 g) having about 90% purity of the title compound. $^1$H NMR (500 MHz, CDCl$_3$): 7.36-7.23 (m, 5H), 3.72-3.65 (m, 8H), 3.39-3.29 (m, 2H), 3.22-3.12 (m, 2H), 2.80-2.70 (m, 2H).

(1-Benzyl-4-hydroxymethyl-pyrrolidin-3-yl)-methanol. To a cooled (0° C.) solution of 1-benzyl-pyrrolidine-3,4-dicarboxylic acid dimethyl ester (8.66 g, 31.2 mmol) in THF (40 mL) was added LAH (2 M in THF, 62 mL, 62 mmol) over a ten minute period. The reaction mixture was stirred while warming (rt, 17 h). The reaction mixture was then cooled (0° C.), and stirred (15 min), and slowly treated sequentially with an addition of H$_2$O (2.8 mL), 2 M NaOH (4.3 mL), and H$_2$O (8.5 mL). The reaction mixture was then heated to reflux (64° C., 1 h). The reaction mixture was cooled and filtered through Celite® and the solid was washed with EtOAc. The filtrate was concentrated in vacuo to afford the title compound as a yellow oil (7.89 g, 100%). $^1$H NMR (500 MHz, CDCl$_3$): 7.38-7.21 (m, 5H), 3.84-3.70 (m, 4H), 3.65-3.59 (m, 2H), 2.70-2.58 (m, 4H), 2.58-2.47 (m, 2H).

5-Benzyl-hexahydro-furo[3,4-c]pyrrole. A solution of (1-benzyl-4-hydroxymethyl-pyrrolidin-3-yl)-methanol (7.89 g, 31.2 mmol) and p-toluenesulfonic acid monohydrate (7.12 g, 37.4 mmol) in toluene (150 mL) was heated under a Dean Stark trap (120° C., 20 h). The reaction mixture was cooled (rt) and treated with 1 N NaOH (50 mL). The aqueous phase was extracted with methyl tert-butyl ether (3×50 mL). The combined organic layers were dried, filtered and concentrated in vacuo. The resulting residue was purified by silica gel column chromatography using MeOH (0.2 M NH$_3$):DCM (0-5%) to afford the title compound as a yellow oil (5.08 g, 80%). $^1$H NMR (500 MHz, CDCl$_3$): 7.37-7.29 (m, 4H), 7.29-7.24 (m, 1H), 3.87-3.79 (m, 2H), 3.65-3.56 (m, 4H), 2.86-2.75 (m, 2H), 2.75-2.66 (m, 2H), 2.34 (dt, J=12.2, 6.1, 2H).

Hexahydro-furo[3,4-c]pyrrole. To a flask charged with a catalytic amount of 10% Pd/C in EtOH (5 mL) was added a solution of 5-benzyl-hexahydro-furo[3,4-c]pyrrole (1.0 g, 4.9 mmol) in EtOH (15 mL). The slurry was stirred (rt, 16 h) under an atmosphere of H$_2$ (g). The reaction mixture was filtered through Celite® and the filtrate was concentrated in vacuo to afford the title compound as a yellow oil (0.6 g, 100%). MS (ESI): mass calcd. for C$_6$H$_{11}$NO, 113.08; m/z found, 114.1 [M+H]$^+$. $^1$H NMR (500 MHz, CDCl$_3$): 3.87-3.77 (m, 2H), 3.59-3.53 (m, 2H), 3.06-2.94 (m, 2H), 2.82-2.66 (m, 4H).

Intermediate 32 was prepared using methods analogous to those described for Example 139.

Intermediate 32: (4R)-1-{1-[6-(Benzothiazol-2-yloxy)-1H-indol-3-ylmethyl]-piperidin-4-yl}-4-(tert-butyl-dimethyl-silanyloxy)-pyrolidin-2-one

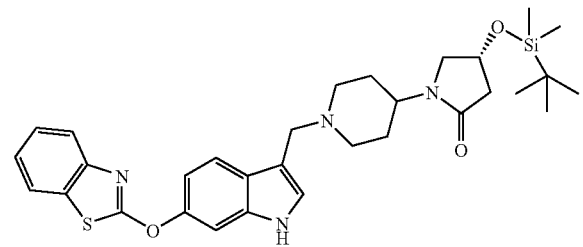 [SMILES: CC(C)(C)[Si](C)(C)O[C@@H]1CC(=O)N(C2CCN(Cc3c[nH]c4cc(Oc5nc6ccccc6s5)ccc34)CC2)C1]

MS (ESI): mass calcd. for O$_{31}$H$_{40}$N$_4$O$_3$SSi, 576.8; m/z found, 577.2 [M+H]$^+$. $^1$H NMR (500 MHz, CDCl$_3$): 8.44 (s, 1H), 7.77 (d, J=8.6, 1H), 7.75 (d, J=8.1, 1H), 7.65 (d, J=7.4, 1H), 7.41-7.37 (m, 2H), 7.27-7.24 (m, 1H), 7.16 (d, J=2.2, 1H), 7.11 (dd, J=8.6, 2.2, 1H), 4.33 (t, J=7.9, 1H), 3.99-3.94 (m, 1H), 3.70 (s, 2H), 3.35 (dt, J=9.2, 2.6, 1H), 3.19-3.14 (m, 1H), 3.06-3.02 (m, 2H), 2.33-2.28 (m, 1H), 2.13-2.08 (m, 2H), 1.89-1.85 (m, 1H), 1.75-1.65 (m, 4H), 0.92 (s, 9H), 0.18 (s, 3H), 0.16 (s, 3H).

Intermediate 33: [5-(Benzothiazol-2-yloxy)-1H-indol-2-yl]-piperidin-1-yl-methanone

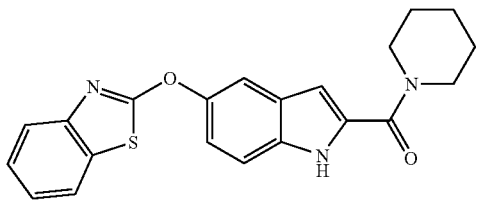 [SMILES: O=C(c1cc2cc(Oc3nc4ccccc4s3)ccc2[nH]1)N1CCCCC1]

5-(Benzothiazol-2-yloxy)-1H-indole-2-carboxylic acid. To a suspension of 5-hydroxyindole-2-carboxylate (5 g, 28.2 mmol), $Cs_2CO_3$ (20 g, 62.1 mmol) in DMSO (56 mL) was added 2-chlorobenzthiazole (3.5 mL, 4.8 g, 28.2 mmol) and the resulting reaction mixture was heated (70° C., 2 d). The reaction mixture was cooled (rt) and partitioned with $H_2O$ and EtOAc (50 mL each). The aqueous layer was treated with concentrated HCl to form a solid. The suspension was filtered and the solid washed with $H_2O$ and dried in vacuo to provide the title compound as a brown solid (7.55 g, 86%). $^1H$ NMR (500 MHz, DMSO-$d_6$): 12.03 (s, 1H), 7.88 (d, J=7.5, 1H), 7.73 (d, J=2.4, 1H), 7.67 (d, J=7.5, 1H), 7.55 (d, J=8.9, 1H), 7.43-7.40 (m, 1H), 7.31-7.28 (m, 2H), 7.15 (d, J=1.4, 1H), the $CO_2H$ proton was not detected.

[5-(Benzothiazol-2-yloxy)-1H-indol-2-yl]-piperidin-1-yl-methanone. To a solution of EDC (370 mg, 1.9 mmol), piperidine (0.24 mL, 0.21 g, 2.4 mmol), DIEA (0.33 mL, 0.25 g, 1.9 mmol) and hydroxybenzotriazole (257 mg, 1.9 mmol) in DCM (15 mL) was added 5-(benzothiazol-2-yloxy)-1H-indole-2-carboxylic acid (500 mg, 1.6 mmol) and the reaction mixture was stirred (rt, 48 h). The reaction mixture was partitioned between saturated $NaHCO_3$ (10 mL) and DCM (20 mL). The organic layer was separated and the aqueous layer was extracted with DCM (2×25 mL). The organic layer was dried, filtered and concentrated in vacuo. The resulting residue was purified by silica gel flash chromatography using EtOAc:hexane (0-70%) to provide the title compound as a colorless solid (374 mg, 63%). MS (ESI): mass calcd. for $C_{21}H_{19}N_3O_2S$, 377.1; m/z found, 378.2 $[M+H]^+$. $^1H$ NMR (400 MHz, $CDCl_3$): 9.77 (5, 1H), 7.74 (d, J=7.6, 1H), 7.67-7.59 (m, 2H), 7.48 (d, J=8.8, 1H), 7.37 (t, J=7.1, 1H), 7.27-7.20 (m, 2H), 6.78 (d, J=1.3, 1H), 3.99-3.74 (m, 4H), 1.90-1.64 (m, J=11.3, 5.8, 6H).

Intermediates 34 to 35 were prepared using methods analogous to those described for Intermediate 33.

Intermediate 34: [6-(Benzothiazol-2-yloxy)-1H-indol-3-yl]-morpholin-4-yl-methanone

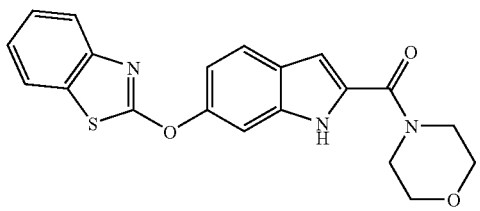 [SMILES: O=C(c1cc2ccc(Oc3nc4ccccc4s3)cc2[nH]1)N1CCOCC1]

MS (ESI): mass calcd. for $C_{20}H_{17}N_3O_3S$, 379.1; m/z found, 380.2 $[M+H]^+$. $^1H$ NMR (500 MHz, $CDCl_3$): 9.62 (5, 1H), 7.73 (d, J=7.5, 1H), 7.64 (dd, J=9.4, 1.5, 2H), 7.48 (d, J=8.9, 1H), 7.38 (td, J=7.8, 1.3, 1H), 7.32-7.18 (m, 2H), 6.79 (5, 1H), 4.02-3.88 (m, 4H), 3.86-3.71 (m, 4H).

Intermediate 35: [5-(Benzothiazol-2-yloxy)-1H-indol-2-yl]-pyrrolidin-1-yl-methanone

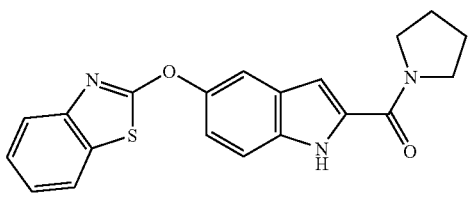 [SMILES: O=C(c1cc2cc(Oc3nc4ccccc4s3)ccc2[nH]1)N1CCCC1]

MS (ESI): mass calcd. for $C_{20}H_{17}N_3O_2S$, 363.1; m/z found, 364.2 $[M+H]^+$. $^1H$ NMR (400 MHz, $CDCl_3$): 9.74 (5, 1H), 7.74 (d, J=8.0, 1H), 7.64 (d, J=8.2, 2H), 7.51 (d, J=8.8, 1H), 7.37 (dd, J=11.3, 4.2, 1H), 7.31-7.19 (m, 2H), 6.91 (d, J=1.5, 1H), 4.01-3.68 (m, 4H), 2.22-1.83 (m, 4H).

Intermediate 36: 6-(Benzothiazol-2-yloxy)-1H-indole-2-carbaldehyde

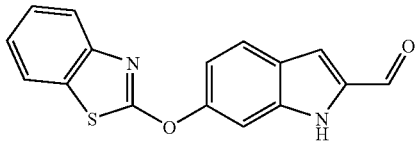

6-Hydroxy-1H-indole-2-carboxylic acid methyl ester. To a solution of 6-hydroxy-1H-indole-2-carboxylic acid (5.0 g, 28.2 mmol) in MeOH (250 mL) was added concentrated HCl (3 mL) and the reaction mixture was heated (90° C., 3 h). The reaction mixture was cooled (rt) and concentrated in vacuo. The resulting residue was partitioned between EtOAc (50 mL) and $H_2O$ (200 mL). The organic layer was separated and the aqueous layer was extracted with EtOAc (2×200 mL). The organic layer was dried, filtered and concentrated in vacuo to provide the title compound as a yellow solid (4.2 g, 77%). MS (ESI): mass calcd. for $C_{10}H_9NO_3$, 191.1; m/z found, 192.1 $[M+H]^+$.

6-(Benzothiazol-2-yloxy)-1H-indole-2-carboxylic acid methyl ester. To a solution 6-hydroxy-1H-indole-2-carboxylic acid methyl ester (4.7 g, 24.5 mmol) in DMF (250 mL) was added $Cs_2CO_3$ (8.0 g, 24.5 mmol) followed by 2-chlorobenzothiazole (3.0 mL, 4.2 g, 24.5 mmol) and the reaction mixture was heated (70° C., 12 h). The reaction mixture was cooled (rt) and concentrated in vacuo. The resulting residue was partitioned between EtOAc (200 mL) and brine (100 mL). The organic layer was separated and the aqueous layer was extracted with EtOAc (2×300 mL). The organic layer was dried, filtered and concentrated in vacuo. The resulting residue was purified by silica gel flash chromatography using EtOAc:hexane (0-40%) to provide the title compound as a colorless foam (3.6 g, 45%). MS (ESI): mass calcd. for $O_{17}H_{12}N_2O_3S$, 324.1; m/z found, 325.0 $[M+H]^+$. $^1H$ NMR (400 MHz, $CDCl_3$): 9.17 (s, 1H), 7.77-7.63 (m, 3H), 7.46-7.42 (m, 1H), 7.42-7.34 (m, 1H), 7.30-7.26 (m, 1H), 7.23-7.19 (m, 1H), 7.14 (dd, J=8.7, 2.1, 1H), 3.94 (s, 3H).

[6-(Benzothiazol-2-yloxy)-1H-indol-2-yl]-methanol. To a cooled (−78° C.) solution of 6-(benzothiazol-2-yloxy)-1H-indole-2-carboxylic acid methyl ester (200 mg, 0.61 mmol) in THF (6 mL) was added LAH (2 M in THF, 0.34 mL, 0.31 g, 0.68 mmol) and the reaction mixture was stirred (−78° C., 1 h). The reaction mixture was treated with $H_2O$ (5 mL) and EtOAc (10 mL). The organic layer was separated and the aqueous layer was extracted with EtOAc (2×25 mL). The organic layer was dried, filtered and concentrated in vacuo. The resulting residue was purified by silica gel flash chromatography using MeOH (0.2 M $NH_3$):DCM (0-4%) to provide the title compound as a beige solid (97 mg, 53%). MS (ESI): mass calcd. for $C_{16}H_{12}N_2O_2S$, 296.1; m/z found, 297.1 $[M+H]^+$. $^1H$ NMR (400 MHz, $CDCl_3$): 8.63 (s, 1H), 7.72 (d, J=8.1, 1H), 7.64 (dd, J=8.0, 0.7, 1H), 7.57 (d, J=8.5, 1H), 7.41-7.31 (m, 2H), 7.27-7.21 (m, 1H), 7.07 (dd, J=8.5, 2.2, 1H), 6.39 (s, 1H), 4.80 (d, J=5.9, 2H), 1.87 (t, J=5.9, 1H).

6-(Benzothiazol-2-yloxy)-1H-indole-2-carbaldehyde. To a solution of [6-(benzothiazol-2-yloxy)-1H-indol-2-yl]-methanol (97 mg, 0.32 mmol) in $CHCl_3$ (5 mL) was added $MnO_2$ (280 mg, 3.2 mmol) and heated (80° C., 2 h). The reaction mixture was cooled (rt), filtered (Celite®) and washed with EtOAc (100 mL). The organic layer was washed with brine (50 mL), dried, filtered and concentrated in vacuo. The resulting residue was purified by silica gel flash chromatography using EtOAc:hexane (0-50%) to provide the title compound as beige solid (47 mg, 49%). MS (ESI): mass calcd. for $C_{16}H_{10}N_2O_2S$, 294.1; m/z found, 295.0 $[M+H]^+$. $^1H$ NMR (400 MHz, $CDCl_3$): 9.80 (s, 1H), 9.80 (s, 1H), 7.79 (d, J=8.8, 1H), 7.73 (d, J=8.1, 1H), 7.68 (d, J=8.0, 1H), 7.49 (s, 1H), 7.40 (dd, J=11.3, 4.1, 1H), 7.31-7.24 (m, 2H), 7.15 (dd, J=8.8, 2.1, 1H).

Intermediate 37: 6-(Thiazolo[4,5-b]pyridin-2-yloxy)-1H-indole-2-carbaldehyde

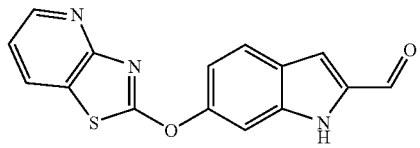 [SMILES: O=Cc1cc2ccc(Oc3nc4ncccc4s3)cc2[nH]1]

6-(Thiazolo[4,5-b]pyridin-2-yloxy)-1H-indole-2-carboxylic acid methyl ester. To a solution 6-hydroxy-1H-indole-2-carboxylic acid methyl ester (4.0 g, 21 mmol) and 2-chloro-thiazolo[4,5-b]pyridine hydrochloride (4.3 g, 21 mmol) in MeCN:DMF (4:1, 250 mL) was added $Cs_2CO_3$ (13.8 g, 42 mmol) and the reaction mixture was heated (60° C., 4 h). The reaction mixture was cooled (rt) and partitioned between EtOAc (300 mL) and saturated $NH_4Cl$ (200 mL). The organic layer was separated and the aqueous layer was extracted with EtOAc (2×200 mL). The organic layer was dried, filtered and concentrated in vacuo. The resulting residue was purified by silica gel flash chromatography using MeOH (0.2 M $NH_3$):DCM (0-15%) to provide the title compound as a brown solid (3.6 g, 53%). MS (ESI): mass calcd. for $C_{16}H_{11}N_3O_3S$, 325.1; m/z found, 326.0$[M+H]^+$. $^1H$ NMR (400 MHz, $DMSO-d_6$): 12.18 (s, 1H), 8.52 (dd, J=4.8, 1.7, 1H), 8.39 (dd, J=8.0, 1.7, 1H), 7.82 (d, J=8.7, 1H), 7.53 (d, J=2.2, 1H), 7.34 (dd, J=8.0, 4.8, 1H), 7.26 (dd, J=2.2, 0.9, 1H), 7.19 (dd, J=8.7, 2.2, 1H), 3.88 (s, 3H).

[6-(Thiazolo[4,5-b]pyridin-2-yloxy)-1H-indol-2-yl]-methanol. To a cooled (0° C.) solution of 6-(thiazolo[4,5-b]pyridin-2-yloxy)-1H-indole-2-carboxylic acid methyl ester (1.0 g, 3.1 mmol) in DCM (30 mL) was added DIBALH (1 M in THF, 15.4 mL, 13.2 g, 15.4 mmol) and the reaction mixture was stirred (0° C., 2 h). The reaction mixture was treated with saturated aqueous $NH_4Cl$ (1 mL), partitioned with EtOAc (50 mL) and saturated aqueous Rochelle's salt (50 mL). The organic layer was separated and the aqueous layer was extracted with EtOAc (2×50 mL). The organic layer was dried, filtered and concentrated in vacuo. The resulting residue was purified by silica gel flash chromatography using MeOH (0.2 M $NH_3$):DCM (0-15%) to provide the title compound as yellow solid (287 mg, 31%). MS (ESI): mass calcd. for $C_{16}H_{11}N_3O_2S$, 297.1; m/z found, 298.0 $[M+H]^+$. $^1H$ NMR (400 MHz, $CDCl_3/CD_3OD$ 10:1): 8.49 (dd, J=4.9, 1.6, 1H), 7.99 (dd, J=7.9, 1.6, 1H), 7.53 (d, J=8.5, 1H), 7.43 (d, J=2.0, 1H), 7.20 (dd, J=7.9, 4.9, 1H), 6.99 (dd, J=8.5, 2.2, 1H), 6.36 (s, 1H), 4.77 (s, 2H).

6-(Thiazolo[4,5-b]pyridin-2-yloxy)-1H-indole-2-carbaldehyde. To a solution of [6-(thiazolo[4,5-b]pyridin-2-yloxy)-1H-indol-2-yl]-methanol (0.89 g, 3.0 mmol) in $CHCl_3$ (30 mL) was added $MnO_2$ (2.6 g, 30 mmol) and the reaction mixture was heated (80° C., 3 h). The reaction mixture was cooled (rt), filtered (Celite®) and washed with isopropanol:DCM (15%, 300 mL). The filtrate was dried, filtered and concentrated in vacuo. The resulting residue was purified by reverse phase HPLC to provide the title compound as a colorless solid (139 mg, 16%). MS (ESI): mass calcd. for $C_{16}H_9N_3O_2S$, 295.0; m/z found, 296.0 $[M+H]^+$. $^1H$ NMR (400 MHz, $DMSO-d_6$): 9.94 (s, 1H), 8.59 (dd, J=4.8, 1.7, 1H), 8.46 (dd, J=8.0, 1.7, 1H), 7.95 (t, J=18.7, 1H), 7.61 (d, J=2.2, 1H), 7.55 (s, 1H), 7.40 (dd, J=8.0, 4.8, 1H), 7.34-7.15 (m, 1H).

Intermediate 38: Methanesulfonic acid 2-[5-(benzothiazol-2-yloxy)-1H-indol-3-yl]-ethyl ester

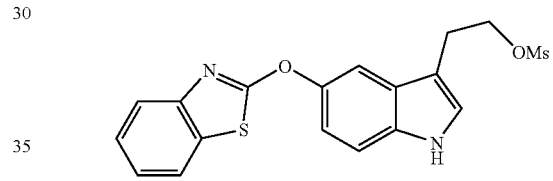

2-[5-(Benzothiazol-2-yloxy)-1H-indol-3-yl-ethanol. To a suspension of 3-(2-hydroxy-ethyl)-1H-indol-5-ol (1.0 g, 5.6 mmol) and $K_2CO_3$ (1.29 g, 9.4 mmol) in DMF (10 mL) was added 2-chlorobenzthiazole (0.58 mL, 4.7 mmol) and the resulting reaction mixture was heated (80° C., 16 h). The reaction mixture was cooled (rt), treated with saturated aqueous $NaHCO_3$ (10 mL) and extracted with DCM (3×15 mL). The organic layer was dried, filtered and concentrated in vacuo. The resulting residue was purified by silica gel flash column chromatography using EtOAc:hexane (20%) to provide the title compound as a white solid (1.05 g, 72%). MS (ESI): mass calcd. for $C_{17}H_{14}N_2O_2S$, 310.3; m/z found, 311.1 $[M+H]^+$. $^1H$ NMR (500 MHz, $CD_3OD$): 7.74 (d, J=7.3, 1H), 7.67 (d, J=7.6, 1H), 7.56 (d, J=2.1, 1H), 7.48-7.40 (m, 2H), 7.32-7.27 (m, 1H), 7.25 (s, 1H), 7.10 (dd, J=8.7, 2.4, 1H), 3.82 (t, J=7.1, 2H), 2.98 (t, J=6.8, 2H).

Methanesulfonic acid 2-[5-(benzothiazol-2-yloxy)-1H-indol-3-yl]-ethyl ester. To a solution of 2-[5-(benzothiazol-2-yloxy)-1H-indol-3-yl]-ethanol (556 mg, 1.79 mmol) and 4-dimethylaminopyridine (43.6 mg, 0.358 mmol) in MeCN (13 mL) was added DIEA (0.74 mL, 4.29 mmol) followed by the addition of MsCl (0.33 mL, 4.29 mmol) and the resulting reaction mixture was stirred (rt, 15 min). The reaction mixture was washed with saturated aqueous $Na_2CO_3$ (10 mL), aqueous 5% sulfuric acid (10 mL) and brine (10 mL). The organic layer was dried, filtered and concentrated in vacuo to provide the title compound as an orange oil (676 mg, 97%). MS (ESI): mass calcd. for $C_{18}H_{16}N_2O_4S_2$, 388.4; m/z found, 389.0 $[M+H]^+$. $^1H$ NMR (500 MHz, $CDCl_3$): 8.92 (s, 1H), 7.68 (dd, J=33.2, 7.9, 2H), 7.52 (d, J=2.2, 1H), 7.44-7.33 (m, 2H), 7.26

(dd, J=13.2, 5.6, 1H), 7.19-7.10 (m, 2H), 4.43 (t, J=6.8, 2H), 2.93-2.76 (m, 3H), 1.28 (t, J=7.1, 2H).

Intermediate 39: 5-(Benzothiazol-2-yloxy)-1-ethyl-1H-indole-2-carbaldehyde

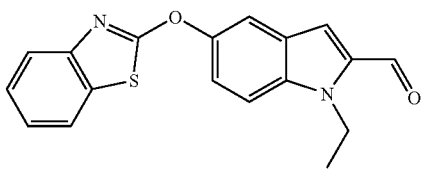 [SMILES: CCn1c(C=O)cc2cc(Oc3nc4ccccc4s3)ccc21]

5-(Benzothiazol-2-yloxy)-1-ethyl-1H-indole-2-carboxylic acid ethyl ester. To a suspension of 5-(benzothiazol-2-yloxy)-1H-indole-2-carboxylic acid (1.24 g, 4 mmol) and $Cs_2CO_3$ (1.3 g, 4 mmol) in DMF (8 mL) was added ethylbromide (0.3 mL, 0.44 g, 4 mmol) and the resulting reaction mixture was stirred (rt, 2 h). The reaction mixture was treated with additional ethylbromide (0.3 mL, 0.44 g, 4 mmol) and $Cs_2CO_3$ (1.3 g, 4 mmol) and stirred (rt, 14 h). The reaction mixture was partitioned with brine and EtOAc (50 mL each). The organic layer was dried, filtered and concentrated in vacuo. The resulting residue was purified by silica gel flash chromatography using EtOAc:hexane (10-60%) to provide the title compound as a tan solid (1.05 g, 72%). MS (ESI): mass calcd. for $C_{20}H_{18}N_2O_3S$, 366.1; m/z found, 367.0 $[M+H]^+$. $^1H$ NMR (500 MHz, $CDCl_3$): 7.76 (d, J=8.0, 1H), 7.67-7.65 (m, 2H), 7.47 (d, J=9.0, 1H), 7.41-7.38 (m, 1H), 7.36-7.34 (m, 2H), 7.28-7.24 (m, 1H), 4.66 (q, J=7.2, 2H), 4.41 (q, J=7.2, 2H), 1.46-1.43 (m, 6H).

[5-(Benzothiazol-2-yloxy)-1-ethyl-1H-indol-2-yl]-methanol. To a cooled (−78° C.) solution of [5-(benzothiazol-2-yloxy)-1-ethyl-1H-indole-2-carboxylic acid ethyl ester (1.05 g, 3.1 mmol) in THF (30 mL) was added LAH (1 M in THF, 0.8 mL, 0.72 g, 7.8 mmol) and the reaction mixture was stirred (−78° C., 1 h) and allowed to warm (rt, 12 h). The reaction mixture was treated with $H_2O$ (10 mL). The organic layer was separated and the aqueous layer was extracted with EtOAc (3×30 mL). The organic layer was dried, filtered and concentrated in vacuo. The resulting residue was purified by silica gel flash chromatography using MeOH:DCM (5-15%) to provide the title compound as a colorless foam (0.5 g, 49%). MS (ESI): mass calcd. for $C_{18}H_{16}N_2O_2S$, 324.0; m/z found, 325.1 $[M+H]^+$. $^1H$ NMR (500 MHz, DMSO-$d_6$): 7.85 (d, J=7.2, 1H), 7.68 (d, J=7.6, 1H), 7.56 (s, 1H), 7.55 (d, J=6.4, 1H), 7.45-7.37 (m, 1H), 7.32-7.25 (m, 1H), 7.16 (dd, J=8.8, 2.4, 1H), 6.44 (s, 1H), 5.32 (s, 1H), 4.67 (s, 2H), 4.29 (q, J=7.1, 2H), 1.33 (t, J=7.1, 3H).

5-(Benzothiazol-2-yloxy)-1-ethyl-1H-indole-2-carbaldehyde. To a solution [5-(benzothiazol-2-yloxy)-1-ethyl-1H-indol-2-yl]-methanol (0.5 g, 1.6 mmol) in $CHCl_3$ (16 mL) was added $MnO_2$ (1.4 g, 16 mmol) and heated (80° C., 3 h). The reaction mixture was cooled (rt), filtered (Celite®) and washed with EtOAc (100 mL). The organic layer was washed with brine (50 mL), dried, filtered and concentrated in vacuo. The resulting residue was recrystallized using EtOAc:hexane (1:3) to provide the title compound as beige solid (0.3 g, 59%). MS (ESI): mass calcd. for $C_{18}H_{14}N_2O_2S$, 322.1; m/z found, 323.1 $[M+H]^+$. $^1H$ NMR (500 MHz, $CDCl_3$): 9.91 (s, 1H), 7.78-7.68 (m, 2H), 7.66 (dd, J=8.0, 0.7, 1H), 7.49 (d, J=9.1, 1H), 7.43-7.34 (m, 2H), 7.30-7.23 (m, 2H), 4.63 (q, J=7.1, 2H), 1.42 (t, J=7.1, 3H).

Intermediate 40: [5-(Benzothiazol-2-yloxy)-benzofuran-2-yl]-methanol

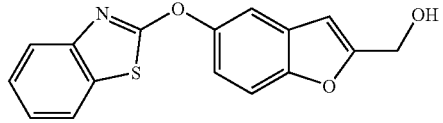 [SMILES: OCc1cc2cc(Oc3nc4ccccc4s3)ccc2o1]

5-hydroxy-benzofuran-2-carboxylic acid. To a cooled (−78° C.) solution of 5-methoxy-benzofuran-2-carboxylic acid (5.0 g, 26.0 mmol) in DCM (100 mL) was added $BBr_3$ (7.4 mL, 19.5 g, 78.0 mmol) and the reaction mixture was stirred (2 h). The reaction mixture was warmed (rt) and subsequently cooled (0° C.) and treated with saturated $NH_4Cl$ (100 mL). The resultant biphasic mixture was partitioned and the aqueous layer was extracted with EtOAc (3×100 mL), dried, filtered and concentrated in vacuo to afford the title compound (4.6 g, 100%).

5-Hydroxy-benzofuran-2-carboxylic acid methyl ester. To a solution of 5-hydroxy-benzofuran-2-carboxylic acid (4.6 g, 26.0 mmol) in MeOH (100 mL) was added concentrated sulfuric acid (1.2 g, 13.0 mmol) and the resultant solution was heated (reflux, 18 h). The reaction was cooled (rt) and concentrated in vacuo. The resultant residue was purified by silica gel flash column chromatography using MeOH:DCM (10%) to provide the title compound (4.14 g, 83%). MS (ESI): mass calcd for $C_{10}H_8O_4$, 192.0; m/z found, 193.1 $[M+H]^+$. $^1H$ NMR (500 MHz, $CD_3OD$): 7.47 (s, 1H), 7.39 (d, J=9.0, 1H), 7.04 (d, J=2.5, 1H), 6.97 (dd, J=9.0, 2.5, 1H), 3.92 (s, 3H).

5-(Benzothiazol-2-yloxy)-benzofuran-2-carboxylic acid methyl ester. To a solution of 5-hydroxy-benzofuran-2-carboxylic acid methyl ester (300 mg, 1.56 mmol) in DMF (5 mL) was added 2-chlorobenzothiazole (263 mg, 1.56 mmol) and $Cs_2CO_3$ (590 mg, 1.87 mmol). The resultant suspension was warmed (50° C., 18 h). The reaction mixture was concentrated under a stream of nitrogen. The resultant residue was purified by silica gel flash chromatography using EtOAc:hexane (10-30%) to provide the title compound (406 mg, 80%). MS (ESI): mass calcd for $C_{17}H_{11}NO_4S$, 325.0; m/z found, 326.1 $[M+H]^+$. $^1H$ NMR (400 MHz, $CDCl_3$): 7.76-7.72 (m, 2H), 7.70 (d, J=8.0, 1H), 7.67 (d, J=9.0, 1H), 7.57 (s, 1H), 7.49-7.44 (m, 1H), 7.43-7.38 (m, 1H), 7.32-7.27 (m, 1H), 4.01 (s, 3H).

[5-(Benzothiazol-2-yloxy)-benzofuran-2-yl]-methanol. To a cooled (0° C.) solution of 5-(benzothiazol-2-yloxy)-benzofuran-2-carboxylic acid methyl ester (170 mg, 0.52 mmol) in DCM (2 mL) was added DIBALH (0.63 mL, 89 mg 0.63 mmol) and the reaction mixture was warmed (rt, 2.5 h). The reaction mixture was treated with saturated aqueous Rochelle's Salt (2 mL) and stirred (rt, 2 h). The biphasic mixture was poured into saturated aqueous $NH_4Cl$ and extracted with DCM (2×50 mL). The organic layer was dried, filtered and concentrated in vacuo. The resultant residue was purified by silica gel flash column chromatography using MeOH:DCM (3-40%) to afford the title compound (55 mg, 36%). MS (ESI): mass calcd for $C_{16}H_{11}NO_3S$, 297.04; m/z found, 298.1 $[M+H]^+$.

Intermediates 41 to 43 were prepared using methods analogous to those described for Intermediate 40.

Intermediate 41: [5-(4-Fluoro-benzothiazol-2-yloxy)-benzofuran-2-yl]-methanol

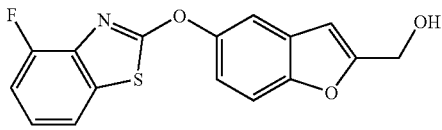 [SMILES: OCc1cc2cc(Oc3nc4c(F)cccc4s3)ccc2o1]

MS (ESI): mass calcd for C$_{16}$H$_{10}$NO$_3$SF, 315.0; m/z found, 316.1 [M+H]$^+$.

Intermediate 42: [5-(Thiazolo[4,5-b]pyridin-2-yloxy)-benzofuran-2-yl]-methanol

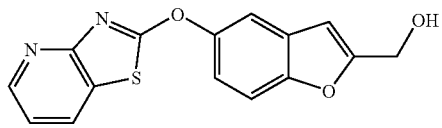 [SMILES: OCc1cc2cc(Oc3nc4ncccc4s3)ccc2o1]

MS (ESI): mass calcd for C$_{15}$H$_{10}$N$_2$O$_3$S, 298.0; m/z found, 299.1 [M+H]$^+$. $^1$H NMR (500 MHz, CD$_3$OD): 8.47 (dd, J=4.9, 1.6, 1H), 8.28 (dd, J=8.0, 1.6, 1H), 7.65 (d, J=2.5, 1H), 7.59 (d, J=8.8, 1H), 7.35-7.29 (m, 2H), 6.79 (s, 1H), 4.71 (s, 2H).

Intermediate 43: [5-(Thiazolo[5,4-b]pyridin-2-yloxy)-benzofuran-2-yl]-methanol

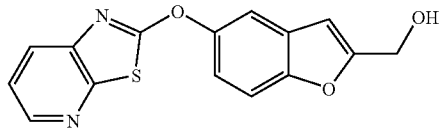 [SMILES: OCc1cc2cc(Oc3nc4cccnc4s3)ccc2o1]

MS (ESI): mass calcd. For C$_{15}$H$_{10}$N$_2$O$_3$S, 298.0; m/z found, 299.1 [M+H]$^+$. $^1$H NMR (400 MHz, CD$_3$OD): 8.39 (dd, J=4.8, 1.5, 1H), 7.99 (dd, J=8.2, 1.5, 1H), 7.62 (d, J=2.5, 1H), 7.58 (d, J=8.8, 1H), 7.46 (dd, J=8.2, 4.8, 1H), 7.29 (dd, J=8.8, 2.5, 1H), 6.79 (d, J=0.8, 1H), 4.71 (d, J=0.6, 2H), 3.54 (t, J=6.6, 1H).

Intermediate 44: [6-(Thiazolo[4,5-b]pyridin-2-yloxy)-benzofuran-2-yl]-methanol

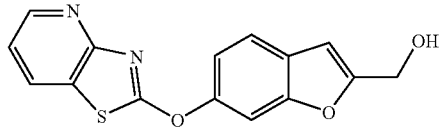 [SMILES: OCc1cc2ccc(Oc3nc4ncccc4s3)cc2o1]

6-Benzyloxy-benzofuran-2-carboxylic acid ethyl ester. To a solution of 4-benzyloxy-2-hydroxy-benzaldehyde (10.0 g, 44 mmol) in DMF (400 mL) is added K$_2$CO$_3$ (18.6 g, 131 mmol) followed by bromo-acetic acid ethyl ester (5.4 mL, 8.1 g, 48 mmol) and the resulting mixture was heated (80° C., 12 h). The reaction mixture was cooled (rt) and treated with H$_2$O (200 mL). The solid was filtered to afforded the title compound as a beige solid (8.1 g, 62%). MS (ESI): mass calcd. for C$_{18}$H$_{16}$O$_4$, 296.1; m/z found, 297.1 [M+H]$^+$. $^1$H NMR (400 MHz, CDCl$_3$): 7.53 (d, J=8.7, 1H), 7.48-7.30 (m, 6H), 7.12 (d, J=2.0, 1H), 7.01 (dt, J=6.1, 3.1, 1H), 5.09 (d, J=28.6, 2H), 4.42 (q, J=7.1, 2H), 1.37 (dt, J=36.6, 9.6, 3H).

6-Hydroxy-benzofuran-2-carboxylic acid ethyl ester. To a solution of 6-benzyloxy-benzofuran-2-carboxylic acid ethyl ester (8.1 g, 27 mmol) in EtOAc/EtOH (3/1, 130 mL) was added Pd/C (0.8 g). The reaction mixture was shaken in a Parr Shaker under H$_2$ (50 psi, 12 h). The reaction mixture was filtered (Celite®), washed with EtOAC (400 mL) and EtOH (100 mL). The filtrate was concentrated and the resulting residue was purified by silica gel flash chromatography using EtOAc:hexanes (0-50%) to provide the title compound as colorless solid (3.9 g, 70%). MS (ESI): mass calcd. for C$_{11}$H$_{10}$O$_4$, 206.1.0; m/z found, 207.1 [M+H]$^+$. $^1$H NMR (400 MHz, CDCl$_3$): 7.50 (d, J=8.6, 1H), 7.46 (d, J=0.8, 1H), 7.25-7.23 (m, 1H), 6.90 (dd, J=8.5, 2.2, 1H), 6.12 (s, 1H), 4.57-4.30 (m, 2H), 1.49-1.31 (m, 3H).

6-(Thiazolo[4,5-b]pyridin-2-yloxy)-benzofuran-2-carboxylic acid ethyl ester. To a solution of 6-hydroxy-benzofuran-2-carboxylic acid ethyl ester (2.0 g, 10 mmol) in MeCN (100 mL) added Cs$_2$CO$_3$ (6.3 g, 19 mmol) followed by 2-chloro-thiazolo[4,5-b]pyridine hydrochloride (2.0 g, 10 mmol) and the reaction mixture was stirred (rt, 12 h). The reaction mixture was treated with H$_2$O (50 mL) and the solid was filtered to afford the title compound as a beige solid (2.3 g, 69%). MS (ESI): mass calcd. for C$_{17}$H$_{12}$N$_2$O$_4$S, 340.1; m/z found, 341.1 [M+H]$^+$. $^1$H NMR (400 MHz, CDCl$_3$): 8.58 (dd, J=4.8, 1.6, 1H), 8.04 (dd, J=7.9, 1.6, 1H), 7.75-7.69 (m, 2H), 7.55 (d, J=0.8, 1H), 7.42 (dd, J=8.6, 2.1, 1H), 7.22 (dd, J=7.9, 4.8, 1H), 4.46 (q, J=7.1, 2H), 1.44 (t, J=7.1, 3H).

[6-(Thiazolo[4,5-b]pyridin-2-yloxy)-benzofuran-2-yl]-methanol. To a cooled (0° C.) solution 6-(thiazolo[4,5-b]pyridin-2-yloxy)-benzofuran-2-carboxylic acid ethyl ester (300 mg, 0.8 mmol) in DCM (8 mL) was added DIBALH (1 M in THF, 3 mL, 3 mmol) and the reaction mixture was warmed (rt, 48 h). The reaction mixture was quenched with saturated aqueous Rochelle's Salt (2 mL) and partitioned with DCM. The organic layer was separated and the aqueous layer was extracted with DCM (2×15 mL). The organic layers were combined, dried, filtered and concentrated in vacuo. The resulting residue was purified by silica gel flash chromatography using MeOH:DCM (0-10%) to provide the title compound as a yellow solid (197 mg, 82%). MS (ESI): mass calcd. for C$_{16}$H$_{10}$N$_2$O$_3$S, 298.1; m/z found, 299.1 [M+H]$^+$. $^1$H NMR (500 MHz, DMSO-d$_6$): 8.53 (dd, J=4.8, 1.7, 1H), 8.40 (dd, J=8.0, 1.7, 1H), 7.84 (d, J=1.7, 1H), 7.74 (d, J=8.4, 1H), 7.44-7.26 (m, 2H), 6.86 (s, 1H), 5.54 (t, J=5.9, 1H), 4.60 (d, J=5.9, 2H).

Intermediate 45 was prepared using methods analogous to those described for Intermediate 44.

Intermediate 45: [6-(Thiazolo[5,4-b]pyridin-2-yloxy)-benzofuran-2-yl]-methanol

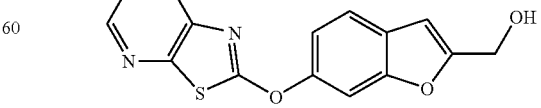

MS (ESI): mass calcd. For C$_{15}$H$_{10}$N$_2$O$_3$S, 298.0; m/z found, 299.1 [M+H]$^+$. $^1$H NMR (400 MHz, CD$_3$OD): 8.39 (dd, J=4.8, 1.5, 1H), 7.99 (dd, J=8.2, 1.5, 1H), 7.67 (d, J=8.4, 1H), 7.63-7.57 (m, 1H), 7.46 (dd, J=8.2, 4.8, 1H), 7.27 (dd, J=8.5, 2.2, 1H), 6.79 (d, J=0.8, 1H), 4.68 (s, J=10.3, 2H).

Intermediate 46: 2-(2-Chloromethyl-benzofuran-5-yloxy)-benzothiazole

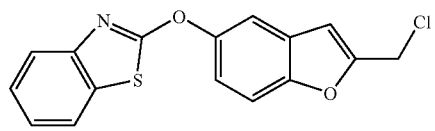 [SMILES: ClCc1cc2cc(Oc3nc4ccccc4s3)ccc2o1]

To a solution of [5-(benzothiazol-2-yloxy)-benzofuran-2-yl]-methanol (55 mg, 0.19 mmol) and DIEA (0.042 mL, 34 mg, 0.24 mmol) in DCM (0.8 mL) was added thionyl chloride (0.017 mL, 26 mg, 0.22 mmol) and the resulting mixture was stirred (rt, 2 h). The reaction mixture was concentrated under a stream of nitrogen to afford the title compound (50 mg, 100%). MS (ESI): mass calcd for $C_{16}H_{10}NO_2SCl$, 315.0; m/z found 316.1 $[M+H]^+$.

Intermediates 47 to 51 were prepared using methods analogous to those described for Intermediate 46.

Intermediate 47: 2-(2-Chloromethyl-benzofuran-5-yloxy)-4-fluoro-benzothiazole

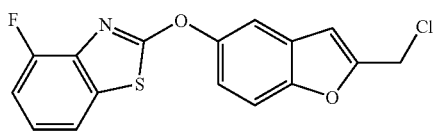 [SMILES: Fc1cccc2sc(Oc3ccc4oc(CCl)cc4c3)nc12]

MS (ESI): mass calcd for $C_{16}H_9NO_2SClF$, 333.0; m/z found, 334.1 $[M+H]^+$.

Intermediate 48: 2-(2-Chloromethyl-benzofuran-5-yloxy)-thiazolo[4,5-b]pyridine

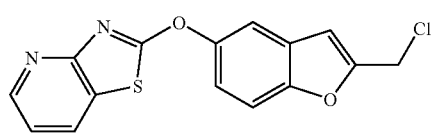

MS (ESI): mass calcd. for $C_{15}H_9N_2O_2SCl$, 316.0; m/z found, 317.1 $[M+H]^+$.

Intermediate 49: 2-(2-Chloromethyl-benzofuran-6-yloxy)-thiazolo[4,5-b]pyridine

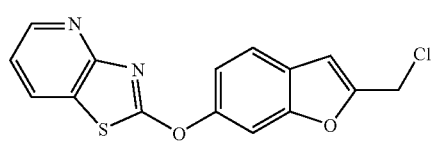

MS (ESI): mass calcd. for $C_{15}H_9ClN_2O_2S$, 316.0; m/z found, 317.0 $[M+H]^+$. $^1$H NMR (400 MHz, DMSO-$d_6$): 8.55 (dd, J=4.9, 1.6, 1H), 8.46 (dd, J=8.0, 1.6, 1H), 7.92 (d, J=1.6, 1H), 7.81 (d, J=8.5, 1H), 7.46-7.35 (m, 2H), 7.12 (s, 1H), 5.03 (s, 2H).

Intermediate 50: 2-(2-Chloromethyl-benzofuran-5-yloxy)-thiazolo[5,4-b]pyridine

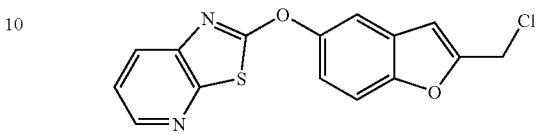

MS (ESI): mass calcd. For $C_{15}H_9ClN_2O_2S$, 316.0; m/z found, 317.1 $[M+H]^+$. $^1$H NMR (400 MHz, CDCl$_3$): 8.52 (dd, J=5.6, 1.2, 1H), 8.42 (dd, J=8.3, 1.2, 1H), 7.83-7.70 (m, 1H), 7.60 (d, J=8.9, 1H), 7.56 (d, J=2.5, 1H), 7.29 (dd, J=8.9, 2.5, 1H), 6.82 (5, 1H), 4.72 (s, 2H).

Intermediate 51: 2-(2-Chloromethyl-benzofuran-6-yloxy)-thiazolo[5,4-b]pyridine

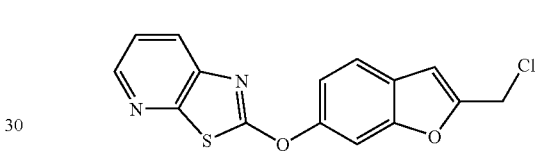

MS (ESI): mass calcd. For $C_{15}H_9ClN_2O_2S$, 316.0; m/z found, 317.0 $[M+H]^+$. $^1$H NMR (400 MHz, CDCl$_3$): 8.51 (dd, J=5.5, 1.1, 1H), 8.39 (dd, J=8.3, 1.2, 1H), 7.73 (dd, J=8.2, 5.6, 1H), 7.66 (d, J=8.5, 1H), 7.56 (d, J=2.0, 1H), 7.28-7.23 (m, 1H), 6.82 (s, 1H), 4.72 (s, 2H).

Intermediate 52: Methanesulfonic acid 2-[6-(benzothiazol-2-yloxy)-benzofuran-3-yl]-ethyl ester

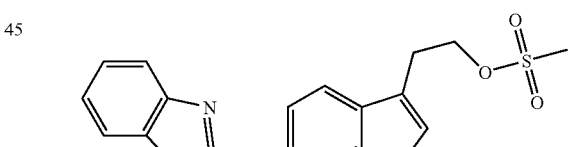

(6-Hydroxy-benzofuran-3-yl)-acetic acid methyl ester. To a suspension of 6-hydroxy-benzofuran-3-one (5.0 g, 33.3 mmol) in xylene (100 mL) was added methyl (triphenylphosphoranylidene)acetate (11.1 g, 33.3 mmol) and the resulting reaction mixture was heated (120° C., 24 h). The reaction mixture was concentrated in vacuo and the residue was treated with 1 M HCl adjusting the pH to 3. The organic layer was extracted with EtOAc (2×100 mL). The combined organic layers were dried, filtered and concentrated in vacuo. The resulting residue was purified by silica gel flash chromatography using EtOAc:hexane (0-70%) to provide the title compound as a clear oil (1.6 g, 23%). MS (ESI): mass calcd. for $C_{10}H_{10}NO_4$, 206.2; m/z found, 207.2 $[M+H]^+$. $^1$H NMR (400 MHz, CDCl$_3$): 7.03-7.07 (m, 1H), 7.37 (d, J=8.4, 1H), 6.93 (d, J=2.2, 1H), 6.77 (dd, J=8.4, 2.2, 1H), 5.20 (br s, 1H), 3.74 (s, 3H), 3.67 (s, 2H).

3-(2-Hydroxy-ethyl)-benzofuran-6-ol. To a cooled (0° C.) solution of (6-hydroxy-benzofuran-3-yl)-acetic acid methyl ester (0.42 g, 2.0 mmol) in THF (18 mL) was added LAH (2 M in THF, 3.1 mL, 6.1 mmol) and the reaction mixture was stirred (0° C., 1 h). The reaction mixture was warmed (rt, 1 h). The reaction mixture was treated with Rochelle's salt (20 mL) and neutralized with saturated $NH_4Cl$ (20 mL). The aqueous layer was extracted with EtOAc (2×50 mL). The combined organic layers were washed with brine, dried, filtered and concentrated in vacuo. The resulting residue was purified by silica gel flash chromatography using MeOH:DCM (0-15%) to provide the title compound as a tan semisolid (0.34 g, 94%). $^1$H NMR (500 MHz, $CDCl_3$): 7.41 (s, 1H), 7.37 (d, J=8.3, 1H), 6.95 (d, J=2.5, 1H), 6.78 (dd, J=8.3, 2.5, 1H), 3.93-3.91 (br s, 2H), 2.92-2.89 (m, 2H), the two hydroxyl protons were not detected.

2-[6-(Benzothiazol-2-yloxy)-benzofuran-3-yl]-ethanol. To a solution of 3-(2-hydroxy-ethyl)-benzofuran-6-ol (0.42 g, 2.4 mmol) in MeCN (10 mL) was added $Cs_2CO_3$ (0.77 g, 2.4 mmol) and 2-chlorobenzthiazole (0.29 mL, 2.4 mmol) and the reaction mixture was stirred (rt, 15 h) and then heated (60° C., 2 h). The reaction mixture was cooled (rt) and partitioned with EtOAc and brine (50 mL each). The aqueous layer was extracted with EtOAc (50 mL). The combined organic layers were washed with brine (50 mL), dried, filtered and concentrated in vacuo. The resulting residue was purified by silica gel flash chromatography using EtOAc:hexane (0-100%) to provide the title compound as an amber oil (0.37 g, 50%). MS (ESI): mass calcd. for $C_{17}H_{13}NO_3S$, 311.4; m/z found, 312.1 [M+H]$^+$. $^1$H NMR (500 MHz, $CDCl_3$): 7.73 (d, J=8.0, 1H), 7.67 (d, J=8.0, 1H), 6.61 (d, J=8.5, 1H), 7.58 (br s, 1H), 7.53 (d, J=2.0, 1H), 7.41-7.37 (m, 1H), 7.29-7.26 (m, 2H), 3.97-3.93 (m, 2H), 3.96 (t, J=6.5, 2H), the hydroxyl proton was not detected.

Methanesulfonic acid 2-[6-(benzothiazol-2-yloxy)-benzofuran-3-yl] ethyl ester. To a solution of 2-[6-(benzothiazol-2-yloxy)-benzofuran-3-yl]-ethanol (0.32 g, 1.0 mmol) in DCM (15 mL) was added 4-dimethylaminopyridine (13 mg, 0.10 mmol), DIEA (0.22 mL, 1.2 mmol) and $Ms_2O$ (0.22 g, 1.2 mmol) and the resulting solution was stirred (rt, 15 min). The reaction mixture was diluted with DCM (40 mL). The organic layer was washed with saturated $NH_4Cl$ (2×50 mL), brine (2×50 mL), dried, filtered and concentrated in vacuo to provide the title compound as a clear oil (0.41 g, 100%). MS (ESI): mass calcd. for $C_{18}H_{15}NO_5S_2$, 389.5; m/z found, 390.1 [M+H]$^+$.

Intermediate 53: Methanesulfonic acid 2-[6-(thiazolo[4,5-b]pyridin-2-yloxy)-benzofuran-3-yl] ethyl ester

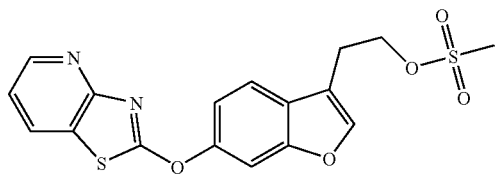 [SMILES: CS(=O)(=O)OCCc1coc2cc(Oc3nc4ncccc4s3)ccc12]

2-[6-(Thiazolo[4,5-b]pyridin-2-yloxy)-benzofuran-3-yl]-ethanol. To a solution of 3-(2-hydroxy-ethyl)-benzofuran-6-ol (0.42 g, 2.4 mmol) in DMF (24 mL) was added $Cs_2CO_3$ (0.77 g, 2.4 mmol) and 2-chloro-thiazolo[4,5-b]pyridine hydrochloride (0.49 g, 2.4 mmol) and the reaction mixture was stirred (rt, 15 h) and then heated (50° C., 2 h). The reaction mixture was cooled (rt) and partitioned with EtOAc and brine (50 mL each). The aqueous layer was extracted with EtOAc (50 mL). The organic layer was washed with brine (50 mL), dried, filtered and concentrated in vacuo. The resulting residue was purified by silica gel flash chromatography using EtOAc:hexane (0-100%) to provide the title compound as an amber oil (0.42 g, 57%). MS (ESI): mass calcd. for $C_{16}H_{12}N_2O_3S$, 312.3; m/z not found. $^1$H NMR (500 MHz, $CDCl_3$): 8.56 (dd, J=4.8, 1.7, 1H), 8.02 (dd, J=8.0, 1.6, 1H), 7.61-7.57 (m, 3H), 7.30 (dd, J=8.4, 2.2, 1H), 7.21 (dd, J=8.0, 4.8, 1H), 3.95 (q, J=6.1, 2H), 2.97-2.94 (m, 2H), 1.75 (t, J=5.5, 1H).

Methanesulfonic acid 2-[6-(thiazolo[4,5-b]pyridin-2-yloxy)-benzofuran-3-yl]-ethyl ester. To a solution of 2-[6-(thiazolo[4,5-b]pyridin-2-yloxy)-benzofuran-3-yl]-ethanol (0.4 g, 1.3 mmol) in DCM (13 mL) was added 4-dimethylaminopyridine (16 mg, 0.13 mmol), DIEA (0.27 mL, 1.5 mmol) and $Ms_2O$ (0.27 g, 1.5 mmol) and the resulting solution was stirred (rt, 15 min). The reaction mixture was diluted with DCM (40 mL). The organic layer was washed with saturated $NH_4Cl$ (2×50 mL), brine (2×50 mL), dried, filtered and concentrated in vacuo to provide the title compound as a clear oil (0.52 g, 100%). MS (ESI): mass calcd. for $C_{17}H_{14}N_2O_5S_2$, 390.4; m/z found, 391.1 [M+H]$^+$.

Intermediate 54: 2-(2-Chloromethyl-benzo[b]thiophen-6-yloxy)-benzothiazole

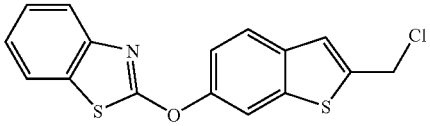 [SMILES: ClCc1cc2ccc(Oc3nc4ccccc4s3)cc2s1]

6-Methoxy-benzo[b]thiophene-2-carboxylic acid methyl ester. To a solution of 2-fluoro-4-methoxy-benzaldehyde (4.0 g, 26 mmol) in DMSO (200 mL) was added mercapto-acetic acid methyl ester (3.6 mL, 3.9 g, 39 mmol) and $Et_3N$ (10.8 mL, 7.8 g, 78 mmol) and the reaction mixture was heated (80° C., 12 h). The reaction mixture was cooled (rt) and treated with $H_2O$ (100 mL). The suspension was filtered to afford the title compound as a yellow solid (4.1 g, 71%). MS (ESI): mass calcd. for $C_{11}H_{10}O_3S$, 222.0; m/z found, 223.0 [M+H]$^+$. $^1$H NMR (400 MHz, $CDCl_3$): 7.97 (d, J=0.6, 1H), 7.74 (d, J=8.8, 1H), 7.28 (d, J=2.3, 1H), 7.02 (dt, J=8.7, 4.3, 1H), 3.92 (s, 3H), 3.89 (s, 3H).

6-(Benzothiazol-2-yloxy)-benzo[b]thiophene-2-carboxylic acid methyl ester. To a cooled (-78° C.) solution of 6-methoxy-benzo[b]thiophene-2-carboxylic acid methyl ester (4.7 g, 21 mmol) in DCM (210 mL) was added $BBr_3$ (6.0 mL, 15.9 g, 63 mmol) dropwise and the reaction mixture was allowed to warm (rt, 4 h). The reaction mixture was cooled (0° C.), diluted with EtOAc (200 mL) and treated with $H_2O$ (25 mL). The organic layer was separated and the aqueous layer was extracted with EtOAc (2×100 mL). The organic layer was dried, filtered and concentrated in vacuo. The resulting residue was dissolved in MeCN (150 mL) and treated with $Cs_2CO_3$ (9.8 g, 30 mmol) and 2-chlorobenzothiazole (1.9 mL, 2.5 g, 15 mmol) and the reaction mixture was heated (60° C., 4 h). The reaction mixture was cooled (rt) and treated with 1 M HCl (50 mL) and partitioned between EtOAc (100 mL) and $H_2O$ (50 mL). The organic layer was separated and the aqueous layer was extracted with EtOAc (2×100 mL). The organic layer was dried, filtered and concentrated in vacuo. The resulting residue was purified by silica gel flash chromatography using EtOAc:hexane (0-60%) to provide the title compound as a colorless foam (0.27 g, 5%). MS (ESI): mass calcd. for $O_{11}H_{10}O_3S_2$, 341.0; m/z found, 342.0 [M+H]$^+$. $^1$H NMR (400 MHz, $CDCl_3$): 8.07 (s, J=0.6, 1H), 7.93 (dd, J=5.4, 3.2, 2H), 7.75 (dd, J=8.1, 0.6, 1H), 7.70 (dd, J=8.0, 0.7, 1H), 7.50-7.37 (m, 2H), 7.35-7.27 (m, 1H), 3.96 (s, 3H).

[6-(Benzothiazol-2-yloxy)-benzo[b]thiophen-2-yl]-methanol. To a cooled (0° C.) solution 6-(benzothiazol-2-yloxy)-benzo[b]thiophene-2-carboxylic acid methyl ester (274 mg, 0.8 mmol) in DCM (8 mL) was added LAH (2 M in THF, 0.4 mL, 0.3 g, 0.8 mmol) and the reaction mixture was stirred (0° C., 3 h). The reaction mixture was treated with saturated aqueous NH$_4$Cl (2 mL) and partitioned with DCM (20 mL). The organic layer was separated and the aqueous layer was extracted with DCM (2×15 mL). The organic layer was dried, filtered and concentrated in vacuo to provide the title compound as a yellow solid (259 mg, 77%). MS (ESI): mass calcd. for C$_{16}$H$_{11}$O$_2$S$_2$, 313.0; m/z found, 314.0 [M+H]$^+$.

2-(2-Chloromethyl-benzo[b]thiophen-6-yloxy)-benzothiazole. To a cooled (0° C.) solution [6-(benzothiazol-2-yloxy)-benzo[b]thiophen-2-yl]-methanol (256 mg, 0.8 mmol) in DCM (8 mL) was added thionyl chloride (60 μL, 98 mg, 0.8 mmol) and the reaction mixture was stirred (0° C., 2 h). The reaction mixture was partitioned between EtOAc (20 mL) and saturated NaHCO$_3$ (10 mL). The organic layer was separated and the aqueous layer was extracted with EtOAc (2×20 mL). The organic layer was dried, filtered and concentrated in vacuo. The resulting residue was purified by silica gel flash chromatography using EtOAc:hexane (0-40%) to provide the title compound as yellow solid (0.17 g, 65%). MS (ESI): mass calcd. for C$_{16}$H$_{10}$ClNOS$_2$, 331.0; m/z found, 332.0 [M+H]$^+$. $^1$H NMR (400 MHz, CDCl$_3$): 7.84 (d, J=2.2, 1H), 7.78 (d, J=8.7, 1H), 7.74 (dd, J=8.1, 0.6, 1H), 7.68 (dd, J=8.0, 0.7, 1H), 7.43-7.26 (m, 4H), 4.86 (s, 2H).

Intermediate 55: 2-(2-Chloromethyl-benzo[b]thiophen-6-yloxy)-thiazolo[4,5-b]pyridine

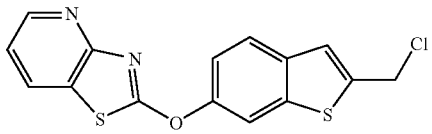 [SMILES: ClCc1cc2ccc(Oc3nc4ncccc4s3)cc2s1]

4-Benzyloxy-2-fluoro-benzaldehyde. To a solution of 2-fluoro-4-hydroxy-benzaldehyde (1.0 g, 7.1 mmol) in DMF (70 mL) was added benzylbromide (0.85 mL, 1.2 g, 7.1 mmol) and K$_2$CO$_3$ (1.1 g, 7.9 mmol) and the reaction mixture was stirred (rt, 12 h). The reaction mixture was treated with H$_2$O (50 mL) and filtered to afford the title compound as a colorless solid (1.4 g, 85%). MS (ESI): mass calcd. for C$_{14}$H$_{11}$FO$_2$, 230.1; m/z found, 231.1 [M+H]$^+$. $^1$H NMR (400 MHz, CDCl$_3$): 10.21 (s, 1H), 7.82 (t, J=8.8, 1H), 7.48-7.32 (m, 5H), 6.85 (dd, J=8.8, 2.3, 1H), 6.71 (dd, J=12.3, 2.3, 1H), 5.11 (d, J=14.8, 2H).

6-Benzyloxy-benzo[b]thiophene-2-carboxylic acid methyl ester. To a solution of 4-benzyloxy-2-fluoro-benzaldehyde (1.3 g, 5.6 mmol) in DMSO (55 mL) was added mercapto-acetic acid methyl ester (1.2 mL, 11.3 mmol) and Et$_3$N (2.4 mL, 1.7 g, 16.8 mmol) and the reaction mixture was heated (80° C., 12 h). The reaction mixture was cooled (rt), treated with H$_2$O (100 mL) and filtered. The resulting residue was purified by silica gel flash chromatography using EtOAc:hexane (0-30%) to provide the title compound as yellow solid (1.6 g, 96%). MS (ESI): mass calcd. for C$_{17}$H$_{14}$O$_3$S, 298.1; m/z found, 299.1 [M+H]$^+$. $^1$H NMR (500 MHz, CDCl$_3$): 7.98 (s, 1H), 7.75 (d, J=8.8, 1H), 7.53-7.30 (m, 6H), 7.10 (dd, J=8.8, 2.3, 1H), 5.14 (s, 2H), 3.92 (s, 3H).

6-Hydroxy-benzo[b]thiophene-2-carboxylic acid methyl ester. To a solution of 4-benzyloxy-2-fluoro-benzaldehyde (0.6 g, 2.2 mmol) in ethanol:AcOH (3:2, 25 mL) was added Pd/C (10%, 0.1 g) and AcOH (0.10 mL). The reaction mixture was placed on a Parr shaker under H$_2$ gas (55 psi, 24 h). Additional Pd/C (2×0.1 g) and AcOH (2×0.10 mL) was added to drive reaction to completion. The reaction mixture was filtered (Celite®), washed with ethanol (200 mL) and the filtrate was concentrated in vacuo. The resulting residue was purified by silica gel flash chromatography using EtOAc:hexane (0-50%) to provide the title compound as a yellow solid (0.2 g, 44%). MS (ESI): mass calcd. for C$_{10}$H$_8$O$_3$S, 208.0; m/z found, 209.1 [M+H]$^+$. $^1$H NMR (400 MHz, CDCl$_3$): 7.95 (s, 1H), 7.70 (d, J=8.7, 1H), 7.24 (d, J=2.2, 1H), 6.96 (dd, J=8.7, 2.2, 1H), 3.92 (s, 3H), 2.30 (s, 1H).

6-(Thiazolo[4,5-b]pyridin-2-yloxy)-benzo[b]thiophene-2-carboxylic acid methyl ester. To a solution of 6-hydroxy-benzo[b]thiophene-2-carboxylic acid methyl ester (0.18 g, 0.9 mmol) in MeCN (9 mL) was added Cs$_2$CO$_3$ (0.6 g, 1.8 mmol), 2-chloro-thiazolo[4,5-b]pyridine hydrochloride (0.18 g, 0.9 mmol) and the reaction mixture was stirred (rt, 3 h). The reaction mixture was filtered and concentrated in vacuum to provide the title compound as pink solid (0.18 g, 60%). MS (ESI): mass calcd. for C$_{11}$H$_{10}$N$_2$O$_3$S$_2$, 342.0; m/z found, 343.0 [M+H]$^+$. $^1$H NMR (400 MHz, CDCl$_3$): 8.58 (dd, J=4.8, 1.6, 1H), 8.12-8.00 (m, 3H), 7.92 (d, J=8.8, 1H), 7.46 (dd, J=8.8, 2.2, 1H), 7.24-7.18 (m, 1H), 3.96 (s, 3H).

[6-(Thiazolo[4,5-b]pyridin-2-yloxy)-benzo[b]thiophen-2-yl]-methanol. To a cooled (0° C.) solution of 6-(thiazolo[4,5-b]pyridin-2-yloxy)-benzo[b]thiophene-2-carboxylic acid methyl ester (0.18 g, 0.5 mmol) in DCM (5 mL) was added LAH (2 M in THF, 0.3 mL, 0.3 g, 0.5 mmol) and the reaction mixture was stirred (0° C., 1 h). The reaction mixture was treated with saturated aqueous Rochelle's salt (2 mL) and partitioned with EtOAc (15 mL). The organic layer was separated and the aqueous layer was extracted with EtOAc (2×15 mL). The organic layer was dried, filtered and concentrated in vacuo to provide the title compound as an orange solid (0.13 mg, 82%). MS (ESI): mass calcd. for C$_{15}$H$_{10}$O$_2$S$_2$, 314.0; m/z found, 315.0 [M+H]$^+$. $^1$H NMR (400 MHz, CDCl$_3$): 8.57 (dd, J=4.8, 1.7, 1H), 8.02 (dd, J=7.9, 1.6, 1H), 7.95 (d, J=2.2, 1H), 7.76 (d, J=8.7, 1H), 7.38 (dd, J=8.6, 2.3, 1H), 7.21 (dd, J=7.9, 4.9, 2H), 4.94 (s, 2H), 2.14 (s, 1H).

2-(2-Chloromethyl-benzo[b]thiophen-6-yloxy)-thiazolo[4,5-b]pyridine. To a cooled (0° C.) solution of [6-(thiazolo[4,5-b]pyridin-2-yloxy)-benzo[b]thiophen-2-yl]-methanol (0.13 g, 0.4 mmol) in DCM (5 mL) was added thionyl chloride (30 μL, 49 mg, 0.4 mmol) and the reaction mixture was stirred (0° C., 3 h). The reaction mixture was partitioned between DCM (20 mL) and saturated NaHCO$_3$ (10 mL). The organic layer was separated and the aqueous layer was extracted with DCM (2×20 mL). The organic layer was dried, filtered and concentrated in vacuo to provide the title compound as a yellow solid (0.11 g, 77%). MS (ESI): mass calcd. for C$_{15}$H$_9$ClN$_2$OS$_2$, 332.0; m/z found, 333.0 [M+H]$^+$. $^1$H NMR (400 MHz, CDCl$_3$): 8.57 (dd, J=4.8, 1.6, 1H), 8.07-7.91 (m, 2H), 7.77 (d, J=8.7, 1H), 7.40 (dd, J=8.7, 2.2, 1H), 7.31 (d, J=0.4, 1H), 7.25-7.14 (m, 1H), 4.86 (s, 2H).

Intermediate 56: 2-(3-Chloromethyl-benzofuran-6-yloxy)-thiazolo[4,5-b]pyridine

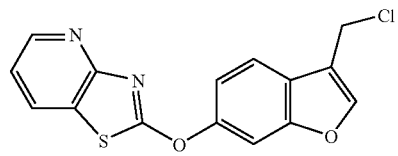 [SMILES: ClCc1coc2cc(Oc3nc4ncccc4s3)ccc12]

6-(tert-Butyl-dimethyl-silanyloxy)-benzofuran-3-one. To a solution of tert-butyl-chloro-dimethyl-silane (12.6 g, 83.9 mmol) in DMF (120 mL) was added DIEA (18.4 g, 24.9 mL, 142.7 mmol) and the mixture was stirred (rt, 0.5 h). The reaction mixture was treated with 6-hydroxy-benzofuran-3-one (12.0 g, 79.9 mmol) and stirred (rt, 0.25 h). The reaction mixture was treated with water (100 mL) to form a solid. The solid was filtered to afford the title compound as a yellow solid (20.4 g, 98%). MS (ESI): mass calcd. for $C_{14}H_{20}O_3Si$, 264.1; m/z found, 265.0 [M+H]$^+$. $^1$H NMR (400 MHz, CDCl$_3$): 7.55 (d, J=8.4, 1H), 6.57 (dd, J=8.5, 2.0, 1H), 6.51 (d, J=1.9, 1H), 4.60 (s, 2H), 0.99 (s, 9H), 0.26 (s, 6H).

Trifluoro-methanesulfonic acid 6-(tert-butyl-dimethyl-silanyloxy)-benzofuran-3-yl ester. To a cooled (0° C.) solution of 6-(tert-butyl-dimethyl-silanyloxy)-benzofuran-3-one (20.4 g, 77.0 mmol) in DCM (385 mL) was added DIEA (18.4 g, 24.9 mL, 142.7 mmol) followed by triflic anhydride (23.9 g, 84.7 mmol) and the mixture was stirred (0° C., 1 h). The reaction mixture was partitioned between EtOAc (250 mL) and water (150 mL). The organic layer was separated, dried, filtered and concentrated in vacuo. The resulting residue was purified by silica gel flash chromatography using EtOAc: hexanes (0-30%) to provide the title compound as a colorless liquid (23.5 g, 77%). MS (ESI): mass calcd. for $C_{15}H_{19}F_3O_5SSi$, 396.07; m/z found, 396.9 [M+H]$^+$. $^1$H NMR (400 MHz, CDCl$_3$): 7.71 (s, 1H), 7.42 (d, J=8.5, 1H), 6.95 (d, J=1.9, 1H), 6.89 (dd, J=8.5, 2.0, 1H), 1.00 (s, J=3.0, 9H), 0.23 (s, 6H).

Preparation of 6-(tert-Butyl-dimethyl-silanyloxy)-benzofuran-3-carboxylic acid methyl ester. To a solution of trifluoro-methanesulfonic acid 6-(tert-butyl-dimethyl-silanyloxy)-benzofuran-3-yl ester (2.4 g, 6.1 mmol) in DMSO (20 mL) and DCE (7 mL) was added TEA (1.2 g, 1.7 mL, 6.1 mmol) and the resulting solution was purged with N$_2$ (g) (20 min). The reaction mixture was treated with Pd(OAc)$_2$ (81.5 mg, 0.36 mmol) and dppp (149.8 mg, 0.36 mmol) and purged with N$_2$ (g). Degassed MeOH (3.0 mL) was added the reaction mixture was purged with a stream of CO (g) and stirred (70° C., 2 h). The reaction mixture was cooled (rt) filtered through Celite® and washed with EtOAc (500 mL). The filtrate was washed with brine (3×200 mL), dried, filtered and concentrated in vacuo. The resulting residue was purified by silica gel flash chromatography using EtOAc:hexanes (0-40%) to provide the title compound as clear oil (0.85 g, 46%). MS (ESI): mass calcd. for $C_{16}H_{22}O_4Si$, 306.13; m/z found, 326.0 [M+H]$^+$. $^1$H NMR (400 MHz, CDCl$_3$): 8.15 (s, 1H), 7.86 (d, J=8.5, 1H), 6.99 (d, J=2.0, 1H), 6.89 (dd, J=8.5, 2.1, 1H), 3.92 (s, 3H), 1.00 (s, J=3.0, 9H), 0.22 (s, 6H).

6-Hydroxy-benzofuran-3-carboxylic acid methyl ester. To 6-(tert-butyl-dimethyl-silanyloxy)-benzofuran-3-carboxylic acid methyl ester (2.4 g, 7.7 mmol) was added 1% HCl in MeOH (70 mL) and the resulting solution was stirred (rt, 14 h). The reaction mixture was concentrated in vacuo. The resulting solid was dissolved in DCM (100 mL) and sat. NaHCO$_3$ (50 mL) was added. A solid formed and was filtered to afford the title compound as a white solid (1.4 g, 94%). MS (ESI): mass calcd. for $C_{10}H_8O_4$, 192.04; m/z found, 193.1 [M+H]$^+$. $^1$H NMR (400 MHz, CD$_3$OD): 8.24 (s, 1H), 7.77 (d, J=8.5, 1H), 6.94 (d, J=1.4, 1H), 6.86 (dd, J=8.5, 1.7, 1H), 3.90 (s, 3H).

6-(Thiazolo[4,5-b]pyridin-2-yloxy)-benzofuran-3-carboxylic acid methyl ester. To a solution of 6-hydroxy-benzofuran-3-carboxylic acid methyl ester (1.7 g, 8.8 mmol) in DMF (88 mL) was added Cs$_2$CO$_3$ (8.6 g, 1.8 mmol) followed by 2-chloro-thiazolo[4,5-b]pyridine hydrochloride (1.8 g, 8.8 mmol) and the reaction mixture was stirred (rt, 3 h). The reaction mixture was treated with water (50 mL) to form a solid. The solid was filtered to provide the title compound as a white solid (2.5 g, 87%). MS (ESI): mass calcd. for $C_{16}H_{10}N_2O_4S$, 326.0; m/z found, 327.0 [M+H]$^+$. $^1$H NMR (400 MHz, CDCl$_3$): 8.57 (dd, J=4.8, 1.6, 1H), 8.30 (s, 1H), 8.11 (d, J=8.6, 1H), 8.03 (dd, J=7.9, 1.6, 1H), 7.75 (d, J=2.1, 1H), 7.41 (dd, J=8.6, 2.1, 1H), 7.22 (dd, J=7.9, 4.8, 1H), 3.97 (s, 3H).

[6-(Thiazolo[4,5-b]pyridin-2-yloxy)-benzofuran-3-yl]-methanol. To a cooled (0° C.) solution of 6-(thiazolo[4,5-b]pyridin-2-yloxy)-benzofuran-2-carboxylic acid methyl ester (6.0 g, 18.3 mmol) in DCM (183 mL) was added DIBALH (1 M in THF, 54.8 mL, 54.8 g, 54.8 mmol) and the reaction mixture was stirred (0° C., 1 h). The reaction mixture was treated with saturated aqueous Rochelle's salt (100 mL) and partitioned with DCM (50 mL). The organic layer was separated and the aqueous layer was extracted with DCM (2×100 mL). The organic layer was dried, filtered and concentrated in vacuo to provide the title compound as yellow solid (4.9 g, 90%). MS (ESI): mass calcd. for $C_{16}H_{10}N_2O_3S$, 298.04; m/z found, 299.0 [M+H]$^+$. $^1$H NMR (500 MHz, DMSO-d$_6$): 8.53 (dd, J=4.8, 1.7, 1H), 8.40 (dd, J=8.0, 1.7, 1H), 8.00 (s, 1H), 7.86 (d, J=2.1, 1H), 7.84 (s, 1H), 7.45-7.37 (m, 1H), 7.38-7.31 (m, 1H), 5.25 (t, J=5.5, 1H), 4.67 (dd, J=5.5, 0.8, 2H).

2-(3-Chloromethyl-benzofuran-6-yloxy)-thiazolo[4,5-b]pyridine. To a solution of [6-(thiazolo[4,5-b]pyridin-2-yloxy)-benzofuran-3-yl]-methanol (1.0 g, 3.4 mmol) in DCM (34 mL) was added SOCl$_2$ (0.49 mL, 0.83 g, 7.0 mmol) and the reaction mixture was stirred (rt, 2 h). The reaction mixture was filtered to afford the hydrochloride salt of the title compound as a yellow solid (1.0 g, 84%). MS (ESI): mass calcd. for $C_{15}H_9ClN_2O_2S$, 316.01; m/z found, 317.0 [M+H]$^+$. $^1$H NMR (400 MHz, CD$_3$OD): 8.93 (dd, J=8.1, 1.4, 1H), 8.69 (dd, J=5.9, 1.4, 1H), 8.02 (s, 1H), 7.90 (d, J=8.5, 1H), 7.81-7.75 (m, 2H), 7.45 (dd, J=8.5, 2.2, 1H), 4.90 (s, 2H).

Intermediate 57 was prepared using procedures analogous to those described for Intermediate 56.

Intermediate 57: 2-(3-Chloromethyl-benzofuran-6-yloxy)-benzothiazole

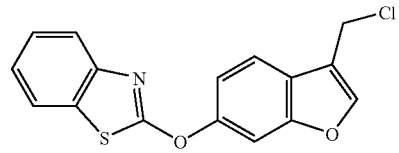 [SMILES: ClCc1coc2cc(Oc3nc4ccccc4s3)ccc12]

6-(Benzothiazol-2-yloxy)-benzofuran-3-carboxylic acid methyl ester. MS (ESI): mass calcd. for $C_{17}H_{11}NO_4S$, 325.0; m/z found, 326.0 [M+H]$^+$. $^1$H NMR (400 MHz, CDCl$_3$): 8.30 (s, 1H), 8.12 (d, J=8.6, 1H), 7.74 (d, J=7.5, 1H), 7.69 (d, J=6.7, 1H), 7.65 (d, J=1.9, 1H), 7.43-7.36 (m, 2H), 7.31-7.26 (m, 1H), 3.96 (s, 3H).

[6-(Benzothiazol-2-yloxy)-benzofuran-3-yl]-methanol. MS (ESI): mass calcd. for $C_{16}H_{11}NO_3S$, 297.1; m/z found, 297.9 [M+H]$^+$. $^1$H NMR (400 MHz, CDCl$_3$): 7.76-7.64 (m, 4H), 7.56 (d, J=2.0, 1H), 7.42-7.36 (m, 1H), 7.31-7.26 (m, 2H), 4.86 (dd, J=5.6, 0.7, 2H), 1.67 (t, J=5.7, 1H).

2-(3-Chloromethyl-benzofuran-6-yloxy)-benzothiazole. MS (ESI): mass calcd. for $C_{16}H_{10}ClNO_2S$, 315.0; m/z found, 315.9 [M+H]$^+$. $^1$H NMR (400 MHz, CDCl$_3$): 7.77-7.70 (m, 3H), 7.70-7.66 (m, 1H), 7.58 (d, J=2.0, 1H), 7.42-7.36 (m, 1H), 7.33 (dd, J=8.5, 2.1, 1H), 7.30-7.26 (m, 1H), 4.75 (s, J=0.8, 2H).

Intermediate 58: Acetic acid 3-chloromethyl-benzofuran-6-yl ester

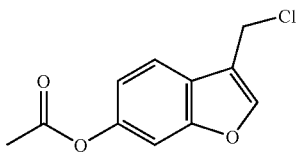

6-Methoxy-benzofuran-3-carboxylic acid ethyl ester. To a solution of 2-hydroxy-4-methoxybenzaldehyde (45 g, 295.76 mmol) in DCM (80 mL) was added catalytic $HBF_4$ etherate (4 mL, 29.4 mmol) and stirred (rt, 10 min). The reaction mixture was cooled (0° C.) and slowly treated drop wise with ethyl diazoacetate (86 ml, 704.7 mmol) over a 30 minute period while maintaining a controlled temperature (0° C. to 23° C.). The resulting mixture was stirred (rt, 1 h). The reaction mixture was concentrated in vacuo and the resulting dark oil was azeotroped with toluene (200 mL) via rotovap (60° C.). Using a Dean Stark trap, the crude mixture was refluxed (24 h). The reaction was cooled (rt) and concentrated in vacuo. The resulting dark oil was purified by flash column chromatography using EtOAc:hexanes (10%) to provide the title compound as a white solid (24.9 g, 38.2%). MS (ESI): mass calcd. for $C_{12}H_{12}O_4$, 220.2; m/z found, 221.2 [M+H]$^+$. $^1$H NMR (400 MHz, CDCl$_3$): 8.16 (s, 1H), 7.90 (d, J=8.6, 1H), 7.03 (d, J=2.2, 1H), 6.98 (dd, J=6.4, 2.3, 1H), 4.39 (q, J=7.2, 2H), 3.86 (s, 3H), 1.41 (t, J=7.2, 3H).

6-Hydroxy-benzofuran-3-carboxylic acid ethyl ester. To a cooled (0° C.) solution of 6-methoxy-benzofuran-3-carboxylic acid ethyl ester (90.0 g, 408.67 mmol) in DCM (700 mL) was slowly added BBr$_3$ (159.0 g, 634.67 mmol) in DCM (200 mL) maintaining a controlled temperature (<5° C.). The resulting mixture was stirred (10° C., 6 h). The reaction mixture was slowly poured into ice/water with vigorous stirring followed by stirring in a temperature gradient (0° C.–rt, 18 h). The solids were filtered off and the filtrate was extracted with EtOAc (2×250 mL). The solids were dissolved (required heat) with the combined organic phase. The organic phase was washed with saturated NaHCO$_3$ (700 mL), H$_2$O (700 mL), dried, filtered and concentrated in vacuo to provide a yellow solid. The crude solid was suspended in EtOAc:hexane (20%), stirred (24 h) and filtered to provide the title compound as a solid (75.6 g). The filtrate was concentrated in vacuo and the resulting residue was purified by flash column chromatography using EtOAc:hexanes (20%) to provide the title compound (2.4 g) as a white solid (93% combined yield). MS (ESI): mass calcd. for $C_{11}H_{10}O_4$, 206.2; m/z found, 207.1 [M+H]$^+$. $^1$H NMR (400 MHz, CDCl$_3$): 8.15 (s, 1H), 7.88 (d, J=8.5, 1H), 7.01 (s, 1H), 6.90 (dd, J=8.5, 2.3, 1H), 5.05 (s, 1H), 4.4 (q, J=7.1, 2H) 1.42 (t, J=7.2, 3H).

3-Hydroxymethyl-benzofuran-6-ol. To a cooled (0° C.) solution of 6-hydroxy-benzofuran-3-carboxylic acid ethyl ester (5.85 g, 28.4 mmol) in THF (250 mL) was added DIBALH as a solution in THF (100 mL, 100 mmol) and the reaction mixture was allowed to warm (rt, 1 h). The reaction was cooled (−78° C.) and treated dropwise with Rochelles salt (120 mL). The resulting mixture was stirred (rt, o/n). The layers were separated and the aqueous layer was extracted with DCM (2×200 mL) and EtOAc (2×200 mL). The organic layers were combined, dried, filtered and concentrated in vacuo to provide the title compound as a white solid (4.72 g, 100%). $^1$H NMR (500 MHz, CD$_3$OD): 7.53 (s, 1H), 7.45 (d, J=8.4, 1H), 6.85 (d, J=2.1, 1H), 6.76 (dd, J=8.4, 2.1, 1H), 4.70 (s, 2H).

Acetic acid 3-chloromethyl-benzofuran-6-yl ester. To a solution of 3-hydroxymethyl-benzofuran-6-ol (4.72 g, 28.6 mmol) in iPrOH (120 mL) was added NaOH (2.30 g, 57.5 mmol) in H$_2$O (25 mL) followed by acetic anhydride (5.4 mL, 57.5 mmol) and the reaction mixture was stirred (rt, 1 h). The reaction was concentrated in vacuo and the resulting residue was partitioned with saturated NaHCO$_3$ (100 mL) and EtOAc (100 mL). The layers were separated and the aqueous layer was extracted with EtOAc (3×100 mL). The organic layers were combined, dried, filtered and concentrated in vacuo. The residue was dissolved in DCM (150 mL) and treated with CCl$_4$ (3.2 mL, 32.9 mmol) and triphenylphosphine (8.64 g, 32.9 mmol) as a solution in CH$_2$Cl$_2$ (50 mL) and stirred (rt, 12 h). The reaction mixture was concentrated in vacuo and the resulting residue was purified by silica gel flash chromatography using DCM:hexanes (0-100%) to provide the title compound as a white solid (3.45 g, 65%). MS (ESI): mass calcd. for $O_{11}H_9Cl_3$, 224.0; m/z found, 225.0 [M+H]$^+$. $^1$H NMR (400 MHz, CDCl$_3$): 7.68-7.64 (m, 2H), 7.28 (d, J=2.0, 1H), 7.05 (dd, J=8.5, 2.0, 1H), 4.73 (d, J=0.8, 2H), 2.33 (s, 3H).

Intermediate 59: N-[1-(6-Hydroxy-benzofuran-3-ylmethyl)-piperidin-4-yl]-acetamide

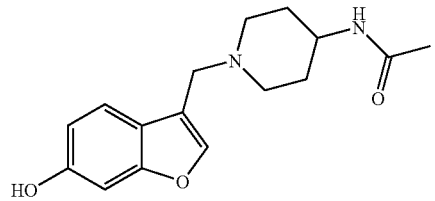 [SMILES: CC(=O)NC1CCN(Cc2coc3cc(O)ccc23)CC1]

To a solution of 4-acetamidopiperidine (429 mg, 3.00 mmol) and K$_2$CO$_3$ (1.14 g, 8.25 mmol) in MeCN (5 mL) was added a solution of acetic acid 3-chloromethyl-benzofuran-6-yl ester (450 mg, 2.0 mmol) in MeCN (5 mL). The reaction mixture was further diluted with MeCN (10 mL) and heated (50° C., 15 h). The solvent was removed in vacuo and the remaining residue was suspended in 5-10% CH$_3$OH in water and enough concentrated acetic acid was added until all solids were dissolved (pH ~7-8). The solution was slowly basified using 4 N KOH until precipitate was observed. The precipitate was filtered and rinsed with water. The pH of the mother liquor was further adjusted (4 N KOH and concentrated acetic acid) to produce additional precipitate, which was filtered and rinsed with water. This process of pH adjustment and solid filtration was repeated until no additional precipitate was observed. The precipitate was combined and dried in vacuo to provide the title compound as an off white solid (419 mg, 73%). MS (ESI): mass calcd. for $C_{16}H_{20}N_2O_3$, 288.15; m/z found, 289.1 [M+H]$^+$. $^1$H NMR (400 MHz, DMSO-d$_6$): 9.44 (s, 1H), 7.69 (d, J=7.6, 1H), 7.63 (s, 1H), 7.47 (d, J=8.4, 1H), 6.86 (d, J=2.0, 1H), 6.72 (dd, J=8.4, 2.1, 1H), 3.56-3.44 (m, 3H), 2.86-2.74 (m, 2H), 1.99 (t, J=10.6, 2H), 1.76 (s, 3H), 1.74-1.62 (m, 2H), 1.43-1.27 (m, 2H).

Intermediates 60 to 63 were prepared using procedures analogous to those described for Intermediate 59.

Intermediate 60: 3-[4-(1-Hydroxy-1-methyl-ethyl)-piperidin-1-ylmethyl]-benzofuran-6-ol

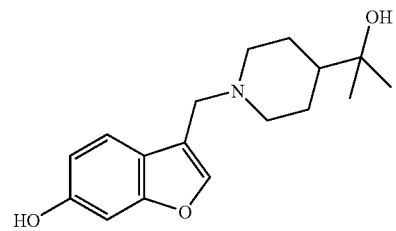 [SMILES: CC(C)(O)C1CCN(Cc2coc3cc(O)ccc23)CC1]

MS (ESI): mass calcd. for $C_{17}H_{23}NO_3$, 289.2; m/z found, 290.1 [M+H]$^+$. $^1$H NMR (500 MHz, CD$_3$OD): 7.52 (s, 1H), 7.46 (d, J=8.4, 1H), 6.85 (d, J=2.0, 1H), 6.75 (dd, J=8.4, 2.1, 1H), 3.60 (s, 2H), 3.06 (d, J=11.6, 2H), 2.03 (t, J=10.9, 2H), 1.75 (d, J=13.0, 2H), 1.39 (qd, J=12.5, 3.6, 2H), 1.30-1.24 (m, 1H), 1.12 (s, 6H).

Intermediate 61: 1-[1-(6-Hydroxy-benzofuran-3-ylmethyl)-piperidin-4-yl]-pyrrolidin-2-one

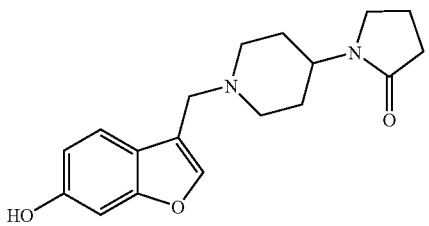 [SMILES: O=C1CCCN1C1CCN(Cc2coc3cc(O)ccc23)CC1]

MS (ESI): mass calcd. for $C_{18}H_{22}N_2O_3$, 314.16; m/z found, 315.0 [M+H]$^+$. $^1$H NMR (400 MHz, DMSO-$d_6$): 9.44 (s, 1H), 7.64 (s, 1H), 7.47 (d, J=8.4, 1H), 6.86 (d, J=2.0, 1H), 6.73 (dd, J=8.4, 2.1, 1H), 3.77-3.64 (m, 1H), 3.52 (s, 2H), 2.99-2.87 (m, 2H), 2.19 (t, J=8.1, 2H), 2.05-1.94 (m, 2H), 1.94-1.82 (m, 2H), 1.71-1.55 (m, 2H), 1.53-1.44 (m, 2H). The remaining protons were not detected and are believed to be hidden in the solvent peak.

Intermediate 62: meso-endo-N-[8-(6-Hydroxy-benzofuran-3-ylmethyl)-8-aza-bicyclo[3.2.1]oct-3-yl]-acetamide trifluoroacetate

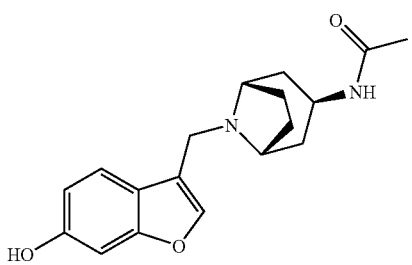 [SMILES: CC(=O)N[C@H]1C[C@H]2CC[C@@H](C1)N2Cc1coc2cc(O)ccc12]

MS (ESI): mass calcd. for $C_{18}H_{22}N_2O_3$, 314.2; m/z found, 315.0 [M+H]$^+$. $^1$H NMR (400 MHz, CD$_3$OD): 7.91 (s, 1H), 7.58 (d, J=8.5, 1H), 6.96 (d, J=1.9, 1H), 6.88 (dd, J=8.5, 2.1, 1H), 4.34 (s, 2H), 4.04 (s, 2H), 3.92 (t, J=6.4, 1H), 2.47 (dd, J=30.0, 10.4, 4H), 2.32 (d, J=16.7, 2H), 2.16 (d, J=16.3, 2H), 1.98 (s, 3H).

Intermediate 63: (1R,4R)-5-(6-Hydroxy-benzofuran-3-ylmethyl)-2,5-diaza-bicyclo[2.2.1]heptane-2-carboxylic acid amide trifluoroacetate

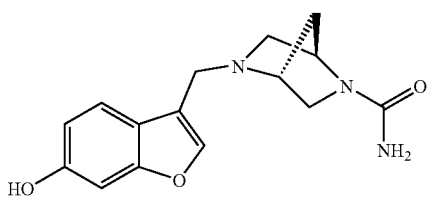 [SMILES: NC(=O)N1C[C@H]2C[C@@H]1CN2Cc1coc2cc(O)ccc12]

MS (ESI): mass calcd. for $C_{15}H_{17}N_3O_3$, 287.1; m/z found, 288.0 [M+H]$^+$. $^1$H NMR (500 MHz, CD$_3$OD): 7.91 (s, 1H), 7.59 (d, J=8.5, 1H), 6.95 (d, J=1.8, 1H), 6.87 (dd, J=8.5, 1.9, 1H), 4.67 (s, 1H), 4.61 (d, J=13.8, 1H), 4.51 (d, J=17.5, 1H), 3.62 (s, 2H), 3.57 (s, J=20.5, 2H), 3.45 (s, 1H), 2.40 (s, 1H), 2.20 (s, J=11.3, 1H).

Intermediate 64: (1S,4S)-1-[5-(6-Hydroxy-benzofuran-3-ylmethyl)-2,5-diaza-bicyclo[2.2.1]hept-2-yl]-ethanone

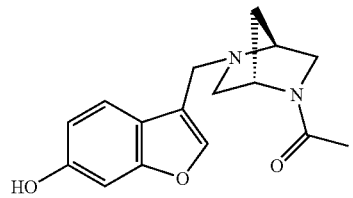 [SMILES: CC(=O)N1C[C@@H]2C[C@H]1CN2Cc1coc2cc(O)ccc12]

To a solution of (1S,4S)-1-(2,5-diaza-bicyclo[2.2.1]hept-2-yl)-ethanone hydrochloride (330 mg, 2.35 mmol) and K$_2$CO$_3$ (0.831 g, 6.01 mmol) in MeCN (20 mL) was added acetic acid 3-chloromethyl-benzofuran-6-yl ester (450 mg, 2.00 mmol) and the reaction mixture was heated (50° C., 20 h). The solvent was removed in vacuo and the remaining residue was dissolved in water (10 mL) and 2-3 mL of 4 M KOH was slowly added to reach pH 13-14. The dark green solution was stirred (10 min) and treated with concentrated acetic acid until the solution reached pH 10. The aqueous mixture was extracted with 20% IPA/DCM (4×30 mL). The organic layer was dried, filtered and concentrated in vacuo to provide the title compound as a gummy yellow solid (540 mg, 94%). MS (ESI): mass calcd. for $C_{16}H_{18}N_2O_3$, 286.1; m/z found, 287.1 [M+H]$^+$. $^1$H NMR (500 MHz, CD$_3$OD): 7.54-7.51 (m, 1H), 7.48 (dd, J=8.4, 2.5, 1H), 6.84 (t, J=1.8, 1H), 6.75 (ddd, J=8.4, 2.9, 2.2, 1H), 4.66 (s, 0.5H), 4.44 (s, 0.5H), 3.89-3.75 (m, 2H), 3.69-3.58 (m, 2H), 3.40 (dd, J=9.8, 2.3, 0.5H), 3.23 (dd, J=11.4, 2.0, 0.5H), 2.96 (dd, J=10.0, 2.2, 0.5H), 2.88 (dd, J=9.9, 2.2, 0.5H), 2.73 (dd, J=9.4, 7.0, 1H), 2.09 (s, 1.5H), 2.03-1.92 (m, 2.5H), 1.80 (d, J=10.1, 0.5H), 1.71 (d, J=10.1, 0.5H).

Intermediate 65: (2S,4S,5S)—N-(2-Aza-bicyclo[2.2.1]hept-5-yl)-acetamide hydrochloride

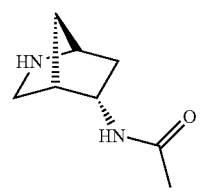

To a solution of (2S,4S,5S)-5-amino-2-aza-bicyclo[2.2.1] heptane-2-carboxylic acid tert-butyl ester (0.29 g, 1.4 mmol) in DCM (8 mL) was added acetic anhydride (0.14 mL, 1.5 mmol, 1.1 equiv.) and the reaction mixture was stirred (rt, 1 h). The reaction mixture was concentrated in vacuo. The resulting clear oil was dissolved in DCM (15 mL) and treated with HCl (4 M in dioxane, 3 mL, 7.9 equiv.) and the solution was stirred (rt, 1.5 h). The reaction mixture was concentrated in vacuo to provide the desired product as a tan solid (0.30 g, 104%). [Note: the mass recovery of 104% was attributed to additional HCl that could not be removed by standard evapo-

Intermediate 66:
1-(3,9-Diaza-spiro[5.5]undec-3-yl)-ethanone hydrochloride

To a solution of 3,9-diaza-spiro[5.5]undecane-3-carboxylic acid tert-butyl ester (400 mg, 1.57 mmol) in DCM (16 mL) was added acetic anhydride (177 μL, 1.88 mmol) and triethylamine (656 μL, 4.71 mmol) and the mixture was stirred (rt, 16 h). The reaction mixture was diluted with DCM (16 mL), washed with water (3×10 mL) and brine (1×10 mL). The organic layer was dried, filtered and concentrated in vacuo to provide the 9-acetyl-3,9-diaza-spiro[5.5]undecane-3-carboxylic acid tert-butyl ester (466 mg, 100%). This intermediate was dissolved in DCM (4 mL), treated with HCl (4 M in dioxane, 4 mL) and stirred (rt, 16 h). The dispersion was concentrated in vacuo to provide the title compound as a white powder (365 mg, 100%). MS (ESI): mass calcd. for $C_{11}H_{20}N_2O$, 196.16; m/z found, 197.1 $[M+H]^+$. $^1H$ NMR (400 MHz, MeOD): 3.63-3.51 (m, 4H), 3.23-3.17 (m, 4H), 2.13 (s, 3H), 1.82-1.73 (m, 4H), 1.67-1.53 (m, 4H).

Intermediate 67:
1-(2,7-Diaza-spiro[4.5]dec-7-yl)ethanone hydrochloride

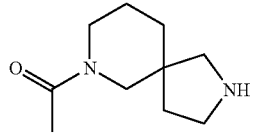

To a solution of 2,7-diaza-spiro[4.5]decane-2-carboxylic acid tert-butyl ester (140 mg, 0.58 mmol) in DCM (5.8 mL) was added acetic anhydride (82 μL, 0.87 mmol) and triethylamine (244 μL, 1.75 mmol) and the reaction mixture was stirred (rt, 16 h). The reaction mixture was diluted with DCM (6 mL), washed with water (3×4 mL) and brine (1×4 mL). The organic layer was dried, filtered and concentrated in vacuo to provide 7-acetyl-2,7-diaza-spiro[4.5]decane-2-carboxylic acid tert-butyl ester as a brown oil (164 mg, 100%). This intermediate was dissolved in DCM (0.75 mL), treated with HCl (4M in dioxane, 0.75 mL) and stirred (rt, 16 h). The dispersion was concentrated in vacuo to yield then desired product (128 mg, 100%). MS (ESI): mass calcd. for $C_{10}H_{18}N_2O$, 182.14; m/z found, 183.1 $[M+H]^+$.

Intermediate 68:
(S,S)-1-(2,5-Diaza-bicyclo[2.2.2]oct-2-yl)ethanone hydrochloride

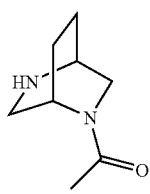

To a solution of (S,S)-2,5-diaza-bicyclo[2.2.2]octane-2-carboxylic acid tert-butyl ester hydrochloride (645 mg, 2.59 mmol) in DCM (26 mL) was added acetic anhydride (490 μL, 5.19 mmol) and triethylamine (1.08 mL, 7.77 mmol) and the mixture was stirred (rt, 16 h). The reaction mixture was washed with water (3×8 mL) and brine (1×8 mL). The organic layer was dried, filtered and concentrated in vacuo to provide (S,S)-5-acetyl-2,5-diaza-bicyclo[2.2.2]octane-2-carboxylic acid tert-butyl ester (658 mg, 100%). This intermediate was dissolved in DCM (3.5 mL), treated with HCl (4 M in dioxane, 3.5 mL) and stirred (rt, 16 h). The dispersion was concentrated in vacuo to provide the title compound as a beige powder (494 mg, 100%). MS (ESI): mass calcd. for $C_8H_{14}N_2O$, 154.11; m/z found, 155.2 $[M+H]^+$. $^1H$ NMR (500 MHz, MeOD): 4.71 (s, 0.5H), 4.25 (s, 0.5H), 3.97 (dt, J=12.1, 2.8, 0.5H), 3.87 (d, J=2.6, 1H), 3.84-3.73 (m, 1H), 3.68 (m, 1H), 3.64 (dd, J=13.8, 1.6, 0.5H), 3.54 (m, 0.5H), 3.45 (m, 1.5H), 2.12 (m, 4.5H), 2.06-1.91 (m, 2.5H).

Intermediate 69: 6-(Thiazolo[4,5-b]pyridin-2-yloxy)-benzofuran-3-carboxylic acid formate

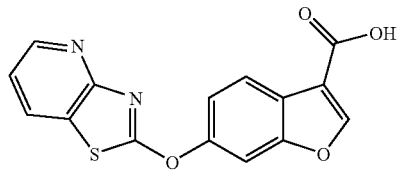 [SMILES: O=C(O)c1coc2cc(Oc3nc4ncccc4s3)ccc12]

To a solution of 6-(thiazolo[4,5-b]pyridin-2-yloxy)-benzofuran-3-carboxylic acid ethyl ester (200 mg, 0.59 mmol) in THF (6 mL) was added 4 N LiOH (0.15 mL, 0.59 mmol). Two additional aliquots of 4 N LiOH (each 0.30 mL) were added over 2 h. The mixture was stirred (rt, 24 h). The reaction mixture was partially concentrated in vacuo. The remaining aqueous solution was purified by reverse phase HPLC to provide the title compound as a white solid (92 mg, 44%). MS (ESI): mass calcd. for $C_{15}H_8N_2O_4S$, 312.02; m/z found, 312.9 $[M+H]^+$. $^1H$ NMR (400 MHz, DMSO-$d_6$): 8.78 (s, 1H), 8.53 (dd, J=4.8, 1.7, 1H), 8.43 (dd, J=8.0, 1.7, 1H), 8.09 (d, J=8.6, 1H), 8.04 (d, J=2.1, 1H), 7.56-7.50 (m, 1H), 7.41-7.32 (m, 1H). The remaining proton was not detected and is believed to be hidden in the solvent peak.

Intermediates 70 to 71 were prepared using methods analogous to those described for Intermediate 9.

Intermediate 70:
2-Chloro-6-methyl-thiazolo[4,5-b]pyridine

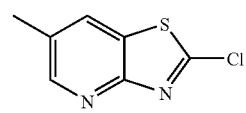

MS (ESI): mass calculated for $C_7H_5ClN_2S$, 183.99; m/z found, 184.95 $[M+H]^+$. $^1H$ NMR (400 MHz, DMSO-$d_6$): 8.61 (d, J=2.0, 1H), 8.46 (dd, J=2.1, 0.8, 1H), 2.50 (s, 3H).

Intermediate 71:
2-Chloro-5-methyl-thiazolo[4,5-b]pyridine

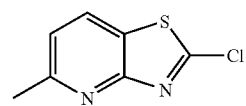

MS (ESI): mass calculated for $C_7H_5ClN_2S$, 183.99; m/z found, 185.00 $[M+H]^+$. $^1H$ NMR (500 MHz, DMSO-$d_6$): 8.46 (d, J=8.3, 1H), 7.42 (d, J=8.3, 1H), 2.61 (s, 3H).

Intermediate 72: [6-(Thiazolo[4,5-b]pyridin-2-yloxy)-furo[3,2-b]pyridin-2-yl]-methanol

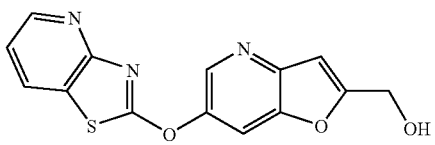 [SMILES: OCc1cc2ncc(Oc3nc4ncccc4s3)cc2o1]

To a mixture of 2-(hydroxymethyl)furo[3,2-b]pyridin-6-ol (200 mg, 1.21 mmol), 2-chloro-thiazolo-[4,5-b]pyridine hydrochloride (300 mg, 1.45 mmol) and Cs$_2$CO$_3$ (800 mg, 2.46 mmol) was added DMF (12 mL). The suspension was stirred (rt, 16 h) and then poured into ice-cold sat'd. aq. NH$_4$Cl. The resultant precipitate was filtered, rinsed with water and dried to provide the product as a beige solid (326 mg, 90%). MS (ESI): mass calcd. for C$_{14}$H$_9$N$_3$O$_3$S, 299.04; m/z found, 300.0 [M+H]$^+$. $^1$H NMR (600 MHz, CD$_3$OD): 8.63 (d, J=2.3, 1H), 8.49 (dd, J=4.9, 1.6, 1H), 8.36 (dd, J=8.0, 1.6, 1H), 8.23 (dd, J=2.3, 0.9, 1H), 7.37 (dd, J=8.0, 4.9, 1H), 6.95 (s, 1H), 4.76 (s, 2H).

Intermediate 73: 2-(2-Chloromethyl-furo[3,2-b]pyridin-6-yloxy)-thiazolo[4,5-b]pyridine

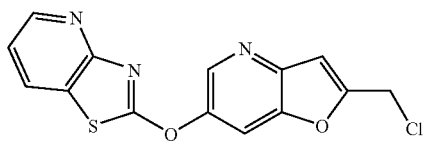 [SMILES: ClCc1cc2ncc(Oc3nc4ncccc4s3)cc2o1]

To a suspension of [6-(thiazolo[4,5-b]pyridin-2-yloxy)-furo[3,2-b]pyridin-2-yl]-methanol (50 mg, 0.17 mmol) in DCM (1.6 mL) was added thionyl chloride (0.020 mL, 0.25 mmol). After 5 min, more thionyl chloride (0.020 mL, 0.25 mmol) was added to the suspension. After 2 h, additional thionyl chloride (0.020 mL, 0.25 mmol) was added. The solution was stirred (rt, 16 h) and concentrated to remove all volatiles to provide the product as a beige solid (53 mg, 99%). MS (ESI): mass calcd. for C$_{14}$H$_8$ClN$_3$O$_2$S, 317.00; m/z found, 317.9 [M+H]$^+$.

Intermediate 74: 2-(3-Azidomethyl-benzofuran-6-yloxy)-thiazolo[4,5-b]pyridine

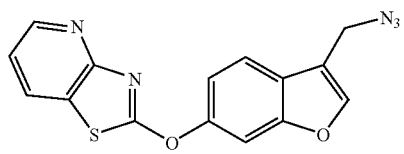 [SMILES: [N-]=[N+]=NCc1coc2cc(Oc3nc4ncccc4s3)ccc12]

To a solution of 2-(3-chloromethyl-benzofuran-6-yloxy)-thiazolo[4,5-b]pyridine (2.7 g, 8.5 mmol) in DMF (42 mL) at 0° C. was added sodium azide (0.61 g, 9.3 mmol). The mixture was stirred at (rt, 3 h), partitioned between ethyl acetate and brine, dried, filtered and concentrated. Upon addition of ethyl acetate and hexanes, precipitate was formed and filtered. Concentration and purification by silica gel flash chromatography using ethyl acetate/hexanes provided a solid that was combined with the previously filtered precipitate to provide the title compound (1.8 g, 65%). MS (ESI): mass calcd. for C$_{15}$H$_9$N$_5$O$_2$S, 323.05; m/z found, 324.0 [M+H]$^+$. $^1$H NMR (400 MHz, CDCl$_3$): 8.57 (dd, J=4.8, 1.6, 1H), 8.09-7.95 (m, 1H), 7.74-7.64 (m, 3H), 7.36 (dd, J=8.5, 2.1, 1H), 7.22 (dd, J=7.9, 4.8, 1H), 4.50 (s, 2H).

Intermediate 75: 2 [6-(Thiazolo[4,5-b]pyridin-2-yloxy)-benzofuran-3-ylmethyl]-carbamic acid tert-butyl ester

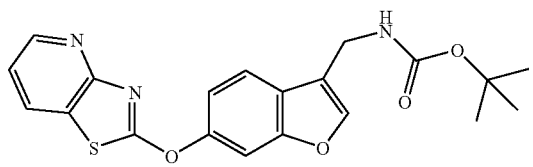 [SMILES: CC(C)(C)OC(=O)NCc1coc2cc(Oc3nc4ncccc4s3)ccc12]

To a solution of 2-(3-azidomethyl-benzofuran-6-yloxy)-thiazolo[4,5-b]pyridine (1.8 g, 5.5 mmol) and triphenylphosphine (1.6 g, 6.1 mmol) in THF (55 mL) was added water (0.3 mL). The mixture was stirred (55° C., 3 h). Incomplete reaction as monitored by TLC led to the addition of more triphenylphosphine (80 mg). After 30 min at 55° C., the reaction was complete and was cooled to rt. To this mixture was added di-tert-butyl dicarbonate (1.2 g, 5.5 mmol). The reaction mixture was stirred (rt, 3 h), then filtered to remove triphenylphosphine oxide. The solution was diluted with ethyl acetate, washed with brine, dried, and concentrated. Purification by silica gel flash chromatography (ethyl acetate/hexanes) led to the title compound as a colorless foam (1.2 g, 52%). MS (ESI): mass calcd. for C$_{20}$H$_{19}$N$_3$O$_4$S, 397.11; m/z found, 398.1 [M+H]$^+$.

Intermediate 76: C-[6-(Thiazolo[4,5-b]pyridin-2-yloxy)-benzofuran-3-yl]-methylamine hydrochloride

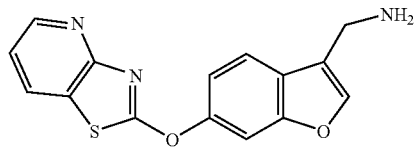 [SMILES: NCc1coc2cc(Oc3nc4ncccc4s3)ccc12]

To a solution of 2 [6-(thiazolo[4,5-b]pyridin-2-yloxy)-benzofuran-3-ylmethyl]-carbamic acid tert-butyl ester (0.10 g, 0.25 mmol) in DCM (1.2 mL) was added 2 M HCl in diethyl ether (0.38 mL). The reaction was stirred (rt, 16 h) before additional HCl (0.38 mL) was added. The reaction was stirred (rt, 24 h) and concentrated to provide the title compound as a white solid (98 mg, 130%). Additional mass is likely due to retained HCl and/or solvent. MS (ESI): mass calcd. for C$_{15}$H$_{11}$N$_3$O$_2$S, 297.06; m/z found, 298.1 [M+H]$^+$.

Intermediate 77: N-Cyclopropyl-N-piperidin-4-yl-acetamide hydrochloride

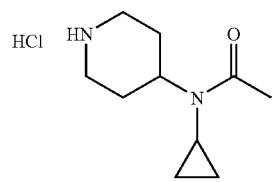

4-(Acetyl-cyclopropyl-amino)-piperidine-1-carboxylic acid tert-butyl ester. To a solution of 4-cyclopropylamino-piperidine-1-carboxylic acid tert-butyl ester (1.0 g, 4.2 mmol)

in DCM (22 mL) was added DIEA (0.8 mL, 4.6 mmol) and acetic anhydride (0.42 mL, 4.4 mmol). The mixture was stirred (rt, 16 h). After washing the solution with 1 N NaOH and brine, the organic layer was dried and concentrated to an orange oil (1.15 g, 98%). MS (ESI): mass calcd. for $C_{15}H_{26}N_2O_3$, 282.19; m/z found, 283.2 [M+H]$^+$.

N-Cyclopropyl-N-piperidin-4-yl-acetamide hydrochloride. To a solution of 4-(acetyl-cyclopropyl-amino)-piperidine-1-carboxylic acid tert-butyl ester (0.50 g, 1.8 mmol) in DCM (9 mL) was added 2 M HCl in diethyl ether (4.5 mL). The reaction mixture was stirred (30° C., 16 h). The mixture was concentrated to an orange solid and used without additional purification. MS (ESI): mass calcd. for $C_{10}H_{18}N_2O$, 182.14; m/z found, 183.2 [M+H]$^+$. $^1$H NMR (500 MHz, CD$_3$OD): 4.07-3.95 (m, 1H), 3.48-3.40 (m, 2H), 3.11-2.98 (m, 2H), 2.77 (s, 1H), 2.49-2.36 (m, 2H), 2.22 (s, 3H), 1.97-1.89 (m, 2H), 1.00-0.94 (m, 2H), 0.90-0.82 (m, 2H).

Intermediate 78:
N-Isopropyl-N-piperidin-4-yl-acetamide hydrochloride

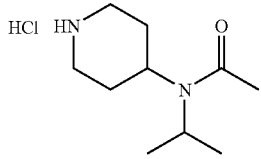

This compound was prepared using methods analogous to those described for Intermediate 77. MS (ESI): mass calcd. for $C_{10}H_{20}N_2O$, 184.16; m/z found, 185.1 [M+H]$^+$.

Intermediate 79:
N-Ethyl-N-piperidin-4-yl-acetamide hydrochloride

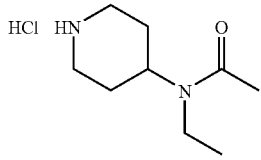

This compound was prepared using methods analogous to those described for Intermediate 77. MS (ESI): mass calculated for $C_9H_{18}N_2O$, 170.14; m/z found, 171.1 [M+H]$^+$. $^1$H NMR (500 MHz, CD$_3$OD): 4.39-4.18 (m, 1H), 3.78-3.72 (m, 0.4H), 3.71-3.64 (m, 0.6H), 3.61-3.56 (m, 0.25H), 3.56-3.40 (m, 3.75H), 3.33-3.30 (m, 0.4H), 3.27-3.18 (m, 0.6H), 3.15-3.06 (m, 1H), 2.36 (s, 1H), 2.33-2.11 (m, 3H), 2.09-2.02 (m, 1H), 1.98-1.91 (m, 1H), 1.27 (t, J=7.2, 1.75H), 1.19 (t, J=7.1, 1.25H).

Intermediate 80: meso-endo-1-(3-Amino-8-aza-bicyclo[3.2.1]oct-8-yl)-ethanone

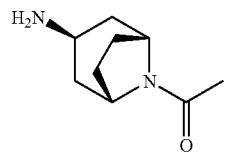

meso-endo-(8-Acetyl-8-aza-bicyclo[3.2.1]oct-3-yl)-carbamic acid tert-butyl ester. To a solution of meso-endo-(8-aza-bicyclo[3.2.1]oct-3-yl)-carbamic acid tert-butyl ester (300 mg, 1.3 mmol) in DCM (6.5 mL) was added DIEA (0.35 mL, 2.0 mmol) and acetic anhydride (0.135 mL, 1.4 mmol). The reaction mixture was stirred (rt, 16 h), washed with 1 N NaOH and extracted with DCM. The organic layer was dried and concentrated to a white solid (341 mg, 96%). MS (ESI): mass calcd. for $C_{14}H_{24}N_2O_3$, 268.18; m/z found, 269.1 [M+H]$^+$. $^1$H NMR (400 MHz, CDCl$_3$): 5.00-4.77 (m, 1H), 4.73-4.62 (m, 1H), 4.17-4.06 (m, 1H), 3.94-3.76 (m, 1H), 2.32-2.19 (m, 1H), 2.15-1.96 (m, 7H), 1.95-1.82 (m, 2H), 1.74-1.65 (m, 1H), 1.45 (s, 9H).

meso-endo-1-(3-Amino-8-aza-bicyclo[3.2.1]oct-8-yl) ethanone. To a solution of meso-endo-(8-acetyl-8-aza-bicyclo[3.2.1]oct-3-yl)-carbamic acid tert-butyl ester (341 mg, 1.3 mmol) in DCM (5 mL) was added 4 N HCl in dioxane (1 mL). The mixture was stirred (rt, 19 h) and concentrated. The residue was re-dissolved in DCM (20 mL). Silica gel-bound carbonate (3 g, loading level 0.71 mmol/g) was added to the mixture and gently agitated on an orbital shaker (rt, 16 h). Another portion of silica gel-bound carbonate (1 g) was added and the mixture agitated for another 6 h. The silica gel was filtered and eluted with DCM and with 1:9:90 2 N NH$_3$ in MeOH/MeOH/DCM. The filtrate was concentrated to provide the title compound as a yellow oil (229 mg, 108%). Additional mass is likely due to excess solvent. MS (ESI): mass calcd. for $C_9H_{16}N_2O$, 168.13; m/z found, 169.2 [M+H]$^+$. $^1$H NMR (400 MHz, CD$_3$OD): 4.61-4.47 (m, 1H), 4.28-4.18 (m, 1H), 3.20-3.05 (m, 1H), 2.26-2.00 (m, 8H), 2.00-1.85 (m, 1H), 1.72-1.52 (m, 2H).

Intermediate 81: meso-exo-1-(3-Amino-8-aza-bicyclo[3.2.1]oct-8-yl)-ethanone

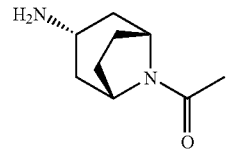

This compound was prepared using methods analogous to those described for Intermediate 80. MS (ESI): mass calcd. for $C_9H_{16}N_2O$, 168.13; m/z found, 169.1 [M+H]$^+$. $^1$H NMR (400 MHz, CD$_3$OD): 4.66-4.54 (m, 1H), 4.38-4.26 (m, 1H), 3.46-3.35 (m, 1H), 2.15-1.67 (m, 9H), 1.59-1.42 (m, 2H).

Intermediate 82:
meso-1-(3,8-Diaza-bicyclo[3.2.1]oct-8-yl)ethanone

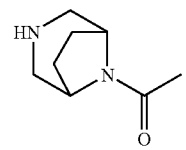

meso-1-(3-Benzyl-3,8-diaza-bicyclo[3.2.1]oct-8-yl)ethanone. To a solution of meso-3-benzyl-3,8-diaza-bicyclo [3.2.1]octane (1.0 g, 4.9 mmol) in DCM (24 mL) was added acetic anhydride (0.55 mL, 5.4 mmol). The reaction mixture was stirred (rt, 2 h), washed with 1 N NaOH, and extracted with DCM. The organic layer was dried and concentrated to a yellow waxy solid (1.1 g, 89%). MS (ESI): mass calcd. for $C_{15}H_{20}N_2O$, 244.16; m/z found, 245.1 [M+H]$^+$. $^1$H NMR (500 MHz, CDCl$_3$): 7.35-7.28 (m, 4H), 7.28-7.22 (m, 1H), 4.63 (d, J=7.0, 1H), 4.01 (d, J=6.4, 1H), 3.56-3.42 (m, 2H), 2.77-2.60 (m, 2H), 2.37-2.19 (m, 2H), 2.05 (s, 3H), 2.04-1.73 (m, 4H).

meso-1-(3,8-Diaza-bicyclo[3.2.1]oct-8-yl)ethanone. To a solution of 20% Pd(OH)$_2$/C (130 mg) in EtOH (5 mL), was added a solution of meso-1-(3-benzyl-3,8-diaza-bicyclo [3.2.1]oct-8-yl)-ethanone (1.1 g, 4.5 mmol) in EtOH (10 mL). The mixture was diluted with additional EtOH (10 mL) and stirred under 1 atm H$_2$ (g) (rt, 14 h). The mixture was filtered through a Celite pad, rinsed with MeOH and concentrated to provide the title compound as a pale yellow waxy solid (726 mg, 96%). MS (ESI): mass calcd. for C$_8$H$_{14}$N$_2$O, 154.11; m/z found, 155.1 [M+H]$^+$. $^1$H NMR (500 MHz, CD$_3$OD): 4.51-4.42 (m, 1H), 4.19-4.09 (m, 1H), 2.93-2.81 (m, 2H), 2.78-2.61 (m, 2H), 2.13-1.83 (m, 7H).

Intermediate 83:
1-(3,7-Diaza-bicyclo[3.3.1]non-3-yl)-ethanone

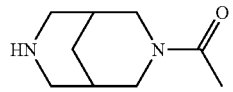

This compound was prepared using methods analogous to those described for Intermediate 82. MS (ESI): mass calculated for C$_9$H$_{16}$N$_2$O, 168.13; m/z found, 169.20 [M+H]$^+$. $^1$H NMR (500 MHz, CDCl$_3$): 4.58 (d, J=13.8, 1H), 3.87 (d, J=12.5, 1H), 3.46-3.40 (m, 1H), 3.14-3.08 (m, 2H), 3.08-3.02 (m, 1H), 2.97 (dd, J=13.3, 2.9, 2H), 2.13 (s, 3H), 2.10-1.98 (m, 1H), 1.97-1.90 (m, 1H), 1.87-1.80 (m, 1H), 1.80-1.69 (m, 2H).

Intermediate 84: 5-(Thiazolo[4,5-b]pyridin-2-yloxy)-benzofuran-2-carboxylic acid

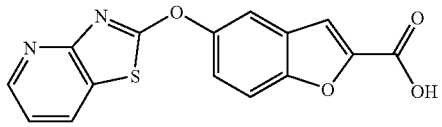 [SMILES: O=C(O)c1cc2cc(Oc3nc4ncccc4s3)ccc2o1]

5-Hydroxy-benzofuran-2-carboxylic acid methyl ester. To a solution of 4-(2-methoxy-propenyl)-furan-2-carboxylic acid (10.0 g, 52 mmol) in CH$_2$Cl$_2$ (520 mL) at –78° C. was added dropwise BBr$_3$ (24.6 mL, 260 mmol). The reaction mixture was allowed to warm up (rt, 4 h). The reaction mixture was cooled (0° C.) and treated with sat'd. aq. NH$_4$Cl (300 mL). The resulting mixture was filtered to give 7.9 g of orange solid. The crude solid was dissolved in MeOH (500 mL) and conc. HCl was added (2 mL). The resulting reaction mixture was heated (70° C., 10 h). The reaction mixture was cooled (rt), the volume was reduced 50%, sat'd. aq. NaHCO$_3$ (100 mL) was added and the solid was filtered. The filtrate was extracted with CH$_2$Cl$_2$ (3×200 mL), dried, concentrated, and combined with the filtered solid to provide the title compound as a yellow solid (6.5 g, 65%). MS (ESI): mass calcd. for C$_{10}$H$_8$O$_4$, 192.0; m/z found, 193.1 [M+H]$^+$. $^1$H NMR (400 MHz, DMSO-d$_6$): 7.61 (s, 1H), 7.51 (d, J=8.9, 1H), 7.06 (d, J=2.5, 1H), 6.98 (dd, J=8.9, 2.5, 1H), 3.94-3.82 (m, 3H), 3.25 (br s, 1H).

5-(Thiazolo[4,5-b]pyridin-2-yloxy)-benzofuran-2-carboxylic acid methyl ester. To a solution of 5-hydroxy-benzofuran-2-carboxylic acid methyl ester (1.5 g, 7.8 mmol) in DMF (78 mL) was added Cs$_2$CO$_3$ (7.6 g, 26 mmol) and 2-chloro-thiazolo[4,5-b]pyridine (1.6 g, 7.8 mmol). The reaction mixture was heated (50° C., 10 h), cooled (rt) and water was added (50 mL). The resulting solid was filtered to provide the title compound as a colorless solid (2.6 g, 100%). MS (ESI): mass calcd. for C$_{16}$H$_{10}$N$_2$O$_4$S, 326.0; m/z found, 327.0 [M+H]$^+$. $^1$H NMR (400 MHz, CDCl$_3$): 8.57 (dd, J=4.8, 1.6, 1H), 8.03 (dd, J=7.9, 1.6, 1H), 7.84 (d, J=2.4, 1H), 7.64 (d, J=9.0, 1H), 7.54 (d, J=0.9, 1H), 7.47 (dd, J=9.0, 2.5, 1H), 7.22 (dd, J=7.9, 4.8, 1H), 4.04-3.86 (m, 3H).

Thiazolo[4,5-b]pyridin-2-yloxy)-benzofuran-2-carboxylic acid. To a solution of 5-(thiazolo[4,5-b]pyridin-2-yloxy)-benzofuran-2-carboxylic acid methyl ester (0.5 g, 1.5 mmol) in IPA (15 mL) was added 2M KOH in water (0.8 mL, 15 mmol), and the reaction mixture was stirred (rt, 1 h). The pH was adjusted to 6 and the reaction mixture was extracted with CH$_2$Cl$_2$:IPA (10:1, 3×20 mL). The organic layers were combined, dried, and concentrated to provide the title compound as a colorless solid (0.5 g, 102%). MS (ESI): mass calcd. for O$_{16}$H$_8$N$_2$O$_4$S, 312.0; m/z found, 312.9 [M+H]$^+$. $^1$H NMR (400 MHz, DMSO-d$_6$): 8.52 (dd, J=4.8, 1.5, 1H), 8.41 (dd, J=8.0, 1.5, 1H), 7.91 (d, J=2.4, 1H), 7.85 (d, J=9.0, 1H), 7.63-7.55 (m, 2H), 7.38-7.31 (m, 1H).

Intermediate 85: 5-(Thiazolo[4,5-b]pyridin-2-yloxy)-benzofuran-2-carbonyl chloride hydrochloride

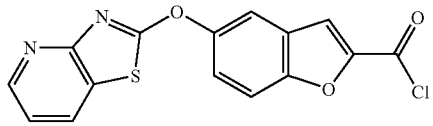 [SMILES: O=C(Cl)c1cc2cc(Oc3nc4ncccc4s3)ccc2o1]

A mixture of 5-(thiazolo[4,5-b]pyridin-2-yloxy)-benzofuran-2-carboxylic acid (326 mg, 1.04 mmol) and thionyl chloride (10 mL) was heated to reflux for 2 h. The crude mixture was concentrated, re-dissolved in CH$_2$Cl$_2$ and concentrated again to provide the product as a yellow solid (375 mg, 98%). $^1$H NMR (400 MHz, DMSO-d$_6$): 8.61-8.51 (m, 2H), 7.97 (d, J=2.5, 1H), 7.94-7.86 (m, 1H), 7.74 (s, 1H), 7.68-7.61 (m, 1H), 7.46-7.38 (m, 1H).

Intermediate 86: 6-(Thiazolo[4,5-b]pyridin-2-yloxy)-benzofuran-3-carbonyl chloride hydrochloride

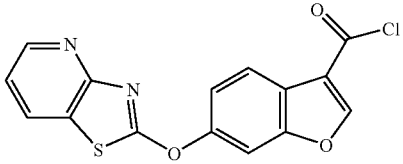 [SMILES: O=C(Cl)c1coc2cc(Oc3nc4ncccc4s3)ccc12]

This compound was prepared using methods analogous to those described for Intermediate 85. MS (ESI): mass calcd. for C$_{15}$H$_7$ClN$_2$O$_3$S, 329.99; m/z found, 330.9 [M+H]$^+$. $^1$H NMR (400 MHz, DMSO-d$_6$): 8.82 (s, 1H), 8.64-8.57 (m, 2H), 8.15-8.04 (m, 2H), 7.58-7.53 (m, 1H), 7.51-7.44 (m, 1H).

Examples 1 to 33 were prepared using methods analogous to those described for Example 139.

Example 1

2-(3-Pyrrolidin-1-ylmethyl-1H-indol-6-yloxy)-benzothiazole

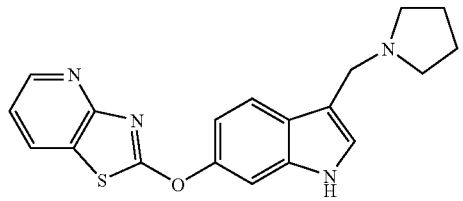 [SMILES: c1cnc2nc(Oc3ccc4c(CN5CCCC5)c[nH]c4c3)sc2c1]

MS (ESI): mass calcd. for $C_{20}H_{19}N_3OS$, 349.4; m/z found, 350.1 [M+H]$^+$. $^1$H NMR (500 MHz, CDCl$_3$): 8.52 (s, 1H), 7.75 (d, J=8.6, 2H), 7.65 (dd, J=8.0, 0.8, 1H), 7.39 (dt, J=7.8, 1.2, 1H), 7.32 (d, J=2.1, 1H), 7.28-7.25 (m, 1H), 7.18 (d, J=2.2, 1H), 7.10 (dd, J=8.6, 2.2, 1H), 3.85 (s, 2H), 2.64-2.61 (m, 4H), 1.84-1.79 (m, 4H).

Example 2

2-(3-Piperidin-1-ylmethyl-1H-indol-6-yloxy)-benzothiazole

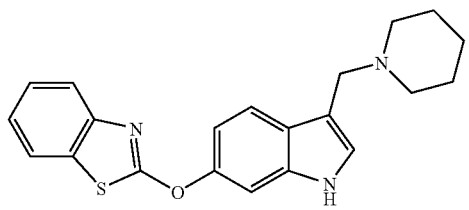

MS (ESI): mass calcd. for $C_{21}H_{21}N_3OS$, 363.4; m/z found, 364.1 [M+H]$^+$. $^1$H NMR (500 MHz, CDCl$_3$): 8.31 (s, 1H), 7.79 (d, J=8.6, 2H), 7.75 (d, J=8.2, 1H), 7.65 (d, J=8.2, 1H), 7.40 (dt, J=8.2, 1.2, 1H), 7.28-7.25 (m, 1H), 7.18 (d, J=2.2, 1H), 7.11 (dd, J=8.6, 2.2, 1H), 3.70 (s, 2H), 2.48 (br s, 4H), 1.63-1.58 (m, 4H), 1.48-1.42 (m, 2H).

Example 3

2-(3-Morpholin-4-ylmethyl-1H-indol-6-yloxy)-benzothiazole

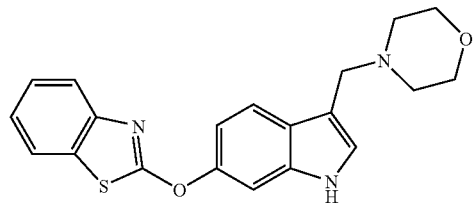 [SMILES: c1ccc2sc(Oc3ccc4c(CN5CCOCC5)c[nH]c4c3)nc2c1]

MS (ESI): mass calcd. for $C_{20}H_{19}N_3O_2S$, 365.4; m/z found, 366.1 [M+H]$^+$. $^1$H NMR (500 MHz, CDCl$_3$): 8.33 (s, 1H), 7.81 (d, J=8.6, 1H), 7.74 (d, J=8.1, 1H), 7.66 (d, J=8.1, 1H), 7.41-7.37 (m, 2H), 7.28-7.25 (m, 1H), 7.18 (d, J=2.2, 1H), 7.12 (dd, J=8.6, 2.2, 1H), 3.74 (t, J=4.6, 4H), 3.71 (s, 2H), 2.52 (br s, 4H).

Example 4

2-[3-(4-Methanesulfonyl-piperidin-1-ylmethyl)-1H-indol-6-yloxy]-benzothiazole

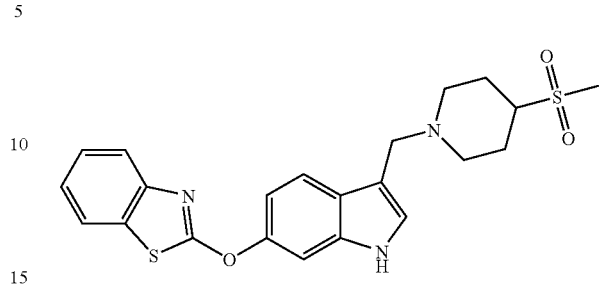

MS (ESI): mass calcd. for $C_{22}H_{23}N_3O_3S_2$, 441.5; m/z found, 442.1 [M+H]$^+$. $^1$H NMR (500 MHz, CDCl$_3$): 8.35 (br s, 1H), 7.75-7.72 (m, 2H), 7.65 (d, J=7.8, 1H), 7.38-7.35 (m, 2H), 7.28-7.24 (m, 1H), 7.14-7.09 (m, 2H), +3.72 (s, 2H), 3.18-3.14 (m, 2H), 2.84-2.80 (m, 1H), 2.82 (s, 3H), 2.14-2.09 (m, 2H), 2.05-2.00 (m, 2H), 1.90-1.86 (m, 2H).

Example 5

[6-(Benzothiazol-2-yloxy)-1H-indol-3-ylmethyl]-benzyl-methyl-amine

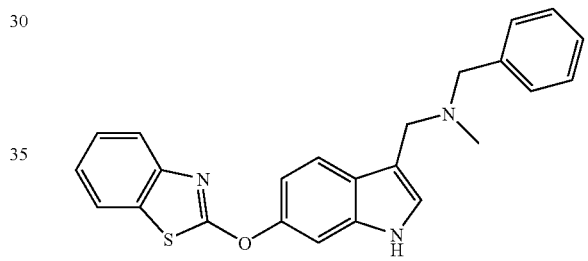

MS (ESI): mass calcd. for $C_{24}H_{21}N_3OS$, 399.5; m/z found, 400.1 [M+H]$^+$. $^1$H NMR (500 MHz, CDCl$_3$): 8.36 (br s, 1H), 7.78-7.44 (m, 2H), 7.65 (d, J=8.0, 1H), 7.41-7.30 (m, 6H), 7.28-7.25 (m, 2H), 7.16 (d, J=1.5, 1H), 7.12-7.10 (m, 1H), 3.72 (s, 2H), 3.58 (s, 2H), 2.24 (s, 3H).

Example 6

2-[3-(1,3-Dihydro-isoindol-2-ylmethyl)-1H-indol-6-yloxy]-benzothiazole

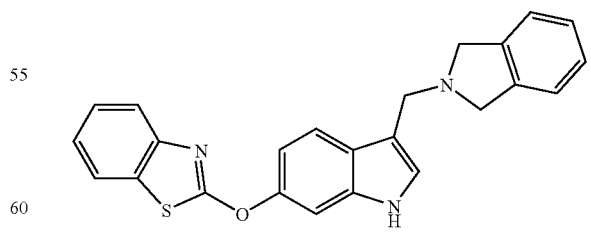

MS (ESI): mass calcd. for $C_{24}H_{19}N_3OS$, 397.5; m/z found, 398.1 [M+H]$^+$. $^1$H NMR (500 MHz, CDCl$_3$): 8.57 (br s, 1H), 7.82 (d, J=8.6, 1H), 7.76-7.75 (m, 1H), 7.67-7.65 (m, 1H), 7.41-7.38 (m, 1H), 7.31 (d, J=2.1, 1H), 7.28-7.25 (m, 1H), 7.21-7.18 (m, 5H), 7.11 (dd, J=8.6, 2.2, 1H), 4.11 (s, 2H), 4.01 (s, 4H).

Example 7

2-[6-(Benzothiazol-2-yloxy)-1H-indol-3-ylmethyl]-1,2,3,4-tetrahydro-isoquinoline

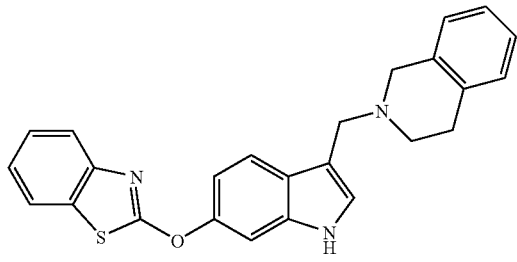 [SMILES: c1ccc2c(c1)CCN(Cc1c[nH]c3cc(Oc4nc5ccccc5s4)ccc13)C2]

MS (ESI): mass calcd. for $C_{25}H_{21}N_3OS$, 411.5; m/z found, 412.1 [M+H]$^+$. $^1$H NMR (500 MHz, CDCl$_3$): 8.28 (br s, 1H), 7.83 (d, J=8.6, 1H), 7.76 (d, J=8.1, 1H), 7.67-7.65 (m, 1H), 7.41-7.38 (m, 2H), 7.28-7.26 (m, 2H), 7.15-7.10 (m, 4H), 7.03-7.01 (m, 1H), 3.91 (s, 2H), 3.73-3.41 (m, 2H), 2.94-2.91 (m, 2H), 2.84-2.81 (s, 2H).

Example 8

2-[3-(4-Phenyl-piperidin-1-ylmethyl)-1H-indol-6-yloxy]-benzothiazole

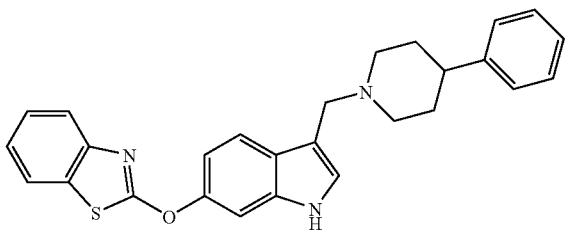 [SMILES: c1ccc(C2CCN(Cc3c[nH]c4cc(Oc5nc6ccccc6s5)ccc34)CC2)cc1]

MS (ESI): mass calcd. for $C_{27}H_{25}N_3OS$, 439.5; m/z found, 440.2 [M+H]$^+$. $^1$H NMR (500 MHz, CDCl$_3$): 8.35 (br s, 1H), 7.82 (d, J=8.6, 1H), 7.76 (d, J=8.2, 1H), 7.68-7.65 (m, 1H), 7.41-7.37 (m, 2H), 7.28-7.19 (m, 7H), 7.13 (dd, J=8.6, 2.1, 1H), 3.79 (s, 2H), 3.16-3.13 (m, 2H), 2.53-2.50 (m, 1H), 2.19-2.14 (m, 2H), 1.86-1.81 (m, 4H).

Example 9

2-(3-Pyrrolidin-1-ylmethyl-1H-indol-5-yloxy)-benzothiazole

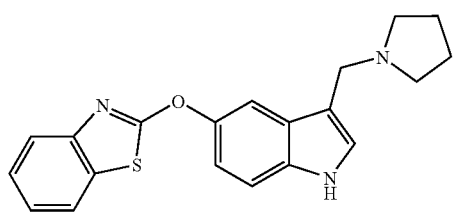 [SMILES: c1ccc2sc(Oc3ccc4[nH]cc(CN5CCCC5)c4c3)nc2c1]

MS (ESI): mass calcd. for $C_{20}H_{19}N_3OS$, 349.4; m/z found, 350.1 [M+H]$^+$. $^1$H NMR (500 MHz, CDCl$_3$): 8.33 (s, 1H), 7.76 (d, J=8.2, 1H), 7.71 (d, J=2.3, 1H), 7.64 (d, J=8.0, 1H), 7.41-7.38 (m, 2H), 7.28-7.24 (m, 2H), 7.18 (dd, J=8.7, 2.3, 1H), 3.82 (s, 2H), 2.60-2.57 (m, 4H), 1.80-1.78 (m, 4H).

Example 10

2-(3-Piperidin-1-ylmethyl-1H-indol-5-yloxy)-benzothiazole

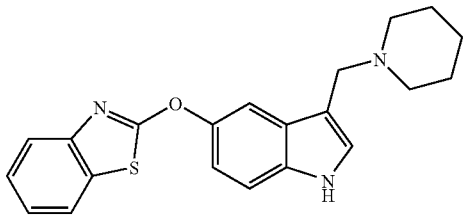 [SMILES: c1ccc2sc(Oc3ccc4[nH]cc(CN5CCCCC5)c4c3)nc2c1]

MS (ESI): mass calcd. for $C_{21}H_{21}N_3OS$, 363.4; m/z found, 364.1 [M+H]$^+$. $^1$H NMR (500 MHz, CDCl$_3$): 8.33 (s, 1H), 7.76 (d, J=8.1, 1H), 7.73 (d, J=2.3, 1H), 7.64 (d, J=7.4, 1H), 7.41-7.38 (m, 2H), 7.28-7.24 (m, 1H), 7.22 (d, J=2.2, 1H), 7.17 (dd, J=8.7, 2.3, 1H), 3.67 (s, 2H), 2.45 (br s, 4H), 1.59-1.55 (m, 4H), 1.46-1.40 (m, 2H).

Example 11

2-(3-Morpholin-4-ylmethyl-1H-indol-5-yloxy)-benzothiazole

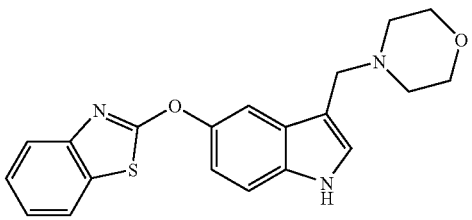 [SMILES: c1ccc2sc(Oc3ccc4[nH]cc(CN5CCOCC5)c4c3)nc2c1]

MS (ESI): mass calcd. for $C_{20}H_{19}N_3O_2S$, 365.4; m/z found, 366.1 [M+H]$^+$. $^1$H NMR (500 MHz, CDCl$_3$): 8.34 (s, 1H), 7.77-7.75 (m, 2H), 7.65 (d, J=7.2, 1H), 7.42-7.38 (m, 2H), 7.28-7.25 (m, 1H), 7.21 (d, J=8.7, 2.4, 1H), 3.71 (t, J=4.6, 4H), 3.69 (s, 2H), 2.50 (br s, 4H).

Example 12

(1S,4S)-2-[3-(2-Oxa-5-aza-bicyclo[2.2.1]hept-5-ylmethyl)-1H-indol-6-yloxy]-benzothiazole

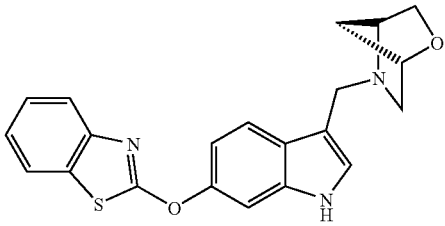

MS (ESI): mass calcd. for $C_{21}H_{19}N_3O_2S$, 377.4; m/z found, 378.1 [M+H]$^+$. $^1$H NMR (500 MHz, CDCl$_3$): 8.26 (br s, 1H), 7.80 (d, J=8.6, 1H), 7.75 (d, J=8.1, 1H), 7.66 (d, J=7.3, 1H), 7.41-7.38 (m, 1H), 7.37 (d, J=2.2, 1H), 7.28-7.25 (m, 1H), 7.19 (d, J=2.1, 1H), 7.12 (dd, J=8.6, 2.2, 1H), 4.45 (5, 1H), 4.16 (d, J=7.7, 1H), 3.99 (d, J=13.4, 1H), 3.92 (d, J=13.4, 1H), 3.67-3.65 (m, 1H), 3.56 (5, 1H), 2.95 (dd, J=10.3, 1.7, 1H), 2.69 (d, J=10.3, 1H), 1.94 (d, J=7.7, 1H), 1.75 (d, J=9.7, 1H).

Example 13 meso-endo-N-{8-[6-(Benzothiazol-2-yloxy)-1H-indol-3-ylmethyl]-8-aza-bicyclo[3.2.1]oct-3-yl}-acetamide

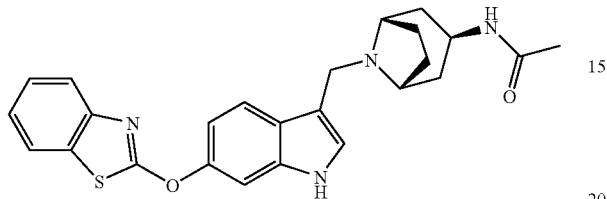

MS (ESI): mass calcd. for $C_{25}H_{26}N_4O_2S$, 446.5; m/z found, 447.2 [M+H]$^+$. $^1$H NMR (500 MHz, CDCl$_3$): 9.05 (br s, 1H), 7.78-7.72 (m, 2H), 7.62 (d, J=7.9, 1H), 7.38-7.35 (m, 1H), 7.29-7.22 (m, 2H), 7.12-7.06 (m, 2H), 5.96 (d, J=6.7, 1H), 4.12-4.07 (m, 1H), 3.67 (s, 2H), 2.28 (s, 2H), 2.22-2.16 (m, 4H), 1.98 (s, 3H), 1.78-1.75 (m, 2H), 1.61-1.58 (m, 2H).

Example 14 meso-endo-N-{8-[6-(4-Fluoro-benzothiazol-2-yloxy)-1H-indol-3-ylmethyl]-8-aza-bicyclo[3.2.1]oct-3-yl}-acetamide

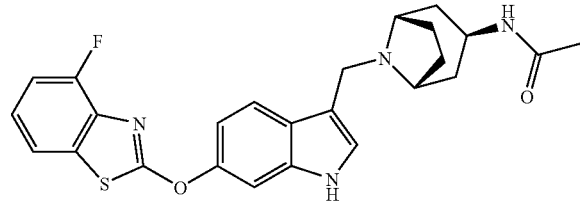 [SMILES: CC(=O)N[C@H]1C[C@H]2CC[C@@H](C1)N2Cc1c[nH]c2cc(Oc3nc4c(F)cccc4s3)ccc12]

MS (ESI): mass calcd. for $C_{25}H_{25}FN_4O_2S$, 464.5; m/z found, 465.2 [M+H]$^+$. $^1$H NMR (500 MHz, CDCl$_3$): 9.23 (br s, 1H), 7.75 (d, J=8.6, 1H), 7.37-7.33 (m, 2H), 7.19-7.16 (m, 2H), 7.11-7.02 (m, 2H), 5.97 (d, J=7.1, 1H), 4.12-4.07 (m, 1H), 3.67 (s, 2H), 2.28 (br s, 2H), 2.20-2.16 (m, 4H), 1.98 (s, 3H), 1.77-1.75 (m, 2H), 1.61-1.58 (m, 2H).

Example 15

2-(3-Piperidin-1-ylmethyl-1H-indol-6-yloxy)-benzooxazole

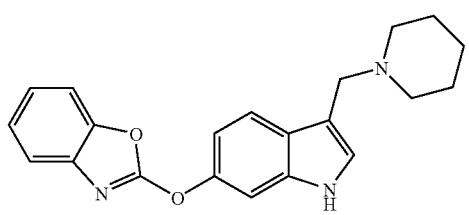 [SMILES: c1ccc2oc(Oc3ccc4c(CN5CCCCC5)c[nH]c4c3)nc2c1]

MS (ESI): mass calculated for $C_{21}H_{21}N_3O_2$, 347.1; m/z found, 348.2 [M+H]$^+$. $^1$H NMR (500 MHz, CD$_3$OD): 7.75 (d, J=8.7, 1H), 7.58-7.40 (m, 3H), 7.38-7.24 (m, 3H), 7.10 (dd, J=8.6, 2.2, 1H), 3.79 (s, 2H), 2.57 (s, 4H), 1.73-1.58 (m, 4H), 1.47 (s, 2H).

Example 16

2-(3-Piperidin-1-ylmethyl-1H-indol-6-yloxy)-thiazolo[4,5-b]pyridine

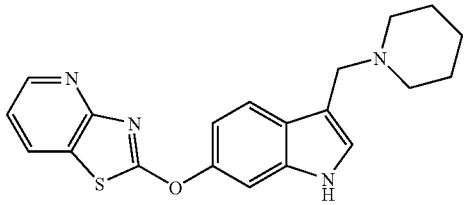

MS (ESI): mass calcd. for $C_{20}H_{20}N_4OS$, 364.1; m/z found, 365.1 [M+H]$^+$. $^1$H NMR (500 MHz, CD$_3$OD): 8.51-8.47 (m, 1H), 8.28-8.23 (m, 1H), 7.78 (d, J=8.6, 1H), 7.45 (d, J=2.2, 1H), 7.37 (5, 1H), 7.35-7.30 (m, 1H), 7.12-7.06 (m, 1H), 3.77 (5, 2H), 2.75-2.41 (m, 4H), 1.76-1.52 (m, 4H), 1.54-1.34 (m, 2H).

Example 17

1-[6-(Thiazolo[4,5-b]pyridin-2-yloxy)-1H-indol-3-ylmethyl]-piperidine-4-carboxylic acid amide

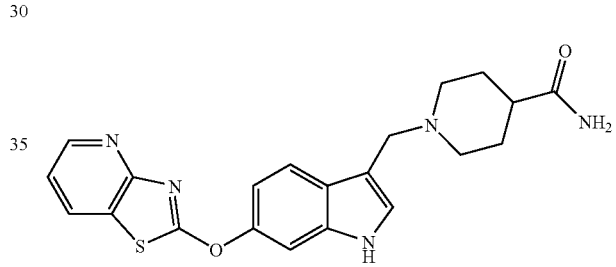

MS (ESI): mass calcd. for $C_{21}H_{21}N_5O_2S$, 407.1; m/z found, 408.1 [M+H]$^+$. $^1$H NMR (400 MHz, DMSO-d$_6$): 11.16 (5, 1H), 8.51 (dd, J=4.8, 1.7, 1H), 8.34 (dd, J=7.9, 1.7, 1H), 7.76 (d, J=8.6, 1H), 7.47 (d, J=2.2, 1H), 7.40-7.22 (m, 2H), 7.15 (5, 1H), 7.07 (dd, J=8.6, 2.2, 1H), 6.65 (5, 1H), 3.63 (5, 2H), 2.90 (d, J=11.3, 2H), 2.14-1.98 (m, 1H), 1.95-1.79 (m, 2H), 1.72-1.42 (m, 4H).

Example 18 meso-endo-N-{8-[6-(Thiazolo[4,5-b]pyridin-2-yloxy)-1H-indol-3-ylmethyl]-8-aza-bicyclo[3.2.1]oct-3-yl}-acetamide

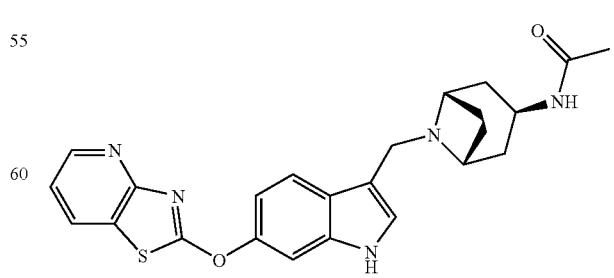

MS (ESI): mass calcd. for $C_{24}H_{25}N_5O_2S$, 447.2; m/z found, 448.1 [M+H]$^+$. $^1$H NMR (400 MHz, CDCl$_3$/CD$_3$OD, 10:1): 8.50-8.40 (m, 1H), 8.26-8.16 (m, 1H), 7.80 (d, J=8.6, 1H), 7.45-7.39 (m, J=2.1, 1H), 7.37 (s, 1H), 7.32-7.26 (m, 1H), 7.04 (s, 1H), 5.48 (s, 2H), 3.97-3.83 (m, 1H), 3.79 (s, 2H), 3.33 (s, 1H), 2.28-2.10 (m, 4H), 2.03-1.86 (m, 5H), 1.72 (d, J=14.5, 2H).

Example 19

(1S,4S)-1-{5-[6-(Thiazolo[4,5-b]pyridin-2-yloxy)-1H-indol-3-ylmethyl]-2,5-diaza-bicyclo[2.2.1]hept-2-yl}-ethanone

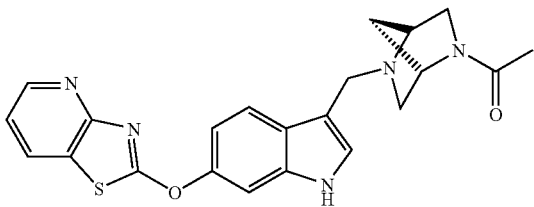

MS (ESI): mass calcd. for C$_{22}$H$_{21}$N$_5$O$_2$S, 419.1; m/z found, 420.1 [M+H]$^+$. $^1$H NMR (400 MHz, CD$_3$OD, 1:1 mixture of rotamers): 8.47 (dd, J=4.9, 1.5, 1H), 8.22 (dd, J=7.9, 1.5, 1H), 7.79 (dd, J=8.6, 3.0, 1H), 7.44-7.39 (m, 1H), 7.37-7.32 (m, 1H), 7.32-7.26 (m, 1H), 7.09-7.02 (m, 1H), 4.68 (s, 0.5H), 4.45 (s, 0.5H), 4.16-4.02 (m, 0.5H), 4.03-3.86 (m, 0.5H), 3.75-3.55 (m, 1.5H), 3.44-3.37 (m, 0.5H), 3.27-3.18 (m, 0.5H), 3.04-2.94 (m, 1H), 2.95-2.85 (m, 1H), 2.83-2.71 (m, 1H), 2.12-1.88 (m, 3H), 1.85-1.65 (m, 1H), 1.26-1.15 (m, 1H).

Example 20

1-{1-[6-(Thiazolo[4,5-b]pyridin-2-yloxy)-1H-indol-3-ylmethyl]-piperidin-4-yl}-pyrrolidin-2-one

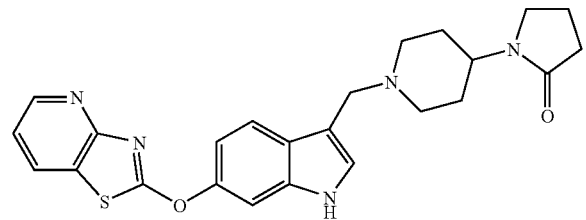 [SMILES: O=C1CCCN1C1CCN(Cc2c[nH]c3cc(Oc4nc5ncccc5s4)ccc23)CC1]

MS (ESI): mass calcd. for C$_{24}$H$_{25}$N$_5$O$_2$S, 447.2; m/z found, 448.2 [M+H]$^+$. $^1$H NMR (400 MHz, CDCl$_3$): 8.78 (s, 1H), 8.61-8.48 (m, 1H), 7.97 (d, J=6.6, 1H), 7.75 (d, J=8.6, 1H), 7.44 (s, 1H), 7.22-6.89 (m, 3H), 4.10-3.88 (m, 1H), 3.70 (s, 2H), 3.34 (t, J=7.0, 2H), 3.09-2.96 (m, 2H), 2.38 (t, J=8.0, 2H), 2.19-2.05 (m, 2H), 2.07-1.87 (m, 2H), 1.82-1.46 (m, 4H).

Example 21

1-[6-(Benzothiazol-2-yloxy)-1H-indol-3-ylmethyl]-piperidine-4-carboxylic acid amide

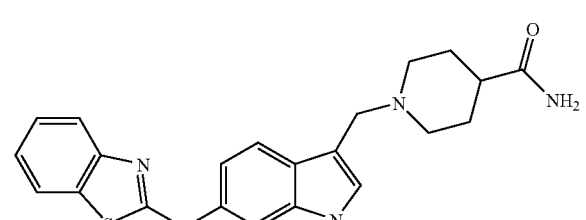

MS (ESI): mass calcd. for C$_{22}$H$_{22}$N$_4$O$_2$S, 406.5; m/z found, 407.1 [M+H]$^+$. $^1$H NMR (500 MHz, CDCl$_3$): 8.21 (s, 1H), 7.79 (d, J=8.6, 1H), 7.76 (d, J=8.1, 1H), 7.66 (d, J=7.6, 1H), 7.40-7.37 (m, 2H), 7.26-7.23 (m, 1H), 7.19 (br s, 1H), 7.12 (dd, J=8.6, 2.1, 1H), 5.46 (br s, 1H), 5.24 (br s, 1H), 3.73 (s, 2H), 3.05 (d, J=11.7, 2H), 2.20-2.17 (m, 1H), 2.04-2.09 (m, 2H), 1.91-1.89 (m, 2H), 1.83-1.79 (m, 2H).

Example 22

1-[6-(Benzothiazol-2-yloxy)-1H-indol-3-ylmethyl]-piperidine-4-carboxylic acid methylamide

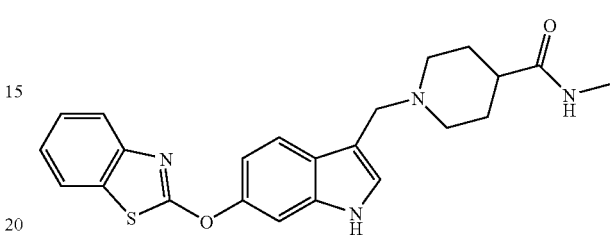

MS (ESI): mass calcd. for C$_{23}$H$_{24}$N$_4$O$_2$S, 420.5; m/z found, 421.1 [M+H]$^+$. $^1$H NMR (500 MHz, CDCl$_3$): 8.45 (s, 1H), 7.78 (d, J=8.6, 1H), 7.74 (d, J=8.1, 1H), 7.65 (d, J=8.0, 1H), 7.41-7.38 (m, 1H), 7.38 (d, J=2.1, 1H), 7.28-7.25 (m, 1H), 7.17 (d, J=2.3, 1H), 7.10 (dd, J=8.6, 2.1, 1H), 5.54 (br s, 1H), 3.71 (s, 2H), 3.05-3.01 (m, 2H), 2.82 (d, J=4.8, 1H), 2.12-2.01 (m, 3H), 1.85-1.69 (m, 6H).

Example 23

{1-[6-(Benzothiazol-2-yloxy)-1H-indol-3-ylmethyl]-piperidin-4-yl}-pyrrolidin-1-yl-methanone

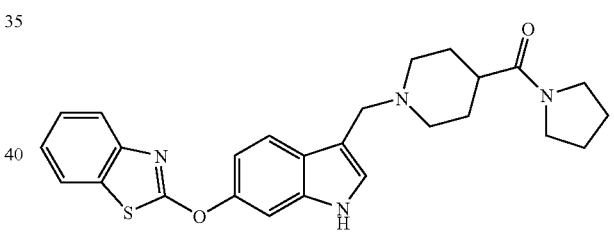

MS (ESI): mass calcd. for C$_{26}$H$_{28}$N$_4$O$_2$S, 460.6; m/z found, 461.2 [M+H]$^+$. $^1$H NMR (500 MHz, CDCl$_3$): 8.72 (br s, 1H), 7.77 (d, J=8.6, 1H), 7.75 (d, J=8.2, 1H), 7.65 (d, J=8.0, 1H), 7.41-7.37 (m, 1H), 7.36 (d, J=2.1, 1H), 7.28-7.25 (m, 1H), 7.19 (d, J=2.3, 1H), 7.10 (dd, J=8.6, 2.2, 1H), 3.73 (s, 2H), 3.49-3.46 (m, 4H), 3.08-3.05 (m, 2H), 2.37-2.31 (m, 1H), 2.07-2.03 (m, 2H), 1.97-1.90 (m, 4H), 1.87-1.82 (m, 2H), 1.72-1.70 (m, 2H).

Example 24

{1-[6-(Benzothiazol-2-yloxy)-1H-indol-3-ylmethyl]-piperidin-4-yl}-piperidin-1-yl-methanone

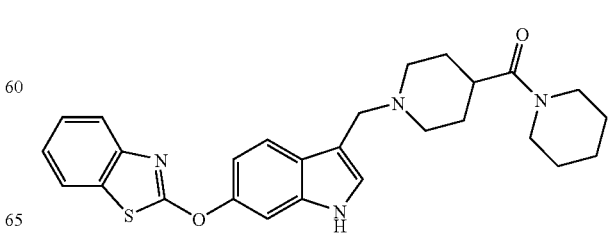

MS (ESI): mass calcd. for $C_{27}H_{30}N_4O_2S$, 474.6; m/z found, 475.2 [M+H]$^+$. $^1$H NMR (500 MHz, CDCl$_3$): 8.42 (br s, 1H), 7.78 (d, J=8.6, 1H), 7.75 (d, J=8.1, 1H), 7.66 (d, J=7.4, 1H), 7.41-7.38 (m, 1H), 7.37 (d, J=2.2, 1H), 7.28-7.25 (m, 1H), 7.20 (d, J=2.3, 1H), 7.11 (dd, J=8.6, 2.2, 1H), 3.74 (s, 2H), 3.58-3.54 (m, 2H), 3.44-3.40 (m, 2H), 3.08-3.04 (m, 2H), 1.48-1.43 (m, 1H), 2.09-2.04 (m, 2H), 1.93-1.88 (m, 2H), 1.70-1.65 (m, 4H), 1.58-1.52 (m, 4H).

Example 25

{1-[6-(Benzothiazol-2-yloxy)-1H-indol-3-ylmethyl]-piperidin-4-yl}-morpholin-4-yl-methanone

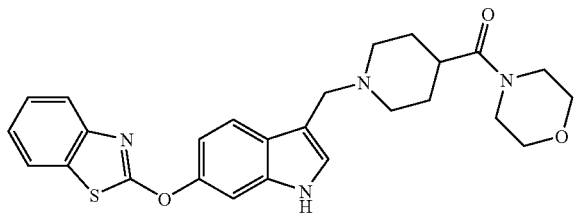 [SMILES: O=C(C1CCN(Cc2c[nH]c3cc(Oc4nc5ccccc5s4)ccc23)CC1)N1CCCCC1]

MS (ESI): mass calcd. for $C_{26}H_{28}N_4O_3S$, 476.6; m/z found, 477.1 [M+H]$^+$. $^1$H NMR (500 MHz, CDCl$_3$): 8.34 (br s, 1H), 7.79 (d, J=8.6, 1H), 7.75 (d, J=8.1, 1H), 7.66 (d, J=7.3, 1H), 7.41-7.38 (m, 1H), 7.37 (d, J=2.3, 1H), 7.28-7.25 (m, 1H), 7.19 (d, J=2.2, 1H), 7.11 (dd, J=8.6, 2.2, 1H), 3.74 (s, 2H), 3.73-3.51 (m, 8H), 3.09-3.04 (m, 2H), 2.46-2.42 (m, 1H), 2.09-2.03 (m, 2H), 1.93-1.89 (m, 2H), 1.70-1.64 (m, 2H).

Example 26

{1-[6-(Benzothiazol-2-yloxy)-1H-indol-3-ylmethyl]-piperidin-4-yl}-(4-methyl-piperazin-1-yl)-methanone

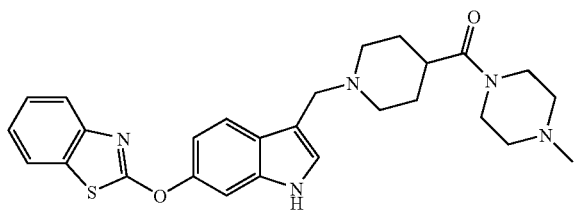 [SMILES: CN1CCN(C(=O)C2CCN(Cc3c[nH]c4cc(Oc5nc6ccccc6s5)ccc34)CC2)CC1]

MS (ESI): mass calcd. for $C_{27}H_{31}N_5O_2S$, 489.6; m/z found, 490.2 [M+H]$^+$. $^1$H NMR (500 MHz, CDCl$_3$): 8.38 (br s, 1H), 7.79 (d, J=8.6, 1H), 7.75 (d, J=8.2, 1H), 7.66 (d, J=8.0, 1H), 7.41-7.38 (m, 1H), 7.37 (d, J=2.2, 1H), 7.28-7.25 (m, 1H), 7.19 (d, J=2.1, 1H), 7.11 (dd, J=8.6, 2.2, 1H), 3.74 (s, 2H), 3.65 (br s, 2H), 3.53-3.49 (m, 2H), 3.08-3.03 (m, 2H), 2.47-2.36 (m, 5H), 2.31 (s, 3H), 2.09-2.03 (m, 2H), 1.94-1.88 (m, 2H), 1.70-1.66 (m, 2H).

Example 27

(3S)-1-[6-(Benzothiazol-2-yloxy)-1H-indol-3-ylmethyl]-piperidine-3-carboxylic acid amide

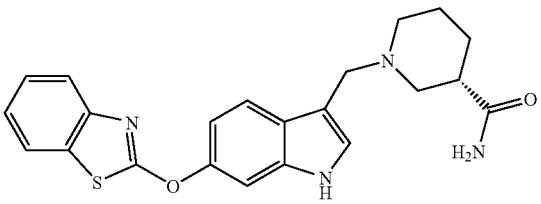 [SMILES: NC(=O)[C@H]1CCCN(Cc2c[nH]c3cc(Oc4nc5ccccc5s4)ccc23)C1]

MS (ESI): mass calcd. for $C_{22}H_{22}N_4O_2S$, 406.5; m/z found, 407.1 [M+H]$^+$. $^1$H NMR (500 MHz, CDCl$_3$): 8.75 (s, 1H), 7.73 (d, J=8.1, 1H), 7.66-7.63 (m, 2H), 7.40-7.37 (m, 2H), 7.28-7.25 (m, 1H), 7.12-7.08 (m, 2H), 5.41 (br s, 1H), 3.72 (d, J=13.3, 1H), 3.60 (d, J=13.3, 1H), 2.93-2.85 (m, 2H), 2.51 (br s, 1H), 2.42 (br s, 1H), 2.26 (br s, 1H), 1.91 (br s, 1H), 1.81-1.76 (m, 2H), 1.65-1.59 (m, 2H).

Example 28

{1-[6-(Benzothiazol-2-yloxy)-1H-indol-3-ylmethyl]-piperidin-4-yl}-methanol

MS (ESI): mass calcd. for $C_{22}H_{23}N_3O_2S$, 393.5; m/z found, 394.1 [M+H]$^+$. $^1$H NMR (500 MHz, CDCl$_3$): 9.01 (s, 1H), 7.72-7.70 (m, 2H), 7.62 (d, J=7.8, 1H), 7.38-7.35 (m, 1H), 7.28-7.23 (m, 2H), 7.10-7.06 (m, 2H), 3.69 (s, 2H), 3.46 (d, J=6.3, 2H), 3.00 (d, J=11.0, 2H), 2.20 (br s, 1H), 2.04-1.99 (m, 2H), 1.72-1.69 (m, 2H), 1.49 (br s, 1H), 1.30-1.27 (m, 2H).

Example 29

{1-[6-(Benzothiazol-2-yloxy)-1H-indol-3-ylmethyl]-piperidin-4-yl}-carbamic acid ethyl ester

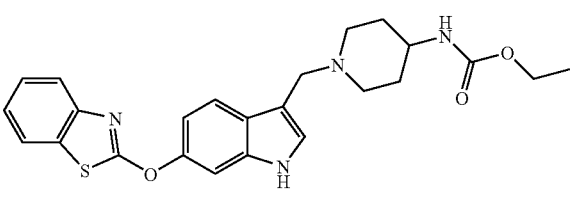 [SMILES: CCOC(=O)NC1CCN(Cc2c[nH]c3cc(Oc4nc5ccccc5s4)ccc23)CC1]

MS (ESI): mass calcd. for $C_{24}H_{26}N_4O_3S$, 450.5; m/z found, 451.1 [M+H]$^+$. $^1$H NMR (500 MHz, CDCl$_3$): 9.14 (s, 1H), 7.71 (d, J=9.0, 2H), 7.62 (d, J=7.5, 1H), 7.38-7.34 (m, 1H), 7.26-7.22 (m, 2H), 7.07-7.04 (m, 2H), 4.68 (br s, 1H), 4.11 (d, J=6.7, 2H), 3.66 (s, 2H), 3.53 (br s, 1H), 2.87 (d, J=10.8, 2H), 2.14 (d, J=10.8, 2H), 1.91 (d, J=10.6, 2H), 1.48-1.42 (m, 2H), 1.24 (t, J=7.0, 3H).

Example 30

1-{1-[6-(Benzothiazol-2-yloxy)-1H-indol-3-ylmethyl]-piperidin-4-yl}-pyrrolidin-2-one

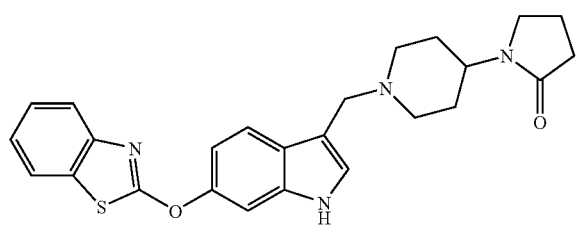

MS (ESI): mass calcd. for $C_{25}H_{26}N_4O_2S$, 446.5; m/z found, 447.1 [M+H]$^+$. $^1$H NMR (500 MHz, CDCl$_3$): 9.01 (s, 1H), 7.75-7.72 (m, 2H), 7.63 (d, J=7.9, 1H), 7.38 (t, J=7.4, 1H), 7.31 (br s, 1H), 7.27-7.23 (m, 1H), 7.11-7.07 (m, 2H), 4.01-3.96 (m, 1H), 3.69 (s, 2H), 3.34 (t, J=6.9, 2H), 3.02 (d, J=11.4, 2H), 2.39 (d, J=8.1, 2H), 2.12-1.97 (m, 4H), 1.75-1.69 (m, 2H), 1.65-1.60 (m, 2H).

Example 31

2-(3-Piperidin-1-ylmethyl-1H-pyrrolo[3,2-b]pyridin-6-yloxy)-benzothiazole

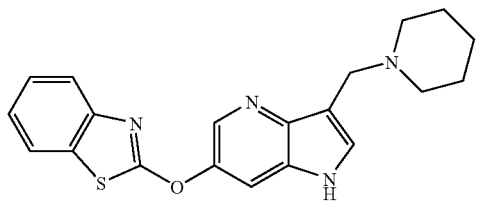 [SMILES: c1ccc2sc(Oc3cnc4c(CN5CCCCC5)c[nH]c4c3)nc2c1]

MS (ESI): mass calcd. for $C_{20}H_{20}N_4OS$, 364.4; m/z found, 365.1 [M+H]$^+$. $^1$H NMR (500 MHz, CDCl$_3$): 9.25 (br s, 1H), 8.52 (d, J=2.4, 1H), 7.69 (dd, J=7.5, 6.0, 1H), 7.63 (d, J=2.4, 1H), 7.41-7.37 (m, 2H), 7.31-7.25 (m, 1H), 3.83 (s, 2H), 2.55 (br s, 4H), 1.62-1.59 (m, 4H), 1.44 (br s, 2H).

Example 32

2-(3-Morpholin-4-ylmethyl-1H-pyrrolo[3,2-b]pyridin-6-yloxy)-benzothiazole

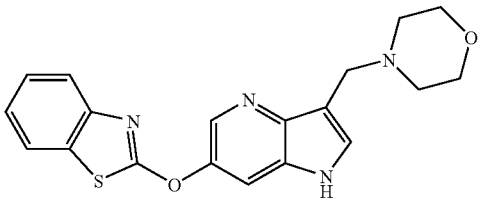 [SMILES: c1ccc2sc(Oc3cnc4c(CN5CCOCC5)c[nH]c4c3)nc2c1]

MS (ESI): mass calcd. for $C_{19}H_{18}N_4O_2S$, 366.4; m/z found, 367.1 [M+H]$^+$. $^1$H NMR (500 MHz, CDCl$_3$): 8.71 (br s, 1H), 8.56 (d, J=2.4, 1H), 7.75 (d, J=2.4, 1H), 7.70 (dd, J=7.7, 0.8, 1H), 7.42-7.39 (m, 2H), 7.32-7.29 (m, 1H), 3.86 (s, 2H), 3.76-3.72 (m, 4H), 3.60 (br s, 4H).

Example 33

1-[6-(Benzothiazol-2-yloxy)-1H-pyrrolo[3,2-b]pyridin-3-ylmethyl]-piperidine-4-carboxylic acid amide

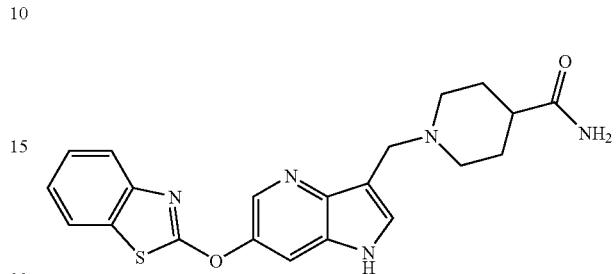

MS (ESI): mass calcd. for $C_{21}H_{21}N_5O_2S$, 407.5; m/z found, 408.1 [M+H]$^+$. $^1$H NMR (500 MHz, CD$_3$OD): 8.44 (d, J=2.4, 1H), 7.94 (d, J=2.4, 1H), 7.81 (d, J=7.4, 1H), 7.70 (br s, 1H), 7.66 (d, J=7.7, 1H), 7.45-7.42 (m, 1H), 7.35-7.32 (m, 1H), 3.91 (s, 2H), 3.11-3.07 (m, 2H), 2.23-2.18 (m, 3H), 1.82-1.76 (m, 4H).

Example 34

2-[6-(Thiazolo[4,5-b]pyridin-2-yloxy)-1H-indol-3-ylmethyl]-1,2,3,4-tetrahydro-benzo[4,5]thieno[3,2-c]pyridine formate

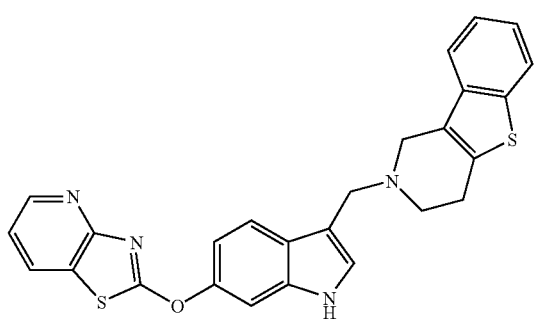 [SMILES: c1cnc2nc(Oc3ccc4c(CN5CCc6sc7ccccc7c6C5)c[nH]c4c3)sc2c1]

To a solution of thiazolo[4,5-b]pyridine (50 mg, 0.19 mmol) in dioxane (0.9 mL) was added 1,2,3,4-tetrahydrobenzo[4,5]thieno[3,2-c]pyridine (35 mg, 0.19 mmol), formaldehyde (35% wt in water, 14 μL, 15 mg, 0.19 mmol) and acetic acid (0.9 mL). The reaction mixture was heated (50° C., 16 h). The reaction mixture was cooled (rt) and concentrated in vacuo. The resulting residue was purified reverse phase HPLC to provide the title compound as a white solid (49 mg, 56%). MS (ESI): mass calcd. for $C_{26}H_{20}N_4OS_2$, 468.1; m/z found, 469.1 [M+H]$^+$. $^1$H NMR (500 MHz, CD$_3$OD): 8.49 (dd, J=4.9, 1.6, 1H), 8.25 (dd, J=8.0, 1.6, 1H), 7.86 (d, J=8.6, 1H), 7.78 (d, J=7.8, 1H), 7.51 (d, J=7.9, 1H), 7.49-7.44 (m, 2H), 7.36-7.30 (m, 2H), 7.30-7.24 (m, 1H), 7.11 (dd, J=8.6, 2.2, 1H), 4.08 (s, 2H), 3.84 (s, 2H), 3.07-2.92 (m, 4H).

Examples 35 to 43 were prepared using methods analogous to those described for Example 34.

Example 35

2-[6-(Thiazolo[4,5-b]pyridin-2-yloxy)-1H-indol-3-ylmethyl]-1,2,3,4-tetrahydro-benzo[4,5]thieno[2,3-c]pyridine

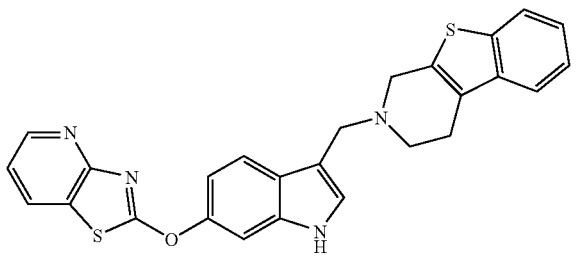 [SMILES: c1cnc2nc(Oc3ccc4c(CN5CCc6c(sc7ccccc67)C5)c[nH]c4c3)sc2c1]

MS (ESI): mass calcd. for $C_{26}H_{20}N_4OS_2$, 468.1; m/z found, 469.1 [M+H]$^+$. $^1$H NMR (500 MHz, CD$_3$OD): 8.49 (dd, J=4.9, 1.6, 1H), 8.26 (dd, J=8.0, 1.6, 1H), 7.85 (d, J=8.6, 1H), 7.79 (d, J=7.9, 1H), 7.63 (d, J=7.9, 1H), 7.52-7.41 (m, 2H), 7.40-7.25 (m, 3H), 7.11 (dd, J=8.6, 2.2, 1H), 4.07 (s, 2H), 3.86 (s, 2H), 3.06 (t, J=5.8, 2H), 2.96-2.89 (m, 2H).

Example 36

8-Chloro-2-[6-(thiazolo[4,5-b]pyridin-2-yloxy)-1H-indol-3-ylmethyl]-1,2,3,4-tetrahydro-benzo[4,5]thieno[3,2-c]pyridine formate

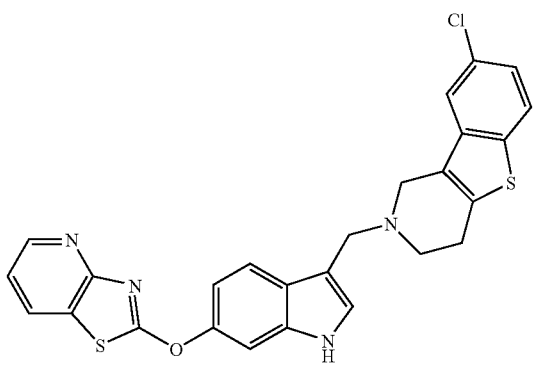 [SMILES: Clc1ccc2sc3c(c2c1)CN(Cc1c[nH]c2cc(Oc4nc5ncccc5s4)ccc12)CC3]

MS (ESI): mass calcd. for $C_{26}H_{19}ClN_4OS_2$, 502.0; m/z found, 503.0 [M+H]$^+$. $^1$H NMR (500 MHz, CD$_3$OD): 8.48 (d, J=4.9, 1H), 8.23 (d, J=7.9, 1H), 7.85 (d, J=8.6, 1H), 7.75 (d, J=8.5, 1H), 7.52 (s, 1H), 7.47 (d, J=8.6, 2H), 7.34-7.29 (m, 1H), 7.28-7.21 (m, 1H), 7.13-7.05 (m, 1H), 4.07 (s, 2H), 3.80 (s, 2H), 3.00 (s, 4H).

Example 37

6-Chloro-2-[6-(thiazolo[4,5-b]pyridin-2-yloxy)-1H-indol-3-ylmethyl]-1,2,3,4-tetrahydro-benzo[4,5]thieno[2,3-c]pyridine formate

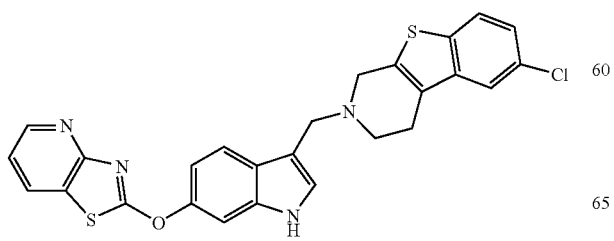

MS (ESI): mass calcd. for $C_{26}H_{19}ClN_4OS_2$, 502.0; m/z found, 503.0 [M+H]$^+$. $^1$H NMR (400 MHz, CD$_3$OD): 8.37 (dd, J=4.9, 1.6, 1H), 8.13 (dd, J=8.0, 1.6, 1H), 7.74 (d, J=8.6, 1H), 7.66 (d, J=8.5, 1H), 7.46-7.38 (m, 3H), 7.26-7.12 (m, 2H), 7.02 (dd, J=8.6, 2.2, 1H), 4.13 (s, 2H), 3.88 (s, 2H), 3.12-3.02 (m, 2H), 3.00-2.91 (m, 2H).

Example 38

8-Fluoro-2-[6-(thiazolo[4,5-b]pyridin-2-yloxy)-1H-indol-3-ylmethyl]-1,2,3,4-tetrahydro-benzo[4,5]thieno[3,2-c]pyridine

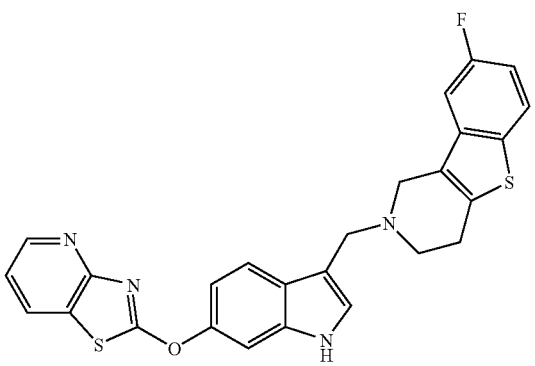 [SMILES: Fc1ccc2sc3c(c2c1)CN(Cc1c[nH]c2cc(Oc4nc5ncccc5s4)ccc12)CC3]

MS (ESI): mass calcd. for $C_{26}H_{19}FN_4OS_2$, 486.1; m/z found, 487.1 [M+H]$^+$. $^1$H NMR (400 MHz, CD$_3$OD): 8.38 (dd, J=4.9, 1.6, 1H), 8.14 (dd, J=8.0, 1.6, 1H), 7.75 (d, J=8.6, 1H), 7.65 (dd, J=8.8, 4.8, 1H), 7.37 (d, J=1.9, 1H), 7.35 (s, 1H), 7.21 (dd, J=8.0, 4.9, 1H), 7.13 (dd, J=9.7, 2.4, 1H), 7.03-6.91 (m, 2H), 3.97 (s, 2H), 3.70 (s, 2H), 2.90 (app s, 4H).

Example 39

2-[6-(Benzothiazol-2-yloxy)-1H-indol-3-ylmethyl]-1,2,3,4-tetrahydro-benzo[4,5]thieno[3,2-c]pyridine formate

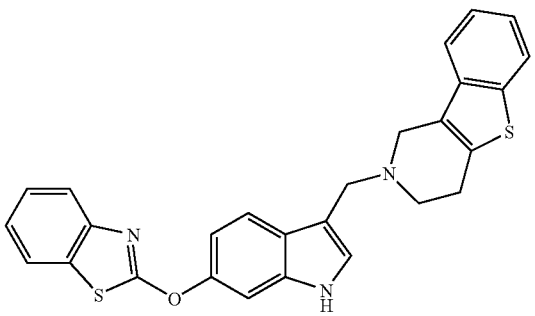

MS (ESI): mass calcd. for $C_{27}H_{21}N_3OS_2$, 467.1; m/z found, 468.1 [M+H]$^+$. $^1$H NMR (400 MHz, CD$_3$OD): 7.71 (d, J=8.6, 1H), 7.68 (d, J=7.4, 1H), 7.61 (d, J=8.0, 1H), 7.52 (d, J=7.6, 1H), 7.44 (s, 1H), 7.41 (d, J=7.2, 1H), 7.34 (d, J=2.0, 1H), 7.31-7.12 (m, 4H), 6.99 (dd, J=8.6, 2.2, 1H), 4.27 (s, 2H), 4.05 (s, 2H), 3.27-3.20 (m, 2H), 3.05-2.94 (m, 2H).

Example 40

2-(3-Morpholin-4-ylmethyl-1H-indol-6-yloxy)-thiazolo[4,5-b]pyridine

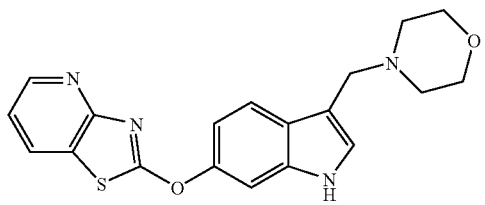 [SMILES: c1cnc2nc(Oc3ccc4c(CN5CCOCC5)c[nH]c4c3)sc2c1]

MS (ESI): mass calcd. for $C_{19}H_{18}N_4O_2S$, 366.4; m/z found, 367.1 [M+H]+. 1H NMR (500 MHz, CDCl3): 8.93 (br s, 1H), 8.57 (dd, J=4.9, 1.7, 1H), 7.99 (dd, J=7.9, 1.7, 1H), 7.77 (d, J=8.6, 1H), 7.46 (br s, 1H), 7.24-7.17 (m, 2H), 7.11 (dd, J=8.6, 2.1, 1H), 3.74 (s, 6H), 2.56 (s, 4H).

Example 41

(3S)-2-[3-(3-Methyl-morpholin-4-ylmethyl)-1H-indol-6-yloxy]-thiazolo[4,5-b]pyridine

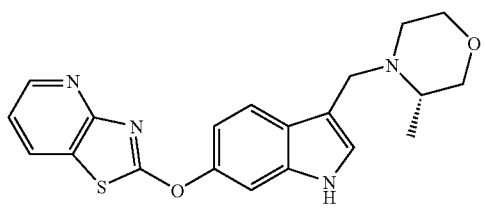 [SMILES: C[C@H]1COCCN1Cc1c[nH]c2cc(Oc3nc4ncccc4s3)ccc12]

MS (ESI): mass calcd. for $C_{20}H_{20}N_4O_2S$, 380.4; m/z found, 381.1 [M+H]+. 1H NMR (400 MHz, CDCl3): 8.56 (dd, J=4.9, 1.7, 1H), 8.50 (br s, 1H), 7.97 (dd, J=7.9, 1.6, 1H), 7.79 (d, J=8.6, 1H), 7.46 (d, J=2.2, 1H), 7.19-7.16 (m, 2H), 7.10 (dd, J=8.6, 2.2, 1H), 4.22 (d, J=13.4, 1H), 3.73-3.70 (m, 2H), 3.57-3.53 (m, 1H), 3.38 (d, J=13.4, 1H), 3.34-3.29 (m, 1H), 2.70-2.67 (m, 1H), 2.53-2.49 (m, 1H), 2.25-2.19 (m, 1H), 1.17 (d, J=6.2, 3H).

Example 42

2-(3-Thiomorpholin-4-ylmethyl-1H-indol-6-yloxy)-thiazolo[4,5-b]pyridine

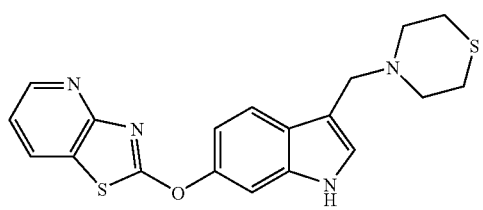 [SMILES: c1cnc2nc(Oc3ccc4c(CN5CCSCC5)c[nH]c4c3)sc2c1]

MS (ESI): mass calcd. for $C_{19}H_{18}N_4OS_2$, 382.5; m/z found, 383.2 [M+H]+. 1H NMR (500 MHz, DMSO-d6): 11.22 (br s, 1H), 8.51 (dd, J=4.8, 1.7, 1H), 8.35 (dd, J=8.0, 1.7, 1H), 7.76 (d, J=8.6, 1H), 7.47 (d, J=2.2, 1H), 7.35-7.30 (m, 2H), 7.07 (dd, J=8.6, 2.2, 1H), 2.67-2.64 (m, 4H), 2.59-2.55 (m, 4H).

Example 43 meso-endo-N-{8-[6-(Thiazolo[5,4-b]pyridin-2-yloxy)-1H-indol-3-ylmethyl]-8-aza-bicyclo[3.2.1]oct-3-yl}-acetamide

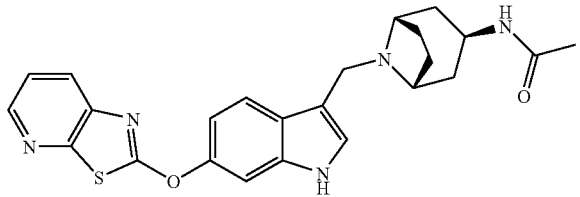 [SMILES: CC(=O)N[C@H]1C[C@H]2CC[C@@H](C1)N2Cc1c[nH]c2cc(Oc3nc4cccnc4s3)ccc12]

MS (ESI): mass calcd. for $C_{24}H_{26}N_6O_2S$, 447.5; m/z found, 448.1 [M+H]+. 1H NMR (500 MHz, CDCl3): 9.18 (br s, 1H), 8.38 (d, J=4.0, 1H), 7.92 (d, J=8.0, 1H), 7.78 (d, J=8.5, 1H), 7.33-7.28 (m, 2H), 7.17 (br s, 1H), 7.07-7.04 (m, 1H), 5.98 (d, J=6.9, 1H), 4.12-4.08 (m, 1H), 3.68 (s, 2H), 3.29 (br s, 2H), 2.20-2.16 (m, 4H), 1.98 (s, 3H), 1.79-1.74 (m, 2H), 1.61-1.58 (m, 2H).

Example 44

(4R)-1-{1-[6-(Benzothiazol-2-yloxy)-1H-indol-3-ylmethyl]-piperidin-4-yl}-4-hydroxy-pyrrolidin-2-one

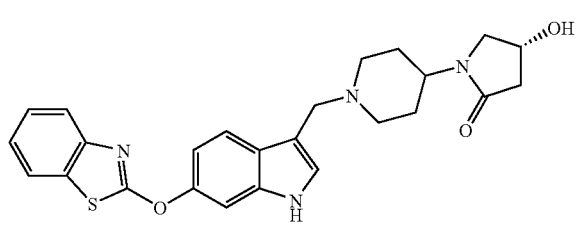 [SMILES: O=C1C[C@@H](O)CN1C1CCN(Cc2c[nH]c3cc(Oc4nc5ccccc5s4)ccc23)CC1]

To a solution of (R)-1-{1-[6-(benzothiazol-2-yloxy)-1H-indol-3-ylmethyl]-piperidin-4-yl}-4-(tert-butyl-dimethyl-silanyloxy)-pyrrolidin-2-one (200 mg, 0.35 mmol) in MeOH:DCM (1:1, 15 mL) was added 4 M HCl in dioxane (5 mL) and the resulting reaction mixture was stirred (rt, 3 h). The reaction mixture was concentrated in vacuo to provide the title compound as a tan solid (112 mg, 70%). MS (ESI): mass calcd. for $C_{25}H_{26}N_4O_3S$, 462.5; m/z found, 463.1 [M+H]+. 1H NMR (500 MHz, CDCl3): 9.00 (br s, 1H), 7.73-7.71 (m, 2H), 7.62 (d, J=7.9, 1H), 7.39-7.33 (m, 2H), 7.28-7.23 (m, 1H), 7.12-7.07 (m, 2H), 4.35 (t, J=8.4, 1H), 3.95-3.90 (m, 1H), 3.69 (s, 2H), 3.37-3.33 (m, 1H), 3.21-3.15 (m, 1H), 3.04-3.02 (m, 2H), 3.41-3.38 (m, 1H), 2.10-2.04 (m, 2H), 1.94-1.89 (m, 1H), 1.77-1.73 (m, 2H), 1.64-1.60 (m, 2H)

Example 45

1-[6-(Benzothiazol-2-yloxy)-1H-indol-3-ylmethyl]-piperidine-4-carboxylic acid

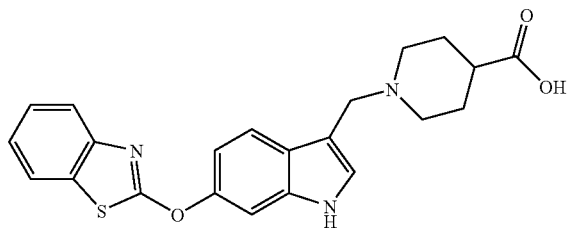 [SMILES: O=C(O)C1CCN(Cc2c[nH]c3cc(Oc4nc5ccccc5s4)ccc23)CC1]

To a solution of 1-[6-(benzothiazol-2-yloxy)-1H-indol-3-ylmethyl]-piperidine-4-carboxylic acid ethyl ester (410 mg, 0.094 mmol) in isopropanol (10 mL) was added aqueous KOH (2 M, 53 mg, 0.42 mL, 0.94 mmol) and the resulting solution was heated (90° C., 24 h). The reaction mixture was diluted with H$_2$O (10 mL) and neutralized with aqueous 1 M HCl. The suspension was filtered and the solid was washed with EtOAc (20 mL) and dried in vacuo to provide the title compound as a tan solid (128 mg, 33%). MS (ESI): mass calcd. for C$_{22}$H$_{21}$N$_3$O$_3$S, 407.4; m/z found, 408.1 [M+H]$^+$. $^1$H NMR (400 MHz, DMSO-d$_6$): 11.18 (5, 1H), 7.88 (d, J=9.7, 1H), 7.73 (d, J=10.8, 1H), 7.68 (d, J=10.0, 1H), 7.44-7.40 (m, 2H), 7.35-7.28 (m, 2H), 7.06-7.03 (m, 1H), 3.66 (5, 2H), 2.88-2.84 (m, 2H), 2.22-2.16 (m, 1H), 2.04-2.00 (m, 2H), 1.80-1.77 (m, 2H), 1.58-1.55 (m, 2H), the CO$_2$H proton was not detected.

Examples 46 to 49 were prepared using methods analogous to those described for Example 45.

Example 46

{1-[6-(Benzothiazol-2-yloxy)-1H-indol-3-ylmethyl]-piperidin-4-yl}-acetic acid

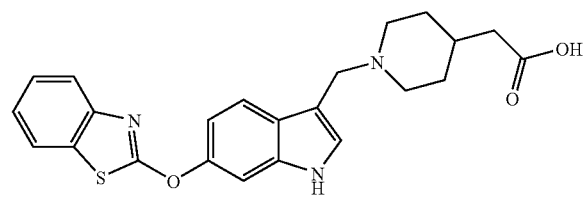 [SMILES: O=C(O)CC1CCN(Cc2c[nH]c3cc(Oc4nc5ccccc5s4)ccc23)CC1]

MS (ESI): mass calcd. for C$_{23}$H$_{23}$N$_3$O$_3$S, 421.5; m/z found, 422.1 [M+H]$^+$. $^1$H NMR (500 MHz, DMSO-d$_6$): 11.70 (br s, 1H), 10.15 (br s, 1H), 7.91-7.89 (m, 2H), 7.70 (d, J=3.1, 1H), 7.67 (d, J=9.5, 1H), 7.54 (d, J=2.7, 1H), 7.44-7.41 (m, 1H), 7.33-7.30 (m, 1H), 7.18 (dd, J=10.8, 2.7, 1H), 4.45-4.40 (m, 2H), 3.46-3.41 (m, 2H), 3.00-2.84 (m, 2H), 2.20-2.17 (m, 2H), 1.90-1.84 (m, 3H), 1.50-1.44 (m, 2H).

Example 47

1-[6-(Benzothiazol-2-yloxy)-1H-indol-3-ylmethyl]-piperidine-3-carboxylic acid

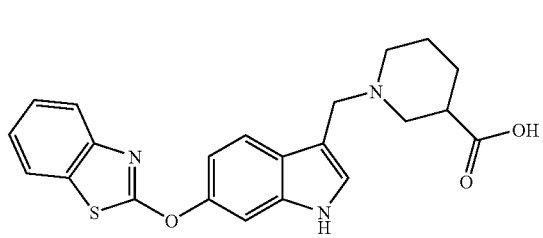 [SMILES: O=C(O)C1CCCN(Cc2c[nH]c3cc(Oc4nc5ccccc5s4)ccc23)C1]

MS (ESI): mass calcd. for C$_{22}$H$_{21}$N$_3$O$_3$S, 407.4; m/z found, 408.1 [M+H]$^+$. $^1$H NMR (500 MHz, DMSO-d$_6$): 11.78 (s, 1H), 10.70 (br 5, 1H), 7.93 (d, J=8.7, 1H), 7.89 (d, J=8.0, 1H), 7.76 (d, J=2.5, 1H), 7.67 (d, J=7.7, 1H), 7.55 (d, J=2.2, 1H), 7.44-7.40 (m, 1H), 7.33-7.30 (m, 1H), 7.18 (dd, J=8.6, 2.2, 1H), 4.52-4.47 (m, 2H), 3.60-3.56 (m, 2H), 2.96-2.92 (m, 3H), 2.06-2.00 (m, 1H), 1.90-1.84 (m, 2H), 1.43-1.40 (m, 1H).

Example 48 meso-endo-(Acetyl-{8-[6-(benzothiazol-2-yloxy)-1H-indol-3-ylmethyl]-8-aza-bicyclo[3.2.1]oct-3-yl}-amino)-acetic acid

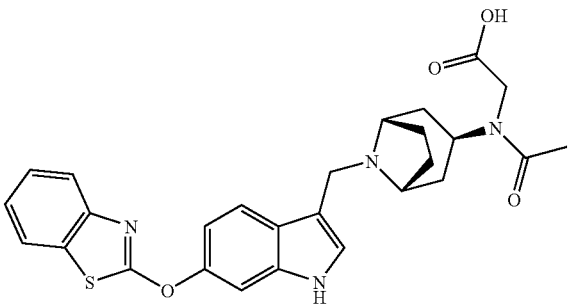 [SMILES: CC(=O)N(CC(=O)O)[C@H]1C[C@H]2CC[C@@H](C1)N2Cc1c[nH]c2cc(Oc3nc4ccccc4s3)ccc12]

MS (ESI): mass calcd. for C$_{27}$H$_{28}$N$_4$O$_4$S, 504.6; m/z found, 505.2 [M+H]$^+$. $^1$H NMR (400 MHz, DMSO-d$_6$): 11.43-11.27 (m, 1H), 8.31 (5, 1H), 7.80-7.88 (m, 2H), 7.66 (d, J=7.8, 1H), 7.57-7.49 (m, 2H), 7.42-7.39 (m, 1H), 7.30-7.26 (m, 1H), 7.16-7.13 (m 1H), 4.70-4.60 (m, 0.5H), 4.26 (br s, 0.5H), 3.95 (br s, 1H), 3.69 (5, 2H), 2.24-2.12 (m, 4H), 1.82-1.60 (m, 5H), 1.35-1.20 (m, 2H), the remaining three protons were not detected and are believed to be hidden in the solvent peaks at 3.39 and 2.50 ppm.

Example 49 meso-endo-(Acetyl-{8-[5-(benzothiazol-2-yloxy)-1H-indol-3-ylmethyl]-8-aza-bicyclo[3.2.1]oct-3-yl}-amino)-acetic acid

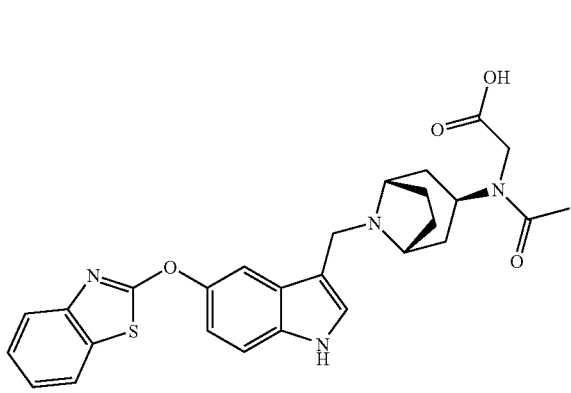 [SMILES: CC(=O)N(CC(=O)O)[C@H]1C[C@H]2CC[C@@H](C1)N2Cc1c[nH]c2ccc(Oc3nc4ccccc4s3)cc12]

MS (ESI): mass calcd. for $C_{27}H_{28}N_4O_4S$, 504.6; m/z found, 505.1 [M+H]$^+$. $^1$H NMR (400 MHz, DMSO-d$_6$): 11.40-11.20 (m, 1H), 8.31 (s, 1H), 7.90-7.83 (m, 2H), 7.67 (d, J=8.1, 1H), 7.48-7.41 (m, 3H), 7.32-7.28 (m, 1H), 7.10-7.05 (m, 1H), 4.76-4.70 (m, 0.5H), 4.35 (br s, 0.5H), 3.98 (br s, 1H), 3.74 (s, 2H), 2.26-2.15 (m, 4H), 2.05 (s, 2H), 1.87 (s, 1H), 1.76-1.60 (m, 2H), 1.32-1.24 (m, 2H), the remaining three protons were not detected and are believed to be hidden in the solvent peaks at 3.39 and 2.50 ppm.

Example 50

1-[6-(Benzothiazol-2-yloxy)-1H-indol-3-ylmethyl]-piperidin-4-ylamine 2HCl

To a solution of {1-[6-(benzothiazol-2-yloxy)-1H-indol-3-ylmethyl]-piperidin-4-yl}-carbamic acid tert-butyl ester (500 mg, 1.04 mmol) in DCM (20 mL) was added 4 M HCl in dioxane (20 mL) and the resulting reaction mixture was stirred (rt, 4 h). The reaction mixture was concentrated in vacuo to provide the title compounds as a tan solid (470 mg, 100%). MS (ESI): mass calcd. for $C_{21}H_{22}N_4OS$, 378.5; m/z found, 379.2 [M+H]$^+$.

Examples 51 to 52 were prepared using methods analogous to those described for Example 50.

Example 51

2-[3-(Hexahydro-pyrrolo[3,4-c]pyrrol-2-ylmethyl)-1H-indol-6-yloxy]-benzothiazole 2HCl

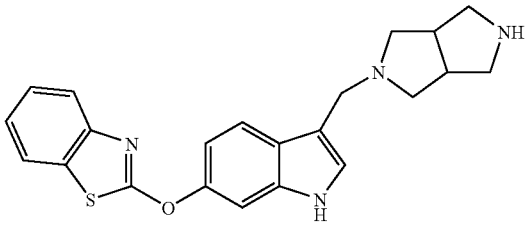 [SMILES: c1ccc2sc(Oc3ccc4c(CN5CC6CNCC6C5)c[nH]c4c3)nc2c1]

MS (ESI): mass calcd. for $C_{22}H_{22}N_4OS$, 390.51; m/z found, 391.2 [M+H]$^+$.

Example 52

(1S,4S)-2-[3-(2,5-Diaza-bicyclo[2.2.1]hept-2-ylmethyl)-1H-indol-6-yloxy]-benzothiazole 2HCl

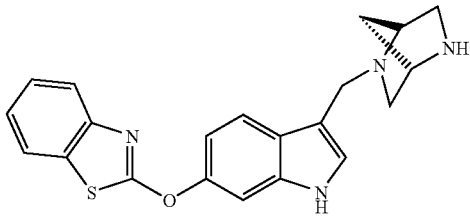

MS (ESI): mass calcd. for $O_{21}H_{20}N_4OS$, 376.48; m/z found, 377.1 [M+H]$^+$.

Example 53

N-{1-[6-(Benzothiazol-2-yloxy)-1H-indol-3-ylmethyl]-piperidin-4-yl}-acetamide

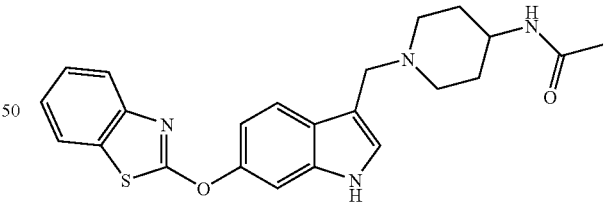

To a suspension of 1-[6-(benzothiazol-2-yloxy)-1H-indol-3-ylmethyl]-piperidin-4-ylamine 2HCl (200 mg, 0.44 mmol) in DCM (4 mL) was added Et$_3$N (0.37 mL, 270 mg, 2.7 mmol) and acetic anhydride (0.067 mL, 68 mg, 0.66 mmol) and the resulting reaction mixture was stirred (rt, 24 h). The reaction mixture was partitioned with EtOAc (50 mL) and brine (50 mL) and the organic layer was dried, filtered and concentrated in vacuo. The resulting residue was purified silica gel flash column chromatography using MeOH (0.2 M NH$_3$):DCM (0-15%) to provide the title compound as a white solid (111 mg, 60%). MS (ESI): mass calcd. for $C_{23}H_{24}N_4O_2S$, 420.5; m/z found, 421.2 [M+H]$^+$. $^1$H NMR (500 MHz, CDCl$_3$): 9.00 (s, 1H), 7.73 (d, J=6.0, 1H), 7.71 (d, J=5.2, 1H), 7.63 (d, J=7.5, 1H), 7.39-7.36 (m, 1H), 7.31 (br s, 1H), 7.26-7.24 (m, 1H), 7.10 (br s, 1H), 7.07 (dd, J=8.6, 2.1, 1H), 5.55 (br d, 1H), 3.80-3.70 (m, 1H), 3.68 (s, 2H), 2.89 (d, J=11.7, 2H), 2.17-2.13 (m, 2H), 1.96 (s, 3H), 1.89 (d, J=11.0, 2H), 1.48-1.40 (m, 2H).

Examples 54 to 55 were prepared using methods analogous to those described for Example 53.

Example 54

1-{5-[6-(Benzothiazol-2-yloxy)-1H-indol-3-ylmethyl]-hexahydro-pyrrolo[3,4-c]pyrrol-2-yl}-ethanone

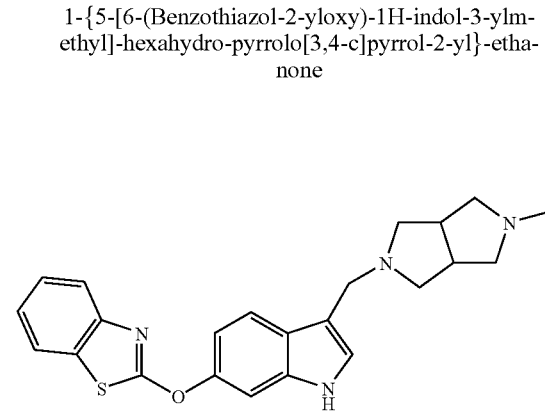

MS (ESI): mass calcd. for $C_{24}H_{24}N_4O_2S$, 432.5; m/z found, 433.2 [M+H]$^+$. $^1$H NMR (500 MHz, CDCl$_3$): 9.48 (s, 1H), 7.71-7.68 (m, 2H), 7.61 (d, J=7.7, 1H), 7.37-7.34 (m, 1H), 7.30 (br s, 1H), 7.24-7.21 (m, 1H), 7.07-7.04 (m, 2H), 3.80-3.78 (m, 1H), 3.72-3.66 (m, 2H), 3.62-3.58 (m, 1H), 3.46-3.41 (m, 1H), 3.29-3.27 (m, 1H), 2.85 (br s, 1H), 2.78 (br s, 1H), 2.65-2.60 (m, 2H), 2.55-2.46 (m, 2H), 2.03 (s, 3H).

Example 55

(1S,4S)-1-{5-[6-(Benzothiazol-2-yloxy)-1H-indol-3-ylmethyl]-2,5-diaza-bicyclo[2.2.1]hept-2-yl}-ethanone

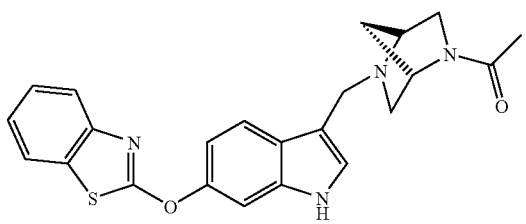

MS (ESI): mass calcd. for $C_{23}H_{22}N_4O_2S$, 418.5; m/z found, 419.2 [M+H]$^+$. $^1$H NMR (500 MHz, CDCl$_3$): 8.27-8.25 (m, 1H), 7.80 (t, J=8.0, 1H), 7.75 (d, J=8.0, 1H), 7.66 (d, J=8.0, 1H), 7.41-7.38 (m, 2H), 7.28-7.26 (m, 1H), 7.18-7.16 (m, 1H), 7.14-7.11 (m, 1H), 4.80 (s, 0.53H), 4.25 (s, 0.47H), 3.99-3.88 (m, 2H), 3.78 (d, J=11.2, 0.53H), 3.63-3.58 (m, 1.47H), 3.23-3.27 (m, 1H), 3.05-3.04 (m, 0.47H), 2.88-2.85 (m, 1H), 2.65 (d, J=9.7, 0.47H), 2.11 (s, 1.44H), 2.02-1.99 (m, 2H), 1.93 (d, J=10.3, 0.53H), 1.79 (d, J=9.6, 0.47H), 1.66 (d, J=9.6, 0.53H).

Example 56

2-(3-Morpholin-4-ylmethyl-1H-indol-6-yloxy)-thiazolo[4,5-b]pyrazine

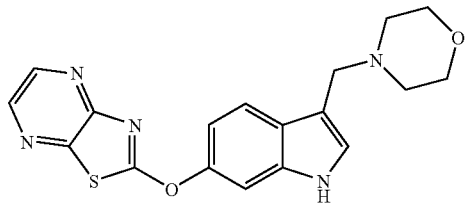 [SMILES: c1cnc2sc(Oc3ccc4c(CN5CCOCC5)c[nH]c4c3)nc2n1]

To a solution of 3-morpholin-4-ylmethyl-1H-indol-6-ol sodium salt (130 mg, 0.51 mmol) and 2-chloro-thiazolo[4,5-b]pyrazine (70 mg, 0.41 mmol) in DMF (1.4 mL) was added Cs$_2$CO$_3$ (43 mg, 0.12 mmol) and the resulting suspension was stirred (rt, 16 h). The reaction mixture was filtered and the solid was rinsed with EtOAc. The reaction mixture was concentrated in vacuo. The resulting residue was purified via reverse phase HPLC to provide the title compound as a white powder (38.3 mg, 26%). MS (ESI): mass calculated for $C_{18}H_{17}N_5O_2S$, 367.1; m/z found, 368.1 [M+H]$^+$. $^1$H NMR (600 MHz, CDCl$_3$): 8.51 (d, J=2.6, 1H), 8.32 (d, J=2.6, 1H), 8.21 (s, 1H), 7.83 (d, J=8.6, 1H), 7.45 (d, J=2.2, 1H), 7.21 (d, J=2.3, 1H), 7.12 (dd, J=8.6, 2.2, 1H), 3.75-3.69 (m, 6H), 2.51 (s, 4H).

Examples 57 to 60 were prepared using methods analogous to those described for Example 56.

Example 57

7-Methyl-2-(3-morpholin-4-ylmethyl-1H-indol-6-yloxy)-thiazolo[4,5-b]pyridine

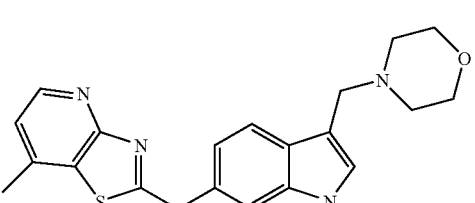

MS (ESI): mass calculated for $C_{20}H_{20}N_4O_2S$, 380.1; m/z found, 381.1 [M+H]$^+$. $^1$H NMR (600 MHz, CDCl$_3$): 8.45 (d, J=5.0, 1H), 8.23 (s, 1H), 7.81 (d, J=8.6, 1H), 7.50 (d, J=2.1, 1H), 7.20 (d, J=2.3, 1H), 7.12 (dd, J=8.6, 2.2, 1H), 7.00 (d, J=5.0, 1H), 3.76-3.68 (m, 6H), 2.51 (s, 4H), 2.47 (s, 3H).

Example 58

6-Fluoro-2-(3-morpholin-4-ylmethyl-1H-indol-6-yloxy)-thiazolo[4,5-b]pyridine

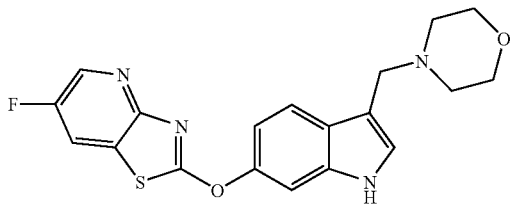 [SMILES: Fc1cnc2nc(Oc3ccc4c(CN5CCOCC5)c[nH]c4c3)sc2c1]

MS (ESI): mass calculated for $C_{19}H_{17}FN_4O_2S$, 384.1; m/z found, 385.1 [M+H]$^+$. $^1$H NMR (400 MHz, CDCl$_3$): 8.42 (dd, J=2.8, 1.1, 1H), 8.24 (s, 1H), 7.81 (d, J=8.6, 1H), 7.73 (dd, J=7.4, 2.8, 1H), 7.47 (d, J=2.1, 1H), 7.19 (d, J=2.3, 1H), 7.11 (dd, J=8.6, 2.2, 1H), 3.76-3.66 (m, 6H), 2.53-2.47 (m, 4H).

Example 59

6-Chloro-2-(3-morpholin-4-ylmethyl-1H-indol-6-yloxy)-thiazolo[4,5-b]pyridine

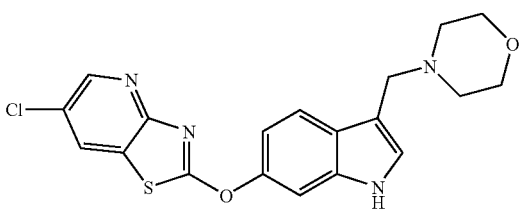 [SMILES: Clc1cnc2nc(Oc3ccc4c(CN5CCOCC5)c[nH]c4c3)sc2c1]

MS (ESI): mass calculated for $C_{19}H_{17}ClN_4O_2S$, 400.0; m/z found, 401.0 [M+H]$^+$. $^1$H NMR (500 MHz, CDCl$_3$): 8.51 (d, J=2.3, 1H), 8.40 (s, 1H), 7.98 (d, J=2.4, 1H), 7.82 (d, J=8.6, 1H), 7.47 (d, J=2.1, 1H), 7.22 (d, J=2.3, 1H), 7.12 (dd, J=8.6, 2.2, 1H), 3.80-3.66 (m, 6H), 2.52 (s, 4H).

Example 60

6-Fluoro-2-(3-morpholin-4-ylmethyl-1H-indol-6-yloxy)-thiazolo[5,4-b]pyridine

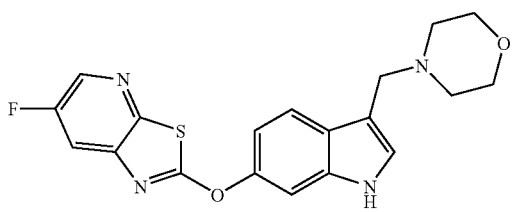 [SMILES: Fc1cnc2sc(Oc3ccc4c(CN5CCOCC5)c[nH]c4c3)nc2c1]

MS (ESI): mass calculated for $C_{19}H_{17}FN_4O_2S$, 384.1; m/z found, 385.1 [M+H]$^+$. $^1$H NMR (500 MHz, CDCl$_3$): 8.32 (dd, J=2.6, 0.9, 1H), 8.21 (s, 1H), 7.86 (d, J=8.6, 1H), 7.70 (dd, J=9.1, 2.6, 1H), 7.38 (d, J=2.1, 1H), 7.23 (d, J=2.3, 1H), 7.12 (dd, J=8.6, 2.2, 1H), 3.77-3.70 (m, 6H), 2.53 (s, 4H).

Example 61

2-(1-Methyl-3-morpholin-4-ylmethyl-1H-indol-6-yloxy)-benzothiazole

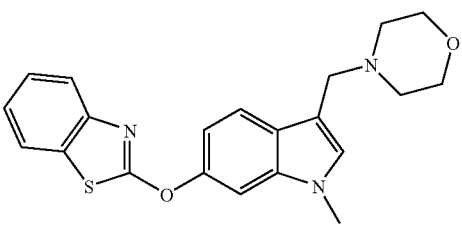 [SMILES: Cn1cc(CN2CCOCC2)c2ccc(Oc3nc4ccccc4s3)cc21]

To a cooled (0° C.) solution of 2-(3-morpholin-4-ylmethyl-1H-indol-6-yloxy)-benzothiazole (280 mg, 0.77 mmol) in DMF (4 mL) was added NaH (95%, 29 mg, 1.15 mmol) and the resulting suspension was stirred (0° C., 15 min) then warmed (rt, 30 min). The reaction mixture was cooled (0° C.) and treated with methyliodide (72 µL, 163 mg, 1.15 mmol) and then warmed (rt, 30 min). The reaction mixture was partitioned with EtOAc and brine (20 mL each). The organic layer was dried, filtered and concentrated in vacuo. The resulting residue was purified by silica gel flash chromatography using MeOH:DCM (0-20%) to provide the title compound as a clear oil (126 mg, 43%). MS (ESI): mass calcd. for $C_{21}H_{21}N_3O_2S$, 379.4; m/z found, 380.1 [M+H]$^+$. $^1$H NMR (500 MHz, CDCl$_3$): 7.79 (d, J=8.6, 1H), 7.76 (d, J=7.7, 1H), 7.66 (d, J=8.0, 1H), 7.41-7.38 (m, 1H), 7.29 (d, J=2.1, 1H), 7.29-7.25 (m, 1H), 7.12 (dd, J=8.6, 2.1, 1H), 3.77 (s, 3H), 3.74 (t, J=4.6, 4H), 3.71 (s, 2H), 2.53 (br s, 4H).

Example 62

2-(1-Ethyl-2-piperidin-1-ylmethyl-1H-indol-5-yloxy)-benzothiazole

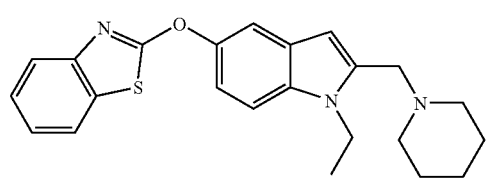 [SMILES: CCn1c(CN2CCCCC2)cc2cc(Oc3nc4ccccc4s3)ccc21]

To a suspension of 5-(benzothiazol-2-yloxy)-1-ethyl-1H-indole-2-carbaldehyde (100 mg, 0.3 mmol) in DCE (3 mL) was added piperidine (0.06 mL, 51 mg, 0.62 mmol), Na(OAc)$_3$BH (131 mg, 0.62 mmol) and the reaction mixture was stirred (rt, 60 h). The reaction mixture was partitioned between saturated NaHCO$_3$ (10 ml) and DCM (20 mL). The organic layer was separated and the aqueous layer was extracted with DCM (2×25 mL). The organic layer was dried, filtered and concentrated in vacuo. The resulting residue was purified by silica gel flash chromatography using MeOH (0.2 M NH$_3$):DCM (0-8%) to provide the title compound as a yellow solid (82 mg, 68%). MS (ESI): mass calcd. for $C_{23}H_{25}N_3OS$, 391.2; m/z found, 392.1 [M+H]$^+$. $^1$H NMR (400 MHz, CDCl$_3$): 7.73 (d, J=8.1, 1H), 7.59 (d, J=7.9, 1H), 7.49 (d, J=2.3, 1H), 7.39-7.29 (m, 2H), 7.23 (d, J=13.2, 1H), 7.12 (dd, J=8.8, 2.4, 1H), 6.35 (s, 1H), 4.36-4.21 (m, 2H), 3.56 (s, 2H), 2.49-2.25 (m, 4H), 1.54 (d, J=5.3, 4H), 1.51-1.32 (m, 5H).

Examples 63 to 64 were prepared using methods analogous to those described for Example 62.

Example 63

2-(1-Ethyl-2-morpholin-4-ylmethyl-1H-indol-5-yloxy)-benzothiazole

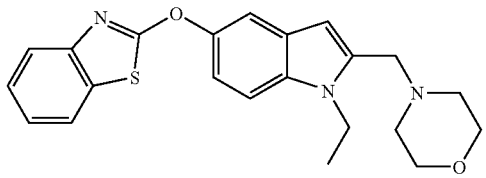 [SMILES: CCn1c(CN2CCOCC2)cc2cc(Oc3nc4ccccc4s3)ccc21]

MS (ESI): mass calcd. for $C_{22}H_{23}N_3O_2S$, 393.2; m/z found, 394.1 [M+H]$^+$. $^1$H NMR (400 MHz, CDCl$_3$): 7.73 (d, J=8.1, 1H), 7.60 (d, J=8.0, 1H), 7.50 (d, J=2.3, 1H), 7.40-7.30 (m, 2H), 7.22 (td, J=7.9, 1.2, 1H), 7.14 (dd, J=8.8, 2.4, 1H), 6.38 (s, 1H), 4.34-4.19 (m, 2H), 3.70 (dd, J=10.0, 5.3, 4H), 3.62 (s, 2H), 2.55-2.39 (m, 4H), 1.42 (t, J=7.2, 3H).

Example 64

2-(1-Ethyl-2-pyrrolidin-1-ylmethyl-1H-indol-5-yloxy)-benzothiazole

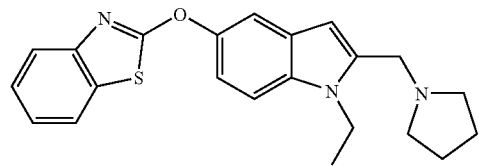 [SMILES: CCn1c(CN2CCCC2)cc2cc(Oc3nc4ccccc4s3)ccc21]

MS (ESI): mass calcd. for $C_{22}H_{23}N_3OS$, 377.2; m/z found, 378.1 [M+H]$^+$. $^1$H NMR (400 MHz, CDCl$_3$): 7.74 (dd, J=8.1, 0.6, 1H), 7.59 (dd, J=7.9, 0.7, 1H), 7.49 (d, J=2.3, 1H), 7.38-7.33 (m, 1H), 7.31 (d, J=8.8, 1H), 7.20 (td, J=7.9, 1.2, 1H), 7.12 (dd, J=8.8, 2.4, 1H), 6.36 (s, 1H), 4.28 (q, J=7.2, 2H), 3.73 (s, 2H), 2.56-2.46 (m, 4H), 1.84-1.66 (m, 4H), 1.37 (t, J=7.2, 3H).

Example 65

2-(2-Piperidin-1-ylmethyl-1H-indol-5-yloxy)-benzothiazole

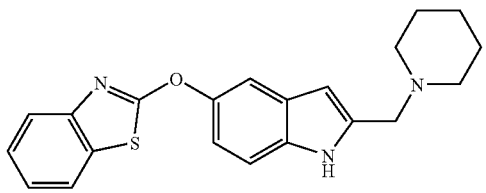

To a cooled (−78° C.) solution of [5-(benzothiazol-2-yloxy)-1H-indol-2-yl]-piperidin-1-yl-methanone (150 mg, 0.40 mmol) in THF (5 mL) was added LAH (2 M in THF, 0.2 mL, 18 mg, 0.40 mmol) and the reaction mixture was stirred (−78° C., 1 h) and allowed to warm (rt, 1 h). The reaction mixture was cooled (0° C.) and treated with H$_2$O (5 mL). The organic layer was separated and the aqueous layer was extracted with EtOAc (3×15 mL). The organic layer was dried, filtered and concentrated in vacuo. The resulting residue was purified by silica gel flash chromatography using MeOH:DCM (0-8%) to provide the title compound as a colorless foam (78 mg, 54%). MS (ESI): mass calcd. for $C_{21}H_{21}N_3OS$, 363.1; m/z found, 364.1 [M+H]$^+$. $^1$H NMR (400 MHz, CDCl$_3$): 8.64 (s, 1H), 7.77-7.70 (m, 1H), 7.61 (dd, J=7.9, 0.7, 1H), 7.48 (d, J=2.3, 1H), 7.40-7.32 (m, 2H), 7.22 (dd, J=11.0, 4.3, 1H), 7.10 (dd, J=8.7, 2.4, 1H), 6.35 (s, 1H), 3.62 (s, 2H), 2.60-2.30 (m, 4H), 1.65-1.54 (m, 4H), 1.53-1.41 (m, 2H).

Example 66 was prepared using methods analogous to those described for Example 65.

Example 66

2-(2-Pyrrolidin-1-ylmethyl-1H-indol-5-yloxy)-benzothiazole

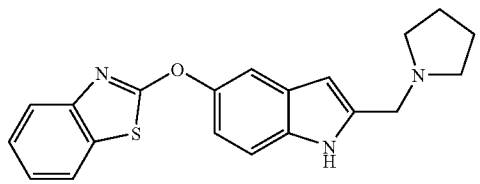 [SMILES: c1ccc2sc(Oc3ccc4[nH]c(CN5CCCC5)cc4c3)nc2c1]

MS (ESI): mass calcd. for $C_{20}H_{19}N_3OS$, 349.1; m/z found, 350.1 [M+H]$^+$. $^1$H NMR (400 MHz, CDCl$_3$): 8.69 (s, 1H), 7.74 (d, J=7.6, 1H), 7.61 (dd, J=7.9, 0.7, 1H), 7.49 (d, J=2.3, 1H), 7.42-7.29 (m, 2H), 7.25-7.18 (m, 1H), 7.10 (dd, J=8.7, 2.4, 1H), 6.36 (d, J=1.1, 1H), 3.79 (s, 2H), 2.69-2.47 (m, 4H), 1.90-1.72 (m, 4H).

Example 67

2-(2-Piperidin-1-ylmethyl-1H-indol-6-yloxy)-benzothiazole

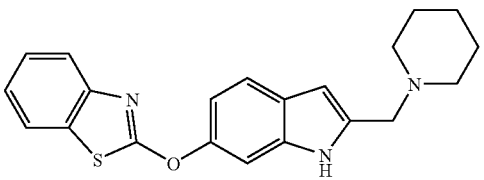

To a suspension of 6-(benzothiazol-2-yloxy)-1H-indole-2-carbaldehyde (47 mg, 0.16 mmol) in DCM (3 mL) was added piperidine (0.14 mL, 0.12 g, 0.48 mmol), Na(OAc)$_3$BH (51 mg, 0.24 mmol) and the reaction mixture was stirred (rt, 12 h). The reaction mixture was partitioned between saturated NaHCO$_3$ (10 ml) and DCM (20 mL). The organic layer was separated and the aqueous layer was extracted with DCM (2×25 mL). The organic layer was dried, filtered and concentrated in vacuo. The resulting residue was purified by silica gel flash chromatography using MeOH (0.2 M):DCM (0-8%) to provide the title compound as a yellow solid (18 mg, 31%). MS (ESI): mass calcd. for $C_{21}H_{21}N_3OS$, 363.1; m/z found, 364.1 [M+H]$^+$. $^1$H NMR (400 MHz, CDCl$_3$): 8.80 (s, 1H), 7.76-7.71 (m, 1H), 7.62 (dd, J=7.9, 0.7, 1H), 7.54 (d, J=8.5, 1H), 7.41-7.33 (m, 1H), 7.30 (d, J=2.0, 1H), 7.25-7.20 (m, 1H), 7.04 (dd, J=8.5, 2.2, 1H), 6.34 (d, J=1.0, 1H), 3.61 (s, J=5.4, 2H), 2.62-2.26 (m, 4H), 1.72-1.53 (m, J=10.9, 5.6, 4H), 1.54-1.30 (m, J=5.1, 2H).

Examples 68 to 70 were prepared using methods analogous to those described for Example 67.

Example 68

2-(2-Pyrrolidin-1-ylmethyl-1H-indol-6-yloxy)-benzothiazole

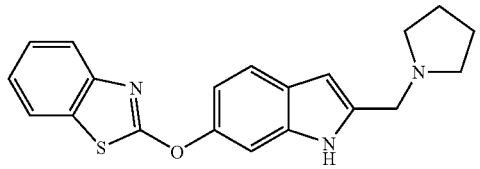 [SMILES: c1ccc2sc(Oc3ccc4cc(CN5CCCC5)[nH]c4c3)nc2c1]

MS (ESI): mass calcd. for $C_{20}H_{19}N_3OS$, 349.1; m/z found, 350.1 [M+H]$^+$. $^1$H NMR (400 MHz, CDCl$_3$): 9.12 (s, 1H), 7.73 (d, J=7.7, 1H), 7.61 (d, J=7.3, 1H), 7.54 (d, J=8.5, 1H), 7.40-7.32 (m, 1H), 7.28 (s, 1H), 7.24-7.20 (m, 1H), 7.03 (dd, J=8.5, 2.2, 1H), 6.35 (s, 1H), 3.78 (s, 2H), 2.70-2.45 (m, 4H), 1.88-1.68 (m, 4H).

Example 69

1-[6-(Benzothiazol-2-yloxy)-1H-indol-2-ylmethyl]-piperidine-4-carboxylic acid amide

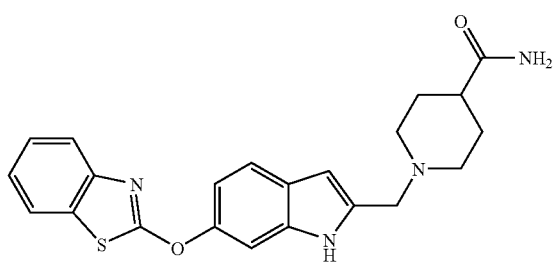 [SMILES: NC(=O)C1CCN(Cc2cc3ccc(Oc4nc5ccccc5s4)cc3[nH]2)CC1]

MS (ESI): mass calcd. for $C_{22}H_{22}N_4O_2S$, 406.1; m/z found, 407.1 [M+H]$^+$. $^1$H NMR (400 MHz, CD$_3$OD): 7.72 (d, J=7.4, 1H), 7.65 (d, J=8.1, 1H), 7.57 (d, J=8.5, 1H), 7.41 (t, J=7.2, 1H), 7.34 (d, J=2.0, 1H), 7.28 (t, J=7.1, 1H), 6.98 (dd, J=8.5, 2.2, 1H), 6.42 (s, 1H), 3.88-3.59 (m, 2H), 2.96-2.68 (m, 2H), 2.60-2.42 (m, 1H), 2.42-2.11 (m, 2H), 1.92-1.43 (m, 4H).

Example 70 meso-endo-N-{8-[6-(Benzothiazol-2-yloxy)-1H-indol-2-ylmethyl]-8-aza-bicyclo[3.2.1]oct-3-yl}-acetamide

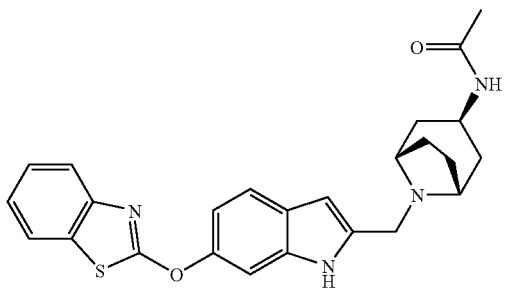 [SMILES: CC(=O)N[C@H]1C[C@H]2CC[C@@H](C1)N2Cc1cc2ccc(Oc3nc4ccccc4s3)cc2[nH]1]

MS (ESI): mass calcd. for $C_{25}H_{26}N_4O_2S$, 446.18; m/z found, 447.2 [M+H]$^+$. $^1$H NMR (400 MHz, CD$_3$OD): 7.71 (d, J=7.9, 1H), 7.65 (d, J=8.0, 1H), 7.55 (d, J=8.5, 1H), 7.44-7.32 (m, 2H), 7.27 (t, J=7.2, 1H), 6.97 (dd, J=8.5, 2.2, 1H), 6.41 (s, 1H), 3.90 (t, J=6.9, 1H), 3.70 (s, 2H), 3.25-3.17 (m, 2H), 2.33-2.01 (m, 4H), 2.01-1.89 (m, 5H), 1.70 (d, J=14.7, 2H).

Example 71

2-(2-Piperidin-1-ylmethyl-1H-indol-6-yloxy)-thiazolo[4,5-b]pyridine

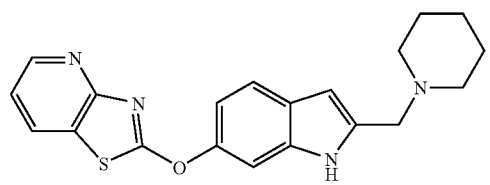

To a suspension of 6-(thiazolo[4,5-b]pyridin-2-yloxy)-1H-indole-2-carbaldehyde (76 mg, 0.26 mmol) in DCM (3 mL) was added piperidine (0.05 mL, 43 mg, 0.51 mmol), Na(OAc)$_3$BH (65 mg, 0.31 mmol) and the reaction mixture was stirred (rt, 12 h). The reaction mixture was partitioned between saturated NaHCO$_3$ (10 ml) and DCM (20 mL). The organic layer was separated and the aqueous layer was extracted with DCM (2×25 mL). The organic layer was dried, filtered and concentrated in vacuo. The resulting residue was purified by reverse phase HPLC to provide the title compound as a colorless solid (12 mg, 13%). MS (ESI): mass calcd. for $C_{20}H_{20}N_4OS$, 364.1; m/z found, 365.1 [M+H]$^+$. $^1$H NMR (500 MHz, CDCl$_3$/CD$_3$OD, 10/1): 8.51 (d, J=4.8, 1H), 7.97 (d, J=7.9, 1H), 7.54 (d, J=8.5, 1H), 7.40 (s, 1H), 7.18 (dd, J=7.9, 4.9, 1H), 7.02 (d, J=8.5, 1H), 6.36 (s, 1H), 3.63 (s, 2H), 2.53-2.47 (m, 2H), 2.47-2.36 (m, 2H), 1.76-1.44 (m, 6H).

Example 72 was prepared using methods analogous to those described for Example 71.

Example 72 meso-endo-N-{8-[6-(Thiazolo[4,5-b]pyridin-2-yloxy)-1H-indol-2-ylmethyl]-8-aza-bicyclo[3.2.1]oct-3-yl}-acetamide

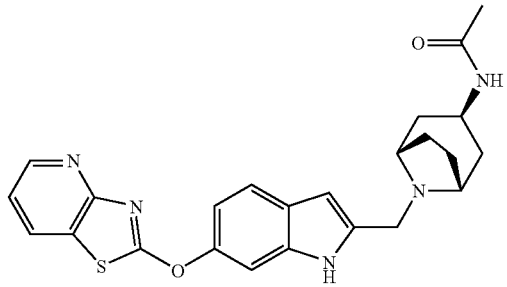 [SMILES: CC(=O)N[C@H]1C[C@H]2CC[C@@H](C1)N2Cc1cc2ccc(Oc3nc4ncccc4s3)cc2[nH]1]

MS (ESI): mass calcd. for $C_{24}H_{25}N_5O_2S$, 447.2; m/z found, 448.2 [M+H]$^+$. $^1$H NMR (400 MHz, CDCl$_3$): 8.55 (dd, J=4.9, 1.6, 1H), 7.98 (dd, J=7.9, 1.7, 1H), 7.55 (d, J=8.6, 1H), 7.46 (d, J=2.1, 1H), 7.18 (dd, J=7.9, 4.9, 1H), 7.05 (dd, J=8.5, 2.2, 1H), 6.34 (s, 1H), 5.90 (s, 1H), 4.23-4.01 (m, 1H), 3.68 (s, 2H), 3.31-3.14 (m, 2H), 2.29-2.10 (m, 4H), 1.99 (s, 3H), 1.89-1.75 (m, 2H), 1.73-1.60 (m, 2H).

Example 73

1-{2-[5-(Benzothiazol-2-yloxy)-1H-indol-3-yl]-ethyl}-piperidine-4-carboxylic acid

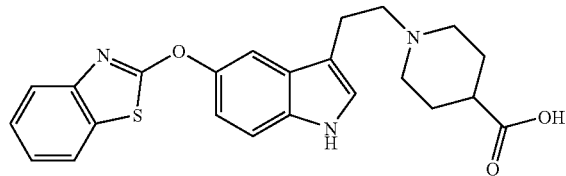 [SMILES: O=C(O)C1CCN(CCc2c[nH]c3ccc(Oc4nc5ccccc5s4)cc23)CC1]

To a solution of 1-{2-[5-(benzothiazol-2-yloxy)-1H-indol-3-yl]-ethyl}-piperidine-4-carboxylic acid ethyl ester (44 mg, 0.098 mmol) in isopropanol (2.5 mL) was added H$_2$O (1.1 mL) followed by KOH (11 mg, 0.19 mmol) in H$_2$O (2.5 mL) and the resulting reaction mixture was stirred (rt, 16 h). The reaction mixture was acidified with 6 N HCl to pH 6 and treated with DCM (10 mL). The layers were separated and the aqueous layer was extracted with 25% isopropanol/DCM (2×10 mL). The combined organic layers were dried, filtered and concentrated in vacuo to afford the title compound as a white solid (43 mg, 100%). MS (ESI): mass calcd. for, C$_{23}$H$_{23}$N$_3$O$_3$S, 421.5; m/z found, 422.1 [M+H]$^+$. $^1$H NMR (500 MHz, CD$_3$OD): 7.76 (d, J=8.0, 1H), 7.66 (m, 2H), 7.51 (d, J=8.7, 1H), 7.43 (m, 1H), 7.36 (s, 1H), 7.31 (m, 1H), 7.16 (dd, J=8.7, 2.3, 1H), 5.20 (s, 2H), 3.94 (m, 1H), 3.30-3.14 (m, 2H), 2.54-2.30 (m, 1H), 2.23-2.04 (m, 2H), 1.30 (s, 2H), 1.17 (d, J=6.2, 4H).

Example 74

2-[3-(2-Piperidin-1-yl-ethyl)-1H-indol-5-yloxy]-benzothiazole

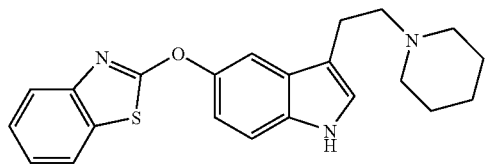 [SMILES: c1ccc2sc(Oc3ccc4[nH]cc(CCN5CCCCC5)c4c3)nc2c1]

To a solution of methanesulfonic acid 2-[5-(benzothiazol-2-yloxy)-1H-indol-3-yl]-ethyl ester (100 mg, 0.26 mmol) in MeCN (3 mL) was added piperidine (0.03 mL, 0.31 mmol) and the reaction mixture was heated (80° C., 2 h). The reaction mixture was cooled (rt), filtered and purified by basic reverse phase HPLC to provide the title compound as a white solid (47.2 mg, 49%). MS (ESI): mass calcd. for C$_{22}$H$_{23}$N$_3$OS, 377.5; m/z found, 378.3 [M+H]$^+$. $^1$H NMR (500 MHz, CDCl$_3$): 8.08 (s, 1H), 7.77 (d, J=7.6, 1H), 7.65 (d, J=8.0, 1H), 7.59 (d, J=2.3, 1H), 7.43-7.36 (m, 2H), 7.26 (s, 1H), 7.18 (dd, J=8.7, 2.3, 1H), 7.14 (s, 1H), 3.02-2.90 (m, 2H), 2.71-2.63 (m, 2H), 2.51 (s, 4H), 1.63 (dd, J=11.3, 5.6, 4H), 1.47 (s, 2H).

Example 75

1-{2-[5-(Benzothiazol-2-yloxy)-1H-indol-3-yl]-ethyl}-piperidine-4-carboxylic acid amide

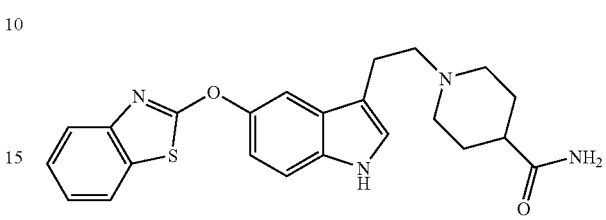

To a solution of methanesulfonic acid 2-[5-(benzothiazol-2-yloxy)-1H-indol-3-yl]-ethyl ester (100 mg, 0.26 mmol) and isonipocotamide (39 mg, 0.31 mmol) in MeCN (3 mL) was added K$_2$CO$_3$ (36 mg, 0.26 mmol) and the reaction mixture was heated (80° C., 16 h). The reaction mixture was cooled (rt), filtered and purified using reverse phase HPLC to provide the title compound as a white solid (8.5 mg, 8%). MS (ESI): mass calcd. for C$_{23}$H$_{24}$N$_4$O$_2$S, 420.5; m/z found, 421.1 [M+H]$^+$. $^1$H NMR (500 MHz, CDCl$_3$): 8.21 (s, 1H), 7.76 (d, J=7.6, 1H), 7.65 (d, J=8.0, 1H), 7.57 (d, J=2.3, 1H), 7.39 (dd, J=11.9, 4.9, 2H), 7.28-7.23 (m, 1H), 7.20-7.13 (m, 2H), 3.09 (d, J=11.8, 2H), 2.99-2.88 (m, 2H), 2.70 (dd, J=8.9, 6.9, 2H), 2.27-2.13 (m, 1H), 2.08 (m, 2H), 1.93 (d, J=11.5, 2H), 1.79 (m, 2H), 1.64 (s, 2H).

Examples 76 to 80 were prepared using methods analogous to those described for Example 45.

Example 76

1-[5-(Benzothiazol-2-yloxy)-benzofuran-2-ylm-ethyl]-piperidine-4-carboxylic acid

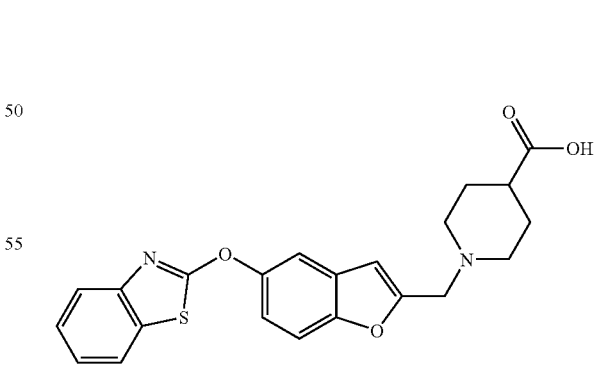

MS (ESI): mass calcd. for C$_{22}$H$_{20}$N$_2$O$_4$S, 408.1; m/z found, 409.0 [M+H]$^+$. $^1$H NMR (400 MHz, CDCl$_3$): 7.72 (d, J=7.6, 1H), 7.66 (d, J=7.2, 1H), 7.55 (d, J=2.4, 1H), 7.51 (d, J=8.9, 1H), 7.40-7.34 (m, 1H), 7.30-7.22 (m, 2H), 6.81 (s, 1H), 3.95 (s, 2H), 3.11 (s, 2H), 2.66-2.29 (m, 3H), 2.17-1.89 (m, 4H), the carboxylate proton was not detected.

Example 77

1-[6-(Benzothiazol-2-yloxy)-benzofuran-2-ylmethyl]-piperidine-4-carboxylic acid

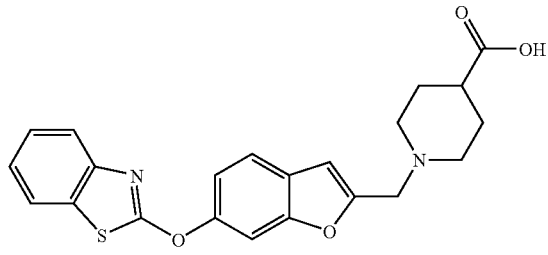 [SMILES: O=C(O)C1CCN(Cc2cc3ccc(Oc4nc5ccccc5s4)cc3o2)CC1]

MS (ESI): mass calcd. for $C_{22}H_{20}N_2O_4S$, 408.1; m/z found, 409.0 [M+H]$^+$. $^1$H NMR (400 MHz, CDCl$_3$): 7.73 (d, J=7.6, 1H), 7.67 (d, J=8.0, 1H), 7.60-7.49 (m, 2H), 7.43-7.33 (m, 1H), 7.30-7.26 (m, 1H), 7.24 (dd, J=8.5, 2.2, 1H), 6.72 (s, 1H), 3.84 (s, 2H), 3.15-2.93 (m, 2H), 2.48-2.23 (m, 3H), 2.01-1.77 (m, 4H), the carboxylate proton was not detected.

Example 78

{1-[6-(Benzothiazol-2-yloxy)-benzofuran-2-ylmethyl]-piperidin-4-yl}-acetic acid formate

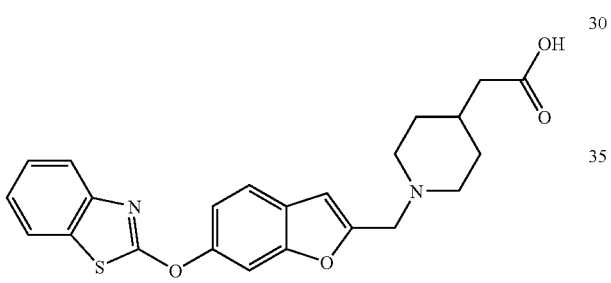

MS (ESI): mass calcd. for $C_{23}H_{22}N_2O_4S$, 422.1; m/z found, 423.1 [M+H]$^+$. $^1$H NMR (400 MHz, CDCl$_3$): 7.73 (d, J=8.0, 1H), 7.67 (d, J=7.9, 1H), 7.61-7.49 (m, 2H), 7.38 (s, 1H), 7.30-7.17 (m, 2H), 6.86 (s, 1H), 4.06 (s, 2H), 3.30 (s, 2H), 2.53-2.38 (m, 2H), 2.32 (s, 2H), 1.88-1.67 (m, 5H).

Example 79

{4-[6-(Benzothiazol-2-yloxy)-benzofuran-2-ylmethyl]-piperazin-1-yl}-acetic acid formate

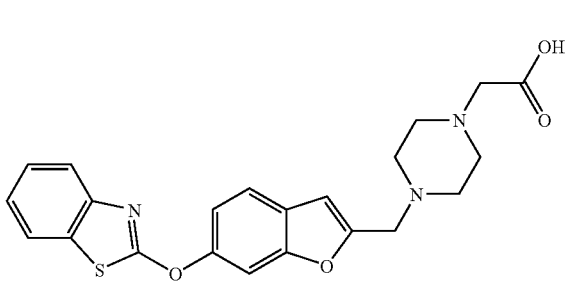 [SMILES: O=C(O)CN1CCN(Cc2cc3ccc(Oc4nc5ccccc5s4)cc3o2)CC1]

MS (ESI): mass calcd. for $C_{22}H_{21}N_3O_4S$, 423.1; m/z found, 424.0 [M+H]$^+$. $^1$H NMR (400 MHz, CDCl$_3$): 7.73 (d, J=7.6, 1H), 7.66 (s, 1H), 7.56 (d, J=8.5, 2H), 7.39 (s, 1H), 7.31-7.18 (m, 2H), 6.65 (s, 1H), 3.76 (s, 2H), 3.59 (s, 1H), 3.37 (s, 2H), 3.09 (s, 4H), 2.81 (s, 4H).

Example 80

1-{2-[6-(Benzothiazol-2-yloxy)-benzofuran-3-yl]-ethyl}-piperidine-4-carboxylic acid

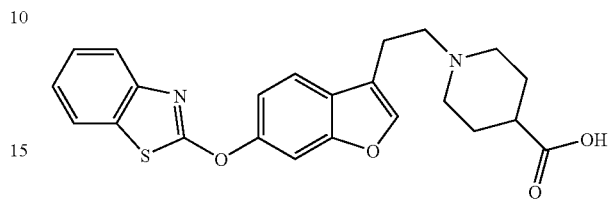

MS (ESI): mass calcd. for $C_{23}H_{22}N_2O_4S$, 422.5; m/z found, 423.0 [M+H]$^+$. $^1$H NMR (500 MHz, DMSO-d$_6$): 7.93-7.91 (m, 2H), 7.77-7.75 (m, 2H), 7.68 (d, J=7.5, 1H), 7.44-7.42 (m, 1H), 7.36-7.31 (m, 2H), 2.91-2.83 (m, 4H), 2.61-2.58 (m, 2H), 2.02-1.96 (m, 3H), 1.77-1.75 (m, 2H), 1.57-1.52 (m, 2H), the carboxylate proton was not detected.

Example 81 meso-endo-{8-[6-(Benzothiazol-2-yloxy)-benzofuran-2-ylmethyl]-8-aza-bicyclo[3.2.1]oct-3-ylamino}-acetic acid

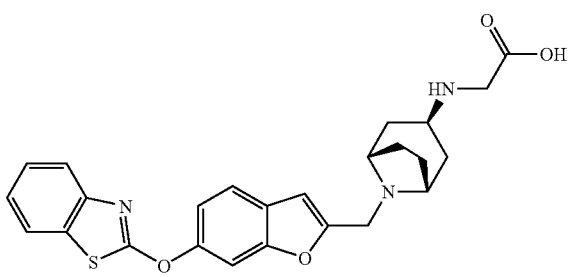 [SMILES: O=C(O)CN[C@H]1C[C@H]2CC[C@@H](C1)N2Cc1cc2ccc(Oc3nc4ccccc4s3)cc2o1]

To a solution ({8-[6-(benzothiazol-2-yloxy)-benzofuran-2-ylmethyl]-8-aza-bicyclo[3.2.1]oct-3-yl}-tert-butoxycarbonyl)-amino)-acetic acid tert-butyl ester (186 mg, 0.3 mmol) in DCM (3 mL) was added TFA (1.3 mL, 1.92 g, 17 mmol) and the reaction mixture was stirred (rt, 12 h). The reaction mixture was neutralized to pH 7 with 1 M NaOH and extracted with DCM:isopropanol (10:1, 3×30 mL). The organic layers were combined, dried, filtered and concentrated in vacuo. The resulting residue was suspended in DMF (5 mL) and a solid is collected and dried to afford the title compound as colorless crystals (22 mg, 15%). MS (ESI): mass calcd. for $C_{25}H_{25}N_3O_4S$, 463.2; m/z found, 464.1 [M+H]$^+$. $^1$H NMR (400 MHz, DMSO-d$_6$): 7.92 (d, J=7.4, 1H), 7.79 (s, 1H), 7.69 (d, J=8.4, 2H), 7.43 (s, 1H), 7.32 (d, J=8.3, 2H), 6.85 (s, 1H), 3.60 (s, 3H), 3.45-3.27 (m, 4H), 2.23-2.07 (m, 2H), 2.08-1.94 (m, 2H), 1.84 (s, 2H), 1.58-1.41 (m, 2H), 1.04 (d, J=6.1, 1H).

Example 82

2-(2-Piperidin-1-ylmethyl-benzofuran-5-yloxy)-benzothiazole formate

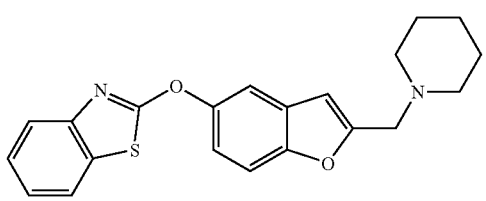

To a suspension of K$_2$CO$_3$ (33 mg, 0.24 mmol) in MeCN (1 mL) was added 2-(2-chloromethyl-benzofuran-5-yloxy)-benzothiazole (27 mg, 0.08 mmol) and piperidine (5 mg, 0.09 mmol) and the reaction mixture was warmed (55° C., 12 h). The reaction mixture was filtered and concentrated and the resultant residue was purified by reverse phase HPLC to afford the title compound (22 mg, 67%). MS (ESI): mass calcd for C$_{21}$H$_{20}$N$_2$O$_2$S, 364.1; m/z found 365.1 [M+H]$^+$. $^1$H NMR (400 MHz, CD$_3$OD): 7.75 (d, J=8.0, 1H), 7.64 (d, J=8.1, 1H), 7.62-7.55 (m, 2H), 7.40 (dt, J=8.0, 1.3, 1H), 7.35-7.18 (m, 2H), 6.85 (5, 1H), 3.85 (5, 2H), 2.76-2.53 (m, 4H), 1.73-1.60 (m, 4H), 1.56-1.42 (m, 2H).

With modifications as stated for each specific Example, if any, Examples 83 to 114 were prepared using methods analogous to those described for Example 82.

Example 83 meso-endo-N-{8-[5-(Benzothiazol-2-yloxy)-benzofuran-2-ylmethyl]-8-aza-bicyclo[3.2.1]oct-3-yl}-acetamide formate

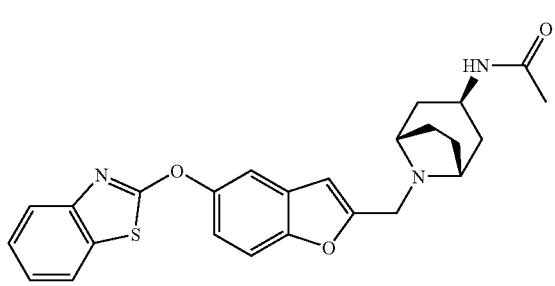 [SMILES: CC(=O)N[C@H]1C[C@H]2CC[C@@H](C1)N2Cc1cc2cc(Oc3nc4ccccc4s3)ccc2o1]

MS (ESI): mass calcd for C$_{25}$H$_{25}$N$_3$O$_3$S, 447.2; m/z found, 448.1 [M+H]$^+$. $^1$H NMR (400 MHz, CD$_3$OD): 7.77 (d, J=8.0, 1H), 7.67-7.61 (m, 3H), 7.42 (dt, J=8.0, 1.3, 1H), 7.37-7.27 (m, 2H), 6.99 (5, 1H), 4.08 (5, 2H), 3.93 (t, J=6.7, 1H), 3.66-3.56 (m, 2H), 2.35-2.23 (m, 4H), 2.23-2.14 (m, 2H), 1.97 (5, 3H), 1.95-1.87 (m, 2H).

Example 84

4-Fluoro-2-(2-piperidin-1-ylmethyl-benzofuran-5-yloxy)-benzothiazole formate

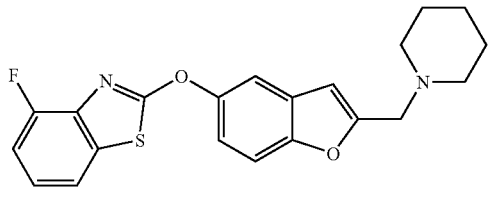 [SMILES: Fc1cccc2sc(Oc3ccc4oc(CN5CCCCC5)cc4c3)nc12]

MS (ESI): mass calcd for C$_{21}$H$_{19}$N$_2$O$_2$SF, 382.1; m/z found, 383.1 [M+H]$^+$. $^1$H NMR (400 MHz, CD$_3$OD): 7.64 (d, J=2.4, 1H), 7.59 (d, J=8.9, 1H), 7.55 (dd, J=8.0, 1.0, 1H), 7.35-7.23 (m, 2H), 7.16 (ddd, J=10.7, 8.2, 1.0, 1H), 6.87 (s, 1H), 3.89 (s, 2H), 2.83-2.53 (m, 4H), 1.76-1.60 (m, 4H), 1.57-1.44 (m, 2H).

Example 85 meso-endo-N-{8-[5-(4-Fluoro-benzothiazol-2-yloxy)-benzofuran-2-ylmethyl]-8-aza-bicyclo[3.2.1]oct-3-yl}-acetamide

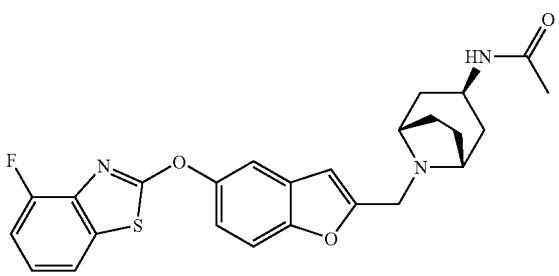 [SMILES: CC(=O)N[C@H]1C[C@H]2CC[C@@H](C1)N2Cc1cc2cc(Oc3nc4c(F)cccc4s3)ccc2o1]

MS (ESI): mass calcd for C$_{25}$H$_{24}$N$_3$O$_3$SF, 465.1; m/z found, 466.1 [M+H]$^+$. $^1$H NMR (400 MHz, CD$_3$OD): 7.68 (d, J=2.3, 1H), 7.63 (d, J=8.9, 1H), 7.58 (dd, J=8.0, 1.0, 1H), 7.36 (dd, J=8.9, 2.5, 1H), 7.30 (dt, J=8.0, 4.7, 1H), 7.18 (ddd, J=10.7, 8.2, 1.0, 1H), 6.99 (s, 1H), 4.08 (s, 2H), 3.98-3.87 (m, 1H), 3.66-3.51 (m, 2H), 2.37-2.22 (m, 4H), 2.22-2.10 (m, 2H), 1.96 (5, 3H), 1.95-1.84 (m, 2H).

Example 86

2-(2-Piperidin-1-ylmethyl-benzofuran-5-yloxy)-thiazolo[4,5-b]pyridine

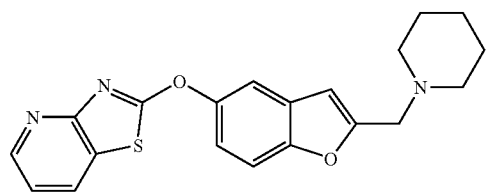 [SMILES: c1cnc2nc(Oc3ccc4oc(CN5CCCCC5)cc4c3)sc2c1]

MS (ESI): mass calcd for C$_{20}$H$_{19}$N$_3$O$_2$S, 365.1; m/z found, 366.1 [M+H]$^+$. $^1$H NMR (400 MHz, CD$_3$OD): 8.50 (dd, J=4.9, 1.6, 1H), 8.30 (dd, J=8.0, 1.6, 1H), 7.67 (d, J=2.3, 1H), 7.61 (d, J=8.8, 1H), 7.39-7.26 (m, 2H), 6.83 (s, 1H), 3.75 (s, 2H), 2.65-2.45 (m, 4H), 1.73-1.58 (m, 4H), 1.56-1.42 (m, 2H).

Example 87 meso-endo-N-{8-[5-(Thiazolo[4,5-b]pyridin-2-yloxy)-benzofuran-2-ylmethyl]-8-aza-bicyclo[3.2.1]oct-3-yl}-acetamide

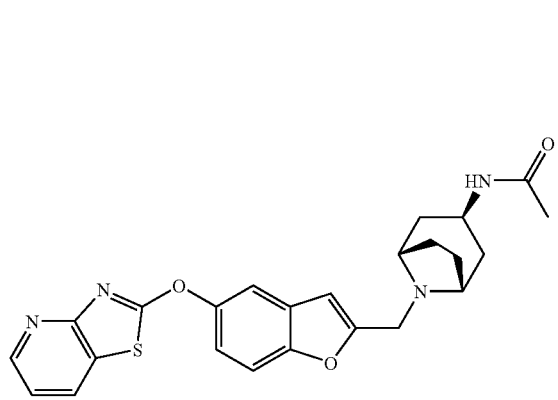 [SMILES: CC(=O)N[C@H]1C[C@H]2CC[C@@H](C1)N2Cc1cc2cc(Oc3nc4ncccc4s3)ccc2o1]

MS (ESI): mass calcd for $C_{24}H_{24}N_4O_3S$, 448.16; m/z found, 449.10 [M+H]$^+$. $^1$H NMR (400 MHz, CD$_3$OD): 8.50 (d, J=4.9, 1.6, 1H), 8.30 (dd, J=8.0, 1.6, 1H), 7.67 (d, J=2.3, 1H), 7.61 (d, J=8.8, 1H), 7.38-7.27 (m, 2H), 6.84 (s, 1H), 4.00-3.82 (m, 1H), 3.77 (s, 2H), 2.30-2.09 (m, 4H), 2.09-1.98 (m, 2H), 1.96 (s, 3H), 1.83-1.67 (m, 2H).

Example 88

1-[5-(Thiazolo[4,5-b]pyridin-2-yloxy)-benzofuran-2-ylmethyl]-piperidine-4-carboxylic acid amide

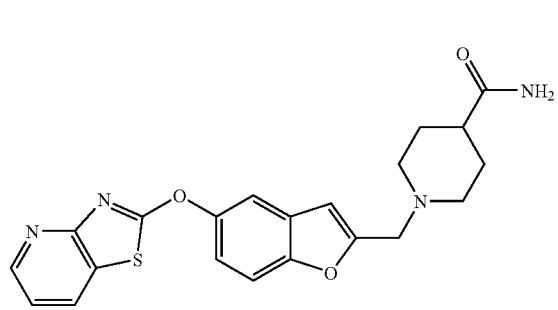 [SMILES: NC(=O)C1CCN(Cc2cc3cc(Oc4nc5ncccc5s4)ccc3o2)CC1]

MS (ESI): mass calcd for $C_{21}H_{20}N_4O_3S$, 408.1; m/z found 409.1 [M+H]$^+$. $^1$H NMR (600 MHz, CDCl$_3$): 8.56 (dd, J=4.8, 1.7, 1H), 8.00 (dd, J=7.9, 1.7, 1H), 7.65-7.57 (m, 1H), 7.57-7.45 (m, 1H), 7.25 (dd, J=8.8, 2.5, 1H), 7.20 (dd, J=7.9, 4.8, 1H), 6.62 (s, 1H), 5.46 (s, 1H), 5.28 (s, 1H), 3.72 (5, 2H), 3.07-2.99 (m, 2H), 2.20-2.12 (m, 3H), 1.98-1.88 (m, 2H), 1.87-1.78 (m, 2H).

Example 89

2-{2-[4-(Pyrimidin-2-yloxy)-piperidin-1-ylmethyl]-benzofuran-5-yloxy}-thiazolo[4,5-b]pyridine MS (ESI): mass calcd for $C_{24}H_{21}N_5O_3S$, 459.1; m/z found, 460.1 [M+H]$^+$. $^1$H NMR (600 MHz, CDCl$_3$): 8.56 (dd, J=4.8, 1.7, 1H), 8.50-8.49 (m, 2H), 8.00 (dd, J=7.9, 1.7, 1H), 7.60-7.59 (m, 1H), 7.54-7.51 (m, 1H), 7.26-7.23 (m, 1H), 7.19 (dd, J=7.9, 4.8, 1H), 6.91-6.89 (m, 1H), 6.64 (s, 1H), 5.13-5.05 (m, 1H), 3.75 (s, 2H), 2.91-2.82 (m, 2H), 2.56-2.46 (m, 2H), 2.15-2.06 (m, 2H), 2.03-1.93 (m, 2H).

Example 90

1-{5-[5-(Thiazolo[4,5-b]pyridin-2-yloxy)-benzofuran-2-ylmethyl]-hexahydro-pyrrolo[3,4-c]pyrrol-2-yl}-ethanone MS (ESI): mass calcd for $C_{23}H_{22}N_4O_3S$, 434.1; m/z found, 435.1 [M+H]$^+$. $^1$H NMR (600 MHz, CDCl$_3$): 8.56 (dd, J=4.8, 1.7, 1H), 8.01 (dd, J=7.9, 1.6, 1H), 7.61-7.58 (m, 1H), 7.52-7.47 (m, 1H), 7.24 (dd, J=6.9, 3.3, 1H), 7.20 (dd, J=7.9, 4.8, 1H), 6.60 (5, 1H), 3.81-3.76 (m, 2H), 3.70-3.63 (m, 2H), 3.51-3.44 (m, 1H), 3.38-3.32 (m, 1H), 3.00-2.91 (m, 1H), 2.91-2.83 (m, 3H), 2.56-2.46 (m, 2H), 2.05 (5, 3H).

Example 91

5-[5-(Thiazolo[4,5-b]pyridin-2-yloxy)-benzofuran-2-ylmethyl]-hexahydro-pyrrolo[3,4-c]pyrrole-2-carboxylic acid amide

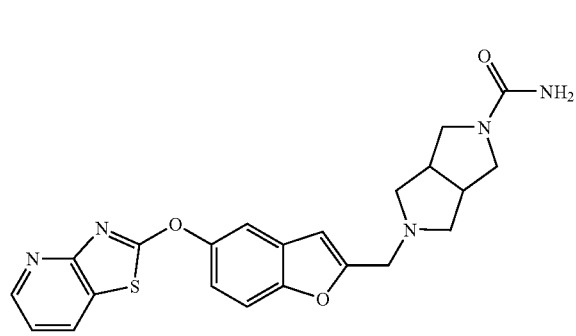 [SMILES: NC(=O)N1CC2CN(Cc3cc4cc(Oc5nc6ncccc6s5)ccc4o3)CC2C1]

MS (ESI): mass calcd for $C_{22}N_{21}N_5O_3S$, 435.1; m/z found, 436.1 [M+H]$^+$. $^1$H NMR (600 MHz, CDCl$_3$): 8.56 (dd, J=4.8, 1.6, 1H), 8.01 (dd, J=7.9, 1.7, 1H), 7.60-7.58 (m, 1H), 7.51-7.48 (m, 1H), 7.25 (dd, J=8.8, 2.5, 1H), 7.20 (dd, J=7.9, 4.8, 1H), 6.61 (s, 1H), 4.40 (s, 2H), 3.80 (s, 2H), 3.61-3.53 (m, 2H), 3.35-3.25 (m, 2H), 2.97-2.92 (m, 2H), 2.91-2.86 (m, 2H), 2.56-2.48 (m, 2H).

Example 92

2-[2-(4-Methanesulfonyl-piperidin-1-ylmethyl)-benzofuran-5-yloxy]-thiazolo[4,5-b]pyridine

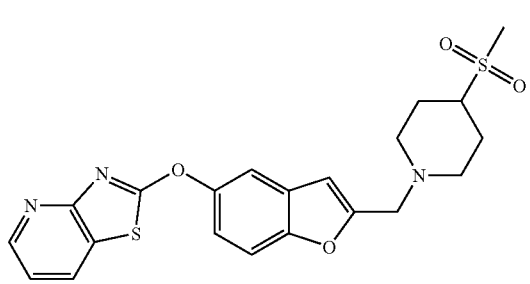 [SMILES: CS(=O)(=O)C1CCN(Cc2cc3cc(Oc4nc5ncccc5s4)ccc3o2)CC1]

MS (ESI): mass calcd for $C_{21}H_{21}N_3O_4S_2$, 443.1; m/z found, 444.1 [M+H]$^+$. $^1$H NMR (600 MHz, CDCl$_3$): 8.56 (dd, J=4.8, 1.6, 1H), 8.01 (dd, J=7.9, 1.7, 1H), 7.63-7.59 (m, 1H), 7.53-7.49 (m, 1H), 7.28-7.25 (m, 1H), 7.20 (dd, J=7.9, 4.8, 1H), 6.64 (s, 1H), 3.75 (s, 2H), 3.20-3.12 (m, 2H), 2.84-2.79 (m, 4H), 2.23-2.14 (m, 4H), 1.98-1.89 (m, 2H).

Example 93 meso-1-{8-[5-(Thiazolo[4,5-b]pyridin-2-yloxy)-benzofuran-2-ylmethyl]-3,8-diaza-bicyclo[3.2.1]oct-3-yl}-ethanone

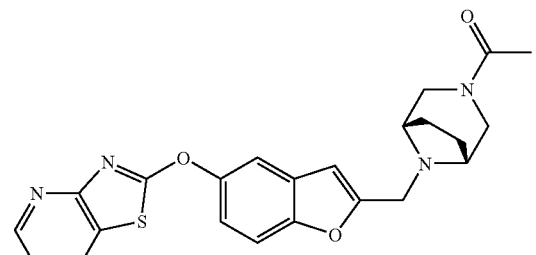

MS (ESI): mass calcd for $C_{23}H_{22}N_4O_3S$, 434.1; m/z found, 435.1 [M+H]$^+$. $^1$H NMR (500 MHz, CDCl$_3$): 8.57-8.53 (m, 1H), 8.03-7.98 (m, 1H), 7.62-7.58 (m, 1H), 7.54-7.49 (m, 1H), 7.29-7.24 (m, 1H), 7.22-7.17 (m, 1H), 6.66 (s, 1H), 4.24-4.18 (m, 1H), 3.68 (s, 2H), 3.43 (s, 2H), 3.38-3.29 (m, 2H), 2.99-2.91 (m, 1H), 2.07 (s, 3H), 2.04-1.96 (m, 2H), 1.73-1.62 (m, 2H).

Example 94 meso-8-[5-(Thiazolo[4,5-b]pyridin-2-yloxy)-benzofuran-2-ylmethyl]-3,8-diaza-bicyclo[3.2.1]octane-3-carboxylic acid amide

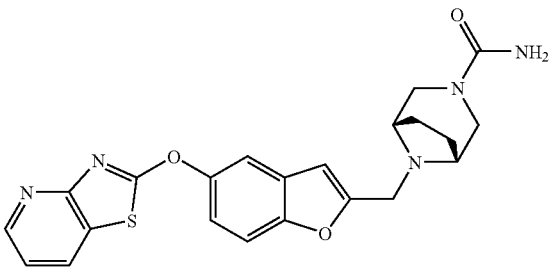 [SMILES: NC(=O)N1C[C@H]2CC[C@@H](C1)N2Cc1cc2cc(Oc3nc4ncccc4s3)ccc2o1]

MS (ESI): mass calcd for $C_{22}H_{21}N_5O_3S$, 435.1; m/z found, 436.1 [M+H]$^+$. $^1$H NMR (500 MHz, CDCl$_3$): 8.58-8.54 (m, 1H), 8.03-7.98 (m, 1H), 7.62-7.59 (m, 1H), 7.53-7.49 (m, 1H), 7.26-7.23 (m, 1H), 7.20 (dd, J=7.9, 4.9, 1H), 6.66 (s, 1H), 4.43 (s, 2H), 3.70 (s, 2H), 3.60-3.48 (m, 2H), 3.36-3.30 (m, 2H), 3.25-3.19 (m, 2H), 2.07-2.01 (m, 2H), 1.81-1.74 (m, 2H).

Example 95

(1S,4S)-1-{5-[5-(Thiazolo[4,5-b]pyridin-2-yloxy)-benzofuran-2-ylmethyl]-2,5-diaza-bicyclo[2.2.1]hept-2-yl}-ethanone

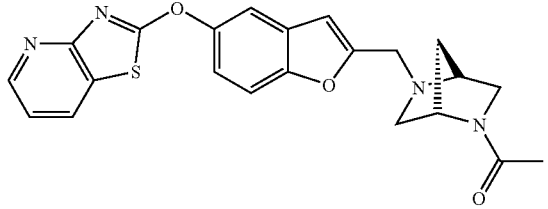

MS (ESI): mass calcd for $C_{22}H_{20}N_4O_3S$, 420.1; m/z found, 421.1 [M+H]$^+$. $^1$H NMR (500 MHz, CDCl$_3$): 8.58-8.53 (m, 1H), 8.03-7.98 (m, 1H), 7.62-7.58 (m, 1H), 7.52-7.46 (m, 1H), 7.26-7.23 (m, 1H), 7.22-7.17 (m, 1H), 6.65-6.60 (m, 1H), 4.82-4.78 (m, 0.5H), 4.27-4.22 (m, 0.5H), 3.93-3.90 (m, 1H), 3.90-3.87 (m, 1H), 3.81-3.75 (m, 0.5H), 3.69-3.65 (m, 1H), 3.63-3.58 (m, 0.5H), 3.38-3.33 (m, 0.5H), 3.33-3.27 (m, 0.5H), 3.19-3.12 (m, 0.5H), 2.98-2.88 (m, 1H), 2.70-2.64 (m, 0.5H), 2.10 (s, 1H), 2.00 (s, 2H), 1.92-1.81 (m, 1H), 1.76-1.65 (m, 1H).

Example 96

1-{1-[5-(Thiazolo[4,5-b]pyridin-2-yloxy)-benzofuran-2-ylmethyl]-piperidin-4-yl}-pyrrolidin-2-one

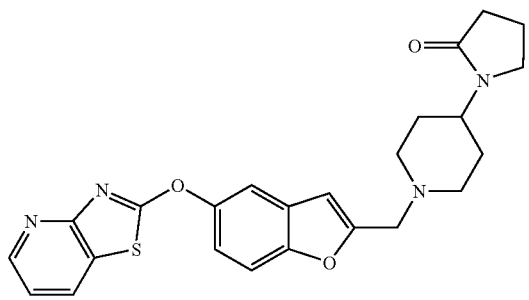 [SMILES: O=C1CCCN1C1CCN(Cc2cc3cc(Oc4nc5ncccc5s4)ccc3o2)CC1]

MS (ESI): mass calcd for $C_{24}H_{24}N_4O_3S$, 448.2; m/z found, 449.1 [M+H]$^+$. $^1$H NMR (500 MHz, CDCl$_3$): 8.59-8.54 (m, 1H), 8.02-7.97 (m, 1H), 7.61-7.58 (m, 1H), 7.53-7.49 (m, 1H), 7.26-7.24 (m, 1H), 7.19 (dd, J=7.9, 4.8, 1H), 6.63 (s, 1H), 4.07-3.95 (m, 1H), 3.70 (s, 2H), 3.40-3.31 (m, 2H), 3.08-2.99 (m, 2H), 2.44-2.35 (m, 2H), 2.28-2.16 (m, 2H), 2.05-1.93 (m, 2H), 1.86-1.75 (m, 2H), 1.72-1.63 (m, 2H).

Example 97

2-(2-Morpholin-4-ylmethyl-benzofuran-5-yloxy)-thiazolo[4,5-b]pyridine

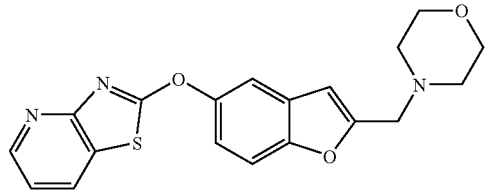 [SMILES: c1cnc2nc(Oc3ccc4oc(CN5CCOCC5)cc4c3)sc2c1]

MS (ESI): mass calcd. for $C_{19}H_{17}N_3O_3S$, 367.1; m/z found, 368.1 [M+H]$^+$. $^1$H NMR (400 MHz, CDCl$_3$): 8.55 (dd, J=4.8, 1.7, 1H), 8.00 (dd, J=7.9, 1.6, 1H), 7.60 (d, J=2.4, 1H), 7.51 (d, J=8.9, 1H), 7.25 (dd, J=8.9, 2.5, 1H), 7.19 (dd, J=7.9, 4.8, 1H), 6.64 (d, J=0.6, 1H), 3.80-3.73 (m, 4H), 3.70 (s, 2H), 2.61-2.50 (m, 4H).

Example 98

(3S)-2-[2-(3-Methyl-morpholin-4-ylmethyl)-benzofuran-5-yloxy]-thiazolo[4,5-b]pyridine

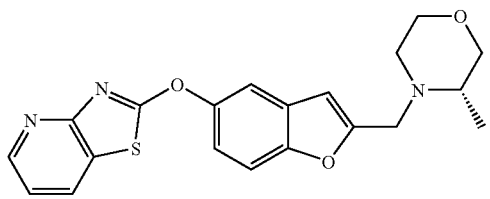 [SMILES: C[C@H]1COCCN1Cc1cc2cc(Oc3nc4ncccc4s3)ccc2o1]

MS (ESI): mass calcd. for $C_{20}H_{19}N_3O_3S$, 381.1; m/z found, 382.0 [M+H]$^+$. $^1$H NMR (400 MHz, CDCl$_3$): 8.55 (dd, J=4.8, 1.7, 1H), 7.99 (dd, J=7.9, 1.7, 1H), 7.59 (d, J=2.4, 1H), 7.50 (d, J=8.8, 1H), 7.25 (dd, J=8.8, 2.5, 1H), 7.18 (dd, J=7.9, 4.8, 1H), 6.63 (s, 1H), 4.03 (d, J=14.8, 1H), 3.80 (dt, J=11.3, 2.5, 1H), 3.77-3.58 (m, 3H), 3.38-3.24 (m, 1H), 2.74 (dt, J=11.7, 2.5, 1H), 2.61-2.40 (m, 2H), 1.11 (d, J=6.3, 3H).

Example 99

(1S,4S)-2-[2-(2-Oxa-5-aza-bicyclo[2.2.1]hept-5-ylmethyl)-benzofuran-5-yloxy]-thiazolo[4,5-b]pyridine

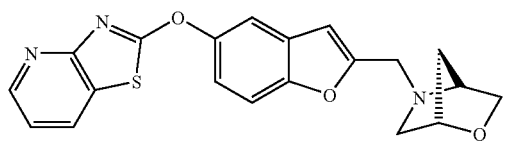

MS (ESI): mass calcd. for $C_{20}H_{17}N_3O_3S$, 379.1; m/z found, 380.1 [M+H]$^+$. $^1$H NMR (400 MHz, CDCl$_3$): 8.55 (dd, J=4.8, 1.6, 1H), 7.99 (dd, J=7.9, 1.7, 1H), 7.59 (d, J=2.4, 1H), 7.50 (d, J=8.8, 1H), 7.24 (dd, J=8.8, 2.5, 1H), 7.18 (dd, J=7.9, 4.8, 1H), 6.62 (d, J=0.6, 1H), 4.44 (s, 1H), 4.13 (d, J=8.0, 1H), 3.92 (q, J=14.4, 2H), 3.68 (dd, J=8.0, 1.7, 1H), 3.59 (s, 1H), 3.01 (dd, J=10.2, 1.6, 1H), 2.71 (d, J=10.2, 1H), 1.94 (dd, J=9.9, 1.9, 1H), 1.83-1.72 (m, 1H).

Example 100

(1S,4S)-5-[5-(Thiazolo[4,5-b]pyridin-2-yloxy)-benzofuran-2-ylmethyl]-2,5-diaza-bicyclo[2.2.1]heptane-2-carboxylic acid amide

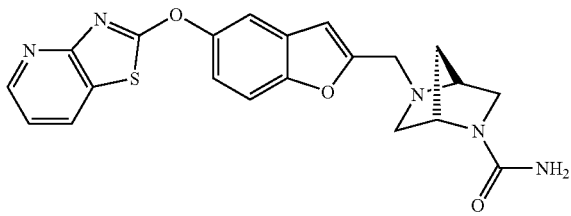

MS (ESI): mass calcd. for $C_{21}H_{19}N_5O_3S$, 421.1; m/z found, 422.1 [M+H]$^+$. $^1$H NMR (400 MHz, CDCl$_3$): 8.55 (dd, J=4.8, 1.6, 1H), 8.00 (dd, J=7.9, 1.6, 1H), 7.58 (d, J=2.5, 1H), 7.49 (d, J=8.9, 1H), 7.24 (dd, J=8.9, 2.5, 1H), 7.19 (dd, J=7.9, 4.8, 1H), 6.62 (s, 1H), 4.54 (s, 2H), 3.96-3.84 (m, 2H), 3.71-3.60 (m, 1H), 3.57 (s, 1H), 3.27 (dd, J=9.1, 2.1, 1H), 3.27 (dd, J=9.1, 2.1, 1H), 3.02 (dd, J=9.7, 1.8, 1H), 2.86 (d, J=9.7, 1H), 1.93 (d, J=9.8, 1H), 1.78 (d, J=9.8, 1H).

Example 101

(1R,4R)-5-[5-(Thiazolo[4,5-b]pyridin-2-yloxy)-benzofuran-2-ylmethyl]-2,5-diaza-bicyclo[2.2.1]heptane-2-carboxylic acid amide

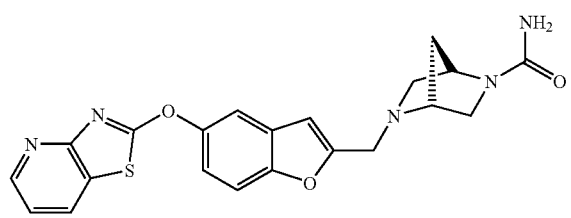

MS (ESI): mass calcd. for $C_{21}H_{19}N_5O_3S$, 421.1; m/z found, 422.1 [M+H]$^+$. $^1$H NMR (400 MHz, CDCl$_3$): 8.55 (dd, J=4.8, 1.7, 1H), 7.99 (dd, J=7.9, 1.7, 1H), 7.59 (d, J=2.4, 1H), 7.50 (d, J=8.8, 1H), 7.30-7.21 (m, 1H), 7.21-7.14 (m, 1H), 6.63 (s, 1H), 4.09-3.99 (m, 1H), 3.85-3.75 (m, 1H), 3.75-3.60 (m, 3H), 3.37-3.25 (m, 1H), 2.80-2.69 (m, 1H), 2.62-2.45 (m, 2H), 1.13 (d, J=6.3, 3H).

Example 102

(1R,4R)-1-{5-[5-(Thiazolo[4,5-b]pyridin-2-yloxy)-benzofuran-2-ylmethyl]-2,5-diaza-bicyclo[2.2.1]hept-2-yl}-ethanone

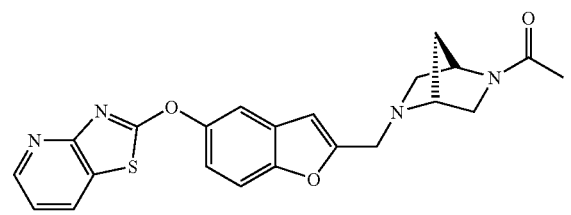

MS (ESI): mass calcd. for $C_{22}H_{20}N_4O_3S$, 420.1; m/z found, 421.0 [M+H]$^+$. $^1$H NMR (400 MHz, CD$_3$OD, mixture of rotamers 1:1): 8.55 (dd, J=4.8, 1.6, 1H), 8.00 (dt, J=7.9, 1.5, 1H), 7.60 (dd, J=3.8, 2.5, 1H), 7.49 (d, J=8.8, 1H), 7.25 (dt, J=8.9, 2.3, 1H), 7.19 (ddd, J=7.9, 4.8, 0.9, 1H), 6.65-6.58 (m, 1H), 4.80 (s, 0.5H), 4.26 (s, 0.5H), 3.91 (s, 1H), 3.88 (s, 1H), 3.78 (d, J=11.6, 0.5H), 3.67 (s, 1H), 3.60 (d, J=9.5, 0.5H), 3.36 (dd, J=9.5, 2.3, 0.5H), 3.31 (dd, J=11.6, 1.9, 0.5H), 3.15 (dd, J=9.6, 2.1, 0.5H), 2.99-2.83 (m, 1H), 2.69-2.64 (m, 0.5H), 2.09 (s, 1H), 2.01 (d, J=9.8, 2H), 1.90-1.77 (m, J=22.6, 9.9, 1.5H), 1.70 (d, J=10.0, 0.5H).

Example 103 meso-endo-N-{8-[5-(Thiazolo[4,5-b]pyridin-2-yloxy)-benzofuran-2-ylmethyl]-8-aza-bicyclo[3.2.1]oct-3-yl}-urea

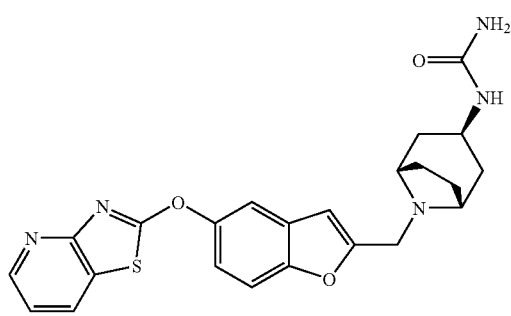 [SMILES: NC(=O)N[C@H]1C[C@H]2CC[C@@H](C1)N2Cc1cc2cc(Oc3nc4ncccc4s3)ccc2o1]

MS (ESI): mass calcd. For $C_{23}H_{23}N_5O_3S$, 449.2; m/z found, 450.1 [M+H]$^+$. $^1$H NMR (400 MHz, CDCl$_3$): 8.54 (d, J=4.7, 1H), 8.00 (dd, J=7.9, 1.4, 1H), 7.55 (s, 1H), 7.49 (d, J=8.8, 1H), 7.24-7.15 (m, 2H), 6.62 (s, 1H), 5.54 (s, 1H), 4.79 (s, 2H), 3.95-3.78 (m, 1H), 3.66 (s, 2H), 3.26 (s, 2H), 2.34-2.14 (m, 2H), 2.13-1.99 (m, 2H), 1.97-1.80 (m, 2H), 1.68 (d, J=14.3, 2H).

Example 104 meso-exo-N-{8-[5-(Thiazolo[4,5-b]pyridin-2-yloxy)-benzofuran-2-ylmethyl]-8-aza-bicyclo[3.2.1]oct-3-yl}-acetamide

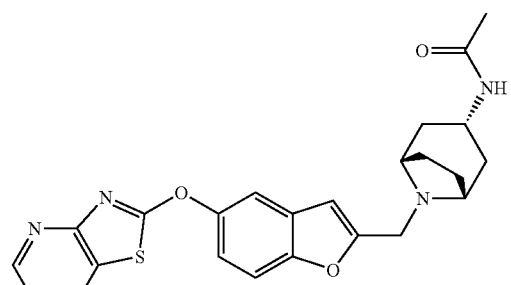

MS (ESI): mass calcd. for $C_{24}H_{24}N_4O_3S$, 448.2; m/z found, 449.1 [M+H]$^+$. $^1$H NMR (400 MHz, CDCl$_3$): 8.56 (dd, J=4.8, 1.7, 1H), 8.00 (dd, J=7.9, 1.7, 1H), 7.59 (d, J=2.5, 1H), 7.50 (d, J=8.8, 1H), 7.25-7.17 (m, 2H), 5.16 (s, 1H), 4.25-4.03 (m, 1H), 3.68 (s, 2H), 3.41-3.25 (m, 2H), 2.16-1.99 (m, 2H), 1.91 (s, 3H), 1.89-1.71 (m, 4H), 1.65-1.52 (m, 3H).

Example 105

1-[5-(Benzothiazol-2-yloxy)-benzofuran-2-ylmethyl]-piperidine-4-carboxylic acid amide

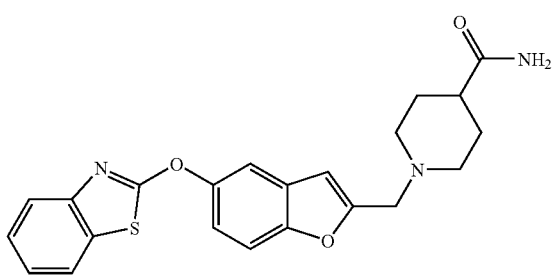 [SMILES: NC(=O)C1CCN(Cc2cc3cc(Oc4nc5ccccc5s4)ccc3o2)CC1]

MS (ESI): mass calcd. for $C_{22}H_{21}N_3O_3S$, 407.1; m/z found, 408.0 [M+H]$^+$. $^1$H NMR (400 MHz, CDCl$_3$): 7.72 (d, J=8.0, 1H), 7.65 (d, J=7.8, 1H), 7.51 (dd, J=5.4, 3.0, 2H), 7.37 (t, J=7.4, 1H), 7.29-7.17 (m, 2H), 6.61 (5, 1H), 5.61 (5, 2H), 3.70 (5, 2H), 3.08-2.91 (m, 2H), 2.24-2.03 (m, 3H), 1.99-1.66 (m, 4H).

Example 106 meso-exo-N-{8-[6-(Thiazolo[4,5-b]pyridin-2-yloxy)-benzofuran-2-ylmethyl]-8-aza-bicyclo[3.2.1]oct-3-yl}-acetamide

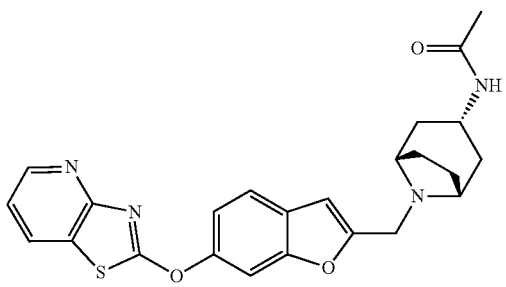 [SMILES: CC(=O)N[C@@H]1C[C@H]2CC[C@@H](C1)N2Cc1cc2ccc(Oc3nc4ncccc4s3)cc2o1]

With respect to the synthesis procedure as described for Example 82, a solvent of 1:5 DMF/CH$_3$CN with K$_2$CO$_3$ at 50° C. was used instead of MeCN with K$_2$CO$_3$ at 55° C. MS (ESI): mass calcd. for $C_{24}H_{24}N_4O_3S$, 448.1; m/z found, 449.1 [M+H]$^+$. $^1$H NMR (500 MHz, CDCl$_3$): 8.56 (dd, J=4.8, 1.6, 1H), 8.02 (dd, J=7.9, 1.6, 1H), 7.56 (d, J=1.7, 1H), 7.54 (d, J=8.5, 1H), 7.25 (dd, J=8.4, 2.2, 1H), 7.20 (dd, J=8.4, 2.2, 1H), 6.61 (d, J=2.2, 1H), 5.48 (d, J=8.3, 1H), 4.23-4.08 (m, 1H), 3.67 (s, 2H), 3.37-3.30 (m, 2H), 2.10-2.02 (m, 2H), 1.94 (s, 3H), 1.88-1.81 (m, 2H), 1.80-1.74 (m, 2H), 1.61-1.52 (m, 2H).

Example 107

(1R,4R)-1-{5-[6-(Thiazolo[4,5-b]pyridin-2-yloxy)-benzofuran-2-ylmethyl]-2,5-diaza-bicyclo[2.2.1]hept-2-yl}-ethanone

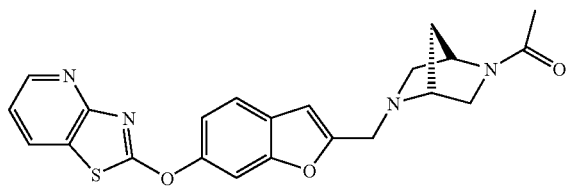

With respect to the synthesis procedure as described for Example 82, a solvent of 1:5 DMF/CH$_3$CN with K$_2$CO$_3$ at rt was used instead of MeCN with K$_2$CO$_3$ at 55° C. MS (ESI): mass calcd. for $C_{22}H_{20}N_4O_3S$, 420.1; m/z found, 421.1 [M+H]$^+$. $^1$H NMR (500 MHz, CDCl$_3$, mixture of rotamers): 8.56 (dd, J=4.8, 1.6, 1H), 8.04-7.99 (m, 1H), 7.58-7.53 (m, 2H), 7.28-7.24 (m, 1H), 7.22-7.18 (m, 1H), 6.65-6.61 (m, 1H), 4.80 (s, 0.5H), 4.26 (s, 0.5H), 3.91 (s, 1H), 3.88 (s, 1H), 3.80-3.76 (m, 0.5H), 3.70-3.66 (m, 1H), 3.62-3.59 (m, 0.5H), 3.37 (dd, J=9.5, 2.3, 0.5H), 3.31 (dd, J=11.6, 1.8, 0.5H), 3.16 (dd, J=9.7, 2.1, 0.5H), 2.96-2.90 (m, 1H), 2.68 (dd, J=9.7, 0.9, 0.5H), 2.10 (s, 1.3H), 2.03-2.00 (m, 0.5H), 2.00 (s, 1.7H), 1.89 (d, J=10.0, 0.5H), 1.83 (d, J=9.8, 0.5H), 1.72-1.68 (m, 0.5H).

Example 108

1-{1-[6-(Thiazolo[4,5-b]pyridin-2-yloxy)-benzofuran-2-ylmethyl]-piperidin-4-yl}-pyrrolidin-2-one formate

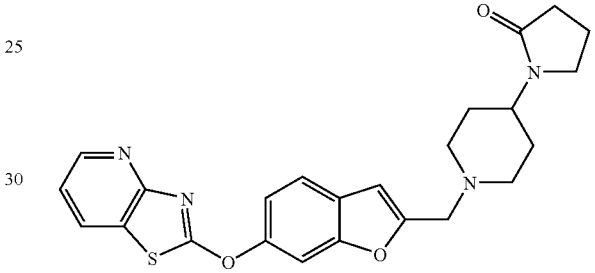

With respect to the synthesis procedure as described for Example 82, a solvent of DMF with K$_2$CO$_3$ at 50° C. was used instead of MeCN with K$_2$CO$_3$ at 55° C. MS (ESI): mass calcd. for $C_{24}H_{24}N_4O_3S$, 448.1; m/z found, 449.1 [M+H]$^+$. $^1$H NMR (400 MHz, CD$_3$OD): 8.49 (s, 1H), 8.30 (dd, J=8.0, 1.6, 1H), 7.74 (d, J=8.5, 1H), 7.72-7.70 (m, 1H), 7.37-7.32 (m, 2H), 7.07 (s, 1H), 4.20 (s, 2H), 4.06-3.94 (m, 1H), 3.45 (t, J=7.0, 2H), 3.41-3.34 (m, 2H), 2.83-2.71 (m, 2H), 2.37 (t, J=8.1, 2H), 2.08-1.94 (m, 4H), 1.86-1.76 (m, 2H).

Example 109

(1S,4S)-2-[2-(2-Oxa-5-aza-bicyclo[2.2.1]hept-5-ylmethyl)-benzofuran-6-yloxy]-thiazolo[4,5-b]pyridine formate

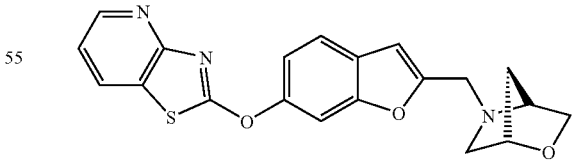

With respect to the synthesis procedure as described for Example 82, a solvent of DMF with K$_2$CO$_3$ at 50° C. was used instead of MeCN with K$_2$CO$_3$ at 55° C. MS (ESI): mass calcd. for $C_{20}H_{17}N_3O_3S$, 379.1; m/z found, 380.1 [M+H]$^+$. $^1$H NMR (400 MHz, CD$_3$OD): 8.53-8.45 (m, 1H), 8.30 (dd, J=8.0, 1.5, 1H), 7.76-7.69 (m, 2H), 7.37-7.30 (m, 2H), 7.14 (s, 1H), 4.63-4.59 (m, 1H), 4.50 (d, J=14.4, 1H), 4.41 (d, J=14.4, 1H), 4.25-4.16 (m, 2H), 3.79 (dd, J=9.4, 1.8, 1H), 3.30-3.24 (m, 2H), 2.25-2.16 (m, 1H), 2.07-2.01 (m, 1H).

Example 110

2-[2-(Tetrahydro-furo[3,4-c]pyrrol-5-ylmethyl)-benzofuran-6-yloxy]-thiazolo[4,5-b]pyridine formate

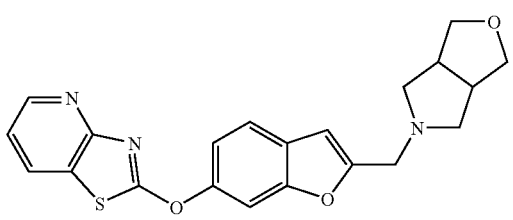 [SMILES: c1cnc2nc(Oc3ccc4cc(CN5CC6COCC6C5)oc4c3)sc2c1]

With respect to the synthesis procedure as described for Example 82, a solvent of DMF with $K_2CO_3$ at 50° C. was used instead of MeCN with $K_2CO_3$ at 55° C. MS (ESI): mass calcd. for $C_{21}H_{19}N_3O_3S$, 393.1; m/z found, 394.1 [M+H]$^+$. $^1$H NMR (400 MHz, CD$_3$OD): 8.51-8.45 (m, 1H), 8.30 (dd, J=8.0, 1.6, 1H), 7.76-7.69 (m, 2H), 7.37-7.31 (m, 2H), 7.09 (s, 1H), 4.35 (s, 2H), 3.77 (d, J=8.4, 2H), 3.66-3.60 (m, 2H), 3.54-3.47 (m, 2H), 3.11-3.06 (m, 2H), 2.90-2.82 (m, 2H).

Example 111

2-[2-(4-Fluoro-piperidin-1-ylmethyl)-benzofuran-5-yloxy]-thiazolo[4,5-b]pyridine

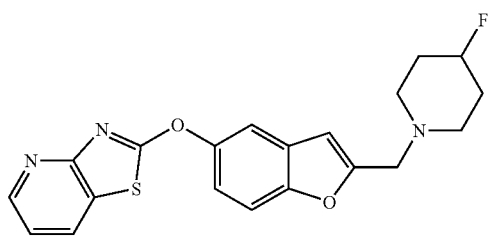 [SMILES: FC1CCN(Cc2cc3cc(Oc4nc5ncccc5s4)ccc3o2)CC1]

MS (ESI): mass calcd. For $C_{20}H_{18}FN_3O_2S$, 383.1; m/z found, 384.1 [M+H]$^+$. $^1$H NMR (400 MHz, CDCl$_3$): 8.58-8.52 (m, 1H), 8.00 (d, J=7.9, 1H), 7.60 (d, J=2.4, 1H), 7.51 (d, J=8.9, 1H), 7.26-7.15 (m, 2H), 6.62 (s, 1H), 4.81-4.56 (m, 1H), 3.71 (s, 2H), 2.76-2.64 (m, J=6.4, 2H), 2.61-2.45 (m, J=5.7, 2H), 2.10-1.87 (m, 4H).

Example 112

Dimethyl-[5-(thiazolo[4,5-b]pyridin-2-yloxy)-benzofuran-2-ylmethyl]-amine

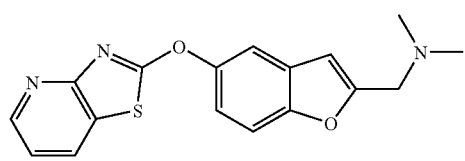 [SMILES: CN(C)Cc1cc2cc(Oc3nc4ncccc4s3)ccc2o1]

MS (ESI): mass calcd. For $C_{17}H_{15}N_3O_2S$, 325.1; m/z found, 326.1 [M+H]$^+$. $^1$H NMR (400 MHz, CDCl$_3$): 8.56 (dd, J=4.8, 1.5, 1H), 7.99 (dd, J=7.9, 1.6, 1H), 7.60 (d, J=2.5, 1H), 7.50 (d, J=8.8, 1H), 7.24 (dd, J=8.8, 2.5, 1H), 7.19 (dd, J=7.9, 4.8, 1H), 6.61 (s, 1H), 3.63 (s, 2H), 2.35 (s, 6H).

Example 113

2-[2-(Tetrahydro-furo[3,4-c]pyrrol-5-ylmethyl)-benzofuran-5-yloxy]-thiazolo[4,5-b]pyridine

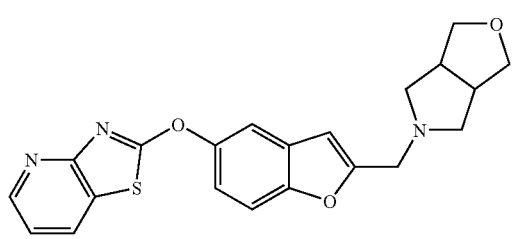 [SMILES: c1cnc2nc(Oc3ccc4oc(CN5CC6COCC6C5)cc4c3)sc2c1]

MS (ESI): mass calcd. For $C_{21}H_{19}N_3O_3S$, 393.1; m/z found, 394.1 [M+H]$^+$. $^1$H NMR (400 MHz, CDCl$_3$): 8.56 (dd, J=4.8, 1.7, 1H), 7.99 (dd, J=7.9, 1.7, 1H), 7.59 (d, J=2.5, 1H), 7.49 (d, J=8.8, 1H), 7.24 (dd, J=8.8, 2.5, 1H), 7.19 (dd, J=7.9, 4.9, 1H), 6.60 (d, J=0.6, 1H), 3.77 (s, 2H), 3.77-3.73 (m, 2H), 3.64 (dd, J=8.9, 2.7, 2H), 2.95-2.81 (m, 4H), 2.41-2.33 (m, 2H).

Example 114

Benzyl-methyl-[5-(thiazolo[4,5-b]pyridin-2-yloxy)-benzofuran-2-ylmethyl]-amine

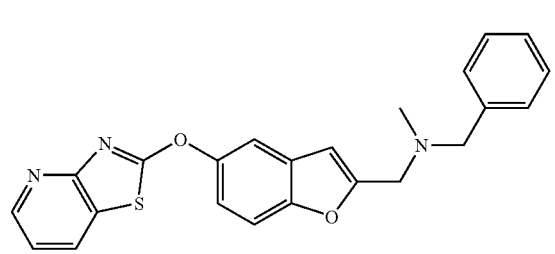 [SMILES: CN(Cc1ccccc1)Cc1cc2cc(Oc3nc4ncccc4s3)ccc2o1]

MS (ESI): mass calcd. For $C_{23}H_{19}N_3O_2S$, 401.1; m/z found, 402.1 [M+H]$^+$. $^1$H NMR (400 MHz, CDCl$_3$): 8.56 (dd, J=4.8, 1.6, 1H), 7.99 (dd, J=7.9, 1.6, 1H), 7.60 (d, J=2.5, 1H), 7.51 (d, J=8.8, 1H), 7.42-7.30 (m, 4H), 7.30-7.21 (m, 2H), 7.19 (dd, J=7.9, 4.8, 1H), 6.63 (s, 1H), 3.74 (s, 2H), 3.64 (s, 2H), 2.34 (s, 3H).

Example 115

2-(2-Morpholin-4-ylmethyl-benzofuran-6-yloxy)-thiazolo[4,5-b]pyridine

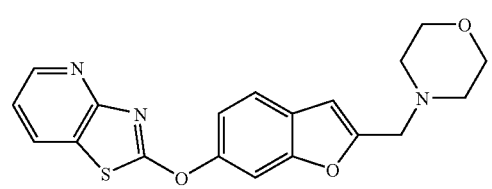

To a solution 2-(2-chloromethyl-benzofuran-6-yloxy)-thiazolo[4,5-b]pyridine (110 mg, 0.3 mmol) in MeCN (3 mL) was added DIEA (209 μL, 0.155 mg, 0.8 mmol) followed by morpholine (27 μL, 27 mg, 0.3 mmol) and stirred (rt, 12 h). The reaction mixture was partitioned between DCM (15 mL) and saturated NaHCO$_3$ (5 mL). The organic layer was washed with saturated NH$_4$Cl (10 mL), dried, filtered and concentrated in vacuo. The resulting residue was purified by reverse phase chromatography to provide the title compound as colorless crystals (41 mg, 37%). MS (ESI): mass calcd. for C$_{19}$H$_{17}$N$_3$O$_3$S, 367.1; m/z found, 368.1.0 [M+H]$^+$. $^1$H NMR (400 MHz, CDCl$_3$): 8.56 (dd, J=4.8, 1.7, 1H), 8.01 (dd, J=7.9, 1.7, 1H), 7.59-7.51 (m, 2H), 7.28-7.25 (m, 1H), 7.20 (dd, J=8.0, 4.8, 1H), 6.65 (s, 1H), 3.75 (dd, J=15.5, 10.8, 4H), 3.70 (s, 2H), 2.62-2.49 (m, 4H).

Examples 116 to 126 were prepared using methods analogous to those described for Example 115.

Example 116

1-[6-(Thiazolo[4,5-b]pyridin-2-yloxy)-benzofuran-2-ylmethyl]-piperidine-4-carboxylic acid amide

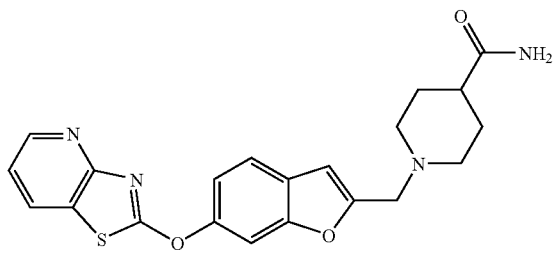 [SMILES: NC(=O)C1CCN(Cc2cc3ccc(Oc4nc5ncccc5s4)cc3o2)CC1]

MS (ESI): mass calcd. for C$_{21}$H$_{20}$N$_4$O$_3$S, 408.1; m/z found, 409.0 [M+H]$^+$. $^1$H NMR (400 MHz, CDCl$_3$): 8.56 (d, J=4.9, 1H), 8.01 (d, J=8.0, 1H), 7.55 (d, J=9.2, 2H), 7.26-7.16 (m, J=7.9, 4.9, 2H), 6.62 (5, 1H), 5.25 (5, 2H), 3.71 (5, 2H), 3.03 (d, J=11.6, 2H), 2.17 (t, J=11.5, 3H), 1.86 (m, 4H).

Example 117

(1S,4S)-5-[6-(Thiazolo[4,5-b]pyridin-2-yloxy)-benzofuran-2-ylmethyl]-2,5-diaza-bicyclo[2.2.1]heptane-2-carboxylic acid amide

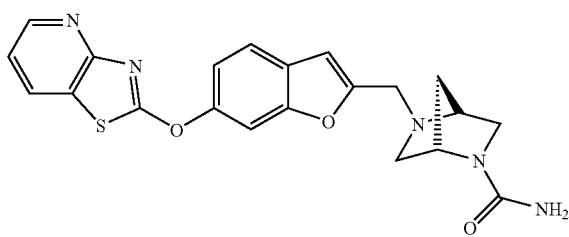

MS (ESI): mass calcd. for C$_{21}$H$_{19}$N$_5$O$_3$S, 421.1; m/z found, 422.2 [M+H]$^+$. $^1$H NMR (400 MHz, CD$_3$OD): 8.48 (dd, J=4.9, 1.6, 1H), 8.29 (dt, J=6.5, 3.2, 1H), 7.65 (dd, J=12.9, 4.9, 2H), 7.38-7.23 (m, 2H), 6.81 (s, 1H), 4.40 (s, 1H), 3.94 (s, 2H), 3.78-3.48 (m, 2H), 3.29-3.24 (m, 1H), 2.99 (dd, J=9.9, 2.0, 1H), 2.83 (d, J=9.9, 1H), 1.94-1.75 (m, 2H).

Example 118 meso-endo-N-{8-[6-(Thiazolo[4,5-b]pyridin-2-yloxy)-benzofuran-2-ylmethyl]-8-aza-bicyclo[3.2.1]oct-3-yl}-acetamide

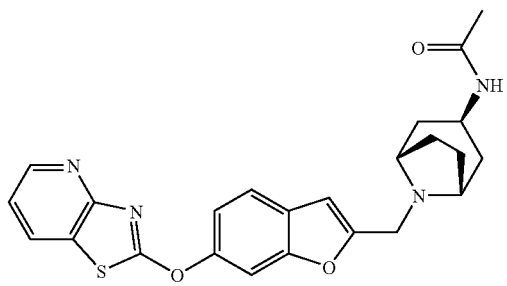 [SMILES: CC(=O)N[C@H]1C[C@H]2CC[C@@H](C1)N2Cc1cc2ccc(Oc3nc4ncccc4s3)cc2o1]

MS (ESI): mass calcd. For C$_{24}$H$_{24}$N$_4$O$_3$S, 448.2; m/z found, 449.0 [M+H]$^+$. $^1$H NMR (500 MHz, CDCl$_3$): 8.56 (dd, J=4.8, 1.6, 1H), 8.01 (dd, J=7.9, 1.6, 1H), 7.55 (d, J=8.5, 2H), 7.25 (d, J=2.2, 1H), 7.23-7.18 (m, 1H), 6.64 (5, 1H), 5.84 (5, 1H), 4.18-4.03 (m, 1H), 3.68 (s, 2H), 3.38-3.26 (m, 2H), 2.33-2.09 (m, 4H), 1.97 (s, 3H), 1.83 (m, 2H), 1.72-1.60 (m, 2H).

Example 119 meso-1-{8-[6-(Thiazolo[4,5-b]pyridin-2-yloxy)-benzofuran-2-ylmethyl]-3,8-diaza-bicyclo[3.2.1]oct-3-yl}-ethanone

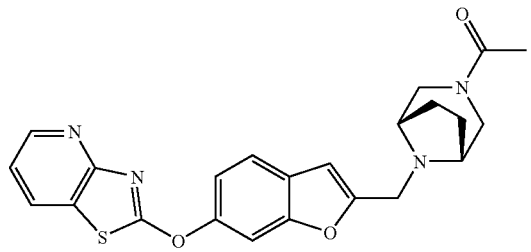 [SMILES: CC(=O)N1C[C@H]2CC[C@@H](C1)N2Cc1cc2ccc(Oc3nc4ncccc4s3)cc2o1]

MS (ESI): mass calcd. For C$_{23}$H$_{22}$N$_4$O$_3$S, 434.1; m/z found, 435.1 [M+H]$^+$. $^1$H NMR (400 MHz, CDCl$_3$): 8.57 (d, J=4.8, 1H), 8.02 (d, J=7.9, 1H), 7.63-7.48 (m, 2H), 7.30-7.23 (m, 1H), 7.20 (dd, J=7.9, 4.8, 1H), 4.22 (d, J=12.8, 1H), 3.68 (s, 2H), 3.44 (s, 2H), 3.34 (s, 2H), 2.95 (d, J=12.6, 1H), 2.07 (s, 4H), 2.07-1.97 (m, 2H), 1.68 (m, 2H).

Example 120

N-(1-{[6-([1,3]thiazolo[4,5-b]pyridin-2-yloxy)-1-benzofuran-2-yl]methyl}pyrrolidin-3-yl)acetamide formate

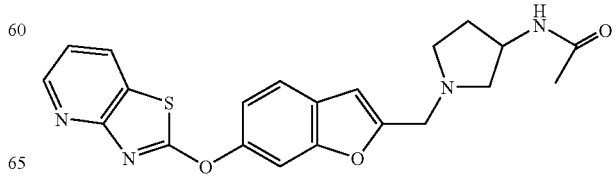

MS (ESI): mass calcd. for $C_{21}H_{20}N_4O_3S$, 408.1; m/z found, 409.1 [M+H]$^+$. $^1$H NMR (400 MHz, CD$_3$OD): 8.49 (d, J=4.0, 1H), 8.31 (dd, J=8.0, 1.5, 1H), 7.76-7.71 (m, 2H), 7.39-7.31 (m, 2H), 7.18 (s, 1H), 4.53 (s, 2H), 4.50-4.43 (m, 1H), 3.62-3.52 (m, 2H), 3.36-3.33 (m, 2H), 2.48-2.36 (m, 1H), 2.10-2.02 (m, 1H), 1.93 (s, 3H).

Example 121

(1S,4S)-1-{5-[5-(Thiazolo[5,4-b]pyridin-2-yloxy)-benzofuran-2-ylmethyl]-2,5-diaza-bicyclo[2.2.1]hept-2-yl}-ethanone

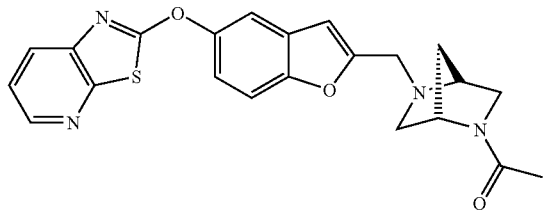

MS (ESI): mass calcd. for $C_{22}H_{20}N_4O_3S$, 420.1; m/z found, 421.0 [M+H]$^+$. $^1$H NMR (400 MHz, CDCl$_3$, mixture of rotamers, 1:1): 8.39 (dd, J=4.8, 1.4, 1H), 7.92 (dd, J=8.1, 1.5, 1H), 7.56-7.48 (m, 2H), 7.32 (dd, J=8.2, 4.8, 1H), 7.25-7.18 (m, 1H), 6.64 (dd, J=4.9, 0.6, 1H), 4.80 (s, 0.5H), 4.26 (s, 0.5H), 3.90 (d, J=11.1, 2H), 3.78 (dd, J=11.6, 1.4, 0.5H), 3.68 (s, 1H), 3.60 (dd, J=9.5, 1.0, 0.5H), 3.36 (dd, J=9.5, 2.3, 0.5H), 3.31 (dd, J=11.7, 1.9, 0.5H), 3.16 (dd, J=9.6, 2.1, 0.5H), 3.00-2.87 (m, 1H), 2.67 (dd, J=9.6, 1.2, 0.5H), 2.09 (s, 1H), 2.06-2.00 (m, 0.5H), 2.00 (s, 2H), 1.94-1.87 (m, 0.5H), 1.88-1.80 (m, 0.5H), 1.74-1.67 (m, 0.5H).

Example 122

(1S,4S)-1-{5-[6-(Thiazolo[5,4-b]pyridin-2-yloxy)-benzofuran-2-ylmethyl]-2,5-diaza-bicyclo[2.2.1]hept-2-yl}-ethanone

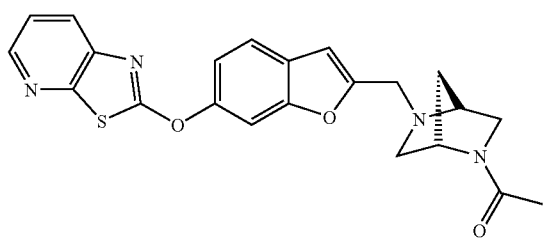

MS (ESI): mass calcd. for $C_{22}H_{20}N_4O_3S$, 420.1; m/z found, 421.0 [M+H]$^+$. $^1$H NMR (400 MHz, CDCl$_3$, mixture of rotamers, 1:1): 8.43-8.37 (m, 1H), 7.94 (dd, J=8.1, 1.5, 1H), 7.58 (dd, J=8.4, 2.0, 1H), 7.52 (s, 1H), 7.33 (dd, J=8.1, 4.8, 1H), 7.23 (dt, J=8.4, 2.3, 1H), 6.65 (dd, J=12.3, 6.9, 1H), 4.80 (s, 0.5H), 4.26 (s, 0.5H), 3.90 (d, J=8.0, 1H), 3.89 (s, 1H), 3.79 (d, J=11.7, 0.5H), 3.68 (s, 1H), 3.64-3.56 (m, 0.5H), 3.37 (dd, J=9.5, 2.2, 0.5H), 3.31 (d, J=11.7, 1.7, 0.5H), 3.17 (dd, J=9.7, 2.1, 0.5H), 3.00-2.86 (m, 1H), 2.67 (dd, J=9.7, 0.9, 0.5H), 2.10 (s, 1.5H), 2.04-2.01 (m, 0.5H), 2.00 (s, 1.5H), 1.90-1.81 (m, 0.5H), 1.71 (d, J=10.1, 0.5H).

Example 123 meso-1-{8-[5-(Thiazolo[5,4-b]pyridin-2-yloxy)-benzofuran-2-ylmethyl]-3,8-diaza-bicyclo[3.2.1]oct-3-yl}-ethanone

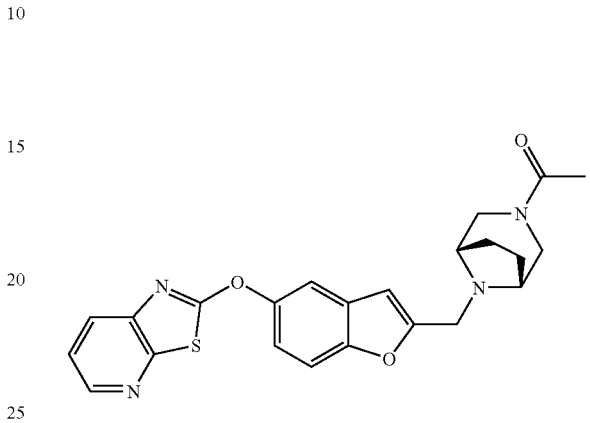

MS (ESI): mass calcd. For $C_{23}H_{22}N_4O_3S$, 434.1; m/z found, 435.0 [M+H]$^+$. $^1$H NMR (400 MHz, CDCl$_3$): 8.39 (dd, J=4.8, 1.6, 1H), 7.92 (dd, J=8.1, 1.5, 1H), 7.54 (d, J=8.8, 1H), 7.52 (d, J=2.4, 1H), 7.32 (dd, J=8.1, 4.8, 1H), 7.23 (dd, J=8.8, 2.5, 1H), 4.21 (dd, J=12.8, 2.6, 1H), 3.78-3.64 (m, 2H), 3.43 (d, J=2.2, 2H), 3.38-3.28 (m, 2H), 2.94 (d, J=12.4, 1H), 2.07 (s, 3H), 2.06-1.95 (m, 3H), 1.80-1.57 (m, 2H).

Example 124 meso-1-{8-[6-(Thiazolo[5,4-b]pyridin-2-yloxy)-benzofuran-2-ylmethyl]-3,8-diaza-bicyclo[3.2.1]oct-3-yl}-ethanone

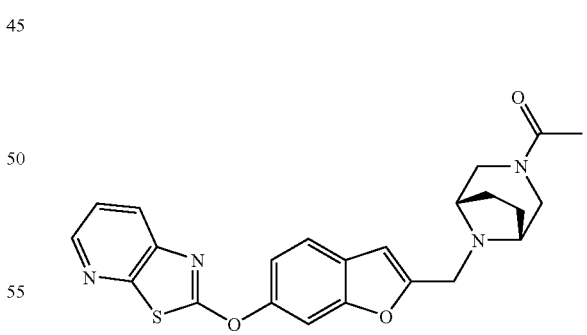

MS (ESI): mass calcd. For $C_{23}H_{22}N_4O_3S$, 434.1; m/z found, 435.0 [M+H]$^+$. $^1$H NMR (400 MHz, CDCl$_3$): 8.41 (dd, J=4.8, 1.5, 1H), 7.94 (dd, J=8.1, 1.5, 1H), 7.59 (d, J=8.4, 1H), 7.54 (d, J=1.7, 1H), 7.34 (dd, J=8.1, 4.8, 1H), 7.23 (dd, J=8.4, 2.2, 1H), 6.67 (s, 1H), 4.27-4.15 (m, 1H), 3.72-3.64 (m, 2H), 3.44 (d, J=2.1, 2H), 3.39-3.27 (m, 2H), 2.95 (d, J=12.5, 1H), 2.14-2.06 (m, 3H), 2.06-1.99 (m, 2H), 1.73-1.59 (m, 2H).

Example 125 meso-endo-N-{8-[5-(Thiazolo[5,4-b]pyridin-2-yloxy)-benzofuran-2-ylmethyl]-8-aza-bicyclo[3.2.1]oct-3-yl}-acetamide

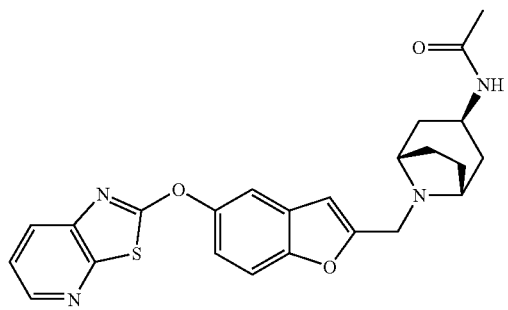 [SMILES: CC(=O)N[C@H]1C[C@H]2CC[C@@H](C1)N2Cc1cc2cc(Oc3nc4cccnc4s3)ccc2o1]

MS (ESI): mass calcd. For $C_{24}H_{24}N_4O_3S$, 448.2; m/z found, 449.0 [M+H]$^+$. $^1$H NMR (400 MHz, CDCl$_3$): 8.39 (dd, J=4.8, 1.5, 1H), 7.93 (dd, J=8.1, 1.5, 1H), 7.52 (d, J=8.8, 1H), 7.50 (d, J=2.4, 1H), 7.32 (dd, J=8.2, 4.8, 1H), 7.21 (dd, J=8.8, 2.5, 1H), 6.64 (s, 1H), 5.77 (s, 1H), 4.21-4.04 (m, 1H), 3.69 (s, 2H), 3.32 (s, 2H), 2.38-2.07 (m, 4H), 1.97 (s, 3H), 1.87-1.76 (m, 2H), 1.64 (d, J=14.9, 2H).

Example 126 meso-endo-N-{8-[6-(Thiazolo[5,4-b]pyridin-2-yloxy)-benzofuran-2-ylmethyl]-8-aza-bicyclo[3.2.1]oct-3-yl}-acetamide

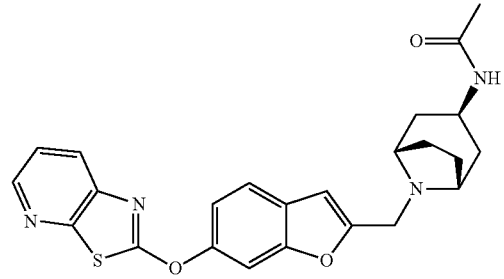 [SMILES: CC(=O)N[C@H]1C[C@H]2CC[C@@H](C1)N2Cc1cc2ccc(Oc3nc4cccnc4s3)cc2o1]

MS (ESI): mass calcd. For $C_{24}H_{24}N_4O_3S$, 448.2; m/z found, 449.0 [M+H]$^+$. $^1$H NMR (500 MHz, CDCl$_3$): 8.45-8.35 (m, 1H), 7.94 (dt, J=8.1, 1.5, 1H), 7.61-7.55 (m, 1H), 7.53 (s, 1H), 7.36-7.31 (m, 1H), 7.26-7.17 (m, 1H), 6.65 (s, 1H), 5.85 (d, J=6.3, 1H), 4.19-4.04 (m, 1H), 3.67 (d, J=10.9, 2H), 3.32 (s, 2H), 2.34-2.22 (m, 2H), 2.21-2.09 (m, 2H), 1.97 (d, J=1.4, 3H), 1.85-1.77 (m, 2H), 1.65 (d, J=14.4, 2H).

Example 127

1-(1-{[6-([1,3]Thiazolo[4,5-b]pyridin-2-yloxy)-1-benzofuran-2-yl]methyl}pyrrolidin-3-yl)urea formate

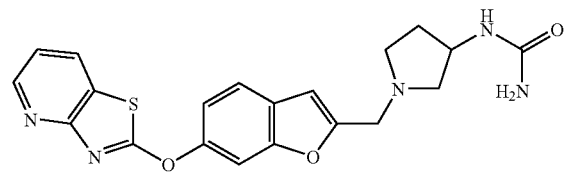 [SMILES: NC(=O)NC1CCN(Cc2cc3ccc(Oc4nc5ncccc5s4)cc3o2)C1]

To a suspension of 1-[6-(thiazolo[4,5-b]pyridin-2-yloxy)-benzofuran-2-ylmethyl]-pyrrolidin-3-ylamine hydrochloride (70 mg, 0.174 mmol) in DCM (3 mL), was added Et$_3$N (0.12 mL, 0.869 mmol), followed by trimethylsilyl isocyanate (0.19 mL, 1.39 mmol) and the resulting solution was stirred (rt, 14 h). The reaction mixture was concentrated and the resulting residue was purified by reverse phase HPLC to afford the title compound as a white solid (33 mg, 42%). MS (ESI): mass calcd. for $C_{20}H_{19}N_5O_3S$, 409.1; m/z found, 410.1 [M+H]$^+$. $^1$H NMR (400 MHz, CD$_3$OD): 8.49 (bs, 1H), 8.31 (dd, J=8.0, 1.4, 1H), 7.74 (d, J=8.5, 1H), 7.70 (d, J=1.8, 1H), 7.38-7.32 (m, 2H), 7.10 (s, 1H), 4.36-4.29 (m, 2H), 4.33 (s, 1H), 3.52-3.38 (m, 2H), 3.25-3.14 (m, 2H), 2.45-2.34 (m, 1H), 1.99-1.89 (m, 1H).

Example 128

N-(1-{[6-([1,3]thiazolo[4,5-b]pyridin-2-yloxy)-1-benzofuran-2-yl]methyl}pyrrolidin-3-yl)methanesulfonamide formate

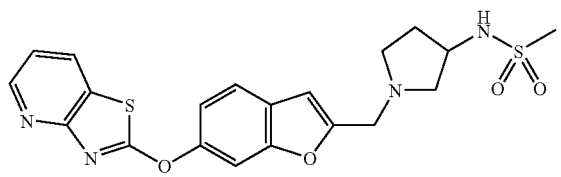 [SMILES: CS(=O)(=O)NC1CCN(Cc2cc3ccc(Oc4nc5ncccc5s4)cc3o2)C1]

To a solution of 1-[6-(thiazolo[4,5-b]pyridin-2-yloxy)-benzofuran-2-ylmethyl]-pyrrolidin-3-ylamine (126 mg, 0.313 mmol) in DMF (2 mL) was added DIEA (125 μL, 0.938 mmol) followed by MsCl (72 μL, 0.938 mmol) and the resulting solution was stirred (rt, 1 h). The reaction mixture was filtered (Celite®) and concentrated in vacuo.

The resulting residue was purified by reverse phase HPLC to afford the title compound as a white solid (46 mg, 30%). MS (ESI): mass calcd. for $C_{20}H_{20}N_4O_4S_2$, 444.1; m/z found, 445.1 [M+H]$^+$. $^1$H NMR (400 MHz, CD$_3$OD): 8.49 (d, J=3.9, 1H), 8.30 (dd, J=8.0, 1.6, 1H), 7.72 (d, J=8.5, 1H), 7.70 (d, J=1.9, 1H), 7.37-7.32 (m, 2H), 7.01 (s, 1H), 4.26 (s, 2H), 4.16-4.07 (m, 1H), 3.41-3.34 (m, 1H), 3.24-3.17 (m, 1H), 3.14-3.03 (m, 2H), 2.97 (s, 3H), 2.45-2.35 (m, 1H), 1.99-1.90 (m, 1H).

Examples 129 to 131 were prepared using methods analogous to those described for Example 149.

Example 129 meso-endo-N-(8-{2-[6-(Benzothiazol-2-yloxy)-benzofuran-3-yl]-ethyl}-8-aza-bicyclo[3.2.1]oct-3-yl)-acetamide

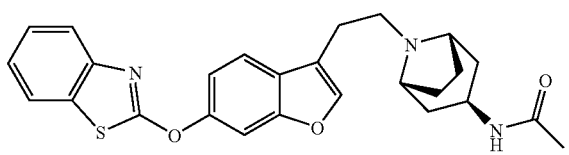 [SMILES: CC(=O)N[C@H]1C[C@H]2CC[C@@H](C1)N2CCc1coc2cc(Oc3nc4ccccc4s3)ccc12]

MS (ESI): mass calcd. for $C_{26}H_{27}N_3O_3S$, 461.6; m/z found, 462.2 [M+H]$^+$. $^1$H NMR (500 MHz, CDCl$_3$): 7.75-7.74 (m, 1H), 7.68-7.66 (m, 1H), 7.59 (d, J=8.5, 1H), 7.54 (s, 1H), 7.52 (d, J=2.0, 1H), 7.41-7.37 (m, 1H), 7.29-7.25 (m, 2H), 5.81-5.79 (m, 1H), 4.13-4.10 (m, 1H), 3.33 (br s, 2H), 2.87-2.83 (m, 2H), 2.70-2.66 (m, 2H), 2.26-2.21 (m, 2H), 2.11-2.08 (m, 2H), 1.97 (s, 3H), 1.79-1.75 (m, 2H), 1.65-1.62 (m, 2H).

Example 130 meso-1-(8-{2-[6-(Thiazolo[4,5-b]pyridin-2-yloxy)-benzofuran-3-yl]-ethyl}-3,8-diaza-bicyclo[3.2.1]oct-3-yl)-ethanone

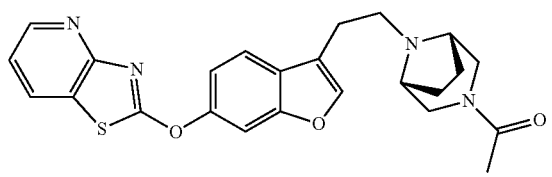 [SMILES: CC(=O)N1C[C@H]2CC[C@@H](C1)N2CCc1coc2cc(Oc3nc4ncccc4s3)ccc12]

MS (ESI): mass calcd. For $C_{24}H_{24}N_4O_3S$, 448.6; m/z found, 449.1 [M+H]$^+$. $^1$H NMR (500 MHz, CDCl$_3$): 8.56 (dd, J=4.8, 1.5, 1H), 8.02 (dd, J=7.9, 1.5, 1H), 7.59-7.57 (m, 3H), 7.30-7.28 (m, 1H), 7.22-7.19 (m, 1H), 4.19 (d, J=12, 1H), 3.44-3.27 (m, 4H), 2.92-2.86 (m, 3H), 2.68 (t, J=7.5, 2H) 2.07 (s, 3H), 1.97-1.91 (m, 2H), 1.65-1.57 (m, 2H).

Example 131 meso-endo-N-(8-{2-[6-(Thiazolo[4,5-b]pyridin-2-yloxy)-benzofuran-3-yl]-ethyl}-8-aza-bicyclo[3.2.1]oct-3-yl)acetamide

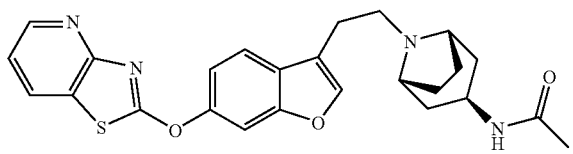 [SMILES: CC(=O)N[C@H]1C[C@H]2CC[C@@H](C1)N2CCc1coc2cc(Oc3nc4ncccc4s3)ccc12]

MS (ESI): mass calcd. for $C_{25}H_{26}N_4O_3S$, 462.6; m/z found, 463.1 [M+H]$^+$. $^1$H NMR (500 MHz, CDCl$_3$): 855 (br s, 1H), 8.02 (d, J=7.7, 1H), 7.59-7.55 (m, 3H), 7.29-7.21 (m, 2H), 5.95 (br s, 1H), 4.09 (br s, 1H), 3.32 (s, 2H), 2.85-2.83 (m, 2H), 2.68-2.65 (m, 2H), 2.22 (br s, 2H), 2.07 (br s, 2H), 1.97 (s, 3H), 1.79-1.77 (m, 2H), 1.66-1.62 (m, 2H).

Example 132

2-(2-Piperidin-1-ylmethyl-benzo[b]thiophen-6-yloxy)-benzothiazole

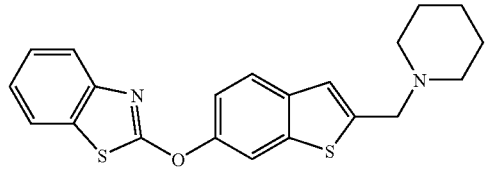 [SMILES: c1ccc2sc(Oc3ccc4cc(CN5CCCCC5)sc4c3)nc2c1]

To a solution 2-(2-chloromethyl-benzo[b]thiophen-6-yloxy)-benzothiazole (86 mg, 0.26 mmol) in MeCN (3 mL) was added DIEA (0.014 mL, 11 mg, 0.8 mmol) followed by piperidine (0.051 mL, 44 mg, 0.52 mmol) and stirred (rt, 12 h). The reaction mixture was partitioned between DCM (15 mL) and saturated NaHCO$_3$(5 mL). The organic layer was washed with saturated NH$_4$Cl (10 mL), dried, filtered and concentrated in vacuo. The resulting residue was purified by reverse phase chromatography to provide the title compound as colorless solid (48 mg, 49%). MS (ESI): mass calcd. for $C_{21}H_{20}N_2OS_2$, 380.1; m/z found, 381.1[M+H]$^+$. $^1$H NMR (400 MHz, CDCl$_3$): 7.79 (d, J=2.3, 1H), 7.75-7.72 (m, 1H), 7.70 (d, J=8.6, 1H), 7.65 (dd, J=8.0, 0.7, 1H), 7.40-7.35 (m, 1H), 7.29 (dd, J=8.6, 2.3, 1H), 7.28-7.21 (m, 1H), 7.13 (5, 1H), 3.75 (5, 2H), 2.55-2.40 (m, 4H), 1.69-1.54 (m, 4H), 1.52-1.32 (m, 2H).

Examples 133 to 134 were prepared using methods analogous to those described for Example 132.

Example 133

(2-Morpholin-4-ylmethyl-benzo[b]thiophen-6-yloxy)-benzothiazole

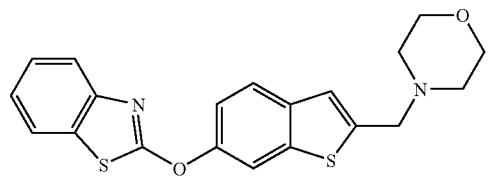

MS (ESI): mass calcd. for $C_{20}H_{18}N_2O_2S_2$, 382.1; m/z found, 383.0 [M+H]$^+$. $^1$H NMR (400 MHz, CDCl$_3$): 7.80 (d, J=2.3, 1H), 7.77-7.69 (m, 2H), 7.66 (ddd, J=7.9, 1.2, 0.5, 1H), 7.42-7.35 (m, 1H), 7.33-7.25 (m, 2H), 7.16 (5, 1H), 3.78 (5, 2H), 3.76-3.70 (m, 4H), 2.67-2.34 (m, 4H).

Example 134 meso-endo-N-{8-[6-(Benzothiazol-2-yloxy)-benzo[b]thiophen-2-ylmethyl]-8-aza-bicyclo[3.2.1]oct-3-yl}-acetamide

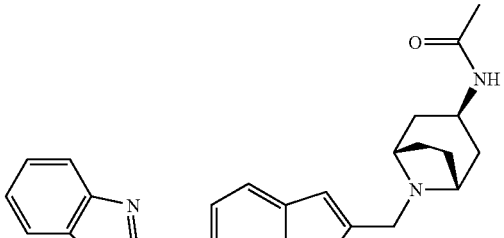

MS (ESI): mass calcd. for $C_{25}H_{25}N_3O_2S_2$, 463.1; m/z found, 464.1 [M+H]$^+$. $^1$H NMR (400 MHz, CDCl$_3$): 7.83-7.79 (m, 1H), 7.76-7.63 (m, J=16.3, 14.9, 7.8, 3H), 7.42-7.35 (m, 1H), 7.33-7.23 (m, 2H), 7.14-7.11 (m, 1H), 5.90-5.68 (m, J=3.8, 3.2, 1H), 4.20-4.03 (m, 1H), 3.88-3.72 (m, 2H), 3.36-3.15 (m, 2H), 2.33-2.20 (m, 2H), 2.20-2.08 (m, 2H), 1.96 (s, 3H), 1.84-1.74 (m, 2H), 1.67-1.58 (m, 2H).

Example 135 meso-endo-N-{8-[6-(Thiazolo[4,5-b]pyridin-2-yloxy)-benzo[b]thiophen-2-ylmethyl]-8-aza-bicyclo[3.2.1]oct-3-yl}-acetamide

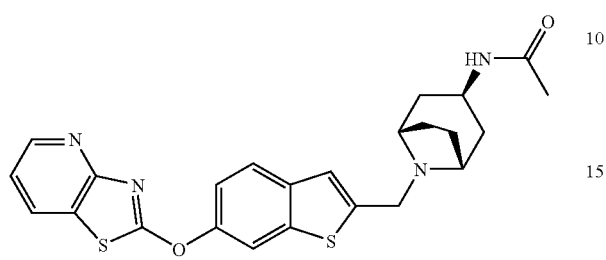

To a solution 2-(2-chloromethyl-benzo[b]thiophen-6-yloxy)-benzothiazole (56 mg, 0.17 mmol) in MeCN (3 mL) was added DIEA (0.058 mL, 44 mg, 0.33 mmol), N-(8-aza-bicyclo[3.2.1]oct-3-yl)-acetamide (28 mg, 0.17 mmol) and the reaction mixture stirred (rt, 12 h). The reaction mixture was partitioned between DCM (15 mL) and saturated NaHCO$_3$ (5 mL). The organic layer was separated and washed with saturated NH$_4$Cl (10 mL). The organic layer was dried, filtered and concentrated in vacuo. The resulting residue was purified by reverse phase chromatography to provide the title compound as a colorless solid (14 mg, 18%). MS (ESI): mass calcd. for $C_{24}H_{24}N_4O_2S_2$, 464.13; m/z found, 465.2 [M+H]$^+$. $^1$H NMR (500 MHz, CDCl$_3$): 8.57 (dd, J=4.8, 1.5, 1H), 8.01 (dd, J=7.9, 1.6, 1H), 7.88 (d, J=2.1, 1H), 7.70 (d, J=8.6, 1H), 7.34 (dd, J=8.6, 2.2, 1H), 7.20 (dd, J=7.9, 4.8, 1H), 7.13 (s, 1H), 5.81 (s, 1H), 4.18-4.05 (m, J=6.9, 1H), 3.80 (s, 2H), 3.30 (s, 2H), 2.38-2.05 (m, 4H), 1.99 (s, J=25.8, 3H), 1.88-1.53 (m, 4H).

Examples 136 to 138 were prepared using methods analogous to those described for Example 135.

Example 136

2-(2-Piperidin-1-ylmethyl-benzo[b]thiophen-6-yloxy)-thiazolo[4,5-b]pyridine

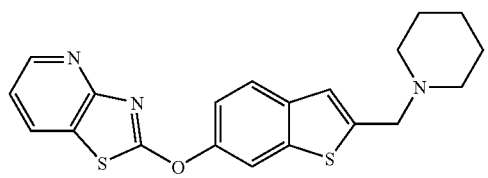 [SMILES: c1cnc2nc(Oc3ccc4cc(CN5CCCCC5)sc4c3)sc2c1]

MS (ESI): mass calcd. for $C_{20}H_{19}N_3OS_2$, 381.1; m/z found, 382.0 [M+H]$^+$. $^1$H NMR (400 MHz, CDCl$_3$): 8.57 (dd, J=4.8, 1.7 Hz, 1H), 8.04-7.95 (m, 1H), 7.88 (d, J=2.25 Hz, 1H), 7.73-7.69 (m, 1H), 7.33 (dd, J=8.6, 2.3 Hz, 1H), 7.20 (dd, J=8.0, 4.8 Hz, 1H), 7.14 (s, 1H), 3.76 (s, 2H), 2.48 (s, 4H), 1.68-1.53 (m, 4H), 1.53-1.39 (m, 2H).

Example 137

2-(3-Morpholin-4-ylmethyl-benzo[b]thiophen-6-yloxy)-thiazolo[4,5-b]pyridine

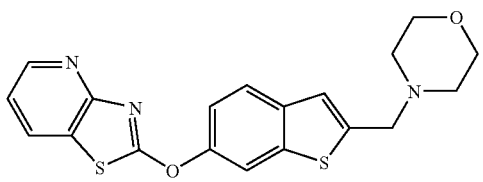 [SMILES: c1cnc2nc(Oc3ccc4cc(CN5CCOCC5)sc4c3)sc2c1]

MS (ESI): mass calcd. for $C_{19}H_{17}N_3O_2S_2$, 383.1; m/z found, 384.0 [M+H]$^+$. $^1$H NMR (400 MHz, CDCl$_3$): 8.57 (dd, J=4.8, 1.6 Hz, 1H), 7.90 (d, J=2.2 Hz, 1H), 8.01 (dd, J=7.9, 1.6 Hz, 1H), 7.72 (d, J=8.6 Hz, 1H), 7.35 (dd, J=8.6, 2.3 Hz, 1H), 7.20 (dd, J=7.9, 4.9 Hz, 2H), 7.17 (s, 1H), 3.79 (s, 1H), 3.77-3.72 (m, 4H), 2.62-2.39 (m, 4H).

Example 138

1-[6-(Thiazolo[4,5-b]pyridin-2-yloxy)-benzo[b]thiophen-2-ylmethyl]-piperidine-4-carboxylic acid amide

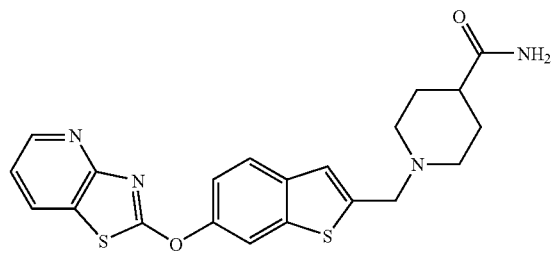 [SMILES: NC(=O)C1CCN(Cc2cc3ccc(Oc4nc5ncccc5s4)cc3s2)CC1]

MS (ESI): mass calcd. for $O_{21}H_{20}N_4O_2S_2$, 424.1; m/z found, 425.1 [M+H]$^+$. $^1$H NMR (400 MHz, CDCl$_3$): 8.57 (dd, J=4.8, 1.6 Hz, 1H), 8.01 (dd, J=7.9, 1.6 Hz, 1H), 7.89 (d, J=2.2 Hz, 1H), 7.71 (d, J=8.6 Hz, 1H), 7.34 (dd, J=8.6, 2.2 Hz, 1H), 7.20 (dd, J=7.9, 4.8 Hz, 1H), 7.15 (s, 1H), 5.61-5.17 (m, 2H), 3.79 (s, 2H), 3.11-2.93 (m, 2H), 2.29-2.05 (m, 3H), 2.04-1.65 (m, 4H).

Example 139

1-[6-(Benzothiazol-2-yloxy)-1H-indol-3-ylmethyl]-piperidine-4-carboxylic acid ethyl ester

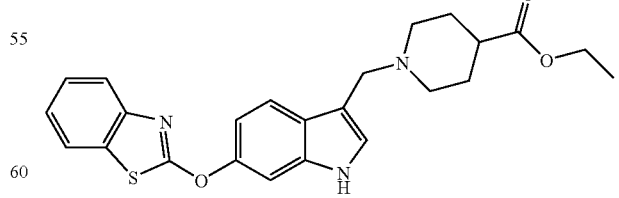

To a solution of 2-(1H-Indo)-6-yloxy)-benzothiazole (500 mg, 1.9 mmol) in dioxane:AcOH (1:1, 19 mL) was added piperidine-4-carboxylic acid ethyl ester (0.29 mL, 296 mg, 1.9 mmol) followed by formaldehyde (140 µL, 56 mg, 1.9 mmol) and the resulting solution was stirred (rt, 18 h). The reaction mixture was partially concentrated and partitioned with 1 M NaOH and EtOAc (100 mL each). The organic layer was dried, filtered and concentrated in vacuo. The resulting residue was purified by silica gel column chromatography using MeOH (0.2M NH$_3$):DCM (0-20%) to afford the title compound as a tan solid (568 mg, 69%). MS (ESI): mass calcd. for C$_{24}$H$_{25}$N$_3$O$_3$S, 435.5; m/z found, 436.2 [M+H]$^+$. $^1$H NMR (500 MHz, CDCl$_3$): 8.31 (5, 1H), 7.79 (d, J=8.6, 1H), 7.75 (d, J=7.6, 1H), 7.66 (dd, J=8.0, 0.7, 1H), 7.41-7.36 (m, 2H), 7.28-7.25 (m, 1H), 7.16 (d, J=2.3, 1H), 7.11 (dd, J=8.6, 2.2, 1H), 4.14 (q, J=7.2, 2H), 3.71 (s, 2H), 2.98-2.95 (m, 2H), 2.31-2.27 (m, 1H), 2.11-2.07 (m, 2H), 1.92-1.88 (m, 2H), 1.81-1.75 (m, 2H), 1.26 (t, J=7.2, 3H).

Examples 140 to 147 were prepared using methods analogous to those described for Example 139.

Example 140

1-[6-(Thiazolo[5,4-b]pyridin-2-yloxy)-1H-indol-3-ylmethyl]-piperidine-4-carboxylic acid ethyl ester

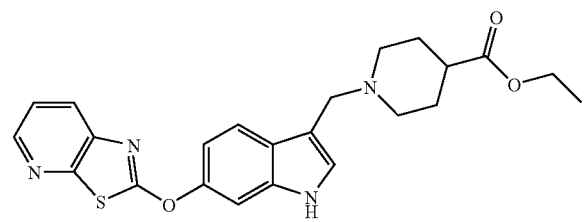 [SMILES: CCOC(=O)C1CCN(Cc2c[nH]c3cc(Oc4nc5ccccc5s4)ccc23)CC1]

MS (ESI): mass calcd. for C$_{23}$H$_{24}$N$_4$O$_3$S, 436.5; m/z found, 437.1 [M+H]$^+$.

Example 141

{1-[6-(Benzothiazol-2-yloxy)-1H-indol-3-ylmethyl]-piperidin-4-yl}-acetic acid methyl ester

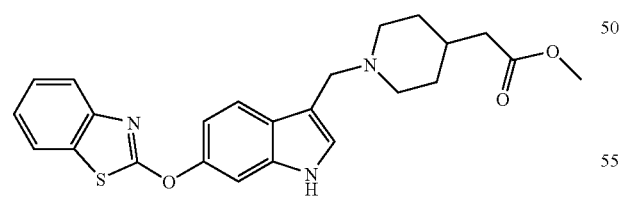

MS (ESI): mass calcd. for C$_{24}$H$_{25}$N$_3$O$_3$S, 435.5; m/z found, 436.1 [M+H]$^+$. $^1$H NMR (500 MHz, CDCl$_3$): 8.37 (s, 1H), 7.76 (t, J=8.9, 2H), 7.65 (d, J=8.0, 1H), 7.41-7.38 (m, 1H), 7.34 (d, J=2.2, 1H), 7.28-7.25 (m, 1H), 7.16 (d, J=2.2, 1H), 7.11 (dd, J=8.6, 2.2, 1H), 3.71 (s, 2H), 3.68 (s, 3H), 2.97 (d, J=11.6, 2H), 2.25 (d, J=7.1, 2H), 2.07-2.03 (m, 2H), 1.81-1.77 (m, 1H), 1.72-1.68 (m, 2H), 1.37-1.31 (m, 2H).

Example 142 meso-endo-(Acetyl-{8-[6-(benzothiazol-2-yloxy)-1H-indol-3-ylmethyl]-8-aza-bicyclo[3.2.1]oct-3-yl}-amino)-acetic acid ethyl ester

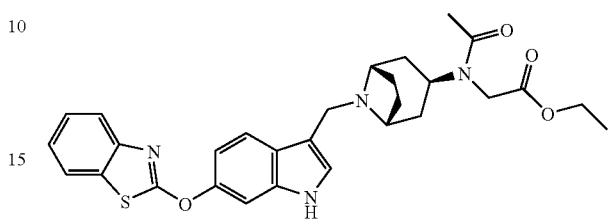

MS (ESI): mass calcd. for C$_{29}$H$_{32}$N$_4$O$_4$S, 532.2; m/z found, 533.2 [M+H]$^+$.

Example 143 meso-endo-(Acetyl-{8-[5-(benzothiazol-2-yloxy)-1H-indol-3-ylmethyl]-8-aza-bicyclo[3.2.1]oct-3-yl}-amino)-acetic acid ethyl ester

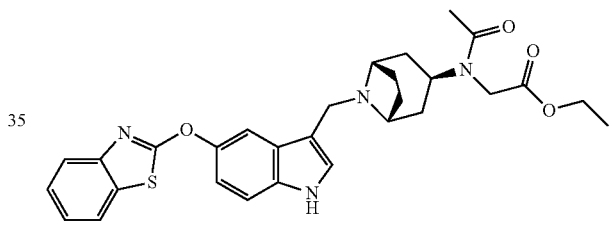

MS (ESI): mass calcd. for C$_{29}$H$_{32}$N$_4$O$_4$S, 532.2; m/z found, 533.1 [M+H]$^+$.

Example 144

(3R)-1-[6-(Benzothiazol-2-yloxy)-1H-indol-3-ylmethyl]-piperidine-3-carboxylic acid ethyl ester

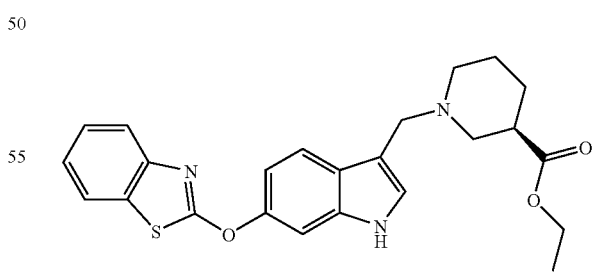

MS (ESI): mass calcd. for C$_{24}$H$_{25}$N$_3$O$_3$S, 435.5; m/z found, 436.1 [M+H]$^+$. $^1$H NMR (500 MHz, CDCl$_3$): 8.37 (s, 1H), 7.77 (d, J=8.6, 1H), 7.76 (d, J=8.1, 1H), 7.65 (d, J=7.9, 1H), 7.41-7.38 (m, 1H), 7.35 (d, J=2.1, 1H), 7.28-7.25 (m, 1H), 7.14 (d, J=2.0, 1H), 7.10 (dd, J=8.6, 2.1, 1H), 4.14-4.08 (m, 2H), 3.73 (d, J=13.6, 1H), 3.71 (d, J=13.6, 1H), 3.05 (d, J=9.5, 1H), 2.84-2.81 (m, 1H), 2.62-2.58 (m, 1H), 3.11-3.08

(m, 1H), 2.12-2.08 (m, 1H), 1.95-1.90 (m, 1H), 1.76-1.73 (m, 1H), 1.62-1.58 (m, 2H), 1.52-1.48 (m, 1H), 1.23 (t, J=7.1, 1H).

Example 145

{1-[6-(Benzothiazol-2-yloxy)-1H-indol-3-ylmethyl]-piperidin-4-yl}-carbamic acid tert-butyl ester

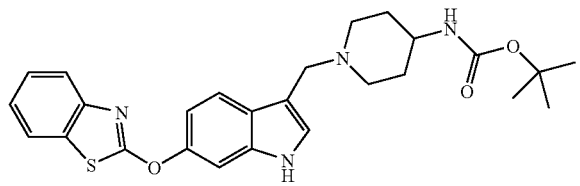 [SMILES: CC(C)(C)OC(=O)NC1CCN(Cc2c[nH]c3cc(Oc4nc5ccccc5s4)ccc23)CC1]

MS (ESI): mass calcd. for $C_{26}H_{30}N_4O_3S$, 478.6; m/z found, 479.2 [M+H]$^+$. $^1$H NMR (500 MHz, CDCl$_3$): 8.30 (s, 1H), 7.79-7.75 (m, 2H), 7.66 (d, J=8.0, 1H), 7.41-7.37 (m, 2H), 7.28-7.25 (m, 1H), 7.17 (br s, 1H), 7.11 (dd, J=8.6, 2.1, 1H), 4.44 (br s, 1H), 3.70 (s, 2H), 3.50 (br s, 1H), 2.89 (br d, 2H), 2.18-2.13 (br t, 2H), 1.93 (br d, 2H), 1.48-1.44 (m, 2H), 1.46 (s, 9H).

Example 146

5-[6-(Benzothiazol-2-yloxy)-1H-indol-3-ylmethyl]-hexahydro-pyrrolo[3,4-c]pyrrole-2-carboxylic acid tert-butyl ester

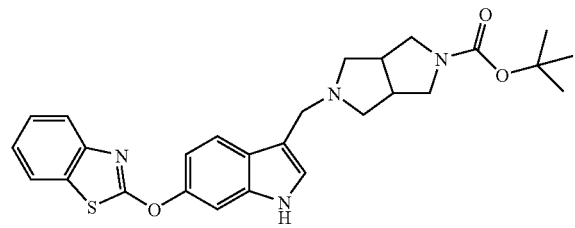 [SMILES: CC(C)(C)OC(=O)N1CC2CN(Cc3c[nH]c4cc(Oc5nc6ccccc6s5)ccc34)CC2C1]

MS (ESI): mass calcd. for $C_{27}H_{30}N_4O_3S$, 490.6; m/z found, 491.2 [M+H]$^+$. $^1$H NMR (500 MHz, CDCl$_3$): 8.34 (s, 1H), 7.77-7.74 (m, 2H), 7.65 (d, J=8.0, 1H), 7.41-7.37 (m, 2H), 7.27-7.25 (m, 1H), 7.16 (br d, J=2.3, 1H), 7.11 (dd, J=8.6, 2.2, 1H), 3.80 (s, 2H), 3.55 (br s, 2H), 2.27 (br s, 2H), 2.81 (br m, 2H), 2.74-2.70 (m, 2H), 2.48 (br s, 2H), 1.47 (s, 9H).

Example 147

(1S,4S)-5-[6-(Benzothiazol-2-yloxy)-1H-indol-3-ylmethyl]-2,5-diaza-bicyclo[2.2.1]heptane-2-carboxylic acid tert-butyl ester

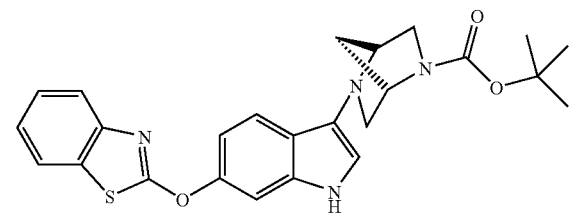

MS (ESI): mass calcd. for $C_{26}H_{28}N_4O_3S$, 476.6; m/z found, 477.2 [M+H]$^+$. $^1$H NMR (500 MHz, CDCl$_3$): 8.27 (s, 1H), 7.81-7.75 (m, 2H), 7.65 (d, J=8.0, 1H), 7.41-7.38 (m, 2H), 7.28-7.25 (m, 1H), 7.18 (br s, 1H), 7.11 (d, J=8.6, 1H), 4.41 (s, 0.46H), 4.27 (s, 0.54H), 3.95-3.8 (m, 2H), 3.66 (d, J=10.5, 0.54H), 3.55-3.50 (m, 1.46H), 3.20-3.16 (m, 1H), 2.97-3.89 (m, 1H), 2.83-2.80 (m, 0.46H), 2.66-2.63 (m, 0.54H), 1.88 (d, J=9.3, 1H), 1.74-1.70 (m, 1H), 1.49 (s, 9H).

Example 148

1-{2-[5-(Benzothiazol-2-yloxy)-1H-indol-3-yl]-ethyl}-piperidine-4-carboxylic acid ethyl ester

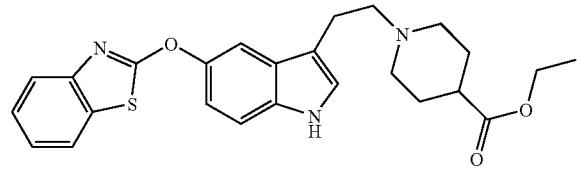 [SMILES: CCOC(=O)C1CCN(CCc2c[nH]c3ccc(Oc4nc5ccccc5s4)cc23)CC1]

To a solution of methanesulfonic acid 2-[5-(benzothiazol-2-yloxy)-1H-indol-3-yl]-ethyl ester (250 mg, 0.64 mmol) in MeCN (7 mL) was added ethyl isonipocoate (0.11 mL, 0.77 mmol) and the reaction mixture was stirred (rt, 16 h). The reaction mixture was filtered and purified using reverse phase HPLC to provide the title compound as an off white solid (44.3 mg, 15%). MS (ESI): mass calcd. for $C_{25}H_{27}N_3O_3S$, 449.5; m/z found, 450.1 [M+H]$^+$. $^1$H NMR (500 MHz, CDCl$_3$): 8.19 (s, 1H), 7.76 (d, J=7.6, 1H), 7.65 (d, J=7.3, 1H), 7.57 (d, J=2.3, 1H), 7.39 (dd, J=10.3, 5.0, 2H), 7.27-7.22 (m, 1H), 7.20-7.11 (m, 2H), 4.15 (q, J=7.1, 2H), 3.07-2.91 (m, 5H), 2.73-2.63 (m, 2H), 2.32 (s, 1H), 2.13 (s, 2H), 1.95 (d, J=10.1, 3H), 1.87-1.74 (m, 3H).

Example 149

1-{2-[6-(Benzothiazol-2-yloxy)-benzofuran-3-yl]-ethyl}-piperidine-4-carboxylic acid ethyl ester

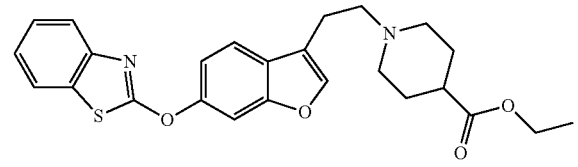 [SMILES: CCOC(=O)C1CCN(CCc2coc3cc(Oc4nc5ccccc5s4)ccc23)CC1]

To a suspension of methanesulfonic acid 2-[6-(benzothiazol-2-yloxy)-benzofuran-3-yl]-ethyl ester (200 mg, 0.5 mmol) and K$_2$CO$_3$ (78 mg, 0.6 mmol) in MeCN (5.2 mL) was added ethyl isonipecotate (0.08 mL, 0.5 mmol) and the reaction mixture was heated (70° C., 48 h). The reaction mixture was filtered, concentrated in vacuo and the resulting residue was partitioned between EtOAc and brine (20 mL each). The organic layer was dried, filtered and concentrated in vacuo. The resulting residue was purified by silica gel flash chromatography using EtOAc:hexane (20-80%) to provide the title compound as a clear oil (108 mg, 47%). MS (ESI): mass calcd. for $C_{25}H_{26}N_2O_4S$, 450.6; m/z found, 451.2 [M+H]$^+$. $^1$H NMR (500 MHz, CDCl$_3$): 7.43 (d, J=8.5, 1H), 7.65 (d, J=8.0, 1H), 7.58 (d, J=8.5, 1H), 7.54 (s, 1H), 7.51 (d, J=1.5, 1H), 7.39-7.36 (m, 1H), 7.27-7.24 (m, 2H), 4.14 (q, J=7.0, 2H), 2.98 (d, J=11.5, 2H), 2.89-2.85 (m, 2H), 2.69-2.66 (m, 2H), 2.34-2.29 (m, 1H), 2.14-2.10 (m, 2H), 1.96-2.94 (m, 2H), 1.85-1.77 (m, 2H), 1.26 (t, J=7.0, 3H).

Example 150 meso-endo-({8-[6-(Benzothiazol-2-yloxy)-benzofuran-2-ylmethyl]-8-aza-bicyclo[3.2.1]oct-3-yl}-tert-butoxycarbonyl-amino)-acetic acid tert-butyl ester

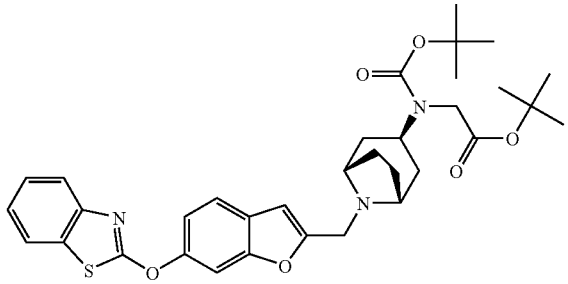 [SMILES: CC(C)(C)OC(=O)CN(C(=O)OC(C)(C)C)[C@H]1C[C@H]2CC[C@@H](C1)N2Cc1cc2ccc(Oc3nc4ccccc4s3)cc2o1]

To a solution 2-(2-chloromethyl-benzofuran-6-yloxy)-benzothiazole (200 mg, 0.6 mmol) in MeCN (6 mL) was added K$_2$CO$_3$ (236 mg, 1.7 mmol) followed by meso-endo-[(8-aza-bicyclo[3.2.1]oct-3-yl)-tert-butoxycarbonyl-amino]-acetic acid tert-butyl ester (194 mg, 0.6 mmol) and stirred (rt, 12 h). The reaction mixture was partitioned with EtOAc (30 mL) and saturated NaHCO$_3$ (10 mL). The aqueous phase was extracted with EtOAc (3×30 mL). The organic layers were combined, dried, filtered and concentrated in vacuo. The resulting residue was purified by flash column chromatography using EtOAc:hexane (0-50%) to provide the title compound as colorless crystals (186 mg, 53%). MS (ESI): mass calcd. for C$_{34}$H$_{41}$N$_3$O$_6$S, 619.3; m/z found, 620.3 [M+H]$^+$. $^1$H NMR (400 MHz, CDCl$_3$): 7.74 (d, J=7.6, 1H), 7.66 (d, J=7.3, 1H), 7.55 (d, J=8.4, 1H), 7.49 (d, J=1.7, 1H), 7.42-7.34 (m, 1H), 7.29-7.23 (m, 2H), 7.21 (dd, J=8.4, 2.1, 1H), 3.68 (5, 2H), 3.52 (5, 2H), 3.38 (5, 2H), 2.39 (dd, J=21.8, 8.9, 2H), 2.13 (d, J=4.4, 2H), 1.57 (5, 1H), 1.43 (5, 18H), 1.34-1.19 (m, 3H), 1.01-0.80 (m, 1H).

Example 151 was prepared using methods analogous to those described for Example 150.

Example 151

{1-[6-(Thiazolo[4,5-b]pyridin-2-yloxy)-benzofuran-2-ylmethyl]-pyrrolidin-3-yl}-carbamic acid tert-butyl ester formate

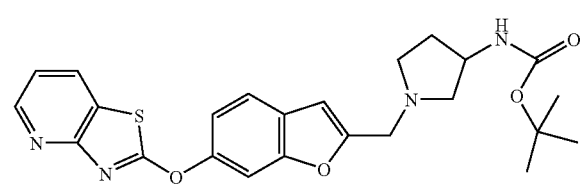 [SMILES: CC(C)(C)OC(=O)NC1CCN(Cc2cc3ccc(Oc4nc5ncccc5s4)cc3o2)C1]

MS (ESI): mass calcd. for C$_{24}$H$_{26}$N$_4$O$_4$S, 466.2; m/z found, 467.1 [M+H]$^+$.

Example 152

1-[6-(Thiazolo[4,5-b]pyridin-2-yloxy)-benzofuran-2-ylmethyl]-pyrrolidin-3-ylamine hydrochloride

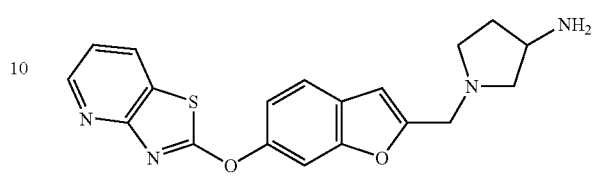

To a suspension of {1-[6-(thiazolo[4,5-b]pyridin-2-yloxy)-benzofuran-2-ylmethyl]-pyrrolidin-3-yl}-carbamic acid tert-butyl ester formate (435 mg, 0.849 mmol) in DCM (10 mL) was added 4 M HCl in dioxane (1.06 mL, 4.25 mmol) and the reaction mixture was stirred (rt, 14 h). The reaction mixture was concentrated in vacuo to afford the title compound as a yellow solid (320 mg, 95%). MS (ESI): mass calcd. for C$_{19}$H$_{18}$N$_4$O$_2$S, 366.1; m/z found, 367.1 [M+H]$^+$.

Example 153

1-{8-[6-(Thiazolo[4,5-b]pyridin-2-yloxy)-benzofuran-3-ylmethyl]-3,8-diaza-bicyclo[3.2.1]oct-3-yl}-ethanone

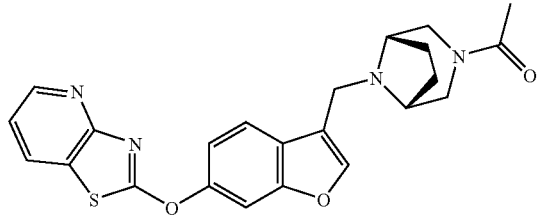 [SMILES: CC(=O)N1C[C@H]2CC[C@@H](C1)N2Cc1coc2cc(Oc3nc4ncccc4s3)ccc12]

To a solution of 2-(3-chloromethyl-benzofuran-6-yloxy)-thiazolo[4,5-b]pyridine (120 mg, 0.31 mmol) in CH$_3$CN/DMF (4:1, 3 mL) was added K$_2$CO$_3$ (169 mg, 1.2 mmol) followed by 1-(3,8-diaza-bicyclo[3.2.1]oct-3-yl)-ethanone (47 mg, 0.31 mmol) and the reaction mixture was stirred (rt, 48 h). The reaction mixture was partitioned between DCM (10 mL) and sat. NaHCO$_3$ (5 mL). The organic layer was separated and concentrated in vacuo. The resulting residue was purified by reverse phase HPLC to provide the title compound as a colorless solid (47 mg, 35%). MS (ESI): mass calcd. for C$_{23}$H$_{22}$N$_4$O$_3$S, 434.14; m/z found, 435.0 [M+H]$^+$. $^1$H NMR (400 MHz, CDCl$_3$): 8.56 (dd, J=4.8, 1.7, 1H), 8.02 (dd, J=7.9, 1.7, 1H), 7.84 (d, J=8.5, 1H), 7.63-7.56 (m, 2H), 7.29 (dd, J=8.5, 2.1, 1H), 7.21 (dd, J=7.9, 4.8, 1H), 4.20 (dd, J=12.7, 1.5, 1H), 3.72-3.58 (m, 2H), 3.48-3.19 (m, 4H), 2.89 (d, J=12.3, 1H), 2.06 (s, J=2.8, 3H), 2.03-1.93 (m, 2H), 1.72-1.63 (m, 2H).

Examples 154 to 189 were prepared using methods analogous to those described for Example 153.

Example 154

(1S,4S)-1-{5-[6-(Thiazolo[4,5-b]pyridin-2-yloxy)-benzofuran-3-ylmethyl]-2,5-diaza-bicyclo[2.2.1]hept-2-yl}-ethanone

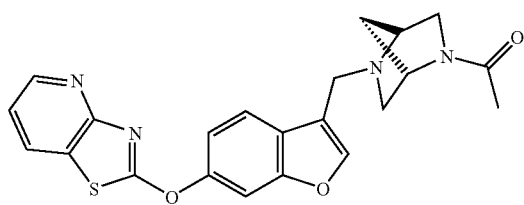

MS (ESI): mass calcd. for $C_{22}H_{20}N_4O_3S$, 420.13; m/z found, 421.0 [M+H]$^+$. $^1$H NMR (400 MHz, CDCl$_3$, 1:1 mixture of rotamers): 8.56 (dd, J=4.8, 1.6, 1H), 8.02 (dt, J=7.9, 1.6, 1H), 7.75 (d, J=8.5, 1H), 7.61-7.56 (m, 2H), 7.32-7.26 (m, 1H), 7.20 (ddd, J=7.9, 4.8, 1.1, 1H), 4.80 (s, 0.5H), 4.24 (s, 0.5H), 3.93-3.78 (m, 2H), 3.76-3.71 (m, 0.5H), 3.62-3.57 (m, 1H), 3.57-3.52 (m, 1H), 3.32 (dd, J=9.3, 2.3, 0.5H), 3.28 (dd, J=11.5, 2.0, 0.5H), 3.02 (dd, J=9.6, 2.1, 0.5H), 2.85 (s, J=1.2, 1H), 2.65-2.59 (m, 0.5H), 2.09 (s, 1.5H), 2.00 (s, 1.5H), 1.99-1.86 (m, 1H), 1.84-1.77 (m, 0.5H), 1.70-1.66 (m, 1H).

Example 155 meso-endo-N-{8-[6-(Thiazolo[4,5-b]pyridin-2-yloxy)-benzofuran-3-ylmethyl]-8-aza-bicyclo[3.2.1]oct-3-yl}-acetamide

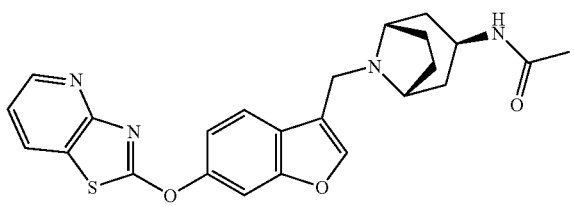 [SMILES: CC(=O)N[C@H]1C[C@H]2CC[C@@H](C1)N2Cc1coc2cc(Oc3nc4ncccc4s3)ccc12]

MS (ESI): mass calcd. for $C_{24}H_{24}N_4O_3S$, 448.16; m/z found, 449.0 [M+H]$^+$. $^1$H NMR (400 MHz, CDCl$_3$): 8.56 (dd, J=4.8, 1.6, 1H), 8.02 (dd, J=7.9, 1.6, 1H), 7.81 (d, J=8.5, 1H), 7.58 (d, J=1.7, 2H), 7.29-7.27 (m, 1H), 7.21 (dd, J=7.9, 4.8, 1H), 5.83 (d, J=6.9, 1H), 4.16-4.02 (m, 1H), 3.63 (s, J=4.0, 2H), 3.27 (s, 2H), 2.26-2.10 (m, 4H), 1.97 (s, 3H), 1.82-1.75 (m, 2H), 1.62 (d, J=14.1, 2H).

Example 156

2-(3-Morpholin-4-ylmethyl-benzofuran-6-yloxy)-thiazolo[4,5-b]pyridine

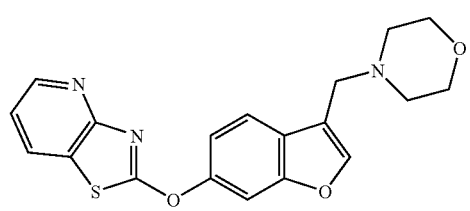 [SMILES: c1cnc2nc(Oc3ccc4c(CN5CCOCC5)coc4c3)sc2c1]

MS (ESI): mass calcd. for $C_{19}H_{17}N_3O_3S$, 367.16; m/z found, 368.0 [M+H]$^+$. $^1$H NMR (400 MHz, CDCl$_3$): 8.56 (dd, J=4.8, 1.6, 1H), 8.02 (dd, J=7.9, 1.6, 1H), 7.79 (d, J=8.5, 1H), 7.60 (s, 1H), 7.58 (d, J=2.0, 1H), 7.29 (dd, J=8.5, 2.1, 1H), 7.21 (dd, J=7.9, 4.8, 1H), 3.75-3.70 (m, 4H), 3.63 (d, J=0.7, 2H), 2.55-2.42 (m, 4H).

Example 157

(1R,4R)-1-{5-[6-(Thiazolo[4,5-b]pyridin-2-yloxy)-benzofuran-3-ylmethyl]-2,5-diaza-bicyclo[2.2.1]hept-2-yl}-ethanone

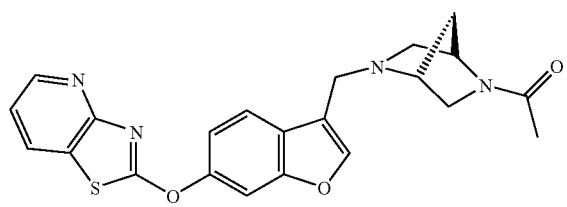

MS (ESI): mass calcd. for $C_{22}H_{20}N_4O_3S$, 420.13; m/z found, 421.1 [M+H]$^+$. $^1$H NMR (400 MHz, CDCl$_3$, 1:1 mixture of rotamers): 8.56 (d, J=4.8, 1H), 8.02 (d, J=7.1, 1H), 7.75 (d, J=8.4, 1H), 7.59 (d, J=1.6, 2H), 7.30 (d, J=7.0, 1H), 7.25-7.15 (m, 1H), 4.79 (s, 0.5H), 4.24 (s, 0.5H), 3.97-3.77 (m, 2H), 3.74 (d, J=11.4, 0.5H), 3.59 (d, J=6.3, 1H), 3.54 (d, J=9.4, 0.5H), 3.38-3.23 (m, 1H), 3.02 (d, J=9.6, 0.5H), 2.85 (s, 1H), 2.62 (d, J=9.6, 0.5H), 2.08 (s, 1.5H), 2.00 (s, 1.5H), 1.98-1.78 (m, 1.5H), 1.70-1.66 (m, 0.5H).

Example 158

(1S,4S)-2-[3-(2-Oxa-5-aza-bicyclo[2.2.1]hept-5-ylmethyl)-benzofuran-6-yloxy]-thiazolo[4,5-b]pyridine

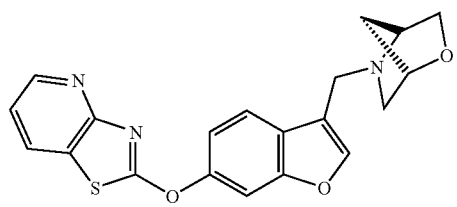

MS (ESI): mass calcd. for $C_{20}H_{17}N_3O_3S$, 379.10; m/z found, 380.1 [M+H]$^+$. $^1$H NMR (400 MHz, CDCl$_3$): 8.56 (dd, J=4.8, 1.6, 1H), 8.01 (dd, J=7.9, 1.6, 1H), 7.76 (d, J=8.5, 1H), 7.60-7.57 (m, 2H), 7.28 (dd, J=8.5, 2.1, 1H), 7.20 (dd, J=7.9, 4.8, 1H), 4.43 (s, 1H), 4.10 (d, J=7.7, 1H), 3.87 (dd, J=17.7, 1.0, 2H), 3.66 (dd, J=7.7, 1.8, 1H), 3.52 (s, 1H), 2.90 (dd, J=10.1, 1.7, 1H), 2.66 (d, J=10.2, 1H), 1.89 (d, J=1.9, 1H), 1.77-1.72 (m, 1H).

Example 159

(S)-2-[3-(3-Methyl-morpholin-4-ylmethyl)-benzofuran-6-yloxy]-thiazolo[4,5-b]pyridine

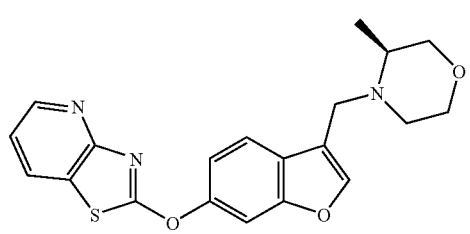 [SMILES: C[C@H]1COCCN1Cc1coc2cc(Oc3nc4ncccc4s3)ccc12]

MS (ESI): mass calcd. for $C_{20}H_{19}N_3O_3S$, 381.11; m/z found, 382.1 [M+H]+. 1H NMR (400 MHz, CDCl3): 8.56 (dd, J=4.8, 1.7, 1H), 8.01 (dd, J=7.9, 1.6, 1H), 7.79 (d, J=8.5, 1H), 7.61-7.55 (m, 2H), 7.29 (dd, J=8.5, 2.1, 1H), 7.20 (dd, J=7.9, 4.8, 1H), 4.13 (dd, J=13.7, 1.1, 1H), 3.82-3.67 (m, 2H), 3.64-3.53 (m, 1H), 3.40-3.24 (m, 2H), 2.68 (dt, J=11.8, 2.7, 1H), 2.56-2.46 (m, 1H), 2.32-2.15 (m, 1H), 1.15 (d, J=6.3, 3H).

Example 160

(1R,4R)-5-[6-(Thiazolo[4,5-b]pyridin-2-yloxy)-benzofuran-3-ylmethyl]-2,5-diaza-bicyclo[2.2.1]heptane-2-carboxylic acid amide

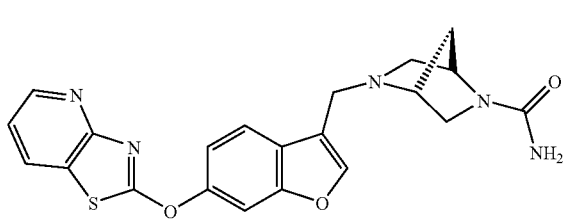

MS (ESI): mass calcd. for $C_{21}H_{19}N_5O_3S$, 421.12; m/z found, 422.0 [M+H]+. 1H NMR (400 MHz, CDCl3): 8.56 (dd, J=4.8, 1.6, 1H), 8.02 (dd, J=7.9, 1.6, 1H), 7.75 (d, J=8.5, 1H), 7.58 (d, J=2.2, 2H), 7.29 (dd, J=8.5, 2.1, 1H), 7.20 (dd, J=8.0, 4.8, 1H), 4.42 (s, 1H), 4.35 (s, 2H), 3.85 (qd, J=13.8, 1.0, 2H), 3.58 (5, 1H), 3.51 (d, J=8.6, 1H), 3.23 (dd, J=8.8, 2.2, 1H), 3.00-2.73 (m, 2H), 1.92 (d, J=9.7, 1H), 1.75 (d, J=9.6, 1H).

Example 161

5-[6-(Thiazolo[4,5-b]pyridin-2-yloxy)-benzofuran-3-ylmethyl]-hexahydro-pyrrolo[3,4-c]pyrrole-2-carboxylic acid amide

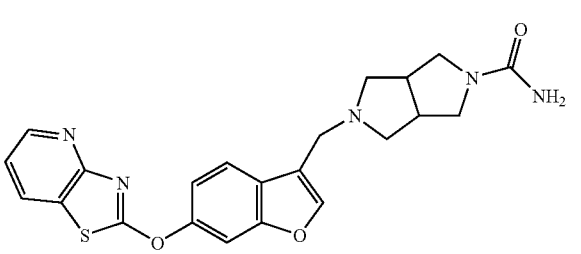 [SMILES: NC(=O)N1CC2CN(Cc3coc4cc(Oc5nc6ncccc6s5)ccc34)CC2C1]

MS (ESI): mass calcd. for $C_{22}H_{21}N_5O_3S$, 435.14; m/z found, 435.9 [M+H]+. 1H NMR (400 MHz, CDCl3): 8.56 (dd, J=4.8, 1.6, 1H), 8.02 (dd, J=7.9, 1.7, 1H), 7.74 (d, J=8.5, 1H), 7.58 (d, J=2.2, 2H), 7.28 (dd, J=8.3, 2.0, 1H), 7.20 (dd, J=8.0, 4.8, 1H), 4.35 (s, 2H), 3.73 (s, 2H), 3.65-3.54 (m, 2H), 3.27 (dd, J=10.3, 3.2, 2H), 2.95-2.83 (m, 2H), 2.68-2.51 (m, 4H).

Example 162

N-{1-[6-(Thiazolo[4,5-b]pyridin-2-yloxy)-benzofuran-3-ylmethyl]-piperidin-4-ylmethyl}-acetamide

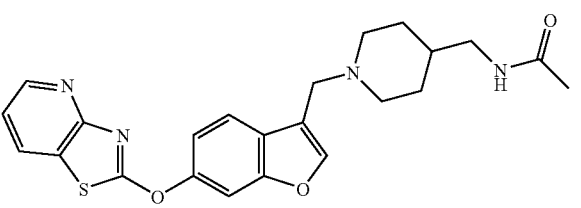 [SMILES: CC(=O)NCC1CCN(Cc2coc3cc(Oc4nc5ncccc5s4)ccc23)CC1]

MS (ESI): mass calcd. for $C_{23}H_{24}N_4O_3S$, 436.16; m/z found, 437.0 [M+H]+. 1H NMR (400 MHz, CDCl3): 8.56 (dd, J=4.8, 1.7, 1H), 8.01 (dd, J=7.9, 1.6, 1H), 7.75 (d, J=8.5, 1H), 7.63-7.52 (m, 2H), 7.29-7.27 (m, 1H), 7.20 (dd, J=7.9, 4.8, 1H), 5.65 (5, 1H), 3.62 (d, J=0.8, 2H), 3.14 (t, J=6.4, 2H), 2.94 (d, J=11.5, 2H), 2.06-1.95 (m, 5H), 1.72 (d, J=26.9, 2H), 1.56-1.43 (m, 1H), 1.35-1.22 (m, 2H).

Example 163

2-[3-(4-Trifluoromethyl-piperidin-1-ylmethyl)-benzofuran-6-yloxy]-thiazolo[4,5-b]pyridine

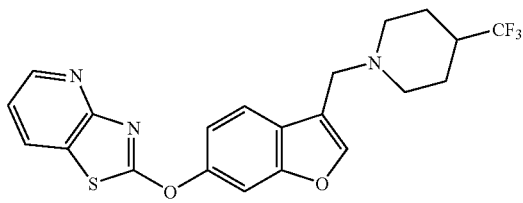 [SMILES: FC(F)(F)C1CCN(Cc2coc3cc(Oc4nc5ncccc5s4)ccc23)CC1]

MS (ESI): mass calcd. for $C_{21}H_{18}F_3N_3O_2S$, 433.11; m/z found, 434.0 [M+H]+. 1H NMR (400 MHz, CDCl3): 8.56 (dd, J=4.8, 1.6, 1H), 8.01 (dd, J=7.9, 1.7, 1H), 7.75 (d, J=8.5, 1H), 7.61-7.54 (m, 2H), 7.29 (dd, J=8.5, 2.1, 1H), 7.20 (dd, J=7.9, 4.8, 1H), 3.64 (d, J=0.8, 2H), 3.09-2.97 (m, 2H), 2.08-1.92 (m, 3H), 1.90-1.80 (m, 2H), 1.69-1.56 (m, 2H).

Example 164

(1S,4S)-1-{5-[6-(Benzothiazol-2-yloxy)-benzofuran-3-ylmethyl]-2,5-diaza-bicyclo[2.2.1]hept-2-yl}-ethanone

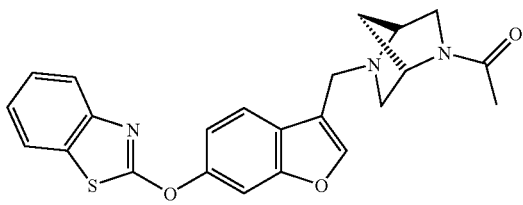

MS (ESI): mass calcd. for $C_{23}H_{21}N_3O_3S$, 419.13; m/z found, 420.0 [M+H]+. 1H NMR (400 MHz, CDCl3, 1:1 mixture of rotamers): 7.77-7.71 (m, 2H), 7.67 (d, J=8.0, 1H), 7.58 (d, J=6.4, 1H), 7.55-7.52 (m, 1H), 7.39 (t, J=7.5, 1H), 7.31-7.23 (m, 2H), 4.80 (5, 0.5H), 4.24 (5, 0.5H), 3.98-3.71 (m, 2.5H), 3.61 (5, 1.0H), 3.55 (d, J=9.1, 0.5H), 3.37-3.24 (m, 1H), 3.02 (dd, J=9.6, 2.1, 0.5H), 2.91-2.80 (m, 1H), 2.63 (d, J=10.7, 0.5H), 2.09 (5, 1.5H), 2.00 (5, 1.5H), 1.99-1.86 (m, 1H), 1.81 (d, J=9.8, 0.5H), 1.73-1.63 (m, 0.5H).

Example 165

2-(3-Morpholin-4-ylmethyl-benzofuran-6-yloxy)-benzothiazole

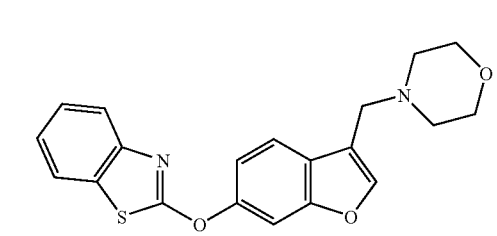 [SMILES: c1ccc2sc(Oc3ccc4c(CN5CCOCC5)coc4c3)nc2c1]

MS (ESI): mass calcd. for C$_{20}$H$_{18}$N$_2$O$_3$S, 366.10; m/z found, 367.0 [M+H]$^+$. $^1$H NMR (400 MHz, CDCl$_3$): 7.77 (d, J=8.5, 1H), 7.73 (d, J=8.1, 0.4, 1H), 7.67-7.63 (m, 1H), 7.57 (s, 1H), 7.53 (d, J=2.1, 1H), 7.41-7.34 (m, 1H), 7.30-7.21 (m, 2H), 3.75-3.67 (m, 4H), 3.61 (s, 2H), 2.53-2.41 (m, 4H).

Example 166

1-{2-[5-(Thiazolo[4,5-b]pyridin-2-yloxy)-benzofuran-2-ylmethyl]-2,7-diaza-spiro[4.5]dec-7-yl}-ethanone

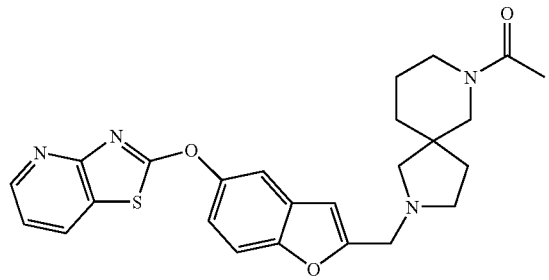 [SMILES: CC(=O)N1CCCC2(CCN(Cc3cc4cc(Oc5nc6ncccc6s5)ccc4o3)C2)C1]

MS (ESI): mass calcd. For C$_{25}$H$_{26}$N$_4$O$_3$S, 476.2; m/z found, 477.1 [M+H]$^+$. $^1$H NMR (500 MHz, CDCl$_3$, mixture of rotamers 1:2): 8.60-8.52 (m, 1H), 8.00 (ddd, J=7.9, 2.8, 1.7, 1H), 7.59 (dd, J=13.2, 2.4, 1H), 7.53-7.45 (m, 1H), 7.24 (td, J=8.9, 2.5, 1H), 7.21-7.17 (m, 1H), 6.62 (s, 0.4H), 6.59 (s, 0.6H), 3.83 (t, J=13.0, 1.6H), 3.73 (t, J=15.0, 1H), 3.49 (s, 0.4H), 3.45 (s, 1H), 3.38-3.31 (m, 0.6H), 3.24-3.14 (m, 0.6H), 3.09 (d, J=13.0, 0.6H), 3.03-2.94 (m, 0.6H), 2.87-2.78 (m, 0.4H), 2.73 (d, J=9.4, 0.6H), 2.72-2.66 (m, 0.4H), 2.58-2.49 (m, 1H), 2.42 (d, J=9.4, 0.4H), 2.13 (d, J=9.4, 0.6H), 2.10 (s, 1H), 2.04 (s, 2H), 1.76-1.51 (m, 5.6H), 1.51-1.38 (m, 0.6H).

Example 167

1-{9-[5-(Thiazolo[4,5-b]pyridin-2-yloxy)-benzofuran-2-ylmethyl]-3,9-diaza-spiro[5.5]undec-3-yl}-ethanone

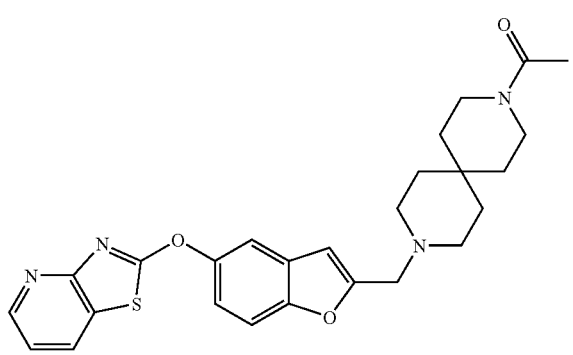 [SMILES: CC(=O)N1CCC2(CCN(Cc3cc4cc(Oc5nc6ncccc6s5)ccc4o3)CC2)CC1]

MS (ESI): mass calcd. For C$_{26}$H$_{28}$N$_4$O$_3$S, 476.2; m/z found, 477.1 [M+H]$^+$. $^1$H NMR (500 MHz, CDCl$_3$): 8.56 (dd, J=4.8, 1.6, 1H), 8.01 (dd, J=7.9, 1.6, 1H), 7.60 (d, J=2.4, 1H), 7.51 (d, J=8.8, 1H), 7.24 (dd, J=8.8, 2.5, 1H), 7.20 (dd, J=7.9, 4.8, 1H), 6.61 (s, 1H), 3.72 (s, 2H), 3.63-3.45 (m, 2H), 3.44- 3.28 (m, 2H), 2.53 (d, J=5.2, 4H), 2.08 (d, J=8.6, 3H), 1.60 (t, J=5.5, 4H), 1.52-1.40 (m, 4H).

Example 168

(1S,4S)-1-{5-[6-(Thiazolo[4,5-b]pyridin-2-yloxy)-benzofuran-2-ylmethyl]-2,5-diaza-bicyclo[2.2.1]hept-2-yl}-ethanone

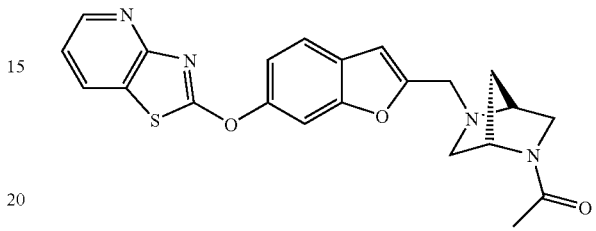

MS (ESI): mass calcd. for C$_{22}$H$_{20}$N$_4$O$_3$S, 420.1; m/z found, 421.0 [M+H]$^+$. $^1$H NMR (400 MHz, CD$_3$OD, mixture of rotamers 1:1): 8.59-8.51 (m, 1H), 8.04-7.99 (m, 1H), 7.61-7.51 (m, 2H), 7.26 (ddd, J=8.5, 2.1, 0.7, 1H), 7.23-7.17 (m, 1H), 6.63 (dd, J=6.8, 0.7, 1H), 4.80 (s, 0.5H), 4.26 (s, 0.5H), 3.89 (d, J=13.8, 2H), 3.78 (d, J=11.6, 0.5H), 3.68 (s, 1H), 3.61 (d, J=10.4, 0.5H), 3.37 (dd, J=9.5, 2.3, 0.5H), 3.31 (dd, J=11.6, 1.9, 0.5H), 3.16 (dd, J=9.7, 2.1, 0.5H), 2.99-2.87 (m, 1H), 2.72-2.64 (m, 0.5H), 2.10 (s, 1.5H), 2.05-1.96 (m, 2H), 1.86 (m, 1H), 1.70 (d, J=10.1, 0.5H).

Example 169 meso-1-{5-[5-(Thiazolo[4,5-b]pyridin-2-yloxy)-benzofuran-2-ylmethyl]-2,5-diaza-bicyclo[2.2.2]oct-2-yl}-ethanone

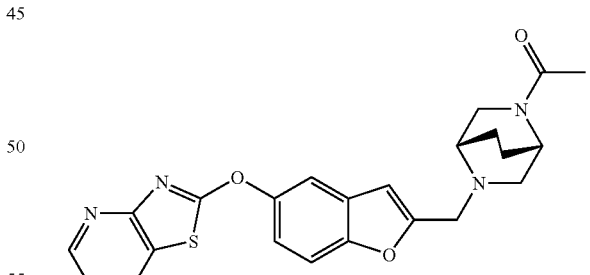

MS (ESI): mass calcd. For C$_{23}$H$_{22}$N$_4$O$_3$S, 434.1; m/z found, 435.1 [M+H]$^+$. $^1$H NMR (400 MHz, CDCl$_3$; mixture of rotamers): 8.55 (dd, J=4.8, 1.7, 1H), 8.04-7.93 (m, 1H), 7.60 (t, J=2.8, 1H), 7.50 (d, J=8.9, 1H), 7.27-7.22 (m, J=8.9, 2.5, 1.3, 1H), 7.19 (ddd, J=8.0, 4.8, 0.8, 1H), 6.63 (d, J=3.0, 1H), 4.59 (s, 0.5H), 3.98-3.76 (m, 3.5H), 3.44 (ddd, J=12.5, 11.6, 2.0, 1H), 3.20-3.07 (m, 1H), 3.05-2.91 (m, 2H), 2.23-2.09 (m, 1H), 2.08 (s, 1.5H), 2.03 (s, 1.5H), 1.94-1.77 (m, 2H), 1.73-1.58 (m, 1H).

Example 170 meso-1-{5-[6-(Thiazolo[4,5-b]pyridin-2-yloxy)-benzofuran-2-ylmethyl]-2,5-diaza-bicyclo[2.2.2]oct-2-yl}-ethanone

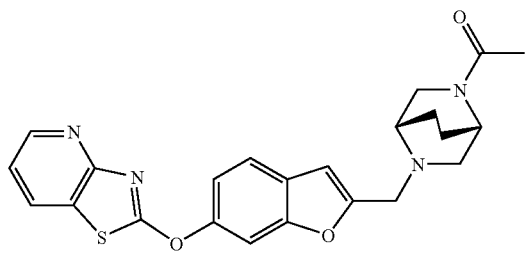 [SMILES: CC(=O)N1C[C@@H]2CC[C@H]1CN2Cc1cc2ccc(Oc3nc4ncccc4s3)cc2o1]

MS (ESI): mass calcd. For $C_{23}H_{22}N_4O_3S$, 434.1; m/z found, 435.1 [M+H]+. $^1$H NMR (400 MHz, CDCl$_3$; mixture of rotamers, 1:1): 8.56 (dd, J=4.8, 1.6, 1H), 8.04-7.96 (m, 1H), 7.60-7.48 (m, 2H), 7.29-7.24 (m, 1H), 7.20 (dd, J=7.9, 4.8, 1H), 6.64 (d, J=3.6, 1H), 4.59 (s, 0.5H), 3.97-3.72 (m, 3.5H), 3.47 (d, J=12.7, 0.5H), 3.40 (dd, J=10.5, 2.0, 0.5H), 3.21-3.06 (m, 1H), 3.06-2.92 (m, 2H), 2.25-2.09 (m, 0.5H), 2.08 (s, 1.5H), 2.03 (s, 1.5H), 1.95-1.78 (m, 2H), 1.68 (s, 1.5H).

Example 171

1-{4-[6-(Thiazolo[4,5-b]pyridin-2-yloxy)-benzofuran-2-ylmethyl]-piperazin-1-yl}-ethanone

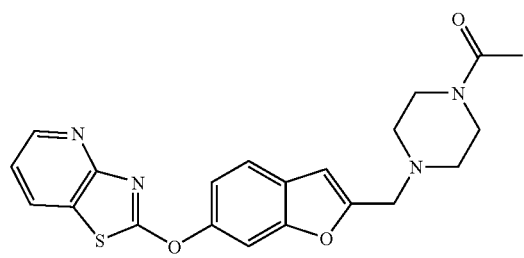 [SMILES: CC(=O)N1CCN(Cc2cc3ccc(Oc4nc5ncccc5s4)cc3o2)CC1]

MS (ESI): mass calcd. For $C_{21}H_{20}N_4O_3S$, 408.1; m/z found, 409.1 [M+H]+. $^1$H NMR (400 MHz, CDCl$_3$): 8.56 (dd, J=4.8, 1.6, 1H), 8.02 (dd, J=7.9, 1.7, 1H), 7.57 (dd, J=10.1, 5.1, 2H), 7.31-7.26 (m, J=2.1, 1H), 7.20 (dd, J=7.9, 4.8, 1H), 6.64 (s, 1H), 3.73 (s, 2H), 3.72-3.60 (m, 2H), 3.58-3.45 (m, 2H), 2.64-2.46 (m, J=10.7, 6.1, 4H), 2.09 (s, 3H).

Example 172 meso-endo-{8-[6-(Thiazolo[4,5-b]pyridin-2-yloxy)-benzofuran-2-ylmethyl]-8-aza-bicyclo[3.2.1]oct-3-yl}-urea

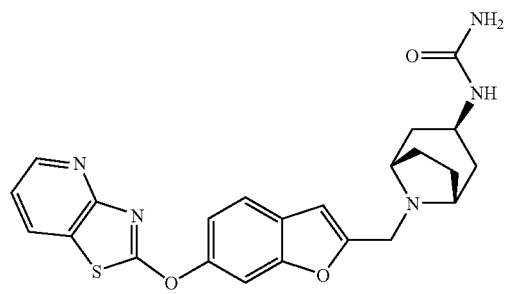 [SMILES: NC(=O)N[C@H]1C[C@H]2CC[C@@H](C1)N2Cc1cc2ccc(Oc3nc4ncccc4s3)cc2o1]

MS (ESI): mass calcd. For $C_{23}H_{23}N_5O_3S$, 449.2; m/z found, 450.1 [M+H]+. $^1$H NMR (400 MHz, CDCl$_3$): 8.54 (dd, J=4.9, 1.6, 1H), 8.04 (dd, J=7.9, 1.6, 1H), 7.55 (dd, J=7.9, 5.0, 2H), 7.28-7.19 (m, 2H), 6.67 (s, 1H), 3.84 (s, 1H), 3.69 (5, 2H), 3.30 (s, 2H), 2.50 (5, 3H), 2.32-2.04 (m, 4H), 1.92 (t, J=7.3, 2H), 1.67 (d, J=14.3, 2H).

Example 173 meso-8-[5-(Benzothiazol-2-yloxy)-benzofuran-2-ylmethyl]-3,8-diaza-bicyclo[3.2.1]octane-3-carboxylic acid amide

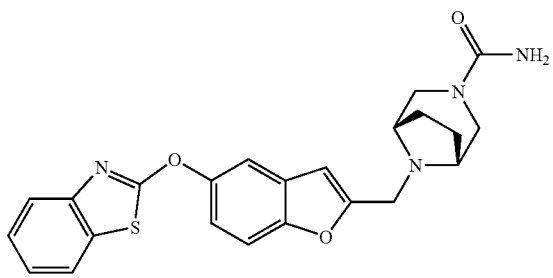 [SMILES: NC(=O)N1C[C@H]2CC[C@@H](C1)N2Cc1cc2cc(Oc3nc4ccccc4s3)ccc2o1]

MS (ESI): mass calcd. For $C_{23}H_{22}N_4O_3S$, 434.1; m/z found, 435.1 [M+H]+. $^1$H NMR (400 MHz, CDCl$_3$): 7.73 (d, J=8.0, 1H), 7.65 (d, J=7.4, 1H), 7.52 (dd, J=5.7, 3.1, 2H), 7.38 (t, J=7.2, 1H), 7.30-7.25 (m, 1H), 7.25-7.19 (m, 1H), 6.65 (s, 1H), 4.48 (s, 2H), 3.69 (s, 2H), 3.52 (s, 1H), 3.33 (s, 2H), 3.22 (d, J=11.6, 2H), 2.12-1.95 (m, J=8.1, 3H), 1.84-1.70 (m, J=7.0, 2H).

Example 174

(1S,4S)-5-[5-(Thiazolo[4,5-b]pyridin-2-yloxy)-benzofuran-2-ylmethyl]-2,5-diaza-bicyclo[2.2.1]heptane-2-carboxylic acid amide

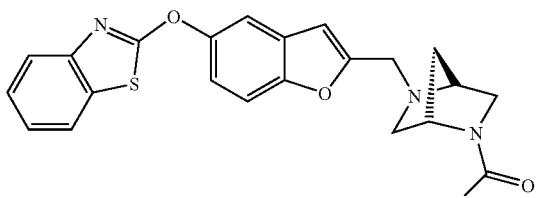

MS (ESI): mass calcd. for $C_{22}H_{20}N_4O_3S$, 420.1; m/z found, 421.0 [M+H]+. $^1$H NMR (400 MHz, CDCl$_3$): 7.73 (d, J=8.1, 1H), 7.65 (d, J=8.0, 1H), 7.57-7.48 (m, 2H), 7.44-7.33 (m, 1H), 7.30-7.24 (m, 1H), 7.24-7.19 (m, 1H), 6.61 (s, 1H), 3.69 (s, 2H), 2.94 (d, J=11.7, 2H), 2.36-2.22 (m, 1H), 2.18 (dd, J=11.2, 8.5, 2H), 2.06-1.73 (m, 5H).

Example 175 meso-endo-{8-[6-(Thiazolo[4,5-b]pyridin-2-yloxy)-benzofuran-3-ylmethyl]-8-aza-bicyclo[3.2.1]oct-3-yl}-urea

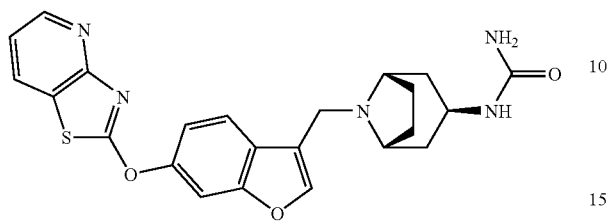

MS (ESI): mass calcd. for $C_{23}H_{23}N_5O_3S$, 449.2; m/z found, 450.1 [M+H]$^+$. $^1$H NMR (400 MHz, CD$_3$Cl$_3$): 8.56 (dd, J=4.8, 1.6, 1H), 8.02 (dd, J=7.9, 1.7, 1H), 7.81 (d, J=8.5, 1H), 7.58-7.54 (m, 2H), 7.29-7.25 (m, 1H), 7.20 (dd, J=7.9, 4.9, 1H), 5.04 (d, J=6.8, 1H), 4.44 (s, 2H), 3.88-3.80 (m, 1H), 3.62 (d, J=0.9, 2H), 3.25 (s, 2H), 2.26-2.05 (m, 4H), 1.88-1.78 (m, 2H), 1.73-1.65 (m, 2H).

Example 176

Furan-2-ylmethyl-methyl-[6-(thiazolo[4,5-b]pyridin-2-yloxy)-benzofuran-3-ylmethyl]-amine

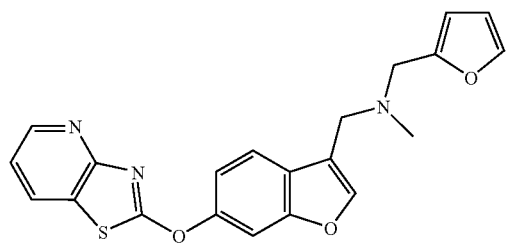 [SMILES: CN(Cc1ccco1)Cc1coc2cc(Oc3nc4ncccc4s3)ccc12]

MS (ESI): mass calcd. for $C_{21}H_{17}N_3O_3S$, 391.10; m/z found, 392.0 [M+H]$^+$. $^1$H NMR (400 MHz, CDCl$_3$): 8.56 (dd, J=4.8, 1.7, 1H), 8.00 (dd, J=7.9, 1.6, 1H), 7.71 (d, J=8.5, 1H), 7.64-7.54 (m, 2H), 7.42 (dd, J=1.8, 0.8, 1H), 7.28 (dd, J=8.5, 2.1, 1H), 7.19 (dd, J=7.9, 4.8, 1H), 6.36-6.33 (m, 1H), 6.25-6.20 (m, 1H), 3.66 (s, 2H), 3.65 (s, 2H), 2.30 (s, 3H).

Example 177

Methyl-pyridin-4-ylmethyl-[6-(thiazolo[4,5-b]pyridin-2-yloxy)-benzofuran-3-ylmethyl]-amine

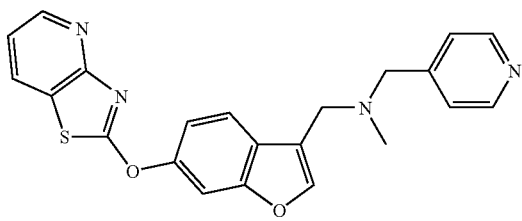 [SMILES: CN(Cc1ccncc1)Cc1coc2cc(Oc3nc4ncccc4s3)ccc12]

MS (ESI): mass calcd. for $C_{22}H_{18}N_4O_2S$, 402.12; m/z found, 403.0 [M+H]$^+$. $^1$H NMR (400 MHz, CDCl$_3$): 8.59-8.53 (m, 3H), 8.01 (dd, J=7.9, 1.7, 1H), 7.83-7.72 (m, 1H), 7.62-7.59 (m, 2H), 7.32 (dd, J=8.5, 2.1, 1H), 7.30-7.27 (m, 2H), 7.20 (dd, J=7.9, 4.8, 1H), 3.74-3.66 (m, 2H), 3.54 (d, J=16.9, 2H), 2.28 (d, J=21.8, 3H).

Example 178

Methyl-pyridin-3-ylmethyl-[6-(thiazolo[4,5-b]pyridin-2-yloxy)-benzofuran-3-ylmethyl]-amine

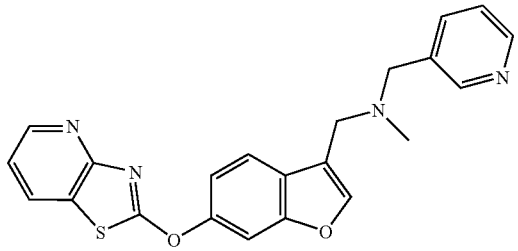 [SMILES: CN(Cc1cccnc1)Cc1coc2cc(Oc3nc4ncccc4s3)ccc12]

MS (ESI): mass calcd. for $C_{22}H_{18}N_4O_2S$, 402.1; m/z found, 403.0 [M+H]$^+$. $^1$H NMR (400 MHz, CDCl$_3$): 8.60-8.55 (m, 2H), 8.51 (dd, J=4.8, 1.5, 1H), 8.01 (dd, J=7.9, 1.7, 1H), 7.74 (d, J=8.5, 1H), 7.71-7.65 (m, 1H), 7.62-7.59 (m, 2H), 7.33-7.24 (m, 2H), 7.20 (dd, J=7.9, 4.8, 1H), 3.68 (s, J=0.6, 2H), 3.58 (s, 2H), 2.24 (s, 3H).

Example 179

1-{1-[6-(Benzothiazol-2-yloxy)-benzofuran-3-ylmethyl]-piperidin-4-yl}-pyrrolidin-2-one

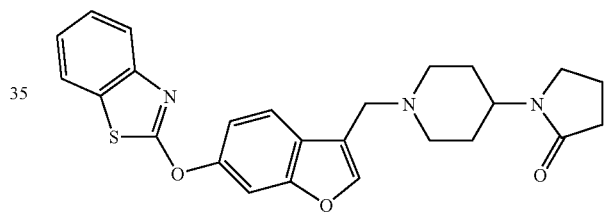

MS (ESI): mass calcd. for $C_{25}H_{25}N_3O_3S$, 447.2; m/z found, 448.0 [M+H]$^+$. $^1$H NMR (400 MHz, CDCl$_3$): 7.78-7.72 (m, 2H), 7.67 (d, J=7.3, 1H), 7.58 (s, 1H), 7.53 (d, J=2.1, 1H), 7.39 (td, J=7.8, 1.2, 1H), 7.32-7.21 (m, 2H), 4.09-3.93 (m, 1H), 3.63 (s, 2H), 3.36 (t, J=7.0, 2H), 3.02 (d, J=11.3, 2H), 2.38 (t, J=8.1, 2H), 2.15 (t, J=10.4, 2H), 2.07-1.91 (m, 2H), 1.81-1.61 (m, 4H).

Example 180

N-{1-[6-(Benzothiazol-2-yloxy)-benzofuran-3-ylmethyl]-piperidin-4-yl}-acetamide

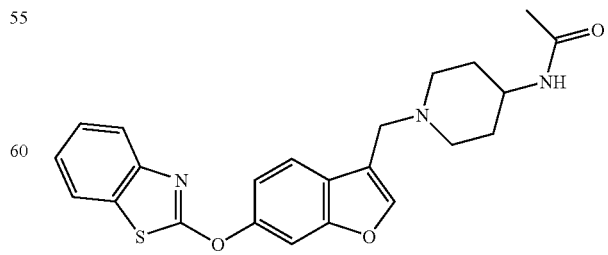

MS (ESI): mass calcd. for $C_{23}H_{23}N_3O_3S$, 421.2; m/z found, 422.0 [M+H]$^+$. $^1$H NMR (400 MHz, CDCl$_3$): 7.78-7.71 (m, 2H), 7.67 (dd, J=7.9, 0.8, 1H), 7.57 (s, 1H), 7.53 (d, J=2.1, 1H), 7.39 (td, J=7.8, 1.3, 1H), 7.42-7.36 (m, 1H), 7.30-7.22 (m, 1H), 5.36-5.20 (m, 1H), 3.88-3.74 (m, 1H), 3.62 (s, J=0.6, 2H), 2.97-2.78 (m, 2H), 2.17 (t, J=10.4, 2H), 1.96 (s, 3H), 1.96-1.89 (m, 2H), 1.49-1.37 (m, 2H).

Example 181 meso-endo-N-{8-[6-(Benzothiazol-2-yloxy)-benzo-furan-3-ylmethyl]-8-aza-bicyclo[3.2.1]oct-3-yl}-acetamide

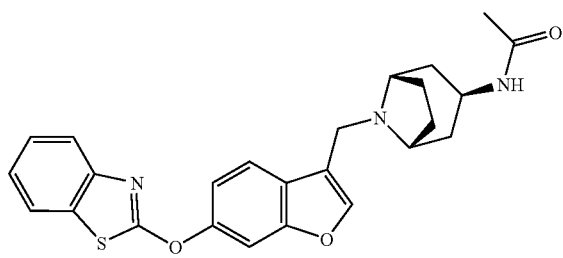 [SMILES: CC(=O)N[C@H]1C[C@H]2CC[C@@H](C1)N2Cc1coc2cc(Oc3nc4ccccc4s3)ccc12]

MS (ESI): mass calcd. for $C_{25}H_{25}N_3O_3S$, 447.2; m/z found, 448.0 [M+H]$^+$. $^1$H NMR (400 MHz, CDCl$_3$): 7.80 (d, J=8.5, 1H), 7.74 (d, J=8.1, 1H), 7.67 (dd, J=7.9, 0.7, 1H), 7.56 (s, 1H), 7.52 (d, J=2.1, 1H), 7.39 (td, J=7.8, 1.3, 1H), 7.31-7.22 (m, 2H), 5.78 (s, 1H), 4.23-3.98 (m, 1H), 3.63 (s, 2H), 3.28 (s, 2H), 2.36-2.06 (m, 4H), 1.96 (s, 3H), 1.84-1.72 (m, 2H), 1.62 (d, J=14.2, 2H).

Example 182

1-{4-[6-(Thiazolo[4,5-b]pyridin-2-yloxy)-benzofu-ran-3-ylmethyl]-[1,4]diazepan-1-yl}-ethanone

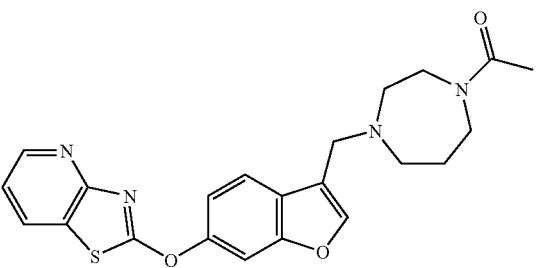 [SMILES: CC(=O)N1CCCN(Cc2coc3cc(Oc4nc5ncccc5s4)ccc23)CC1]

MS (ESI): mass calcd. for $C_{22}H_{22}N_4O_3S$, 422.14; m/z found, 423.0 [M+H]$^+$. $^1$H NMR (400 MHz, CDCl$_3$, 1:1 mixture of rotamers): 8.56 (dd, J=4.8, 1.7, 1H), 8.04-7.99 (m, 1H), 7.76 (dd, J=8.5, 5.0, 1H), 7.64-7.54 (m, 2H), 7.30-7.27 (m, 1H), 7.24-7.15 (m, 1H), 3.76 (dd, J=5.7, 0.8, 2H), 3.72-3.60 (m, 2H), 3.58-3.43 (m, 2H), 2.78-2.60 (m, 4H), 2.10 (s, 1.5H), 2.07 (s, 1.5H), 1.93-1.82 (m, 2H).

Example 183

2-[3-(4-Methanesulfonyl-piperidin-1-ylmethyl)-ben-zofuran-6-yloxy]-thiazolo[4,5-b]pyridine

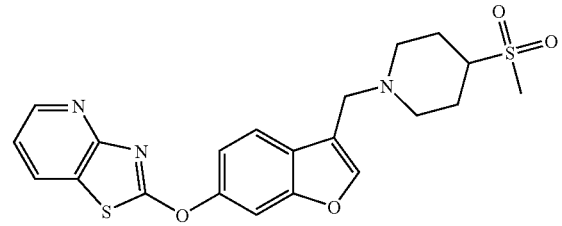 [SMILES: CS(=O)(=O)C1CCN(Cc2coc3cc(Oc4nc5ncccc5s4)ccc23)CC1]

MS (ESI): mass calcd. for $C_{21}H_{21}N_3O_4S_2$, 443.55; m/z found, 444.0 [M+H]$^+$. $^1$H NMR (500 MHz, CDCl$_3$): 8.56 (dd, J=4.8, 1.6, 1H), 8.03 (dd, J=7.9, 1.6, 1H), 7.75 (d, J=8.5, 1H), 7.61-7.55 (m, 2H), 7.28 (dd, J=8.3, 1.9, 1H), 7.21 (dd, J=7.9, 4.8, 1H), 3.66 (s, 2H), 3.13 (d, J=11.6, 2H), 2.90-2.76 (m, 4H), 2.19-2.01 (m, 4H), 1.87 (qd, J=12.4, 3.9, 2H).

Example 184

(2-Methoxy-ethyl)-methyl-[6-(thiazolo[4,5-b]pyri-din-2-yloxy)-benzofuran-3-ylmethyl]-amine

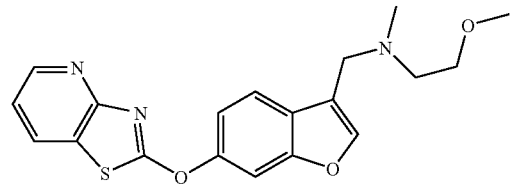 [SMILES: COCCN(C)Cc1coc2cc(Oc3nc4ncccc4s3)ccc12]

MS (ESI): mass calcd. for $C_{21}H_{21}N_3O_{452}$, 369.1; m/z found, 370.1 [M+H]$^+$. $^1$H NMR (500 MHz, CDCl$_3$): 8.56 (dd, J=4.8, 1.6, 1H), 8.01 (dd, J=7.9, 1.6, 1H), 7.74 (d, J=8.5, 1H), 7.64-7.55 (m, 2H), 7.28 (dd, J=8.3, 2.3, 1H), 7.20 (dd, J=7.9, 4.8, 1H), 3.71 (5, 2H), 3.56 (t, J=5.7, 2H), 3.37 (d, J=7.1, 3H), 2.67 (t, J=5.7, 2H), 2.32 (5, 3H).

Example 185

2-(3-Pyrrolidin-1-ylmethyl-benzofuran-6-yloxy)-thiazolo[4,5-b]pyridine

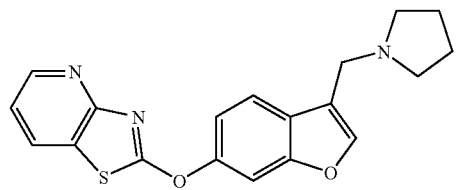 [SMILES: c1cnc2nc(Oc3ccc4c(CN5CCCC5)coc4c3)sc2c1]

MS (ESI): mass calcd. for $C_{19}H_{17}N_3O_2S$, 351.43; m/z found, 352.1 [M+H]$^+$. $^1$H NMR (500 MHz, CDCl$_3$): 8.56 (dd, J=4.8, 1.6, 1H), 8.01 (dd, J=7.9, 1.6, 1H), 7.73 (d, J=8.5, 1H), 7.62 (5, 1H), 7.58 (d, J=2.1, 1H), 7.31-7.26 (m, 1H), 7.20 (dd, J=7.9, 4.8, 1H), 3.76 (s, 2H), 2.58 (t, J=5.8, 4H), 1.81 (dt, J=6.6, 3.1, 4H).

Example 186

(2S)-2-[3-(2-Methoxymethyl-pyrrolidin-1-ylmethyl)-benzofuran-6-yloxy]-thiazolo[4,5-b]pyridine

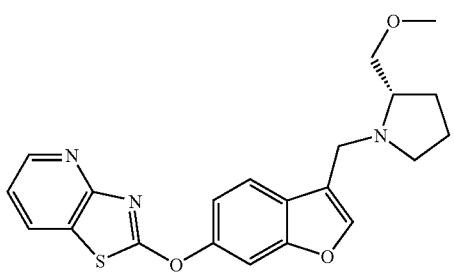 [SMILES: COC[C@@H]1CCCN1Cc1coc2cc(Oc3nc4ncccc4s3)ccc12]

MS (ESI): mass calcd. for $C_{21}H_{21}N_3O_3S$, 395.48; m/z found, 396.0 [M+H]$^+$. $^1$H NMR (500 MHz, CDCl$_3$): 8.56 (dd, J=4.8, 1.5, 1H), 8.01 (dd, J=7.9, 1.6, 1H), 7.76 (d, J=8.5, 1H), 7.60 (s, 1H), 7.57 (d, J=2.0, 1H), 7.32-7.25 (m, 1H), 7.19 (dd, J=7.9, 4.8, 1H), 4.22 (d, J=13.8, 1H), 3.62 (d, J=13.8, 1H), 3.56-3.47 (m, 1H), 3.46-3.36 (m, 4H), 3.00 (dd, J=11.2, 4.7, 1H), 2.78 (dq, J=11.8, 5.9, 1H), 2.28 (dt, J=16.8, 8.4, 1H), 1.94 (tt, J=12.2, 11.7, 1H), 1.81-1.67 (m, 2H), 1.66-1.56 (m, 1H).

Example 187

(1S,4S,5S)—N-{2-[6-(Thiazolo[4,5-b]pyridin-2-yloxy)-benzofuran-3-ylmethyl]-2-aza-bicyclo[2.2.1]hept-5-yl}-acetamide

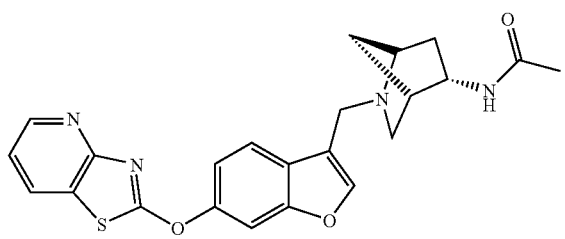

MS (ESI): mass calcd. for $C_{23}H_{22}N_4O_3S$, 434.52; m/z found, 435.0 [M+H]$^+$. $^1$H NMR (400 MHz, CDCl$_3$): 8.56 (dd, J=4.8, 1.6, 1H), 8.02 (dd, J=7.9, 1.6, 1H), 7.72 (d, J=8.5, 1H), 7.61-7.52 (m, 2H), 7.29 (dd, J=8.5, 2.1, 1H), 7.20 (dd, J=7.9, 4.8, 1H), 5.83 (s, 1H), 4.21 (dd, J=10.6, 6.5, 1H), 3.82 (dd, J=13.7, 0.9, 1H), 3.66 (dd, J=13.8, 0.8, 1H), 3.21 (5, 1H), 2.89 (d, J=10.2, 1H), 2.67 (5, 1H), 2.55-2.42 (m, 2H), 2.06 (ddd, J=11.2, 9.3, 3.4, 1H), 1.99 (5, 3H), 1.80 (d, J=10.2, 1H), 1.44 (d, J=10.3, 1H), 1.25 (dt, J=12.9, 3.7, 1H).

Example 188

(1S,4S,5S)—N-{2-[5-(Thiazolo[4,5-b]pyridin-2-yloxy)-benzofuran-2-ylmethyl]-2-aza-bicyclo[2.2.1]hept-5-yl}-acetamide

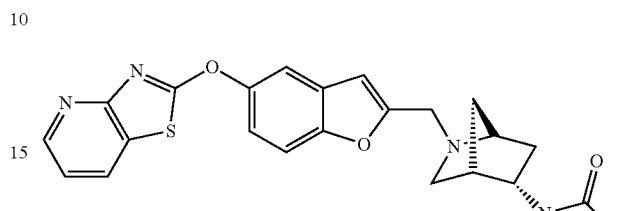

MS (ESI): mass calcd. for $C_{23}H_{22}N_4O_3S$, 434.52; m/z found, 435.0 [M+H]$^+$. $^1$H NMR (500 MHz, CDCl$_3$): 8.60-8.51 (m, 1H), 8.01 (d, J=7.9, 1H), 7.59 (s, 1H), 7.49 (d, J=8.4, 1H), 7.26-7.16 (m, 2H), 6.62 (s, 1H), 6.17 (s, 1H), 4.22 (s, 1H), 3.86 (d, J=14.4, 1H), 3.76 (d, J=14.3, 1H), 3.29 (s, 1H), 3.03 (d, J=10.0, 1H), 2.71 (s, 1H), 2.59 (d, J=10.3, 1H), 2.14-2.02 (m, 1H), 1.98 (s, 3H), 1.77 (d, J=10.1, 1H), 1.47 (d, J=10.4, 1H), 1.38-1.31 (m, 1H).

Example 189

(1S,4S,5S)—N-{2-[6-(Thiazolo[4,5-b]pyridin-2-yloxy)-benzofuran-2-ylmethyl]-2-aza-bicyclo[2.2.1]hept-5-yl}-acetamide

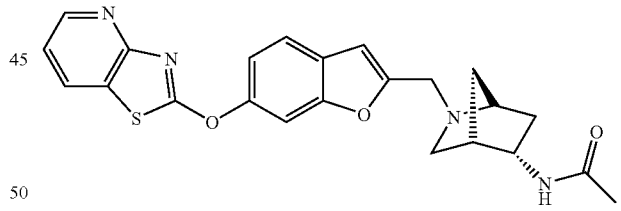

MS (ESI): mass calcd. for $C_{23}H_{22}N_4O_3S$, 434.52; m/z found, 435.0 [M+H]$^+$. $^1$H NMR (500 MHz, CDCl$_3$): 8.57 (d, J=3.2, 1H), 8.07-7.97 (m, 1H), 7.61-7.48 (m, 2H), 7.27-7.17 (m, 2H), 6.62 (d, J=6.6, 1H), 6.31 (d, J=43.9, 1H), 4.22 (s, 1H), 3.86 (d, J=14.4, 1H), 3.75 (dd, J=14.3, 5.4, 1H), 3.30 (s, 1H), 3.08-2.98 (m, 1H), 2.70 (s, 1H), 2.58 (d, J=10.1, 1H), 2.11-1.99 (m, 1H), 1.97 (d, J=3.9, 3H), 1.77 (d, J=10.1, 1H), 1.51-1.42 (m, 1H), 1.36 (d, J=13.5, 1H).

With modifications as stated for each specific Example, if any, Examples 190 to 222 were prepared as Example 153 with the following variation: DMF with $K_2CO_3$ at 50° C. for 16 hr was used instead of 4:1 $CH_3CN$/DMF with $K_2CO_3$ at rt for 48 hr.

Example 190

2-[2-(4-Fluoro-piperidin-1-ylmethyl)-benzofuran-6-yloxy]-thiazolo[4,5-b]pyridine formate

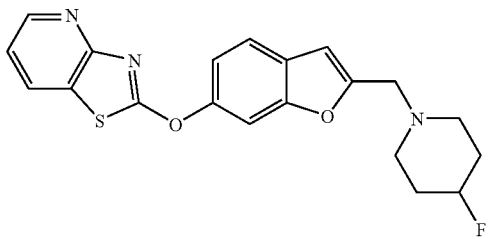 [SMILES: FC1CCN(Cc2cc3ccc(Oc4nc5ncccc5s4)cc3o2)CC1]

MS (ESI): mass calcd. for $C_{20}H_{18}FN_3O_2S$, 383.11; m/z found, 384.0 [M+H]$^+$. $^1$H NMR (500 MHz, CD$_3$OD): 8.48 (d, J=4.0, 1H), 8.30 (dd, J=8.0, 1.3, 1H), 7.71 (dd, J=16.1, 5.0, 2H), 7.37-7.30 (m, 2H), 7.11 (s, 1H), 4.87-4.73 (m, 1H), 4.26 (s, 2H), 3.14-3.00 (m, 4H), 2.21-1.98 (m, 4H).

Example 191

2-[2-(4-Trifluoromethyl-piperidin-1-ylmethyl)-benzofuran-6-yloxy]-thiazolo[4,5-b]pyridine formate

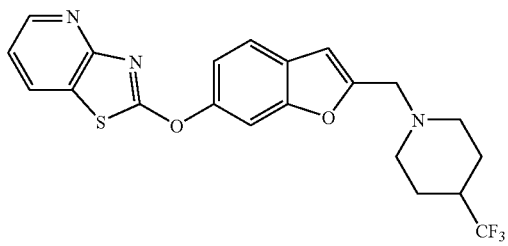 [SMILES: FC(F)(F)C1CCN(Cc2cc3ccc(Oc4nc5ncccc5s4)cc3o2)CC1]

MS (ESI): mass calcd. for $C_{21}H_{18}F_3N_3O_2S$, 433.11; m/z found, 434.0 [M+H]$^+$. $^1$H NMR (500 MHz, CD$_3$OD): 8.51-8.45 (m, 1H), 8.29 (dd, J=8.0, 1.6, 1H), 7.69 (d, J=8.5, 1H), 7.65 (d, J=1.8, 1H), 7.37-7.27 (m, 2H), 6.87 (5, 1H), 3.87 (5, 2H), 3.19-3.10 (m, 2H), 2.35-2.27 (m, 2H), 2.26-2.15 (m, 1H), 1.95-1.86 (m, 2H), 1.74-1.61 (m, 2H).

Example 192

2-(2-Piperidin-1-ylmethyl-benzofuran-6-yloxy)-thiazolo[4,5-b]pyridine formate

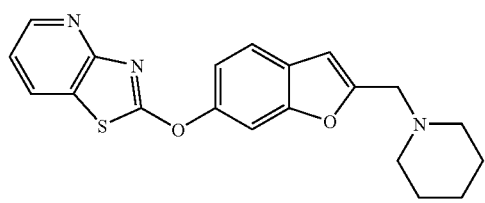 [SMILES: c1cnc2nc(Oc3ccc4cc(CN5CCCCC5)oc4c3)sc2c1]

MS (ESI): mass calcd. for $C_{20}H_{19}N_3O_2S$, 365.12; m/z found, 366.0 [M+H]$^+$. $^1$H NMR (400 MHz, CD$_3$OD): 8.48 (dd, J=4.9, 1.6, 1H), 8.29 (dd, J=8.0, 1.6, 1H), 7.76-7.64 (m, 2H), 7.39-7.26 (m, 2H), 6.95 (5, 1H), 4.04 (5, 2H), 2.93-2.75 (m, 4H), 1.83-1.63 (m, 4H), 1.60-1.47 (m, 2H).

Example 193

(1R,4R)-5-[6-(Thiazolo[4,5-b]pyridin-2-yloxy)-benzofuran-2-ylmethyl]-2,5-diaza-bicyclo[2.2.1]heptane-2-carboxylic acid amide

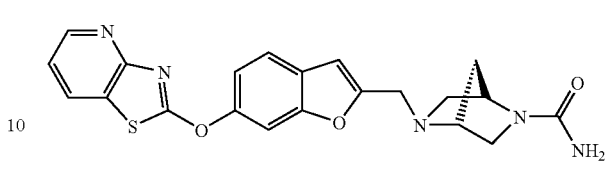

MS (ESI): mass calcd. for $C_{21}H_{19}N_5O_3S$, 421.12; m/z found, 422.0 [M+H]$^+$. $^1$H NMR (600 MHz, CDCl$_3$): 8.52-8.46 (m, 1H), 7.98-7.92 (m, 1H), 7.54-7.47 (m, 2H), 7.22-7.17 (m, 1H), 7.16-7.12 (m, 1H), 6.70 (s, 1H), 4.54-4.38 (m, 2H), 4.00-3.89 (m, 2H), 3.77-3.68 (m, 1H), 3.67-3.57 (m, 1H), 3.25 (d, J=7.8, 1H), 3.10-3.01 (m, 1H), 3.01-2.91 (m, 1H), 1.96-1.87 (m, 1H), 1.76 (d, J=9.6, 1H). The remaining proton was not detected and is believed to be hidden in the solvent peak.

Example 194

5-[6-(Thiazolo[4,5-b]pyridin-2-yloxy)-benzofuran-2-ylmethyl]-hexahydro-pyrrolo[3,4-c]pyrrole-2-carboxylic acid amide

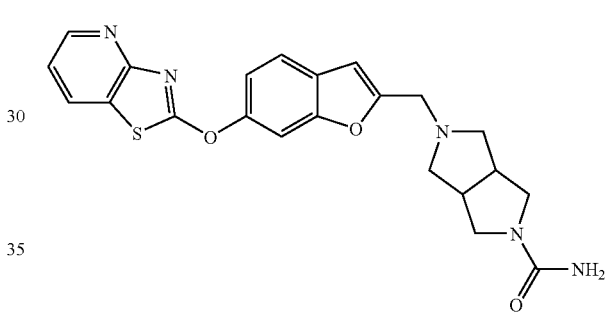

MS (ESI): mass calcd. for $C_{22}H_{21}N_5O_3S$, 435.14; m/z found, 435.9 [M+H]$^+$. $^1$H NMR (500 MHz, CD$_3$OD): 8.47 (dd, J=4.9, 1.6, 1H), 8.28 (dd, J=8.0, 1.6, 1H), 7.69-7.59 (m, 2H), 7.37-7.22 (m, 2H), 6.78 (s, 1H), 3.81 (5, 2H), 3.55-3.46 (m, 2H), 3.30-3.26 (m, 1H), 2.96-2.84 (m, 4H), 2.57-2.44 (m, 2H), 2.03 (d, J=5.2, 1H).

Example 195

1-{5-[6-(Thiazolo[4,5-b]pyridin-2-yloxy)-benzofuran-2-ylmethyl]-hexahydro-pyrrolo[3,4-c]pyrrol-2-yl}-ethanone

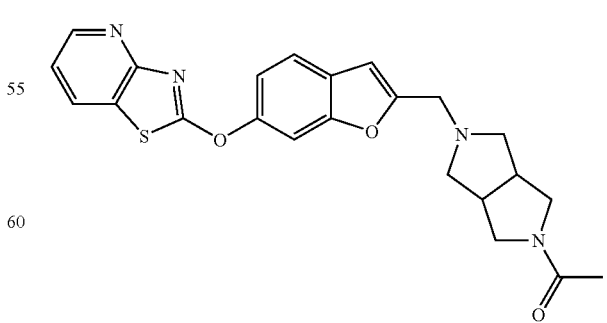

MS (ESI): mass calcd. for $C_{23}H_{22}N_4O_3S$, 434.14; m/z found, 435.0 [M+H]$^+$. $^1$H NMR (500 MHz, CD$_3$OD): 8.51-8.43 (m, 1H), 8.27 (dd, J=8.0, 1.6, 1H), 7.68-7.58 (m, 2H), 7.35-7.24 (m, 2H), 6.77 (s, 1H), 3.81 (s, 2H), 3.75-3.66 (m, 1H), 3.64-3.54 (m, 1H), 3.47-3.36 (m, 2H), 3.02-2.93 (m, 1H), 2.92-2.78 (m, 3H), 2.63-2.54 (m, 2H), 2.03 (s, 3H).

Example 196

1-{4-[6-(Thiazolo[4,5-b]pyridin-2-yloxy)-benzofuran-3-ylmethyl]-piperazin-1-yl}-ethanone formate

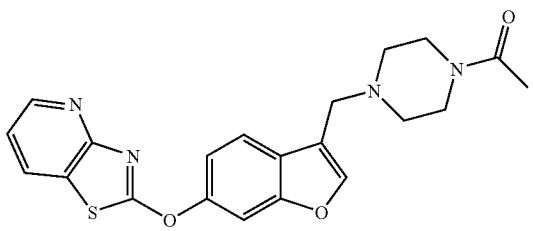 [SMILES: CC(=O)N1CCN(Cc2coc3cc(Oc4nc5ncccc5s4)ccc23)CC1]

MS (ESI): mass calcd. for $C_{21}H_{20}N_4O_3S$, 408.13; m/z found, 409.0 [M+H]$^+$. $^1$H NMR (400 MHz, CD$_3$OD): 8.47 (dd, J=4.9, 1.6, 1H), 8.28 (dd, J=8.0, 1.6, 1H), 7.89-7.84 (m, 1H), 7.82 (s, 1H), 7.65 (d, J=2.1, 1H), 7.36-7.29 (m, 2H), 3.77 (s, 2H), 3.65-3.59 (m, 2H), 3.59-3.52 (m, 2H), 2.63-2.57 (m, 2H), 2.57-2.51 (m, 2H), 2.08 (s, 3H).

Example 197

N-{1-[6-(Thiazolo[4,5-b]pyridin-2-yloxy)-benzofuran-3-ylmethyl]-piperidin-4-yl}-acetamide formate

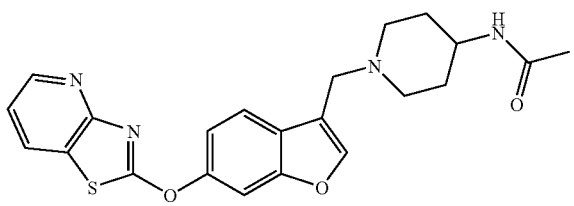 [SMILES: CC(=O)NC1CCN(Cc2coc3cc(Oc4nc5ncccc5s4)ccc23)CC1]

MS (ESI): mass calcd. for $C_{22}H_{22}N_4O_3S$, 422.14; m/z found, 423.0 [M+H]$^+$. $^1$H NMR (400 MHz, CD$_3$OD): 8.51-8.45 (m, 1H), 8.33-8.27 (m, 1H), 7.99 (s, 1H), 7.90-7.80 (m, 1H), 7.75-7.68 (m, 1H), 7.43-7.29 (m, 2H), 4.15 (s, 2H), 3.86-3.73 (m, 1H), 2.86-2.69 (m, 2H), 2.06-1.95 (m, 2H), 1.92 (s, 3H), 1.76-1.60 (m, 2H). The remaining protons were not detected and are believed to be hidden in the solvent peak.

Example 198

Diethyl-[6-(thiazolo[4,5-b]pyridin-2-yloxy)-benzofuran-2-ylmethyl]-amine formate

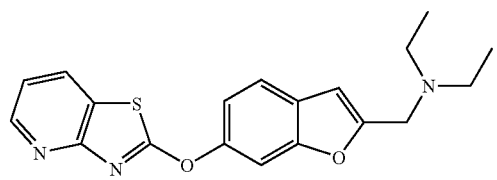 [SMILES: CCN(CC)Cc1cc2ccc(Oc3nc4ncccc4s3)cc2o1]

MS (ESI): mass calcd. for $C_{19}H_{19}N_3O_2S$, 353.1; m/z found, 353.0 [M+H]$^+$. $^1$H NMR (500 MHz, CD$_3$OD): 8.48 (d, J=3.9, 1H), 8.31 (dd, J=8.0, 1.6, 1H), 7.79-7.76 (m, 2H), 7.38 (dd, J=8.5, 2.2, 1H), 7.35 (dd, J=8.0, 4.9, 1H), 7.30 (s, 1H), 4.59 (s, 2H), 3.22 (q, J=7.2, 4H), 1.42 (t, J=7.3, 6H).

Example 199

(1S,4S)-1-{5-[5-(Thiazolo[4,5-c]pyridin-2-yloxy)-benzofuran-2-ylmethyl]-2,5-diaza-bicyclo[2.2.1]hept-2-yl}-ethanone formate

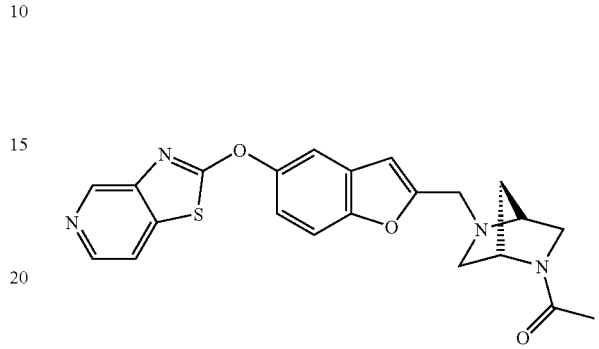

MS (ESI): mass calcd. for $C_{22}H_{20}N_4O_3S$, 420.2; m/z found, 421.1 [M+H]$^+$. $^1$H NMR (400 MHz, CD$_3$OD): 8.82 (s, 1H), 8.36 (d, J=5.4, 1H), 7.91 (d, J=5.3, 1H), 7.64 (d, J=2.4, 1H), 7.59 (d, J=8.9, 1H), 7.31 (ddd, J=8.9, 2.5, 0.7, 1H), 6.84 (s, 1H), 4.71 (s, 0.5H), 4.50 (s, 0.5H), 4.07-3.94 (m, 2H), 3.83-3.62 (m, 2H), 3.48 (dd, J=10.1, 2.3, 0.5H), 3.30-3.25 (m, 0.5H), 3.09 (dd, J=10.1, 2.1, 0.5H), 3.00 (dd, J=10.0, 2.2, 0.5H), 2.90-2.82 (m, 1H), 2.11 (s, 1.5H), 2.03-1.99 (m, 2H), 1.95 (d, J=10.3, 0.5H), 1.91-1.85 (m, 0.5H), 1.79 (d, J=10.3, 0.5H).

Example 200 meso-endo-N-{8-[5-(Thiazolo[4,5-c]pyridin-2-yloxy)-benzofuran-2-ylmethyl]-8-aza-bicyclo[3.2.1]oct-3-yl}-acetamide formate

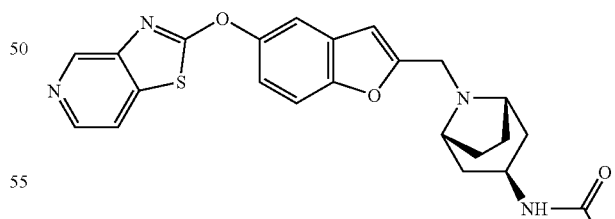

MS (ESI): mass calcd. for $C_{24}H_{24}N_4O_3S$, 448.2; m/z found, 449.1 [M+H]$^+$. $^1$H NMR (400 MHz, CD$_3$OD): 8.81 (s, 1H), 8.43 (br s, 1H), 8.37 (d, J=5.5, 1H), 7.93 (d, J=5.5, 1H), 7.72 (d, J=2.4, 1H), 7.67 (d, J=8.9, 1H), 7.40 (dd, J=8.9, 2.5, 1H), 7.09 (s, 1H), 4.25 (s, 2H), 3.93 (t, J=6.7, 1H), 3.76 (br s, 2H), 2.40-2.24 (m, 6H), 2.02-1.97 (m, 5H).

Example 201 meso-endo-N-{8-[6-(Thiazolo[4,5-c]pyridin-2-yloxy)-benzofuran-2-ylmethyl]-8-aza-bicyclo[3.2.1]oct-3-yl}-acetamide

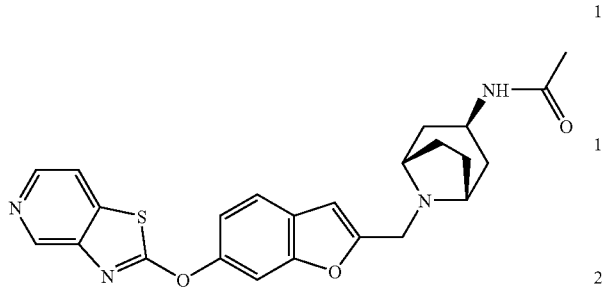

MS (ESI): mass calcd. for $C_{24}H_{24}N_4O_3S$, 448.2; m/z found, 449.1 [M+H]$^+$. $^1$H NMR (500 MHz, CDCl$_3$): 9.00 (s, 1H), 8.44 (d, J=5.3, 1H), 7.64 (d, J=5.3, 1H), 7.58 (d, J=8.4, 1H), 7.54 (d, J=1.5, 1H), 7.23 (dd, J=8.4, 2.1, 1H), 6.65 (s, 1H), 5.81 (d, J=6.2, 1H), 4.11 (q, J=6.9, 1H), 3.68 (s, 2H), 3.33 (br s, 2H), 2.31-2.25 (m, 2H), 2.21-2.14 (m, 2H), 1.97 (s, 3H), 1.85-1.79 (m, 2H), 1.64-1.62 (m, 1H).

Example 202 meso-1-{8-[6-(Thiazolo[4,5-c]pyridin-2-yloxy)-benzofuran-2-ylmethyl]-3,8-diaza-bicyclo[3.2.1]oct-3-yl}ethanone

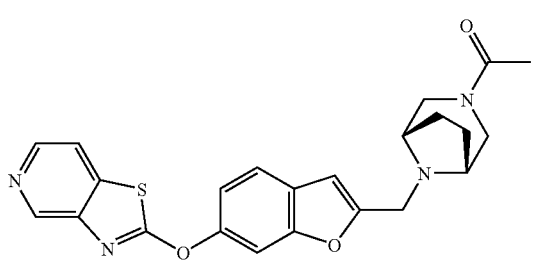 [SMILES: CC(=O)N1C[C@H]2CC[C@@H](C1)N2Cc1cc2ccc(Oc3nc4cnccc4s3)cc2o1]

MS (ESI): mass calcd. for $C_{23}H_{22}N_4O_3S$, 434.1; m/z found, 435.0 [M+H]$^+$. $^1$H NMR (500 MHz, CDCl$_3$): 9.00 (s, 1H), 8.45 (d, J=5.3, 1H), 7.65 (d, J=5.3, 1H), 7.59 (d, J=8.4, 1H), 7.56 (d, J=1.5, 1H), 7.24 (dd, J=8.4, 2.1, 1H), 6.68 (s, 1H), 4.21 (dd, J=12.9, 2.5, 1H), 3.68 (s, 2H), 3.45-3.42 (m, 2H), 3.36-3.31 (m, 2H), 2.94 (d, J=12.9, 1H), 2.07 (s, 3H), 2.05-1.96 (m, 2H), 1.75-1.62 (m, 2H).

Example 203

(1S,4S)-1-{5-[6-(Thiazolo[4,5-c]pyridin-2-yloxy)-benzofuran-2-ylmethyl]-2,5-diaza-bicyclo[2.2.1]hept-2-yl}-ethanone

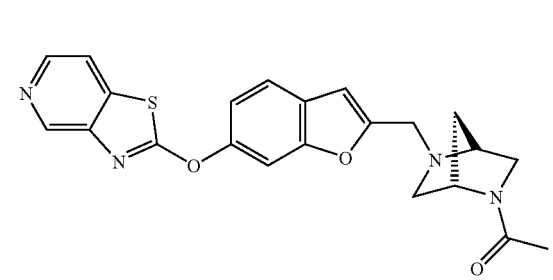

MS (ESI): mass calcd. for $C_{22}H_{20}N_4O_3S$, 420.1; m/z found, 421.0 [M+H]$^+$. $^1$H NMR (400 MHz, CDCl$_3$): 9.00 (d, J=0.8, 1H), 8.45 (d, J=5.4, 1H), 7.66-7.64 (m, 1H), 7.59 (dd, J=8.4, 1.6, 1H), 7.55-7.53 (m, 1H), 7.24 (dt, J=8.4, 2.1, 1H), 6.65 (dd, J=5.0, 0.8, 1H), 4.81 (s, 0.6H), 4.26 (s, 0.4H), 3.91 (s, 1H), 3.88 (s, 1H), 3.79 (dd, J=11.7, 1.4, 0.4H), 3.68 (br s, 1H), 3.61 (dd, J=9.5, 1.0, 0.6H), 3.37 (dd, J=9.5, 2.3, 0.6H), 3.31 (dd, J=11.7, 1.9, 0.4H), 3.17 (dd, J=9.7, 2.1, 0.4H), 2.97-2.88 (m, 1H), 2.67 (dd, J=9.6, 1.2, 0.4H), 2.10 (s, 1.5H), 2.06-1.98 (m, 2.5H), 1.93-1.82 (m, 1H), 1.73-1.69 (m, 1H).

Example 204

1-[6-(Thiazolo[4,5-b]pyridin-2-yloxy)-benzofuran-2-ylmethyl]-piperidine-4-carboxylic acid methylamide

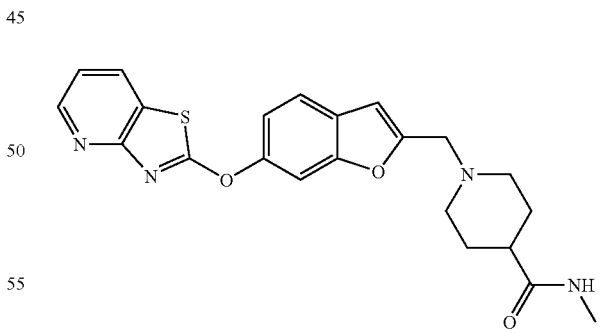

MS (ESI): mass calcd. for $C_{22}H_{22}N_4O_3S$, 422.1; m/z found, 423.0 [M+H]$^+$. $^1$H NMR (400 MHz, CDCl$_3$): 8.56 (dd, J=4.8, 1.6, 1H), 8.01 (dd, J=7.9, 1.7, 1H), 7.60-7.51 (m, 2H), 7.26-7.23 (m, 1H), 7.20 (dd, J=7.9, 4.8, 1H), 6.61 (s, 1H), 5.62 (br s, 1H), 3.70 (s, 2H), 3.04-2.98 (m, 2H), 2.79 (d, J=4.8, 3H), 2.20-2.03 (m, 3H), 1.92-1.75 (m, 4H).

Example 205

Pyrrolidin-1-yl-{1-[6-(thiazolo[4,5-b]pyridin-2-yloxy)-benzofuran-2-ylmethyl]-piperidin-4-yl}-methanone

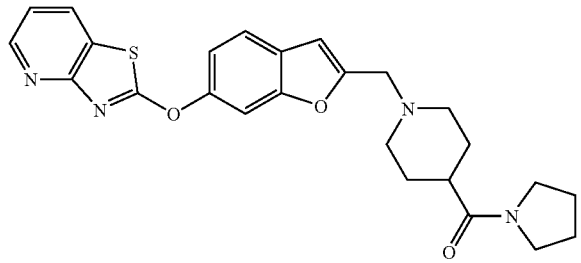 [SMILES: O=C(C1CCN(Cc2cc3ccc(Oc4nc5ncccc5s4)cc3o2)CC1)N1CCCC1]

MS (ESI): mass calcd. for $C_{25}H_{26}N_4O_3S$, 462.2; m/z found, 463.1 [M+H]$^+$. $^1$H NMR (400 MHz, CDCl$_3$): 8.56 (dd, J=4.8, 1.6, 1H), 8.01 (dd, J=7.9, 1.7, 1H), 7.58-7.54 (m, 2H), 7.28-7.23 (m, 1H), 7.20 (dd, J=7.9, 4.8, 1H), 6.61 (s, 1H), 3.74 (s, 2H), 3.46 (t, J=6.8, 4H), 3.07-3.01 (m, 2H), 2.36-2.28 (m, 1H), 2.18 (td, J=11.7, 2.4, 2H), 2.02-1.89 (m, 4H), 1.88-1.78 (m, 2H), 1.73 (d, J=12.4, 2H).

Example 206 meso-1-{8-[5-(Thiazolo[4,5-c]pyridin-2-yloxy)-benzofuran-2-ylmethyl]-3,8-diaza-bicyclo[3.2.1]oct-3-yl}-ethanone

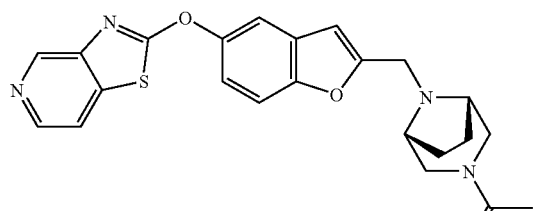

MS (ESI): mass calcd. for $C_{23}H_{22}N_4O_3S$, 434.1; m/z found, 435.0 [M+H]$^+$. $^1$H NMR (500 MHz, CDCl$_3$): 8.99 (d, J=0.7, 1H), 8.44 (d, J=5.3, 1H), 7.64 (dd, J=5.3, 0.8, 1H), 7.56-7.53 (m, 2H), 7.24 (dd, J=8.8, 2.5, 1H), 6.68 (s, 1H), 4.21 (dd, J=12.8, 2.6, 1H), 3.69 (s, 2H), 3.44 (d, J=2.3, 2H), 3.36-3.31 (m, 2H), 2.95 (d, J=11.5, 1H), 2.07 (s, 3H), 2.07-1.99 (m, 2H), 1.74-1.62 (m, 2H).

Example 207 meso-exo-{8-[6-(Thiazolo[4,5-b]pyridin-2-yloxy)-benzofuran-3-ylmethyl]-8-aza-bicyclo[3.2.1]oct-3-yl}-urea

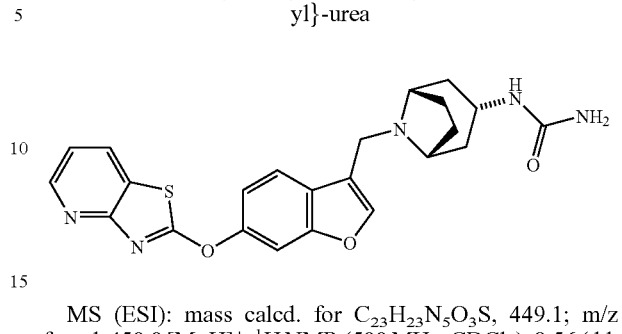

MS (ESI): mass calcd. for $C_{23}H_{23}N_5O_3S$, 449.1; m/z found, 450.0 [M+H]$^+$. $^1$H NMR (500 MHz, CDCl$_3$): 8.56 (dd, J=4.8, 1.6, 1H), 8.06 (dd, J=7.9, 1.6, 1H), 7.87 (d, J=8.5, 1H), 7.55 (s, 1H), 7.51 (d, J=2.0, 1H), 7.31 (dd, J=8.5, 2.1, 1H), 7.24 (dd, J=7.9, 4.8, 1H), 5.48 (br s, 1H), 4.45 (s, 2H), 3.96-3.86 (m, 1H), 3.61 (s, 2H), 3.28 (br s, 1H), 2.07-2.02 (m, 2H), 1.88-1.83 (m, 2H), 1.79-1.70 (m, 1H), 1.48 (t, J=11.0, 2H).

Example 208 meso-exo-N-{8-[6-(Thiazolo[4,5-b]pyridin-2-yloxy)-benzofuran-3-ylmethyl]-8-aza-bicyclo[3.2.1]oct-3-yl}-acetamide

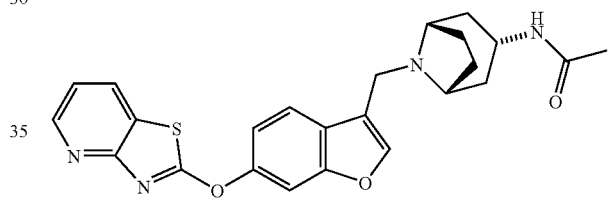

MS (ESI): mass calcd. for $C_{24}H_{24}N_4O_3S$, 448.2; m/z found, 449.1 [M+H]$^+$. $^1$H NMR (500 MHz, CD$_3$OD): 8.48 (dd, J=4.9, 1.5, 1H), 8.29 (dd, J=8.0, 1.6, 1H), 7.92 (d, J=8.5, 1H), 7.81 (s, 1H), 7.65 (d, J=2.1, 1H), 7.36-7.29 (m, 2H), 4.11-4.03 (m, 1H), 3.74 (s, 2H), 3.36-3.31 (m, 2H), 2.19-2.09 (m, 2H), 1.89 (s, 3H), 1.81-1.69 (m, 4H), 1.63-1.57 (m, 2H).

Example 209

(1S,4S)-5-[6-(Thiazolo[4,5-b]pyridin-2-yloxy)-benzofuran-3-ylmethyl]-2,5-diaza-bicyclo[2.2.1]heptane-2-carboxylic acid amide formate

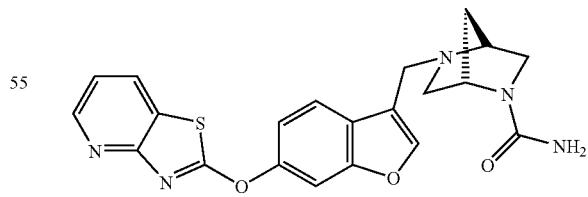

MS (ESI): mass calcd. for $C_{21}H_{19}N_5O_3S$, 421.1; m/z found, 422.0 [M+H]$^+$. $^1$H NMR (500 MHz, CD$_3$OD): 8.48 (dd, J=4.9, 1.6, 1H), 8.30 (dd, J=8.0, 1.6, 1H), 7.95 (s, 1H), 7.88 (d, J=8.5, 1H), 7.70 (d, J=2.1, 1H), 7.38-7.31 (m, 2H), 4.50 (s, 1H), 4.21 (d, J=13.9, 1H), 4.13 (d, J=13.9, 1H), 3.97 (s, 1H), 3.62 (d, J=10.3, 1H), 3.36 (dd, J=10.4, 2.2, 1H), 3.14-3.06 (m, 2H), 2.13 (d, J=10.5, 1H), 1.93 (d, J=10.5, 1H).

Example 210 meso-8-[6-(Thiazolo[4,5-b]pyridin-2-yloxy)-benzofuran-3-ylmethyl]-3,8-diaza-bicyclo[3.2.1]octane-3-carboxylic acid amide

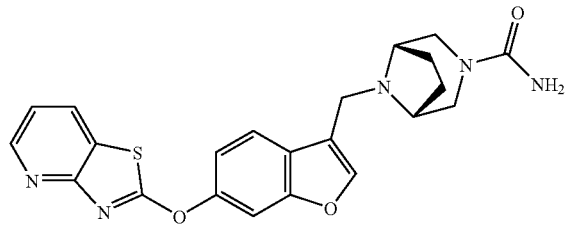 [SMILES: NC(=O)N1C[C@H]2CC[C@@H](C1)N2Cc1coc2cc(Oc3nc4ncccc4s3)ccc12]

MS (ESI): mass calcd. for $C_{22}H_{21}N_5O_3S$, 435.1; m/z found, 436.0 [M+H]$^+$. $^1$H NMR (400 MHz, CD$_3$OD): 8.48 (dd, J=4.9, 1.6, 1H), 8.30 (dd, J=8.0, 1.7, 1H), 7.95 (d, J=8.5, 1H), 7.83 (5, 1H), 7.65 (d, J=2.2, 1H), 7.36-7.32 (m, 2H), 3.73 (d, J=0.8, 2H), 3.60 (d, J=10.7, 2H), 3.06 (d, J=11.8, 2H), 2.14-2.06 (m, 2H), 1.73-1.66 (m, 2H). The remaining protons were not detected and are believed to be hidden in the solvent peak.

Example 211 meso-1-{5-[6-(Thiazolo[4,5-b]pyridin-2-yloxy)-benzofuran-3-ylmethyl]-hexahydro-pyrrolo[3,4-c]pyrrol-2-yl}-ethanone

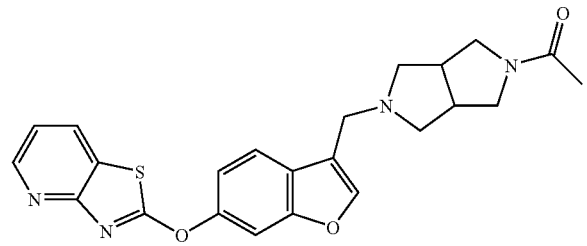 [SMILES: CC(=O)N1CC2CN(Cc3coc4cc(Oc5nc6ncccc6s5)ccc34)CC2C1]

MS (ESI): mass calcd. for $C_{23}H_{22}N_4O_3S$, 434.1; m/z found, 435.0 [M+H]$^+$. $^1$H NMR (400 MHz, CD$_3$OD): 8.48 (dd, J=4.9, 1.6, 1H), 8.31-8.24 (m, 1H), 7.83 (d, J=8.5, 1H), 7.80 (s, 1H), 7.65 (d, J=2.0, 1H), 7.35-7.29 (m, 2H), 3.83-3.69 (m, 3H), 3.61 (dd, J=12.4, 8.5, 1H), 3.46-3.38 (m, 2H), 3.01-2.82 (m, 2H), 2.72-2.57 (m, 4H), 2.03 (s, 3H).

Example 212

2-(3-Piperidin-1-ylmethyl-benzofuran-6-yloxy)-thiazolo[4,5-b]pyridine

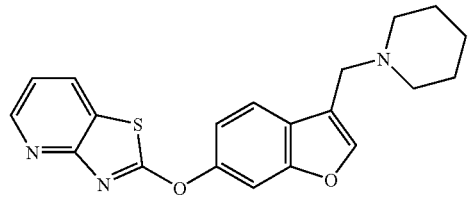 [SMILES: c1cnc2nc(Oc3ccc4c(CN5CCCCC5)coc4c3)sc2c1]

MS (ESI): mass calcd. for $C_{20}H_{19}N_3O_2S$, 365.1; m/z found, 366.0 [M+H]$^+$. $^1$H NMR (400 MHz, CD$_3$OD): 8.48 (dd, J=4.9, 1.6, 1H), 8.30 (dd, J=8.0, 1.7, 1H), 7.85 (d, J=8.5, 1H), 7.82 (s, 1H), 7.66 (d, J=2.3, 1H), 7.37-7.31 (m, 2H), 3.69 (d, J=0.7, 2H), 2.52 (br s, 4H), 1.66-1.59 (m, 4H), 1.51-1.43 (m, 2H).

Example 213

1-[6-(Thiazolo[4,5-b]pyridin-2-yloxy)-benzofuran-3-ylmethyl]-piperidine-4-carboxylic acid amide

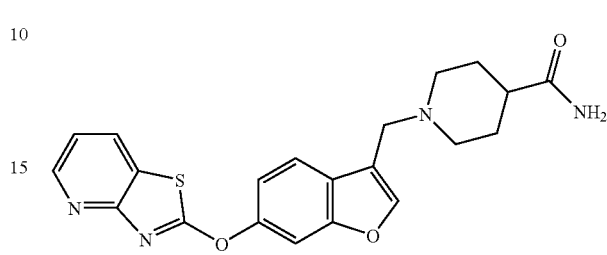

MS (ESI): mass calcd. for $C_{21}H_{20}N_4O_3S$, 408.1; m/z found, 409.0 [M+H]$^+$. $^1$H NMR (400 MHz, CD$_3$OD): 8.48 (dd, J=4.9, 1.6, 1H), 8.29 (dd, J=8.0, 1.6, 1H), 7.87 (d, J=8.5, 1H), 7.81 (s, 1H), 7.66 (d, J=2.1, 1H), 7.35-7.31 (m, 2H), 3.71 (s, 2H), 3.06-3.00 (m, 2H), 2.26-2.17 (m, 1H), 2.12 (td, J=11.4, 3.2, 2H), 1.85-1.70 (m, 4H).

Example 214

1-[6-(Thiazolo[4,5-b]pyridin-2-yloxy)-benzofuran-3-ylmethyl]-piperidine-4-carboxylic acid methylamide

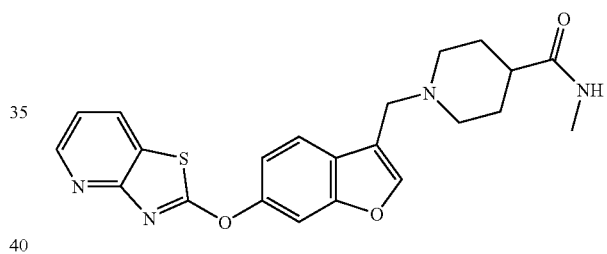

MS (ESI): mass calcd. for $C_{22}H_{22}N_4O_3S$, 422.1; m/z found, 423.0 [M+H]$^+$. $^1$H NMR (400 MHz, CD$_3$OD): 8.48 (dd, J=4.9, 1.6, 1H), 8.30 (dd, J=8.0, 1.6, 1H), 7.87 (d, J=8.5, 1H), 7.81 (5, 1H), 7.66 (d, J=1.9, 1H), 7.36-7.31 (m, 2H), 3.71 (5, 2H), 3.06-3.00 (m, 2H), 2.69 (s, 3H), 2.20-2.06 (m, 3H), 1.80-1.72 (m, 4H).

Example 215

1-{1-[6-(Thiazolo[4,5-b]pyridin-2-yloxy)-benzofuran-3-ylmethyl]-piperidin-4-yl}-pyrrolidin-2-one

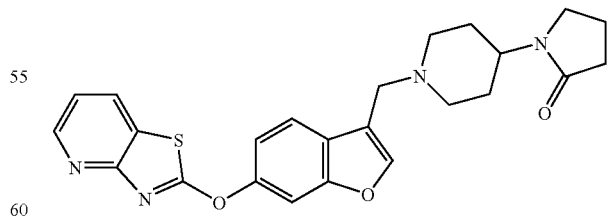

In this example, and after the 16-hour heating, 2 eq of TEA was added while heating the solution to 70° C. Partitioning and succeeding steps were performed as described in Example 153. MS (ESI): mass calcd. for $C_{24}H_{24}N_4O_3S$, 448.2; m/z found, 449.0 [M+H]$^+$. $^1$H NMR (400 MHz, CD$_3$OD): 8.38 (dd, J=4.9, 1.6, 1H), 8.20 (dd, J=8.0, 1.6, 1H), 7.77 (d, J=8.5, 1H), 7.73 (5, 1H), 7.57 (d, J=2.0, 1H), 7.26-

7.22 (m, 2H), 3.78 (tt, J=12.1, 4.2, 1H), 3.63 (5, 2H), 3.34 (t, J=7.0, 2H), 3.01-2.95 (m, 2H), 2.27 (t, J=8.1, 2H), 2.09 (td, J=11.9, 2.3, 2H), 1.96-1.87 (m, 2H), 1.70 (qd, J=12.4, 3.9, 2H), 1.60-1.52 (m, 2H).

Example 216

(3S)-1-[6-(Thiazolo[4,5-b]pyridin-2-yloxy)-benzofuran-3-ylmethyl]-piperidine-3-carboxylic acid amide

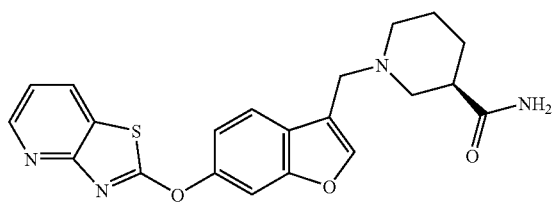 [SMILES: NC(=O)[C@@H]1CCCN(Cc2coc3cc(Oc4nc5ncccc5s4)ccc23)C1]

MS (ESI): mass calcd. for $C_{21}H_{20}N_4O_3S$, 408.1; m/z found, 409.0 [M+H]$^+$. $^1$H NMR (400 MHz, CD$_3$OD): 8.39 (dd, J=4.9, 1.6, 1H), 8.20 (dd, J=8.0, 1.6, 1H), 7.77-7.72 (m, 2H), 7.57 (d, J=1.9, 1H), 7.26-7.22 (m, 2H), 3.62 (s, 2H), 2.81 (d, J=9.5, 1H), 2.75-2.68 (m, 1H), 2.45-2.36 (m, 1H), 2.30-2.10 (m, 2H), 1.77-1.62 (m, 2H), 1.59-1.37 (m, 2H).

Example 217

2-{3-[4-(Pyrimidin-2-yloxy)-piperidin-1-ylmethyl]-benzofuran-6-yloxy}-thiazolo[4,5-b]pyridine

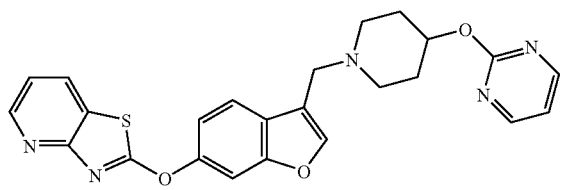 [SMILES: c1cnc(OC2CCN(Cc3coc4cc(Oc5nc6ncccc6s5)ccc34)CC2)nc1]

MS (ESI): mass calcd. for $C_{24}H_{21}N_5O_3S$, 459.1; m/z found, 460.0 [M+H]$^+$. $^1$H NMR (400 MHz, CD$_3$OD): 8.53 (d, J=4.8, 2H), 8.48 (dd, J=4.9, 1.6, 1H), 8.29 (dd, J=8.0, 1.6, 1H), 7.88 (d, J=8.5, 1H), 7.83 (5, 1H), 7.66 (d, J=2.1, 1H), 7.37-7.30 (m, 2H), 7.05 (t, J=4.8, 1H), 5.15-5.08 (m, 1H), 3.76 (5, 2H), 2.91-2.84 (m, 2H), 2.52-2.43 (m, 2H), 2.15-2.04 (m, 2H), 1.93-1.83 (m, 2H).

Example 218

2-{1-[6-(Thiazolo[4,5-b]pyridin-2-yloxy)-benzofuran-3-ylmethyl]-piperidin-4-yl}-propan-2-ol

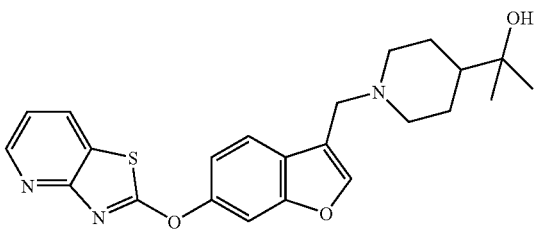 [SMILES: CC(C)(O)C1CCN(Cc2coc3cc(Oc4nc5ncccc5s4)ccc23)CC1]

MS (ESI): mass calcd. for $C_{23}H_{25}N_3O_3S$, 423.2; m/z found, 424.1 [M+H]$^+$. $^1$H NMR (400 MHz, CD$_3$OD): 8.48 (dd, J=4.9, 1.6, 1H), 8.29 (dd, J=8.0, 1.6, 1H), 7.85 (d, J=8.5, 1H), 7.82 (s, 1H), 7.65 (d, J=2.1, 1H), 7.36-7.30 (m, 2H), 3.71 (s, 2H), 3.12-3.05 (m, 2H), 2.07 (t, J=11.7, 2H), 1.77 (d, J=12.7, 2H), 1.42 (qd, J=12.4, 3.6, 2H), 1.34-1.26 (m, 1H), 1.14 (s, 6H).

Example 219

Diethyl-[6-(thiazolo[4,5-b]pyridin-2-yloxy)-benzofuran-3-ylmethyl]-amine

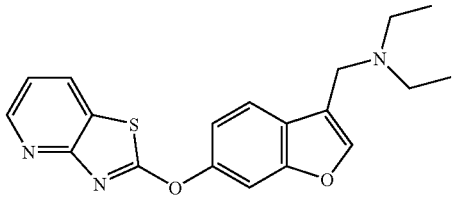 [SMILES: CCN(CC)Cc1coc2cc(Oc3nc4ncccc4s3)ccc12]

MS (ESI): mass calcd. for $C_{19}H_{19}N_3O_2S$, 353.1; m/z found, 354.0 [M+H]$^+$. $^1$H NMR (400 MHz, CD$_3$OD): 8.48 (dd, J=4.9, 1.6, 1H), 8.29 (dd, J=8.0, 1.6, 1H), 7.84 (d, J=8.5, 1H), 7.81 (s, 1H), 7.65 (d, J=2.1, 1H), 7.35-7.31 (m, 2H), 3.79 (s, 2H), 2.61 (q, J=7.2, 4H), 1.13 (t, J=7.2, 6H).

Example 220

1-[6-(Thiazolo[4,5-b]pyridin-2-yloxy)-benzofuran-3-ylmethyl]-1,2,3,4,5,6-hexahydro-[4,4']bipyridinyl

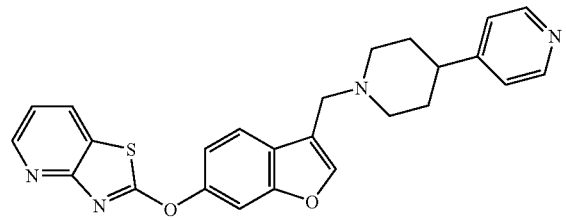 [SMILES: c1cnc2nc(Oc3ccc4c(CN5CCC(c6ccncc6)CC5)coc4c3)sc2c1]

MS (ESI): mass calcd. for $C_{25}H_{22}N_4O_2S$, 442.1; m/z found, 443.0 [M+H]$^+$. $^1$H NMR (400 MHz, CD$_3$OD): 8.48 (d, J=3.6, 1H), 8.42 (br s, 2H), 8.29 (dd, J=8.0, 1.6, 1H), 7.89 (d, J=8.5, 1H), 7.84 (s, 1H), 7.66 (d, J=2.0, 1H), 7.38-7.30 (m, 4H), 3.77 (s, 2H), 3.17-3.11 (m, 2H), 2.62 (tt, J=11.8, 3.9, 1H), 2.25 (td, J=11.7, 2.6, 2H), 1.93-1.74 (m, 4H).

Example 221

(1S,4S)-1-{5-[6-(Thiazolo[5,4-b]pyridin-2-yloxy)-benzofuran-3-ylmethyl]-2,5-diaza-bicyclo[2.2.1]hept-2-yl}-ethanone

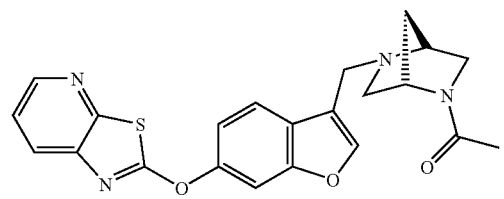

MS (ESI): mass calcd. for $C_{22}H_{20}N_4O_3S$, 420.1; m/z found, 421.1 [M+H]$^+$. $^1$H NMR (400 MHz, CD$_3$OD): 8.40 (dd, J=4.8, 1.5, 1H), 8.00 (dd, J=8.2, 1.5, 1H), 7.86 (dd, J=8.5, 2.2, 1H), 7.83-7.80 (m, 1H), 7.63-7.60 (m, 1H), 7.46 (dd, J=8.2, 4.8, 1H), 7.30 (dt, J=8.5, 2.1, 1H), 4.69 (s, 0.5H), 4.46

(s, 0.5H), 3.99-3.85 (m, 2H), 3.71-3.61 (m, 2H), 3.43 (dd, J=9.9, 2.3, 0.5H), 3.26 (dd, J=11.4, 2.0, 0.5H), 2.98 (dd, J=9.9, 2.1, 0.5H), 2.91 (dd, J=9.8, 2.2, 0.5H), 2.79-2.71 (m, 1H), 2.10 (s, 1.5H), 2.05-1.95 (m, 2.5H), 1.83 (d, J=10.1, 0.5H), 1.74 (d, J=10.0, 0.5H).

Example 222

(1S,4S)-1-{5-[6-(Thiazolo[4,5-c]pyridin-2-yloxy)-benzofuran-3-ylmethyl]-2,5-diaza-bicyclo[2.2.1]hept-2-yl}-ethanone

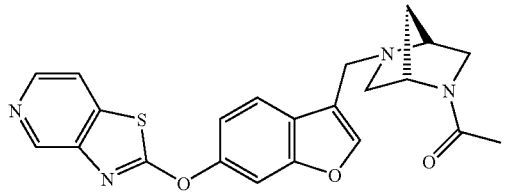

MS (ESI): mass calcd. for $C_{22}H_{20}N_4O_3S$, 420.1; m/z found, 420.9 [M+H]+. 1H NMR (500 MHz, CD3OD): 7.52 (d, J=4.2, 1H), 7.48 (dd, J=8.4, 2.5, 1H), 6.84 (t, J=1.8, 1H), 6.75 (ddd, J=8.4, 2.9, 2.2, 1H), 4.66 (s, 0.5H), 4.44 (s, 0.5H), 3.89-3.75 (m, 2H), 3.69-3.58 (m, 2H), 3.40 (dd, J=9.8, 2.3, 0.5H), 3.23 (dd, J=11.4, 2.0, 0.5H), 2.96 (dd, J=10.0, 2.2, 0.5H), 2.88 (dd, J=9.9, 2.2, 0.5H), 2.73 (dd, J=9.4, 7.0, 1H), 2.09 (s, 1.5H), 2.03-1.92 (m, 2.5H), 1.80 (d, J=10.1, 0.5H), 1.71 (d, J=10.1, 0.5H).

With modifications as stated for each specific Example, if any, Examples 223 to 230 were prepared using methods analogous to those described for Example 153.

Example 223

1-[6-(Benzothiazol-2-yloxy)-benzofuran-3-ylmethyl]-piperidine-4-carboxylic acid ethyl ester

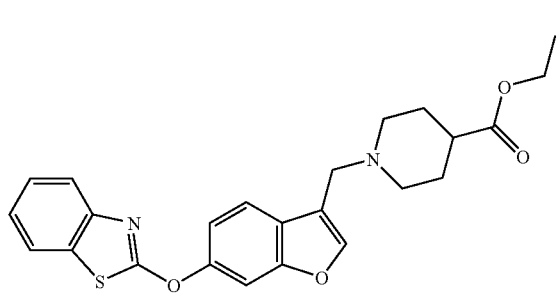 [SMILES: CCOC(=O)C1CCN(Cc2coc3cc(Oc4nc5ccccc5s4)ccc23)CC1]

MS (ESI): mass calcd. for $C_{24}H_{24}N_2O_4S$, 436.2; m/z found, 437.0 [M+H]+. 1H NMR (400 MHz, CDCl3): 7.77 (d, J=8.5, 1H), 7.74 (dd, J=8.2, 0.5, 1H), 7.67 (dd, J=7.9, 0.8, 1H), 7.56 (s, 1H), 7.52 (d, J=2.1, 1H), 7.39 (td, J=7.8, 1.3, 1H), 7.30-7.23 (m, 2H), 4.13 (d, J=7.1, 2H), 3.62 (s, J=0.6, 2H), 2.97-2.88 (m, 2H), 2.34-2.23 (m, 1H), 2.08 (td, J=11.3, 2.2, 2H), 1.94-1.85 (m, 2H), 1.84-1.71 (m, 2H), 1.25 (t, J=7.1, 3H).

Example 224

1-[6-(Thiazolo[4,5-b]pyridin-2-yloxy)-benzofuran-3-ylmethyl]-piperidine-4-carboxylic acid ethyl ester

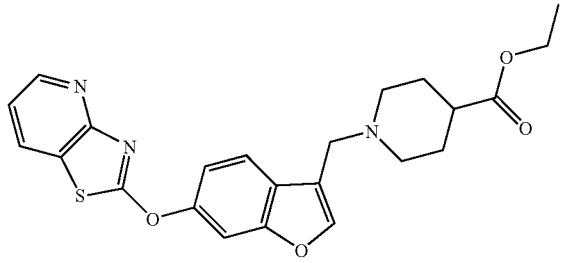 [SMILES: CCOC(=O)C1CCN(Cc2coc3cc(Oc4nc5ncccc5s4)ccc23)CC1]

MS (ESI): mass calcd. for $C_{23}H_{23}N_3O_4S$, 437.1; m/z found, 438.0 [M+H]+. 1H NMR (400 MHz, CDCl3): 8.56 (dd, J=4.8, 1.6, 1H), 8.02 (dd, J=7.9, 1.7, 1H), 7.78 (d, J=8.5, 1H), 7.60-7.56 (m, 2H), 7.27 (dd, J=8.5, 2.1, 1H), 7.20 (dd, J=7.9, 4.8, 1H), 4.23-4.02 (m, 2H), 3.61 (t, J=10.5, 2H), 2.92 (s, J=11.5, 2H), 2.36-2.21 (m, 1H), 2.15-2.04 (m, 2H), 1.90 (dd, J=13.2, 3.2, 2H), 1.77 (ddd, J=24.5, 11.4, 3.7, 2H), 1.32-1.14 (m, 3H).

Example 225

1-[6-(Thiazolo[4,5-b]pyridin-2-yloxy)-benzofuran-2-ylmethyl]-piperidine-4-carboxylic acid tert-butyl ester

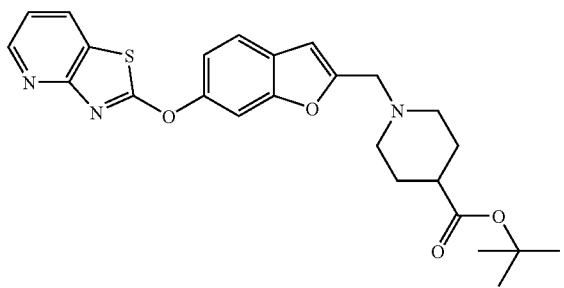 [SMILES: CC(C)(C)OC(=O)C1CCN(Cc2cc3ccc(Oc4nc5ncccc5s4)cc3o2)CC1]

A solvent of DMF with K2CO3 at 50° C. was used instead of 4:1 CH3CN/DMF with K2CO3 at rt. MS (ESI): mass calcd. for $C_{25}H_{27}N_3O_4S$, 465.2; m/z found, 466.1 [M+H]+. 1H NMR (500 MHz, CDCl3): 8.57 (dd, J=4.8, 1.6, 1H), 8.01 (dd, J=7.9, 1.7, 1H), 7.58-7.53 (m, 2H), 7.28-7.24 (m, 1H), 7.20 (dd, J=7.9, 4.8, 1H), 6.62 (s, 1H), 3.69 (s, 2H), 2.96-2.90 (m, 2H), 2.24-2.12 (m, 3H), 1.92-1.86 (m, 2H), 1.84-1.75 (m, 2H), 1.43 (s, 9H).

Example 226

4-[6-(Thiazolo[4,5-b]pyridin-2-yloxy)-benzofuran-3-ylmethyl]-piperazine-1-carboxylic acid tert-butyl ester

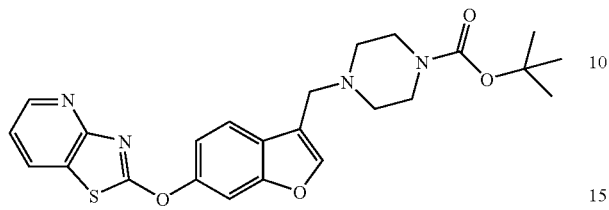

MS (ESI): mass calcd. for $C_{24}H_{26}N_4O_4S$, 466.56; m/z found, 467.0 [M+H]$^+$. $^1$H NMR (400 MHz, CDCl$_3$): 8.56 (dd, J=4.8, 1.6, 1H), 8.02 (dd, J=7.9, 1.7, 1H), 7.77 (d, J=8.5, 1H), 7.59 (d, J=2.4, 2H), 7.29 (dd, J=8.5, 2.1, 1H), 7.20 (dd, J=8.0, 4.8, 1H), 3.65 (d, J=0.7, 2H), 3.49-3.41 (m, 4H), 2.45 (s, 4H), 1.46 (s, 9H).

Example 227

{1-[6-(Thiazolo[4,5-b]pyridin-2-yloxy)-benzofuran-3-ylmethyl]-piperidin-4-yl}-carbamic acid tert-butyl ester

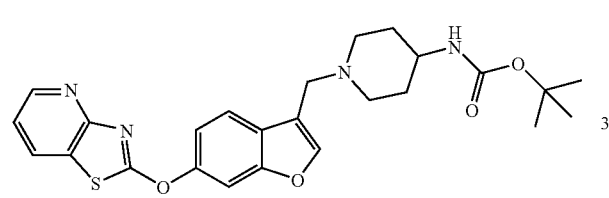

MS (ESI): mass calcd. for $C_{25}H_{28}N_4O_4S$, 480.59; m/z found, 481.1 [M+H]$^+$. $^1$H NMR (400 MHz, CDCl$_3$): 8.56 (dd, J=4.8, 1.7, 1H), 8.01 (dd, J=7.9, 1.7, 1H), 7.75 (d, J=8.5, 1H), 7.57 (d, J=2.3, 2H), 7.31-7.26 (m, 1H), 7.20 (dd, J=8.0, 4.8, 1H), 4.43 (s, 1H), 3.61 (d, J=0.6, 2H), 3.48 (s, 1H), 2.86 (d, J=11.6, 2H), 2.15 (t, J=10.3, 2H), 2.04 (s, 1H), 1.93 (d, J=11.3, 2H), 1.69 (s, 1H), 1.50-1.36 (m, 9H).

Example 228

4-[6-(Thiazolo[4,5-b]pyridin-2-yloxy)-benzofuran-3-ylmethyl]-[1,4]diazepane-1-carboxylic acid tert-butyl ester

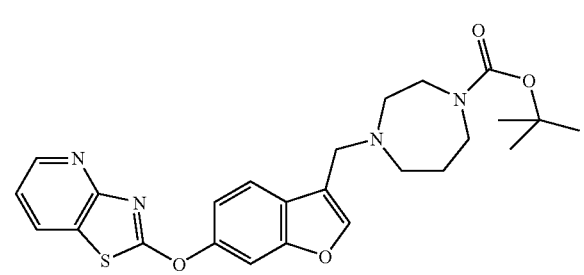 [SMILES: CC(C)(C)OC(=O)N1CCCN(Cc2coc3cc(Oc4nc5ncccc5s4)ccc23)CC1]

MS (ESI): mass calcd. for $C_{25}H_{28}N_4O_4S$, 480.2; m/z found, 481.1 [M+H]$^+$. $^1$H NMR (400 MHz, CDCl$_3$): 8.56 (dd, J=4.8, 1.6, 1H), 8.07-7.97 (m, 1H), 7.76 (t, J=7.4, 1H), 7.58 (s, 2H), 7.27 (d, J=7.1, 1H), 7.23-7.17 (m, 1H), 3.75 (d, J=0.8, 2H), 3.58-3.38 (m, 4H), 2.78-2.59 (m, 4H), 1.90-1.75 (m, 2H), 1.47 (s, J=1.7, 9H).

Example 229

(1S,4S)-5-[6-(Thiazolo[4,5-b]pyridin-2-yloxy)-benzofuran-3-ylmethyl]-2,5-diaza-bicyclo[2.2.2]octane-2-carboxylic acid tert-butyl ester trifluoroacetate

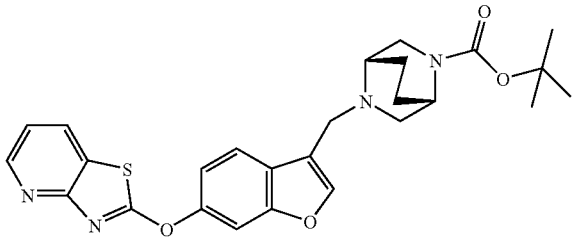 [SMILES: CC(C)(C)OC(=O)N1C[C@@H]2CC[C@H]1CN2Cc1coc2cc(Oc3nc4ncccc4s3)ccc12]

MS (ESI): mass calcd. for $C_{26}H_{28}N_4O_4S$, 492.2; m/z found, 493.1 [M+H]$^+$. $^1$H NMR (400 MHz, CD$_3$OD): 8.50 (dd, J=5.0, 1.6, 1H), 8.35 (dd, J=8.0, 1.6, 1H), 8.22 (s, 1H), 7.95 (d, J=8.6, 1H), 7.82 (d, J=2.1, 1H), 7.48 (dd, J=8.6, 2.1, 1H), 7.37 (dd, J=8.0, 5.0, 1H), 4.75 (s, 2H), 4.36-4.30 (m, 1H), 3.92 (d, J=14.1, 1H), 3.73-3.55 (m, 3H), 2.16-1.94 (m, 3H), 1.48 (d, J=8.3, 9H).

Example 230

4-{Cyclopropyl-[6-(thiazolo[4,5-b]pyridin-2-yloxy)-benzofuran-3-ylmethyl]-amino}-piperidine-1-carboxylic acid tert-butyl ester

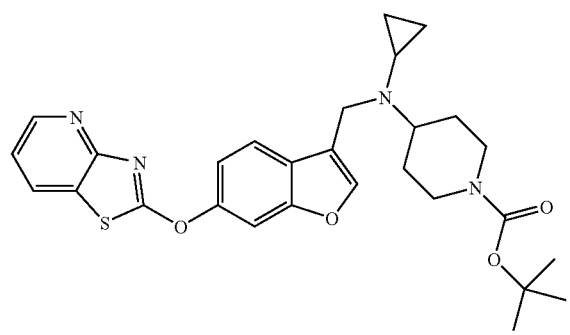 [SMILES: CC(C)(C)OC(=O)N1CCC(N(Cc2coc3cc(Oc4nc5ncccc5s4)ccc23)C2CC2)CC1]

MS (ESI): mass calcd. for $C_{28}H_{32}N_4O_4S$, 520.2; m/z found, 521.1 [M+H]$^+$.

Example 231

2-(3-piperazin-1-ylmethyl-benzofuran-6-yloxy)-thiazolo[4,5-b]pyridine hydrochloride

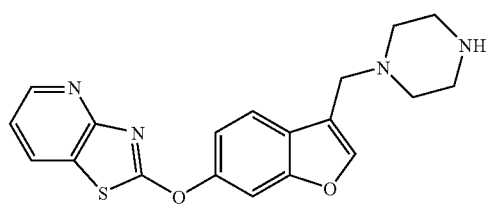 [SMILES: c1cnc2nc(Oc3ccc4c(CN5CCNCC5)coc4c3)sc2c1]

To a solution of 4-[6-(thiazolo[4,5-b]pyridin-2-yloxy)-benzofuran-3-ylmethyl]-piperazine-carboxylic acid tert-butyl ester (0.22 g, 0.47 mmol) in DCM (5 mL) is added HCl (4 M in dioxane, 1 mL, 8.5 equiv.) and the solution was stirred (rt, 1 h). The reaction mixture was concentrated in vacuo to provide the desired product as a white solid (0.25 g, 129%). [Note: the mass recovery of 129% was attributed to additional HCl that could not be removed by standard evaporation under reduced pressure]. MS (ESI): mass calcd. for $C_{19}H_{18}N_4O_2S$, 366.44; m/z found, 367.1 [M+H]$^+$.

Examples 232 to 235 were prepared using methods analogous to those described for Example 231.

Example 232

1-[6-(Thiazolo[4,5-b]pyridin-2-yloxy)-benzofuran-3-ylmethyl]-piperidin-4-ylamine hydrochloride

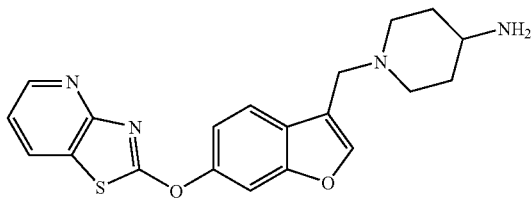 [SMILES: NC1CCN(Cc2coc3cc(Oc4nc5ncccc5s4)ccc23)CC1]

MS (ESI): mass calcd. for $C_{20}H_{20}N_4O_2S$, 380.47; m/z found, 381.0 [M+H]$^+$.

Example 233

2-(3-[1,4]Diazepan-1-ylmethyl-benzofuran-6-yloxy)-thiazolo[4,5-b]pyridine

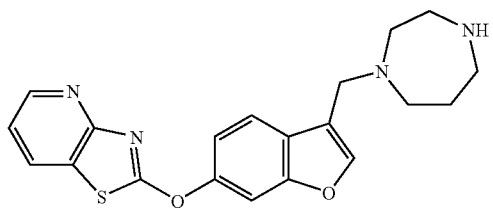 [SMILES: c1cnc2nc(Oc3ccc4c(CN5CCCNCC5)coc4c3)sc2c1]

MS (ESI): mass calcd. for $C_{20}H_{20}N_4O_2S$, 380.1; m/z found, 381.1 [M+H]$^+$.

Example 234

(1S,4S)-2-[6-(Thiazolo[4,5-b]pyridin-2-yloxy)-benzofuran-3-ylmethyl]-2,5-diaza-bicyclo[2.2.2]octane hydrochloride

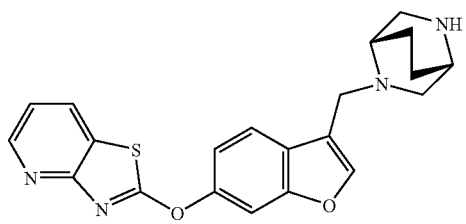 [SMILES: c1cnc2nc(Oc3ccc4c(CN5C[C@@H]6CC[C@H]5CN6)coc4c3)sc2c1]

MS (ESI): mass calcd. for $C_{21}H_{20}N_4O_2S$, 392.1; m/z found, 393.0 [M+H]$^+$.

Example 235

Cyclopropyl-piperidin-4-yl-[6-(thiazolo[4,5-b]pyridin-2-yloxy)-benzofuran-3-ylmethyl]-amine

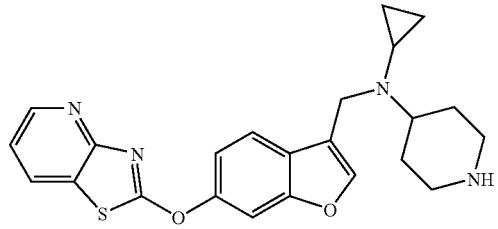 [SMILES: c1cnc2nc(Oc3ccc4c(CN(C5CCNCC5)C5CC5)coc4c3)sc2c1]

MS (ESI): mass calcd. for $C_{23}H_{24}N_4O_2S$, 420.2; m/z found, 421.0 [M+H]$^+$.

Example 236

2,2-Dimethyl-N-{1-[6-(thiazolo[4,5-b]pyridin-2-yloxy)-benzofuran-2-ylmethyl]-pyrrolidin-3-yl}-propionamide formate

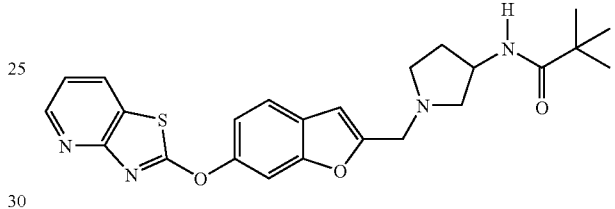

To a solution of 1-[6-(thiazolo[4,5-b]pyridin-2-yloxy)-benzofuran-2-ylmethyl]-pyrrolidin-3-ylamine hydrochloride (65 mg, 0.161 mmol) in DCM (2 mL) was added DIEA (64 μL, 0.484 mmol) followed by pivaloyl chloride (20 μL, 0.484 mmol) and the resulting solution was stirred (rt, 1 h). The reaction mixture was partitioned with DCM (5 mL) and saturated NaHCO$_3$ (5 mL). The layers were separated and the aqueous layer was extracted with DCM (3×10 mL). The organic layers were combined, dried, filtered and concentrated in vacuo. The resulting residue was purified by flash column chromatography using MeOH:DCM (0-10%) followed by reverse phase HPLC to provide the title compound as a yellow solid (32 mg, 40%). MS (ESI): mass calcd. for $C_{24}H_{26}N_4O_3S$, 450.2; m/z found, 451.0 [M+H]$^+$. $^1$H NMR (500 MHz, CD$_3$OD): 8.48 (dd, J=4.8, 1.3, 1H), 8.30 (dd, J=8.0, 1.6, 2H), 7.72-7.68 (m, 2H), 7.38-7.29 (m, 2H), 6.92 (s, 1H), 4.47-4.37 (m, 1H), 4.13-4.02 (m, 2H), 3.19-3.04 (m, 2H), 2.89-2.75 (m, 2H), 2.38-2.30 (m, 1H), 1.84-1.77 (m, 1H), 1.16 (s, 9H).

Examples 237 to 238 were prepared using methods analogous to those described for Example 53.

Example 237

(1S,4S)1-{5-[6-(Thiazolo[4,5-b]pyridin-2-yloxy)-benzofuran-3-ylmethyl]-2,5-diaza-bicyclo[2.2.2]oct-2-yl}-ethanone

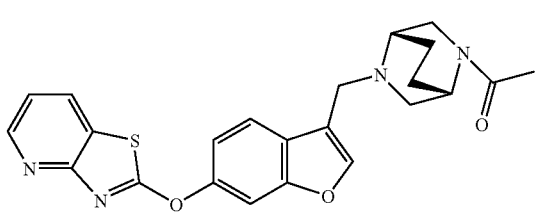 [SMILES: CC(=O)N1C[C@@H]2CC[C@H]1CN2Cc1coc2cc(Oc3nc4ncccc4s3)ccc12]

MS (ESI): mass calcd. for $C_{23}H_{22}N_4O_3S$, 434.1; m/z found, 435.0 [M+H]$^+$. $^1$H NMR (400 MHz, CD$_3$OD): 8.50

(dd, J=4.9, 1.5, 1H), 8.32 (dd, J=8.0, 1.6, 1H), 7.91 (dd, J=8.5, 2.5, 1H), 7.85 (s, 1H), 7.67 (d, J=2.1, 1H), 7.38-7.33 (m, 2H), 4.49-4.44 (m, 0.5H), 4.02-3.89 (m, 3H), 3.84-3.79 (m, 0.5H), 3.52 (dd, J=10.9, 2.0, 0.5H), 3.42 (dd, J=12.6, 1.8, 0.5H), 3.11-2.96 (m, 3H), 2.25-2.14 (m, 1H), 2.10 (s, 1.5H), 2.07 (s, 1.5H), 1.99-1.84 (m, 2H), 1.76-1.63 (m, 1H).

Example 238

1-(4-{Cyclopropyl-[6-(thiazolo[4,5-b]pyridin-2-yloxy)-benzofuran-3-ylmethyl]-amino}-piperidin-1-yl)-ethanone

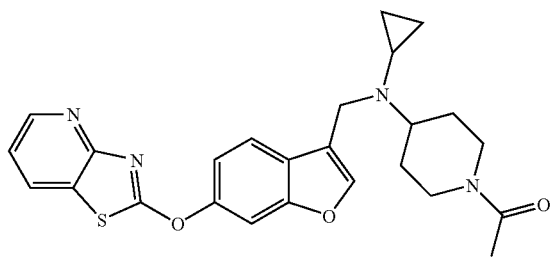 [SMILES: CC(=O)N1CCC(N(Cc2coc3cc(Oc4nc5ncccc5s4)ccc23)C2CC2)CC1]

MS (ESI): mass calcd. for $C_{25}H_{26}N_4O_3S$, 462.2; m/z found, 463.0 [M+H]$^+$. $^1$H NMR (400 MHz, CDCl$_3$): 8.56 (dd, J=4.8, 1.7, 1H), 8.02 (dd, J=7.9, 1.6, 1H), 7.65 (d, J=8.5, 1H), 7.58 (d, J=2.1, 1H), 7.55 (s, 1H), 7.28-7.23 (m, 2H), 7.20 (dd, J=7.9, 4.8, 1H), 4.69 (dd, J=13.2, 2.2, 1H), 3.96 (s, 2H), 3.83 (d, J=13.4, 1H), 2.95 (td, J=13.3, 2.4, 1H), 2.85-2.72 (m, 1H), 2.43 (td, J=13.0, 2.3, 1H), 2.02-1.93 (m, 1H), 1.91-1.78 (m, 2H), 1.73-1.57 (m, 4H), 0.59-0.38 (m, 4H).

Example 239

4-[6-(Thiazolo[4,5-b]pyridin-2-yloxy)-benzofuran-3-ylmethyl]-piperazine-1-carboxylic acid amide

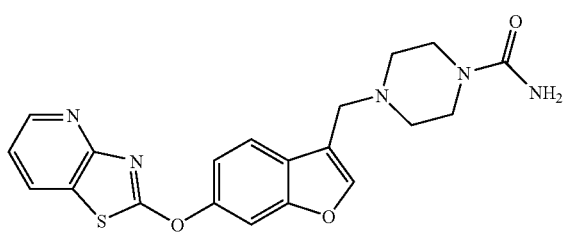 [SMILES: NC(=O)N1CCN(Cc2coc3cc(Oc4nc5ncccc5s4)ccc23)CC1]

To a suspension of 2-(3-piperazin-1-ylmethyl-benzofuran-6-yloxy)-thiazolo[4,5-b]pyridine hydrochloride (122 mg, 0.30 mmol) in DCM (3 mL) was added Et$_3$N (0.21 mL, 1.51 mmol) and the reaction mixture was stirred (rt, 15 min). The resulting solution was treated with trimethylsilyl isocyanate (0.14 mL, 0.91 mmol) and stirred (rt, 4 h). The reaction mixture was concentrated in vacuo and the resulting residue was purified by reverse phase HPLC to afford the title compound as a white solid (55 mg, 44%). MS (ESI): mass calcd. for $C_{20}H_{19}N_5O_3S$, 409.47; m/z found, 410.0 [M+H]$^+$. $^1$H NMR (400 MHz, CDCl$_3$): 8.56 (dd, J=4.8, 1.6, 1H), 8.02 (dd, J=7.9, 1.6, 1H), 7.77 (d, J=8.5, 1H), 7.59 (d, J=1.9, 2H), 7.29 (dd, J=8.5, 2.1, 1H), 7.21 (dd, J=7.9, 4.8, 1H), 4.43 (s, 2H), 3.66 (d, J=0.7, 2H), 3.47-3.36 (m, 4H), 2.55-2.46 (m, 4H).

Examples 240 to 242 were prepared using methods analogous to those described for Example 239.

Example 240

{1-[6-(Thiazolo[4,5-b]pyridin-2-yloxy)-benzofuran-3-ylmethyl]-piperidin-4-yl}-urea

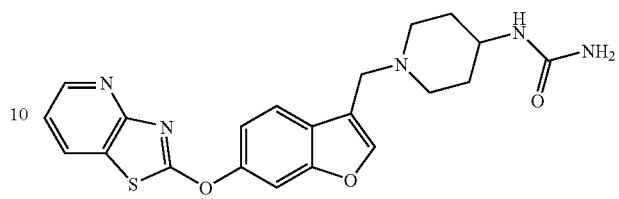

MS (ESI): mass calcd. for $C_{21}H_{21}N_5O_3S$, 423.50; m/z found, 424.0 [M+H]$^+$. $^1$H NMR (400 MHz, CDCl$_3$): 8.54 (dd, J=4.8, 1.6, 1H), 8.04 (dd, J=7.9, 1.6, 1H), 7.75 (d, J=8.5, 1H), 7.57 (5, 1H), 7.53 (d, J=2.1, 1H), 7.28-7.19 (m, 2H), 5.30 (d, J=7.5, 1H), 4.50 (5, 2H), 3.65 (5, 2H), 3.63-3.46 (m, 1H), 2.83 (d, J=11.6, 2H), 2.20 (t, J=9.9, 2H), 1.99-1.85 (m, 2H), 1.57-1.40 (m, 2H).

Example 241

(1S,4S)-5-[6-(Thiazolo[4,5-b]pyridin-2-yloxy)-benzofuran-3-ylmethyl]-2,5-diaza-bicyclo[2.2.2]octane-2-carboxylic acid amide formate

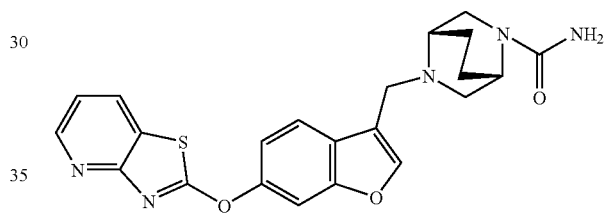

MS (ESI): mass calcd. for $C_{22}H_{21}N_5O_3S$, 435.1; m/z found, 435.9 [M+H]$^+$. $^1$H NMR (500 MHz, CD$_3$OD): 8.48 (dd, J=4.9, 1.6, 1H), 8.30 (dd, J=8.0, 1.6, 1H), 7.92-7.89 (m, 2H), 7.69 (d, J=2.0, 1H), 7.38-7.31 (m, 2H), 4.18-4.05 (m, 3H), 3.87-3.83 (m, 1H), 3.41-3.36 (m, 1H), 3.22 (s, 1H), 3.17-3.08 (m, 2H), 2.25-2.17 (m, 1H), 2.00-1.82 (m, 2H), 1.78-1.72 (m, 1H).

Example 242

4-{Cyclopropyl-[6-(thiazolo[4,5-b]pyridin-2-yloxy)-benzofuran-3-ylmethyl]-amino}-piperidine-1-carboxylic acid amide

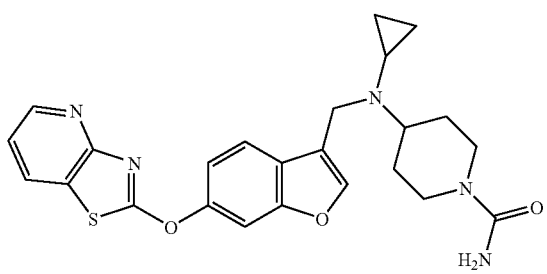 [SMILES: NC(=O)N1CCC(N(Cc2coc3cc(Oc4nc5ncccc5s4)ccc23)C2CC2)CC1]

MS (ESI): mass calcd. for $C_{24}H_{25}N_5O_3S$, 463.17; m/z found, 464.0 [M+H]$^+$. $^1$H NMR (400 MHz, CDCl$_3$): 8.56 (dd, J=4.8, 1.6, 1H), 8.02 (dd, J=7.9, 1.6, 1H), 7.65 (d, J=8.5, 1H), 7.58 (d, J=2.1, 1H), 7.55 (s, 1H), 7.26-7.17 (m, 2H), 4.44 (s, 2H), 4.01 (s, 1H), 3.96 (s, 2H), 2.84-2.65 (m, 3H), 2.04-1.92 (m, 1H), 1.83 (d, J=12.1, 2H), 1.77-1.61 (m, 3H), 0.60-0.38 (m, 4H).

Example 243

2-[3-(4-Methanesulfonyl-piperazin-1-ylmethyl)-benzofuran-6-yloxy]-thiazolo[4,5-b]pyridine

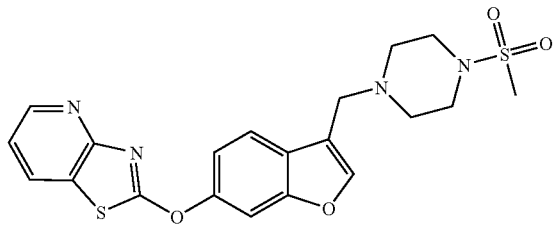 [SMILES: CS(=O)(=O)N1CCN(Cc2coc3cc(Oc4nc5ncccc5s4)ccc23)CC1]

To a suspension of 2-(3-piperazin-1-ylmethyl-benzofuran-6-yloxy)-thiazolo[4,5-b]pyridine hydrochloride (122 mg, 0.30 mmol) in DCM (3 mL) was added DIEA (158 µL, 0.91 mmol) and the reaction mixture was stirred (rt, 15 min). The resulting solution was treated with MsCl (26 µL, 0.33 mmol) and the resulting solution was stirred (rt, 2 h). The reaction mixture was partitioned with EtOAc and brine (20 mL each) and the organic layer was dried, filtered and concentrated in vacuo. The resulting residue was purified by reverse phase HPLC to provide the title compound as a white solid (42 mg, 31%). MS (ESI): mass calcd. for $C_{20}H_{20}N_4O_4S_2$, 444.54; m/z found, 445.0 [M+H]$^+$. $^1$H NMR (400 MHz, CDCl$_3$): 8.56 (dd, J=4.8, 1.6, 1H), 8.03 (dd, J=7.9, 1.7, 1H), 7.74 (d, J=8.5, 1H), 7.62-7.56 (m, 2H), 7.30 (dd, J=8.5, 2.1, 1H), 7.21 (dd, J=8.0, 4.8, 1H), 3.69 (d, J=0.5, 2H), 3.32-3.21 (m, 4H), 2.79 (s, 3H), 2.67-2.54 (m, 4H).

Examples 244 to 247 were prepared using methods analogous to those described for Example 243.

Example 244

N-{1-[6-(Thiazolo[4,5-b]pyridin-2-yloxy)-benzofuran-3-ylmethyl]-piperidin-4-yl}-methanesulfonamide

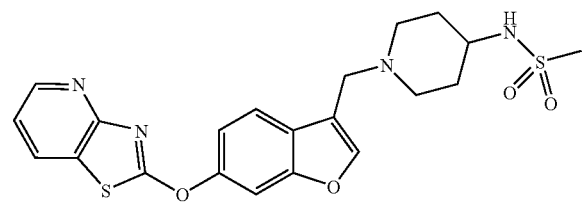 [SMILES: CS(=O)(=O)NC1CCN(Cc2coc3cc(Oc4nc5ncccc5s4)ccc23)CC1]

MS (ESI): mass calcd. for $C_{21}H_{22}N_4O_4S_2$, 458.56; m/z found, 459.0 [M+H]$^+$. $^1$H NMR (500 MHz, CDCl$_3$): 8.56 (dd, J=4.8, 1.6, 1H), 8.03 (dd, J=7.9, 1.6, 1H), 7.74 (d, J=8.5, 1H), 7.58 (d, J=2.1, 2H), 7.28 (dd, J=8.5, 2.1, 1H), 7.21 (dd, J=7.9, 4.8, 1H), 4.40 (dd, J=5.3, 3.6, 1H), 3.64 (s, 2H), 3.42-3.28 (m, 1H), 2.98 (s, 3H), 2.89 (d, J=11.2, 2H), 2.18 (t, J=10.5, 2H), 2.00 (d, J=11.3, 2H), 1.60 (td, J=13.9, 3.6, 2H).

Example 245

(1S,4S)-2-Methanesulfonyl-5-[6-(thiazolo[4,5-b]pyridin-2-yloxy)-benzofuran-3-ylmethyl]-2,5-diaza-bicyclo[2.2.2]octane

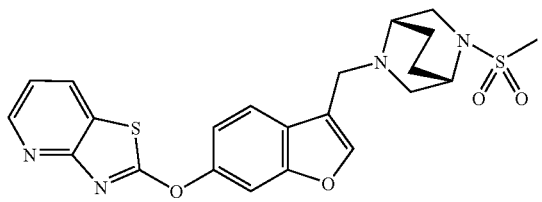 [SMILES: CS(=O)(=O)N1C[C@@H]2CC[C@H]1CN2Cc1coc2cc(Oc3nc4ncccc4s3)ccc12]

MS (ESI): mass calcd. for $C_{22}H_{22}N_4O_4S_2$, 470.1; m/z found, 471.0 [M+H]$^+$. $^1$H NMR (400 MHz, CD$_3$OD): 8.48 (dd, J=4.9, 1.5, 1H), 8.30 (dd, J=8.0, 1.7, 1H), 7.89 (d, J=4.2, 1H), 7.82 (s, 1H), 7.65 (d, J=1.9, 1H), 7.37-7.30 (m, 2H), 3.94 (s, 2H), 3.81-3.76 (m, 2H), 3.34 (d, J=10.1, 2.0, 1H), 3.11 (dt, J=10.7, 2.8, 1H), 3.07-3.02 (m, 1H), 2.95-2.87 (m, 4H), 2.21-2.09 (m, 1H), 2.07-1.95 (m, 1H), 1.90-1.82 (m, 1H), 1.77-1.68, 1H).

Example 246

Cyclopropyl-(1-methanesulfonyl-piperidin-4-yl)-[6-(thiazolo[4,5-b]pyridin-2-yloxy)-benzofuran-3-ylmethyl]-amine

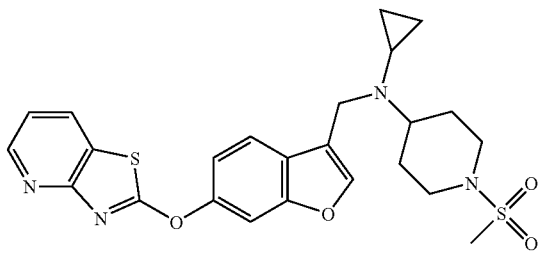 [SMILES: CS(=O)(=O)N1CCC(N(Cc2coc3cc(Oc4nc5ncccc5s4)ccc23)C2CC2)CC1]

MS (ESI): mass calcd. for $C_{24}H_{26}N_4O_4S_2$, 498.1; m/z found, 498.9 [M+H]$^+$. $^1$H NMR (400 MHz, CDCl$_3$): 8.55 (dd, J=4.8, 1.7, 1H), 8.03 (dd, J=7.9, 1.7, 1H), 7.65 (d, J=8.5, 1H), 7.58 (d, J=2.1, 1H), 7.55 (s, 1H), 7.25 (dd, J=8.5, 2.1, 1H), 7.21 (dd, J=7.9, 4.8, 1H), 3.97 (s, J=0.7, 2H), 3.94-3.80 (m, 4H), 2.74 (s, J=4.6, 3H), 2.72-2.51 (m, 2H), 1.95-1.85 (m, 2H), 1.03-0.95 (m, 1H), 0.90-0.80 (m, 1H), 0.61-0.52 (m, 2H), 0.51-0.41 (m, 2H).

Example 247

2-[3-(4-Methanesulfonyl-[1,4]diazepan-1-ylmethyl)-benzofuran-6-yloxy]-thiazolo[4,5-b]pyridine

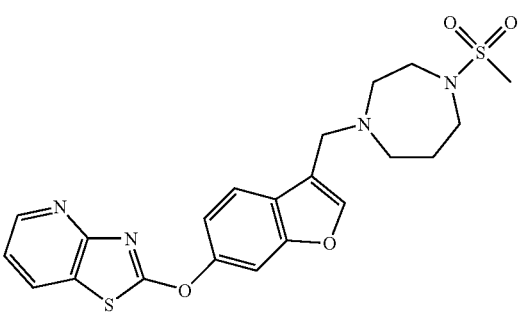 [SMILES: CS(=O)(=O)N1CCCN(Cc2coc3cc(Oc4nc5ncccc5s4)ccc23)CC1]

MS (ESI): mass calcd. for $O_{21}H_{22}N_4O_4S_2$, 458.1; m/z found, 459.0 [M+H]$^+$. $^1$H NMR (400 MHz, CDCl$_3$): 8.56 (dd, J=4.8, 1.6, 1H), 8.02 (dd, J=7.9, 1.6, 1H), 7.75 (d, J=8.5, 1H), 7.59 (d, J=1.6, 2H), 7.29 (dd, J=8.5, 2.1, 1H), 7.21 (dd, J=7.9, 4.8, 1H), 3.83-3.72 (m, 2H), 3.52-3.38 (m, 4H), 2.83 (s, 3H), 2.82-2.75 (m, 4H), 2.00-1.86 (m, 2H).

Example 248

1-[6-(Benzothiazol-2-yloxy)-benzofuran-3-ylmethyl]-piperidine-4-carboxylic acid formate

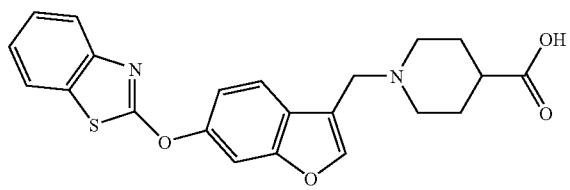 [SMILES: O=C(O)C1CCN(Cc2coc3cc(Oc4nc5ccccc5s4)ccc23)CC1]

To a solution 1-[6-(benzothiazol-2-yloxy)-benzofuran-3-ylmethyl]-piperidine-4-carboxylic acid ethyl ester (342 mg, 0.783 mmol) in IPA (8 mL) was added 2 M KOH (3.9 mL, 7.8 mmol) and stirred (rt, 2 h). The pH of the reaction mixture was adjusted to pH 8 with 1 M HCl (1.7 mL) and partitioned with DCM (30 mL). The aqueous phase was extracted with DCM (3×30 mL). The organic layers were combined, dried, filtered and concentrated in vacuo. The resulting residue was purified by reverse phase HPLC to provide the title compound as a colorless solid (86 mg, 24%). MS (ESI): mass calcd. for $C_{22}H_{20}N_2O_4S$, 408.1; m/z found, 408.9 [M+H]$^+$. $^1$H NMR (400 MHz, CDCl$_3$): 7.78-7.64 (m, 4H), 7.56 (d, J=2.0, 1H), 7.41-7.35 (m, 1H), 7.31-7.27 (m, 1H), 3.90 (s, 2H), 3.61 (s, J=135.2, 1H), 3.17 (d, J=11.3, 3H), 2.36 (t, J=10.9, 3H), 2.11-1.77 (m, 4H).

Example 249

1-[6-(Thiazolo[4,5-b]pyridin-2-yloxy)-benzofuran-3-ylmethyl]-piperidine-4-carboxylic acid

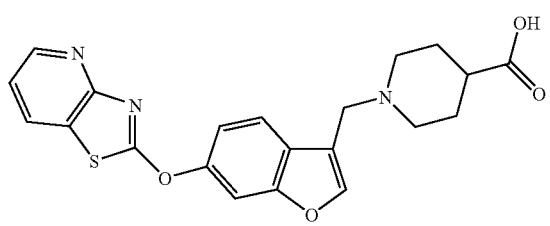 [SMILES: O=C(O)C1CCN(Cc2coc3cc(Oc4nc5ncccc5s4)ccc23)CC1]

To a solution 1-[6-(thiazolo[4,5-b]pyridin-2-yloxy)-benzofuran-3-ylmethyl]-piperidine-4-carboxylic acid ethyl ester (77 mg, 0.18 mmol) in IPA (1.7 mL) was added 2 M KOH (0.9 mL, 1.8 mmol) and stirred (rt, 2 h). The pH of the reaction mixture was adjusted to pH 8 with 1 M HCl (1.7 mL) and partitioned with DCM (30 mL). The aqueous phase was extracted with DCM (3×30 mL). The organic layers were combined, dried, filtered and concentrated in vacuo to provide the title compound as a yellow solid (28 mg, 39%). MS (ESI): mass calcd. for $C_{21}H_{19}N_3O_4S$, 409.1; m/z found, 410.0 [M+H]$^+$. $^1$H NMR (400 MHz, CD$_3$OD): 8.49 (dd, J=4.8, 1.4, 1H), 8.31 (dd, J=8.0, 1.5, 1H), 7.98 (s, 1H), 7.89 (d, J=8.6, 1H), 7.75-7.70 (m, 1H), 7.44-7.29 (m, 2H), 4.06 (s, 2H), 3.28-3.08 (m, 2H), 2.72-2.47 (m, 2H), 2.34-2.22 (m, 1H), 2.09-1.95 (m, 2H), 1.93-1.72 (m, 2H). The remaining proton was not detected (COOH).

Example 250

N-{1-[6-(5-Methyl-thiazolo[4,5-b]pyridin-2-yloxy)-benzofuran-3-ylmethyl]-piperidin-4-yl}-acetamide formate

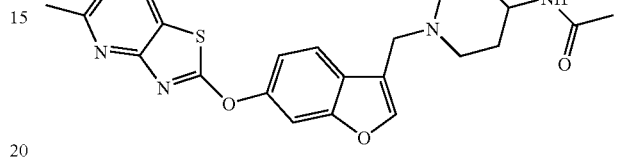

To a suspension of N-[1-(6-hydroxy-benzofuran-3-ylmethyl)-piperidin-4-yl]-acetamide (50 mg, 0.17 mmol), Cs$_2$CO$_3$ (170 mg, 0.52 mmol) in DMF (1.73 mL) was added 2-chloro-5-methyl-thiazolo[4,5-b]pyridine (40 mg, 0.22 mmol) and the reaction mixture was stirred (rt, 16 h). The reaction mixture was filtered and purified via reverse-phase preparative HPLC to provide the title compound as a white solid (67 mg, 79%). MS (ESI): mass calcd. for $C_{23}H_{24}N_4O_3S$, 436.16; m/z found, 437.0 [M+H]$^+$. $^1$H NMR (500 MHz, CDCl$_3$): 7.91 (d, J=8.1, 1H), 7.83 (s, 1H), 7.71 (d, J=8.3, 1H), 7.63 (s, 1H), 7.32 (d, J=7.9, 1H), 7.09 (d, J=8.1, 1H), 5.77 (s, 1H), 3.93 (s, 3H), 3.17 (s, 2H), 2.61 (s, 2H), 2.47 (s, 2H), 1.97 (s, 5H), 1.78 (s, 2H).

Examples 251 to 255 were prepared using methods analogous to those described for Example 250.

Example 251

N-{1-[6-(6-Methyl-thiazolo[4,5-b]pyridin-2-yloxy)-benzofuran-3-ylmethyl]-piperidin-4-yl}-acetamide formate

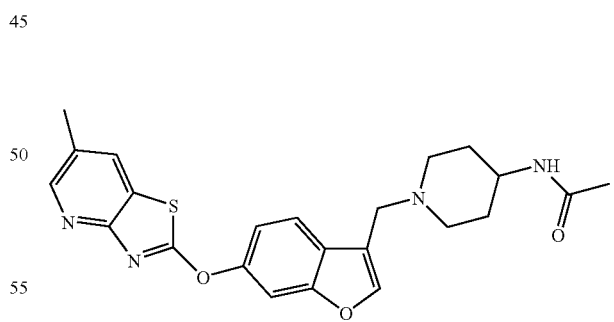

MS (ESI): mass calcd. for $C_{23}H_{24}N_4O_3S$, 436.16; m/z found, 437.0 [M+H]$^+$. $^1$H NMR (600 MHz, CDCl$_3$): 8.43-8.36 (m, 1H), 7.85-7.80 (m, 1H), 7.72 (d, J=8.5, 1H), 7.63 (s, 1H), 7.59 (d, J=2.1, 1H), 7.30 (dd, J=8.5, 2.2, 1H), 5.38 (d, J=7.1, 1H), 3.88-3.79 (m, 1H), 3.72 (s, 2H), 2.98 (d, J=10.6, 2H), 2.43 (s, 3H), 2.26 (t, J=10.9, 2H), 1.98-1.93 (m, 5H), 1.59-1.48 (m, 2H).

Example 252

N-{1-[6-(7-Methyl-thiazolo[4,5-b]pyridin-2-yloxy)-benzofuran-3-ylmethyl]-piperidin-4-yl}-acetamide formate

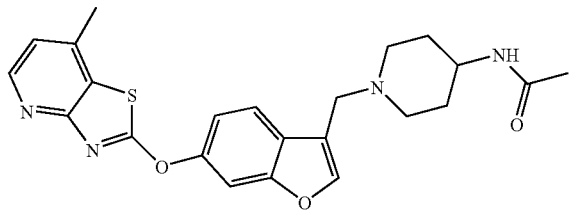 [SMILES: CC(=O)NC1CCN(Cc2coc3cc(Oc4nc5nccc(C)c5s4)ccc23)CC1]

MS (ESI): mass calcd. for $C_{23}H_{24}N_4O_3S$, 436.16; m/z found, 437.0 [M+H]$^+$. $^1$H NMR (600 MHz, CDCl$_3$): 8.45 (d, J=5.0, 1H), 7.72 (d, J=8.5, 1H), 7.66 (s, 1H), 7.60 (d, J=2.0, 1H), 7.31 (dd, J=8.5, 2.1, 1H), 7.03 (dd, J=5.0, 0.7, 1H), 5.47 (d, J=7.9, 1H), 3.90-3.81 (m, 1H), 3.77 (s, 2H), 3.03 (d, J=11.1, 2H), 2.51 (s, 3H), 2.31 (t, J=11.1, 2H), 1.99-1.94 (m, 5H), 1.62-1.54 (m, 2H).

Example 253

N-{1-[6-(Thiazolo[4,5-b]pyrazin-2-yloxy)-benzofuran-3-ylmethyl]-piperidin-4-yl}-acetamide formate

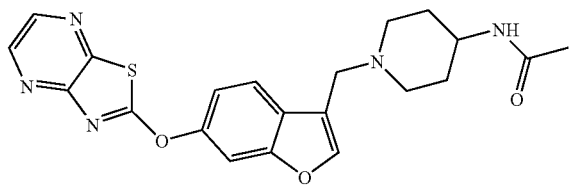 [SMILES: CC(=O)NC1CCN(Cc2coc3cc(Oc4nc5nccnc5s4)ccc23)CC1]

MS (ESI): mass calcd. for $C_{21}H_{21}N_5O_3S$, 423.14; m/z found, 424.0 [M+H]$^+$. $^1$H NMR (500 MHz, CDCl$_3$): 8.52 (d, J=2.6, 1H), 8.35 (d, J=2.5, 1H), 7.77 (d, J=8.5, 1H), 7.66 (s, 1H), 7.58 (d, J=1.8, 1H), 7.32-7.27 (m, 1H), 5.47-5.36 (m, 1H), 3.91-3.78 (m, 1H), 3.73 (s, 2H), 3.07-2.94 (m, 2H), 2.26 (t, J=11.0, 2H), 2.04-1.93 (m, 5H), 1.62-1.48 (m, 2H).

Example 254

N-{1-[6-(6-Chloro-thiazolo[4,5-b]pyridin-2-yloxy)-benzofuran-3-ylmethyl]-piperidin-4-yl}-acetamide formate

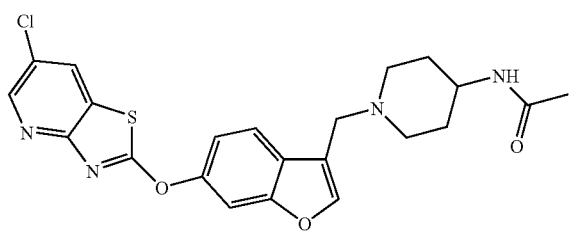 [SMILES: CC(=O)NC1CCN(Cc2coc3cc(Oc4nc5ncc(Cl)cc5s4)ccc23)CC1]

MS (ESI): mass calcd. for $C_{22}H_{21}ClN_4O_3S$, 456.10; m/z found, 456.9 [M+H]$^+$. $^1$H NMR (500 MHz, CDCl$_3$): 8.50 (5, 1H), 8.03 (d, J=2.3, 1H), 7.94 (5, 1H), 7.76 (d, J=8.5, 1H), 7.61 (5, 1H), 7.32 (d, J=8.4, 1H), 6.08 (5, 1H), 4.02 (5, 2H), 3.92 (5, 1H), 3.34-3.17 (m, 2H), 2.63-2.50 (m, 2H), 2.05-1.95 (m, 5H), 1.87 (5, 2H).

Example 255

N-{1-[6-(6-Fluoro-thiazolo[4,5-b]pyridin-2-yloxy)-benzofuran-3-ylmethyl]-piperidin-4-yl}-acetamide formate

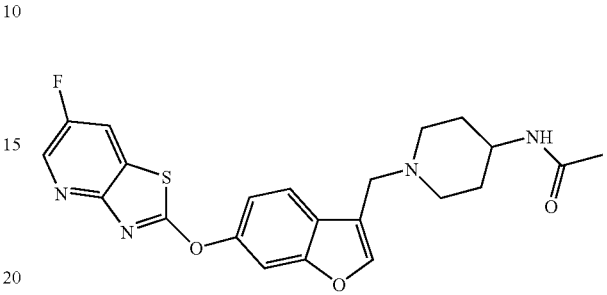

MS (ESI): mass calcd. for $C_{22}H_{21}FN_4O_3S$, 440.13; m/z found, 441.0 [M+H]$^+$. $^1$H NMR (500 MHz, CDCl$_3$): 8.43 (5, 1H), 7.93 (5, 1H), 7.83-7.73 (m, 2H), 7.65-7.61 (m, 1H), 7.33 (dd, J=8.5, 2.0, 1H), 5.98 (s, 1H), 4.01 (s, 2H), 3.98-3.88 (m, 1H), 3.25 (d, J=11.1, 2H), 2.64-2.54 (m, 2H), 2.07-1.95 (m, 5H), 1.93-1.82 (m, 2H).

Examples 256 to 258 were prepared using methods analogous to those described for Example 149.

Example 256

2-[3-(2-Morpholin-4-yl-ethyl)-benzofuran-6-yloxy]-thiazolo[4,5-b]pyridine

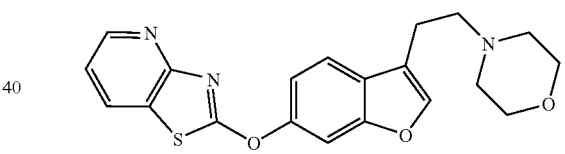

MS (ESI): mass calcd. for $C_{20}H_{19}N_3O_3S$, 381.45; m/z found, 382.1 [M+H]$^+$. $^1$H NMR (500 MHz, CDCl$_3$): 8.57 (dd, J=4.8, 1.5, 1H), 8.01 (dd, J=7.9, 1.5, 1H), 7.58 (dd, J=6.7, 4.4, 3H), 7.30 (dd, J=8.5, 2.0, 1H), 7.20 (dd, J=7.9, 4.8, 1H), 3.82-3.71 (m, 4H), 2.93-2.83 (m, 2H), 2.76-2.67 (m, 2H), 2.56 (s, 4H).

Example 257

1-(4-{2-[6-(Thiazolo[4,5-b]pyridin-2-yloxy)-benzofuran-3-yl]-ethyl}-piperazin-1-yl)-ethanone

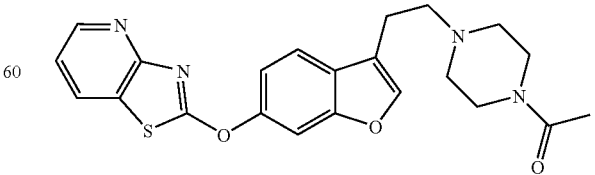

MS (ESI): mass calcd. for $C_{22}H_{22}N_4O_3S$, 422.51; m/z found, 423.0 [M+H]$^+$. $^1$H NMR (500 MHz, CDCl$_3$): 8.57 (dd, J=4.8, 1.6, 1H), 8.02 (dd, J=7.9, 1.6, 1H), 7.58 (d, J=9.3, 3H), 7.30 (dd, J=8.4, 2.1, 1H), 7.21 (dd, J=7.9, 4.8, 1H), 3.71-3.64 (m, 2H), 3.55-3.48 (m, 2H), 2.89 (t, J=7.5, 2H), 2.73 (t, J=7.6, 2H), 2.61-2.48 (m, 4H), 2.11 (s, 3H).

Example 258

(1S,4S)-1-(5-{2-[6-(Thiazolo[4,5-b]pyridin-2-yloxy)-benzofuran-3-yl]-ethyl}-2,5-diaza-bicyclo[2.2.1]hept-2-yl)-ethanone

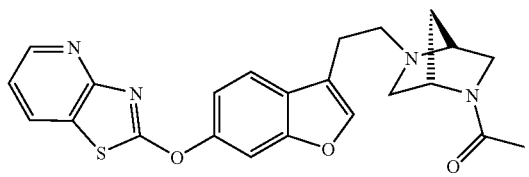

MS (ESI): mass calcd. for $C_{23}H_{22}N_4O_3S$, 434.52; m/z found, 435.0 [M+H]$^+$. $^1$H NMR (500 MHz, CDCl$_3$): 8.57 (dd, J=3.6, 1.2, 1H), 8.04-8.00 (m, 1H), 7.57 (dd, J=13.6, 5.2, 3H), 7.32-7.28 (m, 1H), 7.23-7.18 (m, 1H), 4.79 (s, 0.6H), 4.24 (s, 0.4H), 3.74-3.53 (m, 2H), 3.31 (dd, J=24.7, 10.5, 1H), 3.13 (d, J=9.5, 0.4H), 3.01-2.71 (m, 5.2H), 2.58 (d, J=9.4, 0.4H), 2.09 (s, 1.4H), 2.03-1.93 (m, 1.8H), 1.90 (d, J=10.1, 0.6H), 1.81 (d, J=9.7, 0.6H), 1.69 (d, J=9.5, 0.6H).

Example 259

1-{4-[5-(Thiazolo[4,5-b]pyridin-2-yloxy)-benzofuran-2-ylmethyl]-piperazin-1-yl}ethanone formate This compound was prepared using methods analogous to those described for Example 82, substituting DMF with K$_2$CO$_3$ at 35° C. for MeCN with K$_2$CO$_3$ at 55° C. MS (ESI): mass calcd. for $C_{21}H_{20}N_4O_3S$, 408.13; m/z found, 408.9 [M+H]$^+$. $^1$H NMR (600 MHz, CD$_3$OD): 8.51-8.45 (m, 1H), 8.31-8.25 (m, 1H), 7.65 (d, J=2.5, 1H), 7.59 (d, J=8.8, 1H), 7.36-7.27 (m, 2H), 6.83 (s, 1H), 3.81 (s, 2H), 3.66-3.55 (m, 4H), 2.66-2.53 (m, 4H), 2.09 (s, 3H).

Example 260

5-[6-(Thiazolo[4,5-b]pyridin-2-yloxy)-benzofuran-3-ylmethyl]-hexahydro-pyrrolo[3,4-c]pyrrole-2-carboxylic acid tert-butyl ester This compound was prepared using methods analogous to those described for Example 153, with the following variation: DMF with K$_2$CO$_3$ at 60° C. for 16 hr was used instead of 4:1 CH$_3$CN/DMF with K$_2$CO$_3$ at rt for 48 hr. MS (ESI): mass calculated for $C_{26}H_{28}N_4O_4S$, 492.18; m/z found, 493.0 [M+H]$^+$.

Example 261

(1S,4S)-5-[6-(Thiazolo[4,5-b]pyridin-2-yloxy)-benzofuran-3-ylmethyl]-2,5-diaza-bicyclo[2.2.1]heptane-2-carboxylic acid tert-butyl ester This compound was prepared using methods analogous to those described for Example 153, with the following variation: DMF with K$_2$CO$_3$ at 60° C. for 16 hr was used instead of 4:1 CH$_3$CN/DMF with K$_2$CO$_3$ at rt for 48 hr. MS (ESI): mass calculated for $C_{25}H_{26}N_4O_4S$, 478.17; m/z found, 479.0 [M+H]$^+$.

Example 262

2-[3-(Hexahydro-pyrrolo[3,4-c]pyrrol-2-ylmethyl)-benzofuran-6-yloxy]-thiazolo[4,5-b]pyridine dihydrochloride

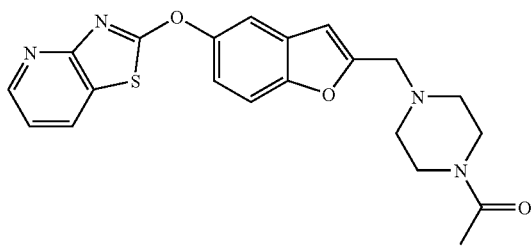 [SMILES: CC(=O)N1CCN(Cc2cc3cc(Oc4nc5ncccc5s4)ccc3o2)CC1]

This compound was prepared using methods analogous to those described for Example 152. MS (ESI): mass calculated for $C_{21}H_{20}N_4O_2S$, 392.13; m/z found, 393.0 [M+H]$^+$.

Example 263

(1S,4S)-2-[3-(2,5-Diaza-bicyclo[2.2.1]hept-2-ylmethyl)-benzofuran-6-yloxy]-thiazolo[4,5-b]pyridine dihydrochloride

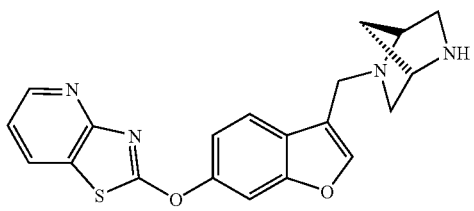

This compound was prepared using methods analogous to those described for Example 152. MS (ESI): mass calculated for $C_{20}H_{18}N_4O_2S$, 378.12; m/z found, 378.9 [M+H]$^+$.

Example 264

2-[3-(2,8-Diaza-spiro[4.5]dec-8-ylmethyl)-benzofuran-6-yloxy]-thiazolo[4,5-b]pyridine

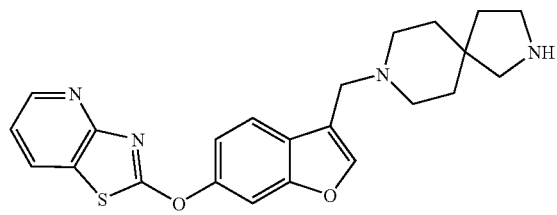 [SMILES: c1cnc2nc(Oc3ccc4c(CN5CCC6(CCNC6)CC5)coc4c3)sc2c1]

This compound was prepared using methods analogous to those described for Example 152. MS (ESI): mass calculated for $C_{23}H_{24}N_4O_2S$, 420.16; m/z found, 421.0 [M+H]$^+$. $^1$H NMR (400 MHz, CD$_3$OD): 9.02 (d, J=8.0, 1H), 8.73 (d, J=5.4, 1H), 8.31 (s, 1H), 8.19-8.13 (m, 1H), 7.90 (d, J=1.7, 1H), 7.83 (dd, J=8.0, 5.9, 1H), 7.58-7.53 (m, 1H), 3.77-3.71 (m, 2H), 3.69-3.64 (m, 2H), 3.64-3.56 (m, 2H), 3.50-3.33 (m, 4H), 2.21-1.92 (m, 6H).

Example 265

1-{8-[6-(Thiazolo[4,5-b]pyridin-2-yloxy)-benzofuran-3-ylmethyl]-2,8-diaza-spiro[4.5]dec-2-yl}-ethanone

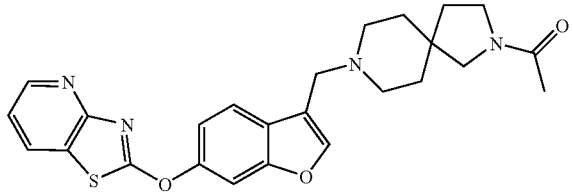 [SMILES: CC(=O)N1CCC2(CCN(Cc3coc4cc(Oc5nc6ncccc6s5)ccc34)CC2)C1]

This compound was prepared using methods analogous to those described for Example 53. MS (ESI): mass calculated for $C_{25}H_{26}N_4O_3S$, 462.17; m/z found, 463.0 [M+H]$^+$. $^1$H NMR (500 MHz, CDCl$_3$): 8.61-8.54 (m, 1H), 8.07-8.01 (m, 1H), 7.76-7.66 (m, 2H), 7.65-7.60 (m, 1H), 7.36-7.29 (m, 1H), 7.25-7.19 (m, 1H), 3.85 (d, J=13.7, 3H), 3.55-3.46 (m, 2H), 3.36 (s, 1.25H), 3.26 (s, 0.75H), 2.88 (s, 1H), 2.65 (s, 1H), 2.52 (s, 1H), 2.05 (s, 3H), 1.84 (t, J=7.1, 1H), 1.79-1.60 (m, 5H).

Examples 266 to 278 were prepared using methods analogous to those described for Example 153, with the following variation: DMF with K$_2$CO$_3$ at 50° C. for 16 hr was used instead of 4:1 CH$_3$CN/DMF with K$_2$CO$_3$ at rt for 48 hr.

Example 266

2-[6-(Thiazolo[4,5-b]pyridin-2-yloxy)-benzofuran-3-ylmethyl]-decahydro-isoquinoline formate

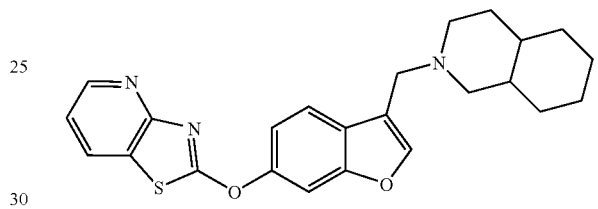

MS (ESI): mass calcd. for $C_{24}H_{25}N_3O_2S$, 419.17; m/z found, 420.0 [M+H]$^+$. $^1$H NMR (600 MHz, CD$_3$OD): 8.48 (dd, J=4.9, 1.6, 1H), 8.31 (dd, J=8.0, 1.6, 1H), 7.95-7.83 (m, 2H), 7.72-7.68 (m, 1H), 7.40-7.36 (m, 1H), 7.36-7.32 (m, 1H), 4.31-0.68 (m, 18H).

Example 267

1-[6-(Thiazolo[4,5-b]pyridin-2-yloxy)-benzofuran-3-ylmethyl]-decahydro-quinoline formate

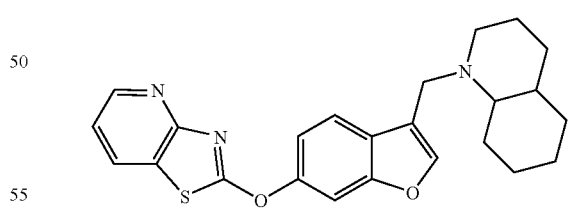

MS (ESI): mass calcd. for $C_{24}H_{25}N_3O_2S$, 419.17; m/z found, 420.0 [M+H]$^+$. $^1$H NMR (600 MHz, CD$_3$OD): 8.50-8.45 (m, 1H), 8.32-8.27 (m, 1H), 7.91-7.88 (m, 1H), 7.82 (d, J=8.5, 1H), 7.71-7.68 (m, 1H), 7.40-7.29 (m, 2H), 4.29 (d, J=14.3, 1H), 3.85 (d, J=14.3, 1H), 3.33-3.29 (m, 1H), 3.13 (d, J=11.0, 1H), 2.51-2.43 (m, 1H), 2.40-2.30 (m, 1H), 2.16-2.07 (m, 1H), 1.96-1.89 (m, 1H), 1.77-1.58 (m, 4H), 1.46-1.23 (m, 4H), 1.14-1.01 (m, 2H).

Example 268

1-[6-(Thiazolo[4,5-b]pyridin-2-yloxy)-benzofuran-3-ylmethyl]-piperidin-4-ol

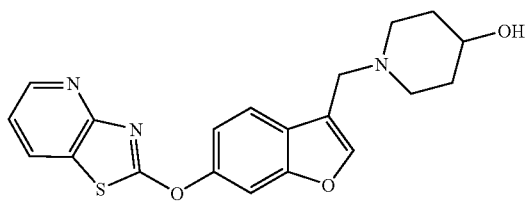 [SMILES: OC1CCN(Cc2coc3cc(Oc4nc5ncccc5s4)ccc23)CC1]

MS (ESI): mass calcd. for $C_{20}H_{19}N_3O_3S$, 381.11; m/z found, 381.9 [M+H]$^+$. $^1$H NMR (600 MHz, CDCl$_3$): 8.57 (dd, J=4.8, 1.6, 1H), 8.02 (dd, J=7.9, 1.7, 1H), 7.77 (d, J=8.5, 1H), 7.60-7.56 (m, 2H), 7.32-7.26 (m, 1H), 7.23-7.17 (m, 1H), 3.73 (s, 1H), 3.67-3.63 (m, 2H), 2.87-2.77 (m, 2H), 2.28-2.19 (m, 2H), 1.95-1.87 (m, 2H), 1.67-1.55 (m, 3H).

Example 269

{1-[6-(Thiazolo[4,5-b]pyridin-2-yloxy)-benzofuran-3-ylmethyl]-piperidin-4-yl}-methanol

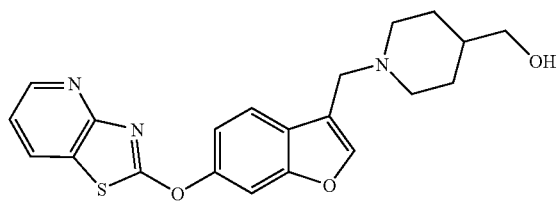 [SMILES: OCC1CCN(Cc2coc3cc(Oc4nc5ncccc5s4)ccc23)CC1]

MS (ESI): mass calcd. for $C_{21}H_{21}N_3O_3S$, 395.13; m/z found, 396.0 [M+H]$^+$. $^1$H NMR (600 MHz, CDCl$_3$): 8.57 (dd, J=4.8, 1.6, 1H), 8.01 (dd, J=7.9, 1.6, 1H), 7.76 (d, J=8.5, 1H), 7.62-7.55 (m, 2H), 7.31-7.24 (m, 1H), 7.23-7.17 (m, 1H), 3.66 (d, J=19.1, 2H), 3.51 (d, J=6.4, 2H), 3.03-2.95 (m, 2H), 2.08-1.99 (m, 2H), 1.78-1.71 (m, 2H), 1.56-1.46 (m, 1.5H), 1.36-1.22 (m, 2.5H).

Example 270

2-[3-(4-Fluoro-piperidin-1-ylmethyl)-benzofuran-6-yloxy]-thiazolo[4,5-b]pyridine formate

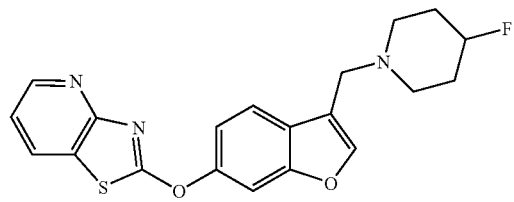 [SMILES: FC1CCN(Cc2coc3cc(Oc4nc5ncccc5s4)ccc23)CC1]

MS (ESI): mass calcd. for $C_{20}H_{18}FN_3O_2S$, 383.11; m/z found, 384.0 [M+H]$^+$. $^1$H NMR (600 MHz, CD$_3$OD): 8.50-8.46 (m, 1H), 8.32-8.28 (m, 1H), 7.94 (s, 1H), 7.89-7.84 (m, 1H), 7.71-7.68 (m, 1H), 7.39-7.32 (m, 2H), 4.80 (s, 0.5H), 4.70 (s, 0.5H), 4.03 (s, 2H), 3.00-2.81 (m, 4H), 2.07-1.91 (m, 4H).

Example 271

2-[3-(4-Methoxy-piperidin-1-ylmethyl)-benzofuran-6-yloxy]-thiazolo[4,5-b]pyridine formate

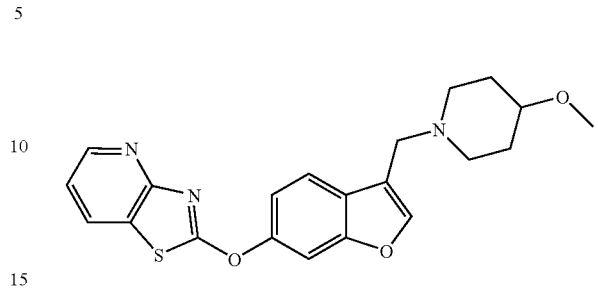

MS (ESI): mass calcd. for $C_{21}H_{21}N_3O_3S$, 395.13; m/z found, 396.2 [M+H]$^+$. $^1$H NMR (600 MHz, CD$_3$OD): 8.50-8.47 (m, 1H), 8.33-8.28 (m, 1H), 8.02 (s, 1H), 7.87 (d, J=8.5, 1H), 7.73 (d, J=2.1, 1H), 7.41-7.37 (m, 1H), 7.36-7.32 (m, 1H), 4.23 (s, 2H), 3.48-3.42 (m, 1H), 3.34 (d, J=11.4, 3H), 3.23-3.15 (m, 2H), 3.01-2.90 (m, 2H), 2.06-1.95 (m, 2H), 1.89-1.78 (m, 2H).

Example 272

1'-[6-(Thiazolo[4,5-b]pyridin-2-yloxy)-benzofuran-3-ylmethyl]-[1,4']bipiperidinyl-2-one formate

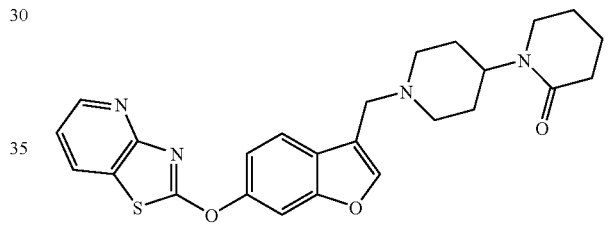

MS (ESI): mass calcd. for $C_{25}H_{26}N_4O_3S$, 462.17; m/z found, 463.1 [M+H]$^+$. $^1$H NMR (400 MHz, CD$_3$OD): 8.49 (dd, J=4.9, 1.6, 1H), 8.31 (dd, J=8.0, 1.6, 1H), 7.98 (s, 1H), 7.91-7.85 (m, 1H), 7.73 (d, J=2.1, 1H), 7.42-7.31 (m, 2H), 4.53-4.40 (m, 1H), 4.11 (s, 2H), 3.42-3.33 (m, 2H), 3.29-3.22 (m, 2H), 2.76-2.62 (m, 2H), 2.41-2.31 (m, 2H), 2.07-1.92 (m, 2H), 1.86-1.69 (m, 6H).

Example 273

N-{1-[6-(Thiazolo[4,5-b]pyridin-2-yloxy)-furo[3,2-b]pyridin-2-ylmethyl]-piperidin-4-yl}-acetamide formate

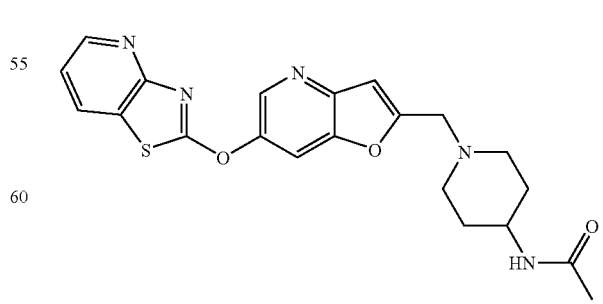

MS (ESI): mass calcd. for $C_{21}H_{21}N_5O_3S$, 423.14; m/z found, 423.9 [M+H]$^+$. $^1$H NMR (600 MHz, CDCl$_3$): 8.63-

8.60 (m, 1H), 8.58 (dd, J=4.8, 1.6, 1H), 8.09 (dd, J=8.0, 1.6, 1H), 8.04 (dd, J=2.3, 0.9, 1H), 7.27-7.24 (m, 1H), 6.92 (d, J=0.5, 1H), 3.94-3.77 (m, 3H), 3.10-2.98 (m, 2H), 2.44-2.32 (m, 2H), 2.02-1.92 (m, 5H), 1.69-1.51 (m, 2H).

Example 274

(1S,4S)-1-{5-[6-(Thiazolo[4,5-b]pyridin-2-yloxy)-furo[3,2-b]pyridin-2-ylmethyl]-2,5-diaza-bicyclo[2.2.1]hept-2-yl}-ethanone formate

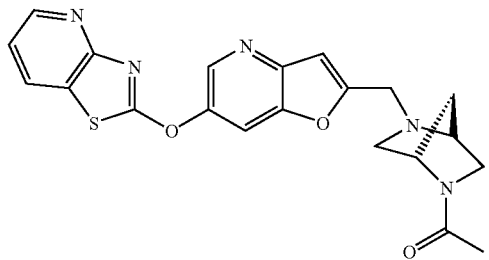

This reaction was heated for 8 hr instead of 16 hr. MS (ESI): mass calcd. for $C_{21}H_{19}N_5O_3S$, 421.12; m/z found, 422.0 [M+H]$^+$. $^1$H NMR (600 MHz, CD$_3$OD): 8.63 (dd, J=2.3, 1.2, 1H), 8.49 (dd, J=4.9, 1.6, 1H), 8.37-8.33 (m, 1H), 8.25-8.22 (m, 1H), 7.36 (dd, J=8.0, 4.9, 1H), 7.01-6.97 (m, 1H), 4.71 (s, 0.5H), 4.51 (s, 0.5H), 4.12-4.01 (m, 2H), 3.79 (d, J=12.8, 1H), 3.74-3.69 (m, 0.5H), 3.68-3.62 (m, 0.5H), 3.51-3.46 (m, 0.5H), 3.33-3.28 (m, 0.5H), 3.14-3.07 (m, 0.5H), 3.05-2.99 (m, 0.5H), 2.91-2.83 (m, 1H), 2.14-1.99 (m, 3.5H), 1.99-1.94 (m, 0.5H), 1.92-1.85 (m, 0.5H), 1.83-1.77 (m, 0.5H).

Example 275

4-Phenyl-1-[6-(thiazolo[4,5-b]pyridin-2-yloxy)-benzofuran-3-ylmethyl]-piperidin-4-ol

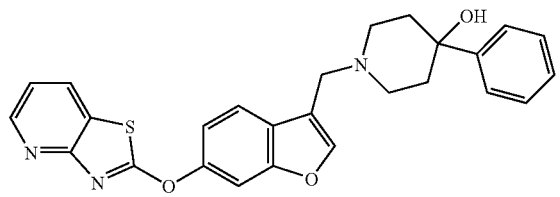 [SMILES: OC1(c2ccccc2)CCN(Cc2coc3cc(Oc4nc5ncccc5s4)ccc23)CC1]

MS (ESI): mass calcd. for $C_{26}H_{23}N_3O_3S$, 457.2; m/z found, 458.1 [M+H]$^+$. $^1$H NMR (400 MHz, CD$_3$OD): 8.50 (dd, J=4.9, 1.6, 1H), 8.32 (dd, J=8.0, 1.6, 1H), 7.92 (d, J=8.5, 1H), 7.90 (s, 1H), 7.70 (d, J=2.1, 1H), 7.53-7.49 (m, 2H), 7.40-7.30 (m, 4H), 7.25-7.20 (m, 1H), 3.83 (s, 2H), 2.93-2.87 (m, 2H), 2.74-2.64 (m, 2H), 2.17 (td, J=13.4, 4.4, 2H), 1.81-1.75 (m, 2H).

Example 276

Cyclopropyl-{4-[6-(thiazolo[4,5-b]pyridin-2-yloxy)-benzofuran-3-ylmethyl]-piperazin-1-yl}-methanone formate

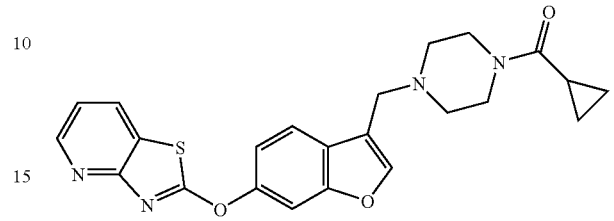

MS (ESI): mass calcd. for $C_{23}H_{22}N_4O_3S$, 434.1; m/z found, 435.0 [M+H]$^+$. $^1$H NMR (400 MHz, CD$_3$OD): 8.48 (dd, J=4.9, 1.6, 1H), 8.30 (dd, J=8.0, 1.6, 1H), 7.90 (d, J=8.5, 1H), 7.85 (s, 1H), 7.67 (d, J=2.1, 1H), 7.37-7.31 (m, 2H), 3.80 (s, 4H), 3.67-3.60 (m, 2H), 2.67-2.54 (m, 4H), 1.98-1.91 (m, 1H), 0.90-0.76 (m, 4H).

Example 277

2-[3-(4-Cyclopropyl-piperazin-1-ylmethyl)-benzofuran-6-yloxy]-thiazolo[4,5-b]pyridine

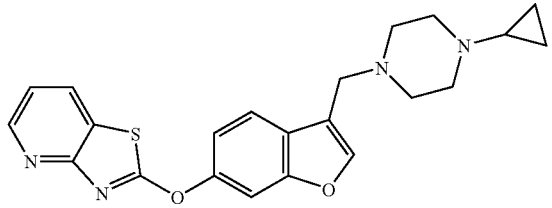 [SMILES: c1cnc2nc(Oc3ccc4c(CN5CCN(C6CC6)CC5)coc4c3)sc2c1]

MS (ESI): mass calcd. for $C_{22}H_{22}N_4O_2S$, 406.2; m/z found, 407.0 [M+H]$^+$. $^1$H NMR (400 MHz, CD$_3$OD): 8.48 (dd, J=4.9, 1.6, 1H), 8.30 (dd, J=8.0, 1.6, 1H), 7.87 (d, J=8.5, 1H), 7.82 (s, 1H), 7.66 (d, J=2.1, 1H), 7.36-7.31 (m, 2H), 3.72 (d, J=0.6, 2H), 2.75-2.45 (m, 8H), 1.70-1.64 m, 1H), 0.51-0.45 (m, 2H), 0.44-0.38 (m, 2H).

Example 278

8-[6-(Thiazolo[4,5-b]pyridin-2-yloxy)-benzofuran-3-ylmethyl]-2,8-diaza-spiro[4.5]decane-2-carboxylic acid tert-butyl ester

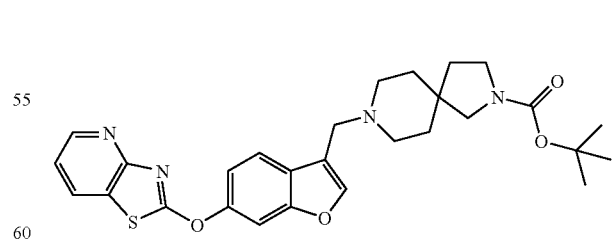

MS (ESI): mass calculated for $C_{28}H_{32}N_4O_4S$, 520.21; m/z found, 521.0 [M+H]$^+$. $^1$H NMR (500 MHz, CDCl$_3$): 8.57 (dd, J=4.8, 1.6, 1H), 8.02 (dd, J=7.9, 1.5, 1H), 7.78-7.73 (m, 1H), 7.62 (s, 1H), 7.59 (d, J=2.1, 1H), 7.30 (dd, J=8.5, 2.1, 1H), 7.21 (dd, J=7.9, 4.8, 1H), 3.70 (s, 2H), 3.42-3.31 (m, 2H), 3.21 (s, 1H), 3.13 (s, 1H), 2.73-2.24 (m, 4H), 1.70 (t, J=7.0, 2H), 1.66-1.57 (m, 4H), 1.49-1.44 (m, 9H).

Examples 279 to 296 were prepared using methods analogous to those described for Example 153, with the following variation: DMF with K₂CO₃ at 35° C. for 16 hr was used instead of 4:1 CH₃CN/DMF with K₂CO₃ at rt for 48 hr.

Example 279

2-[3-(4-Benzyl-piperidin-1-ylmethyl)-benzofuran-6-yloxy]-thiazolo[4,5-b]pyridine

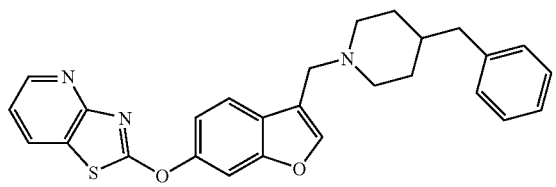 [SMILES: c1ccc(CC2CCN(Cc3coc4cc(Oc5nc6ncccc6s5)ccc34)CC2)cc1]

MS (ESI): mass calcd. for $C_{27}H_{25}N_3O_2S$, 455.17; m/z found, 456.0 [M+H]⁺. ¹H NMR (400 MHz, CDCl₃): 8.57 (dd, J=4.8, 1.6, 1H), 8.01 (dd, J=7.9, 1.7, 1H), 7.75 (d, J=8.5, 1H), 7.60-7.54 (m, 2H), 7.31-7.10 (m, 7H), 3.65-3.60 (m, 2H), 2.98-2.88 (m, 2H), 2.53 (d, J=7.1, 2H), 2.03-1.90 (m, 2H), 1.68-1.60 (m, 2H), 1.58-1.46 (m, 1H), 1.39-1.23 (m, 2H).

Example 280

2-[3-(4-Phenyl-piperidin-1-ylmethyl)-benzofuran-6-yloxy]-thiazolo[4,5-b]pyridine formate

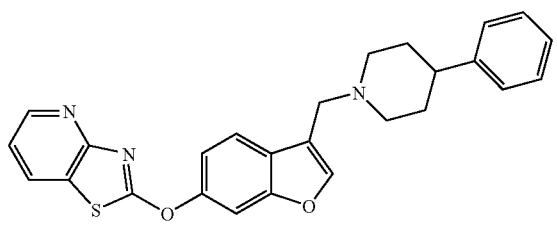 [SMILES: c1ccc(C2CCN(Cc3coc4cc(Oc5nc6ncccc6s5)ccc34)CC2)cc1]

MS (ESI): mass calcd. for $C_{26}H_{23}N_3O_2S$, 441.15; m/z found, 441.9 [M+H]⁺. ¹H NMR (400 MHz, CD₃OD): 8.50-8.46 (m, 1H), 8.34-8.28 (m, 1H), 7.98 (s, 1H), 7.91 (d, J=8.5, 1H), 7.72 (d, J=2.1, 1H), 7.44-7.13 (m, 7H), 4.07 (s, 2H), 3.41-3.27 (m, 2H), 2.72-2.54 (m, 3H), 1.98-1.79 (m, 4H).

Example 281

2-[3-(3,5-Dimethyl-piperidin-1-ylmethyl)-benzofuran-6-yloxy]-thiazolo[4,5-b]pyridine formate

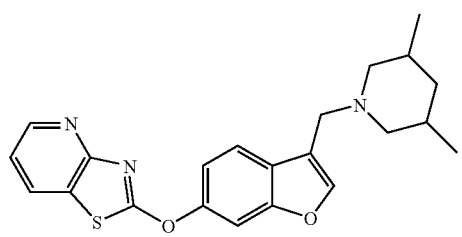 [SMILES: CC1CC(C)CN(Cc2coc3cc(Oc4nc5ncccc5s4)ccc23)C1]

MS (ESI): mass calcd. for $C_{22}H_{23}N_3O_2S$, 393.15; m/z found, 394.1 [M+H]⁺. ¹H NMR (400 MHz, CD₃OD): 8.52-8.46 (m, 1H), 8.35-8.29 (m, 1H), 8.11-7.97 (m, 1H), 7.92-7.87 (m, 1H), 7.78-7.71 (m, 1H), 7.46-7.31 (m, 2H), 4.31 (s, 1.5H), 4.18-4.07 (m, 0.5H), 3.38-3.29 (m, 1.5H), 3.02-2.91 (m, 0.5H), 2.70-2.57 (m, 0.5H), 2.41-2.29 (m, 1.5H), 2.14-2.05 (m, 0.5H), 1.98-1.76 (m, 2H), 1.49-1.39 (m, 0.5H), 1.07-0.89 (m, 6H), 0.85-0.71 (m, 1H).

Example 282

Dimethyl-{1-[6-(thiazolo[4,5-b]pyridin-2-yloxy)-benzofuran-3-ylmethyl]-piperidin-4-yl}-amine formate

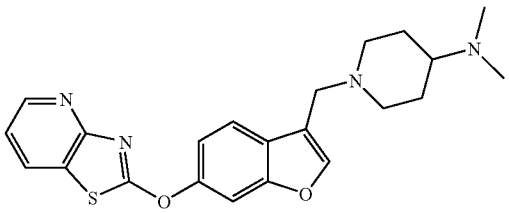 [SMILES: CN(C)C1CCN(Cc2coc3cc(Oc4nc5ncccc5s4)ccc23)CC1]

MS (ESI): mass calcd. for $C_{22}H_{24}N_4O_2S$, 408.16; m/z found, 409.1 [M+H]⁺. ¹H NMR (400 MHz, CD₃OD): 8.48 (dd, J=4.9, 1.6, 1H), 8.31 (dd, J=8.0, 1.6, 1H), 7.91-7.81 (m, 2H), 7.67 (d, J=2.1, 1H), 7.39-7.29 (m, 2H), 3.78 (s, 2H), 3.23-3.10 (m, 3H), 2.83 (s, 6H), 2.27-2.16 (m, 2H), 2.12-2.05 (m, 2H), 1.84-1.69 (m, 2H).

Example 283

2-[3-(4-Pyrrolidin-1-yl-piperidin-1-ylmethyl)-benzofuran-6-yloxy]-thiazolo[4,5-b]pyridine formate

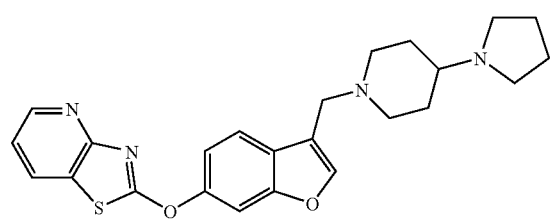 [SMILES: c1cnc2nc(Oc3ccc4c(CN5CCC(N6CCCC6)CC5)coc4c3)sc2c1]

MS (ESI): mass calcd. for $C_{24}H_{26}N_4O_2S$, 434.18; m/z found, 435.3 [M+H]⁺. ¹H NMR (600 MHz, CD₃OD): 8.51-8.47 (m, 1H), 8.33-8.27 (m, 1H), 7.88-7.82 (m, 2H), 7.67 (d, J=2.1, 1H), 7.38-7.30 (m, 2H), 3.77 (s, 2H), 3.42-3.28 (m, 4H), 3.18-3.06 (m, 3H), 2.24-2.11 (m, 4H), 2.10-2.00 (m, 4H), 1.82-1.71 (m, 2H).

Example 284

1'-[6-(Thiazolo[4,5-b]pyridin-2-yloxy)-benzofuran-3-ylmethyl]-[1,4']bipiperidinyl formate

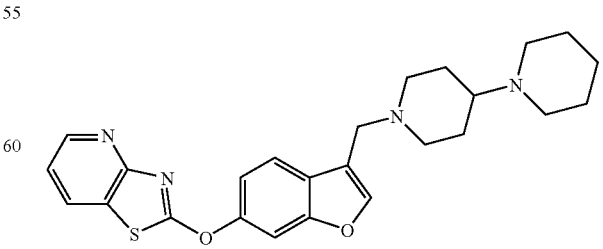

MS (ESI): mass calcd. for $C_{25}H_{28}N_4O_2S$, 448.19; m/z found, 449.1 [M+H]⁺. ¹H NMR (600 MHz, CD₃OD): 8.51-8.46 (m, 1H), 8.33-8.28 (m, 1H), 7.88-7.81 (m, 2H), 7.67 (d, J=2.1, 1H), 7.37-7.30 (m, 2H), 3.79 (s, 2H), 3.32-3.08 (m, 7H), 2.29-2.17 (m, 2H), 2.15-2.07 (m, 2H), 1.93-1.75 (m, 6H), 1.66 (s, 2H).

Example 285

2-[3-(4-Morpholin-4-yl-piperidin-1-ylmethyl)-benzofuran-6-yloxy]-thiazolo[4,5-b]pyridine formate

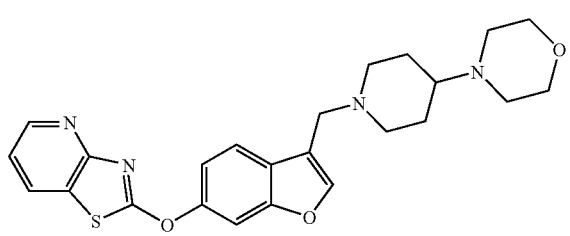 [SMILES: c1cnc2nc(Oc3ccc4c(CN5CCC(N6CCOCC6)CC5)coc4c3)sc2c1]

MS (ESI): mass calcd. for $C_{24}H_{26}N_4O_3S$, 450.17; m/z found, 451.2 [M+H]$^+$. $^1$H NMR (600 MHz, CD$_3$OD): 8.48 (dd, J=4.9, 1.6, 1H), 8.34-8.28 (m, 1H), 7.97 (s, 1H), 7.87 (d, J=8.5, 1H), 7.72 (d, J=2.1, 1H), 7.40-7.32 (m, 2H), 4.09 (s, 2H), 3.80-3.74 (m, 4H), 3.40-3.33 (m, 2H), 2.88-2.80 (m, 4H), 2.74-2.67 (m, 1H), 2.65-2.55 (m, 2H), 2.14-2.06 (m, 2H), 1.82-1.71 (m, 2H).

Example 286

2-[3-(4-Methyl-piperidin-1-ylmethyl)-benzofuran-6-yloxy]-thiazolo[4,5-b]pyridine formate

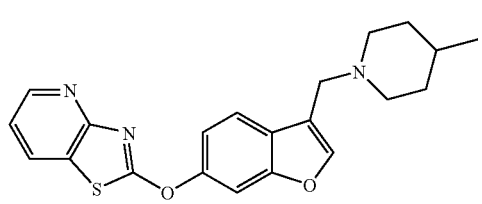 [SMILES: CC1CCN(Cc2coc3cc(Oc4nc5ncccc5s4)ccc23)CC1]

MS (ESI): mass calcd. for $C_{21}H_{21}N_3O_2S$, 379.14; m/z found, 380.1 [M+H]$^+$. $^1$H NMR (600 MHz, CD$_3$OD): 8.50-8.46 (m, 1H), 8.33-8.29 (m, 1H), 8.04 (5, 1H), 7.87 (d, J=8.5, 1H), 7.74 (d, J=2.1, 1H), 7.42-7.38 (m, 1H), 7.37-7.32 (m, 1H), 4.25 (5, 2H), 3.38 (d, J=12.1, 2H), 2.83-2.73 (m, 2H), 1.88-1.79 (m, 2H), 1.66-1.54 (m, 1H), 1.47-1.36 (m, 2H), 1.01-0.96 (m, 3H).

Example 287

2-[3-(4-Phenyl-piperazin-1-ylmethyl)-benzofuran-6-yloxy]-thiazolo[4,5-b]pyridine formate

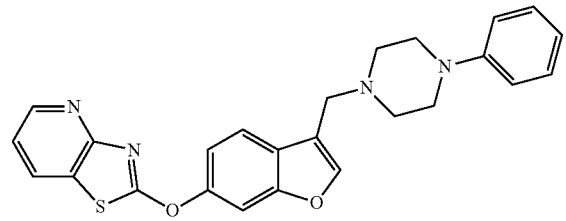 [SMILES: c1ccc(N2CCN(Cc3coc4cc(Oc5nc6ncccc6s5)ccc34)CC2)cc1]

MS (ESI): mass calcd. for $C_{25}H_{22}N_4O_2S$, 442.15; m/z found, 443.0 [M+H]$^+$. $^1$H NMR (500 MHz, CDCl$_3$): 8.57 (dd, J=4.8, 1.7, 1H), 8.02 (dd, J=7.9, 1.7, 1H), 7.80 (d, J=8.5, 1H), 7.64 (s, 1H), 7.60 (d, J=2.0, 1H), 7.32-7.18 (m, 4H), 6.97-6.91 (m, 2H), 6.89-6.83 (m, 1H), 3.72 (s, 2H), 3.27-3.19 (m, 4H), 2.75-2.64 (m, 4H).

Example 288

2-[3-(4-Pyridin-2-yl-piperazin-1-ylmethyl)-benzofuran-6-yloxy]-thiazolo[4,5-b]pyridine formate

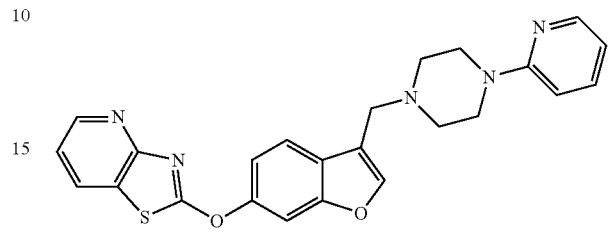

MS (ESI): mass calcd. for $C_{24}H_{21}N_5O_2S$, 443.14; m/z found, 444.0 [M+H]$^+$. $^1$H NMR (500 MHz, CDCl$_3$): 8.59-8.54 (m, 1H), 8.22-8.17 (m, 1H), 8.05-8.00 (m, 1H), 7.82-7.76 (m, 1H), 7.68-7.63 (m, 1H), 7.61 (d, J=2.0, 1H), 7.52-7.45 (m, 1H), 7.30 (dd, J=8.5, 2.1, 1H), 7.24-7.17 (m, 1H), 6.68-6.59 (m, 2H), 3.76 (5, 2H), 3.64-3.54 (m, 4H), 2.74-2.64 (m, 4H).

Example 289

2-[3-(4-Pyridin-4-yl-piperazin-1-ylmethyl)-benzofuran-6-yloxy]-thiazolo[4,5-b]pyridine formate

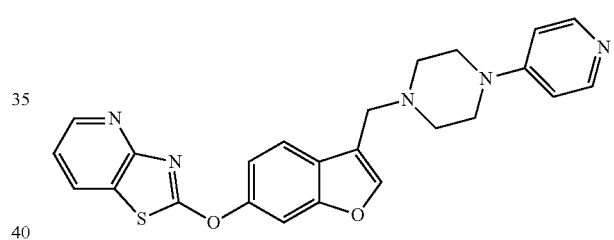

MS (ESI): mass calcd. for $C_{24}H_{21}N_5O_2S$, 443.14; m/z found, 444.0 [M+H]$^+$. $^1$H NMR (500 MHz, CDCl$_3$): 8.56 (dd, J=4.8, 1.6, 1H), 8.31-8.25 (m, 2H), 8.04 (dd, J=7.9, 1.7, 1H), 7.78 (d, J=8.5, 1H), 7.62 (app s, 1H), 7.61 (d, J=2.0, 1H), 7.33-7.29 (m, 1H), 7.24-7.20 (m, 1H), 6.74 (d, J=7.1, 2H), 3.72 (s, 2H), 3.52-3.45 (m, 4H), 2.69-2.62 (m, 4H).

Example 290

2-{3-[4-(4-Methoxy-phenyl)-piperazin-1-ylmethyl]-benzofuran-6-yloxy}-thiazolo[4,5-b]pyridine formate

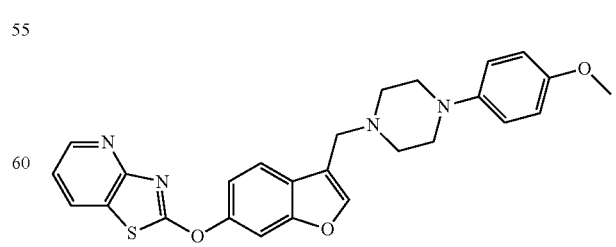

MS (ESI): mass calcd. for $C_{26}H_{24}N_4O_3S$, 472.16; m/z found, 473.0 [M+H]$^+$. $^1$H NMR (500 MHz, CDCl$_3$): 8.57 (dd, J=4.8, 1.6, 1H), 8.03 (dd, J=7.9, 1.7, 1H), 7.78 (d, J=8.5, 1H), 7.67 (s, 1H), 7.61 (d, J=2.0, 1H), 7.31 (dd, J=8.5, 2.1, 1H), 7.24-7.18 (m, 1H), 6.93-6.88 (m, 2H), 6.86-6.81 (m, 2H), 3.79 (s, 2H), 3.77 (s, 3H), 3.18-3.11 (m, 4H), 2.79-2.74 (m, 4H).

Example 291

2-[3-(4-Phenethyl-piperazin-1-ylmethyl)-benzofuran-6-yloxy]-thiazolo[4,5-b]pyridine formate

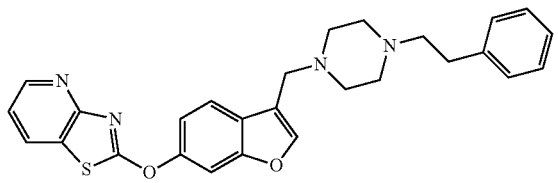 [SMILES: c1ccc(CCN2CCN(Cc3coc4cc(Oc5nc6ncccc6s5)ccc34)CC2)cc1]

MS (ESI): mass calcd. for $C_{27}H_{26}N_4O_2S$, 470.18; m/z found, 471.0 [M+H]$^+$. $^1$H NMR (500 MHz, CDCl$_3$): 8.56 (dd, J=4.8, 1.6, 1H), 8.03 (dd, J=7.9, 1.6, 1H), 7.75 (d, J=8.5, 1H), 7.62 (s, 1H), 7.58 (d, J=2.1, 1H), 7.33-7.25 (m, 3H), 7.25-7.17 (m, 4H), 3.72 (s, 2H), 3.10-2.49 (m, 12H).

Example 292

2-[3-(4-Pyrimidin-2-yl-piperazin-1-ylmethyl)-benzofuran-6-yloxy]-thiazolo[4,5-b]pyridine formate

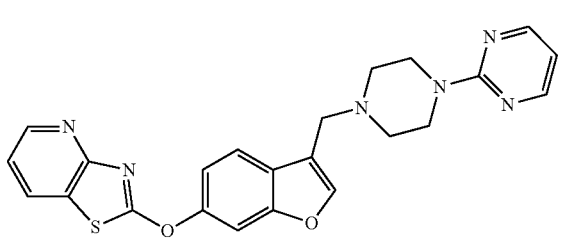 [SMILES: c1cnc(N2CCN(Cc3coc4cc(Oc5nc6ncccc6s5)ccc34)CC2)nc1]

MS (ESI): mass calcd. for $C_{23}H_{20}N_6O_2S$, 444.14; m/z found, 444.9 [M+H]$^+$. $^1$H NMR (400 MHz, CDCl$_3$): 8.57 (dd, J=4.8, 1.6, 1H), 8.30 (d, J=4.8, 2H), 8.02 (dd, J=7.9, 1.7, 1H), 7.81 (d, J=8.5, 1H), 7.64-7.59 (m, 2H), 7.32-7.28 (m, 1H), 7.24-7.17 (m, 1H), 6.48 (t, J=4.7, 1H), 3.89-3.81 (m, 4H), 3.69 (s, 2H), 2.61-2.53 (m, 4H).

Example 293

2-[6-(Thiazolo[4,5-b]pyridin-2-yloxy)-benzofuran-3-ylmethyl]-1,2,3,4-tetrahydro-isoquinoline formate

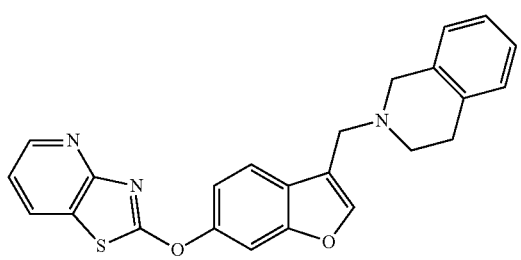 [SMILES: c1ccc2c(c1)CCN(Cc1coc3cc(Oc4nc5ncccc5s4)ccc13)C2]

MS (ESI): mass calcd. for $C_{24}H_{19}N_3O_2S$, 413.12; m/z found, 414.0 [M+H]$^+$. $^1$H NMR (500 MHz, CD$_3$OD): 8.47 (dd, J=4.9, 1.6, 1H), 8.28 (dd, J=8.0, 1.6, 1H), 7.94-7.85 (m, 2H), 7.68 (d, J=2.1, 1H), 7.36-7.30 (m, 2H), 7.15-7.06 (m, 3H), 7.05-6.99 (m, 1H), 3.96 (s, 2H), 3.78 (s, 2H), 2.97-2.88 (m, 4H).

Example 294

Methyl-(1-methyl-piperidin-4-yl)-[6-(thiazolo[4,5-b]pyridin-2-yloxy)-benzofuran-3-ylmethyl]-amine

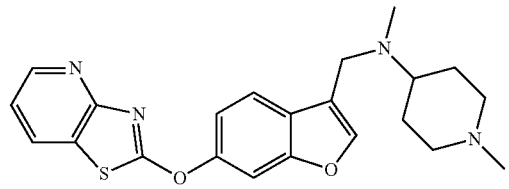 [SMILES: CN1CCC(N(C)Cc2coc3cc(Oc4nc5ncccc5s4)ccc23)CC1]

MS (ESI): mass calcd. for $C_{22}H_{24}N_4O_2S$, 408.16; m/z found, 409.1 [M+H]$^+$. $^1$H NMR (400 MHz, CD$_3$OD): 8.50-8.46 (m, 1H), 8.32-8.27 (m, 1H), 7.86-7.80 (m, 2H), 7.65 (d, J=2.1, 1H), 7.37-7.29 (m, 2H), 3.80 (s, 2H), 3.03-2.91 (m, 2H), 2.61-2.48 (m, 1H), 2.35-2.23 (m, 6H), 2.12-1.99 (m, 2H), 1.97-1.85 (m, 2H), 1.80-1.65 (m, 2H).

Example 295 meso-1-{3-[6-(Thiazolo[4,5-b]pyridin-2-yloxy)-benzofuran-3-ylmethyl]-3,8-diaza-bicyclo[3.2.1]oct-8-yl}-ethanone formate

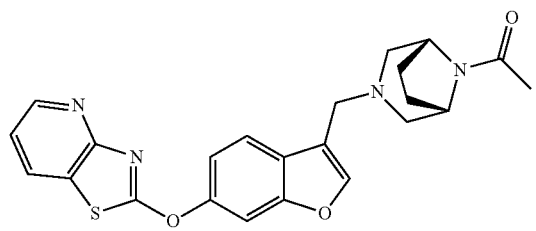 [SMILES: CC(=O)N1[C@@H]2CC[C@H]1CN(Cc1coc3cc(Oc4nc5ncccc5s4)ccc13)C2]

MS (ESI): mass calcd. for $C_{23}H_{22}N_4O_3S$, 434.14; m/z found, 435.0 [M+H]$^+$. $^1$H NMR (400 MHz, CD$_3$OD): 8.48 (dd, J=4.9, 1.6, 1H), 8.30 (dd, J=8.0, 1.6, 1H), 7.91 (d, J=8.5, 1H), 7.78 (s, 1H), 7.66 (d, J=2.1, 1H), 7.39-7.32 (m, 2H), 4.56 (d, J=6.8, 1H), 4.23 (d, J=5.7, 1H), 3.75-3.64 (m, 2H), 2.90-2.72 (m, 2H), 2.35-2.24 (m, 2H), 2.08 (s, 3H), 2.06-1.71 (m, 4H).

Example 296 meso-endo-N-{8-[6-(Thiazolo[4,5-b]pyridin-2-yloxy)-furo[3,2-b]pyridin-2-ylmethyl]-8-aza-bicyclo[3.2.1]oct-3-yl}-acetamide formate

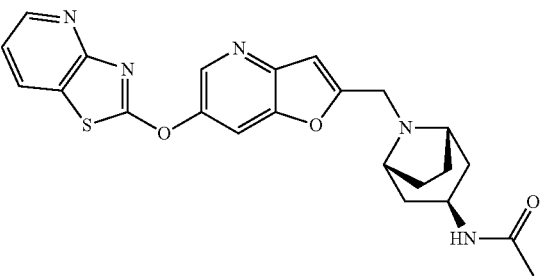 [SMILES: CC(=O)N[C@H]1C[C@H]2CC[C@@H](C1)N2Cc1cc2ncc(Oc3nc4ncccc4s3)cc2o1]

MS (ESI): mass calcd. for $C_{23}H_{23}N_5O_3S$, 449.15; m/z found, 450.0 [M+H]$^+$. $^1$H NMR (600 MHz, CD$_3$OD): 8.70-8.66 (m, 1H), 8.50 (dd, J=4.9, 1.6, 1H), 8.39-8.34 (m, 1H), 8.32-8.28 (m, 1H), 7.41-7.35 (m, 1H), 7.18 (s, 1H), 4.20 (s, 2H), 3.95-3.90 (m, 1H), 3.68 (br s, 2H), 3.33-3.29 (m, 1H), 2.37-2.17 (m, 6H), 2.00-1.92 (m, 5H).

Examples 297 to 301 were prepared using methods analogous to those described for Example 153, with the following variation: DMF with K$_2$CO$_3$ and 5 equivalents of the appropriate amine nucleophile at 35° C. for 16 hr was used instead of 4:1 CH$_3$CN/DMF with K$_2$CO$_3$ and 1 equivalent of the appropriate amine nucleophile at rt for 48 hr.

Example 297

Cyclopropyl-[6-(thiazolo[4,5-b]pyridin-2-yloxy)-benzofuran-3-ylmethyl]-amine

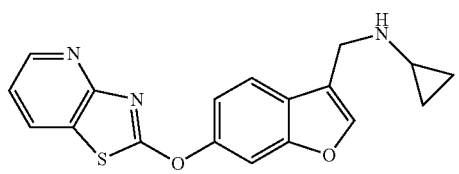 [SMILES: c1cnc2nc(Oc3ccc4c(CNC5CC5)coc4c3)sc2c1]

MS (ESI): mass calcd. for C$_{18}$H$_{15}$N$_3$O$_2$S, 337.09; m/z found, 338.0 [M+H]$^+$. $^1$H NMR (500 MHz, CDCl$_3$): 8.57 (dd, J=4.8, 1.7, 1H), 8.01 (dd, J=7.9, 1.7, 1H), 7.67 (d, J=8.5, 1H), 7.62 (s, 1H), 7.61-7.57 (m, 1H), 7.32-7.28 (m, 1H), 7.23-7.18 (m, 1H), 3.99 (s, 2H), 2.29-2.19 (m, 1H), 0.54-0.39 (m, 4H).

Example 298

Cyclopentyl-[6-(thiazolo[4,5-b]pyridin-2-yloxy)-benzofuran-3-ylmethyl]-amine

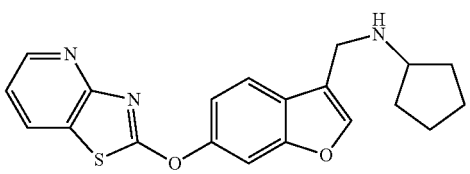 [SMILES: c1cnc2nc(Oc3ccc4c(CNC5CCCC5)coc4c3)sc2c1]

MS (ESI): mass calcd. for C$_{20}$H$_{19}$N$_3$O$_2$S, 365.12; m/z found, 366.0 [M+H]$^+$. $^1$H NMR (500 MHz, CDCl$_3$): 8.57 (dd, J=4.8, 1.7, 1H), 8.01 (dd, J=7.9, 1.7, 1H), 7.67 (d, J=8.5, 1H), 7.62 (d, J=0.9, 1H), 7.59 (d, J=2.0, 1H), 7.30 (dd, J=8.5, 2.1, 1H), 7.23-7.17 (m, 1H), 3.91 (d, J=1.0, 2H), 3.24-3.16 (m, 1H), 1.95-1.35 (m, 9H).

Example 299

Cyclohexyl-[6-(thiazolo[4,5-b]pyridin-2-yloxy)-benzofuran-3-ylmethyl]-amine

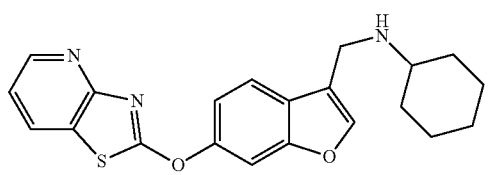 [SMILES: c1cnc2nc(Oc3ccc4c(CNC5CCCCC5)coc4c3)sc2c1]

MS (ESI): mass calcd. for C$_{21}$H$_{21}$N$_3$O$_2$S, 379.14; m/z found, 380.0 [M+H]$^+$. $^1$H NMR (400 MHz, CDCl$_3$): 8.56 (dd, J=4.8, 1.6, 1H), 8.01 (dd, J=7.9, 1.6, 1H), 7.66 (d, J=8.5, 1H), 7.62 (s, 1H), 7.59 (dd, J=7.4, 2.3, 1H), 7.32-7.26 (m, 1H), 7.23-7.17 (m, 1H), 3.96 (s, 2H), 2.63-2.49 (m, 1H), 2.02-1.90 (m, 2H), 1.83-1.71 (m, 2H), 1.69-1.57 (m, 1H), 1.37-1.08 (m, 6H).

Example 300

[6-(Thiazolo[4,5-b]pyridin-2-yloxy)-benzofuran-3-ylmethyl]-thiophen-2-ylmethyl-amine

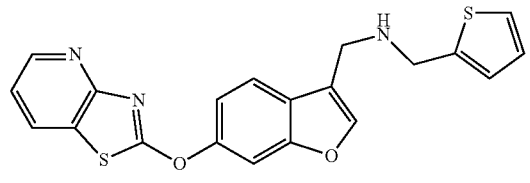 [SMILES: c1csc(CNCc2coc3cc(Oc4nc5ncccc5s4)ccc23)c1]

MS (ESI): mass calcd. for C$_{20}$H$_{15}$N$_3$O$_2$S$_2$, 393.06; m/z found, 393.9 [M+H]$^+$. $^1$H NMR (400 MHz, CDCl$_3$): 8.56 (dd, J=4.8, 1.7, 1H), 8.04-7.98 (m, 1H), 7.71 (d, J=8.5, 1H), 7.63 (d, J=7.2, 1H), 7.59 (d, J=2.1, 1H), 7.32-7.17 (m, 3H), 7.00-6.92 (m, 2H), 4.07 (s, 2H), 3.97 (s, 2H), 1.90 (br s, 1H).

Example 301 tert-Butyl-[6-(thiazolo[4,5-b]pyridin-2-yloxy)-benzofuran-3-ylmethyl]-amine formate

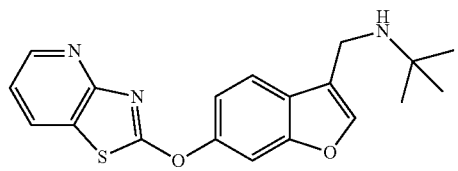 [SMILES: CC(C)(C)NCc1coc2cc(Oc3nc4ncccc4s3)ccc12]

MS (ESI): mass calcd. for C$_{19}$H$_{19}$N$_3$O$_2$S, 353.12; m/z found, 354.0 [M+H]$^+$. $^1$H NMR (400 MHz, CD$_3$OD): 8.46 (dd, J=4.9, 1.6, 1H), 8.30 (dd, J=8.0, 1.6, 1H), 8.12 (s, 1H), 7.88 (d, J=8.6, 1H), 7.75 (d, J=2.1, 1H), 7.41 (dd, J=8.6, 2.1, 1H), 7.37-7.30 (m, 1H), 4.41 (s, 2H), 1.54 (s, 9H).

Example 302

2-[3-(4-tert-Butyl-piperidin-1-ylmethyl)-benzofuran-6-yloxy]-thiazolo[4,5-b]pyridine formate

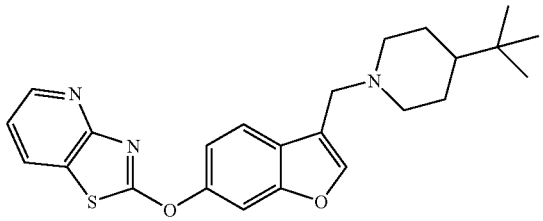 [SMILES: CC(C)(C)C1CCN(Cc2coc3cc(Oc4nc5ncccc5s4)ccc23)CC1]

This compound was prepared using methods analogous to those described for Example 153, with the following variation: DMF with K$_2$CO$_3$ at 35° C. for 15 hr before heating at 50° C. for 8 hr was used instead of 4:1 CH$_3$CN/DMF with K$_2$CO$_3$ at rt for 48 hr. MS (ESI): mass calcd. for $C_{24}H_{27}N_3O_2S$, 421.18; m/z found, 422.0 [M+H]$^+$. $^1$H NMR (400 MHz, CD$_3$OD): 8.51-8.46 (m, 1H), 8.33-8.28 (m, 1H), 7.95 (s, 1H), 7.86 (d, J=8.5, 1H), 7.71 (d, J=2.1, 1H), 7.41-7.30 (m, 2H), 4.01 (s, 2H), 3.35-3.25 (m, 2H), 2.51-2.38 (m, 2H), 1.87-1.76 (m, 2H), 1.52-1.37 (m, 2H), 1.22-1.11 (m, 1H), 0.88 (s, 9H).

Example 303

Propyl-[6-(thiazolo[4,5-b]pyridin-2-yloxy)-benzofuran-3-ylmethyl]-amine formate

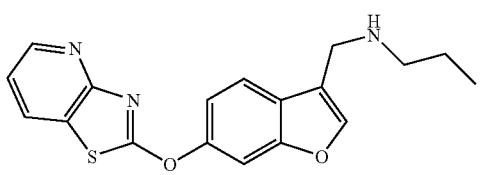 [SMILES: CCCNCc1coc2cc(Oc3nc4ncccc4s3)ccc12]

This compound was prepared using methods analogous to those described for Example 153, with the following variation: DMF with K$_2$CO$_3$ and 1.5 equivalents of the amine nucleophile at rt for 16 hr before adding another 1.5 equivalents of amine and stirring at rt for another 2 hr was used instead of 4:1 CH$_3$CN/DMF with K$_2$CO$_3$ and 1 equivalent of the amine nucleophile at rt for 48 hr. MS (ESI): mass calcd. for $C_{18}H_{17}N_3O_2S$, 339.10; m/z found, 340.0 [M+H]$^+$. $^1$H NMR (500 MHz, CD$_3$OD): 8.48 (dd, J=4.9, 1.6, 1H), 8.31 (dd, J=8.0, 1.6, 1H), 8.03 (s, 1H), 7.87 (d, J=8.5, 1H), 7.73 (d, J=2.0, 1H), 7.40 (dd, J=8.5, 2.1, 1H), 7.37-7.31 (m, 1H), 4.31 (s, 2H), 3.03-2.92 (m, 2H), 1.81-1.67 (m, 2H), 1.06-0.97 (m, 3H).

Example 304

Isobutyl-[6-(thiazolo[4,5-b]pyridin-2-yloxy)-benzofuran-3-ylmethyl]-amine formate

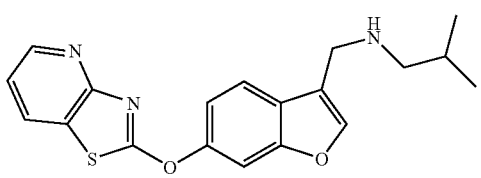 [SMILES: CC(C)CNCc1coc2cc(Oc3nc4ncccc4s3)ccc12]

This compound was prepared using methods analogous to those described for Example 153, with the following variation: DMF with K$_2$CO$_3$ and 1.5 equivalents of the amine nucleophile at rt for 16 hr before adding another 1.5 equivalents of amine and stirring at rt for another 2 hr was used instead of 4:1 CH$_3$CN/DMF with K$_2$CO$_3$ and 1 equivalent of the amine nucleophile at rt for 48 hr. MS (ESI): mass calcd. for $C_{19}H_{19}N_3O_2S$, 353.12; m/z found, 354.0 [M+H]$^+$. $^1$H NMR (400 MHz, CD$_3$OD): 8.48 (dd, J=4.9, 1.6, 1H), 8.34-8.29 (m, 1H), 8.07 (s, 1H), 7.88 (d, J=8.6, 1H), 7.74 (d, J=2.1, 1H), 7.40 (dd, J=8.6, 2.1, 1H), 7.37-7.32 (m, 1H), 4.34 (s, 2H), 2.89 (d, J=7.2, 2H), 2.11-1.96 (m, 1H), 1.02 (d, J=6.7, 6H).

Examples 305 to 316 were prepared using methods analogous to those described for Example 153, with the following variation: DMF with K$_2$CO$_3$ at rt for 16 hr was used instead of 4:1 CH$_3$CN/DMF with K$_2$CO$_3$ at rt for 48 hr.

Example 305

(2-Piperidin-1-yl-ethyl)-[6-(thiazolo[4,5-b]pyridin-2-yloxy)-benzofuran-3-ylmethyl]-amine

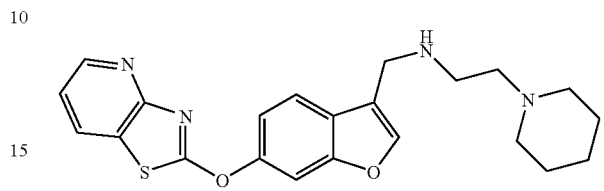

MS (ESI): mass calcd. for $C_{22}H_{24}N_4O_2S$, 408.16; m/z found, 409.1 [M+H]$^+$. $^1$H NMR (400 MHz, CDCl$_3$): 8.60-8.54 (m, 1H), 8.02 (dd, J=7.9, 1.6, 1H), 7.72-7.66 (m, 1H), 7.66-7.56 (m, 2H), 7.32-7.28 (m, 1H), 7.23-7.18 (m, 1H), 3.95 (app s, 2H), 2.84-2.73 (m, 2H), 2.55-2.26 (m, 6H), 1.64-1.36 (m, 6H).

Example 306

(2-Morpholin-4-yl-ethyl)-[6-(thiazolo[4,5-b]pyridin-2-yloxy)-benzofuran-3-ylmethyl]-amine formate

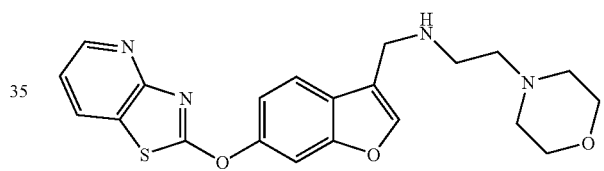

MS (ESI): mass calcd. for $C_{21}H_{22}N_4O_3S$, 410.14; m/z found, 411.0 [M+H]$^+$. $^1$H NMR (500 MHz, CD$_3$OD): 8.50-8.47 (m, 1H), 8.35-8.31 (m, 1H), 8.09 (s, 1H), 7.93-7.90 (m, 1H), 7.78 (d, J=1.9, 1H), 7.46-7.43 (m, 1H), 7.38-7.33 (m, 1H), 4.42 (s, 2H), 3.70-3.65 (m, 4H), 3.22-3.16 (m, 2H), 2.71-2.65 (m, 2H), 2.54-2.45 (m, 4H).

Example 307

N-{1-[6-(Thiazolo[4,5-b]pyridin-2-yloxy)-benzofuran-3-ylmethyl]-pyrrolidin-3-yl}-acetamide formate

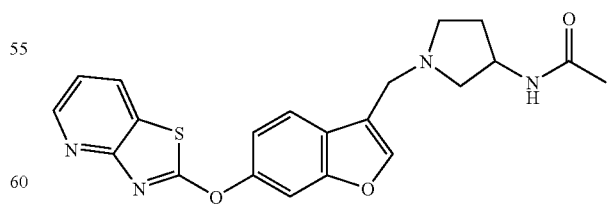

MS (ESI): mass calcd. for $C_{21}H_{20}N_4O_3S$, 408.1; m/z found, 408.9 [M+H]$^+$. $^1$H NMR (500 MHz, CD$_3$OD): 8.49 (dd, J=4.9, 1.6, 1H), 8.31 (dd, J=8.0, 1.6, 1H), 8.01 (s, 1H), 7.90 (d, J=8.5, 1H), 7.74 (d, J=2.0, 1H), 7.40 (dd, J=8.5, 2.1, 1H), 7.35 (dd, J=8.0, 4.9, 1H), 4.40-4.33 (m, 1H), 4.29-4.19

(m, 2H), 3.30-3.21 (m, 2H), 3.04 (dt, J=10.4, 7.7, 1H), 2.98 (dd, J=11.0, 4.7, 1H), 2.41-2.33 (m, 1H), 1.92 (5, 3H), 1.91-1.83 (m, 1H).

Example 308

2-[3-(4-Isobutyl-piperazin-1-ylmethyl)-benzofuran-6-yloxy]-thiazolo[4,5-b]pyridine formate

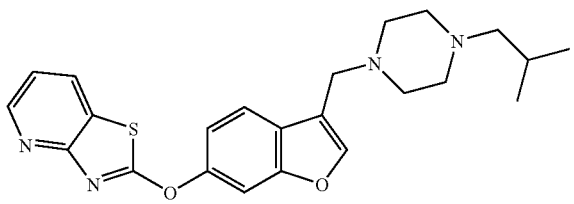 [SMILES: CC(C)CN1CCN(Cc2coc3cc(Oc4nc5ncccc5s4)ccc23)CC1]

MS (ESI): mass calcd. for C₂₃H₂₆N₄O₂S, 422.2; m/z found, 423.0 [M+H]⁺. ¹H NMR (400 MHz, CD₃OD): 8.48 (dd, J=4.9, 1.6, 1H), 8.30 (dd, J=8.0, 1.6, 1H), 7.89-7.83 (m, 2H), 7.67 (d, J=2.1, 1H), 7.36-7.31 (m, 2H), 3.79 (s, 2H), 2.95-2.78 (br s, 4H), 2.78-2.60 (br s, 4H), 2.48 (d, J=7.2, 2H), 2.00-1.89 (m, 1H), 0.96 (s, 3H), 0.95 (s, 3H).

Example 309

N-Methyl-N-{1-[6-(thiazolo[4,5-b]pyridin-2-yloxy)-benzofuran-3-ylmethyl]-pyrrolidin-3-yl}-acetamide

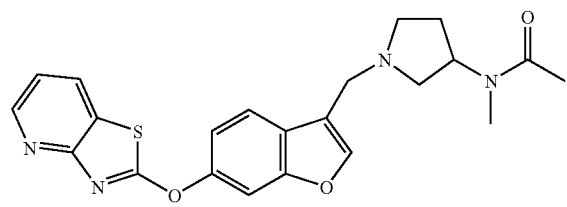 [SMILES: CC(=O)N(C)C1CCN(Cc2coc3cc(Oc4nc5ncccc5s4)ccc23)C1]

MS (ESI): mass calcd. for C₂₂H₂₂N₄O₃S, 422.1; m/z found, 423.0 [M+H]⁺. ¹H NMR (400 MHz, CD₃OD): 8.48 (dd, J=4.9, 1.6, 1H), 8.30 (dd, J=8.0, 1.6, 1H), 7.88-7.80 (m, 2H), 7.67-7.64 (m, 1H), 7.37-7.30 (m, 2H), 5.23-5.12 (m, 0.6H), 4.63-4.53 (m, 0.4H), 3.85-3.70 (m, 2H), 3.03 (s, 1.7H), 3.00-2.91 (m, 1H), 2.89 (s, 1.3H), 2.80-2.64 (m, 1.4H), 2.56 (dd, J=10.2, 8.4, 0.6H), 2.48-2.35 (m, 1H), 2.30-2.13 (m, 1H), 2.12 (s, 1.3H), 2.04 (d, J=4.6, 1.7H), 1.91-1.72 (m, 1H).

Example 310

(S)—N-{1-[6-(Thiazolo[4,5-b]pyridin-2-yloxy)-benzofuran-3-ylmethyl]-pyrrolidin-3-yl}-acetamide

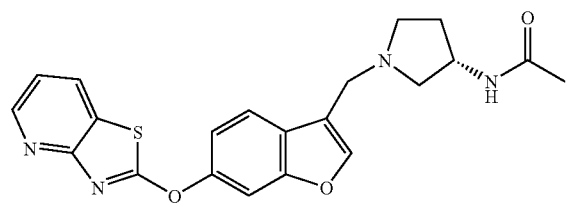 [SMILES: CC(=O)N[C@H]1CCN(Cc2coc3cc(Oc4nc5ncccc5s4)ccc23)C1]

MS (ESI): mass calcd. for C₂₁H₂₀N₄O₃S, 408.1; m/z found, 409.0 [M+H]⁺. ¹H NMR (400 MHz, CD₃OD): 8.48 (dd, J=4.9, 1.6, 1H), 8.30 (dd, J=8.0, 1.6, 1H), 7.86 (d, J=8.5, 1H), 7.83 (s, 1H), 7.66 (d, J=2.1, 1H), 7.36-7.31 (m, 2H), 4.35-4.28 (m, 1H), 3.87-3.78 (m, 2H), 2.91-2.77 (m, 2H), 2.62-2.55 (m, 1H), 2.52 (dd, J=9.8, 4.7, 1H), 2.30-2.20 (m, 1H), 1.90 (s, 3H), 1.72-1.63 (m, 1H).

Example 311

4-(2-{[6-(Benzothiazol-2-yloxy)-benzofuran-3-ylmethyl]-amino}-ethyl)-benzenesulfonamide

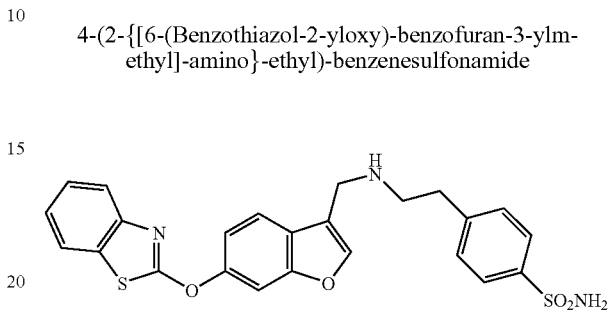

MS (ESI): mass calcd. for C₂₄H₂₁N₃O₄S₂, 479.10; m/z found, 480.1 [M+H]⁺. ¹H NMR (500 MHz, CDCl₃): 7.83 (d, J=8.4, 2H), 7.75 (dd, J=8.1, 0.5, 1H), 7.68 (dd, J=8.0, 0.7, 1H), 7.60-7.54 (m, 2H), 7.51 (d, J=2.0, 1H), 7.42-7.36 (m, 1H), 7.35 (d, J=8.3, 2H), 7.28 (dd, J=10.6, 3.8, 1H), 7.24 (dd, J=8.5, 2.1, 1H), 3.93 (s, 2H), 2.95 (br s, 4H), 1.49 (br s, 3H).

Example 312

(S)-{1-[6-(Benzothiazol-2-yloxy)-benzofuran-3-ylmethyl]-pyrrolidin-2-yl}-methanol

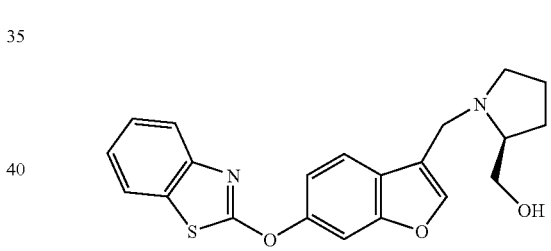

MS (ESI): mass calcd. for O₂₁H₂₀N₂O₃S, 380.12; m/z found, m/z 381.0 [M+H]⁺. ¹H NMR (400 MHz, CDCl₃): 8.50 (s, 1H), 7.83 (s, 1H), 7.74 (d, J=8.5, 2H), 7.70 (d, J=7.1, 1H), 7.61 (d, J=2.1, 1H), 7.43-7.38 (m, 1H), 7.34 (dd, J=8.5, 2.1, 1H), 7.33-7.27 (m, 1H), 4.46 (d, J=14.1, 1H), 4.16 (d, J=14.0, 1H), 3.85 (d, J=5.3, 2H), 3.45-3.29 (m, 2H), 2.85-2.74 (m, 1H), 2.09-1.77 (m, 4H).

Example 313

{1-[6-(Benzothiazol-2-yloxy)-benzofuran-3-ylmethyl]-piperidin-4-yl}-carbamic acid tert-butyl ester

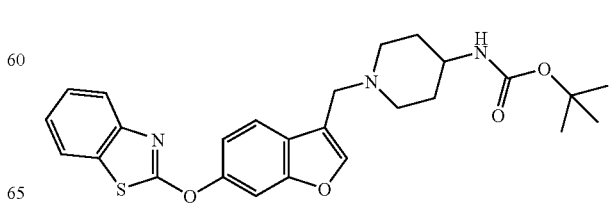

MS (ESI): mass calcd. for C$_{26}$H$_{29}$N$_3$O$_4$S, 479.19; m/z found, 480.0 [M+H]$^+$. $^1$H NMR (500 MHz, CDCl$_3$): 7.78-7.72 (m, 2H), 7.70-7.65 (m, 1H), 7.57 (s, 1H), 7.52 (d, J=2.1, 1H), 7.42-7.37 (m, 1H), 7.30-7.27 (m, 1H), 7.26-7.23 (m, 1H), 4.43 (s, 1H), 3.61 (s, 2H), 3.48 (s, 1H), 2.90-2.81 (m, 2H), 2.15 (t, J=10.8, 2H), 1.93 (d, J=10.3, 2H), 1.44 (s, 9H), 1.48-1.39 (m, 2H).

Example 314

2-[3-(3-Propoxy-azetidin-1-ylmethyl)-benzofuran-6-yloxy]-thiazolo[4,5-b]pyridine

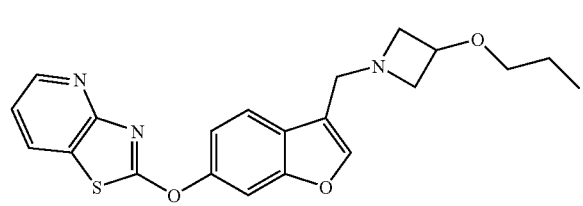 [SMILES: CCCOC1CN(Cc2coc3cc(Oc4nc5ncccc5s4)ccc23)C1]

MS (ESI): mass calcd. for C$_{21}$H$_{21}$N$_3$O$_3$S, 395.48; m/z found, 396.1 [M+H]$^+$. $^1$H NMR (400 MHz, CD$_3$OD): 8.53 (dd, J=4.9, 1.6, 1H), 8.08 (dd, J=8.0, 1.6, 1H), 7.74-7.69 (m, 2H), 7.61 (d, J=2.0, 1H), 7.36-7.30 (m, 1H), 7.26 (dd, J=8.0, 4.9, 1H), 4.20 (t, J=6.0, 1H), 3.93 (s, 2H), 3.88-3.81 (m, 2H), 3.36-3.30 (m, 2H), 3.20 (dd, J=9.0, 6.2, 2H), 1.58 (dd, J=14.2, 6.9, 2H), 0.92 (t, J=7.4, 3H).

Example 315

1-[6-(Thiazolo[4,5-b]pyridin-2-yloxy)-benzofuran-3-ylmethyl]-azetidin-3-ol

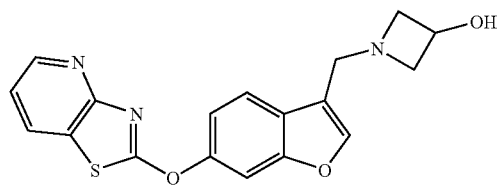 [SMILES: OC1CN(Cc2coc3cc(Oc4nc5ncccc5s4)ccc23)C1]

MS (ESI): mass calcd. for C$_{18}$H$_{15}$N$_3$O$_3$S, 353.40; m/z found, 354.1 [M+H]$^+$. $^1$H NMR (400 MHz, CD$_3$OD): 8.49 (dd, J=4.9, 1.6, 1H), 8.43 (s, 1H), 8.34-8.24 (m, 1H), 7.97-7.69 (m, 2H), 7.44-7.38 (m, 2H), 4.59-4.47 (m, 1H), 4.27 (s, 2H), 4.13-4.01 (m, 2H), 3.67-3.55 (m, 2H).

Example 316

2-[3-(3,3-Difluoro-azetidin-1-ylmethyl)-benzofuran-6-yloxy]-thiazolo[4,5-b]pyridine

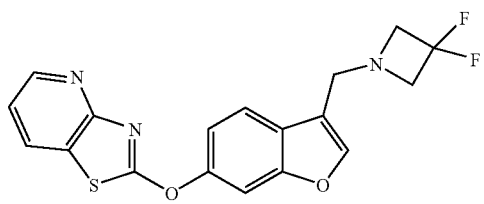 [SMILES: FC1(F)CN(Cc2coc3cc(Oc4nc5ncccc5s4)ccc23)C1]

MS (ESI): mass calcd. for C$_{18}$H$_{13}$F$_2$N$_3$O$_2$S, 373.38; m/z found, 374.1 [M+H]$^+$. $^1$H NMR (400 MHz, CD$_3$OD): 8.57-8.47 (m, 1H), 8.21 (d, J=7.5, 1H), 7.85-7.70 (m, 2H), 7.62 (s, 1H), 7.33 (d, J=8.4, 2H), 3.92 (s, 2H), 3.69 (t, J=12.0, 4H).

Example 317

N,N-Diethyl-N'-[6-(thiazolo[4,5-b]pyridin-2-yloxy)-benzofuran-3-ylmethyl]-ethane-1,2-diamine

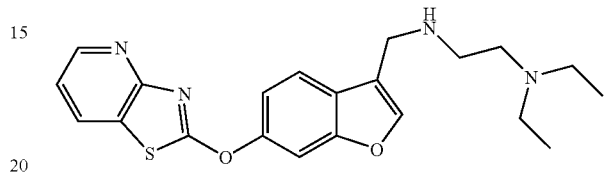

This compound was prepared using methods analogous to those described for Example 153, with the following variation: DMF with K$_2$CO$_3$ and 1.5 equivalents of amine nucleophile at rt for 16 hr before adding another 1.0 equivalent of amine and stirring at rt for 2 h was used instead of 4:1 CH$_3$CN/DMF with K$_2$CO$_3$ and 1 equivalent of the amine nucleophile at rt for 48 hr. MS (ESI): mass calcd. for C$_{21}$H$_{24}$N$_4$O$_2$S, 396.16; m/z found, 397.1 [M+H]$^+$. $^1$H NMR (500 MHz, CDCl$_3$): 8.59-8.56 (m, 1H), 8.01 (dd, J=7.9, 1.6, 1H), 7.68 (d, J=8.5, 1H), 7.63 (d, J=2.8, 1H), 7.59 (d, J=2.1, 1H), 7.29 (dd, J=8.5, 2.1, 1H), 7.24-7.17 (m, 1H), 3.95 (app s, 2H), 2.82-2.71 (m, 2H), 2.64-2.46 (m, 6H), 1.08-0.93 (m, 6H).

Example 318

Cyclohexyl-ethyl-[6-(thiazolo[4,5-b]pyridin-2-yloxy)-benzofuran-3-ylmethyl]-amine formate

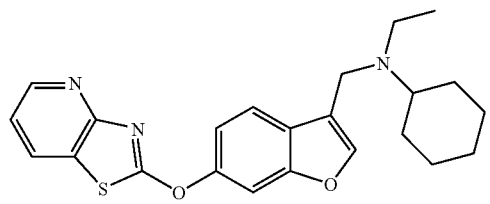 [SMILES: CCN(Cc1coc2cc(Oc3nc4ncccc4s3)ccc12)C1CCCCC1]

This compound was prepared using methods analogous to those described for Example 153, with the following variation: DMF with K$_2$CO$_3$ at 35° C. for 20.5 hr before stirring at 75° C. for 1.5 hr was used instead of 4:1 CH$_3$CN/DMF with K$_2$CO$_3$ at rt for 48 hr. MS (ESI): mass calcd. for C$_{23}$H$_{25}$N$_3$O$_2$S, 407.17; m/z found, 408.0 [M+H]$^+$. $^1$H NMR (500 MHz, CD$_3$OD): 8.48 (dd, J=4.9, 1.6, 1H), 8.30 (dd, J=8.0, 1.6, 1H), 7.97 (s, 1H), 7.87 (d, J=8.5, 1H), 7.71 (d, J=2.1, 1H), 7.40-7.31 (m, 2H), 4.18 (s, 2H), 3.05-2.90 (m, 3H), 2.07-1.97 (m, 2H), 1.94-1.84 (m, 2H), 1.75-1.63 (m, 1H), 1.61-1.45 (m, 2H), 1.41-1.14 (m, 6H).

Examples 319 to 321 were prepared using methods analogous to those described for Example 153, with the following variation: DMF with K$_2$CO$_3$ and 1.5 equivalents of the amine nucleophile at rt for 17 hr before stirring at 35° C. for 3 hr was used instead of 4:1 CH₃CN/DMF with K₂CO₃ and 1 equivalent of the amine nucleophile at rt for 48 hr.

Example 319

(2-Phenoxy-ethyl)-[6-(thiazolo[4,5-b]pyridin-2-yloxy)-benzofuran-3-ylmethyl]-amine formate

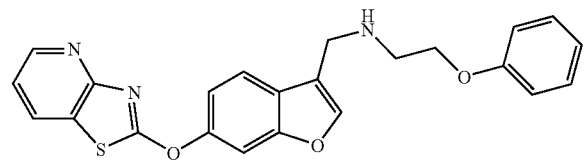 [SMILES: c1ccc(OCCNCc2coc3cc(Oc4nc5ncccc5s4)ccc23)cc1]

MS (ESI): mass calcd. for $C_{23}H_{19}N_3O_3S$, 417.11; m/z found, 417.9 [M+H]⁺. ¹H NMR (400 MHz, CD₃OD): 8.46 (dd, J=4.9, 1.6, 1H), 8.28 (dd, J=8.0, 1.6, 1H), 7.97 (s, 1H), 7.84 (d, J=8.5, 1H), 7.69 (d, J=2.0, 1H), 7.39-7.22 (m, 4H), 6.99-6.87 (m, 3H), 4.26 (s, 2H), 4.23-4.18 (m, 2H), 3.34-3.26 (m, 2H).

Example 320

Indan-2-yl-[6-(thiazolo[4,5-b]pyridin-2-yloxy)-benzofuran-3-ylmethyl]-amine formate

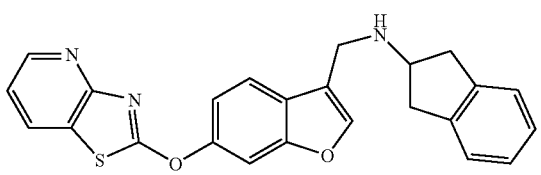 [SMILES: c1ccc2c(c1)CC(NCc1coc3cc(Oc4nc5ncccc5s4)ccc13)C2]

MS (ESI): mass calcd. for $C_{24}H_{19}N_3O_2S$, 413.12; m/z found, 414.0 [M+H]⁺. ¹H NMR (400 MHz, CDCl₃): 8.54 (dd, J=4.8, 1.7, 1H), 8.02 (dd, J=7.9, 1.6, 1H), 7.76-7.66 (m, 2H), 7.57 (d, J=2.1, 1H), 7.31-7.25 (m, 1H), 7.24-7.11 (m, 5H), 4.75 (br s, 1H), 4.03 (s, 2H), 3.83-3.74 (m, 1H), 3.28-3.16 (m, 2H), 3.03-2.91 (m, 2H).

Example 321

Phenethyl-[6-(thiazolo[4,5-b]pyridin-2-yloxy)-benzofuran-3-ylmethyl]-amine formate

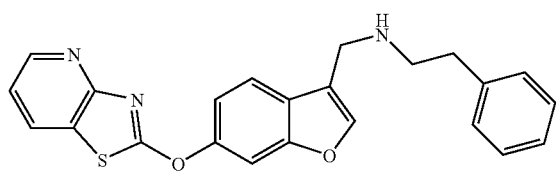 [SMILES: c1ccc(CCNCc2coc3cc(Oc4nc5ncccc5s4)ccc23)cc1]

MS (ESI): mass calcd. for $C_{23}H_{19}N_3O_2S$, 401.12; m/z found, 402.0 [M+H]⁺. ¹H NMR (400 MHz, CD₃OD): 8.47 (dd, J=4.9, 1.6, 1H), 8.30 (dd, J=8.0, 1.6, 1H), 7.90 (s, 1H), 7.76 (d, J=8.5, 1H), 7.69 (d, J=2.0, 1H), 7.38-7.17 (m, 7H), 4.12 (s, 2H), 3.12-3.02 (m, 2H), 2.96-2.87 (m, 2H).

Examples 322 to 331 were prepared using methods analogous to those described for Example 153, with the following variation: DMF with K₂CO₃ at 40° C. for 16 hr was used instead of 4:1 CH₃CN/DMF with K₂CO₃ at rt for 48 hr.

Example 322

N-Cyclopropyl-N-{1-[6-(thiazolo[4,5-b]pyridin-2-yloxy)-benzofuran-3-ylmethyl]-piperidin-4-yl}-acetamide

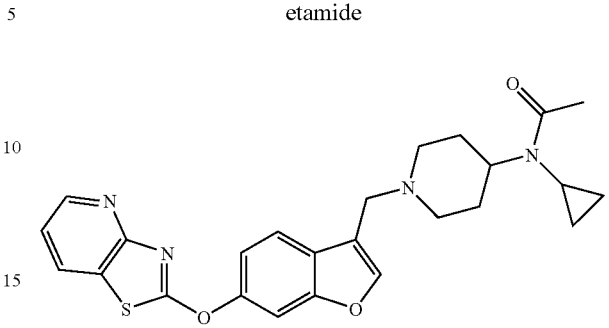

MS (ESI): mass calcd. for $C_{25}H_{26}N_4O_3S$, 462.17; m/z found, 463.1 [M+H]⁺. ¹H NMR (400 MHz, CD₃OD): 8.48 (dd, J=4.9, 1.6, 1H), 8.30 (dd, J=8.0, 1.6, 1H), 7.90-7.81 (m, 2H), 7.67 (d, J=2.0, 1H), 7.40-7.29 (m, 2H), 4.01-3.88 (m, 1H), 3.72 (s, 2H), 3.15-3.01 (m, 2H), 2.71-2.58 (m, 1H), 2.27-2.06 (m, 7H), 1.79-1.62 (m, 2H), 1.00-0.77 (m, 4H).

Example 323

N-Isopropyl-N-{1-[6-(thiazolo[4,5-b]pyridin-2-yloxy)-benzofuran-3-ylmethyl]-piperidin-4-yl}-acetamide

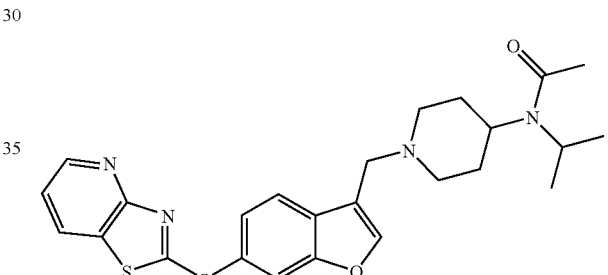

MS (ESI): mass calcd. for $C_{25}H_{28}N_4O_3S$, 464.19; m/z found, 465.0 [M+H]⁺. ¹H NMR (400 MHz, CD₃OD): 8.48 (d, J=4.3, 1H), 8.36-8.27 (m, 1H), 7.88 (dd, J=8.5, 3.8, 1H), 7.83 (d, J=5.0, 1H), 7.70-7.64 (m, 1H), 7.40-7.30 (m, 2H), 4.12-4.00 (m, 1H), 3.73 (d, J=11.9, 2H), 3.64-3.50 (m, 1H), 3.15-2.97 (m, 2H), 2.84-2.67 (m, 1H), 2.26-2.12 (m, 2H), 2.08 (d, J=4.0, 3H), 1.99-1.85 (m, 1H), 1.78-1.67 (m, 1H), 1.52-1.42 (m, 1H), 1.35 (d, J=6.8, 3H), 1.22 (d, J=6.7, 3H).

Example 324

(R)—N-{1-[6-(Thiazolo[4,5-b]pyridin-2-yloxy)-benzofuran-3-ylmethyl]-pyrrolidin-3-yl}-acetamide

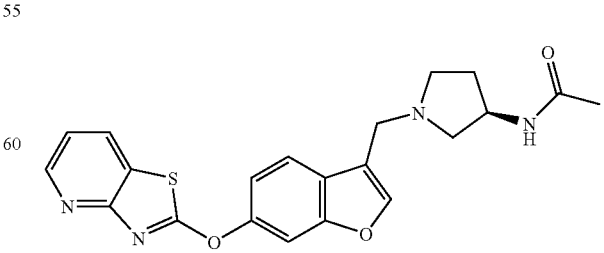

MS (ESI): mass calcd. for $C_{21}H_{20}N_4O_3S$, 408.1; m/z found, 409.1 [M+H]⁺. ¹H NMR (500 MHz, CD₃OD): 8.48

(dd, J=4.9, 1.6, 1H), 8.30 (dd, J=8.0, 1.6, 1H), 7.86 (d, J=8.5, 1H), 7.83 (s, 1H), 7.66 (d, J=2.0, 1H), 7.36-7.32 (m, 2H), 4.35-4.28 (m, 1H), 3.86-3.78 (m, 2H), 2.88 (dd, J=9.8, 7.1, 1H), 2.81 (td, J=8.6, 5.6, 1H), 2.61-2.56 (m, 1H), 2.52 (dd, J=9.8, 4.7, 1H), 2.29-2.22 (m, 1H), 1.90 (s, 3H), 1.71-1.64 (m, 1H).

Example 325

2-[3-(4-Thiophen-2-ylmethyl-piperazin-1-ylmethyl)-benzofuran-6-yloxy]-thiazolo[4,5-b]pyridine

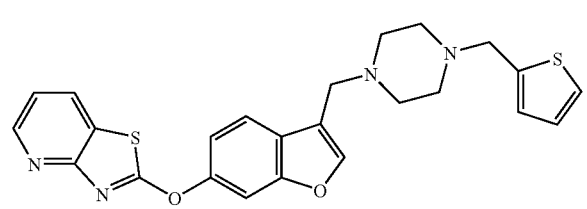 [SMILES: c1csc(CN2CCN(Cc3coc4cc(Oc5nc6ncccc6s5)ccc34)CC2)c1]

MS (ESI): mass calcd. for $C_{24}H_{22}N_4O_2S_2$, 462.1; m/z found, 462.9 [M+H]$^+$. $^1$H NMR (400 MHz, CD$_3$OD): 8.48 (dd, J=4.9, 1.6, 1H), 8.30 (dd, J=8.0, 1.6, 1H), 7.86 (d, J=8.5, 1H), 7.82 (s, 1H), 7.66 (d, J=2.1, 1H), 7.37-7.29 (m, 3H), 6.98-6.92 (m, 2H), 3.75 (s, 2H), 3.72 (d, J=0.6, 2H), 2.57 (br s, 8H).

Example 326

2-[3-(Hexahydro-pyrrolo[1,2-a]pyrazin-2-ylmethyl)-benzofuran-6-yloxy]-thiazolo[4,5-b]pyridine

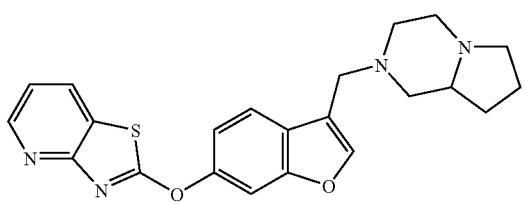 [SMILES: c1cnc2nc(Oc3ccc4c(CN5CCN6CCCC6C5)coc4c3)sc2c1]

MS (ESI): mass calcd. for $C_{22}H_{22}N_4O_2S$, 406.2; m/z found, 407.1 [M+H]$^+$. $^1$H NMR (400 MHz, CD$_3$OD): 8.48 (dd, J=4.9, 1.6, 1H), 8.30 (dd, J=8.0, 1.6, 1H), 7.87 (d, J=8.5, 1H), 7.83 (s, 1H), 7.66 (d, J=2.2, 1H), 7.36-7.31 (m, 2H), 3.83-3.71 (m, 2H), 3.09-3.00 (m, 3H), 2.95-2.90 (m, 1H), 2.39-2.27 (m, 2H), 2.24-2.13 (m, 2H), 1.99 (t, J=10.4, 1H), 1.87-1.72 (m, 3H), 1.45-1.33 (m, 1H).

Example 327

Diethyl-{1-[6-(thiazolo[4,5-b]pyridin-2-yloxy)-benzofuran-3-ylmethyl]-pyrrolidin-3-yl}-amine

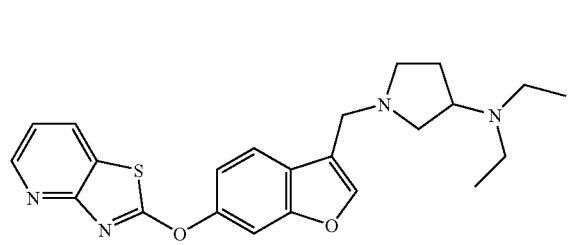 [SMILES: CCN(CC)C1CCN(Cc2coc3cc(Oc4nc5ncccc5s4)ccc23)C1]

MS (ESI): mass calcd. for $C_{23}H_{26}N_4O_2S$, 422.2; m/z found, 423.1 [M+H]$^+$. $^1$H NMR (400 MHz, CD$_3$OD): 8.48 (dd, J=4.9, 1.6, 1H), 8.30 (dd, J=8.0, 1.6, 1H), 7.86-7.82 (m, 2H), 7.66 (d, J=2.1, 1H), 7.37-7.31 (m, 2H), 3.84 (d, J=14.0, 1H), 3.76 (d, J=13.9, 1H), 3.46-3.37 (m, 1H), 2.88 (dd, J=9.3, 7.5, 1H), 2.79-2.56 (m, 6H), 2.51 (dd, J=9.4, 7.2, 1H), 2.10-1.98 (m, 1H), 1.83-1.73 m, 1H), 1.04 (t, J=7.2, 6H).

Example 328

(R)-2-[3-(3-Fluoro-pyrrolidin-1-ylmethyl)-benzofuran-6-yloxy]-thiazolo[4,5-b]pyridine

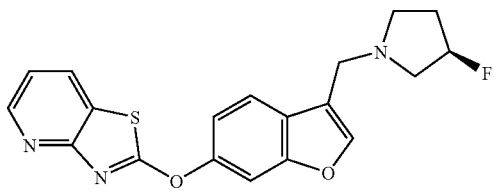 [SMILES: F[C@@H]1CCN(Cc2coc3cc(Oc4nc5ncccc5s4)ccc23)C1]

MS (ESI): mass calcd. for $C_{19}H_{16}FN_3O_2S$, 369.1; m/z found, 370.0 [M+H]$^+$. $^1$H NMR (400 MHz, CD$_3$OD): 8.48 (dd, J=4.9, 1.6, 1H), 8.29 (dd, J=8.0, 1.6, 1H), 7.89-7.81 (m, 2H), 7.66 (d, J=2.0, 1H), 7.37-7.30 (m, 2H), 5.28-5.21 (m, 0.5H), 5.11 (td, J=5.1, 1.6, 0.5H), 3.91-3.79 (m, 2H), 3.02-2.90 (m, 2H), 2.80 (dd, J=11.6, 5.0, 0.5H), 2.73 (dd, J=11.7, 5.0, 0.5H), 2.57-2.47 (m, 1H), 2.31-2.12 (m, 1H), 2.11-1.92 (m, 1H).

Example 329

Diethyl-[5-(thiazolo[4,5-b]pyridin-2-yloxy)-benzofuran-2-ylmethyl]-amine formate

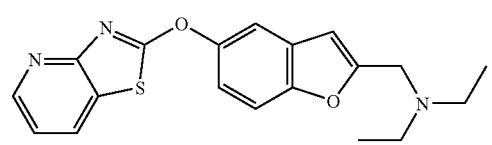 [SMILES: CCN(CC)Cc1cc2cc(Oc3nc4ncccc4s3)ccc2o1]

MS (ESI): mass calcd. for $C_{19}H_{19}N_3O_2S$, 353.1; m/z found, 354.0 [M+H]$^+$. $^1$H NMR (500 MHz, CD$_3$OD): 8.47 (dd, J=4.9, 1.6, 1H), 8.27 (dd, J=8.0, 1.6, 1H), 7.64 (d, J=2.4, 1H), 7.58 (d, J=8.8, 1H), 7.35-7.28 (m, 2H), 6.81 (s, 1H), 3.88 (s, 2H), 2.63 (q, J=7.2, 4H), 1.15 (t, J=7.2, 6H).

Example 330

2-[3-(5-Fluoro-1,3-dihydro-isoindol-2-ylmethyl)-benzofuran-6-yloxy]-thiazolo[4,5-b]pyridine

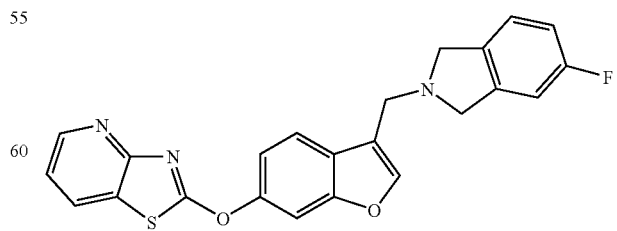

MS (ESI): mass calcd. for $C_{23}H_{16}FN_3O_2S$, 417.09; m/z found, 417.9 [M+H]$^+$. $^1$H NMR (400 MHz, CD$_3$OD): 8.50 (dd, J=4.9, 1.6, 1H), 8.36 (dd, J=8.0, 1.6, 1H), 8.25 (s, 1H), 7.99 (d, J=8.6, 1H), 7.85 (d, J=1.9, 1H), 7.50 (dd, J=8.6, 2.2, 1H), 7.46-7.36 (m, 2H), 7.24-7.13 (m, 2H), 4.83-4.75 (m, 4H).

Example 331

2-[3-(1,3-Dihydro-isoindol-2-ylmethyl)-benzofuran-6-yloxy]-thiazolo[4,5-b]pyridine

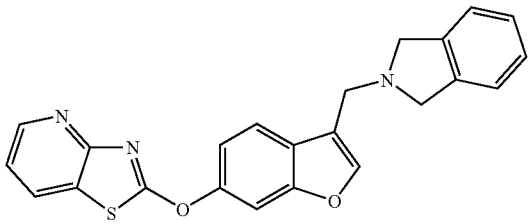 [SMILES: c1ccc2c(c1)CN(Cc1coc3cc(Oc4nc5ncccc5s4)ccc13)C2]

MS (ESI): mass calcd. for C$_{23}$H$_{17}$N$_3$O$_2$S, 399.10; m/z found, 399.9 [M+H]$^+$. $^1$H NMR (400 MHz, CD$_3$OD): 8.50 (dd, J=4.9, 1.6, 1H), 8.35 (dd, J=8.0, 1.6, 1H), 8.25 (s, 1H), 7.99 (d, J=8.6, 1H), 7.85 (d, J=2.0, 1H), 7.50 (dd, J=8.6, 2.1, 1H), 7.46-7.34 (m, 5H), 4.82 (s, 4H).

Example 332 meso-endo-1-(3-{[6-(Thiazolo[4,5-b]pyridin-2-yloxy)-benzofuran-3-ylmethyl]-amino}-8-aza-bicyclo[3.2.1]oct-8-yl)-ethanone formate.

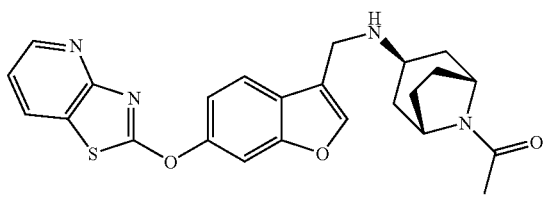 [SMILES: CC(=O)N1[C@@H]2CC[C@H]1C[C@@H](NCc1coc3cc(Oc4nc5ncccc5s4)ccc13)C2]

This compound was prepared using methods analogous to those described for Example 153, with the following variation: DMF with K$_2$CO$_3$ at 75° C. for 1 hr was used instead of 4:1 CH$_3$CN/DMF with K$_2$CO$_3$ at rt for 48 hr. MS (ESI): mass calcd. for C$_{24}$H$_{24}$N$_4$O$_3$S, 448.16; m/z found, 449.1 [M+H]$^+$. $^1$H NMR (400 MHz, CD$_3$OD): 8.48 (dd, J=4.9, 1.6, 1H), 8.33-8.28 (m, 1H), 7.92 (s, 1H), 7.84 (d, J=8.5, 1H), 7.71 (d, J=2.0, 1H), 7.40-7.32 (m, 2H), 4.65-4.58 (m, 1H), 4.33-4.27 (m, 1H), 4.15 (s, 2H), 3.18-3.07 (m, 1H), 2.41-2.27 (m, 2H), 2.18-2.01 (m, 6H), 2.01-1.89 (m, 1H), 1.87-1.67 (m, 2H).

Example 333 meso-exo-1-(3-{[6-(Thiazolo[4,5-b]pyridin-2-yloxy)-benzofuran-3-ylmethyl]-amino}-8-aza-bicyclo[3.2.1]oct-8-yl)-ethanone formate

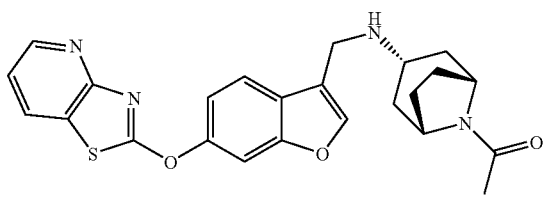 [SMILES: CC(=O)N1[C@@H]2CC[C@H]1C[C@H](NCc1coc3cc(Oc4nc5ncccc5s4)ccc13)C2]

This compound was prepared using methods analogous to those described for Example 153, with the following variation: DMF with K$_2$CO$_3$ at 75° C. for 2 hr before stirring at rt for 16 hr was used instead of 4:1 CH$_3$CN/DMF with K$_2$CO$_3$ at rt for 48 hr. MS (ESI): mass calcd. for C$_{24}$H$_{24}$N$_4$O$_3$S, 448.16; m/z found, 449.1 [M+H]$^+$. $^1$H NMR (400 MHz, CD$_3$OD): 8.49 (dd, J=4.9, 1.6, 1H), 8.32 (dd, J=8.0, 1.6, 1H), 8.06 (s, 1H), 7.88 (d, J=8.6, 1H), 7.77 (d, J=2.0, 1H), 7.48-7.41 (m, 1H), 7.39-7.32 (m, 1H), 4.76-4.68 (m, 1H), 4.49-4.40 (m, 1H), 4.35 (s, 2H), 3.83-3.71 (m, 1H), 2.34-1.66 (m, 11H).

Example 334

3-{Methyl-[6-(thiazolo[4,5-b]pyridin-2-yloxy)-benzofuran-3-ylmethyl]-amino}-propionic acid ethyl ester

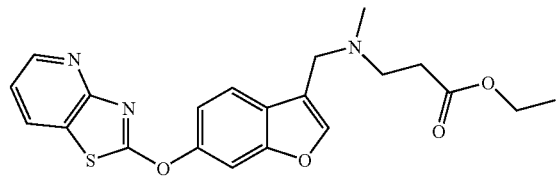 [SMILES: CCOC(=O)CCN(C)Cc1coc2cc(Oc3nc4ncccc4s3)ccc12]

This compound was prepared using methods analogous to those described for Example 153, with the following variation: DMF with K$_2$CO$_3$ at 75° C. for 7 hr was used instead of 4:1 CH$_3$CN/DMF with K$_2$CO$_3$ at rt for 48 hr. MS (ESI): mass calcd. for C$_{21}$H$_{21}$N$_3$O$_4$S, 411.13; m/z found, 411.9 [M+H]$^+$. $^1$H NMR (400 MHz, CDCl$_3$): 8.56 (dd, J=4.8, 1.7, 1H), 8.04-7.98 (m, 1H), 7.76-7.70 (m, 1H), 7.61-7.56 (m, 2H), 7.29-7.24 (m, 1H), 7.23-7.16 (m, 1H), 4.17-4.08 (m, 2H), 3.66 (s, 2H), 2.85-2.75 (m, 2H), 2.59-2.49 (m, 2H), 2.25 (s, 3H), 1.30-1.18 (m, 3H).

Example 335

3-{Methyl-[6-(thiazolo[4,5-b]pyridin-2-yloxy)-benzofuran-3-ylmethyl]-amino}-propionic acid formate

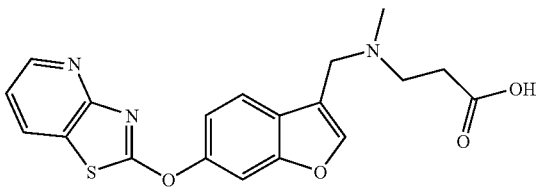 [SMILES: CN(CCC(=O)O)Cc1coc2cc(Oc3nc4ncccc4s3)ccc12]

To a solution of 3-{methyl-[6-(thiazolo[4,5-b]pyridin-2-yloxy)-benzofuran-3-ylmethyl]-amino}-propionic acid ethyl ester (30 mg, 0.07 mmol) in THF (0.75 mL) was added 4 N LiOH (0.1 mL). The mixture was stirred (rt, 6.5 h). Purification by reverse phase HPLC provided the title compound as a white solid (7 mg, 21%). MS (ESI): mass calcd. for C$_{19}$H$_{17}$N$_3$O$_4$S, 383.09; m/z found, 384.9 [M+H]$^+$. $^1$H NMR (400 MHz, CD$_3$OD): 8.49 (dd, J=4.9, 1.6, 1H), 8.32 (dd, J=8.0, 1.6, 1H), 8.15 (s, 1H), 7.97-7.92 (m, 1H), 7.80 (d, J=2.1, 1H), 7.44 (dd, J=8.6, 2.1, 1H), 7.38-7.32 (m, 1H), 4.48 (s, 2H), 3.35 (t, J=6.5, 2H), 2.80 (s, 3H), 2.66 (t, J=6.5, 2H).

Examples 336 to 337 were prepared using methods analogous to those described for Example 153, with the following variation: DMF with 6 equivalents of K$_2$CO$_3$ at 50° C. for 16 hr was used instead of 4:1 CH$_3$CN/DMF with 4 equivalents of K$_2$CO$_3$ at rt for 48 hr.

Example 336 meso-exo-N-{8-[6-(Thiazolo[4,5-b]pyridin-2-yloxy)-furo[3,2-b]pyridin-2-ylmethyl]-8-aza-bicyclo[3.2.1]oct-3-yl}-acetamide

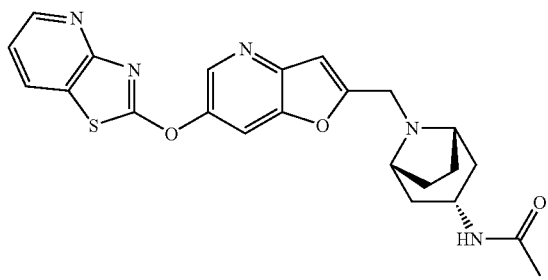 [SMILES: CC(=O)N[C@@H]1C[C@H]2CC[C@@H](C1)N2Cc1cc2ncc(Oc3nc4ncccc4s3)cc2o1]

MS (ESI): mass calcd. for C$_{23}$H$_{23}$N$_5$O$_3$S, 449.15; m/z found, 450.0 [M+H]$^+$. $^1$H NMR (600 MHz, CDCl$_3$): 8.62-8.55 (m, 2H), 8.07 (dd, J=8.0, 1.6, 1H), 8.02-7.99 (m, 1H), 7.28-7.22 (m, 1H), 6.87 (s, 1H), 5.27-5.22 (m, 1H), 4.23-4.13 (m, 1H), 3.72 (s, 2H), 3.39-3.32 (m, 2H), 2.11-2.04 (m, 2H), 1.95 (s, 3H), 1.91-1.84 (m, 2H), 1.84-1.77 (m, 2H), 1.61-1.52 (m, 2H).

Example 337

(1S,4S)-5-[6-(Thiazolo[4,5-b]pyridin-2-yloxy)-furo[3,2-b]pyridin-2-ylmethyl]-2,5-diaza-bicyclo[2.2.1]heptane-2-carboxylic acid amide formate

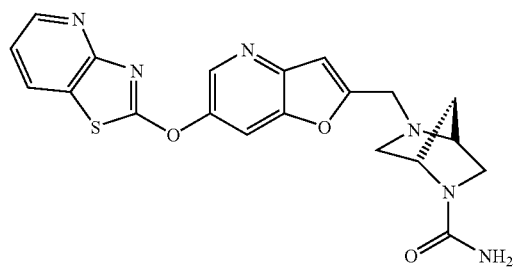

MS (ESI): mass calcd. for C$_{20}$H$_{15}$N$_6$O$_3$S, 422.12; m/z found, 423.0 [M+H]$^+$. $^1$H NMR (600 MHz, CD$_3$OD): 8.67-8.62 (m, 1H), 8.51-8.47 (m, 1H), 8.38-8.32 (m, 1H), 8.27-8.23 (m, 1H), 7.41-7.34 (m, 1H), 7.04-6.99 (m, 1H), 4.44 (br s, 1H), 4.13-4.04 (m, 2H), 3.80 (s, 1H), 3.64-3.56 (m, 1H), 3.37-3.27 (m, 3H), 3.10-3.03 (m, 1H), 2.97-2.90 (m, 1H), 2.02-1.96 (m, 1H), 1.89-1.82 (m, 1H).

Examples 338 to 341 were prepared using methods analogous to those described for Example 153, with the following variation: DMF with 6 equivalents of K$_2$CO$_3$ at 75° C. for 1-2 hr was used instead of 4:1 CH$_3$CN/DMF with 4 equivalents of K$_2$CO$_3$ at rt for 48 hr.

Example 338 meso-1-{8-[6-(Thiazolo[4,5-b]pyridin-2-yloxy)-furo[3,2-b]pyridin-2-ylmethyl]-3,8-diaza-bicyclo[3.2.1]oct-3-yl}-ethanone formate

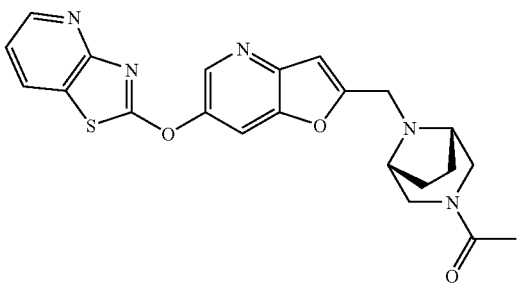 [SMILES: CC(=O)N1C[C@H]2CC[C@@H](C1)N2Cc1cc2ncc(Oc3nc4ncccc4s3)cc2o1]

MS (ESI): mass calcd. for C$_{22}$H$_{21}$N$_5$O$_3$S, 435.14; m/z found, 435.9 [M+H]$^+$. $^1$H NMR (400 MHz, CD$_3$OD): 8.66-8.62 (m, 1H), 8.49 (dd, J=4.9, 1.6, 1H), 8.36 (dd, J=8.0, 1.6, 1H), 8.24 (dd, J=2.3, 0.9, 1H), 7.41-7.33 (m, 1H), 7.07-7.00 (m, 1H), 4.19-4.11 (m, 1H), 3.84 (s, 2H), 3.67-3.59 (m, 1H), 3.47-3.39 (m, 3H), 2.99-2.87 (m, 1H), 2.21-1.98 (m, 5H), 1.82-1.56 (m, 2H).

Example 339

(1S,4S)-1-{5-[6-(Thiazolo[4,5-b]pyridin-2-yloxy)-furo[3,2-b]pyridin-2-ylmethyl]-2,5-diaza-bicyclo[2.2.2]oct-2-yl}-ethanone formate

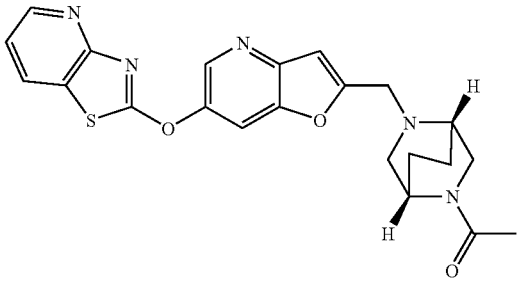 [SMILES: CC(=O)N1C[C@@H]2CC[C@H]1CN2Cc1cc2ncc(Oc3nc4ncccc4s3)cc2o1]

MS (ESI): mass calcd. for C$_{22}$H$_{21}$N$_5$O$_3$S, 435.14; m/z found, 435.9 [M+H]$^+$. $^1$H NMR (400 MHz, CD$_3$OD): 8.63 (d, J=2.3, 1H), 8.49 (dd, J=4.9, 1.6, 1H), 8.35 (dd, J=8.0, 1.6, 1H), 8.25-8.21 (m, 1H), 7.40-7.33 (m, 1H), 7.00 (5, 1H), 4.51-4.45 (m, 0.5H), 4.13-3.93 (m, 3H), 3.84-3.75 (m, 0.5H), 3.59-3.50 (m, 0.5H), 3.48-3.38 (m, 0.5H), 3.19-3.01 (m, 3H), 2.27-1.61 (m, 7H).

Example 340

(1R,4R)-1-{5-[6-(Thiazolo[4,5-b]pyridin-2-yloxy)-furo[3,2-b]pyridin-2-ylmethyl]-2,5-diaza-bicyclo[2.2.1]hept-2-yl}-ethanone formate

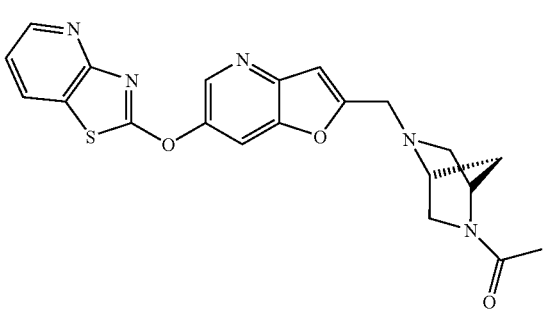

MS (ESI): mass calcd. for $C_{21}H_{19}N_5O_3S$, 421.12; m/z found, 422.0 [M+H]$^+$. $^1$H NMR (400 MHz, CD$_3$OD): 8.66-8.62 (m, 1H), 8.49 (dd, J=4.9, 1.6, 1H), 8.35 (dd, J=8.0, 1.6, 1H), 8.27-8.22 (m, 1H), 7.41-7.33 (m, 1H), 7.00 (s, 1H), 4.71 (app s, 0.5H), 4.51 (app s, 0.5H), 4.14-4.00 (m, 2H), 3.83-3.77 (m, 1H), 3.75-3.62 (m, 1H), 3.53-3.46 (m, 0.5H), 3.15-2.99 (m, 1H), 2.94-2.81 (m, 1H), 2.15-1.75 (m, 5H).

Example 341

1-{1-[6-(Thiazolo[4,5-b]pyridin-2-yloxy)-furo[3,2-b]pyridin-2-ylmethyl]-piperidin-4-yl}-pyrrolidin-2-one

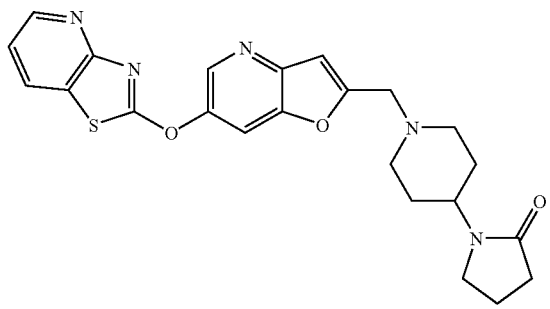 [SMILES: O=C1CCCN1C1CCN(Cc2cc3ncc(Oc4nc5ncccc5s4)cc3o2)CC1]

MS (ESI): mass calcd. for $C_{23}H_{23}N_5O_3S$, 449.15; m/z found, 450.0 [M+H]$^+$. $^1$H NMR (500 MHz, CDCl$_3$): 8.60 (d, J=2.3, 1H), 8.58 (dd, J=4.8, 1.7, 1H), 8.07 (dd, J=8.0, 1.7, 1H), 8.01-7.97 (m, 1H), 7.26-7.22 (m, 1H), 6.86 (d, J=0.6, 1H), 4.09-3.99 (m, 1H), 3.75 (5, 2H), 3.40-3.33 (m, 2H), 3.11-3.00 (m, 2H), 2.43-2.36 (m, 2H), 2.30-2.20 (m, 2H), 2.06-1.96 (m, 2H), 1.89-1.75 (m, 2H), 1.73-1.66 (m, 2H).

Example 342

4-[6-(Thiazolo[4,5-b]pyridin-2-yloxy)-benzofuran-3-ylmethyl]-piperazin-2-one

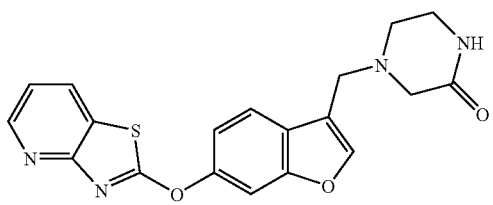 [SMILES: O=C1CN(Cc2coc3cc(Oc4nc5ncccc5s4)ccc23)CCN1]

This compound was prepared using methods analogous to those described for Example 153, with the following variation: DMF with K$_2$CO$_3$ and 2.0 equivalents of the amine nucleophile at rt for 16 hr was used instead of 4:1 CH$_3$CN/DMF with K$_2$CO$_3$ and 1 equivalent of the amine nucleophile at rt for 48 hr. MS (ESI): mass calcd. for $C_{19}H_{16}N_4O_3S$, 380.1; m/z found, 381.0 [M+H]$^+$. $^1$H NMR (400 MHz, CD$_3$OD): 8.48 (dd, J=4.9, 1.6, 1H), 8.30 (dd, J=8.0, 1.7, 1H), 7.90-7.85 (m, 2H), 7.68 (d, J=2.0, 1H), 7.36-7.32 (m, 2H), 3.81 (s, 2H), 3.34-3.31 (m, 2H), 3.17 (s, 2H), 2.76-2.71 (m, 2H).

Example 343

1-{4-[6-(Thiazolo[4,5-b]pyridin-2-yloxy)-furo[3,2-b]pyridin-2-ylmethyl]-piperazin-1-yl}-ethanone formate

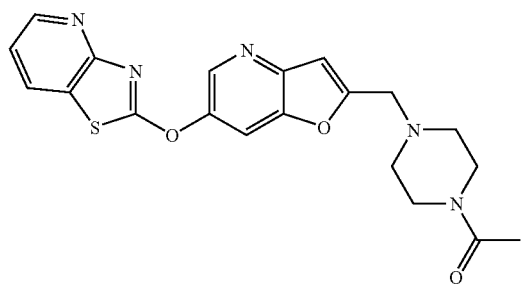 [SMILES: CC(=O)N1CCN(Cc2cc3ncc(Oc4nc5ncccc5s4)cc3o2)CC1]

This compound was prepared using methods analogous to those described for Example 322, utilizing 2.2 equivalents of amine nucleophile. MS (ESI): mass calcd. for $C_{20}H_{19}N_5O_3S$, 409.12; m/z found, 410.0 [M+H]$^+$. $^1$H NMR (600 MHz, CD$_3$OD): 8.63 (dd, J=6.2, 2.3, 1H), 8.49 (dd, J=4.9, 1.6, 1H), 8.38-8.32 (m, 1H), 8.24 (dd, J=2.3, 0.9, 1H), 7.40-7.34 (m, 1H), 7.00 (d, J=0.6, 1H), 3.88 (s, 2H), 3.67-3.55 (m, 4H), 2.69-2.55 (m, 4H), 2.11 (s, 3H).

Examples 344 to 348 were prepared using methods analogous to those described for Example 153, with the following variation: DMF with K$_2$CO$_3$ at 70° C. for 16 hr was used instead of 4:1 CH$_3$CN/DMF with K$_2$CO$_3$ at rt for 48 hr.

Example 344

Benzyl-[6-(thiazolo[4,5-b]pyridin-2-yloxy)-benzofuran-3-ylmethyl]-amine

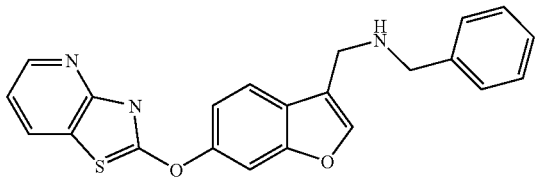

MS (ESI): mass calcd. for $C_{22}H_{17}N_3O_2S$, 387.46; m/z found, 388.0 [M+H]$^+$. $^1$H NMR (500 MHz, CDCl$_3$): 8.49 (dd, J=4.8, 1.6, 1H), 7.96 (dd, J=7.9, 1.5, 1H), 7.65 (s, 1H), 7.56 (d, J=8.4, 1H), 7.46 (d, J=1.7, 1H), 7.33 (d, J=7.5, 2H), 7.31-7.25 (m, 2H), 7.22 (t, J=7.2, 1H), 7.15 (dd, J=7.9, 4.8, 1H), 7.11 (d, J=8.3, 1H), 3.93 (s, 2H), 3.88 (s, 2H).

Example 345

(4-Fluoro-benzyl)-[6-(thiazolo[4,5-b]pyridin-2-yloxy)-benzofuran-3-ylmethyl]-amine

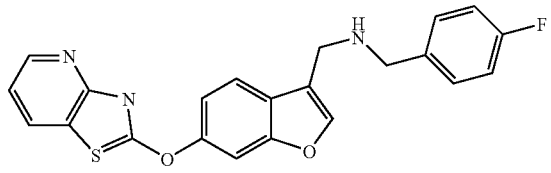

MS (ESI): mass calcd. for $C_{22}H_{16}FN_3O_2S$, 405.45; m/z found, 406.0 [M+H]$^+$. $^1$H NMR (500 MHz, CDCl$_3$): 8.49 (dd, J=4.8, 1.4, 1H), 7.96 (d, J=7.8, 1H), 7.62 (d, J=5.0, 1H), 7.56 (t, J=8.8, 1H), 7.48 (s, 1H), 7.33-7.24 (m, 2H), 7.14 (dd, J=7.7, 5.0, 2H), 7.00-6.92 (m, 2H), 3.90 (s, 2H), 3.82 (s, 2H).

Example 346

(4-Methoxy-benzyl)-[6-(thiazolo[4,5-b]pyridin-2-yloxy)-benzofuran-3-ylmethyl]-amine

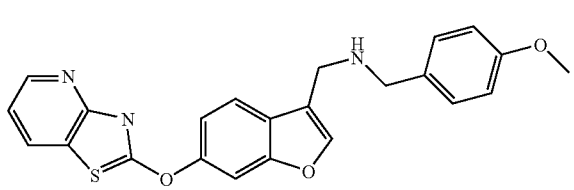

MS (ESI): mass calcd. for $C_{23}H_{19}N_3O_3S$, 417.49; m/z found, 418.0 [M+H]$^+$. $^1$H NMR (500 MHz, CDCl$_3$): 8.49 (dd, J=4.8, 1.6, 1H), 7.99-7.95 (m, 1H), 7.68 (s, 1H), 7.54 (dd, J=7.3, 3.3, 1H), 7.44 (d, J=2.0, 1H), 7.25 (dd, J=12.3, 5.4, 2H), 7.15 (ddd, J=10.0, 8.0, 4.9, 1H), 7.07 (d, J=8.1, 1H), 6.84-6.78 (m, 2H), 3.93 (s, 2H), 3.84 (s, 2H), 3.77-3.71 (m, 3H).

Example 347

4-(4-Chloro-phenyl)-1-[6-(thiazolo[4,5-b]pyridin-2-yloxy)-benzofuran-3-ylmethyl]-piperidin-4-ol

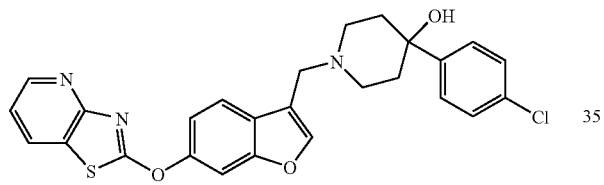

MS (ESI): mass calcd. for $C_{26}H_{22}ClN_3O_3S$, 491.99; m/z found, 492.0 [M+H]$^+$. $^1$H NMR (500 MHz, CDCl$_3$): 8.50-8.44 (m, 1H), 7.96 (dd, J=7.9, 1.5, 1H), 7.71 (d, J=8.5, 1H), 7.65 (d, J=13.9, 1H), 7.51 (d, J=2.0, 1H), 7.41-7.36 (m, 2H), 7.23 (dd, J=8.6, 2.2, 3H), 7.14 (dd, J=7.9, 4.8, 1H), 3.71 (s, 2H), 2.85 (s, 2H), 2.58 (s, 2H), 2.13 (s, 2H), 1.70 (d, J=13.6, 2H).

Example 348

4-(4-Bromo-phenyl)-1-[6-(thiazolo[4,5-b]pyridin-2-yloxy)-benzofuran-3-ylmethyl]-piperidin-4-ol

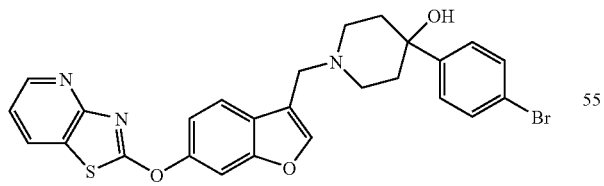

MS (ESI): mass calcd. for $C_{26}H_{22}BrN_3O_3S$, 535.1; m/z found, 535.8 [M+H]$^+$. $^1$H NMR (500 MHz, CDCl$_3$): 8.47 (dd, J=4.8, 1.6, 1H), 7.96 (dd, J=7.9, 1.6, 1H), 7.71 (d, J=8.5, 1H), 7.68-7.63 (m, 1H), 7.51 (d, J=2.1, 1H), 7.42-7.35 (m, 2H), 7.34-7.29 (m, 2H), 7.23 (dd, J=8.5, 2.1, 1H), 7.14 (dd, J=7.9, 4.8, 1H), 3.75 (s, 2H), 2.86 (s, 2H), 2.63 (s, 2H), 2.15 (s, 2H), 1.70 (d, J=13.0, 2H).

Examples 349 to 352 were prepared using methods analogous to those described for Example 153, with the following variation: DMF with Et$_3$N at 50° C. for 16 hr was used instead of 4:1 CH$_3$CN/DMF with K$_2$CO$_3$ at rt for 48 hr.

Example 349

2-[3-(2,6-Dimethyl-morpholin-4-ylmethyl)-benzofuran-6-yloxy]-thiazolo[4,5-b]pyridine

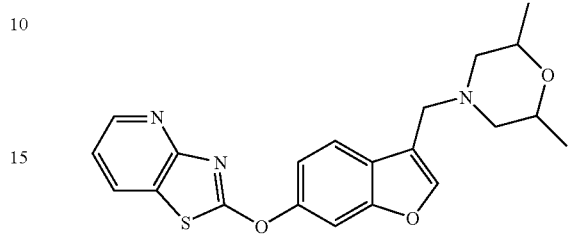

MS (ESI): mass calculated for $C_{21}H_{21}N_3O_3S$, 395.13; m/z found, 396.0 [M+H]$^+$. $^1$H NMR (600 MHz, CDCl$_3$): 8.58-8.56 (m, 1H), 8.02 (dd, J=7.9, 1.6, 1H), 7.81-7.76 (m, 1H), 7.60-7.56 (m, 2H), 7.29 (dd, J=8.4, 2.2, 1H), 7.21 (dd, J=7.9, 4.8, 1H), 4.07-4.01 (m, 0.4H), 3.74-3.66 (m, 1.6H), 3.61 (s, 1.6H), 3.56 (s, 0.4H), 2.77 (d, J=10.4, 1.6H), 2.52 (dd, J=10.9, 2.7, 0.4H), 2.23-2.16 (m, 0.4H), 1.79 (t, J=10.7, 1.6H), 1.24 (d, J=6.4, 1H), 1.16 (d, J=6.3, 5H).

Example 350

2-[3-(3-Fluoro-piperidin-1-ylmethyl)-benzofuran-6-yloxy]-thiazolo[4,5-b]pyridine

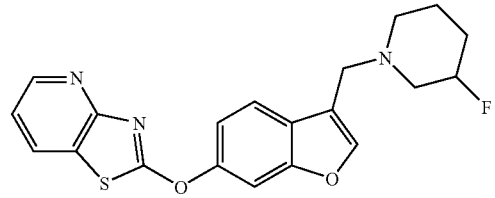 [SMILES: FC1CCCN(Cc2coc3cc(Oc4nc5ncccc5s4)ccc23)C1]

MS (ESI): mass calculated for $C_{20}H_{18}FN_3O_2S$, 383.11; m/z found, 384.0 [M+H]$^+$. $^1$H NMR (500 MHz, CDCl$_3$): 8.57 (dd, J=4.8, 1.6, 1H), 8.02 (dd, J=7.9, 1.6, 1H), 7.76 (d, J=8.5, 1H), 7.63-7.55 (m, 2H), 7.28 (dd, J=8.5, 2.1, 1H), 7.21 (dd, J=7.9, 4.8, 1H), 4.74-4.67 (m, 0.5H), 4.64-4.57 (m, 0.5H), 3.74-3.65 (m, 2H), 2.92-2.78 (m, 1H), 2.61-2.42 (m, 2H), 2.38-2.27 (m, 1H), 1.95-1.79 (m, 2H), 1.70-1.50 (m, 2H).

Example 351

4-{1-[6-(Thiazolo[4,5-b]pyridin-2-yloxy)-benzofuran-3-ylmethyl]-piperidin-4-yl}-2,4-dihydro-[1,2,4]triazol-3-one

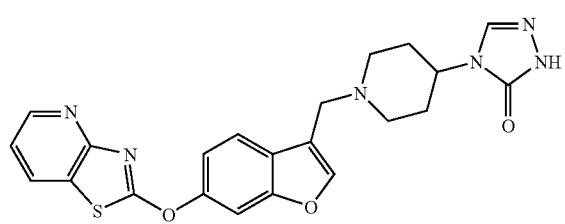 [SMILES: O=c1[nH]ncn1C1CCN(Cc2coc3cc(Oc4nc5ncccc5s4)ccc23)CC1]

MS (ESI): mass calculated for $C_{22}H_{20}N_6O_3S$, 448.13; m/z found, 449.0 [M+H]$^+$. $^1$H NMR (600 MHz, CDCl$_3$): 8.61 (s, 1H), 8.57 (dd, J=4.8, 1.6, 1H), 8.03 (dd, J=7.9, 1.6, 1H), 7.77 (d, J=8.4, 1H), 7.60 (s, 1H), 7.59 (d, J=2.0, 1H), 7.47-7.46 (m, 1H), 7.31 (dd, J=8.5, 2.0, 1H), 7.21 (dd, J=7.9, 4.8, 1H), 3.97-3.91 (m, 1H), 3.68 (s, 2H), 3.11-3.07 (m, 2H), 2.22-2.16 (m, 2H), 2.06-2.01 (m, 2H), 1.85-1.77 (m, 2H).

Example 352

1-{7-[6-(Thiazolo[4,5-b]pyridin-2-yloxy)-benzofuran-3-ylmethyl]-3,7-diaza-bicyclo[3.3.1]non-3-yl}-ethanone

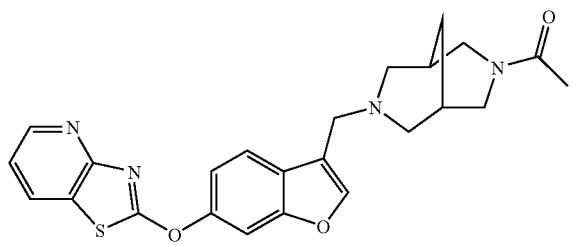 [SMILES: CC(=O)N1CC2CC(CN(Cc3coc4cc(Oc5nc6ncccc6s5)ccc34)C2)C1]

MS (ESI): mass calculated for C$_{24}$H$_{24}$N$_4$O$_3$S, 448.16; m/z found, 449.0 [M+H]$^+$. $^1$H NMR (500 MHz, CDCl$_3$): 8.56 (dd, J=4.8, 1.6, 1H), 8.01 (dd, J=7.9, 1.7, 1H), 7.66 (d, J=8.4, 1H), 7.60-7.55 (m, 2H), 7.28-7.26 (m, 1H), 7.20 (dd, J=7.9, 4.8, 1H), 4.60 (d, J=13.4, 1H), 3.68-3.58 (m, 2H), 3.32 (dd, J=3.8, 1.6, 0.5H), 3.31-3.27 (m, 1H), 3.26 (s, 0.5H), 3.16 (d, J=10.8, 1H), 2.97-2.89 (m, 2H), 2.37-2.32 (m, 1H), 2.21-2.16 (m, 1H), 2.00 (s, 1H), 1.94-1.87 (m, 4H), 1.78-1.70 (m, 1H), 1.70-1.65 (m, 1H).

Example 353

N-Ethyl-N-{1-[6-(thiazolo[4,5-b]pyridin-2-yloxy)-benzofuran-3-ylmethyl]-piperidin-4-yl}-acetamide

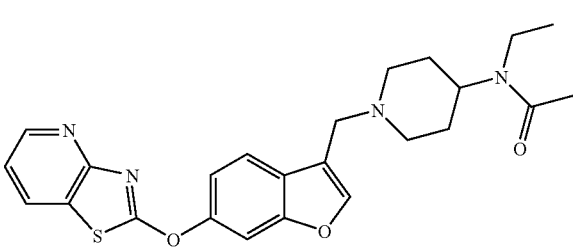 [SMILES: CCN(C(C)=O)C1CCN(Cc2coc3cc(Oc4nc5ncccc5s4)ccc23)CC1]

This compound was prepared using methods analogous to those described for Example 153, with the following variation: DMF with Et$_3$N at rt for 16 hr was used instead of 4:1 CH$_3$CN/DMF with K$_2$CO$_3$ at rt for 48 hr. MS (ESI): mass calculated for C$_{24}$H$_{26}$N$_4$O$_3$S, 450.17; m/z found, 451.0 [M+H]$^+$. $^1$H NMR (400 MHz, CD$_3$OD): 8.48 (dd, J=4.9, 1.6, 1H), 8.32-8.28 (m, 1H), 7.87 (d, J=8.5, 1H), 7.83 (s, 1H), 7.68-7.65 (m, 1H), 7.38-7.31 (m, 2H), 4.31-4.20 (m, 0.5H), 3.73 (d, J=11.0, 2H), 3.70-3.61 (m, 0.5H), 3.39-3.33 (m, 2H), 3.14-3.05 (m, 2H), 2.19 (q, J=11.8, 2H), 2.11 (d, J=3.6, 3H), 1.96-1.78 (m, 2H), 1.78-1.69 (m, 1H), 1.69-1.61 (m, 1H), 1.20 (t, J=7.1, 1.5H), 1.10 (t, J=7.0, 1.5H).

Example 354

(Tetrahydro-furan-3-yl)-{5-[6-(thiazolo[4,5-b]pyridin-2-yloxy)-benzofuran-3-ylmethyl]-hexahydro-pyrrolo[3,4-c]pyrrol-2-yl}-methanone

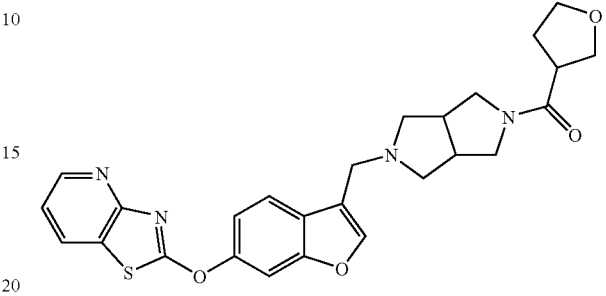

A solution of 2-[3-(hexahydro-pyrrolo[3,4-c]pyrrol-2-ylmethyl)-benzofuran-6-yloxy]-thiazolo[4,5-b]pyridine dihydrochloride (50 mg, 0.11 mmol), N-(3-dimethylaminopropyl)-N'-ethylcarbdiimide hydrochloride (21 mg, 0.11 mmol), 1-hydroxybenzotriazole (73 mg, 0.54 mmol), N-methylmorpholine (33 mg, 0.32 mmol), and tetrahydro-furan-3-carboxylic acid (13 mg, 0.11 mmol) in DMF (0.4 mL) was stirred at rt. Upon reaction completion, the mixture was concentrated, re-dissolved in DMF and purified using reverse phase HPLC to provide the title compound (24 mg, 45%). MS (ESI): mass calculated for C$_{26}$H$_{26}$N$_4$O$_4$S, 490.17; m/z found, 491.0 [M+H]$^+$. $^1$H NMR (400 MHz, CDCl$_3$): 8.56 (dd, J=4.8, 1.6, 1H), 8.03 (dd, J=8.0, 1.5, 1H), 7.70 (dd, J=8.5, 2.9, 1H), 7.59 (dd, J=5.6, 3.4, 2H), 7.27-7.18 (m, 2H), 4.08-3.95 (m, 1H), 3.94-3.60 (m, 7H), 3.53-3.42 (m, 1H), 3.40-3.26 (m, 1H), 3.17-3.06 (m, 1H), 2.99-2.77 (m, 2H), 2.71-2.46 (m, 4H), 2.29-2.14 (m, 1H), 2.14-1.99 (m, 1H).

Example 355

2-Hydroxy-1-{5-[6-(thiazolo[4,5-b]pyridin-2-yloxy)-benzofuran-3-ylmethyl]-hexahydro-pyrrolo[3,4-c]pyrrol-2-yl}-ethanone

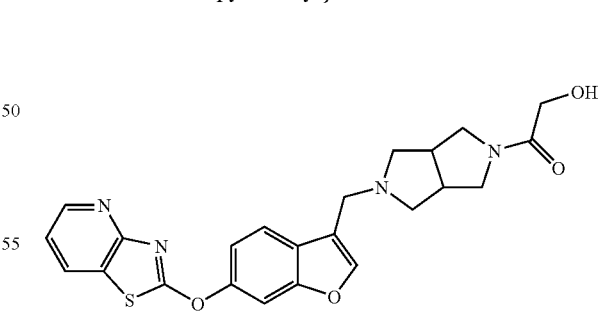

This compound was prepared using methods analogous to those described for Example 354. MS (ESI): mass calculated for C$_{23}$H$_{22}$N$_4$O$_4$S, 450.14; m/z found, 451.0 [M+H]$^+$. $^1$H NMR (400 MHz, CDCl$_3$): 8.56 (dd, J=4.8, 1.6, 1H), 8.03 (dd, J=7.9, 1.6, 1H), 7.69 (d, J=8.5, 1H), 7.62-7.54 (m, 2H), 7.33-7.25 (m, 1H), 7.21 (dd, J=7.9, 4.8, 1H), 4.13-4.00 (m, 2H), 3.86-3.73 (m, 2H), 3.71-3.44 (m, 4H), 3.20-3.09 (m, 1H), 3.00-2.79 (m, 2H), 2.71-2.58 (m, 2H), 2.58-2.51 (m, 2H).

Examples 356 to 359 were prepared using methods analogous to those described for Example 236, substituting Et$_3$N for DIEA.

Example 356

(1S,4S)-Pyrazin-2-yl-{5-[6-(thiazolo[4,5-b]pyridin-2-yloxy)-benzofuran-3-ylmethyl]-2,5-diaza-bicyclo[2.2.1]hept-2-yl}-methanone

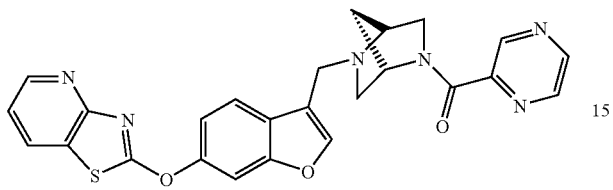

MS (ESI): mass calculated for C$_{25}$H$_{20}$N$_6$O$_3$S, 484.13; m/z found, 485.0 [M+H]$^+$. $^1$H NMR (400 MHz, CD$_3$OD): 9.09-9.00 (m, 1H), 8.73-8.68 (m, 1H), 8.68-8.63 (m, 1H), 8.50-8.45 (m, 1H), 8.34-8.25 (m, 1H), 7.93-7.80 (m, 2H), 7.70-7.63 (m, 1H), 7.39-7.27 (m, 2H), 4.99-4.91 (m, 1H), 4.08-3.88 (m, 2H), 3.87-3.66 (m, 2H), 3.61-3.52 (m, 1H), 3.07-2.90 (m, 2H), 2.12-1.98 (m, 1H), 1.92-1.80 (m, 1H).

Example 357

(1S,4S)-Cyclobutyl-{5-[6-(thiazolo[4,5-b]pyridin-2-yloxy)-benzofuran-3-ylmethyl]-2,5-diaza-bicyclo[2.2.1]hept-2-yl}-methanone

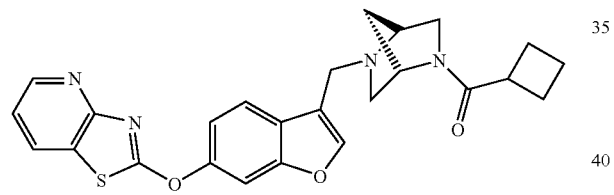

MS (ESI): mass calculated for C$_{25}$H$_{24}$N$_4$O$_3$S, 460.16; m/z found, 461.2 [M+H]$^+$. $^1$H NMR (400 MHz, CDCl$_3$): 8.59-8.53 (m, 1H), 8.05-7.99 (m, 1H), 7.77-7.71 (m, 1H), 7.60-7.55 (m, 2H), 7.32-7.27 (m, 1H), 7.24-7.18 (m, 1H), 4.77 (s, 0.5H), 4.17 (s, 0.5H), 3.89-3.75 (m, 2H), 3.74-3.63 (m, 1H), 3.62-3.53 (m, 1H), 3.51-3.44 (m, 1H), 3.33-3.08 (m, 2H), 3.02-2.96 (m, 0.5H), 2.91-2.83 (m, 0.5H), 2.83-2.75 (m, 0.5H), 2.56-2.48 (m, 0.5H), 2.46-2.26 (m, 2H), 2.24-2.04 (m, 2H), 2.04-1.80 (m, 3H).

Example 358

(1S,4S)-Isoxazol-5-yl-{5-[6-(thiazolo[4,5-b]pyridin-2-yloxy)-benzofuran-3-ylmethyl]-2,5-diaza-bicyclo[2.2.1]hept-2-yl}-methanone

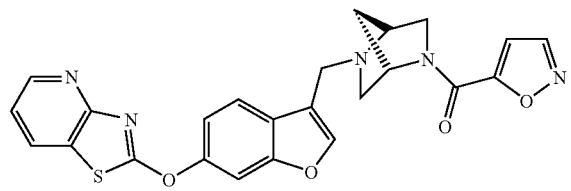

MS (ESI): mass calculated for C$_{24}$H$_{19}$N$_5$O$_4$S, 473.12; m/z found, 474.0 [M+H]$^+$. $^1$H NMR (500 MHz, CD$_3$OD): 8.52 (d, J=1.9, 1H), 8.50-8.46 (m, 1H), 8.32-8.26 (m, 1H), 7.92-7.80 (m, 2H), 7.68-7.63 (m, 1H), 7.37-7.29 (m, 2H), 6.98 (d, J=1.9, 0.5H), 6.94 (d, J=1.9, 0.5H), 5.02-4.88 (m, 1H), 4.07-3.87 (m, 3H), 3.87-3.71 (m, 2H), 3.12-3.05 (m, 0.5H), 3.03-2.96 (m, 0.5H), 2.95-2.84 (m, 1H), 2.16-2.03 (m, 1H), 1.94-1.82 (m, 1H).

Example 359

Furan-3-yl-{5-[6-(thiazolo[4,5-b]pyridin-2-yloxy)-benzofuran-3-ylmethyl]-hexahydro-pyrrolo[3,4-c]pyrrol-2-yl}-methanone

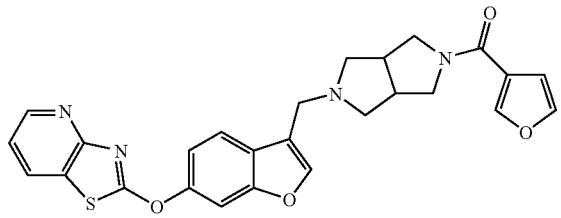 [SMILES: O=C(c1ccoc1)N1CC2CN(Cc3coc4cc(Oc5nc6ncccc6s5)ccc34)CC2C1]

MS (ESI): mass calculated for C$_{26}$H$_{22}$N$_4$O$_4$S, 486.14; m/z found, 486.9 [M+H]$^+$. $^1$H NMR (400 MHz, CDCl$_3$): 8.57 (dd, J=4.8, 1.5, 1H), 8.03 (dd, J=7.9, 1.5, 1H), 7.79-7.68 (m, 2H), 7.63-7.55 (m, 2H), 7.43-7.38 (m, 1H), 7.25-7.15 (m, 2H), 6.70 (s, 1H), 4.06-3.58 (m, 4H), 3.49 (s, 2H), 3.01-2.84 (m, 2H), 2.78-2.44 (m, 4H).

Example 360

(1S,4S)-4-{5-[6-(Thiazolo[4,5-b]pyridin-2-yloxy)-benzofuran-3-ylmethyl]-2,5-diaza-bicyclo[2.2.1]hept-2-ylmethyl}-benzoic acid methyl ester

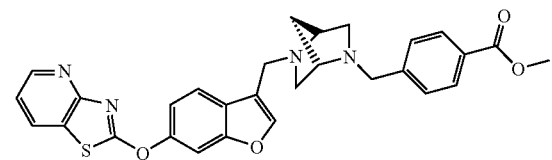

A mixture of (1S,4S)-2-[3-(2,5-diaza-bicyclo[2.2.1]hept-2-ylmethyl)-benzofuran-6-yloxy]-thiazolo[4,5-b]pyridine dihydrochloride (50 mg, 0.11 mmol), 4-bromomethyl-benzoic acid methyl ester (28 mg, 0.12 mmol), and K$_2$CO$_3$ (38 mg, 0.28 mmol) in CH$_3$CN (0.4 mL) was stirred at rt. Upon reaction completion, the mixture was concentrated, re-dissolved in DMF and purified by reverse phase HPLC to provide the title compound (10 mg, 16%). MS (ESI): mass calculated for C$_{29}$H$_{26}$N$_4$O$_4$S, 526.17; m/z found, 527.0 [M+H]$^+$. $^1$H NMR (400 MHz, CDCl$_3$): 8.57 (dd, J=4.8, 1.6, 1H), 8.05-7.96 (m, 3H), 7.77 (d, J=8.5, 1H), 7.58 (dd, J=7.8, 4.3, 2H), 7.45 (d, J=8.3, 2H), 7.32-7.28 (m, 1H), 7.21 (dd, J=7.9, 4.8, 1H), 3.91 (s, 3H), 3.90-3.69 (m, 2H), 3.41-3.27 (m, 2H), 2.96-2.90 (m, 1H), 2.85-2.81 (m, 1H), 2.74-2.66 (m, 2H), 1.77 (s, 2H), 1.47 (s, 2H).

Example 361

Dimethyl-[6-(thiazolo[4,5-b]pyridin-2-yloxy)-benzofuran-3-ylmethyl]-amine

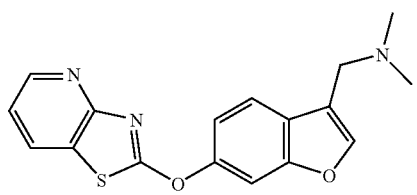 [SMILES: CN(C)Cc1coc2cc(Oc3nc4ncccc4s3)ccc12]

To a solution of C-[6-(thiazolo[4,5-b]pyridin-2-yloxy)-benzofuran-3-yl]-methylamine hydrochloride (67 mg, 0.20 mmol) in methanol (1.7 mL) was added formaldehyde (20 μL, 0.34 mmol) and sodium triacetoxyborohydride (143 mg, 0.67 mmol). Monitoring by LCMS showed the reaction to be incomplete. More formaldehyde (20 μL) was added to enable reaction completion. The mixture was washed with sat'd. aq. NaHCO$_3$, extracted with DCM, dried, and concentrated. Purification by reverse phase HPLC provided the title compound as a slightly yellow oil (29 mg, 43%). MS (ESI): mass calcd. for C$_{17}$H$_{15}$N$_3$O$_2$S, 325.09; m/z found, 326.0 [M+H]$^+$. $^1$H NMR (400 MHz, CDCl$_3$): 8.57 (dd, J=4.8, 1.6, 1H), 8.01 (dd, J=7.9, 1.6, 1H), 7.73 (d, J=8.5, 1H), 7.63-7.57 (m, 2H), 7.29 (dd, J=8.5, 2.2, 1H), 7.21 (dd, J=7.9, 4.9, 1H), 3.56 (s, 2H), 2.30 (s, 6H).

Example 362

(2-{1-[6-(Benzothiazol-2-yloxy)-benzofuran-3-ylmethyl]-piperidin-4-yl}-ethyl)-carbamic acid tert-butyl ester

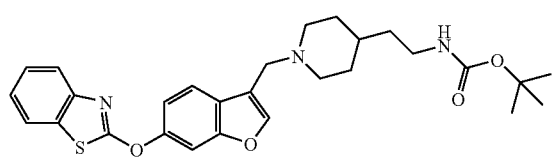 [SMILES: CC(C)(C)OC(=O)NCCC1CCN(Cc2coc3cc(Oc4nc5ccccc5s4)ccc23)CC1]

This compound was prepared using methods analogous to those described for Example 153, with the following variation: DMF with K$_2$CO$_3$ at rt for 16 hr was used instead of 4:1 CH$_3$CN/DMF with K$_2$CO$_3$ at rt for 48 hr. MS (ESI): mass calcd. for C$_{28}$H$_{33}$N$_3$O$_4$S, 507.22; m/z found, 508.0 [M+H]$^+$. $^1$H NMR (500 MHz, CDCl$_3$): 7.80-7.71 (m, 2H), 7.67 (d, J=8.0, 1H), 7.57 (s, 1H), 7.52 (d, J=1.9, 1H), 7.39 (t, J=7.7, 1H), 7.31-7.21 (m, 2H), 3.62 (s, 2H), 3.15 (d, J=5.9, 2H), 2.97-2.89 (m, 2H), 1.99 (t, J=10.4, 2H), 1.68 (d, J=10.0, 2H), 1.44 (s, 9H), 1.47-1.37 (m, 2H), 1.34-1.21 (m, 4H).

Example 363

N-{1-[6-(Benzothiazol-2-yloxy)-benzofuran-3-ylmethyl]-piperidin-4-yl}-methanesulfonamide

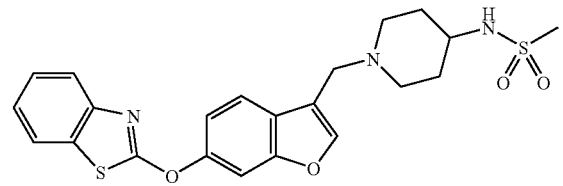 [SMILES: CS(=O)(=O)NC1CCN(Cc2coc3cc(Oc4nc5ccccc5s4)ccc23)CC1]

To a solution of {1-[6-(benzothiazol-2-yloxy)-benzofuran-3-ylmethyl]-piperidin-4-yl}-carbamic acid tert-butyl ester (110 mg, 0.23 mmol) in DCM (1.1 mL) was added 2 M HCl in diethyl ether (0.34 mL). The reaction mixture was stirred (rt, 16 h) and then heated to 40° C. (24 h). Additional HCl (1 mL) was added, and the mixture was heated (40° C., 4 h). After concentration, the residue was re-dissolved in DCM (1.5 mL). To this solution was added Et$_3$N (0.16 mL, 0.92 mmol) and methanesulfonic anhydride (44 mg, 0.25 mmol). The mixture was stirred (rt, 16 h). Additional methanesulfonic anhydride was added, and the reaction mixture was stirred (rt, 30 min). After concentration, the crude material was purified by reverse phase HPLC to provide the title compound as a white solid (22 mg, 21%). MS (ESI): mass calcd. for C$_{22}$H$_{23}$N$_3$O$_4$S$_2$, 457.11; m/z found, 458.0 [M+H]$^+$. $^1$H NMR (400 MHz, CDCl$_3$): 7.77-7.72 (m, 2H), 7.68 (dd, J=7.9, 0.7, 1H), 7.57 (s, 1H), 7.53 (d, J=2.1, 1H), 7.42-7.36 (m, 1H), 7.32-7.22 (m, 2H), 4.31 (d, J=7.6, 1H), 3.63 (s, 2H), 3.43-3.30 (m, 1H), 2.98 (s, 3H), 2.89 (d, J=11.5, 2H), 2.23-2.12 (m, 2H), 2.00 (d, J=11.2, 2H), 1.68-1.52 (m, 2H).

Example 364

N-(2-{1-[6-(Benzothiazol-2-yloxy)-benzofuran-3-ylmethyl]-piperidin-4-yl}-ethyl)-methanesulfonamide

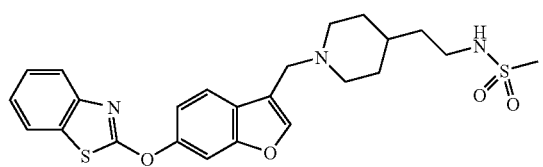 [SMILES: CS(=O)(=O)NCCC1CCN(Cc2coc3cc(Oc4nc5ccccc5s4)ccc23)CC1]

This compound was prepared using methods analogous to those described for Example 363. MS (ESI): mass calcd. for C$_{24}$H$_{27}$N$_3$O$_4$S$_2$, 485.14; m/z found, 486.0 [M+H]$^+$. $^1$H NMR (400 MHz, CDCl$_3$): 7.78-7.70 (m, 2H), 7.67 (dd, J=8.0, 0.7, 1H), 7.58 (s, 1H), 7.52 (d, J=2.1, 1H), 7.43-7.35 (m, 1H), 7.31-7.21 (m, 2H), 4.23 (t, J=5.7, 1H), 3.63 (s, 2H), 3.22-3.12 (m, 2H), 2.95 (s, 3H), 3.01-2.92 (m, 2H), 2.00 (d, J=11.2, 2H), 1.68 (d, J=12.1, 2H), 1.52 (dd, J=14.1, 6.9, 2H), 1.37-1.22 (m, 3H).

Example 365

5-(Thiazolo[4,5-b]pyridin-2-yloxy)-benzofuran-2-carboxylic acid benzyl-methyl-amide

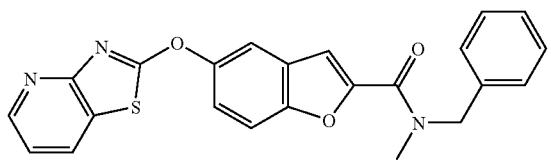 [SMILES: CN(Cc1ccccc1)C(=O)c1cc2cc(Oc3nc4ncccc4s3)ccc2o1]

To a solution of 5-(thiazolo[4,5-b]pyridin-2-yloxy)-benzofuran-2-carbonyl chloride hydrochloride (150 mg, 0.43 mmol) in $CH_2Cl_2$ (4.3 mL) was added N-benzyl-N-methylamine (55 μL, 0.43 mmol) and $Et_3N$ (0.12 mL, 0.86 mmol). The reaction mixture was stirred (rt, 2 h) before additional N-benzyl-N-methylamine (55 μL, 0.43 mmol) was added. The mixture was concentrated and purified by reverse phase chromatography to provide the title product as an orange oil (27 mg, 15%). MS (ESI): mass calcd. for $C_{23}H_{17}N_3O_3S$, 415.10; m/z found, 416.0 [M+H]$^+$. $^1$H NMR (400 MHz, CDCl$_3$): 8.60 (d, J=3.7, 1H), 8.09 (dd, J=7.9, 1.5, 1H), 7.75 (br s, 1H), 7.66-7.49 (m, 1H), 7.46-7.28 (m, 8H), 5.05-4.62 (m, 2H), 3.45-2.94 (m, 3H).

Example 366

(1R,4R)-1-{5-[5-(Thiazolo[4,5-b]pyridin-2-yloxy)-benzofuran-2-carbonyl]-2,5-diaza-bicyclo[2.2.1]hept-2-yl}-ethanone

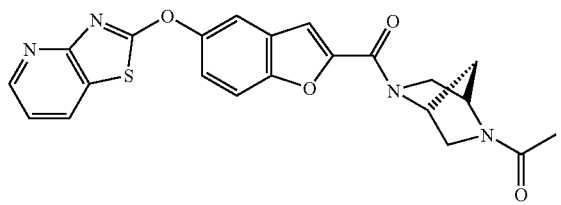

This compound was prepared using methods analogous to those described for Example 365. MS (ESI): mass calcd. for $C_{22}H_{18}N_4O_4S$, 434.10; m/z found, 435.0 [M+H]$^+$. $^1$H NMR (400 MHz, CD$_3$OD): 8.52 (d, J=4.2, 1H), 8.42 (d, J=8.0, 1H), 7.90-7.82 (m, 1H), 7.81-7.68 (m, 1H), 7.61-7.48 (m, 2H), 7.47-7.36 (m, 1H), 5.48 (d, J=21.1, OH), 5.10 (d, J=14.0, 1H), 5.02-4.90 (m, 1H), 4.21-3.92 (m, 1H), 3.88-3.41 (m, 3H), 2.27-1.89 (m, 5H).

Example 367

6-(Thiazolo[4,5-b]pyridin-2-yloxy)-benzofuran-3-carboxylic acid methylamide

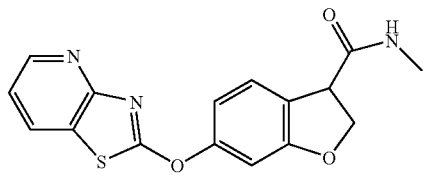 [SMILES: CNC(=O)C1COc2cc(Oc3nc4ncccc4s3)ccc21]

To a solution of 6-(thiazolo[4,5-b]pyridin-2-yloxy)-benzofuran-3-carbonyl chloride hydrochloride (256 mg, 0.77 mmol) in $CH_2Cl_2$ (7.7 mL) was added $Et_3N$ (0.32 mL, 2.32 mmol) and methylamine dihydrochloride (81 mg, 0.77 mmol). The reaction mixture was stirred (rt, 1 h). Water followed by sat'd. aq. NaHCO$_3$ was added to the mixture. The resultant precipitate was filtered and concentrated to provide the title compound (115 mg, 45%). MS (ESI): mass calcd. for $C_{16}H_{11}N_3O_3S$, 325.05; m/z found, 326.0 [M+H]$^+$. $^1$H NMR (400 MHz, CDCl$_3$): 8.57 (dd, J=4.8, 1.6, 1H), 8.23 (s, 1H), 8.17-8.01 (m, 2H), 7.37 (dd, J=8.6, 2.2, 1H), 7.24 (dd, J=7.9, 4.8, 1H), 7.01 (d, J=26.5, 1H), 3.00 (d, J=4.8, 3H).

Examples 368 to 369 were prepared using methods analogous to those described for Example 367.

Example 368

N-{1-[6-(Thiazolo[4,5-b]pyridin-2-yloxy)-benzofuran-3-carbonyl]-piperidin-4-yl}-acetamide

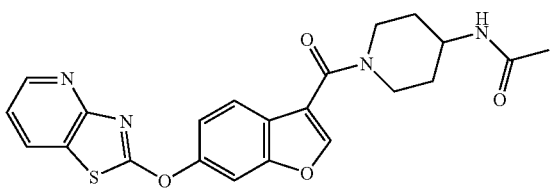 [SMILES: CC(=O)NC1CCN(C(=O)c2coc3cc(Oc4nc5ncccc5s4)ccc23)CC1]

MS (ESI): mass calcd. for $C_{22}H_{20}N_4O_4S$, 436.12; m/z found, 437.0 [M+H]$^+$. $^1$H NMR (400 MHz, CDCl$_3$): 8.57 (dd, J=4.9, 1.6, 1H), 8.05 (dd, J=7.9, 1.6, 1H), 7.90 (s, 1H), 7.76-7.65 (m, 2H), 7.38 (dd, J=8.5, 2.2, 1H), 7.28-7.15 (m, 1H), 5.69-5.53 (m, 1H), 4.18-3.99 (m, 1H), 3.14 (s, 2H), 2.15-1.92 (m, 5H), 1.85-1.58 (m, 2H), 1.54-1.31 (m, 2H).

Example 369 meso-endo-N-{8-[6-(Thiazolo[4,5-b]pyridin-2-yloxy)-benzofuran-3-carbonyl]-8-aza-bicyclo[3.2.1]oct-3-yl}-acetamide

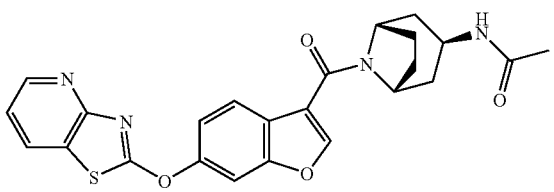 [SMILES: CC(=O)N[C@H]1C[C@H]2CC[C@@H](C1)N2C(=O)c1coc2cc(Oc3nc4ncccc4s3)ccc12]

MS (ESI): mass calcd. for $C_{24}H_{22}N_4O_4S$, 462.14; m/z found, 462.9 [M+H]$^+$. $^1$H NMR (400 MHz, CDCl$_3$): 8.56 (dd, J=4.8, 1.6, 1H), 8.05 (dd, J=7.9, 1.6, 1H), 7.95 (s, 1H), 7.78 (d, J=8.5, 1H), 7.70 (d, J=2.1, 1H), 7.38 (dd, J=8.5, 2.1, 1H), 7.26-7.19 (m, 1H), 6.11 (d, J=6.4, 1H), 4.88 (br s, 1H), 4.42 (br s, 1H), 4.25-4.15 (m, 1H), 2.35 (br s, 1H), 2.22-2.11 (m, 2H), 2.06-1.94 (m, 6H), 1.89-1.80 (m, 2H).

Example 370

1-{1-[6-(Thiazolo[4,5-b]pyridin-2-yloxy)-benzofuran-3-carbonyl]-piperidin-4-yl}-pyrrolidin-2-one

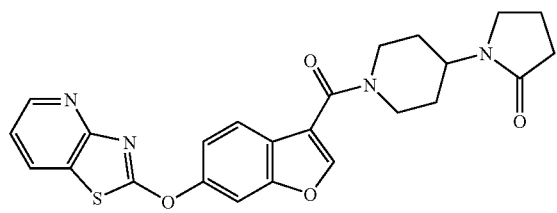 [SMILES: O=C(c1coc2cc(Oc3nc4ncccc4s3)ccc12)N1CCC(N2CCCC2=O)CC1]

This compound was prepared using methods analogous to those described for Example 367, with the modification that the reaction was conducted for 16 hr instead of 1 hr. MS (ESI): mass calcd. for $C_{24}H_{22}N_4O_4S$, 462.14; m/z found, 462.9 [M+H]$^+$. $^1$H NMR (400 MHz, CDCl$_3$): 8.57 (dd, J=4.8, 1.6, 1H), 8.05 (dd, J=7.9, 1.7, 1H), 7.93 (s, 1H), 7.74-7.68 (m, 2H), 7.40 (dd, J=8.6, 2.1, 1H), 7.26-7.19 (m, 1H), 4.36-4.22 (m, 1H), 3.37 (t, J=7.0, 2H), 2.48-2.37 (m, 2H), 2.17 (s, 1H), 2.10-1.96 (m, 2H), 1.85-1.75 (m, 2H), 1.75-1.54 (m, 5H).

Example 371

(1S,4S)-1-{5-[6-(Thiazolo[4,5-b]pyridin-2-yloxy)-benzofuran-3-carbonyl]-2,5-diaza-bicyclo[2.2.1]hept-2-yl}-ethanone

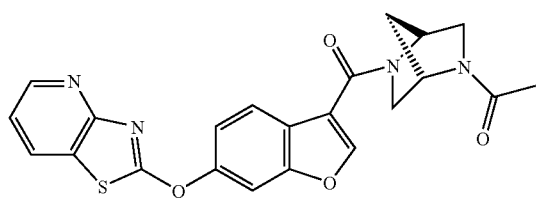

To a mixture of (1S,4S)-1-(2,5-diazo-bicyclo[2.2.1]hept-2-yl)-ethanone hydrochloride (94 mg, 0.53 mmol) in DCM (3.8 mL) was added N-(3-dimethylaminopropyl)-N'-ethylcarbdiimide hydrochloride (103 mg, 0.76 mmol), 1-hydroxybenzotriazole (146 mg, 0.76 mmol), DIEA (0.27 mL, 1.53 mmol), and 6-(thiazolo[4,5-b]pyridine-2-yloxy)-benzofuran-3-carboxylic acid (119 mg, 0.38 mmol). The reaction mixture was stirred (rt, 16 h), concentrated and purified by reverse phase HPLC to provide the title compound as a white solid (35 mg, 21%). MS (ESI): mass calcd. for $C_{22}H_{18}N_4O_4S$, 434.10; m/z found, 435.0 [M+H]$^+$. $^1$H NMR (400 MHz, CDCl$_3$): 8.58 (dd, J=4.8, 1.5, 1H), 8.19 (d, J=8.2, 1H), 8.05 (dd, J=7.9, 1.7, 1H), 7.94 (d, J=8.5, 1H), 7.74 (dd, J=4.1, 2.1, 1H), 7.44-7.35 (m, 1H), 7.23 (dd, J=8.0, 4.8, 1H), 5.29-4.97 (m, 1.4H), 4.85-4.67 (m, 0.3H), 4.56 (s, 0.3H), 3.89-3.44 (m, 4H), 2.25-1.84 (m, 5H).

Examples 372 to 380 were prepared using methods analogous to those described for Example 371.

Example 372

1-{4-[6-(Thiazolo[4,5-b]pyridin-2-yloxy)-benzofuran-3-carbonyl]-[1,4]diazepan-1-yl}-ethanone

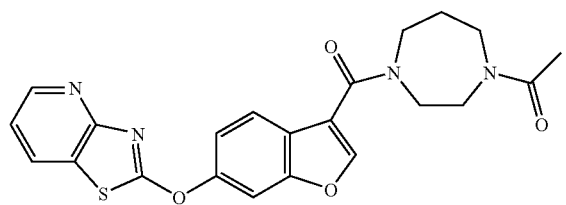 [SMILES: CC(=O)N1CCCN(C(=O)c2coc3cc(Oc4nc5ncccc5s4)ccc23)CC1]

MS (ESI): mass calcd. for $C_{22}H_{20}N_4O_4S$, 436.12; m/z found, 437.0 [M+H]$^+$. $^1$H NMR (400 MHz, CDCl$_3$): 8.57 (dd, J=3.4, 1.4, 1H), 8.08-8.01 (m, 1H), 7.89 (s, 1H), 7.81-7.67 (m, 2H), 7.42-7.33 (m, 1H), 7.26-7.20 (m, 1H), 4.08-3.41 (m, 8H), 2.14 (s, 3H), 2.03-1.66 (m, 2H).

Example 373

6-(Thiazolo[4,5-b]pyridin-2-yloxy)-benzofuran-3-carboxylic acid isopropyl-methyl-amide

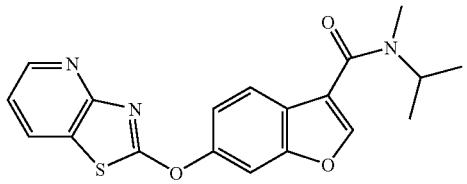 [SMILES: CC(C)N(C)C(=O)c1coc2cc(Oc3nc4ncccc4s3)ccc12]

MS (ESI): mass calcd. for $C_{19}H_{17}N_3O_3S$, 367.10; m/z found, 368.0 [M+H]$^+$. $^1$H NMR (500 MHz, CDCl$_3$): 8.58 (d, J=3.7, 1H), 8.04 (dd, J=7.9, 1.6, 1H), 7.87 (s, 1H), 7.75 (d, J=8.6, 1H), 7.70 (d, J=2.1, 1H), 7.37 (dd, J=8.6, 2.1, 1H), 7.23 (dd, J=7.9, 4.8, 1H), 3.02 (d, J=20.0, 3H), 1.24 (t, J=10.2, 7H).

Example 374 meso-8-[6-(Thiazolo[4,5-b]pyridin-2-yloxy)-benzofuran-3-carbonyl]-3,8-diaza-bicyclo[3.2.1]octane-3-carboxylic acid amide

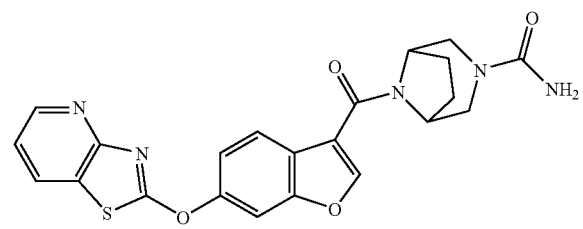 [SMILES: NC(=O)N1CC2CCC(C1)N2C(=O)c1coc2cc(Oc3nc4ncccc4s3)ccc12]

MS (ESI): mass calcd. for $C_{22}H_{19}N_5O_4S$, 449.12; m/z found, 450.0 [M+H]$^+$. $^1$H NMR (500 MHz, CDCl$_3$): 8.62 (dd, J=5.0, 1.5, 1H), 8.15 (dd, J=8.0, 1.6, 1H), 8.00 (s, 1H), 7.78 (d, J=8.6, 1H), 7.73 (d, J=1.9, 1H), 7.41 (dd, J=8.6, 2.1, 1H), 7.32 (dd, J=8.0, 5.0, 1H), 5.45 (s, 2H), 3.76 (s, 4H), 3.30 (s, 2H), 2.16-2.02 (m, 2H), 1.91 (d, J=7.9, 2H).

Example 375

(1S,4S)-5-[6-(Thiazolo[4,5-b]pyridin-2-yloxy)-benzofuran-3-carbonyl]-2,5-diaza-bicyclo[2.2.1]heptane-2-carboxylic acid amide

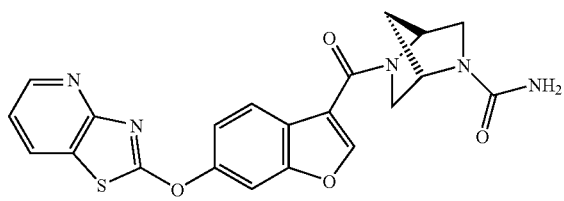

MS (ESI): mass calcd. for C$_{21}$H$_{17}$N$_5$O$_4$S, 435.10; m/z found, 435.9 [M+H]$^+$. $^1$H NMR (500 MHz, CDCl$_3$): 8.60 (dd, J=4.9, 1.5, 1H), 8.20-8.07 (m, 2H), 7.97 (s, 1H), 7.72 (d, J=2.1, 1H), 7.40 (dd, J=8.6, 2.2, 1H), 7.30-7.27 (m, 1H), 5.20 (s, 2H), 4.83 (s, 1H), 3.85-3.72 (m, 3H), 3.66-3.44 (m, 2H), 2.09-1.95 (m, 2H).

Example 376

(4-Fluoro-piperidin-1-yl)-[6-(thiazolo[4,5-b]pyridin-2-yloxy)-benzofuran-3-yl]-methanone

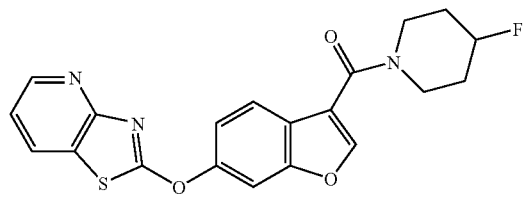 [SMILES: O=C(c1coc2cc(Oc3nc4ncccc4s3)ccc12)N1CCC(F)CC1]

MS (ESI): mass calcd. for C$_{20}$H$_{16}$FN$_3$O$_3$S, 397.09; m/z found, 398.0 [M+H]$^+$. $^1$H NMR (500 MHz, CDCl$_3$): 8.61 (dd, J=5.0, 1.6, 1H), 8.11 (dd, J=8.0, 1.6, 1H), 7.93 (d, J=6.2, 1H), 7.71 (dd, J=5.4, 3.1, 2H), 7.39 (dd, J=8.6, 2.1, 1H), 7.32-7.27 (m, 1H), 5.04-4.96 (m, 0.5H), 4.94-4.87 (m, 0.5H), 3.76-3.64 (m, 2H), 3.38 (5, 2H), 2.04-1.85 (m, 4H).

Example 377

(4-Phenyl-piperidin-1-yl)-[6-(thiazolo[4,5-b]pyridin-2-yloxy)-benzofuran-3-yl]-methanone

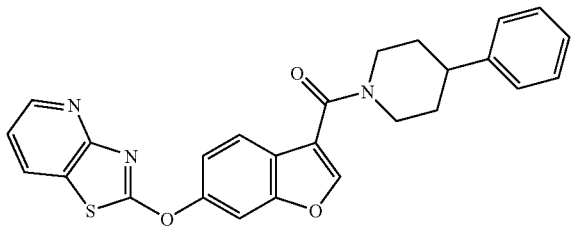 [SMILES: O=C(c1coc2cc(Oc3nc4ncccc4s3)ccc12)N1CCC(c2ccccc2)CC1]

MS (ESI): mass calcd. for C$_{26}$H$_{21}$N$_3$O$_3$S, 455.13; m/z found, 456.0 [M+H]$^+$. $^1$H NMR (500 MHz, CDCl$_3$): 8.60 (dd, J=4.9, 1.6, 1H), 8.12-8.07 (m, 1H), 7.95 (d, J=6.2, 1H), 7.76 (d, J=8.6, 1H), 7.71 (d, J=2.0, 1H), 7.39 (dd, J=8.6, 2.2, 1H), 7.37-7.30 (m, 2H), 7.30-7.27 (m, 1H), 7.25-7.20 (m, 3H), 4.17 (br s, 2H), 3.11 (br s, 2H), 2.89-2.79 (m, 1H), 2.05-1.93 (m, 2H), 1.76 (br s, 2H).

Example 378

1-[6-(Thiazolo[4,5-b]pyridin-2-yloxy)-benzofuran-3-carbonyl]-piperidine-4-carboxylic acid amide

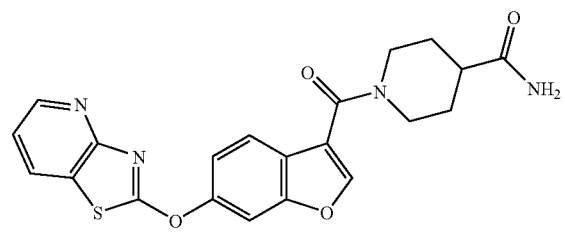 [SMILES: NC(=O)C1CCN(C(=O)c2coc3cc(Oc4nc5ncccc5s4)ccc23)CC1]

MS (ESI): mass calcd. for C$_{21}$H$_{18}$N$_4$O$_4$S, 422.10; m/z found, 423.0 [M+H]$^+$. $^1$H NMR (500 MHz, CDCl$_3$): 8.61 (dd, J=4.9, 1.6, 1H), 8.10 (dd, J=8.0, 1.6, 1H), 7.93 (5, 1H), 7.73-7.69 (m, 2H), 7.38 (dd, J=8.7, 2.1, 1H), 7.28 (dd, J=7.1, 4.0, 1H), 5.83-5.53 (m, 2H), 3.21-2.99 (m, 2H), 2.57-2.44 (m, 1H), 2.07-1.91 (m, 2H), 1.89-1.73 (m, 2H).

Example 379

(4-Cyclohexyl-piperazin-1-yl)-[6-(thiazolo[4,5-b]pyridin-2-yloxy)-benzofuran-3-yl]-methanone

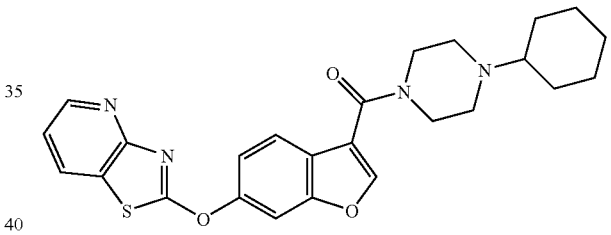

MS (ESI): mass calcd. for C$_{25}$H$_{26}$N$_4$O$_3$S, 462.17; m/z found, 463.1 [M+H]$^+$. $^1$H NMR (500 MHz, CDCl$_3$): 8.60 (dd, J=4.9, 1.5, 1H), 8.13 (dd, J=8.0, 1.6, 1H), 7.99 (5, 1H), 7.73 (dd, J=12.3, 5.3, 2H), 7.44-7.39 (m, 1H), 7.33-7.27 (m, 1H), 3.93-3.65 (m, 1H), 3.65-3.50 (m, 2H), 3.22-3.13 (m, 2H), 2.95-2.76 (m, 3H), 2.19-2.06 (m, 2H), 2.03-1.91 (m, 2H), 1.78-1.69 (m, 1H), 1.53-1.28 (m, 5H), 1.23-1.10 (m, 1H).

Example 380

1-{4-[6-(Thiazolo[4,5-b]pyridin-2-yloxy)-benzofuran-3-carbonyl]-piperazin-1-yl}-ethanone

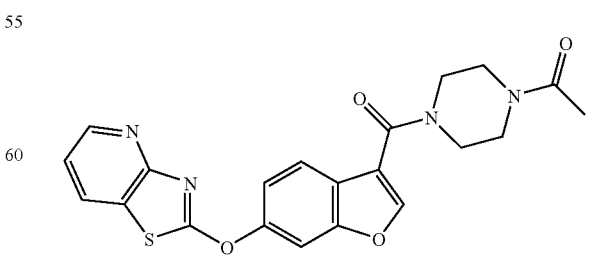

MS (ESI): mass calcd. for C$_{21}$H$_{18}$N$_4$O$_4$S, 422.10; m/z found, 423.0 [M+H]$^+$. $^1$H NMR (500 MHz, CDCl$_3$): 8.64-8.57 (m, 1H), 8.10 (dd, J=8.0, 1.6, 1H), 7.95 (s, 1H), 7.73 (dd, J=9.7, 5.3, 2H), 7.40 (dd, J=8.6, 2.1, 1H), 7.30-7.27 (m, 1H), 3.87-3.66 (m, 5H), 3.57 (s, 2H), 2.17 (s, 4H).

Example 381

6-(Thiazolo[4,5-b]pyridin-2-yloxy)-benzofuran-3-carboxylic acid cyclohexyl-ethyl-amide

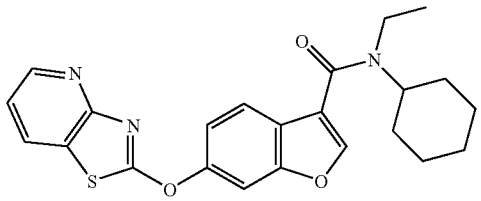 [SMILES: CCN(C(=O)c1coc2cc(Oc3nc4ncccc4s3)ccc12)C1CCCCC1]

This compound was prepared using methods analogous to those described for Example 371, with the modification that the reaction was conducted for 5 days instead of 16 h. MS (ESI): mass calcd. for $C_{23}H_{23}N_3O_3S$, 421.15; m/z found, 422.0 [M+H]$^+$. $^1$H NMR (500 MHz, CDCl$_3$): 8.60-8.56 (m, 1H), 8.07-8.03 (m, 1H), 7.81 (5, 1H), 7.74 (d, J=8.6, 1H), 7.72-7.68 (m, 1H), 7.36 (dd, J=8.6, 2.1, 1H), 7.26-7.20 (m, 1H), 3.49 (5, 2H), 1.90-1.73 (m, 4H), 1.72-1.54 (m, 4H), 1.37-1.02 (m, 6H).

Example 382

[4-(Pyrimidin-2-yloxy)-piperidin-1-yl]-[6-(thiazolo[4,5-b]pyridin-2-yloxy)-benzofuran-3-yl]-methanone

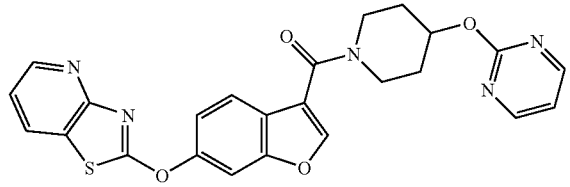 [SMILES: O=C(c1coc2cc(Oc3nc4ncccc4s3)ccc12)N1CCC(Oc2ncccn2)CC1]

This compound was prepared using methods analogous to those described for Example 371, but the reaction was conducted for 30 h and required a second purification by flash column chromatography using MeOH/DCM (0 to 10%). MS (ESI): mass calcd. for $C_{24}H_{19}N_5O_4S$, 473.12; m/z found, 474.0 [M+H]$^+$. $^1$H NMR (400 MHz, CDCl$_3$): 8.58 (dd, J=4.9, 1.6, 1H), 8.53 (d, J=4.8, 2H), 8.05 (dd, J=7.9, 1.6, 1H), 7.94 (s, 1H), 7.72 (dd, J=5.3, 3.0, 2H), 7.38 (dd, J=8.7, 2.1, 1H), 7.23 (dd, J=8.0, 4.9, 1H), 6.96 (t, J=4.8, 1H), 5.35 (q, J=6.9, 3.5, 1H), 4.01 (s, 2H), 3.72 (s, 2H), 2.00 (s, 2H), 1.65-1.52 (m, 2H).

Example 383

Piperidin-1-yl-[6-(thiazolo[4,5-b]pyridin-2-yloxy)-benzofuran-3-yl]-methanone

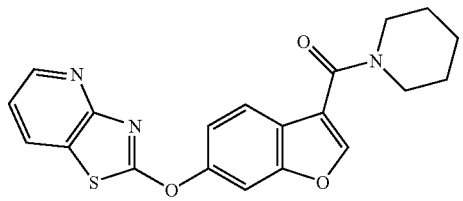 [SMILES: O=C(c1coc2cc(Oc3nc4ncccc4s3)ccc12)N1CCCCC1]

This compound was prepared using methods analogous to those described for Example 371, but the reaction was conducted for 30 h and required a second purification by flash column chromatography using ethyl acetate/hexanes (0 to 60%). MS (ESI): mass calcd. for $C_{20}H_{17}N_3O_3S$, 379.10; m/z found, 380.0 [M+H]$^+$. $^1$H NMR (400 MHz, CDCl$_3$): 8.57 (dd, J=4.8, 1.6, 1H), 8.04 (dd, J=7.9, 1.6, 1H), 7.89 (s, 1H), 7.70 (dd, J=7.4, 5.4, 2H), 7.37 (dd, J=8.6, 2.2, 1H), 7.23 (dd, J=7.9, 4.8, 1H), 3.77-3.54 (m, 4H), 1.75-1.60 (m, 6H).

Example 384

[4-(Piperidine-1-carbonyl)-piperidin-1-yl]-[6-(thiazolo[4,5-b]pyridin-2-yloxy)-benzofuran-3-yl]-methanone

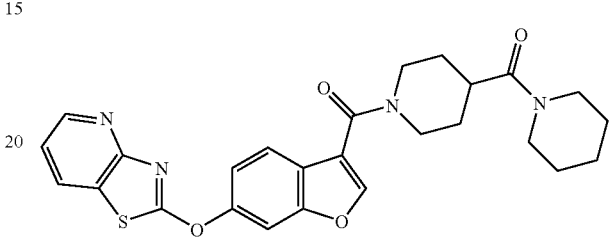

This compound was prepared using methods analogous to those described for Example 371, but the reaction was conducted for 30 h and required a second purification by flash column chromatography using ethyl acetate/hexanes (0 to 60%) and MeOH/DCM (0-5%). MS (ESI): mass calcd. for $C_{26}H_{26}N_4O_4S$, 490.17; m/z found, 491.0 [M+H]$^+$. $^1$H NMR (400 MHz, CDCl$_3$): 8.57 (dd, J=4.8, 1.6, 1H), 8.05 (dd, J=7.9, 1.6, 1H), 7.92 (s, 1H), 7.73-7.69 (m, 2H), 7.37 (dd, J=8.7, 2.0, 1H), 7.23 (dd, J=7.9, 4.8, 1H), 3.61-3.43 (m, 4H), 3.09 (s, 2H), 2.88-2.76 (m, 1H), 1.94-1.74 (m, 4H), 1.72-1.51 (m, 8H).

Example 385

(Octahydro-isoquinolin-2-yl)-[6-(thiazolo[4,5-b]pyridin-2-yloxy)-benzofuran-3-yl]-methanone

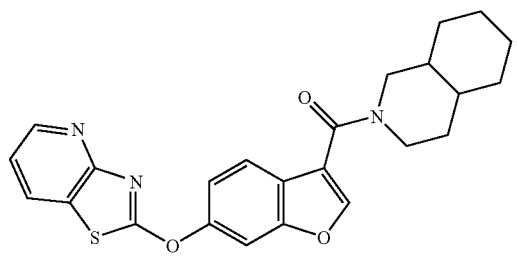 [SMILES: O=C(c1coc2cc(Oc3nc4ncccc4s3)ccc12)N1CCC2CCCCC2C1]

This compound was prepared using methods analogous to those described for Example 371, but the reaction was conducted for 30 h and required additional purification by flash column chromatography using ethyl acetate/hexanes (0 to 70%) followed by additional reverse phase HPLC. MS (ESI): mass calcd. for $C_{24}H_{23}N_3O_3S$, 433.15; m/z found, 434.0 [M+H]$^+$. $^1$H NMR (400 MHz, CDCl$_3$): 8.57 (dd, J=4.8, 1.7, 1H), 8.04 (dd, J=8.0, 1.6, 1H), 7.89 (s, 1H), 7.71 (d, J=8.6, 1H), 7.68 (d, J=2.1, 1H), 7.36 (dd, J=8.6, 2.1, 1H), 7.22 (dd, J=7.9, 4.8, 1H), 3.73-3.41 (m, 3H), 2.32 (d, J=8.0, 1H), 1.89-1.63 (m, 6H), 1.56-1.05 (m, 6H).

Example 386

(3,4-Dihydro-1H-isoquinolin-2-yl)-[6-(thiazolo[4,5-b]pyridin-2-yloxy)-benzofuran-3-yl]-methanone

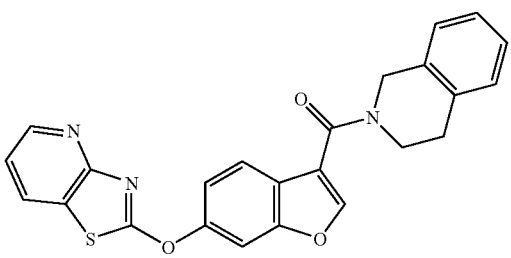 [SMILES: O=C(c1coc2cc(Oc3nc4ncccc4s3)ccc12)N1CCc2ccccc2C1]

This compound was prepared using methods analogous to those described for Example 371, but the reaction was conducted for 30 h and required additional purification by flash column chromatography using ethyl acetate/hexanes (0 to 70%) followed by additional reverse phase HPLC. MS (ESI): mass calcd. for $C_{24}H_{17}N_3O_3S$, 427.10; m/z found, 428.0 [M+H]$^+$. $^1$H NMR (400 MHz, CDCl$_3$): 8.58 (dd, J=4.8, 1.6, 1H), 8.05 (dd, J=7.9, 1.6, 1H), 7.96 (s, 1H), 7.82-7.71 (m, 2H), 7.37 (dd, J=8.6, 2.1, 1H), 7.25-7.15 (m, 5H), 4.88 (s, 2H), 3.94 (s, 2H), 2.93 (d, J=41.7, 2H).

Example 387

(4-Benzoyl-piperidin-1-yl)-[6-(thiazolo[4,5-b]pyridin-2-yloxy)-benzofuran-3-yl]-methanone

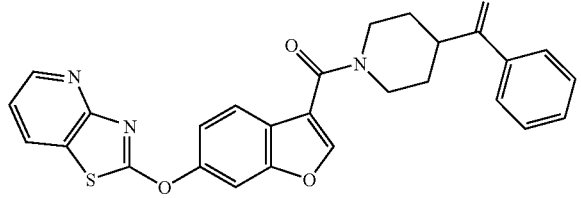

This compound was prepared using methods analogous to those described for Example 371, but the reaction was conducted for 30 h and required a second purification by flash column chromatography using ethyl acetate/hexanes (0 to 60%) and MeOH/DCM (0-5%). MS (ESI): mass calcd. for $C_{27}H_{21}N_3O_4S$, 483.13; m/z found, 484.1 [M+H]$^+$. $^1$H NMR (400 MHz, CDCl$_3$): 8.57 (dd, J=4.8, 1.5, 1H), 8.04 (dd, J=7.9, 1.6, 1H), 8.00-7.92 (m, 3H), 7.73 (d, J=8.8, 2H), 7.60 (t, J=7.4, 1H), 7.50 (t, J=7.6, 2H), 7.38 (dd, J=8.5, 2.2, 1H), 7.22 (dd, J=7.9, 4.8, 1H), 3.66-3.54 (m, 1H), 3.23 (s, 2H), 1.99 (s, 2H), 1.93-1.78 (m, 2H), 1.60 (s, 1H), 1.32-1.21 (m, 1H).

Example 388

6-(Thiazolo[4,5-b]pyridin-2-yloxy)-benzofuran-3-carboxylic acid (3-dimethylamino-propyl)-methyl-amide

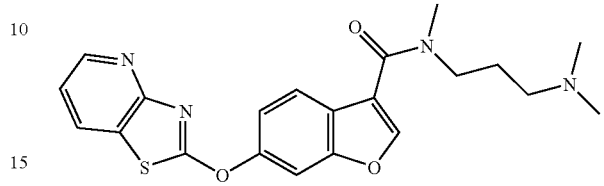

This compound was prepared using methods analogous to those described for Example 371, but the reaction was conducted for 30 h and required a second purification by flash column chromatography using MeOH/DCM (0-20%). MS (ESI): mass calcd. for $C_{21}H_{22}N_4O_3S$, 410.14; m/z found, 411.0 [M+H]$^+$. $^1$H NMR (500 MHz, CDCl$_3$): 8.57 (dd, J=4.8, 1.6, 1H), 8.04 (dd, J=7.9, 1.7, 1H), 7.96 (s, 1H), 7.82 (d, J=8.4, 1H), 7.71 (d, J=2.0, 1H), 7.37 (dd, J=8.6, 2.1, 1H), 7.22 (dd, J=7.9, 4.8, 1H), 3.77-3.48 (m, 2H), 3.19 (s, 3H), 2.62 (s, 3H), 2.60-1.59 (m, 7H).

Example 389 endo-Bicyclo[2.2.1]heptane-2-carboxylic acid [6-(thiazolo[4,5-b]pyridin-2-yloxy)-benzofuran-3-ylmethyl]-amide

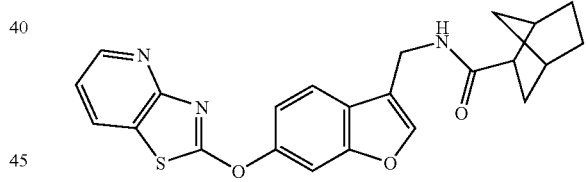

To a mixture of endo-bicyclo[2.2.1]heptane-2-carboxylic acid (38 mg, 0.27 mmol) in DCM (2.7 mL) was added N-(3-dimethylaminopropyl)-N'-ethylcarbdiimide hydrochloride (73 mg, 0.54 mmol), 1-hydroxybenzotriazole (103 mg, 0.54 mmol), DIEA (0.19 mL, 1.08 mmol), and C-[6-(thiazolo[4,5-b]pyridin-2-yloxy)-benzofuran-3-yl]-methylamine hydrochloride (90 mg, 0.27 mmol). The reaction mixture was stirred (rt, 16 h), concentrated and purified by reverse phase HPLC to provide the title compound as a white solid (36 mg, 32%). MS (ESI): mass calcd. for $C_{23}H_{21}N_3O_3S$, 419.13; m/z found, 420.0 [M+H]$^+$. $^1$H NMR (400 MHz, CDCl$_3$): 8.57 (dd, J=4.8, 1.6, 1H), 8.03 (dd, J=7.9, 1.6, 1H), 7.68-7.60 (m, 3H), 7.30 (dd, J=8.5, 2.1, 1H), 7.21 (dd, J=7.9, 4.8, 1H), 5.66 (s, 1H), 4.67-4.54 (m, 2H), 2.69-2.60 (m, 1H), 2.44-2.36 (m, 1H), 2.31-2.24 (m, 1H), 1.75-1.59 (m, 2H), 1.54-1.29 (m, 6H).

Examples 390 to 393 were prepared using methods analogous to those described for Example 389.

Example 390

2-(4-Acetyl-piperazin-1-yl)-N-[6-(thiazolo[4,5-b]pyridin-2-yloxy)-benzofuran-3-ylmethyl]-acetamide

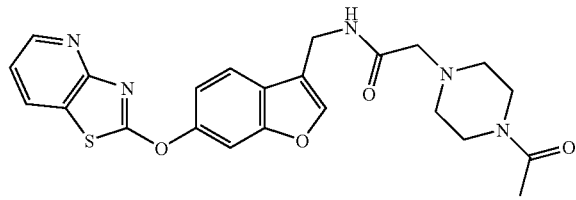 [SMILES: CC(=O)N1CCN(CC(=O)NCc2coc3cc(Oc4nc5ncccc5s4)ccc23)CC1]

MS (ESI): mass calcd. for $C_{23}H_{23}N_5O_4S$, 465.15; m/z found, 466.1 [M+H]⁺. ¹H NMR (400 MHz, CDCl₃): 8.56 (dd, J=4.8, 1.6, 1H), 8.05 (dd, J=7.9, 1.6, 1H), 7.68-7.62 (m, 3H), 7.30 (dd, J=8.5, 2.1, 2H), 7.22 (dd, J=7.9, 4.8, 1H), 4.63 (d, J=6.0, 2H), 3.61-3.54 (m, 2H), 3.46-3.36 (m, 2H), 3.11 (s, 2H), 2.52-2.43 (m, 4H), 2.06 (s, 3H).

Example 391

2-(3-Methyl-isoxazol-5-yl)-N-[6-(thiazolo[4,5-b]pyridin-2-yloxy)-benzofuran-3-ylmethyl]-acetamide

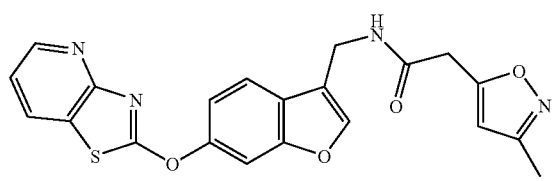 [SMILES: Cc1cc(CC(=O)NCc2coc3cc(Oc4nc5ncccc5s4)ccc23)on1]

MS (ESI): mass calcd. for $C_{21}H_{16}N_4O_4S$, 420.09; m/z found, 420.9 [M+H]⁺. ¹H NMR (400 MHz, CDCl₃): 8.56 (dd, J=4.9, 1.6, 1H), 8.03 (dd, J=7.9, 1.6, 1H), 7.65-7.57 (m, 3H), 7.28 (dd, J=8.6, 2.1, 1H), 7.22 (dd, J=7.9, 4.8, 1H), 6.19-6.13 (m, 1H), 6.08 (s, 1H), 4.58 (d, J=5.7, 2H), 3.74 (s, 2H), 2.28 (s, 3H).

Example 392

4-Hydroxy-cyclohexanecarboxylic acid [6-(thiazolo[4,5-b]pyridin-2-yloxy)-benzofuran-3-ylmethyl]-amide

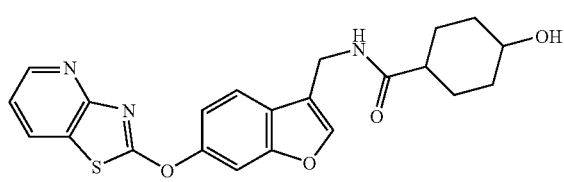 [SMILES: O=C(NCc1coc2cc(Oc3nc4ncccc4s3)ccc12)C1CCC(O)CC1]

MS (ESI): mass calcd. for $C_{22}H_{21}N_3O_4S$, 423.13; m/z found, 423.9 [M+H]⁺. ¹H NMR (400 MHz, CDCl₃): 8.57-8.54 (m, 1H), 8.03 (dd, J=7.9, 1.6, 1H), 7.65-7.59 (m, 3H), 7.31-7.27 (m, 1H), 7.22 (m, 1H), 5.93-5.78 (m, 1H), 4.58 (t, J=5.2, 2H), 4.04-3.95 (m, 0.6H), 3.67-3.55 (m, 0.4H), 2.28-2.15 (m, 0.6H), 2.14-1.98 (m, 1.4H), 1.97-1.75 (m, 3.6H), 1.72-1.65 (m, 1.4H), 1.54 (m, 2H), 1.34-1.18 (m, 1H).

Example 393

N-[6-(Thiazolo[4,5-b]pyridin-2-yloxy)-benzofuran-3-ylmethyl]-terephthalamic acid methyl ester

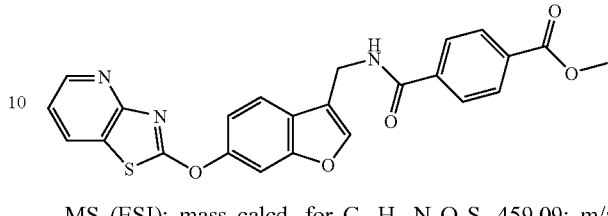

MS (ESI): mass calcd. for $C_{24}H_{17}N_3O_5S$, 459.09; m/z found, 459.9 [M+H]⁺. ¹H NMR (400 MHz, CDCl₃): 8.54 (dd, J=4.8, 1.6, 1H), 8.12-8.07 (m, 2H), 8.03 (dd, J=7.9, 1.6, 1H), 7.89-7.83 (m, 2H), 7.69 (dd, J=11.7, 2.9, 2H), 7.61 (d, J=2.1, 1H), 7.31-7.26 (m, 2H), 7.21 (dd, J=8.0, 4.8, 1H), 4.78 (d, J=5.5, 2H), 3.94 (d, J=5.9, 3H).

Example 394

2-(4-Chloro-phenyl)-N-[6-(thiazolo[4,5-b]pyridin-2-yloxy)-benzofuran-3-ylmethyl]-acetamide

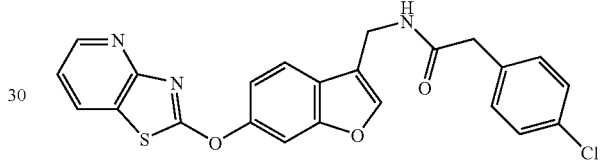

To C-[6-(thiazolo[4,5-b]pyridin-2-yloxy)-benzofuran-3-yl]-methylamine hydrochloride (100 mg, 0.30 mmol) in DCM (3 mL) was added 4-chlorophenylacetyl chloride (57 mg, 0.30 mmol) and Et₃N (0.13 mL, 0.90 mmol). The reaction mixture was stirred (rt, 16 h). Another equivalent of 4-chlorophenylacetyl chloride (57 mg, 0.30 mmol) was added, but the reaction remained at 50% conversion. Two equivalents of 4-chlorophenylacetyl chloride (114 mg, 0.60 mmol) and three equivalents of Et₃N (0.13 mL, 0.90 mmol) were added. Upon reaction completion, the mixture was washed with sat'd. aq. NaHCO₃ and extracted with DCM. After drying and concentration, the residue was purified by reverse phase HPLC to provide the title compound (47 mg, 35%). MS (ESI): mass calcd. for $C_{23}H_{16}ClN_3O_3S$, 449.06; m/z found, 449.9 [M+H]⁺. ¹H NMR (500 MHz, CDCl₃): 8.56 (dd, J=4.8, 1.6, 1H), 8.04 (dd, J=7.9, 1.6, 1H), 7.60 (d, J=2.0, 1H), 7.58-7.53 (m, 2H), 7.33-7.29 (m, 2H), 7.28-7.24 (m, 1H), 7.24-7.18 (m, 3H), 5.70 (s, 1H), 4.55 (d, J=5.8, 2H), 3.58 (s, 2H).

Example 395

N-[6-(Thiazolo[4,5-b]pyridin-2-yloxy)-benzofuran-3-ylmethyl]-acetamide

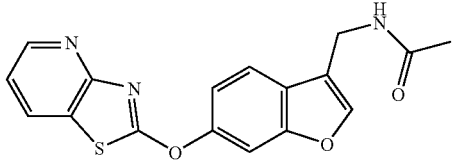 [SMILES: CC(=O)NCc1coc2cc(Oc3nc4ncccc4s3)ccc12]

This compound was prepared using methods analogous to those described for Example 394, but no additional equivalents of reagents were necessary for reaction completion. MS (ESI): mass calcd. for $C_{17}H_{13}N_3O_3S$, 339.07; m/z found, 339.9 [M+H]+. 1H NMR (500 MHz, CDCl3): 8.55 (dd, J=4.8, 1.6, 1H), 8.03 (dd, J=7.9, 1.6, 1H), 7.65 (d, J=8.5, 1H), 7.63 (s, 1H), 7.60 (d, J=2.0, 1H), 7.28 (dd, J=8.5, 2.1, 1H), 7.21 (dd, J=7.9, 4.8, 1H), 5.92 (s, 1H), 4.73-4.44 (m, 2H), 2.14-1.90 (m, 3H).

Example 396

N-[6-(Thiazolo[4,5-b]pyridin-2-yloxy)-benzofuran-3-ylmethyl]-terephthalamic acid

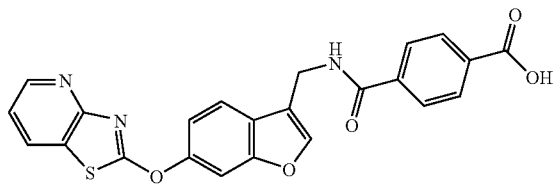 [SMILES: O=C(O)c1ccc(C(=O)NCc2coc3cc(Oc4nc5ncccc5s4)ccc23)cc1]

This compound was prepared using methods analogous to those described for Example 248. MS (ESI): mass calcd. for $C_{23}H_{15}N_3O_5S$, 445.07; m/z found, 446.0 [M+H]+. 1H NMR (500 MHz, CDCl3): 8.59 (dd, J=4.9, 1.6, 1H), 8.12-8.06 (m, 3H), 7.86 (d, J=8.4, 2H), 7.69 (s, 1H), 7.67 (d, J=8.5, 1H), 7.58 (d, J=2.0, 1H), 7.33-7.27 (m, 3H), 6.73 (s, 1H), 4.77 (d, J=5.6, 2H).

Example 397

1-[6-(Thiazolo[4,5-b]pyridin-2-yloxy)-benzofuran-3-ylmethyl]-3,4-dihydro-1H-quinolin-2-one

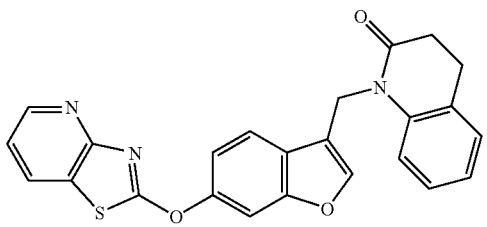 [SMILES: O=C1CCc2ccccc2N1Cc1coc2cc(Oc3nc4ncccc4s3)ccc12]

To a solution of 60% NaH (68 mg, 1.7 mmol) in DMF (2.5 mL) at 0° C. was added a solution of 3,4-dihydro-1H-quinolin-2-one (208 mg, 1.4 mmol) in DMF (2.0 mL). The reaction mixture was stirred (0° C., 30 min) before the addition of 2-(3-chloromethyl-benzofuran-6-yloxy)-thiazolo[4,5-b]pyridine hydrochloride (50 mg, 0.14 mmol). The reaction mixture was stirred (rt, 30 min), washed with water, extracted with ethyl acetate, dried, filtered and concentrated. The residue was purified by reverse phase HPLC to provide the title compound (22 mg, 36%). MS (ESI): mass calcd. for $C_{24}H_{17}N_3O_3S$, 427.10; m/z found, 428.0 [M+H]+. 1H NMR (500 MHz, CD3OD): 8.54-8.48 (m, 1H), 8.43-8.36 (m, 1H), 7.88-7.81 (m, 1H), 7.78 (d, J=8.5, 1H), 7.64 (d, J=2.1, 1H), 7.44-7.38 (m, 2H), 7.36-7.30 (m, 1H), 7.30-7.16 (m, 2H), 7.05-6.98 (m, 1H), 5.38 (s, 2H), 2.98-2.85 (m, 2H), 2.79-2.70 (m, 2H).

Examples 398 to 403 were prepared using methods analogous to those described for Example 397.

Example 398

1-[6-(Thiazolo[4,5-b]pyridin-2-yloxy)-benzofuran-3-ylmethyl]-6-trifluoromethyl-1,3-dihydro-indol-2-one

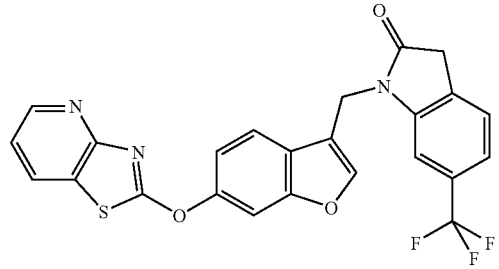 [SMILES: O=C1Cc2ccc(C(F)(F)F)cc2N1Cc1coc2cc(Oc3nc4ncccc4s3)ccc12]

MS (ESI): mass calcd. for $C_{24}H_{14}F_3N_3O_3S$, 481.07; m/z found, 482.0 [M+H]+. 1H NMR (400 MHz, CD3OD): 8.51 (dd, J=5.1, 1.6, 1H), 8.43-8.37 (m, 1H), 7.73 (d, J=8.6, 1H), 7.61 (d, J=2.0, 1H), 7.50 (s, 1H), 7.46-7.34 (m, 2H), 7.33-7.24 (m, 2H), 7.03 (s, 1H), 4.04-3.94 (m, 1H), 3.59-3.49 (m, 1H), 3.42-3.35 (m, 1H).

Example 399

1-[6-(Thiazolo[4,5-b]pyridin-2-yloxy)-benzofuran-3-ylmethyl]-1,3-dihydro-indol-2-one

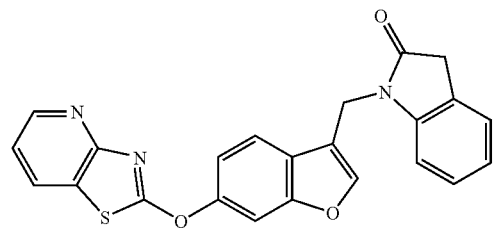 [SMILES: O=C1Cc2ccccc2N1Cc1coc2cc(Oc3nc4ncccc4s3)ccc12]

MS (ESI): mass calcd. for $C_{23}H_{15}N_3O_3S$, 413.08; m/z found, 413.9 [M+H]+. 1H NMR (500 MHz, CDCl3): 8.63 (dd, J=5.0, 1.6, 1H), 8.12 (dd, J=8.0, 1.6, 1H), 7.64 (s, 1H), 7.61 (d, J=8.5, 1H), 7.55 (d, J=1.9, 1H), 7.34-7.28 (m, 2H), 7.25-7.18 (m, 2H), 7.13-7.08 (m, 1H), 7.06-6.99 (m, 1H), 6.84-6.78 (m, 1H), 3.90-3.80 (m, 1H), 3.52-3.36 (m, 1H), 3.34-3.24 (m, 1H).

Example 400

1-[6-(Thiazolo[4,5-b]pyridin-2-yloxy)-benzofuran-3-ylmethyl]-5-trifluoromethyl-1,3-dihydro-indol-2-one

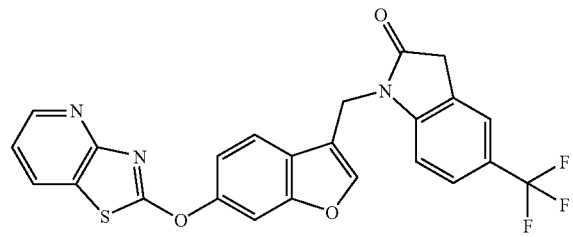 [SMILES: O=C1Cc2cc(C(F)(F)F)ccc2N1Cc1coc2cc(Oc3nc4ncccc4s3)ccc12]

MS (ESI): mass calcd. for $C_{24}H_{14}F_3N_3O_3S$, 481.07; m/z found, 482.0 [M+H]+. 1H NMR (500 MHz, CDCl3): 8.62 (dd, J=5.0, 1.6, 1H), 8.11 (dd, J=7.9, 1.6, 1H), 7.73 (s, 1H), 7.57

(d, J=8.6, 1H), 7.53 (d, J=2.1, 1H), 7.51-7.46 (m, 1H), 7.41 (s, 1H), 7.32-7.27 (m, 2H), 7.25-7.20 (m, 1H), 6.87 (d, J=8.1, 1H), 3.91-3.83 (m, 1H), 3.50-3.33 (m, 2H).

Example 401

5-Chloro-1-[6-(thiazolo[4,5-b]pyridin-2-yloxy)-benzofuran-3-ylmethyl]-1,3-dihydro-indol-2-one

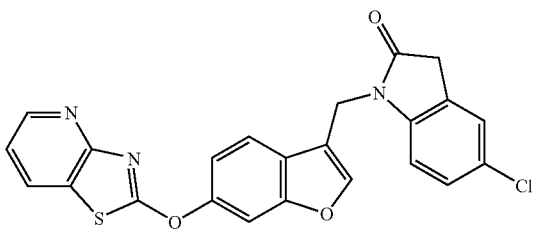 [SMILES: O=C1Cc2cc(Cl)ccc2N1Cc1coc2cc(Oc3nc4ncccc4s3)ccc12]

MS (ESI): mass calcd. for $C_{23}H_{14}ClN_3O_3S$, 447.04; m/z found, 447.9 [M+H]$^+$. $^1$H NMR (500 MHz, CDCl$_3$): 8.66-8.60 (m, 1H), 8.13 (dd, J=7.9, 1.5, 1H), 7.68 (s, 1H), 7.62 (d, J=8.6, 1H), 7.54 (d, J=2.1, 1H), 7.37-7.29 (m, 3H), 7.21-7.15 (m, 1H), 7.15-7.10 (m, 1H), 6.74 (d, J=8.2, 1H), 3.88-3.77 (m, 1H), 3.45-3.37 (m, 1H), 3.38-3.28 (m, 1H).

Example 402

6-Chloro-1-[6-(thiazolo[4,5-b]pyridin-2-yloxy)-benzofuran-3-ylmethyl]-1,3-dihydro-indol-2-one

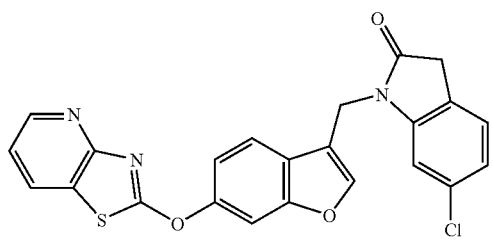 [SMILES: O=C1Cc2ccc(Cl)cc2N1Cc1coc2cc(Oc3nc4ncccc4s3)ccc12]

MS (ESI): mass calcd. for $C_{23}H_{14}ClN_3O_3S$, 447.04; m/z found, 447.9 [M+H]$^+$. $^1$H NMR (500 MHz, CDCl$_3$): 8.66-8.60 (m, 1H), 8.17-8.12 (m, 1H), 8.00 (s, 1H), 7.63 (dd, J=12.0, 5.4, 1H), 7.56-7.53 (m, 1H), 7.36-7.29 (m, 2H), 7.26-7.23 (m, 1H), 7.02-6.96 (m, 2H), 6.84 (s, 1H), 3.87-3.74 (m, 1H), 3.49-3.37 (m, 1H), 3.33-3.20 (m, 1H).

Example 403

5-Fluoro-1-[6-(thiazolo[4,5-b]pyridin-2-yloxy)-benzofuran-3-ylmethyl]-1,3-dihydro-indol-2-one

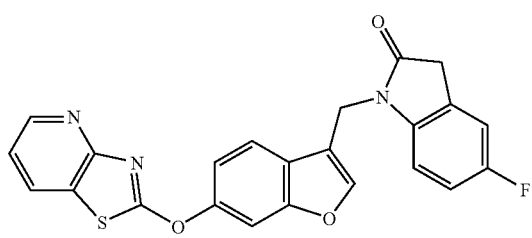 [SMILES: O=C1Cc2cc(F)ccc2N1Cc1coc2cc(Oc3nc4ncccc4s3)ccc12]

MS (ESI): mass calcd. for $C_{23}H_{14}FN_3O_3S$, 431.07; m/z found, 431.9 [M+H]$^+$. $^1$H NMR (500 MHz, CDCl$_3$): 8.69-8.56 (m, 1H), 8.16-8.06 (m, 2H), 7.62 (d, J=8.5, 1H), 7.54 (d, J=2.1, 1H), 7.38-7.28 (m, 2H), 7.26-7.20 (m, 1H), 6.96-6.82 (m, 2H), 6.81-6.70 (m, 1H), 3.89-3.78 (m, 1H), 3.47-3.38 (m, 1H), 3.34-3.24 (m, 1H).

Example 404

(R)—N-(1-Aza-bicyclo[2.2.2]oct-3-yl)-N-[6-(thiazolo[4,5-b]pyridin-2-yloxy)-benzofuran-3-ylmethyl]-acetamide formate

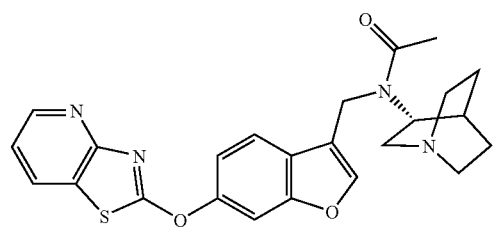 [SMILES: CC(=O)N(Cc1coc2cc(Oc3nc4ncccc4s3)ccc12)[C@H]1CN2CCC1CC2]

(R)-(1-Aza-bicyclo[2.2.2]oct-3-yl)-[6-(thiazolo[4,5-b]pyridin-2-yloxy)-benzofuran-3-ylmethyl]-amine. This compound was prepared using methods analogous to those described for Example 153, with the following variation: DMF with Et$_3$N at 50° C. for 16 hr was used instead of 4:1 CH$_3$CN/DMF with K$_2$CO$_3$ at rt for 48 hr. Crude material was used in the next step without additional purification. MS (ESI): mass calcd. for $C_{22}H_{22}N_4O_2S$, 406.15; m/z found, 407.0 [M+H]$^+$.

(R)—N-(1-Aza-bicyclo[2.2.2]oct-3-yl)-N-[6-(thiazolo[4,5-b]pyridin-2-yloxy)-benzofuran-3-ylmethyl]-acetamide formate. This compound was prepared using methods analogous to those described for Example 53, but using 10 equivalents of acetyl chloride and 10 equivalents of Et$_3$N. MS (ESI): mass calcd. for $C_{24}H_{24}N_4O_3S$, 448.16; m/z found, 449.0 [M+H]$^+$. $^1$H NMR (400 MHz, CD$_3$OD): 8.52-8.46 (m, 1H), 8.34 (dd, J=8.0, 1.6, 1H), 8.25 (s, 1H), 7.94-7.84 (m, 2H), 7.55-7.47 (m, 1H), 7.41-7.32 (m, 1H), 4.70-4.59 (m, 2H), 4.31-4.20 (m, 1H), 4.05-3.90 (m, 1H), 3.70-3.44 (m, 5H), 2.28-2.16 (m, 2H), 2.16-2.04 (m, 2H), 2.04-1.87 (m, 4H).

Example 405

2-(3-Piperidin-1-ylmethyl-benzofuran-6-yloxy)-benzothiazole

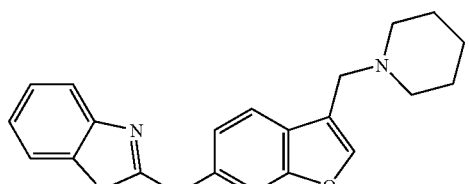

This compound was prepared using methods analogous to those described for Example 153, with the following variation: DMF with K$_2$CO$_3$ at rt for 16 hr was used instead of 4:1 CH$_3$CN/DMF with K$_2$CO$_3$ at rt for 48 hr. MS (ESI): mass calcd. for $C_{21}H_{20}N_2O_2S$, 364.1; m/z found, 364.9 [M+H]$^+$. $^1$H NMR (400 MHz, CD$_3$OD): 7.83 (d, J=8.5, 1H), 7.81 (5, 1H), 7.79-7.76 (m, 1H), 7.67-7.64 (m, 1H), 7.60 (d, J=2.1, 1H), 7.44-7.42 (m, 1H), 7.33-7.28 (m, 2H), 3.70 (5, 2H), 2.54 (br s, 4H), 1.70-1.57 (m, 4H), 1.47 (d, J=4.9, 2H).

Example 406

2-(2-Piperidin-1-ylmethyl-benzofuran-6-yloxy)-benzothiazole

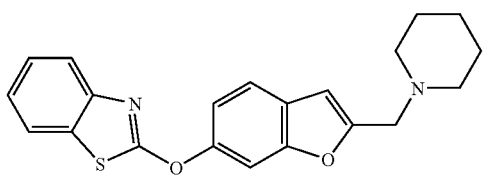 [SMILES: c1ccc2sc(Oc3ccc4cc(CN5CCCCC5)oc4c3)nc2c1]

This compound was prepared using methods analogous to those described for Example 153, with the following variation: DMF with $K_2CO_3$ at rt for 16 hr was used instead of 4:1 $CH_3CN/DMF$ with $K_2CO_3$ at rt for 48 hr. MS (ESI): mass calcd. for $C_{21}H_{20}N_2O_2S$, 364.1; m/z found, 364.9 $[M+H]^+$. $^1$H NMR (400 MHz, $CD_3OD$): 7.77-7.74 (m, 1H), 7.65 (d, J=8.5, 2H), 7.57 (d, J=1.9, 1H), 7.43-7.38 (m, 1H), 7.32-7.27 (m, 1H), 7.24 (dd, J=8.5, 2.2, 1H), 6.79 (5, 1H), 3.71 (5, 2H), 2.54 (br s, 4H), 1.67-1.58 (m, 4H), 1.51-1.41 (m, 2H).

Biological Methods:

Compounds of the invention were tested in the following assays in their free base ('), hydrochloride ("), or formate (^) salt forms.

Assay 1: Recombinant Human $LTA_4$ Hydrolase Assay for $LTA_4$ Hydrolase Inhibitor Activity Compounds of the present invention were tested for $LTA_4$ hydrolase inhibitor activity against recombinant human $LTA_4$ hydrolase ($rhLTA_4H$). Vectors were prepared and used to express $rhLTA_4H$ essentially as follows: $LTA_4$ hydrolase encoding DNA was amplified by polymerase chain reaction (PCR) using a human placental cDNA library as a template. Oligonucleotide primers for the PCR reaction were based on the 5'-end, and the complement of the 3'-end, of the published nucleotide sequence for the coding region of the human $LTA_4$ hydrolase gene (C. D. Funk et al., Proc. Natl. Acad. Sci. USA 1987, 84:6677-6681). The amplified 1.9 kb DNA fragment encoding $LTA_4$ hydrolase was isolated and cloned into the pFastBac1 vector (Invitrogen). Recombinant baculovirus was generated as described by the manufacturer, and used to infect *Spodoptera frugiperda* (Sf-9) cells. Recombinant $LTA_4$ hydrolase enzyme was purified from the infected Sf-9 cells essentially as described by J. K. Gierse et al. (Protein Expression and Purification 1993, 4:358-366). The purified enzyme solution was adjusted to contain 0.29 mg/mL $LTA_4$ hydrolase, 50 mM Tris (pH 8.0), 150 mM NaCl, 5 mM dithiothreitol, 50% glycerol, and EDTA-free Complete protease inhibitor cocktail (Roche). The specific activity of the enzyme was about 3.8 µmol/min/mg.

$LTA_4$ substrate was prepared from the methyl ester of $LTA_4$ (Cayman Chemical) by treatment with 67 equiv of NaOH under nitrogen at rt for 40 min. The $LTA_4$ substrate in its free acid form was kept frozen at −80° C. until needed. Each compound was diluted to different concentrations in assay buffer (from Assay Designs) containing 10% DMSO. A 25-µL aliquot of each compound dilution was incubated for 10 min at rt with an equal volume of assay buffer containing 10 ng of recombinant human $LTA_4H$. The solution was then adjusted to 200 µL with assay buffer. $LTA_4$ (free acid) was thawed and diluted in assay buffer to a concentration of 313 ng/mL, and 25 µL (8 ng) of $LTA_4$ substrate was added to the reaction mixture (total volume=225 µL) at time zero. Each reaction was carried out at rt for 30 min. The reaction was stopped by diluting 10 µL of the reaction mixture with 200 µL of assay buffer. $LTB_4$ was quantified in the diluted sample by a commercially available enzyme-linked immunoassay (Cayman Chemical Co.), as recommended by the manufacturer. Positive controls, under essentially identical conditions but without addition of an inhibitor compound, and negative controls, containing all assay components except enzyme, were routinely run in each experiment. $IC_{50}$ values were determined by nonlinear regression of the activity data at different compound concentrations using Graphpad Prism 4.0, one site binding competition.

The $IC_{50}$ values obtained for compounds tested in this assay are presented in Table 1. Such values should be expected to fall within the typical three-fold variability of assays of this type. The values presented here are the result of a single determination or an average of two or more determinations. Compounds that were not tested are indicated as such by a "NT" designation.

TABLE 1

| Example | $IC_{50}$ (µM) |
|---|---|
| Inter. 17 | 0.037' |
| 1 | 0.012' |
| 2 | 0.019' |
| 3 | 0.016' |
| 4 | 0.023' |
| 5 | 0.054' |
| 6 | 0.017' |
| 7 | 0.042' |
| 8 | 0.011' |
| 9 | 0.591' |
| 10 | 0.415' |
| 11 | 1.398' |
| 12 | 0.013' |
| 13 | 0.002' |
| 14 | 0.000' |
| 15 | 0.013' |
| 16 | 0.003' |
| 17 | 0.002' |
| 18 | 0.001' |
| 19 | 0.002' |
| 20 | 0.002' |
| 21 | 0.005' |
| 22 | 0.002' |
| 23 | 0.005' |
| 24 | 0.002' |
| 25 | 0.002' |
| 26 | 0.007' |
| 27 | 0.019' |
| 28 | 0.015' |
| 29 | 0.015' |
| 30 | 0.011' |
| 31 | 0.055' |
| 32 | 0.096' |
| 33 | 0.042' |
| 34 | 0.020^or' |
| 35 | 0.034' |
| 36 | 0.077' |
| 37 | 0.008^ |
| 38 | 0.029' |
| 39 | 0.275^ |
| 40 | 0.002' |
| 41 | 0.004' |
| 42 | <0.001' |
| 43 | 0.006' |
| 44 | 0.006' |
| 45 | 0.006' |
| 46 | 0.015' |
| 47 | 0.021' |
| 48 | 0.679' |
| 49 | 0.013' |
| 50 | 0.028" |
| 51 | 0.045" |
| 52 | 0.023" |
| 53 | 0.008' |
| 54 | 0.004' |

TABLE 1-continued

| Example | IC$_{50}$ (μM) |
|---|---|
| 55 | 0.003' |
| 56 | 0.081' |
| 57 | 0.093' |
| 58 | 0.010' |
| 59 | 0.111' |
| 60 | 0.169' |
| 61 | 0.610' |
| 62 | 0.382' |
| 63 | 1.639' |
| 64 | 0.093' |
| 65 | 0.100' |
| 66 | 0.030' |
| 67 | 0.034' |
| 68 | 0.020' |
| 69 | 0.047' |
| 70 | 0.001' |
| 71 | 0.017' |
| 72 | 0.027' |
| 73 | 3.460' |
| 74 | 2.026' |
| 75 | 0.714' |
| 76 | 0.028' |
| 77 | 0.035' |
| 78 | 0.226^ |
| 79 | 0.460^ |
| 80 | 0.048' |
| 81 | 0.029' |
| 82 | 0.190^ |
| 83 | 0.070^ |
| 84 | 0.236^ |
| 85 | 0.017^ |
| 86 | 0.068' |
| 87 | 0.035' |
| 88 | 0.011' |
| 89 | 0.149' |
| 90 | 0.035' |
| 91 | 0.088' |
| 92 | 0.051' |
| 93 | 0.003' |
| 94 | 0.102' |
| 95 | 0.005' |
| 96 | 0.140' |
| 97 | 0.194' |
| 98 | 0.153' |
| 99 | 0.037' |
| 100 | 0.069' |
| 101 | 0.052' |
| 102 | 0.012' |
| 103 | 0.004' |
| 104 | 0.010' |
| 105 | 0.097' |
| 106 | 0.007' |
| 107 | 0.065' |
| 108 | 0.145^ |
| 109 | 0.186^ |
| 110 | 0.207^ |
| 111 | 0.281' |
| 112 | 0.042' |
| 113 | 0.283' |
| 114 | 0.015' |
| 115 | 0.327' |
| 116 | 0.044' |
| 117 | 0.118' |
| 118 | 0.023' |
| 119 | 0.036' |
| 120 | 0.145 |
| 121 | 0.488 |
| 122 | 3.430 |
| 123 | 0.089 |
| 124 | 1.467 |
| 125 | 0.200 |
| 126 | 0.610' |
| 127 | 0.062' |
| 128 | 0.084' |
| 129 | 0.013' |
| 130 | 0.005' |
| 131 | 0.005' |
| 132 | 0.720' |
| 133 | 0.473' |
| 134 | 0.043' |
| 135 | 0.003' |
| 136 | 0.117' |
| 137 | 0.248' |
| 138 | 0.169' |
| 139 | 0.012' |
| 140 | 0.021' |
| 141 | 0.02' |
| 142 | NT |
| 143 | NT |
| 144 | 0.078' |
| 145 | 0.0097' |
| 146 | 0.017' |
| 147 | 0.012' |
| 148 | NT |
| 149 | 0.17' |
| 150 | NT |
| 151 | NT |
| 152 | NT |
| 153 | 0.002' |
| 154 | 0.007' |
| 155 | 0.002' |
| 156 | 0.017' |
| 157 | 0.008' |
| 158 | 0.006' |
| 159 | 0.016' |
| 160 | 0.005' |
| 161 | 0.009' |
| 162 | 0.001' |
| 163 | 0.107' |
| 164 | 0.026' |
| 165 | 0.095' |
| 166 | 0.286' |
| 167 | 0.088' |
| 168 | 0.036' |
| 169 | 0.003' |
| 170 | 0.005' |
| 171 | 0.059' |
| 172 | 0.009' |
| 173 | 0.187' |
| 174 | 0.130' |
| 175 | 0.002' |
| 176 | 0.060' |
| 177 | 0.013' |
| 178 | 0.020' |
| 179 | 0.011' |
| 180 | 0.021' |
| 181 | 0.003' |
| 182 | 0.009' |
| 183 | 0.006' |
| 184 | 0.008' |
| 185 | 0.004' |
| 186 | 0.001' |
| 187 | 0.001' |
| 188 | 0.026' |
| 189 | 0.003' |
| 190 | 0.116^ |
| 191 | 0.010^ |
| 192 | 0.043^ |
| 193 | 0.052' |
| 194 | 0.039' |
| 195 | 0.080' |
| 196 | 0.011^ |
| 197 | 0.004^or' |
| 198 | 0.011^ |
| 199 | 0.338^ |
| 200 | 1.134^ |
| 201 | 0.236' |
| 202 | 1.517' |
| 203 | 2.567' |
| 204 | 0.169' |
| 205 | 0.120' |
| 206 | 0.147' |
| 207 | 0.001' |
| 208 | 0.001' |
| 209 | 0.053^or' |
| 210 | 0.005' |

TABLE 1-continued

| Example | IC$_{50}$ (μM) |
|---|---|
| 211 | 0.011' |
| 212 | 0.004' |
| 213 | 0.005' |
| 214 | 0.002' |
| 215 | 0.003' |
| 216 | 0.003' |
| 217 | 0.004' |
| 218 | 0.005' |
| 219 | 0.002' |
| 220 | 0.005' |
| 221 | 0.227' |
| 222 | 0.365' |
| 223 | 0.175' |
| 224 | 0.002' |
| 225 | 0.765' |
| 236 | 0.060^ |
| 237 | 0.002' |
| 238 | 0.005' |
| 239 | 0.006' |
| 240 | 0.005' |
| 241 | 0.004^ or ' |
| 242 | 0.032' |
| 243 | 0.006' |
| 244 | 0.005' |
| 245 | 0.004' |
| 246 | 0.014' |
| 247 | 0.009' |
| 248 | 0.012^ or ' |
| 249 | 0.012' |
| 250 | 0.467^ |
| 251 | 0.027^ |
| 252 | 0.024^ |
| 253 | 0.039^ |
| 254 | 0.108^ |
| 255 | 0.031^ |
| 256 | 0.061' |
| 257 | 0.003' |
| 258 | 0.022' |
| 259 | 0.005^ |
| 265 | <0.001^ |
| 266 | 0.002^ |
| 267 | 0.009^ |
| 268 | 0.008' |
| 269 | 0.004' |
| 270 | 0.026^ |
| 271 | 0.005^ |
| 272 | 0.005^ |
| 273 | 0.160^ |
| 274 | 0.250^ |
| 275 | 0.002' |
| 276 | 0.003^ |
| 277 | 0.012' |
| 279 | 0.044' |
| 280 | 0.010^ |
| 281 | 0.028^ |
| 282 | 0.017^ |
| 283 | 0.035^ |
| 284 | 0.024^ |
| 285 | 0.016^ |
| 286 | 0.001^ |
| 287 | 0.026^ |
| 288 | 0.019^ |
| 289 | 0.004^ |
| 290 | 0.040^ |
| 291 | 0.014^ |
| 292 | 0.040^ |
| 293 | 0.019^ |
| 294 | 0.024' |
| 295 | 0.004^ |
| 296 | 0.850^ |
| 297 | 0.019' |
| 298 | 0.012' |
| 299 | 0.016' |
| 300 | 0.020' |
| 301 | 0.015^ |
| 302 | 0.020^ |
| 303 | 0.011^ |
| 304 | 0.003^ |
| 305 | 0.031' |
| 306 | 0.095^ |
| 307 | 0.005^ |
| 308 | 0.009^ |
| 309 | 0.005' |
| 310 | 0.013' |
| 311 | 0.230' |
| 312 | 0.022^ |
| 314 | 0.015' |
| 315 | 0.010' |
| 316 | 0.029' |
| 317 | 0.035' |
| 318 | <0.001^ |
| 319 | 0.052^ |
| 320 | 0.015^ |
| 321 | 0.040^ |
| 322 | 0.006' |
| 323 | 0.009' |
| 324 | 0.008' |
| 325 | 0.026' |
| 326 | 0.021' |
| 327 | 0.029' |
| 328 | 0.012' |
| 329 | 0.054^ |
| 330 | 0.054' |
| 331 | 0.054' |
| 332 | 0.008^ |
| 333 | 0.006^ |
| 334 | 0.020' |
| 335 | 0.005^ |
| 336 | 0.110' |
| 337 | 0.270^ |
| 338 | 0.450^ |
| 339 | 0.012^ |
| 340 | 0.012^ |
| 341 | 0.470' |
| 342 | 0.016' |
| 343 | 0.250^ |
| 344 | 0.021' |
| 345 | 0.007' |
| 346 | 0.013' |
| 347 | 0.024' |
| 348 | 0.067^ |
| 349 | 0.026^ |
| 350 | 0.026' |
| 351 | 0.002^ |
| 352 | 0.050' |
| 353 | 0.006' |
| 354 | 0.007' |
| 355 | 0.003' |
| 356 | 0.018' |
| 357 | 0.007' |
| 358 | 0.009' |
| 359 | 0.008' |
| 360 | 0.017' |
| 361 | 0.020' |
| 363 | 0.037' |
| 364 | 0.018' |
| 365 | 0.110' |
| 366 | 0.020' |
| 367 | 0.160' |
| 368 | 0.026' |
| 369 | 0.019' |
| 370 | 0.009' |
| 371 | 0.025' |
| 372 | 0.030' |
| 373 | 0.034' |
| 374 | 0.011' |
| 375 | 0.041' |
| 376 | 0.013' |
| 377 | 0.020' |
| 378 | 0.022' |
| 379 | 0.010' |
| 380 | 0.007' |
| 381 | 0.110' |
| 382 | 0.010' |
| 383 | 0.050' |
| 384 | 0.012' |

TABLE 1-continued

| Example | IC$_{50}$ (μM) |
|---|---|
| 385 | 1.530' |
| 386 | 0.210' |
| 387 | 0.150' |
| 388 | 0.150' |
| 389 | 0.120' |
| 390 | 0.027' |
| 391 | 0.074' |
| 392 | 0.029' |
| 393 | 0.100' |
| 394 | 0.085' |
| 395 | 0.085' |
| 396 | 0.052' |
| 397 | 0.016' |
| 398 | 0.470' |
| 399 | 0.013' |
| 400 | 1.120' |
| 401 | 1.020' |
| 402 | 0.032' |
| 403 | 0.047' |
| 404 | 0.002' |
| 405 | 0.077' |
| 406 | 0.492' |

Assay 2: LTB$_4$ Production by Calcium Ionophore-Stimulated Murine Blood for LTA$_4$H Inhibitor Activity CD-1 mice were sacrificed, and blood was collected in heparin-containing syringes by cardiac puncture. The blood was diluted 1 in 15 with RPMI-1640 medium, and 200-μL aliquots of the diluted blood were added to wells of a 96-well microtiter plate. LTA$_4$H inhibitor test compounds were prepared at different concentrations in RPMI-1640 medium containing 1% DMSO, and 20 μL of each test solution was added to a well containing diluted whole blood (final DMSO concentration of 0.1°)/0). After the microtiter plate contents were incubated for 15 min at 37° C. in a humidified incubator, calcium ionophore A23187 (Sigma Chemical Co., St. Louis, Mo.) was added to each sample well (final concentration=7 μg/mL). The incubation was continued under the same conditions for an additional 30 min to allow LTB$_4$ formation. The reaction was terminated by centrifugation (833×g, 10 min at 4° C.), and supernatants were analyzed for LTB$_4$ by a commercially available enzyme-linked immunoassay (Cayman Chemical Co.) according to the manufacturer's instructions. Positive controls, under essentially identical conditions but without addition of an inhibitor compound, and negative unstimulated controls, containing all assay components except calcium ionophore, were routinely run in each experiment. IC$_{50}$ values for compounds tested in this assay were determined by nonlinear regression of the activity data at different compound concentrations using Graphpad Prism 4.0, one site binding competition and are presented in Table 2. The values presented here are the result of a single determination or an average of two or more determinations.

TABLE 2

| Example | IC$_{50}$ (μM) |
|---|---|
| Inter. 17 | 1.005' |
| 1 | 0.068' |
| 2 | 0.078' |
| 3 | 0.303' |
| 4 | 0.190' |
| 5 | 0.901' |
| 6 | 0.968' |
| 7 | 0.476' |
| 8 | 1.140' |
| 12 | 0.250' |
| 13 | 0.100' |
| 14 | 0.066' |
| 15 | 0.152' |

TABLE 2-continued

| Example | IC$_{50}$ (μM) |
|---|---|
| 16 | 0.017' |
| 17 | 0.118' |
| 18 | 0.301' |
| 19 | 0.104' |
| 20 | 0.081' |
| 21 | 0.161' |
| 22 | 0.079' |
| 23 | 0.114' |
| 24 | 0.341' |
| 25 | 0.100' |
| 26 | 0.188' |
| 27 | 0.136' |
| 28 | 0.079' |
| 29 | 0.234' |
| 30 | 0.143' |
| 31 | 0.188' |
| 32 | 0.258' |
| 33 | 1.518' |
| 34 | 0.401' |
| 35 | 0.234' |
| 36 | 0.423' |
| 37 | 0.310' |
| 38 | 0.350' |
| 40 | 0.023' |
| 41 | 0.034' |
| 42 | 0.027' |
| 43 | 0.409' |
| 44 | 0.222' |
| 45 | 1.344' |
| 46 | 0.667' |
| 47 | 0.870' |
| 49 | 10.000' |
| 50 | 0.739" |
| 51 | 0.180" |
| 52 | 0.411" |
| 53 | 0.204' |
| 54 | 0.165' |
| 55 | 0.129' |
| 56 | 0.290' |
| 57 | 0.444' |
| 58 | 0.250' |
| 64 | 2.430' |
| 65 | 1.113' |
| 66 | 1.134' |
| 67 | 0.295' |
| 68 | 0.450' |
| 69 | 1.222' |
| 70 | 0.076' |
| 71 | 0.087' |
| 72 | 0.100' |
| 76 | 0.048' |
| 77 | 0.030' |
| 80 | 0.350' |
| 81 | 0.450' |
| 83 | 0.119' |
| 85 | 0.210' |
| 86 | 0.085' |
| 87 | 0.077' |
| 88 | 0.320' |
| 90 | 0.022' |
| 91 | 0.097' |
| 92 | 0.400' |
| 93 | 0.023' |
| 94 | 0.202' |
| 95 | 0.026' |
| 96 | 0.110' |
| 99 | 0.063' |
| 100 | 0.160' |
| 101 | 0.202' |
| 102 | 0.293' |
| 103 | 0.132' |
| 104 | 0.016' |
| 105 | 0.488' |
| 106 | 0.014' |
| 107 | 0.276' |
| 112 | 0.070' |
| 114 | 0.085' |
| 116 | 0.055' |

TABLE 2-continued

| Example | IC$_{50}$ (μM) |
|---|---|
| 118 | 0.050' |
| 119 | 0.220' |
| 129 | 0.180' |
| 134 | 0.740' |
| 135 | 0.110' |
| 139 | 0.467' |
| 140 | 8.506' |
| 141 | 0.640' |
| 144 | 2.443' |
| 145 | 0.171' |
| 146 | 0.582' |
| 147 | 0.568' |
| 153 | 0.025' |
| 154 | 0.026' |
| 155 | 0.009' |
| 156 | 0.021' |
| 157 | 0.016' |
| 158 | 0.032' |
| 159 | 0.079' |
| 160 | 0.049' |
| 161 | 0.069' |
| 162 | 0.026' |
| 164 | 0.230' |
| 165 | 0.840' |
| 167 | 0.220' |
| 168 | 0.210' |
| 169 | 0.023' |
| 170 | 0.080' |
| 171 | 0.280' |
| 172 | 0.230' |
| 175 | 0.176' |
| 176 | 0.200' |
| 177 | 0.110' |
| 178 | 0.290' |
| 179 | 0.075' |
| 180 | 0.038' |
| 181 | 0.033' |
| 182 | 0.039' |
| 183 | 0.057' |
| 184 | 0.049' |
| 185 | 0.012' |
| 186 | 0.006' |
| 187 | 0.021' |
| 188 | 0.063' |
| 189 | 0.070' |
| 191 | 0.833^ |
| 192 | 0.120^ |
| 193 | 0.260' |
| 194 | 0.260' |
| 195 | 0.151' |
| 196 | 0.038^ |
| 197 | 0.015^,or, |
| 198 | 0.110^ |
| 202 | 2.700' |
| 206 | 0.340' |
| 207 | 0.160' |
| 208 | 0.024' |
| 209 | 0.054^,or, |
| 210 | 0.034' |
| 211 | 0.013' |
| 212 | 0.019' |
| 213 | 0.025' |
| 214 | 0.019' |
| 215 | 0.021' |
| 216 | 0.028' |
| 217 | 0.036' |
| 218 | 0.053' |
| 219 | 0.020' |
| 220 | 0.012' |
| 224 | 0.366' |
| 236 | 0.190^ |
| 237 | 0.022' |
| 238 | 0.044' |
| 239 | 0.018' |
| 240 | 0.070' |
| 241 | 0.069^,or, |
| 242 | 0.068' |
| 243 | 0.080' |
| 244 | 0.024' |
| 245 | 0.032' |
| 246 | 0.090' |
| 247 | 0.024' |
| 248 | 0.020^,or, |
| 249 | 0.054' |
| 251 | 0.220^ |
| 252 | 0.048^ |
| 253 | 0.091^ |
| 255 | 0.072^ |
| 256 | 0.260' |
| 257 | 0.169' |
| 258 | 0.088' |
| 259 | 0.074^ |
| 266 | 0.100^ |
| 267 | 0.044^ |
| 268 | 0.150' |
| 269 | 0.012' |
| 270 | 0.100^ |
| 271 | 0.079^ |
| 272 | 0.015^ |
| 275 | 0.034' |
| 276 | 0.077^ |
| 277 | 0.130' |
| 279 | 0.130' |
| 280 | 0.130^ |
| 281 | 0.077^ |
| 282 | 0.072^ |
| 283 | 0.130^ |
| 284 | 0.160^ |
| 285 | 0.050^ |
| 286 | 0.055^ |
| 287 | 0.240^ |
| 288 | 0.170^ |
| 289 | 0.040^ |
| 290 | 0.170^ |
| 291 | 0.130^ |
| 295 | 0.055^ |
| 297 | 0.240' |
| 298 | 0.017' |
| 299 | 0.012' |
| 300 | 0.150' |
| 301 | 0.004^ |
| 302 | 0.078^ |
| 303 | 0.015^ |
| 304 | 0.024^ |
| 306 | 0.010^ |
| 307 | 0.008^ |
| 308 | 0.071^ |
| 309 | 0.066' |
| 310 | 0.036' |
| 312 | 0.160^ |
| 314 | 0.028' |
| 315 | 0.034' |
| 316 | 0.120' |
| 321 | 0.051^ |
| 322 | 0.030' |
| 323 | 0.041' |
| 324 | 0.016' |
| 325 | 0.078' |
| 326 | 0.120' |
| 327 | 0.130' |
| 328 | 0.093' |
| 330 | 1.040' |
| 331 | 1.060' |
| 332 | 0.100^ |
| 333 | 0.024^ |
| 335 | 0.200^ |
| 339 | 0.070^ |
| 340 | 0.610^ |
| 342 | 0.230' |
| 344 | 0.100' |
| 345 | 0.072' |
| 347 | 0.130' |
| 348 | 0.360' |
| 349 | 0.860^ |
| 350 | 0.038' |
| 351 | 0.094^ |

TABLE 2-continued

| Example | IC$_{50}$ (μM) |
|---|---|
| 352 | 0.110' |
| 353 | 0.022' |
| 354 | 0.200' |
| 355 | 0.068' |
| 356 | 0.260' |
| 357 | 0.220' |
| 358 | 0.014' |
| 359 | 0.190' |
| 360 | 0.350' |
| 361 | 0.010' |
| 363 | 0.400' |
| 364 | 0.310' |
| 366 | 0.061' |
| 368 | 0.170' |
| 369 | 0.100' |
| 370 | 0.030' |
| 371 | 0.084' |
| 372 | 0.047' |
| 373 | 0.100' |
| 374 | 0.050' |
| 375 | 0.610' |
| 376 | 0.085' |
| 377 | 0.410' |
| 378 | 0.110' |
| 379 | 0.150' |
| 380 | 0.035' |
| 382 | 0.060' |
| 383 | 0.200' |
| 384 | 0.120' |
| 390 | 0.270' |
| 391 | 0.560' |
| 392 | 0.290' |
| 397 | 0.820' |
| 399 | 0.300' |
| 402 | 0.400' |
| 403 | 0.690' |

Assay 3: Murine Arachidonic Acid-Induced Inflammation Model

LTA$_4$H inhibitor compounds of the present invention were dissolved in 20% cyclodextran/H$_2$O at a concentration of 3 mg/mL. The solutions were administered by oral gavage to female Balb/c mice weighing approximately 20 grams each (0.2 mL per mouse, 30 mg of LTA$_4$H inhibitor compound per kg). Sixty minutes after being administered an LTA$_4$ inhibitor, each mouse received topical application of 20 μL of arachidonic acid (100 mg/mL in acetone) to the left ear and 20 μL of acetone only to the right ear. After 3 h, the mice were sacrificed, blood was withdrawn in heparinized syringes, and 8 mm ear biopsies were taken. Ear biopsies were weighed to determine edema and then frozen at −80° C. until needed for determination of neutrophil influx.

One hundred-microliter aliquots of heparinized blood were added to wells of a microtiter plate, along with equal volumes of RPMI-1640 medium, and calcium ionophore A23187 was added to each sample well (final concentration=7 μg/μL). The microtiter plate contents were incubated for 30 min at 37° C. in a humidified incubator. The reaction was terminated by centrifugation (833×g, 10 min at 4° C.). Supernatants were analyzed for LTB$_4$ by a commercially available enzyme-linked immunoassay (Cayman Chemical Co.) in accordance with the manufacturer's instructions. The percent inhibition of ex vivo stimulated LTB$_4$ production (% Inh. LTB$_4$) was determined by comparison to animals treated identically except that the solution administered by oral gavage was devoid of inhibitor compound.

Neutrophil influx was quantified by measuring the activity of myeloperoxidase (MPO), a neutrophil-specific enzyme. The ear biopsies were homogenized in 0.5 mL extraction buffer (0.3 M sucrose, 0.22% (w/v) hexadecyl trimethyl ammonium bromide (CTAB), and 2.5 mM citrate prepared from 0.5 M citrate stock solution (pH 5.0)), in a Fast-Prep-24 (MP™) (40 seconds at 6 mps). Debris was removed by centrifugation at 14000×g for 10 min. Aliquots of 10 μL of the resulting supernatant were added to wells of a microtiter plate, along with 90-μL aliquots of dilution buffer (10 mM citrate, 0.22% CTAB), followed by addition of 20 μL TMB liquid substrate system (Sigma Chemical Co.) to each sample well. The microtiter plate contents were held at room temperature until the sample with the highest concentration of MPO reached an absorbance value of 0.4 at 650 nm. The reaction was stopped by addition of 50 μL 1 M H$_2$SO$_4$ to each sample well, and the myeloperoxidase activity in each sample was determined from the absorbance at 405 nm. The background value from the right ear, treated only with acetone, was subtracted from that for the left ear, treated with arachidonic acid in acetone, for each animal. The percent inhibition of neutrophil influx (% Inh. MPO) by compounds of the invention was determined by comparison to animals treated identically, except that the solution administered by oral gavage was devoid of inhibitor compound. Results for compounds tested in this assay are presented in Table 3. All compounds were assayed in their free base form.

TABLE 3

| Ex | % Inh. MPO | % Inh. LTB$_4$ |
|---|---|---|
| 41 | 62' | 65' |
| 56 | 45' | 40' |
| 58 | 57' | 84' |
| 76 | 89' | 85' |
| 77 | 77' | 85' |
| 90 | 50' | 61' |
| 93 | 87' | 85' |
| 95 | 79' | 80' |
| 96 | 53' | 66' |
| 99 | 58' | 15' |
| 100 | 33' | 44' |
| 101 | 65' | 53' |
| 103 | 18' | 0' |
| 104 | 92' | 83' |
| 106 | 81' | 85' |
| 107 | 82' | 75' |
| 112 | 17' | 56' |
| 116 | 66' | 76' |
| 118 | 97' | 89' |
| 119 | 83' | 78' |
| 135 | 42' | 85' |
| 153 | 82' | 84' |
| 154 | 83' | 83' |
| 155 | 88' | 85' |
| 156 | 86' | 91' |
| 157 | 93' | 97' |
| 158 | 87' | 95' |
| 159 | 78' | 83' |
| 160 | 77' | 90' |
| 162 | 87' | 90' |
| 167 | 77' | 78' |
| 168 | 74' | 70' |
| 169 | 92' | 85' |
| 170 | 70' | 76' |
| 177 | 12' | 70' |
| 182 | 67' | 85' |
| 183 | 85' | 83' |
| 184 | 53' | 82' |
| 185 | 64' | 75' |
| 186 | 79' | 86' |
| 187 | 88' | 83' |
| 188 | 78' | 73' |
| 189 | 84' | 76' |
| 196 | 93^ | 91^ |
| 197 | 92^ori | 91^ori |
| 198 | 74^ | 80^ |
| 208 | 92' | 93' |
| 209 | 82^ori | 68^ori |
| 211 | 86' | 92' |
| 213 | 92' | 80' |
| 214 | 88' | 90' |
| 215 | 78' | 88' |

TABLE 3-continued

| Ex | % Inh. MPO | % Inh. LTB₄ |
|---|---|---|
| 216 | 87' | 87' |
| 218 | 98' | 83' |
| 236 | 34^ | 39^ |
| 237 | 81' | 90' |
| 238 | 77' | 93' |
| 239 | 90' | 71' |
| 240 | 0' | 50' |
| 241 | 85^or' | 77^or' |
| 244 | 89' | 80.7' |
| 248 | 90^or' | 83.0^or' |
| 256 | 83' | 68.4' |
| 257 | 87' | 68.7' |
| 258 | 72' | 70.9' |
| 269 | 92' | 74' |
| 307 | 78^ | 81^ |
| 309 | 81' | 70' |
| 339 | 50^ | 50^ |
| 366 | 50' | 78' |
| 369 | 76' | 58' |
| 370 | 69' | 78' |
| 371 | 82' | 54' |
| 372 | 53' | 62' |
| 374 | 37' | 7' |

While the invention has been illustrated by reference to examples, it is understood that the invention is intended not to be limited to the foregoing detailed description.

What is claimed is:

1. A chemical entity selected from compounds of Formula (I), pharmaceutically acceptable salts of compounds of Formula (I), and pharmaceutically acceptable prodrugs of compounds of Formula (I)

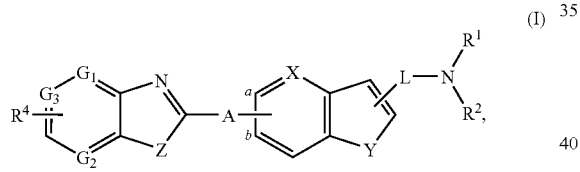
(I)

wherein

A is O, bound at site a or at site b;

Z is O or S;

G₁, G₂ and G₃ are each independently CR⁴ or N;

R⁴ is H, —C₁₋₄alkyl, or halo;

X is CH or N;

Y is O, S, or NR³;

R³ is H or —C₁₋₄alkyl;

when Y is O, then L is —CH₂—, —CH₂CH₂—, or —C(O)—;

when Y is S or NR³, then L is —CH₂— or —CH₂CH₂—;

R¹ and R² are each independently H, —C₁₋₄alkyl, —C(O)R^i, —(CH₂)₂C(O)OR³, —(CH₂)₂N(CH₂CH₃)₂, —(CH₂)₃N(CH₃)₂, —C₃₋₆cycloalkyl, —(CH₂)₁₋₄OCH₃, indan-2-yl,

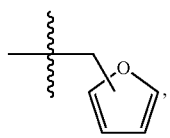 , 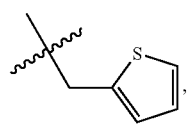 , 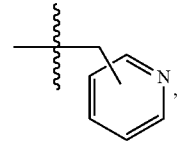 ,

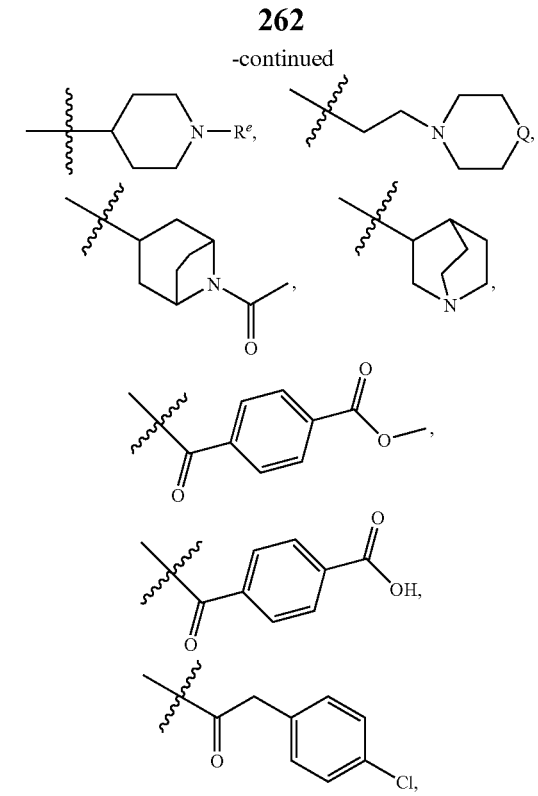

or —(CH₂)₀₋₂—(O)₀₋₁-phenyl wherein said phenyl is optionally substituted with halo, —OCH₃, or —SO₂NH₂; provided that R¹ and R² are not both H simultaneously;

R^i is —CH₃, 4-acetyl-piperazin-1-ylmethyl, 3-methyl-isoxazol-5-ylmethyl, 4-hydroxy-cyclohexyl, or

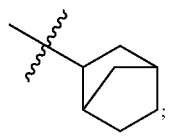 [SMILES: *C1CC2CCC1C2 ; ";"] ;

or

R¹ and R² are taken together as in one of the following assignments (i) and (ii);

(i) R¹ and R² taken together with the nitrogen member to which they are attached form an unbridged monocyclic moiety, said moiety optionally containing one additional heteroatom member selected from N, O, and S; said moiety being optionally substituted with R⁵ and (R⁵')ₘ;

m is 0 or 1;

when m is 1, R⁵' is —C₁₋₄alkyl, halo, or OH;

R⁵ is selected from H; halo; =O; —OH; —OR³; —CF₃; —S(O)(O)CH₃; —C₁₋₄alkyl; —OC₁₋₄alkyl; —C(CH₃)₂OH; —(CH₂)₀₋₁C(O)OR³; —N(R³)₂; —CH₂OH; —CH₂OCH₃; —(CH₂)₀₋₂NR⁹C(O)R⁷; —(CH₂)₀₋₂NHS(O)(O)CH₃; —C(O)R⁸; —C₃₋₆cycloalkyl; pyrimidin-2-yloxy; 1-piperidinyl; 1-piperidinyl-2-one; 1-pyrrolidinyl; 4-morpholinyl; pyridinyl; pyrimidyl; thiophenylmethyl; 5-oxo-1; 5-dihydro-[1,2,4]triazol-4-yl; —(CH₂)₀₋₂-phenyl wherein said phenyl is optionally substituted with halo or OCH₃; and 1-pyrrolidinyl-2-one optionally substituted with —OH;

Q is CH₂ or O;

R⁷ is —C₁₋₄alkyl, —NH₂, or —OC₁₋₄alkyl;

R⁸ is —C₁₋₄alkyl; —NH₂; —NHCH₃; —C₃₋₆cycloalkyl; —(CH₂)₀₋₁phenyl wherein said phenyl is optionally substituted with halo or CO₂H; 1-pyrrolidinyl; or

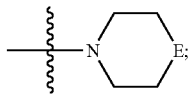

E is CH₂, O, or N(CH₃);
R⁹ is H, —C₁₋₄alkyl, or —C₃₋₆cycloalkyl;
(ii) R¹ and R² taken together with the nitrogen member to which they are attached form one of the following

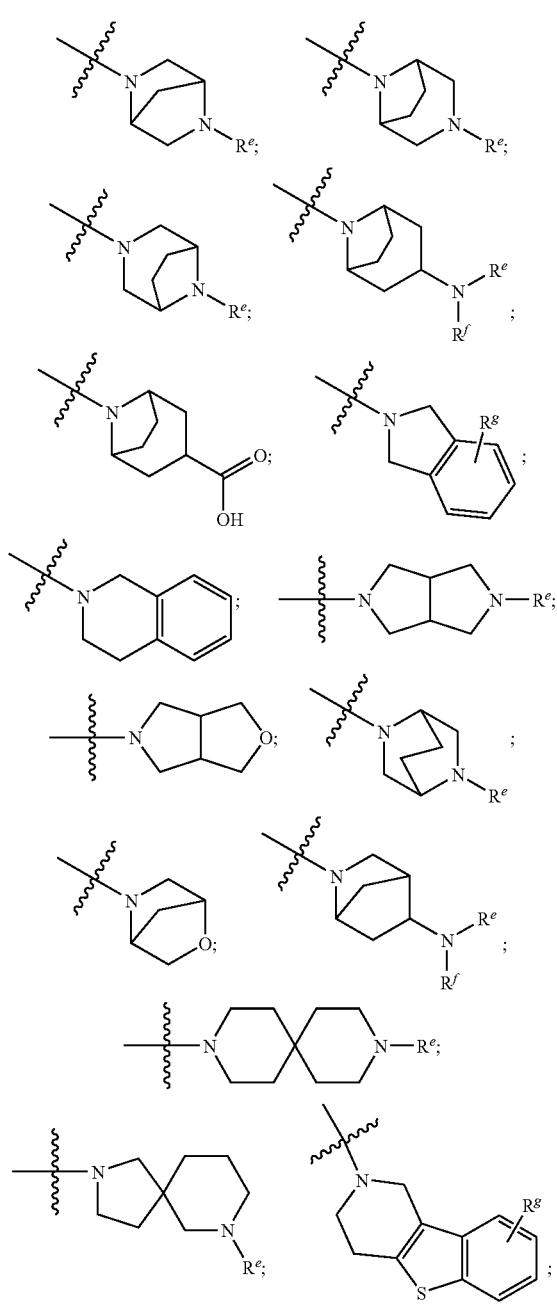

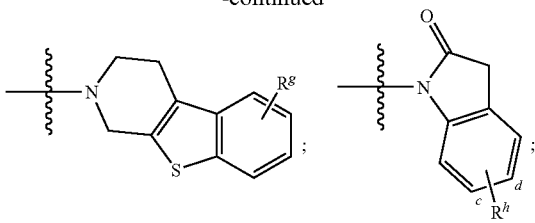

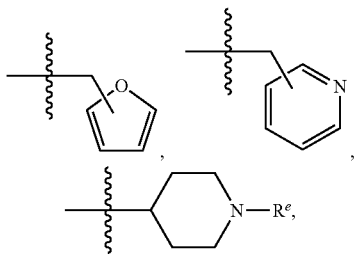

Rᵉ is H, —C₁₋₄alkyl, —C(O)C₁₋₄alkyl, —C(O)OC₁₋₄alkyl, —C(O)NH₂, —C(O)-tetrahydrofuranyl, —C(O)CH₂OH, —C(O)isoxazol-5-yl, —C(O)furan-3-yl, —C(O)pyrazin-2-yl, —C(O)cyclobutyl, —S(O)(O)CH₃, or 4-methoxycarbonyl-benzyl;
Rᶠ is H, —CH₃, or —CH₂C(O)OR³;
Rᵍ is H or halo; and
Rʰ is bound at site c or d and is selected from H, CF₃, and halo.

2. A chemical entity as in claim 1,
wherein
L is —CH₂— or —CH₂CH₂—;
R¹ and R² are each independently H, —C₁₋₄alkyl, —C₃₋₆cycloalkyl, —(CH₂)₁₋₄OCH₃, or benzyl, provided that R¹ and R² are not both H simultaneously; or
R¹ and R² are taken together as in one of the following assignments (i) and (ii);
(i) R¹ and R² taken together with the nitrogen member to which they are attached form an unbridged monocyclic moiety, said moiety optionally containing one additional heteroatom member selected from N, O, and S; said moiety being optionally substituted with $R^5$;

$R^5$ is selected from H, halo, —$CF_3$, —S(O)(O)$CH_3$, —$C_{1-4}$alkyl, —C($CH_3$)$_2$OH, —($CH_2$)$_{0-1}$C(O)$OR^3$, —$NH_2$, —$CH_2$OH, —$CH_2$O$CH_3$, —($CH_2$)$_{0-1}$NHC(O)$R^7$, —NHS(O)(O)$CH_3$, —C(O)$R^8$, phenyl, pyridinyl, pyrimidin-2-yloxy, and 1-pyrrolidinyl-2-one optionally substituted with —OH;

$R^7$ is —$C_{1-4}$alkyl, —$NH_2$, or —$OC_{1-4}$alkyl;

$R^8$ is —$C_{1-4}$alkyl, —$NH_2$, —$NHCH_3$, 1-pyrrolidinyl, or

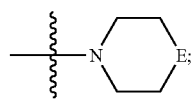

E is $CH_2$, O, or N($CH_3$); or (ii) $R^1$ and $R^2$ taken together with the nitrogen member to which they are attached form one of the following

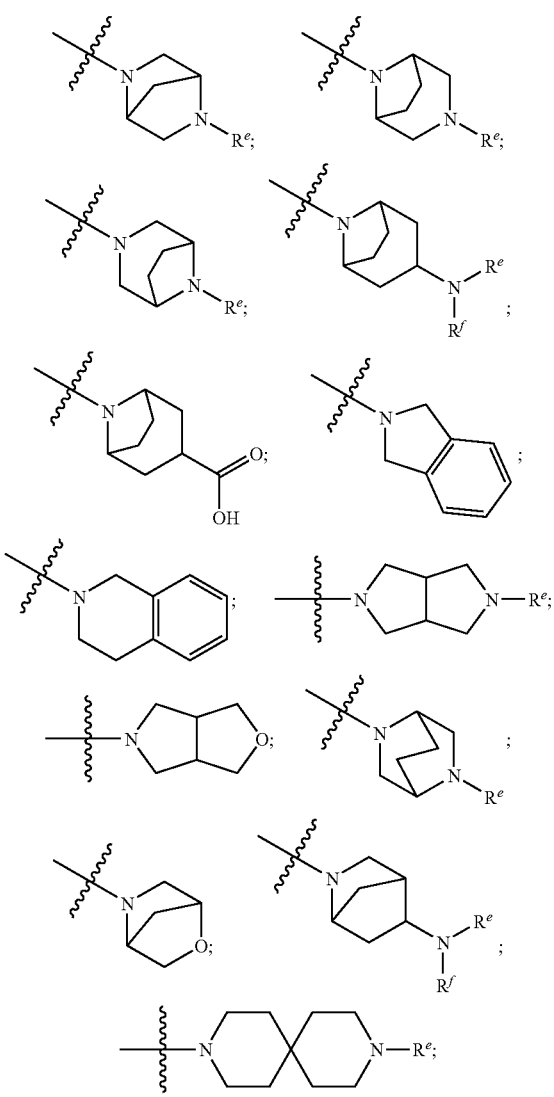

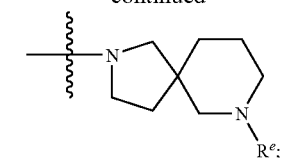

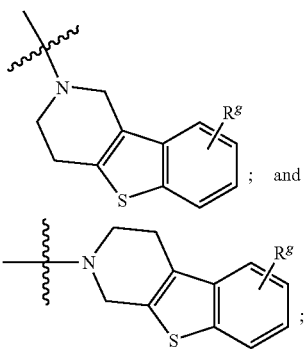

$R^e$ is H, —C(O)$C_{1-4}$alkyl, —C(O)O$C_{1-4}$alkyl, —S(O)(O)$CH_3$, or —C(O)$NH_2$;

$R^f$ is H, —$CH_3$, or —$CH_2$C(O)$OR^3$; and $R^g$ is H or halo.

3. A chemical entity as in claim 1, wherein

L is —$CH_2$— or —$CH_2CH_2$—;

$R^1$ and $R^2$ are each independently H, —$C_{1-4}$alkyl, or benzyl, provided that $R^1$ and $R^2$ are not both H simultaneously; or $R^1$ and $R^2$ are taken together as in one of the following assignments (i) and (ii);

(i) $R^1$ and $R^2$ taken together with the nitrogen member to which they are attached form an unbridged monocyclic moiety, said moiety optionally containing one additional heteroatom member selected from N, O, and S; said moiety being optionally substituted with $R^5$;

$R^5$ is selected from H, halo, —S(O)(O)$CH_3$, —$C_{1-4}$alkyl, —($CH_2$)$_{0-1}$C(O)$OR^3$, —$NH_2$, —$CH_2$OH, —NHC(O)$R^7$, —NHS(O)(O)$CH_3$, —C(O)$R^8$, phenyl, pyrimidin-2-yloxy, and 1-pyrrolidinyl-2-one optionally substituted with —OH;

$R^7$ is —$CH_3$, —$NH_2$, or —$OC_{1-4}$alkyl;

$R^8$ is —$C_{1-4}$alkyl, —$NH_2$, —$NHCH_3$, 1-pyrrolidinyl, or

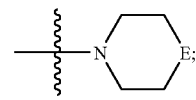

E is $CH_2$, O, or N($CH_3$); or (ii) $R^1$ and $R^2$ taken together with the nitrogen member to which they are attached form one of the following

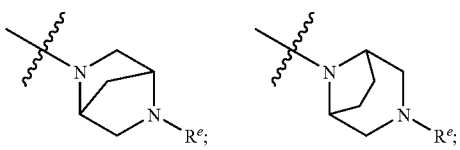

-continued

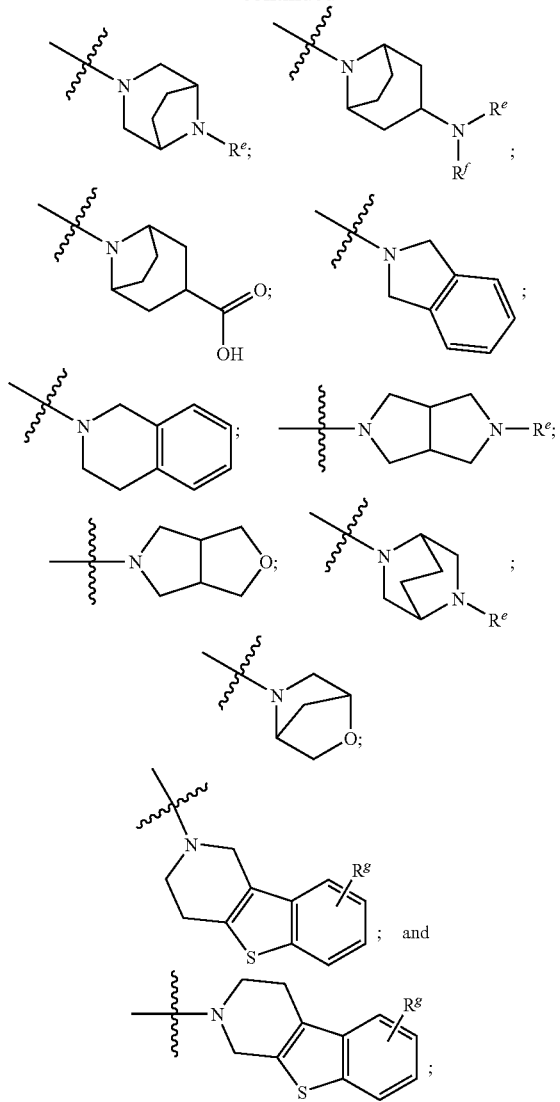

$R^e$ is H, —C(O)C$_{1-4}$alkyl, —C(O)OC$_{1-4}$alkyl, or —C(O)NH$_2$;
$R^f$ is H, —CH$_3$, or —CH$_2$C(O)OR$^3$; and
$R^g$ is H or halo.

4. A chemical entity as in claim 1, wherein Z is O.
5. A chemical entity as in claim 1, wherein Z is S.
6. A chemical entity as in claim 1, wherein G$_1$ is N.
7. A chemical entity as in claim 1, wherein G$_1$ is CR$^4$.
8. A chemical entity as in claim 1, wherein G$_2$ is N.
9. A chemical entity as in claim 1, wherein G$_2$ is CR$^4$.
10. A chemical entity as in claim 4, wherein G$_1$ is N.
11. A chemical entity as in claim 5, wherein G$_1$ is N.
12. A chemical entity as in claim 11, wherein X is CH.
13. A chemical entity as in claim 1, wherein Y is NR$^3$.
14. A chemical entity as in claim 13, wherein R$^3$ is H.
15. A chemical entity as in claim 1, wherein Y is O.
16. A chemical entity as in claim 1, wherein Y is S.
17. A chemical entity as in claim 1, wherein L is —CH$_2$—.
18. A chemical entity as in claim 1, wherein L is —CH$_2$CH$_2$—.
19. A chemical entity as in claim 11, wherein A is bound at site b.
20. A chemical entity as in claim 1, wherein said R$^1$ and R$^2$ taken together with the nitrogen member to which they are attached form one of the following

21. A chemical entity as in claim 1, wherein said R$^1$ and R$^2$ taken together with the nitrogen member to which they are attached form one of the following

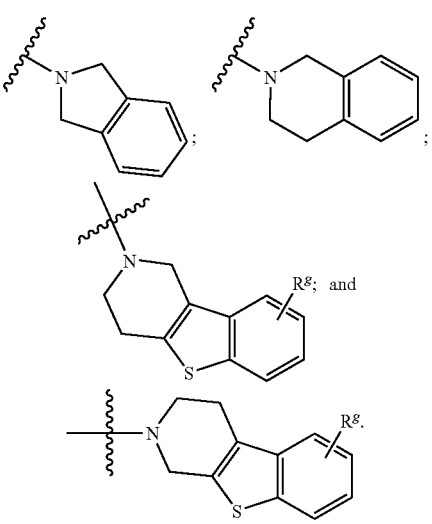

22. A chemical entity as in claim 1, wherein said R$^1$ and R$^2$ are each independently H, C$_{1-4}$alkyl, or benzyl.
23. A chemical entity as in claim 1, wherein said R$^1$ and R$^2$ taken together with the nitrogen member to which they are attached form an unbridged monocyclic moiety, said moiety optionally containing one additional heteroatom member selected from N, O, and S; said moiety being optionally substituted with R$^5$.
24. A chemical entity as in claim 1, wherein R$^1$ and R$^2$ taken together with the nitrogen member to which they are attached form one of the following moieties; azetidine, pyrrolidine, piperidine, piperazine, or [1,4]-diazepane, wherein each of said moieties is optionally substituted with $R^5$ and $(R^5)_m$.

25. A chemical entity as in claim 1, wherein said $R^1$ and $R^2$ taken together with the nitrogen member to which they are attached form one of the following

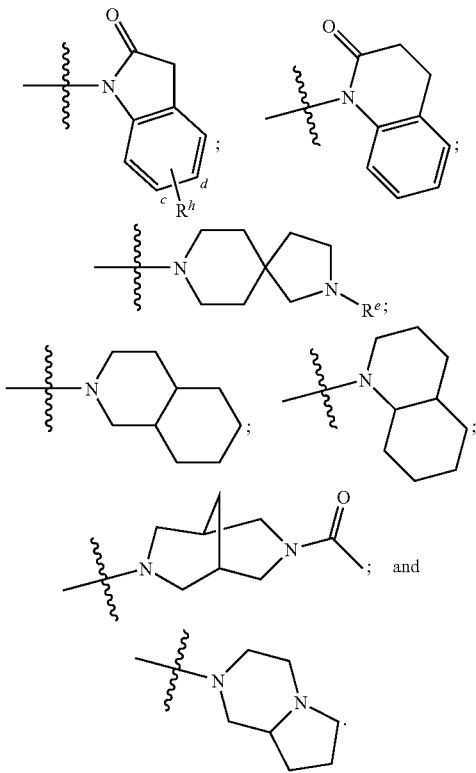

26. A chemical entity selected from the group consisting of
2-(3-pyrrolidin-1-ylmethyl-1H-indol-6-yloxy)-benzothiazole;
2-(3-piperidin-1-ylmethyl-1H-indol-6-yloxy)-benzothiazole;
2-(3-morpholin-4-ylmethyl-1H-indol-6-yloxy)-benzothiazole;
2-[3-(4-methanesulfonyl-piperidin-1-ylmethyl)-1H-indol-6-yloxy]-benzothiazole;
[6-(benzothiazol-2-yloxy)-1H-indol-3-ylmethyl]-benzyl-methyl-amine;
2-[3-(1,3-dihydro-isoindol-2-ylmethyl)-1H-indol-6-yloxy]-benzothiazole;
2-[6-(benzothiazol-2-yloxy)-1H-indol-3-ylmethyl]-1,2,3,4-tetrahydro-isoquinoline;
2-[3-(4-phenyl-piperidin-1-ylmethyl)-1H-indol-6-yloxy]-benzothiazole;
2-(3-pyrrolidin-1-ylmethyl-1H-indol-5-yloxy)-benzothiazole;
2-(3-piperidin-1-ylmethyl-1H-indol-5-yloxy)-benzothiazole;
2-(3-morpholin-4-ylmethyl-1H-indol-5-yloxy)-benzothiazole;
(1S,4S)-2-[3-(2-oxa-5-aza-bicyclo[2.2.1]hept-5-ylmethyl)-1H-indol-6-yloxy]-benzothiazole;
meso-endo-N-{8-[6-(benzothiazol-2-yloxy)-1H-indol-3-ylmethyl]-8-aza-bicyclo[3.2.1]oct-3-yl}-acetamide;
meso-endo-N-{8-[6-(4-fluoro-benzothiazol-2-yloxy)-1H-indol-3-ylmethyl]-8-aza-bicyclo[3.2.1]oct-3-yl}-acetamide;
2-(3-piperidin-1-ylmethyl-1H-indol-6-yloxy)-benzooxazole;
2-(3-piperidin-1-ylmethyl-1H-indol-6-yloxy)-thiazolo[4,5-b]pyridine;
1-[6-(thiazolo[4,5-b]pyridin-2-yloxy)-1H-indol-3-ylmethyl]-piperidine-4-carboxylic acid amide;
meso-endo-N-{8-[6-(thiazolo[4,5-b]pyridin-2-yloxy)-1H-indol-3-ylmethyl]-8-aza-bicyclo[3.2.1]oct-3-yl}-acetamide;
(1S,4S)-1-{5-[6-(thiazolo[4,5-b]pyridin-2-yloxy)-1H-indol-3-ylmethyl]-2,5-diaza-bicyclo[2.2.1]hept-2-yl}-ethanone;
1-{1-[6-(thiazolo[4,5-b]pyridin-2-yloxy)-1H-indol-3-ylmethyl]-piperidin-4-yl}-pyrrolidin-2-one;
1-[6-(benzothiazol-2-yloxy)-1H-indol-3-ylmethyl]-piperidine-4-carboxylic acid amide;
1-[6-(benzothiazol-2-yloxy)-1H-indol-3-ylmethyl]-piperidine-4-carboxylic acid methylamide;
{1-[6-(benzothiazol-2-yloxy)-1H-indol-3-ylmethyl]-piperidin-4-yl}-pyrrolidin-1-yl-methanone;
{1-[6-(benzothiazol-2-yloxy)-1H-indol-3-ylmethyl]-piperidin-4-yl}-piperidin-1-yl-methanone;
{1-[6-(benzothiazol-2-yloxy)-1H-indol-3-ylmethyl]-piperidin-4-yl}-morpholin-4-yl-methanone;
{1-[6-(benzothiazol-2-yloxy)-1H-indol-3-ylmethyl]-piperidin-4-yl}-(4-methyl-piperazin-1-yl)-methanone;
(3S)-1-[6-(benzothiazol-2-yloxy)-1H-indol-3-ylmethyl]-piperidine-3-carboxylic acid amide;
{1-[6-(benzothiazol-2-yloxy)-1H-indol-3-ylmethyl]-piperidin-4-yl}-methanol;
{1-[6-(benzothiazol-2-yloxy)-1H-indol-3-ylmethyl]-piperidin-4-yl}-carbamic acid ethyl ester;
1-{1-[6-(benzothiazol-2-yloxy)-1H-indol-3-ylmethyl]-piperidin-4-yl}-pyrrolidin-2-one;
2-(3-piperidin-1-ylmethyl-1H-pyrrolo[3,2-b]pyridin-6-yloxy)-benzothiazole;
2-(3-morpholin-4-ylmethyl-1H-pyrrolo[3,2-b]pyridin-6-yloxy)-benzothiazole;
1-[6-(benzothiazol-2-yloxy)-1H-pyrrolo[3,2-b]pyridin-3-ylmethyl]-piperidine-4-carboxylic acid amide;
2-[6-(thiazolo[4,5-b]pyridin-2-yloxy)-1H-indol-3-ylmethyl]-1,2,3,4-tetrahydro-benzo[4,5]thieno[3,2-c]pyridine;
2-[6-(thiazolo[4,5-b]pyridin-2-yloxy)-1H-indol-3-ylmethyl]-1,2,3,4-tetrahydro-benzo[4,5]thieno[2,3-c]pyridine;
8-chloro-2-[6-(thiazolo[4,5-b]pyridin-2-yloxy)-1H-indol-3-ylmethyl]-1,2,3,4-tetrahydro-benzo[4,5]thieno[3,2-c]pyridine;
6-chloro-2-[6-(thiazolo[4,5-b]pyridin-2-yloxy)-1H-indol-3-ylmethyl]-1,2,3,4-tetrahydro-benzo[4,5]thieno[2,3-c]pyridine;
8-fluoro-2-[6-(thiazolo[4,5-b]pyridin-2-yloxy)-1H-indol-3-ylmethyl]-1,2,3,4-tetrahydro-benzo[4,5]thieno[3,2-c]pyridine;
2-[6-(benzothiazol-2-yloxy)-1H-indol-3-ylmethyl]-1,2,3,4-tetrahydro-benzo[4,5]thieno[3,2-c]pyridine;
2-(3-morpholin-4-ylmethyl-1H-indol-6-yloxy)-thiazolo[4,5-b]pyridine;
(3S)-2-[3-(3-Methyl-morpholin-4-ylmethyl)-1H-indol-6-yloxy]-thiazolo[4,5-b]pyridine;
2-(3-thiomorpholin-4-ylmethyl-1H-indol-6-yloxy)-thiazolo[4,5-b]pyridine;
meso-endo-N-{8-[6-(Thiazolo[5,4-b]pyridin-2-yloxy)-1H-indol-3-ylmethyl]-8-aza-bicyclo[3.2.1]oct-3-yl}-acetamide;
(4R)-1-{1-[6-(benzothiazol-2-yloxy)-1H-indol-3-ylmethyl]-piperidin-4-yl}-4-hydroxy-pyrrolidin-2-one;
1-[6-(benzothiazol-2-yloxy)-1H-indol-3-ylmethyl]-piperidine-4-carboxylic acid;

{1-[6-(benzothiazol-2-yloxy)-1H-indol-3-ylmethyl]-piperidin-4-yl}-acetic acid;
1-[6-(benzothiazol-2-yloxy)-1H-indol-3-ylmethyl]-piperidine-3-carboxylic acid;
meso-endo-(acetyl-{8-[6-(benzothiazol-2-yloxy)-1H-indol-3-ylmethyl]-8-aza-bicyclo[3.2.1]oct-3-yl}-amino)-acetic acid;
meso-endo-(acetyl-{8-[5-(benzothiazol-2-yloxy)-1H-indol-3-ylmethyl]-8-aza-bicyclo[3.2.1]oct-3-yl}-amino)-acetic acid;
1-[6-(benzothiazol-2-yloxy)-1H-indol-3-ylmethyl]-piperidin-4-ylamine;
2-[3-(hexahydro-pyrrolo[3,4-c]pyrrol-2-ylmethyl)-1H-indol-6-yloxy]-benzothiazole;
(1S,4S)-2-[3-(2,5-diaza-bicyclo[2.2.1]hept-2-ylmethyl)-1H-indol-6-yloxy]-benzothiazole;
N-{1-[6-(benzothiazol-2-yloxy)-1H-indol-3-ylmethyl]-piperidin-4-yl}-acetamide;
1-{5-[6-(benzothiazol-2-yloxy)-1H-indol-3-ylmethyl]-hexahydro-pyrrolo[3,4-c]pyrrol-2-yl}-ethanone;
(1S,4S)-1-{5-[6-(benzothiazol-2-yloxy)-1H-indol-3-ylmethyl]-2,5-diaza-bicyclo[2.2.1]hept-2-yl}-ethanone;
2-(3-morpholin-4-ylmethyl-1H-indol-6-yloxy)-thiazolo[4,5-b]pyrazine;
7-methyl-2-(3-morpholin-4-ylmethyl-1H-indol-6-yloxy)-thiazolo[4,5-b]pyridine;
6-fluoro-2-(3-morpholin-4-ylmethyl-1H-indol-6-yloxy)-thiazolo[4,5-b]pyridine;
6-chloro-2-(3-morpholin-4-ylmethyl-1H-indol-6-yloxy)-thiazolo[4,5-b]pyridine;
6-fluoro-2-(3-morpholin-4-ylmethyl-1H-indol-6-yloxy)-thiazolo[5,4-b]pyridine;
2-(1-methyl-3-morpholin-4-ylmethyl-1H-indol-6-yloxy)-benzothiazole;
2-(1-ethyl-2-piperidin-1-ylmethyl-1H-indol-5-yloxy)-benzothiazole;
2-(1-ethyl-2-morpholin-4-ylmethyl-1H-indol-5-yloxy)-benzothiazole;
2-(1-ethyl-2-pyrrolidin-1-ylmethyl-1H-indol-5-yloxy)-benzothiazole;
2-(2-piperidin-1-ylmethyl-1H-indol-5-yloxy)-benzothiazole;
2-(2-pyrrolidin-1-ylmethyl-1H-indol-5-yloxy)-benzothiazole;
2-(2-piperidin-1-ylmethyl-1H-indol-6-yloxy)-benzothiazole;
2-(2-pyrrolidin-1-ylmethyl-1H-indol-6-yloxy)-benzothiazole;
1-[6-(benzothiazol-2-yloxy)-1H-indol-2-ylmethyl]-piperidine-4-carboxylic acid amide;
meso-endo-N-{8-[6-(benzothiazol-2-yloxy)-1H-indol-2-ylmethyl]-8-aza-bicyclo[3.2.1]oct-3-yl}-acetamide;
2-(2-piperidin-1-ylmethyl-1H-indol-6-yloxy)-thiazolo[4,5-b]pyridine;
meso-endo-N-{8-[6-(thiazolo[4,5-b]pyridin-2-yloxy)-1H-indol-2-ylmethyl]-8-aza-bicyclo[3.2.1]oct-3-yl}-acetamide;
1-{2-[5-(benzothiazol-2-yloxy)-1H-indol-3-yl]-ethyl}-piperidine-4-carboxylic acid;
2-[3-(2-piperidin-1-yl-ethyl)-1H-indol-5-yloxy]-benzothiazole;
1-{2-[5-(benzothiazol-2-yloxy)-1H-indol-3-yl]-ethyl}-piperidine-4-carboxylic acid amide;
1-[5-(benzothiazol-2-yloxy)-benzofuran-2-ylmethyl]-piperidine-4-carboxylic acid;
1-[6-(benzothiazol-2-yloxy)-benzofuran-2-ylmethyl]-piperidine-4-carboxylic acid;
{1-[6-(benzothiazol-2-yloxy)-benzofuran-2-ylmethyl]-piperidin-4-yl}-acetic acid;
{4-[6-(benzothiazol-2-yloxy)-benzofuran-2-ylmethyl]-piperazin-1-yl}-acetic acid;
1-{2-[6-(benzothiazol-2-yloxy)-benzofuran-3-yl]-ethyl}-piperidine-4-carboxylic acid;
meso-endo-{8-[6-(benzothiazol-2-yloxy)-benzofuran-2-ylmethyl]-8-aza-bicyclo[3.2.1]oct-3-ylamino}-acetic acid;
2-(2-piperidin-1-ylmethyl-benzofuran-5-yloxy)-benzothiazole;
meso-endo-N-{8-[5-(benzothiazol-2-yloxy)-benzofuran-2-ylmethyl]-8-aza-bicyclo[3.2.1]oct-3-yl}-acetamide;
4-fluoro-2-(2-piperidin-1-ylmethyl-benzofuran-5-yloxy)-benzothiazole;
meso-endo-N-{8-[5-(4-fluoro-benzothiazol-2-yloxy)-benzofuran-2-ylmethyl]-8-aza-bicyclo[3.2.1]oct-3-yl}-acetamide;
2-(2-piperidin-1-ylmethyl-benzofuran-5-yloxy)-thiazolo[4,5-b]pyridine;
meso-endo-N-{8-[5-(thiazolo[4,5-b]pyridin-2-yloxy)-benzofuran-2-ylmethyl]-8-aza-bicyclo[3.2.1]oct-3-yl}-acetamide;
1-[5-(thiazolo[4,5-b]pyridin-2-yloxy)-benzofuran-2-ylmethyl]-piperidine-4-carboxylic acid amide;
2-{2-[4-(pyrimidin-2-yloxy)-piperidin-1-ylmethyl]-benzofuran-5-yloxy}-thiazolo[4,5-b]pyridine;
1-{5-[5-(thiazolo[4,5-b]pyridin-2-yloxy)-benzofuran-2-ylmethyl]-hexahydro-pyrrolo[3,4-c]pyrrol-2-yl}-ethanone;
5-[5-(thiazolo[4,5-b]pyridin-2-yloxy)-benzofuran-2-ylmethyl]-hexahydro-pyrrolo[3,4-c]pyrrole-2-carboxylic acid amide;
2-[2-(4-methanesulfonyl-piperidin-1-ylmethyl)-benzofuran-5-yloxy]-thiazolo[4,5-b]pyridine;
meso-1-{8-[5-(thiazolo[4,5-b]pyridin-2-yloxy)-benzofuran-2-ylmethyl]-3,8-diaza-bicyclo[3.2.1]oct-3-yl}-ethanone;
meso-8-[5-(thiazolo[4,5-b]pyridin-2-yloxy)-benzofuran-2-ylmethyl]-3,8-diaza-bicyclo[3.2.1]octane-3-carboxylic acid amide;
(1S,4S)-1-{5-[5-(thiazolo[4,5-b]pyridin-2-yloxy)-benzofuran-2-ylmethyl]-2,5-diaza-bicyclo[2.2.1]hept-2-yl}-ethanone;
1-{1-[5-(thiazolo[4,5-b]pyridin-2-yloxy)-benzofuran-2-ylmethyl]-piperidin-4-yl}-pyrrolidin-2-one;
2-(2-morpholin-4-ylmethyl-benzofuran-5-yloxy)-thiazolo[4,5-b]pyridine;
(3S)-2-[2-(3-methyl-morpholin-4-ylmethyl)-benzofuran-5-yloxy]-thiazolo[4,5-b]pyridine;
(1S,4S)-2-[2-(2-oxa-5-aza-bicyclo[2.2.1]hept-5-ylmethyl)-benzofuran-5-yloxy]thiazolo[4,5-b]pyridine;
(1S,4S)-5-[5-(thiazolo[4,5-b]pyridin-2-yloxy)-benzofuran-2-ylmethyl]-2,5-diaza-bicyclo[2.2.1]heptane-2-carboxylic acid amide;
(1R,4R)-5-[5-(thiazolo[4,5-b]pyridin-2-yloxy)-benzofuran-2-ylmethyl]-2,5-diaza-bicyclo[2.2.1]heptane-2-carboxylic acid amide;
(1R,4R)-1-{5-[5-(thiazolo[4,5-b]pyridin-2-yloxy)-benzofuran-2-ylmethyl]-2,5-diaza-bicyclo[2.2.1]hept-2-yl}-ethanone;
meso-endo-N-{8-[5-(thiazolo[4,5-b]pyridin-2-yloxy)-benzofuran-2-ylmethyl]-8-aza-bicyclo[3.2.1]oct-3-yl}-urea;
meso-exo-N-{8-[5-(thiazolo[4,5-b]pyridin-2-yloxy)-benzofuran-2-ylmethyl]-8-aza-bicyclo[3.2.1]oct-3-yl}-acetamide;
1-[5-(benzothiazol-2-yloxy)-benzofuran-2-ylmethyl]-piperidine-4-carboxylic acid amide;
meso-exo-N-{8-[6-(thiazolo[4,5-b]pyridin-2-yloxy)-benzofuran-2-ylmethyl]-8-aza-bicyclo[3.2.1]oct-3-yl}-acetamide;

(1R,4R)-1-{5-[6-(thiazolo[4,5-b]pyridin-2-yloxy)-benzofuran-2-ylmethyl]-2,5-diaza-bicyclo[2.2.1]hept-2-yl}-ethanone;
1-{1-[6-(thiazolo[4,5-b]pyridin-2-yloxy)-benzofuran-2-ylmethyl]-piperidin-4-yl}-pyrrolidin-2-one;
(1S,4S)-2-[2-(2-oxa-5-aza-bicyclo[2.2.1]hept-5-ylmethyl)-benzofuran-6-yloxy]-thiazolo[4,5-b]pyridine;
2-[2-(tetrahydro-furo[3,4-c]pyrrol-5-ylmethyl)-benzofuran-6-yloxy]-thiazolo[4,5-b]pyridine;
2-[2-(4-fluoro-piperidin-1-ylmethyl)-benzofuran-5-yloxy]-thiazolo[4,5-b]pyridine;
dimethyl-[5-(thiazolo[4,5-b]pyridin-2-yloxy)-benzofuran-2-ylmethyl]-amine;
2-[2-(tetrahydro-furo[3,4-c]pyrrol-5-ylmethyl)-benzofuran-5-yloxy]-thiazolo[4,5-b]pyridine;
benzyl-methyl-[5-(thiazolo[4,5-b]pyridin-2-yloxy)-benzofuran-2-ylmethyl]-amine;
2-(2-morpholin-4-ylmethyl-benzofuran-6-yloxy)-thiazolo[4,5-b]pyridine;
1-[6-(thiazolo[4,5-b]pyridin-2-yloxy)-benzofuran-2-ylmethyl]-piperidine-4-carboxylic acid amide;
(1S,4S)-5-[6-(thiazolo[4,5-b]pyridin-2-yloxy)-benzofuran-2-ylmethyl]-2,5-diaza-bicyclo[2.2.1]heptane-2-carboxylic acid amide;
meso-endo-N-{8-[6-(thiazolo[4,5-b]pyridin-2-yloxy)-benzofuran-2-ylmethyl]-8-aza-bicyclo[3.2.1]oct-3-yl}-acetamide;
meso-1-{8-[6-(thiazolo[4,5-b]pyridin-2-yloxy)-benzofuran-2-ylmethyl]-3,8-diaza-bicyclo[3.2.1]oct-3-yl}-ethanone;
N-(1-{[6-([1,3]thiazolo[4,5-b]pyridin-2-yloxy)-1-benzofuran-2-yl]methyl}pyrrolidin-3-yl)acetamide;
(1S,4S)-1-{5-[5-(thiazolo[5,4-b]pyridin-2-yloxy)-benzofuran-2-ylmethyl]-2,5-diaza-bicyclo[2.2.1]hept-2-yl}-ethanone;
(1S,4S)-1-{5-[6-(thiazolo[5,4-b]pyridin-2-yloxy)-benzofuran-2-ylmethyl]-2,5-diaza-bicyclo[2.2.1]hept-2-yl}-ethanone;
meso-1-{8-[5-(thiazolo[5,4-b]pyridin-2-yloxy)-benzofuran-2-ylmethyl]-3,8-diaza-bicyclo[3.2.1]oct-3-yl}-ethanone;
meso-1-{8-[6-(thiazolo[5,4-b]pyridin-2-yloxy)-benzofuran-2-ylmethyl]-3,8-diaza-bicyclo[3.2.1]oct-3-yl}-ethanone;
meso-endo-N-{8-[5-(thiazolo[5,4-b]pyridin-2-yloxy)-benzofuran-2-ylmethyl]-8-aza-bicyclo[3.2.1]oct-3-yl}-acetamide;
meso-endo-N-{8-[6-(thiazolo[5,4-b]pyridin-2-yloxy)-benzofuran-2-ylmethyl]-8-aza-bicyclo[3.2.1]oct-3-yl}-acetamide;
1-(1-{[6-([1,3]thiazolo[4,5-b]pyridin-2-yloxy)-1-benzofuran-2-yl]methyl}pyrrolidin-3-yl)urea;
N-(1-{[6-([1,3]thiazolo[4,5-b]pyridin-2-yloxy)-1-benzofuran-2-yl]methyl}pyrrolidin-3-yl)methanesulfonamide;
meso-endo-N-(8-{2-[6-(benzothiazol-2-yloxy)-benzofuran-3-yl]-ethyl}-8-aza-bicyclo[3.2.1]oct-3-yl)-acetamide;
meso-1-(8-{2-[6-(thiazolo[4,5-b]pyridin-2-yloxy)-benzofuran-3-yl]-ethyl}-3,8-diaza-bicyclo[3.2.1]oct-3-yl)-ethanone;
meso-endo-N-(8-{2-[6-(thiazolo[4,5-b]pyridin-2-yloxy)-benzofuran-3-yl]-ethyl}-8-aza-bicyclo[3.2.1]oct-3-yl)-acetamide;
2-(2-piperidin-1-ylmethyl-benzo[b]thiophen-6-yloxy)-benzothiazole;
(2-morpholin-4-ylmethyl-benzo[b]thiophen-6-yloxy)-benzothiazole;
meso-endo-N-{8-[6-(benzothiazol-2-yloxy)-benzo[b]thiophen-2-ylmethyl]-8-aza-bicyclo[3.2.1]oct-3-yl}-acetamide;
meso-endo-N-{8-[6-(thiazolo[4,5-b]pyridin-2-yloxy)-benzo[b]thiophen-2-ylmethyl]-8-aza-bicyclo[3.2.1]oct-3-yl}-acetamide;
2-(2-piperidin-1-ylmethyl-benzo[b]thiophen-6-yloxy)-thiazolo[4,5-b]pyridine;
2-(3-morpholin-4-ylmethyl-benzo[b]thiophen-6-yloxy)-thiazolo[4,5-b]pyridine;
1-[6-(thiazolo[4,5-b]pyridin-2-yloxy)-benzo[b]thiophen-2-ylmethyl]-piperidine-4-carboxylic acid amide;
1-[6-(benzothiazol-2-yloxy)-1H-indol-3-ylmethyl]-piperidine-4-carboxylic acid ethyl ester;
1-[6-(thiazolo[5,4-b]pyridin-2-yloxy)-1H-indol-3-ylmethyl]-piperidine-4-carboxylic acid ethyl ester;
{1-[6-(benzothiazol-2-yloxy)-1H-indol-3-ylmethyl]-piperidin-4-yl}-acetic acid methyl ester;
meso-endo-(acetyl-{8-[6-(benzothiazol-2-yloxy)-1H-indol-3-ylmethyl]-8-aza-bicyclo[3.2.1]oct-3-yl}-amino)-acetic acid ethyl ester;
meso-endo-(acetyl-{8-[5-(benzothiazol-2-yloxy)-1H-indol-3-ylmethyl]-8-aza-bicyclo[3.2.1]oct-3-yl}-amino)-acetic acid ethyl ester;
(3R)-[6-(benzothiazol-2-yloxy)-1H-indol-3-ylmethyl]-piperidine-3-carboxylic acid ethyl ester;
{1-[6-(benzothiazol-2-yloxy)-1H-indol-3-ylmethyl]-piperidin-4-yl}-carbamic acid tert-butyl ester;
5-[6-(benzothiazol-2-yloxy)-1H-indol-3-ylmethyl]-hexahydro-pyrrolo[3,4-c]pyrrole-2-carboxylic acid tert-butyl ester;
(1S,4S)-5-[6-(benzothiazol-2-yloxy)-1H-indol-3-ylmethyl]-2,5-diaza-bicyclo[2.2.1]heptane-2-carboxylic acid tert-butyl ester;
1-{2-[5-(benzothiazol-2-yloxy)-1H-indol-3-yl]-ethyl}-piperidine-4-carboxylic acid ethyl ester;
1-{2-[6-(benzothiazol-2-yloxy)-benzofuran-3-yl]-ethyl}-piperidine-4-carboxylic acid ethyl ester;
meso-endo-({8-[6-(benzothiazol-2-yloxy)-benzofuran-2-ylmethyl]-8-aza-bicyclo[3.2.1]oct-3-yl}-tert-butoxycarbonyl-amino)-acetic acid tert-butyl ester;
{1-[6-(thiazolo[4,5-b]pyridin-2-yloxy)-benzofuran-2-ylmethyl]-pyrrolidin-3-yl}-carbamic acid tert-butyl ester;
1-[6-(thiazolo[4,5-b]pyridin-2-yloxy)-benzofuran-2-ylmethyl]-pyrrolidin-3-ylamine;
1-{8-[6-(thiazolo[4,5-b]pyridin-2-yloxy)-benzofuran-3-ylmethyl]-3,8-diaza-bicyclo[3.2.1]oct-3-yl}-ethanone;
(1S,4S)-1-{5-[6-(thiazolo[4,5-b]pyridin-2-yloxy)-benzofuran-3-ylmethyl]-2,5-diaza-bicyclo[2.2.1]hept-2-yl}-ethanone;
meso-endo-N-{8-[6-(thiazolo[4,5-b]pyridin-2-yloxy)-benzofuran-3-ylmethyl]-8-aza-bicyclo[3.2.1]oct-3-yl}-acetamide;
2-(3-morpholin-4-ylmethyl-benzofuran-6-yloxy)-thiazolo[4,5-b]pyridine;
(1R,4R)-1-{5-[6-(thiazolo[4,5-b]pyridin-2-yloxy)-benzofuran-3-ylmethyl]-2,5-diaza-bicyclo[2.2.1]hept-2-yl}-ethanone;
(1S,4S)-2-[3-(2-oxa-5-aza-bicyclo[2.2.1]hept-5-ylmethyl)-benzofuran-6-yloxy]-thiazolo[4,5-b]pyridine;
(S)-2-[3-(3-methyl-morpholin-4-ylmethyl)-benzofuran-6-yloxy]-thiazolo[4,5-b]pyridine;
(1R,4R)-5-[6-(thiazolo[4,5-b]pyridin-2-yloxy)-benzofuran-3-ylmethyl]-2,5-diaza-bicyclo[2.2.1]heptane-2-carboxylic acid amide;
5-[6-(thiazolo[4,5-b]pyridin-2-yloxy)-benzofuran-3-ylmethyl]-hexahydro-pyrrolo[3,4-c]pyrrole-2-carboxylic acid amide;
N-{1-[6-(thiazolo[4,5-b]pyridin-2-yloxy)-benzofuran-3-ylmethyl]-piperidin-4-ylmethyl}-acetamide;

2-[3-(4-trifluoromethyl-piperidin-1-ylmethyl)-benzofuran-6-yloxy]-thiazolo[4,5-b]pyridine;
(1S,4S)-1-{5-[6-(benzothiazol-2-yloxy)-benzofuran-3-ylmethyl]-2,5-diaza-bicyclo[2.2.1]hept-2-yl}-ethanone;
2-(3-morpholin-4-ylmethyl-benzofuran-6-yloxy)-benzothiazole;
1-{2-[5-(thiazolo[4,5-b]pyridin-2-yloxy)-benzofuran-2-ylmethyl]-2,7-diaza-spiro[4.5]dec-7-yl}-ethanone;
1-{9-[5-(thiazolo[4,5-b]pyridin-2-yloxy)-benzofuran-2-ylmethyl]-3,9-diaza-spiro[5.5]undec-3-yl}-ethanone;
(1S,4S)-1-{5-[6-(thiazolo[4,5-b]pyridin-2-yloxy)-benzofuran-2-ylmethyl]-2,5-diaza-bicyclo[2.2.1]hept-2-yl}-ethanone;
meso-1-{5-[5-(thiazolo[4,5-b]pyridin-2-yloxy)-benzofuran-2-ylmethyl]-2,5-diaza-bicyclo[2.2.2]oct-2-yl}-ethanone;
meso-1-{5-[6-(thiazolo[4,5-b]pyridin-2-yloxy)-benzofuran-2-ylmethyl]-2,5-diaza-bicyclo[2.2.2]oct-2-yl}-ethanone;
1-{4-[6-(thiazolo[4,5-b]pyridin-2-yloxy)-benzofuran-2-ylmethyl]-piperazin-1-yl}-ethanone;
meso-endo-{8-[6-(thiazolo[4,5-b]pyridin-2-yloxy)-benzofuran-2-ylmethyl]-8-aza-bicyclo[3.2.1]oct-3-yl}-urea;
meso-8-[5-(benzothiazol-2-yloxy)-benzofuran-2-ylmethyl]-3,8-diaza-bicyclo[3.2.1]octane-3-carboxylic acid amide;
(1S,4S)-5-[5-(thiazolo[4,5-b]pyridin-2-yloxy)-benzofuran-2-ylmethyl]-2,5-diaza-bicyclo[2.2.1]heptane-2-carboxylic acid amide;
meso-endo-{8-[6-(thiazolo[4,5-b]pyridin-2-yloxy)-benzofuran-3-ylmethyl]-8-aza-bicyclo[3.2.1]oct-3-yl}-urea;
furan-2-ylmethyl-methyl-[6-(thiazolo[4,5-b]pyridin-2-yloxy)-benzofuran-3-ylmethyl]-amine;
methyl-pyridin-4-ylmethyl-[6-(thiazolo[4,5-b]pyridin-2-yloxy)-benzofuran-3-ylmethyl]amine;
methyl-pyridin-3-ylmethyl-[6-(thiazolo[4,5-b]pyridin-2-yloxy)-benzofuran-3-ylmethyl]-amine;
1-{1-[6-(benzothiazol-2-yloxy)-benzofuran-3-ylmethyl]-piperidin-4-yl}-pyrrolidin-2-one;
N-{1-[6-(benzothiazol-2-yloxy)-benzofuran-3-ylmethyl]-piperidin-4-yl}-acetamide;
meso-endo-N-{8-[6-(benzothiazol-2-yloxy)-benzofuran-3-ylmethyl]-8-aza-bicyclo[3.2.1]oct-3-yl}-acetamide;
1-{4-[6-(thiazolo[4,5-b]pyridin-2-yloxy)-benzofuran-3-ylmethyl]-[1,4]diazepan-1-yl}-ethanone;
2-[3-(4-methanesulfonyl-piperidin-1-ylmethyl)-benzofuran-6-yloxy]-thiazolo[4,5-b]pyridine;
(2-methoxy-ethyl)-methyl-[6-(thiazolo[4,5-b]pyridin-2-yloxy)-benzofuran-3-ylmethyl]-amine;
2-(3-pyrrolidin-1-ylmethyl-benzofuran-6-yloxy)-thiazolo[4,5-b]pyridine;
(2S)-2-[3-(2-methoxymethyl-pyrrolidin-1-ylmethyl)-benzofuran-6-yloxy]-thiazolo[4,5-b]pyridine;
(1S,4S,5S)—N-{2-[6-(thiazolo[4,5-b]pyridin-2-yloxy)-benzofuran-3-ylmethyl]-2-aza-bicyclo[2.2.1]hept-5-yl}-acetamide;
(1S,4S,5S)—N-{2-[5-(thiazolo[4,5-b]pyridin-2-yloxy)-benzofuran-2-ylmethyl]-2-aza-bicyclo[2.2.1]hept-5-yl}-acetamide;
(1S,4S,5S)—N-{2-[6-(thiazolo[4,5-b]pyridin-2-yloxy)-benzofuran-2-ylmethyl]-2-aza-bicyclo[2.2.1]hept-5-yl}-acetamide;
2-[2-(4-fluoro-piperidin-1-ylmethyl)-benzofuran-6-yloxy]-thiazolo[4,5-b]pyridine;
2-[2-(4-trifluoromethyl-piperidin-1-ylmethyl)-benzofuran-6-yloxy]-thiazolo[4,5-b]pyridine;
2-(2-piperidin-1-ylmethyl-benzofuran-6-yloxy)-thiazolo[4,5-b]pyridine;
(1R,4R)-5-[6-(thiazolo[4,5-b]pyridin-2-yloxy)-benzofuran-2ylmethyl]-2,5-diaza-bicyclo[2.2.1]heptane-2-carboxylic acid amide;
5-[6-(thiazolo[4,5-b]pyridin-2-yloxy)-benzofuran-2-ylmethyl]-hexahydro-pyrrolo[3,4-c]pyrrole-2-carboxylic acid amide;
1-{5-[6-(thiazolo[4,5-b]pyridin-2-yloxy)-benzofuran-2-ylmethyl]-hexahydro-pyrrolo[3,4-c]pyrrol-2-yl}-ethanone;
1-{4-[6-(thiazolo[4,5-b]pyridin-2-yloxy)-benzofuran-3-ylmethyl]-piperazin-1-yl}-ethanone;
N-{1-[6-(thiazolo[4,5-b]pyridin-2-yloxy)-benzofuran-3-ylmethyl]-piperidin-4-yl}-acetamide;
diethyl-[6-(thiazolo[4,5-b]pyridin-2-yloxy)-benzofuran-2-ylmethyl]-amine;
(1S,4S)-1-{5-[5-(thiazolo[4,5-c]pyridin-2-yloxy)-benzofuran-2-ylmethyl]-2,5-diaza-bicyclo[2.2.1]hept-2-yl}-ethanone;
meso-endo-N-{8-[5-(thiazolo[4,5-c]pyridin-2-yloxy)-benzofuran-2-ylmethyl]-8-aza-bicyclo[3.2.1]oct-3-yl}-acetamide;
meso-endo-N-{8-[6-(thiazolo[4,5-c]pyridin-2-yloxy)-benzofuran-2-ylmethyl]-8-aza-bicyclo[3.2.1]oct-3-yl}-acetamide;
meso-1-{8-[6-(thiazolo[4,5-c]pyridin-2-yloxy)-benzofuran-2-ylmethyl]-3,8-diaza-bicyclo[3.2.1]oct-3-yl}-ethanone;
(1S,4S)-1-{5-[6-(thiazolo[4,5-c]pyridin-2-yloxy)-benzofuran-2-ylmethyl]-2,5-diaza-bicyclo[2.2.1]hept-2-yl}-ethanone;
1-[6-(thiazolo[4,5-b]pyridin-2-yloxy)-benzofuran-2-ylmethyl]-piperidine-4-carboxylic acid methylamide;
pyrrolidin-1-yl-{1-[6-(thiazolo[4,5-b]pyridin-2-yloxy)-benzofuran-2-ylmethyl]-piperidin-4-yl}-methanone;
meso-1-{8-[5-(thiazolo[4,5-c]pyridin-2-yloxy)-benzofuran-2-ylmethyl]-3,8-diaza-bicyclo[3.2.1]oct-3-yl}-ethanone;
meso-exo-{8-[6-(thiazolo[4,5-b]pyridin-2-yloxy)-benzofuran-3-ylmethyl]-8-aza-bicyclo[3.2.1]oct-3-yl}-urea;
meso-exo-N-{8-[6-(thiazolo[4,5-b]pyridin-2-yloxy)-benzofuran-3-ylmethyl]-8-aza-bicyclo[3.2.1]oct-3-yl}-acetamide;
(1S,4S)-5-[6-(thiazolo[4,5-b]pyridin-2-yloxy)-benzofuran-3-ylmethyl]-2,5-diaza-bicyclo[2.2.1]heptane-2-carboxylic acid amide;
meso-8-[6-(thiazolo[4,5-b]pyridin-2-yloxy)-benzofuran-3-ylmethyl]-3,8-diaza-bicyclo[3.2.1]octane-3-carboxylic acid amide;
meso-1-{5-[6-(thiazolo[4,5-b]pyridin-2-yloxy)-benzofuran-3-ylmethyl]-hexahydro-pyrrolo[3,4-c]pyrrol-2-yl}-ethanone;
2-(3-piperidin-1-ylmethyl-benzofuran-6-yloxy)-thiazolo[4,5-b]pyridine;
1-[6-(thiazolo[4,5-b]pyridin-2-yloxy)-benzofuran-3-ylmethyl]-piperidine-4-carboxylic acid amide;
1-[6-(thiazolo[4,5-b]pyridin-2-yloxy)-benzofuran-3-ylmethyl]-piperidine-4-carboxylic acid methylamide;
1-{1-[6-(thiazolo[4,5-b]pyridin-2-yloxy)-benzofuran-3-ylmethyl]-piperidin-4-yl}-pyrrolidin-2-one;
(3-S)-1-[6-(thiazolo[4,5-b]pyridin-2-yloxy)-benzofuran-3-ylmethyl]-piperidine-3-carboxylic acid amide;
2-{3-[4-(pyrimidin-2-yloxy)-piperidin-1-ylmethyl]-benzofuran-6-yloxy}-thiazolo[4,5-b]-pyridine;
2-{1-[6-(thiazolo[4,5-b]pyridin-2-yloxy)-benzofuran-3-ylmethyl]-piperidin-4-yl}-propan-2-ol;
diethyl-[6-(thiazolo[4,5-b]pyridin-2-yloxy)-benzofuran-3-ylmethyl]-amine;
1-[6-(thiazolo[4,5-b]pyridin-2-yloxy)-benzofuran-3-ylmethyl]-1,2,3,4,5,6-hexahydro-[4,4']bipyridinyl;

(1S,4S)-1-{5-[6-(thiazolo[5,4-b]pyridin-2-yloxy)-benzofuran-3-ylmethyl]-2,5-diaza-bicyclo[2.2.1]hept-2-yl}-ethanone;
(1S,4S)-1-{5-[6-(thiazolo[4,5-c]pyridin-2-yloxy)-benzofuran-3-ylmethyl]-2,5-diaza-bicyclo[2.2.1]hept-2-yl}-ethanone;
1-[6-(benzothiazol-2-yloxy)-benzofuran-3-ylmethyl]-piperidine-4-carboxylic acid ethyl ester;
1-[6-(thiazolo[4,5-b]pyridin-2-yloxy)-benzofuran-3-ylmethyl]-piperidine-4-carboxylic acid ethyl ester;
1-[6-(thiazolo[4,5-b]pyridin-2-yloxy)-benzofuran-2-ylmethyl]-piperidine-4-carboxylic acid tert-butyl ester;
4-[6-(thiazolo[4,5-b]pyridin-2-yloxy)-benzofuran-3-ylmethyl]-piperazine-1-carboxylic acid tert-butyl ester;
{1-[6-(thiazolo[4,5-b]pyridin-2-yloxy)-benzofuran-3-ylmethyl]-piperidin-4-yl}-carbamic acid tert-butyl ester;
4-[6-(thiazolo[4,5-b]pyridin-2-yloxy)-benzofuran-3-ylmethyl]-[1,4]diazepane-1-carboxylic acid tert-butyl ester;
(1S,4S)-5-[6-(thiazolo[4,5-b]pyridin-2-yloxy)-benzofuran-3-ylmethyl]-2,5-diaza-bicyclo[2.2.2]octane-2-carboxylic acid tert-butyl ester;
4-{cyclopropyl-[6-(thiazolo[4,5-b]pyridin-2-yloxy)-benzofuran-3-ylmethyl]-amino}-piperidine-1-carboxylic acid tert-butyl ester;
2-(3-piperazin-1-ylmethyl-benzofuran-6-yloxy)-thiazolo[4,5-b]pyridine;
1-[6-(thiazolo[4,5-b]pyridin-2-yloxy)-benzofuran-3-ylmethyl]-piperidin-4-ylamine;
2-(3-[1,4]diazepan-1-ylmethyl-benzofuran-6-yloxy)-thiazolo[4,5-b]pyridine;
(1S,4S)-2-[6-(thiazolo[4,5-b]pyridin-2-yloxy)-benzofuran-3-ylmethyl]-2,5-diaza-bicyclo[2.2.2]octane;
cyclopropyl-piperidin-4-yl-[6-(thiazolo[4,5-b]pyridin-2-yloxy)-benzofuran-3-ylmethyl]-amine;
2,2-dimethyl-N-{1-[6-(thiazolo[4,5-b]pyridin-2-yloxy)-benzofuran-2-ylmethyl]-pyrrolidin-3-yl}-propionamide;
(1S,4S)1-{5-[6-(thiazolo[4,5-b]pyridin-2-yloxy)-benzofuran-3-ylmethyl]-2,5-diaza-bicyclo[2.2.2]oct-2-yl}-ethanone;
1-(4-{cyclopropyl-[6-(thiazolo[4,5-b]pyridin-2-yloxy)-benzofuran-3-ylmethyl]-amino}-piperidin-1-yl)-ethanone;
4-[6-(thiazolo[4,5-b]pyridin-2-yloxy)-benzofuran-3-ylmethyl]-piperazine-1-carboxylic acid amide;
{1-[6-(thiazolo[4,5-b]pyridin-2-yloxy)-benzofuran-3-ylmethyl]-piperidin-4-yl}-urea;
(1S,4S)-5-[6-(thiazolo[4,5-b]pyridin-2-yloxy)-benzofuran-3-ylmethyl]-2,5-diaza-bicyclo[2.2.2]octane-2-carboxylic acid amide;
4-{cyclopropyl-[6-(thiazolo[4,5-b]pyridin-2-yloxy)-benzofuran-3-ylmethyl]-amino}-piperidine-1-carboxylic acid amide;
2-[3-(4-methanesulfonyl-piperazin-1-ylmethyl)-benzofuran-6-yloxy]-thiazolo[4,5-b]pyridine;
N-{1-[6-(thiazolo[4,5-b]pyridin-2-yloxy)-benzofuran-3-ylmethyl]-piperidin-4-yl}-methanesulfonamide;
(1S,4S)-2-methanesulfonyl-5-[6-(thiazolo[4,5-b]pyridin-2-yloxy)-benzofuran-3-ylmethyl]-2,5-diaza-bicyclo[2.2.2]octane;
cyclopropyl-(1-methanesulfonyl-piperidin-4-yl)-[6-(thiazolo[4,5-b]pyridin-2-yloxy)-benzofuran-3-ylmethyl]-amine;
2-[3-(4-methanesulfonyl-[1,4]diazepan-1-ylmethyl)-benzofuran-6-yloxy]-thiazolo[4,5-b]pyridine;
1-[6-(benzothiazol-2-yloxy)-benzofuran-3-ylmethyl]-piperidine-4-carboxylic acid;
1-[6-(thiazolo[4,5-b]pyridin-2-yloxy)-benzofuran-3-ylmethyl]-piperidine-4-carboxylic acid;
N-{1-[6-(5-methyl-thiazolo[4,5-b]pyridin-2-yloxy)-benzofuran-3-ylmethyl]-piperidin-4-yl}-acetamide;
N-{1-[6-(6-methyl-thiazolo[4,5-b]pyridin-2-yloxy)-benzofuran-3-ylmethyl]-piperidin-4-yl}-acetamide;
N-{1-[6-(7-methyl-thiazolo[4,5-b]pyridin-2-yloxy)-benzofuran-3-ylmethyl]-piperidin-4-yl}-acetamide;
N-{1-[6-(thiazolo[4,5-b]pyrazin-2-yloxy)-benzofuran-3-ylmethyl]-piperidin-4-yl}-acetamide;
N-{1-[6-(6-chloro-thiazolo[4,5-b]pyridin-2-yloxy)-benzofuran-3-ylmethyl]-piperidin-4-yl}-acetamide;
N-{1-[6-(6-fluoro-thiazolo[4,5-b]pyridin-2-yloxy)-benzofuran-3-ylmethyl]-piperidin-4-yl}-acetamide;
2-[3-(2-morpholin-4-yl-ethyl)-benzofuran-6-yloxy]-thiazolo[4,5-b]pyridine;
1-(4-{2-[6-(thiazolo[4,5-b]pyridin-2-yloxy)-benzofuran-3-yl]-ethyl}-piperazin-1-yl)-ethanone;
(1S,4S)-1-(5-{2-[6-(thiazolo[4,5-b]pyridin-2-yloxy)-benzofuran-3-yl]-ethyl}-2,5-diaza-bicyclo[2.2.1]hept-2-yl)-ethanone;
and pharmaceutically acceptable salts and prodrugs thereof.

27. A chemical entity selected from the group consisting of
1-{4-[5-(thiazolo[4,5-b]pyridin-2-yloxy)-benzofuran-2-ylmethyl]-piperazin-1-yl}-ethanone;
5-[6-(thiazolo[4,5-b]pyridin-2-yloxy)-benzofuran-3-ylmethyl]-hexahydro-pyrrolo[3,4-c]pyrrole-2-carboxylic acid tert-butyl ester;
(1S,4S)-5-[6-(thiazolo[4,5-b]pyridin-2-yloxy)-benzofuran-3-ylmethyl]-2,5-diaza-bicyclo[2.2.1]heptane-2-carboxylic acid tert-butyl ester;
2-[3-(hexahydro-pyrrolo[3,4-c]pyrrol-2-ylmethyl)-benzofuran-6-yloxy]-thiazolo[4,5-b]pyridine;
(1S,4S)-2-[3-(2,5-diaza-bicyclo[2.2.1]hept-2-ylmethyl)-benzofuran-6-yloxy]-thiazolo[4,5-b]pyridine;
2-[3-(2,8-diaza-spiro[4.5]dec-8-ylmethyl)-benzofuran-6-yloxy]-thiazolo[4,5-b]pyridine;
1-{8-[6-(thiazolo[4,5-b]pyridin-2-yloxy)-benzofuran-3-ylmethyl]-2,8-diaza-spiro[4.5]dec-2-yl}-ethanone;
2-[6-(thiazolo[4,5-b]pyridin-2-yloxy)-benzofuran-3-ylmethyl]-decahydro-isoquinoline;
1-[6-(thiazolo[4,5-b]pyridin-2-yloxy)-benzofuran-3-ylmethyl]-decahydro-quinoline;
1-[6-(thiazolo[4,5-b]pyridin-2-yloxy)-benzofuran-3-ylmethyl]-piperidin-4-ol;
{1-[6-(thiazolo[4,5-b]pyridin-2-yloxy)-benzofuran-3-ylmethyl]-piperidin-4-yl}-methanol;
2-[3-(4-fluoro-piperidin-1-ylmethyl)-benzofuran-6-yloxy]-thiazolo[4,5-b]pyridine;
2-[3-(4-methoxy-piperidin-1-ylmethyl)-benzofuran-6-yloxy]-thiazolo[4,5-b]pyridine;
1'-[6-(thiazolo[4,5-b]pyridin-2-yloxy)-benzofuran-3-ylmethyl]-[1,4]bipiperidinyl-2-one;
N-{1-[6-(thiazolo[4,5-b]pyridin-2-yloxy)-furo[3,2-b]pyridin-2-ylmethyl]-piperidin-4-yl}-acetamide;
(1S,4S)-1-{5-[6-(thiazolo[4,5-b]pyridin-2-yloxy)-furo[3,2-b]pyridin-2-ylmethyl]-2,5-diaza-bicyclo[2.2.1]hept-2-yl}-ethanone;
4-phenyl-1-[6-(thiazolo[4,5-b]pyridin-2-yloxy)-benzofuran-3-ylmethyl]-piperidin-4-ol,
cyclopropyl-{4-[6-(thiazolo[4,5-b]pyridin-2-yloxy)-benzofuran-3-ylmethyl]-piperazin-1-yl}-methanone;
2-[3-(4-cyclopropyl-piperazin-1-ylmethyl)-benzofuran-6-yloxy]-thiazolo[4,5-b]pyridine;
8-[6-(thiazolo[4,5-b]pyridin-2-yloxy)-benzofuran-3-ylmethyl]-2,8-diaza-spiro[4.5]decane-2-carboxylic acid tert-butyl ester;
2-[3-(4-benzyl-piperidin-1-ylmethyl)-benzofuran-6-yloxy]-thiazolo[4,5-b]pyridine;
2-[3-(4-phenyl-piperidin-1-ylmethyl)-benzofuran-6-yloxy]-thiazolo[4,5-b]pyridine;

2-[3-(3,5-dimethyl-piperidin-1-ylmethyl)-benzofuran-6-yloxy]-thiazolo[4,5-b]pyridine;
dimethyl-{1-[6-(thiazolo[4,5-b]pyridin-2-yloxy)-benzofuran-3-ylmethyl]-piperidin-4-yl}-amine;
2-[3-(4-pyrrolidin-1-yl-piperidin-1-ylmethyl)-benzofuran-6-yloxy]-thiazolo[4,5-b]pyridine;
1'-[6-(thiazolo[4,5-b]pyridin-2-yloxy)-benzofuran-3-ylmethyl]-[1,4]bipiperidinyl;
2-[3-(4-morpholin-4-yl-piperidin-1-ylmethyl)-benzofuran-6-yloxy]-thiazolo[4,5-b]pyridine;
2-[3-(4-methyl-piperidin-1-ylmethyl)-benzofuran-6-yloxy]-thiazolo[4,5-b]pyridine;
2-[3-(4-phenyl-piperazin-1-ylmethyl)-benzofuran-6-yloxy]-thiazolo[4,5-b]pyridine;
2-[3-(4-pyridin-2-yl-piperazin-1-ylmethyl)-benzofuran-6-yloxy]-thiazolo[4,5-b]pyridine;
2-[3-(4-pyridin-4-yl-piperazin-1-ylmethyl)-benzofuran-6-yloxy]-thiazolo[4,5-b]pyridine;
2-{3-[4-(4-methoxy-phenyl)-piperazin-1-ylmethyl]-benzofuran-6-yloxy}-thiazolo[4,5-b]pyridine;
2-[3-(4-phenethyl-piperazin-1-ylmethyl)-benzofuran-6-yloxy]-thiazolo[4,5-b]pyridine;
2-[3-(4-pyridin-2-yl-piperazin-1-ylmethyl)-benzofuran-6-yloxy]-thiazolo[4,5-b]pyridine;
2-[6-(thiazolo[4,5-b]pyridin-2-yloxy)-benzofuran-3-ylmethyl]-1,2,3,4-tetrahydro-isoquinoline;
methyl-(1-methyl-piperidin-4-yl)-[6-(thiazolo[4,5-b]pyridin-2-yloxy)-benzofuran-3-ylmethyl]-amine;
meso-1-{3-[6-(thiazolo[4,5-b]pyridin-2-yloxy)-benzofuran-3-ylmethyl]-3,8-diaza-bicyclo[3.2.1]oct-8-yl}-ethanone;
meso-endo-N-{8-[6-(thiazolo[4,5-b]pyridin-2-yloxy)-furo[3,2-b]pyridin-2-ylmethyl]-8-aza-bicyclo[3.2.1]oct-3-yl}-acetamide;
cyclopropyl-[6-(thiazolo[4,5-b]pyridin-2-yloxy)-benzofuran-3-ylmethyl]-amine;
cyclopentyl-[6-(thiazolo[4,5-b]pyridin-2-yloxy)-benzofuran-3-ylmethyl]-amine;
cyclohexyl-[6-(thiazolo[4,5-b]pyridin-2-yloxy)-benzofuran-3-ylmethyl]-amine;
[6-(thiazolo[4,5-b]pyridin-2-yloxy)-benzofuran-3-ylmethyl]-thiophen-2-ylmethyl-amine;
tert-butyl-[6-(thiazolo[4,5-b]pyridin-2-yloxy)-benzofuran-3-ylmethyl]-amine;
2-[3-(4-tert-butyl-piperidin-1-ylmethyl)-benzofuran-6-yloxy]-thiazolo[4,5-b]pyridine;
propyl-[6-(thiazolo[4,5-b]pyridin-2-yloxy)-benzofuran-3-ylmethyl]-amine;
isobutyl-[6-(thiazolo[4,5-b]pyridin-2-yloxy)-benzofuran-3-ylmethyl]-amine;
(2-piperidin-1-yl-ethyl)-[6-(thiazolo[4,5-b]pyridin-2-yloxy)-benzofuran-3-ylmethyl]-amine;
(2-morpholin-4-yl-ethyl)-[6-(thiazolo[4,5-b]pyridin-2-yloxy)-benzofuran-3-ylmethyl]-amine;
N-{1-[6-(thiazolo[4,5-b]pyridin-2-yloxy)-benzofuran-3-ylmethyl]-pyrrolidin-3-yl}-acetamide;
2-[3-(4-isobutyl-piperazin-1-ylmethyl)-benzofuran-6-yloxy]-thiazolo[4,5-b]pyridine;
N-methyl-N-{1-[6-(thiazolo[4,5-b]pyridin-2-yloxy)-benzofuran-3-ylmethyl]-pyrrolidin-3-yl}-acetamide;
(S)—N-{1-[6-(thiazolo[4,5-b]pyridin-2-yloxy)-benzofuran-3-ylmethyl]-pyrrolidin-3-yl}-acetamide;
4-(2-{[6-(benzothiazol-2-yloxy)-benzofuran-3-ylmethyl]-amino}-ethyl)-benzenesulfonamide;
(S)-{1-[6-(benzothiazol-2-yloxy)-benzofuran-3-ylmethyl]-pyrrolidin-2-yl}-methanol;
{1-[6-(benzothiazol-2-yloxy)-benzofuran-3-ylmethyl]-piperidin-4-yl}-carbamic acid tert-butyl ester;
2-[3-(3-propoxy-azetidin-1-ylmethyl)-benzofuran-6-yloxy]-thiazolo[4,5-b]pyridine;
1-[6-(thiazolo[4,5-b]pyridin-2-yloxy)-benzofuran-3-ylmethyl]-azetidin-3-ol;
2-[3-(3,3-difluoro-azetidin-1-ylmethyl)-benzofuran-6-yloxy]-thiazolo[4,5-b]pyridine;
N,N-diethyl-N'-[6-(thiazolo[4,5-b]pyridin-2-yloxy)-benzofuran-3-ylmethyl]-ethane-1,2-diamine;
cyclohexyl-ethyl-[6-(thiazolo[4,5-b]pyridin-2-yloxy)-benzofuran-3-ylmethyl]-amine;
(2-phenoxy-ethyl)-[6-(thiazolo[4,5-b]pyridin-2-yloxy)-benzofuran-3-ylmethyl]-amine;
indan-2-yl-[6-(thiazolo[4,5-b]pyridin-2-yloxy)-benzofuran-3-ylmethyl]-amine;
phenethyl-[6-(thiazolo[4,5-b]pyridin-2-yloxy)-benzofuran-3-ylmethyl]-amine;
N-cyclopropyl-N-{1-[6-(thiazolo[4,5-b]pyridin-2-yloxy)-benzofuran-3-ylmethyl]-piperidin-4-yl}-acetamide;
N-isopropyl-N-{1-[6-(thiazolo[4,5-b]pyridin-2-yloxy)-benzofuran-3-ylmethyl]-piperidin-4-yl}-acetamide;
(R)—N-{1-[6-(thiazolo[4,5-b]pyridin-2-yloxy)-benzofuran-3-ylmethyl]-pyrrolidin-3-yl}-acetamide;
2-[3-(4-thiophen-2-ylmethyl-piperazin-1-ylmethyl)-benzofuran-6-yloxy]-thiazolo[4,5-b]pyridine;
2-[3-(hexahydro-pyrrolo[1,2-a]pyrazin-2-ylmethyl)-benzofuran-6-yloxy]-thiazolo[4,5-b]pyridine;
diethyl-{1-[6-(thiazolo[4,5-b]pyridin-2-yloxy)-benzofuran-3-ylmethyl]-pyrrolidin-3-yl}-amine;
(R)-2-[3-(3-fluoro-pyrrolidin-1-ylmethyl)-benzofuran-6-yloxy]-thiazolo[4,5-b]pyridine;
diethyl-[5-(thiazolo[4,5-b]pyridin-2-yloxy)-benzofuran-2-ylmethyl]-amine;
2-[3-(5-fluoro-1,3-dihydro-isoindol-2-ylmethyl)-benzofuran-6-yloxy]-thiazolo[4,5-b]-pyridine;
2-[3-(1,3-dihydro-isoindol-2-ylmethyl)-benzofuran-6-yloxy]-thiazolo[4,5-b]pyridine;
meso-endo-1-(3-{[6-(thiazolo[4,5-b]pyridin-2-yloxy)-benzofuran-3-ylmethyl]-amino}-8-aza-bicyclo[3.2.1]oct-8-yl)-ethanone;
meso-exo-1-(3-{[6-(thiazolo[4,5-b]pyridin-2-yloxy)-benzofuran-3-ylmethyl]-amino}-8-aza-bicyclo[3.2.1]oct-8-yl)-ethanone;
3-{methyl-[6-(thiazolo[4,5-b]pyridin-2-yloxy)-benzofuran-3-ylmethyl]-amino}-propionic acid ethyl ester;
3-{methyl-[6-(thiazolo[4,5-b]pyridin-2-yloxy)-benzofuran-3-ylmethyl]-amino}-propionic acid;
meso-exo-N-{8-[6-(thiazolo[4,5-b]pyridin-2-yloxy)-furo[3,2-b]pyridin-2-ylmethyl]-8-aza-bicyclo[3.2.1]oct-3-yl}-acetamide;
(1S,4S)-5-[6-(thiazolo[4,5-b]pyridin-2-yloxy)-furo[3,2-b]pyridin-2-ylmethyl]-2,5-diaza-bicyclo[2.2.1]heptane-2-carboxylic acid amide;
meso-1-{8-[6-(thiazolo[4,5-b]pyridin-2-yloxy)-furo[3,2-b]pyridin-2-ylmethyl]-3,8-diaza-bicyclo[3.2.1]oct-3-yl}-ethanone;
(1S,4S)-1-{5-[6-(thiazolo[4,5-b]pyridin-2-yloxy)-furo[3,2-b]pyridin-2-ylmethyl]-2,5-diaza-bicyclo[2.2.2]oct-2-yl}-ethanone;
(1R,4R)-1-{5-[6-(thiazolo[4,5-b]pyridin-2-yloxy)-furo[3,2-b]pyridin-2-ylmethyl]-2,5-diaza-bicyclo[2.2.1]hept-2-yl}-ethanone;
1-{1-[6-(thiazolo[4,5-b]pyridin-2-yloxy)-furo[3,2-b]pyridin-2-ylmethyl]-piperidin-4-yl}-pyrrolidin-2-one;
4-[6-(thiazolo[4,5-b]pyridin-2-yloxy)-benzofuran-3-ylmethyl]-piperazin-2-one;
1-{4-[6-(thiazolo[4,5-b]pyridin-2-yloxy)-furo[3,2-b]pyridin-2-ylmethyl]-piperazin-1-yl}-ethanone;
benzyl-[6-(thiazolo[4,5-b]pyridin-2-yloxy)-benzofuran-3-ylmethyl]-amine;
(4-fluoro-benzyl)-[6-(thiazolo[4,5-b]pyridin-2-yloxy)-benzofuran-3-ylmethyl]-amine;

(4-methoxy-benzyl)-[6-(thiazolo[4,5-b]pyridin-2-yloxy)-benzofuran-3-ylmethyl]-amine;
4-(4-chloro-phenyl)-1-[6-(thiazolo[4,5-b]pyridin-2-yloxy)-benzofuran-3-ylmethyl]-piperidin-4-ol;
4-(4-bromo-phenyl)-1-[6-(thiazolo[4,5-b]pyridin-2-yloxy)-benzofuran-3-ylmethyl]-piperidin-4-ol;
2-[3-(2,6-dimethyl-morpholin-4-ylmethyl)-benzofuran-6-yloxy]-thiazolo[4,5-b]pyridine;
2-[3-(3-fluoro-piperidin-1-ylmethyl)-benzofuran-6-yloxy]-thiazolo[4,5-b]pyridine;
4-{1-[6-(thiazolo[4,5-b]pyridin-2-yloxy)-benzofuran-3-ylmethyl]-piperidin-4-yl}-2,4-dihydro-[1,2,4]triazol-3-one;
1-{7-[6-(thiazolo[4,5-b]pyridin-2-yloxy)-benzofuran-3-ylmethyl]-3,7-diaza-bicyclo[3.3.1]non-3-yl}-ethanone;
N-ethyl-N-{1-[6-(thiazolo[4,5-b]pyridin-2-yloxy)-benzofuran-3-ylmethyl]-piperidin-4-yl}-acetamide;
(tetrahydro-furan-3-yl)-{5-[6-(thiazolo[4,5-b]pyridin-2-yloxy)-benzofuran-3-ylmethyl]-hexahydro-pyrrolo[3,4-c]pyrrol-2-yl}-methanone;
2-hydroxy-1-{5-[6-(thiazolo[4,5-b]pyridin-2-yloxy)-benzofuran-3-ylmethyl]-hexahydro-pyrrolo[3,4-c]pyrrol-2-yl}-ethanone;
(1S,4S)-pyrazin-2-yl-{5-[6-(thiazolo[4,5-b]pyridin-2-yloxy)-benzofuran-3-ylmethyl]-2,5-diaza-bicyclo[2.2.1]hept-2-yl}-methanone;
(1S,4S)-cyclobutyl-{5-[6-(thiazolo[4,5-b]pyridin-2-yloxy)-benzofuran-3-ylmethyl]-2,5-diaza-bicyclo[2.2.1]hept-2-yl}-methanone;
(1S,4S)-isoxazol-5-yl-{5-[6-(thiazolo[4,5-b]pyridin-2-yloxy)-benzofuran-3-ylmethyl]-2,5-diaza-bicyclo[2.2.1]hept-2-yl}-methanone;
furan-3-yl-{5-[6-(thiazolo[4,5-b]pyridin-2-yloxy)-benzofuran-3-ylmethyl]hexahydro-pyrrolo[3,4-c]pyrrol-2-yl}-methanone;
(1S,4S)-4-{5-[6-(thiazolo[4,5-b]pyridin-2-yloxy)-benzofuran-3-ylmethyl]-2,5-diaza-bicyclo[2.2.1]hept-2-ylmethyl}-benzoic acid methyl ester;
dimethyl-[6-(thiazolo[4,5-b]pyridin-2-yloxy)-benzofuran-3-ylmethyl]-amine;
(2-{1-[6-(benzothiazol-2-yloxy)-benzofuran-3-ylmethyl]-piperidin-4-yl}-ethyl)-carbamic acid tert-butyl ester;
N-{1-[6-(benzothiazol-2-yloxy)-benzofuran-3-ylmethyl]-piperidin-4-yl}-methanesulfonamide;
N-(2-{1-[6-(benzothiazol-2-yloxy)-benzofuran-3-ylmethyl]-piperidin-4-yl}-ethyl)-methanesulfonamide;
5-(thiazolo[4,5-b]pyridin-2-yloxy)-benzofuran-2-carboxylic acid benzyl-methyl-amide;
(1R,4R)-1-{5-[5-(thiazolo[4,5-b]pyridin-2-yloxy)-benzofuran-2-carbonyl]-2,5-diaza-bicyclo[2.2.1]hept-2-yl}-ethanone;
6-(thiazolo[4,5-b]pyridin-2-yloxy)-benzofuran-3-carboxylic acid methylamide;
N-{1-[6-(thiazolo[4,5-b]pyridin-2-yloxy)-benzofuran-3-carbonyl]-piperidin-4-yl}-acetamide;
meso-endo-N-{8-[6-(thiazolo[4,5-b]pyridin-2-yloxy)-benzofuran-3-carbonyl]-8-aza-bicyclo[3.2.1]oct-3-yl}-acetamide;
1-{1-[6-(thiazolo[4,5-b]pyridin-2-yloxy)-benzofuran-3-carbonyl]-piperidin-4-yl}-pyrrolidin-2-one;
(1S,4S)-1-{5-[6-(thiazolo[4,5-b]pyridin-2-yloxy)-benzofuran-3-carbonyl]-2,5-diaza-bicyclo[2.2.1]hept-2-yl}-ethanone;
1-{4-[6-(thiazolo[4,5-b]pyridin-2-yloxy)-benzofuran-3-carbonyl]-[1,4]diazepan-1-yl}-ethanone;
6-(thiazolo[4,5-b]pyridin-2-yloxy)-benzofuran-3-carboxylic acid isopropyl-methyl-amide;
meso-8-[6-(thiazolo[4,5-b]pyridin-2-yloxy)-benzofuran-3-carbonyl]-3,8-diaza-bicyclo[3.2.1]octane-3-carboxylic acid amide;
(1S,4S)-5-[6-(thiazolo[4,5-b]pyridin-2-yloxy)-benzofuran-3-carbonyl]-2,5-diaza-bicyclo[2.2.1]heptane-2-carboxylic acid amide;
(4-fluoro-piperidin-1-yl)-[6-(thiazolo[4,5-b]pyridin-2-yloxy)-benzofuran-3-yl]-methanone;
(4-phenyl-piperidin-1-yl)-[6-(thiazolo[4,5-b]pyridin-2-yloxy)-benzofuran-3-yl]-methanone;
1-[6-(thiazolo[4,5-b]pyridin-2-yloxy)-benzofuran-3-carbonyl]-piperidine-4-carboxylic acid amide;
(4-cyclohexyl-piperazin-1-yl)-[6-(thiazolo[4,5-b]pyridin-2-yloxy)-benzofuran-3-yl]-methanone;
1-{4-[6-(thiazolo[4,5-b]pyridin-2-yloxy)-benzofuran-3-carbonyl]-piperazin-1-yl}-ethanone;
6-(thiazolo[4,5-b]pyridin-2-yloxy)-benzofuran-3-carboxylic acid cyclohexyl-ethyl-amide;
[4-(pyrimidin-2-yloxy)-piperidin-1-yl]-[6-(thiazolo[4,5-b]pyridin-2-yloxy)-benzofuran-3-yl]-methanone;
piperidin-1-yl-[6-(thiazolo[4,5-b]pyridin-2-yloxy)-benzofuran-3-yl]-methanone;
[4-(piperidine-1-carbonyl)-piperidin-1-yl]-[6-(thiazolo[4,5-b]pyridin-2-yloxy)-benzofuran-3-yl]-methanone;
(octahydro-isoquinolin-2-yl)-[6-(thiazolo[4,5-b]pyridin-2-yloxy)-benzofuran-3-yl]-methanone;
(3,4-dihydro-1H-isoquinolin-2-yl)-[6-(thiazolo[4,5-b]pyridin-2-yloxy)-benzofuran-3-yl]-methanone;
(4-benzoyl-piperidin-1-yl)-[6-(thiazolo[4,5-b]pyridin-2-yloxy)-benzofuran-3-yl]-methanone;
6-(thiazolo[4,5-b]pyridin-2-yloxy)-benzofuran-3-carboxylic acid (3-dimethylamino-propyl)-methyl-amide;
endo-bicyclo[2.2.1]heptane-2-carboxylic acid [6-(thiazolo[4,5-b]pyridin-2-yloxy)-benzofuran-3-ylmethyl]-amide;
2-(4-acetyl-piperazin-1-yl)-N-[6-(thiazolo[4,5-b]pyridin-2-yloxy)-benzofuran-3-ylmethyl]-acetamide;
2-(3-methyl-isoxazol-5-yl)-N-[6-(thiazolo[4,5-b]pyridin-2-yloxy)-benzofuran-3-ylmethyl]-acetamide;
4-hydroxy-cyclohexanecarboxylic acid [6-(thiazolo[4,5-b]pyridin-2-yloxy)-benzofuran-3-ylmethyl]-amide;
N-[6-(thiazolo[4,5-b]pyridin-2-yloxy)-benzofuran-3-ylmethyl]-terephthalamic acid methyl ester;
2-(4-chloro-phenyl)-N-[6-(thiazolo[4,5-b]pyridin-2-yloxy)-benzofuran-3-ylmethyl]-acetamide;
N-[6-(thiazolo[4,5-b]pyridin-2-yloxy)-benzofuran-3-ylmethyl]-acetamide;
N-[6-(thiazolo[4,5-b]pyridin-2-yloxy)-benzofuran-3-ylmethyl]-terephthalamic acid;
1-[6-(thiazolo[4,5-b]pyridin-2-yloxy)-benzofuran-3-ylmethyl]-3,4-dihydro-1H-quinolin-2-one;
1-[6-(thiazolo[4,5-b]pyridin-2-yloxy)-benzofuran-3-ylmethyl]-6-trifluoromethyl-1,3-dihydro-indol-2-one;
1-[6-(thiazolo[4,5-b]pyridin-2-yloxy)-benzofuran-3-ylmethyl]-1,3-dihydro-indol-2-one;
1-[6-(thiazolo[4,5-b]pyridin-2-yloxy)-benzofuran-3-ylmethyl]-5-trifluoromethyl-1,3-dihydro-indol-2-one;
5-chloro-1-[6-(thiazolo[4,5-b]pyridin-2-yloxy)-benzofuran-3-ylmethyl]-1,3-dihydro-indol-2-one;
6-chloro-1-[6-(thiazolo[4,5-b]pyridin-2-yloxy)-benzofuran-3-ylmethyl]-1,3-dihydro-indol-2-one;
5-fluoro-1-[6-(thiazolo[4,5-b]pyridin-2-yloxy)-benzofuran-3-ylmethyl]-1,3-dihydro-indol-2-one;
(R)—N-(1-aza-bicyclo[2.2.2]oct-3-yl)-N-[6-(thiazolo[4,5-b]pyridin-2-yloxy)-benzofuran-3-ylmethyl]-acetamide;
2-(3-piperidin-1-ylmethyl-benzofuran-6-yloxy)-benzothiazole;
2-(2-piperidin-1-ylmethyl-benzofuran-6-yloxy)-benzothiazole;

and pharmaceutically acceptable salts and prodrugs thereof.

28. A pharmaceutical composition comprising an effective amount of at least one chemical entity selected from the group consisting of compounds of Formula (I), pharmaceutically acceptable salts of compounds of Formula (I), and pharmaceutically acceptable prodrugs of compounds of Formula (I)

wherein
A is O, bound at site a or at site b;
Z is O or S;
$G_1$, $G_2$ and $G_3$ are each independently $CR^4$ or N;
$R^4$ is H, —$C_{1-4}$alkyl, or halo;
X is CH or N;
Y is O, S, or $NR^3$;
$R^3$ is H or —$C_{1-4}$alkyl;
when Y is O, then L is —$CH_2$—, —$CH_2CH_2$—, or —C(O)—;
when Y is S or $NR^3$, then L is —$CH_2$— or —$CH_2CH_2$—;
$R^1$ and $R^2$ are each independently H, —$C_{1-4}$alkyl, —C(O)$R^i$, —$(CH_2)_2$C(O)O$R^3$, —$(CH_2)_2$N($CH_2CH_3$)$_2$, —$(CH_2)_3$N($CH_3$)$_2$, —$C_{3-6}$cycloalkyl, —$(CH_2)_{1-4}$O$CH_3$, indan-2-yl, or —$(CH_2)_{0-2}$—(O)$_{0-1}$-phenyl wherein said phenyl is optionally substituted with halo, —$OCH_3$, or —$SO_2NH_2$; provided that $R^1$ and $R^2$ are not both H simultaneously;

$R^i$ is —$CH_3$, 4-acetyl-piperazin-1-ylmethyl, 3-methyl-isoxazol-5-ylmethyl, 4-hydroxy-cyclohexyl, or or
$R^1$ and $R^2$ are taken together as in one of the following assignments (i) and (ii);
(i) $R^1$ and $R^2$ taken together with the nitrogen member to which they are attached form an unbridged monocyclic moiety, said moiety optionally containing one additional heteroatom member selected from N, O, and S; said moiety being optionally substituted with $R^5$ and $(R^{5'})_m$;
m is 0 or 1;
when m is 1, $R^{5'}$ is —$C_{1-4}$alkyl, halo, or OH;
$R^5$ is selected from H; halo; =O; —OH; —O$R^3$; —$CF_3$; —S(O)(O)$CH_3$; —$C_{1-4}$alkyl; —O$C_{1-4}$alkyl; —C($CH_3$)$_2$OH; —$(CH_2)_{0-1}$C(O)O$R^3$; —N($R^3$)$_2$; —$CH_2$OH; —$CH_2$O$CH_3$; —$(CH_2)_{0-2}$N$R^9$C(O)$R^7$; —$(CH_2)_{0-2}$NHS(O)(O)$CH_3$; —C(O)$R^8$; —$C_{3-6}$cycloalkyl; pyrimidin-2-yloxy; 1-piperidinyl; 1-piperidinyl-2-one; 1-pyrrolidinyl; 4-morpholinyl; pyridinyl; pyrimidyl; thiophenylmethyl; 5-oxo-1; 5-dihydro-[1,2,4]triazol-4-yl; —$(CH_2)_{0-2}$-phenyl wherein said phenyl is optionally substituted with halo or $OCH_3$; and 1-pyrrolidinyl-2-one optionally substituted with —OH;
Q is $CH_2$ or O;
$R^7$ is —$C_{1-4}$alkyl, —$NH_2$, or —O$C_{1-4}$alkyl;
$R^8$ is —$C_{1-4}$alkyl; —$NH_2$; —$NHCH_3$; —$C_{3-6}$cycloalkyl; —$(CH_2)_{0-1}$phenyl wherein said phenyl is optionally substituted with halo or $CO_2H$; 1-pyrrolidinyl; or E is $CH_2$, O, or N($CH_3$);
$R^9$ is H, —$C_{1-4}$alkyl, or —$C_{3-6}$cycloalkyl;
(ii) $R^1$ and $R^2$ taken together with the nitrogen member to which they are attached form one of the following -continued

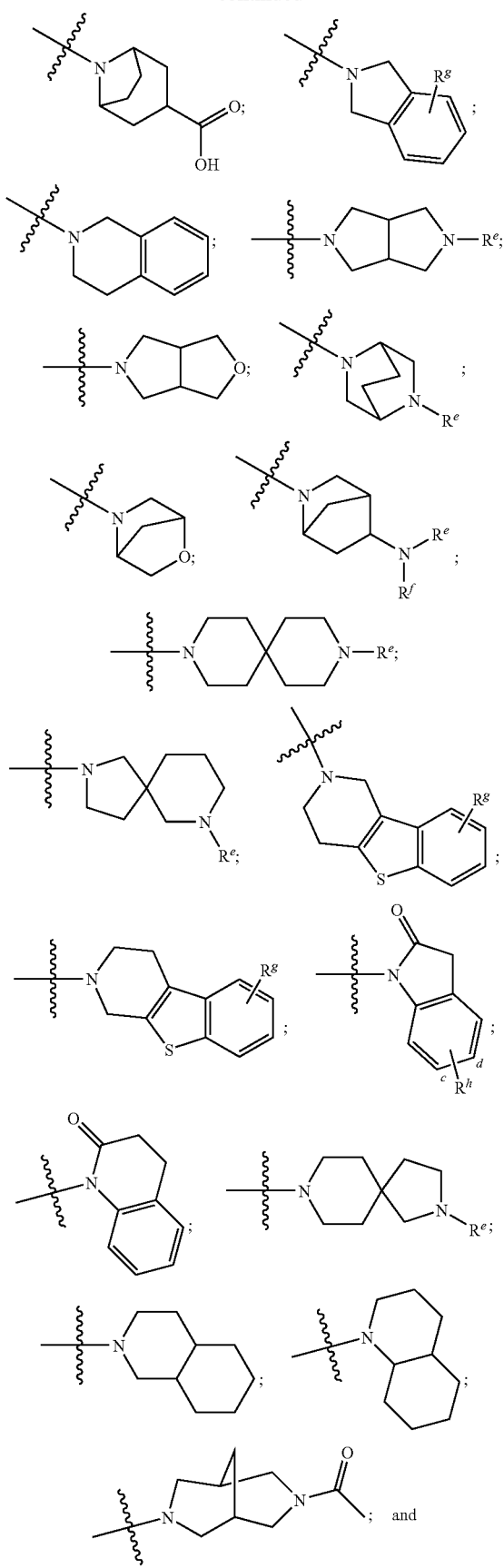

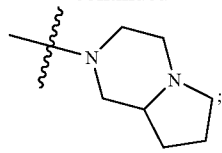

-continued $R^e$ is H, —$C_{1-4}$alkyl, —C(O)$C_{1-4}$alkyl, —C(O)O$C_{1-4}$alkyl, —C(O)NH$_2$, —C(O)-tetrahydrofuranyl, —C(O)CH$_2$OH, —C(O)isoxazol-5-yl, —C(O)furan-3-yl, —C(O)pyrazin-2-yl, —C(O)cyclobutyl, —S(O)(O)CH$_3$, or 4-methoxycarbonyl-benzyl;

$R^f$ is H, —CH$_3$, or —CH$_2$C(O)O$R^3$;

$R^g$ is H or halo; and $R^h$ is bound at site c or d and is selected from H, CF$_3$, and halo.

29. A pharmaceutical composition as in claim 28, wherein said chemical entity is selected from the group consisting of
2-(3-pyrrolidin-1-ylmethyl-1H-indol-6-yloxy)-benzothiazole;
2-(3-piperidin-1-ylmethyl-1H-indol-6-yloxy)-benzothiazole;
2-(3-morpholin-4-ylmethyl-1H-indol-6-yloxy)-benzothiazole;
2-[3-(4-methanesulfonyl-piperidin-1-ylmethyl)-1H-indol-6-yloxy]-benzothiazole;
[6-(benzothiazol-2-yloxy)-1H-indol-3-ylmethyl]-benzyl-methyl-amine;
2-[3-(1,3-dihydro-isoindol-2-ylmethyl)-1H-indol-6-yloxy]-benzothiazole;
2-[6-(benzothiazol-2-yloxy)-1H-indol-3-ylmethyl]-1,2,3,4-tetrahydro-isoquinoline;
2-[3-(4-phenyl-piperidin-1-ylmethyl)-1H-indol-6-yloxy]-benzothiazole;
2-(3-pyrrolidin-1-ylmethyl-1H-indol-5-yloxy)-benzothiazole;
2-(3-piperidin-1-ylmethyl-1H-indol-5-yloxy)-benzothiazole;
2-(3-morpholin-4-ylmethyl-1H-indol-5-yloxy)-benzothiazole;
(1S,4S)-2-[3-(2-oxa-5-aza-bicyclo[2.2.1]hept-5-ylmethyl)-1H-indol-6-yloxy]-benzothiazole;
meso-endo-N-{8-[6-(benzothiazol-2-yloxy)-1H-indol-3-ylmethyl]-8-aza-bicyclo[3.2.1]oct-3-yl}-acetamide;
meso-endo-N-{8-[6-(4-fluoro-benzothiazol-2-yloxy)-1H-indol-3-ylmethyl]-8-aza-bicyclo[3.2.1]oct-3-yl}-acetamide;
2-(3-piperidin-1-ylmethyl-1H-indol-6-yloxy)-benzooxazole;
2-(3-piperidin-1-ylmethyl-1H-indol-6-yloxy)-thiazolo[4,5-b]pyridine;
1-[6-(thiazolo[4,5-b]pyridin-2-yloxy)-1H-indol-3-ylmethyl]-piperidine-4-carboxylic acid amide;
meso-endo-N-{8-[6-(thiazolo[4,5-b]pyridin-2-yloxy)-1H-indol-3-ylmethyl]-8-aza-bicyclo[3.2.1]oct-3-yl}-acetamide;
(1S,4S)-1-{5-[6-(thiazolo[4,5-b]pyridin-2-yloxy)-1H-indol-3-ylmethyl]-2,5-diaza-bicyclo[2.2.1]hept-2-yl}-ethanone;
1-{1-[6-(thiazolo[4,5-b]pyridin-2-yloxy)-1H-indol-3-ylmethyl]-piperidin-4-yl}-pyrrolidin-2-one;
1-[6-(benzothiazol-2-yloxy)-1H-indol-3-ylmethyl]-piperidine-4-carboxylic acid amide;
1-[6-(benzothiazol-2-yloxy)-1H-indol-3-ylmethyl]-piperidine-4-carboxylic acid methylamide;
{1-[6-(benzothiazol-2-yloxy)-1H-indol-3-ylmethyl]-piperidin-4-yl}-pyrrolidin-1-yl-methanone;

{1-[6-(benzothiazol-2-yloxy)-1H-indol-3-ylmethyl]-piperidin-4-yl}-piperidin-1-yl-methanone;
{1-[6-(benzothiazol-2-yloxy)-1H-indol-3-ylmethyl]-piperidin-4-yl}-morpholin-4-yl-methanone;
{1-[6-(benzothiazol-2-yloxy)-1H-indol-3-ylmethyl]-piperidin-4-yl}-(4-methyl-piperazin-1-yl)-methanone;
(3S)-1-[6-(benzothiazol-2-yloxy)-1H-indol-3-ylmethyl]-piperidine-3-carboxylic acid amide;
{1-[6-(benzothiazol-2-yloxy)-1H-indol-3-ylmethyl]-piperidin-4-yl}-methanol;
{1-[6-(benzothiazol-2-yloxy)-1H-indol-3-ylmethyl]-piperidin-4-yl}-carbamic acid ethyl ester;
1-{1-[6-(benzothiazol-2-yloxy)-1H-indol-3-ylmethyl]-piperidin-4-yl}-pyrrolidin-2-one;
2-(3-piperidin-1-ylmethyl-1H-pyrrolo[3,2-b]pyridin-6-yloxy)-benzothiazole;
2-(3-morpholin-4-ylmethyl-1H-pyrrolo[3,2-b]pyridin-6-yloxy)-benzothiazole;
1-[6-(benzothiazol-2-yloxy)-1H-pyrrolo[3,2-b]pyridin-3-ylmethyl]-piperidine-4-carboxylic acid amide;
2-[6-(thiazolo[4,5-b]pyridin-2-yloxy)-1H-indol-3-ylmethyl]-1,2,3,4-tetrahydro-benzo[4,5]thieno[3,2-c]pyridine;
2-[6-(thiazolo[4,5-b]pyridin-2-yloxy)-1H-indol-3-ylmethyl]-1,2,3,4-tetrahydro-benzo[4,5]thieno[2,3-c]pyridine;
8-chloro-2-[6-(thiazolo[4,5-b]pyridin-2-yloxy)-1H-indol-3-ylmethyl]-1,2,3,4-tetrahydro-benzo[4,5]thieno[3,2-c]pyridine;
6-chloro-2-[6-(thiazolo[4,5-b]pyridin-2-yloxy)-1H-indol-3-ylmethyl]-1,2,3,4-tetrahydro-benzo[4,5]thieno[2,3-c]pyridine;
8-fluoro-2-[6-(thiazolo[4,5-b]pyridin-2-yloxy)-1H-indol-3-ylmethyl]-1,2,3,4-tetrahydro-benzo[4,5]thieno[3,2-c]pyridine;
2-[6-(benzothiazol-2-yloxy)-1H-indol-3-ylmethyl]-1,2,3,4-tetrahydro-benzo[4,5]thieno[3,2-c]pyridine;
2-(3-morpholin-4-ylmethyl-1H-indol-6-yloxy)-thiazolo[4,5-b]pyridine;
(3S)-2-[3-(3-Methyl-morpholin-4-ylmethyl)-1H-indol-6-yloxy]-thiazolo[4,5-b]pyridine;
2-(3-thiomorpholin-4-ylmethyl-1H-indol-6-yloxy)-thiazolo[4,5-b]pyridine;
meso-endo-N-{8-[6-(Thiazolo[5,4-b]pyridin-2-yloxy)-1H-indol-3-ylmethyl]-8-aza-bicyclo[3.2.1]oct-3-yl}-acetamide;
(4R)-1-{1-[6-(benzothiazol-2-yloxy)-1H-indol-3-ylmethyl]-piperidin-4-yl}-4-hydroxy-pyrrolidin-2-one;
1-[6-(benzothiazol-2-yloxy)-1H-indol-3-ylmethyl]-piperidine-4-carboxylic acid;
{1-[6-(benzothiazol-2-yloxy)-1H-indol-3-ylmethyl]-piperidin-4-yl}-acetic acid;
1-[6-(benzothiazol-2-yloxy)-1H-indol-3-ylmethyl]-piperidine-3-carboxylic acid;
meso-endo-(acetyl-{8-[6-(benzothiazol-2-yloxy)-1H-indol-3-ylmethyl]-8-aza-bicyclo[3.2.1]oct-3-yl}-amino)-acetic acid;
meso-endo-(acetyl-{8-[5-(benzothiazol-2-yloxy)-1H-indol-3-ylmethyl]-8-aza-bicyclo[3.2.1]oct-3-yl}-amino)-acetic acid;
1-[6-(benzothiazol-2-yloxy)-1H-indol-3-ylmethyl]-piperidin-4-ylamine;
2-[3-(hexahydro-pyrrolo[3,4-c]pyrrol-2-ylmethyl)-1H-indol-6-yloxy]-benzothiazole;
(1S,4S)-2-[3-(2,5-diaza-bicyclo[2.2.1]hept-2-ylmethyl)-1H-indol-6-yloxy]-benzothiazole;
N-{1-[6-(benzothiazol-2-yloxy)-1H-indol-3-ylmethyl]-piperidin-4-yl}-acetamide;
1-{5-[6-(benzothiazol-2-yloxy)-1H-indol-3-ylmethyl]-hexahydro-pyrrolo[3,4-c]pyrrol-2-yl}-ethanone;
(1S,4S)-1-{5-[6-(benzothiazol-2-yloxy)-1H-indol-3-ylmethyl]-2,5-diaza-bicyclo[2.2.1]hept-2-yl}-ethanone;
2-(3-morpholin-4-ylmethyl-1H-indol-6-yloxy)-thiazolo[4,5-b]pyrazine;
7-methyl-2-(3-morpholin-4-ylmethyl-1H-indol-6-yloxy)-thiazolo[4,5-b]pyridine;
6-fluoro-2-(3-morpholin-4-ylmethyl-1H-indol-6-yloxy)-thiazolo[4,5-b]pyridine;
6-chloro-2-(3-morpholin-4-ylmethyl-1H-indol-6-yloxy)-thiazolo[4,5-b]pyridine;
6-fluoro-2-(3-morpholin-4-ylmethyl-1H-indol-6-yloxy)-thiazolo[5,4-b]pyridine;
2-(1-methyl-3-morpholin-4-ylmethyl-1H-indol-6-yloxy)-benzothiazole;
2-(1-ethyl-2-piperidin-1-ylmethyl-1H-indol-5-yloxy)-benzothiazole;
2-(1-ethyl-2-morpholin-4-ylmethyl-1H-indol-5-yloxy)-benzothiazole;
2-(1-ethyl-2-pyrrolidin-1-ylmethyl-1H-indol-5-yloxy)-benzothiazole;
2-(2-piperidin-1-ylmethyl-1H-indol-5-yloxy)-benzothiazole;
2-(2-pyrrolidin-1-ylmethyl-1H-indol-5-yloxy)-benzothiazole;
2-(2-piperidin-1-ylmethyl-1H-indol-6-yloxy)-benzothiazole;
2-(2-pyrrolidin-1-ylmethyl-1H-indol-6-yloxy)-benzothiazole;
1-[6-(benzothiazol-2-yloxy)-1H-indol-2-ylmethyl]-piperidine-4-carboxylic acid amide;
meso-endo-N-{8-[6-(benzothiazol-2-yloxy)-1H-indol-2-ylmethyl]-8-aza-bicyclo[3.2.1]oct-3-yl}-acetamide;
2-(2-piperidin-1-ylmethyl-1H-indol-6-yloxy)-thiazolo[4,5-b]pyridine;
meso-endo-N-{8-[6-(thiazolo[4,5-b]pyridin-2-yloxy)-1H-indol-2-ylmethyl]-8-aza-bicyclo[3.2.1]oct-3-yl}-acetamide;
1-{2-[5-(benzothiazol-2-yloxy)-1H-indol-3-yl]-ethyl}-piperidine-4-carboxylic acid;
2-[3-(2-piperidin-1-yl-ethyl)-1H-indol-5-yloxy]-benzothiazole;
1-{2-[5-(benzothiazol-2-yloxy)-1H-indol-3-yl]-ethyl}-piperidine-4-carboxylic acid amide;
1-[5-(benzothiazol-2-yloxy)-benzofuran-2-ylmethyl]-piperidine-4-carboxylic acid;
1-[6-(benzothiazol-2-yloxy)-benzofuran-2-ylmethyl]-piperidine-4-carboxylic acid;
{1-[6-(benzothiazol-2-yloxy)-benzofuran-2-ylmethyl]-piperidin-4-yl}-acetic acid;
{4-[6-(benzothiazol-2-yloxy)-benzofuran-2-ylmethyl]-piperazin-1-yl}-acetic acid;
1-{2-[6-(benzothiazol-2-yloxy)-benzofuran-3-yl]-ethyl}-piperidine-4-carboxylic acid;
meso-endo-{8-[6-(benzothiazol-2-yloxy)-benzofuran-2-ylmethyl]-8-aza-bicyclo[3.2.1]oct-3-ylamino}-acetic acid;
2-(2-piperidin-1-ylmethyl-benzofuran-5-yloxy)-benzothiazole;
meso-endo-N-{8-[5-(benzothiazol-2-yloxy)-benzofuran-2-ylmethyl]-8-aza-bicyclo[3.2.1]oct-3-yl}-acetamide;
4-fluoro-2-(2-piperidin-1-ylmethyl-benzofuran-5-yloxy)-benzothiazole;
meso-endo-N-{8-[5-(4-fluoro-benzothiazol-2-yloxy)-benzofuran-2-ylmethyl]-8-aza-bicyclo[3.2.1]oct-3-yl}-acetamide;
2-(2-piperidin-1-ylmethyl-benzofuran-5-yloxy)-thiazolo[4,5-b]pyridine;
meso-endo-N-{8-[5-(thiazolo[4,5-b]pyridin-2-yloxy)-benzofuran-2-ylmethyl]-8-aza-bicyclo[3.2.1]oct-3-yl}-acetamide;

1-[5-(thiazolo[4,5-b]pyridin-2-yloxy)-benzofuran-2-ylmethyl]-piperidine-4-carboxylic acid amide;
2-{2-[4-(pyrimidin-2-yloxy)-piperidin-1-ylmethyl]-benzofuran-5-yloxy}-thiazolo[4,5-b]-pyridine;
1-{5-[5-(thiazolo[4,5-b]pyridin-2-yloxy)-benzofuran-2-ylmethyl]-hexahydro-pyrrolo[3,4-c]pyrrol-2-yl}-ethanone;
5-[5-(thiazolo[4,5-b]pyridin-2-yloxy)-benzofuran-2-ylmethyl]-hexahydro-pyrrolo[3,4-c]pyrrole-2-carboxylic acid amide;
2-[2-(4-methanesulfonyl-piperidin-1-ylmethyl)-benzofuran-5-yloxy]-thiazolo[4,5-b]pyridine;
meso-1-{8-[5-(thiazolo[4,5-b]pyridin-2-yloxy)-benzofuran-2-ylmethyl]-3,8-diaza-bicyclo[3.2.1]oct-3-yl}-ethanone;
meso-8-[5-(thiazolo[4,5-b]pyridin-2-yloxy)-benzofuran-2-ylmethyl]-3,8-diaza-bicyclo[3.2.1]octane-3-carboxylic acid amide;
(1S,4S)-1-{5-[5-(thiazolo[4,5-b]pyridin-2-yloxy)-benzofuran-2-ylmethyl]-2,5-diaza-bicyclo[2.2.1]hept-2-yl}-ethanone;
1-{1-[5-(thiazolo[4,5-b]pyridin-2-yloxy)-benzofuran-2-ylmethyl]-piperidin-4-yl}-pyrrolidin-2-one;
2-(2-morpholin-4-ylmethyl-benzofuran-5-yloxy)-thiazolo[4,5-b]pyridine;
(3S)-2-[2-(3-methyl-morpholin-4-ylmethyl)-benzofuran-5-yloxy]-thiazolo[4,5-b]-pyridine;
(1S,4S)-2-[2-(2-oxa-5-aza-bicyclo[2.2.1]hept-5-ylmethyl)-benzofuran-5-yloxy]-thiazolo[4,5-b]pyridine;
(1S,4S)-5-[5-(thiazolo[4,5-b]pyridin-2-yloxy)-benzofuran-2-ylmethyl]-2,5-diaza-bicyclo[2.2.1]heptane-2-carboxylic acid amide;
(1R,4R)-5-[5-(thiazolo[4,5-b]pyridin-2-yloxy)-benzofuran-2-ylmethyl]-2,5-diaza-bicyclo[2.2.1]heptane-2-carboxylic acid amide;
(1R,4R)-1-{5-[5-(thiazolo[4,5-b]pyridin-2-yloxy)-benzofuran-2-ylmethyl]-2,5-diaza-bicyclo[2.2.1]hept-2-yl}-ethanone;
meso-endo-N-{8-[5-(thiazolo[4,5-b]pyridin-2-yloxy)-benzofuran-2-ylmethyl]-8-aza-bicyclo[3.2.1]oct-3-yl}-urea;
meso-exo-N-{8-[5-(thiazolo[4,5-b]pyridin-2-yloxy)-benzofuran-2-ylmethyl]-8-aza-bicyclo[3.2.1]oct-3-yl}-acetamide;
1-[5-(benzothiazol-2-yloxy)-benzofuran-2-ylmethyl]-piperidine-4-carboxylic acid amide;
meso-exo-N-{8-[6-(thiazolo[4,5-b]pyridin-2-yloxy)-benzofuran-2-ylmethyl]-8-aza-bicyclo[3.2.1]oct-3-yl}-acetamide;
(1R,4R)-1-{5-[6-(thiazolo[4,5-b]pyridin-2-yloxy)-benzofuran-2-ylmethyl]-2,5-diaza-bicyclo[2.2.1]hept-2-yl}-ethanone;
1-{1-[6-(thiazolo[4,5-b]pyridin-2-yloxy)-benzofuran-2-ylmethyl]-piperidin-4-yl}-pyrrolidin-2-one;
(1S,4S)-2-[2-(2-oxa-5-aza-bicyclo[2.2.1]hept-5-ylmethyl)-benzofuran-6-yloxy]-thiazolo[4,5-b]pyridine;
2-[2-(tetrahydro-furo[3,4-c]pyrrol-5-ylmethyl)-benzofuran-6-yloxy]-thiazolo[4,5-b]pyridine;
2-[2-(4-fluoro-piperidin-1-ylmethyl)-benzofuran-5-yloxy]-thiazolo[4,5-b]pyridine;
dimethyl-[5-(thiazolo[4,5-b]pyridin-2-yloxy)-benzofuran-2-ylmethyl]-amine;
2-[2-(tetrahydro-furo[3,4-c]pyrrol-5-ylmethyl)-benzofuran-5-yloxy]-thiazolo[4,5-b]pyridine;
benzyl-methyl-[5-(thiazolo[4,5-b]pyridin-2-yloxy)-benzofuran-2-ylmethyl]-amine;
2-(2-morpholin-4-ylmethyl-benzofuran-6-yloxy)-thiazolo[4,5-b]pyridine;
1-[6-(thiazolo[4,5-b]pyridin-2-yloxy)-benzofuran-2-ylmethyl]-piperidine-4-carboxylic acid amide;
(1S,4S)-5-[6-(thiazolo[4,5-b]pyridin-2-yloxy)-benzofuran-2-ylmethyl]-2,5-diaza-bicyclo[2.2.1]heptane-2-carboxylic acid amide;
meso-endo-N-{8-[6-(thiazolo[4,5-b]pyridin-2-yloxy)-benzofuran-2-ylmethyl]-8-aza-bicyclo[3.2.1]oct-3-yl}-acetamide;
meso-1-{8-[6-(thiazolo[4,5-b]pyridin-2-yloxy)-benzofuran-2-ylmethyl]-3,8-diaza-bicyclo[3.2.1]oct-3-yl}-ethanone;
N-(1-{[6-([1,3]thiazolo[4,5-b]pyridin-2-yloxy)-1-benzofuran-2-yl]methyl}pyrrolidin-3-yl)acetamide;
(1S,4S)-1-{5-[5-(thiazolo[5,4-b]pyridin-2-yloxy)-benzofuran-2-ylmethyl]-2,5-diaza-bicyclo[2.2.1]hept-2-yl}-ethanone;
(1S,4S)-1-{5-[6-(thiazolo[5,4-b]pyridin-2-yloxy)-benzofuran-2-ylmethyl]-2,5-diaza-bicyclo[2.2.1]hept-2-yl}-ethanone;
meso-1-{8-[5-(thiazolo[5,4-b]pyridin-2-yloxy)-benzofuran-2-ylmethyl]-3,8-diaza-bicyclo[3.2.1]oct-3-yl}-ethanone;
meso-1-{8-[6-(thiazolo[5,4-b]pyridin-2-yloxy)-benzofuran-2-ylmethyl]-3,8-diaza-bicyclo[3.2.1]oct-3-yl}-ethanone;
meso-endo-N-{8-[5-(thiazolo[5,4-b]pyridin-2-yloxy)-benzofuran-2-ylmethyl]-8-aza-bicyclo[3.2.1]oct-3-yl}-acetamide;
meso-endo-N-{8-[6-(thiazolo[5,4-b]pyridin-2-yloxy)-benzofuran-2-ylmethyl]-8-aza-bicyclo[3.2.1]oct-3-yl}-acetamide;
1-(1-{[6-([1,3]thiazolo[4,5-b]pyridin-2-yloxy)-1-benzofuran-2-yl]methyl}pyrrolidin-3-yl)urea;
N-(1-{[6-([1,3]thiazolo[4,5-b]pyridin-2-yloxy)-1-benzofuran-2-yl]methyl}pyrrolidin-3-yl)methanesulfonamide;
meso-endo-N-(8-{2-[6-(benzothiazol-2-yloxy)-benzofuran-3-yl]-ethyl}-8-aza-bicyclo[3.2.1]oct-3-yl)-acetamide;
meso-1-(8-{2-[6-(thiazolo[4,5-b]pyridin-2-yloxy)-benzofuran-3-yl]-ethyl}-3,8-diaza-bicyclo[3.2.1]oct-3-yl)-ethanone;
meso-endo-N-(8-{2-[6-(thiazolo[4,5-b]pyridin-2-yloxy)-benzofuran-3-yl]-ethyl}-8-aza-bicyclo[3.2.1]oct-3-yl)-acetamide;
2-(2-piperidin-1-ylmethyl-benzo[b]thiophen-6-yloxy)-benzothiazole;
(2-morpholin-4-ylmethyl-benzo[b]thiophen-6-yloxy)-benzothiazole;
meso-endo-N-{8-[6-(benzothiazol-2-yloxy)-benzo[b]thiophen-2-ylmethyl]-8-aza-bicyclo[3.2.1]oct-3-yl}-acetamide;
meso-endo-N-{8-[6-(thiazolo[4,5-b]pyridin-2-yloxy)-benzo[b]thiophen-2-ylmethyl]-8-aza-bicyclo[3.2.1]oct-3-yl}-acetamide;
2-(2-piperidin-1-ylmethyl-benzo[b]thiophen-6-yloxy)-thiazolo[4,5-b]pyridine;
2-(3-morpholin-4-ylmethyl-benzo[b]thiophen-6-yloxy)-thiazolo[4,5-b]pyridine;
1-[6-(thiazolo[4,5-b]pyridin-2-yloxy)-benzo[b]thiophen-2-ylmethyl]-piperidine-4-carboxylic acid amide;
1-[6-(benzothiazol-2-yloxy)-1H-indol-3-ylmethyl]-piperidine-4-carboxylic acid ethyl ester;
1-[6-(thiazolo[5,4-b]pyridin-2-yloxy)-1H-indol-3-ylmethyl]-piperidine-4-carboxylic acid ethyl ester;
{1-[6-(benzothiazol-2-yloxy)-1H-indol-3-ylmethyl]-piperidin-4-yl}-acetic acid methyl ester;
meso-endo-(acetyl-{8-[6-(benzothiazol-2-yloxy)-1H-indol-3-ylmethyl]-8-aza-bicyclo[3.2.1]oct-3-yl}-amino)-acetic acid ethyl ester;

meso-endo-(acetyl-{8-[5-(benzothiazol-2-yloxy)-1H-indol-3-ylmethyl]-8-aza-bicyclo[3.2.1]oct-3-yl}-amino)-acetic acid ethyl ester;
(3R)-1-[6-(benzothiazol-2-yloxy)-1H-indol-3-ylmethyl]-piperidine-3-carboxylic acid ethyl ester;
{1-[6-(benzothiazol-2-yloxy)-1H-indol-3-ylmethyl]-piperidin-4-yl}-carbamic acid tert-butyl ester;
5-[6-(benzothiazol-2-yloxy)-1H-indol-3-ylmethyl]-hexahydro-pyrrolo[3,4-c]pyrrole-2-carboxylic acid tert-butyl ester;
(1S,4S)-5-[6-(benzothiazol-2-yloxy)-1H-indol-3-ylmethyl]-2,5-diaza-bicyclo[2.2.1]heptane-2-carboxylic acid tert-butyl ester;
1-{2-[5-(benzothiazol-2-yloxy)-1H-indol-3-yl]-ethyl}-piperidine-4-carboxylic acid ethyl ester;
1-{2-[6-(benzothiazol-2-yloxy)-benzofuran-3-yl]-ethyl}-piperidine-4-carboxylic acid ethyl ester;
meso-endo-({8-[6-(benzothiazol-2-yloxy)-benzofuran-2-ylmethyl]-8-aza-bicyclo[3.2.1]oct-3-yl}-tert-butoxycarbonyl-amino)-acetic acid tert-butyl ester;
{1-[6-(thiazolo[4,5-b]pyridin-2-yloxy)-benzofuran-2-ylmethyl]-pyrrolidin-3-yl}-carbamic acid tert-butyl ester;
1-[6-(thiazolo[4,5-b]pyridin-2-yloxy)-benzofuran-2-ylmethyl]-pyrrolidin-3-ylamine;
1-{8-[6-(thiazolo[4,5-b]pyridin-2-yloxy)-benzofuran-3-ylmethyl]-3,8-diaza-bicyclo[3.2.1]oct-3-yl}-ethanone;
(1S,4S)-1-{5-[6-(thiazolo[4,5-b]pyridin-2-yloxy)-benzofuran-3-ylmethyl]-2,5-diaza-bicyclo[2.2.1]hept-2-yl}-ethanone;
meso-endo-N-{8-[6-(thiazolo[4,5-b]pyridin-2-yloxy)-benzofuran-3-ylmethyl]-8-aza-bicyclo[3.2.1]oct-3-yl}-acetamide;
2-(3-morpholin-4-ylmethyl-benzofuran-6-yloxy)-thiazolo[4,5-b]pyridine;
(1R,4R)-1-{5-[6-(thiazolo[4,5-b]pyridin-2-yloxy)-benzofuran-3-ylmethyl]-2,5-diaza-bicyclo[2.2.1]hept-2-yl}-ethanone;
(1S,4S)-2-[3-(2-oxa-5-aza-bicyclo[2.2.1]hept-5-ylmethyl)-benzofuran-6-yloxy]-thiazolo[4,5-b]pyridine;
(S)-2-[3-(3-methyl-morpholin-4-ylmethyl)-benzofuran-6-yloxy]-thiazolo[4,5-b]pyridine;
(1R,4R)-5-[6-(thiazolo[4,5-b]pyridin-2-yloxy)-benzofuran-3-ylmethyl]-2,5-diaza-bicyclo[2.2.1]heptane-2-carboxylic acid amide;
5-[6-(thiazolo[4,5-b]pyridin-2-yloxy)-benzofuran-3-ylmethyl]-hexahydro-pyrrolo[3,4-c]pyrrole-2-carboxylic acid amide;
N-{1-[6-(thiazolo[4,5-b]pyridin-2-yloxy)-benzofuran-3-ylmethyl]-piperidin-4-ylmethyl}-acetamide;
2-[3-(4-trifluoromethyl-piperidin-1-ylmethyl)-benzofuran-6-yloxy]-thiazolo[4,5-b]pyridine;
(1S,4S)-1-{5-[6-(benzothiazol-2-yloxy)-benzofuran-3-ylmethyl]-2,5-diaza-bicyclo[2.2.1]hept-2-yl}-ethanone;
2-(3-morpholin-4-ylmethyl-benzofuran-6-yloxy)-benzothiazole;
1-{2-[5-(thiazolo[4,5-b]pyridin-2-yloxy)-benzofuran-2-ylmethyl]-2,7-diaza-spiro[4.5]dec-7-yl}-ethanone;
1-{9-[5-(thiazolo[4,5-b]pyridin-2-yloxy)-benzofuran-2-ylmethyl]-3,9-diaza-spiro[5.5]undec-3-yl}-ethanone;
(1S,4S)-1-{5-[6-(thiazolo[4,5-b]pyridin-2-yloxy)-benzofuran-2-ylmethyl]-2,5-diaza-bicyclo[2.2.1]hept-2-yl}-ethanone;
meso-1-{5-[5-(thiazolo[4,5-b]pyridin-2-yloxy)-benzofuran-2-ylmethyl]-2,5-diaza-bicyclo[2.2.2]oct-2-yl}-ethanone;
meso-1-{5-[6-(thiazolo[4,5-b]pyridin-2-yloxy)-benzofuran-2-ylmethyl]-2,5-diaza-bicyclo[2.2.2]oct-2-yl}-ethanone;
1-{4-[6-(thiazolo[4,5-b]pyridin-2-yloxy)-benzofuran-2-ylmethyl]-piperazin-1-yl}-ethanone;
meso-endo-{8-[6-(thiazolo[4,5-b]pyridin-2-yloxy)-benzofuran-2-ylmethyl]-8-aza-bicyclo[3.2.1]oct-3-yl}-urea;
meso-8-[5-(benzothiazol-2-yloxy)-benzofuran-2-ylmethyl]-3,8-diaza-bicyclo[3.2.1]octane-3-carboxylic acid amide;
(1S,4S)-5-[5-(thiazolo[4,5-b]pyridin-2-yloxy)-benzofuran-2-ylmethyl]-2,5-diaza-bicyclo[2.2.1]heptane-2-carboxylic acid amide;
meso-endo-{8-[6-(thiazolo[4,5-b]pyridin-2-yloxy)-benzofuran-3-ylmethyl]-8-aza-bicyclo[3.2.1]oct-3-yl}-urea;
furan-2-ylmethyl-methyl-[6-(thiazolo[4,5-b]pyridin-2-yloxy)-benzofuran-3-ylmethyl]-amine;
methyl-pyridin-4-ylmethyl-[6-(thiazolo[4,5-b]pyridin-2-yloxy)-benzofuran-3-ylmethyl]-amine;
methyl-pyridin-3-ylmethyl-[6-(thiazolo[4,5-b]pyridin-2-yloxy)-benzofuran-3-ylmethyl]-amine;
1-{1-[6-(benzothiazol-2-yloxy)-benzofuran-3-ylmethyl]-piperidin-4-yl}-pyrrolidin-2-one;
N-{1-[6-(benzothiazol-2-yloxy)-benzofuran-3-ylmethyl]-piperidin-4-yl}-acetamide;
meso-endo-N-{8-[6-(benzothiazol-2-yloxy)-benzofuran-3-ylmethyl]-8-aza-bicyclo[3.2.1]oct-3-yl}-acetamide;
1-{4-[6-(thiazolo[4,5-b]pyridin-2-yloxy)-benzofuran-3-ylmethyl]-[1,4]diazepan-1-yl}-ethanone;
2-[3-(4-methanesulfonyl-piperidin-1-ylmethyl)-benzofuran-6-yloxy]-thiazolo[4,5-b]pyridine;
(2-methoxy-ethyl)-methyl-[6-(thiazolo[4,5-b]pyridin-2-yloxy)-benzofuran-3-ylmethyl]-amine;
2-(3-pyrrolidin-1-ylmethyl-benzofuran-6-yloxy)-thiazolo[4,5-b]pyridine;
(2S)-2-[3-(2-methoxymethyl-pyrrolidin-1-ylmethyl)-benzofuran-6-yloxy]-thiazolo[4,5-b]pyridine;
(1S,4S,5S)—N-{2-[6-(thiazolo[4,5-b]pyridin-2-yloxy)-benzofuran-3-ylmethyl]-2-aza-bicyclo[2.2.1]hept-5-yl}-acetamide;
(1S,4S,5S)—N-{2-[5-(thiazolo[4,5-b]pyridin-2-yloxy)-benzofuran-2-ylmethyl]-2-aza-bicyclo[2.2.1]hept-5-yl}-acetamide;
(1S,4S,5S)—N-{2-[6-(thiazolo[4,5-b]pyridin-2-yloxy)-benzofuran-2-ylmethyl]-2-aza-bicyclo[2.2.1]hept-5-yl}-acetamide;
2-[2-(4-fluoro-piperidin-1-ylmethyl)-benzofuran-6-yloxy]-thiazolo[4,5-b]pyridine;
2-[2-(4-trifluoromethyl-piperidin-1-ylmethyl)-benzofuran-6-yloxy]-thiazolo[4,5-b]-pyridine;
2-(2-piperidin-1-ylmethyl-benzofuran-6-yloxy)-thiazolo[4,5-b]pyridine;
(1R,4R)-5-[6-(thiazolo[4,5-b]pyridin-2-yloxy)-benzofuran-2ylmethyl]-2,5-diaza-bicyclo[2.2.1]heptane-2-carboxylic acid amide;
5-[6-(thiazolo[4,5-b]pyridin-2-yloxy)-benzofuran-2-ylmethyl]-hexahydro-pyrrolo[3,4-c]pyrrole-2-carboxylic acid amide;
1-{5-[6-(thiazolo[4,5-b]pyridin-2-yloxy)-benzofuran-2-ylmethyl]-hexahydro-pyrrolo[3,4-c]pyrrol-2-yl}-ethanone;
1-{4-[6-(thiazolo[4,5-b]pyridin-2-yloxy)-benzofuran-3-ylmethyl]-piperazin-1-yl}-ethanone;
N-{1-[6-(thiazolo[4,5-b]pyridin-2-yloxy)-benzofuran-3-ylmethyl]-piperidin-4-yl}-acetamide;
diethyl-[6-(thiazolo[4,5-b]pyridin-2-yloxy)-benzofuran-2-ylmethyl]-amine;
(1S,4S)-1-{5-[5-(thiazolo[4,5-c]pyridin-2-yloxy)-benzofuran-2-ylmethyl]-2,5-diaza-bicyclo[2.2.1]hept-2-yl}-ethanone;
meso-endo-N-{8-[5-(thiazolo[4,5-c]pyridin-2-yloxy)-benzofuran-2-ylmethyl]-8-aza-bicyclo[3.2.1]oct-3-yl}-acetamide;

meso-endo-N-{8-[6-(thiazolo[4,5-c]pyridin-2-yloxy)-benzofuran-2-ylmethyl]-8-aza-bicyclo[3.2.1]oct-3-yl}-acetamide;
meso-1-{8-[6-(thiazolo[4,5-c]pyridin-2-yloxy)-benzofuran-2-ylmethyl]-3,8-diaza-bicyclo[3.2.1]oct-3-yl}-ethanone;
(1S,4S)-1-{5-[6-(thiazolo[4,5-c]pyridin-2-yloxy)-benzofuran-2-ylmethyl]-2,5-diaza-bicyclo[2.2.1]hept-2-yl}-ethanone;
1-[6-(thiazolo[4,5-b]pyridin-2-yloxy)-benzofuran-2-ylmethyl]-piperidine-4-carboxylic acid methylamide;
pyrrolidin-1-yl-{1-[6-(thiazolo[4,5-b]pyridin-2-yloxy)-benzofuran-2-ylmethyl]-piperidin-4-yl}-methanone;
meso-1-{8-[5-(thiazolo[4,5-c]pyridin-2-yloxy)-benzofuran-2-ylmethyl]-3,8-diaza-bicyclo[3.2.1]oct-3-yl}-ethanone;
meso-exo-{8-[6-(thiazolo[4,5-b]pyridin-2-yloxy)-benzofuran-3-ylmethyl]-8-aza-bicyclo[3.2.1]oct-3-yl}-urea;
meso-exo-N-{8-[6-(thiazolo[4,5-b]pyridin-2-yloxy)-benzofuran-3-ylmethyl]-8-aza-bicyclo[3.2.1]oct-3-yl}-acetamide;
(1S,4S)-5-[6-(thiazolo[4,5-b]pyridin-2-yloxy)-benzofuran-3-ylmethyl]-2,5-diaza-bicyclo[2.2.1]heptane-2-carboxylic acid amide;
meso-8-[6-(thiazolo[4,5-b]pyridin-2-yloxy)-benzofuran-3-ylmethyl]-3,8-diaza-bicyclo[3.2.1]octane-3-carboxylic acid amide;
meso-1-{5-[6-(thiazolo[4,5-b]pyridin-2-yloxy)-benzofuran-3-ylmethyl]-hexahydro-pyrrolo[3,4-c]pyrrol-2-yl}-ethanone;
2-(3-piperidin-1-ylmethyl-benzofuran-6-yloxy)-thiazolo[4,5-b]pyridine;
1-[6-(thiazolo[4,5-b]pyridin-2-yloxy)-benzofuran-3-ylmethyl]-piperidine-4-carboxylic acid amide;
1-[6-(thiazolo[4,5-b]pyridin-2-yloxy)-benzofuran-3-ylmethyl]-piperidine-4-carboxylic acid methylamide;
1-{1-[6-(thiazolo[4,5-b]pyridin-2-yloxy)-benzofuran-3-ylmethyl]-piperidin-4-yl}-pyrrolidin-2-one;
(3-S)-1-[6-(thiazolo[4,5-b]pyridin-2-yloxy)-benzofuran-3-ylmethyl]-piperidine-3-carboxylic acid amide;
2-{3-[4-(pyrimidin-2-yloxy)-piperidin-1-ylmethyl]-benzofuran-6-yloxy}-thiazolo[4,5-b]pyridine;
2-{1-[6-(thiazolo[4,5-b]pyridin-2-yloxy)-benzofuran-3-ylmethyl]-piperidin-4-yl}-propan-2-ol;
diethyl-[6-(thiazolo[4,5-b]pyridin-2-yloxy)-benzofuran-3-ylmethyl]-amine;
1-[6-(thiazolo[4,5-b]pyridin-2-yloxy)-benzofuran-3-ylmethyl]-1,2,3,4,5,6-hexahydro-[4,4']bipyridinyl;
(1S,4S)-1-{5-[6-(thiazolo[5,4-b]pyridin-2-yloxy)-benzofuran-3-ylmethyl]-2,5-diaza-bicyclo[2.2.1]hept-2-yl}-ethanone;
(1S,4S)-1-{5-[6-(thiazolo[4,5-c]pyridin-2-yloxy)-benzofuran-3-ylmethyl]-2,5-diaza-bicyclo[2.2.1]hept-2-yl}-ethanone;
1-[6-(benzothiazol-2-yloxy)-benzofuran-3-ylmethyl]-piperidine-4-carboxylic acid ethyl ester;
1-[6-(thiazolo[4,5-b]pyridin-2-yloxy)-benzofuran-3-ylmethyl]-piperidine-4-carboxylic acid ethyl ester;
1-[6-(thiazolo[4,5-b]pyridin-2-yloxy)-benzofuran-2-ylmethyl]-piperidine-4-carboxylic acid tert-butyl ester;
4-[6-(thiazolo[4,5-b]pyridin-2-yloxy)-benzofuran-3-ylmethyl]-piperazine-1-carboxylic acid tert-butyl ester;
{1-[6-(thiazolo[4,5-b]pyridin-2-yloxy)-benzofuran-3-ylmethyl]-piperidin-4-yl}-carbamic acid tert-butyl ester;
4-[6-(thiazolo[4,5-b]pyridin-2-yloxy)-benzofuran-3-ylmethyl]-[1,4]diazepane-1-carboxylic acid tert-butyl ester;
(1S,4S)-5-[6-(thiazolo[4,5-b]pyridin-2-yloxy)-benzofuran-3-ylmethyl]-2,5-diaza-bicyclo[2.2.2]octane-2-carboxylic acid tert-butyl ester;
4-{cyclopropyl-[6-(thiazolo[4,5-b]pyridin-2-yloxy)-benzofuran-3-ylmethyl]-amino}-piperidine-1-carboxylic acid tert-butyl ester;
2-(3-piperazin-1-ylmethyl-benzofuran-6-yloxy)-thiazolo[4,5-b]pyridine;
1-[6-(thiazolo[4,5-b]pyridin-2-yloxy)-benzofuran-3-ylmethyl]-piperidin-4-ylamine;
2-(3-[1,4]diazepan-1-ylmethyl-benzofuran-6-yloxy)-thiazolo[4,5-b]pyridine;
(1S,4S)-2-[6-(thiazolo[4,5-b]pyridin-2-yloxy)-benzofuran-3-ylmethyl]-2,5-diaza-bicyclo[2.2.2]octane;
cyclopropyl-piperidin-4-yl-[6-(thiazolo[4,5-b]pyridin-2-yloxy)-benzofuran-3-ylmethyl]-amine,
2,2-dimethyl-N-{1-[6-(thiazolo[4,5-b]pyridin-2-yloxy)-benzofuran-2-ylmethyl]-pyrrolidin-3-yl}-propionamide;
(1S,4S)1-{5-[6-(thiazolo[4,5-b]pyridin-2-yloxy)-benzofuran-3-ylmethyl]-2,5-diaza-bicyclo[2.2.2]oct-2-yl}-ethanone;
1-(4-{cyclopropyl-[6-(thiazolo[4,5-b]pyridin-2-yloxy)-benzofuran-3-ylmethyl]-amino}-piperidin-1-yl)-ethanone;
4-[6-(thiazolo[4,5-b]pyridin-2-yloxy)-benzofuran-3-ylmethyl]-piperazine-1-carboxylic acid amide;
{1-[6-(thiazolo[4,5-b]pyridin-2-yloxy)-benzofuran-3-ylmethyl]-piperidin-4-yl}-urea;
(1S,4S)-5-[6-(thiazolo[4,5-b]pyridin-2-yloxy)-benzofuran-3-ylmethyl]-2,5-diaza-bicyclo[2.2.2]octane-2-carboxylic acid amide;
4-{cyclopropyl-[6-(thiazolo[4,5-b]pyridin-2-yloxy)-benzofuran-3-ylmethyl]-amino}-piperidine-1-carboxylic acid amide;
2-[3-(4-methanesulfonyl-piperazin-1-ylmethyl)-benzofuran-6-yloxy]-thiazolo[4,5-b]pyridine;
N-{1-[6-(thiazolo[4,5-b]pyridin-2-yloxy)-benzofuran-3-ylmethyl]-piperidin-4-yl}-methanesulfonamide;
(1S,4S)-2-methanesulfonyl-5-[6-(thiazolo[4,5-b]pyridin-2-yloxy)-benzofuran-3-ylmethyl]-2,5-diaza-bicyclo[2.2.2]octane;
cyclopropyl-(1-methanesulfonyl-piperidin-4-yl)-[6-(thiazolo[4,5-b]pyridin-2-yloxy)-benzofuran-3-ylmethyl]-amine;
2-[3-(4-methanesulfonyl-[1,4]diazepan-1-ylmethyl)-benzofuran-6-yloxy]-thiazolo[4,5-b]pyridine;
1-[6-(benzothiazol-2-yloxy)-benzofuran-3-ylmethyl]-piperidine-4-carboxylic acid;
1-[6-(thiazolo[4,5-b]pyridin-2-yloxy)-benzofuran-3-ylmethyl]-piperidine-4-carboxylic acid;
N-{1-[6-(5-methyl-thiazolo[4,5-b]pyridin-2-yloxy)-benzofuran-3-ylmethyl]-piperidin-4-yl}-acetamide;
N-{1-[6-(6-methyl-thiazolo[4,5-b]pyridin-2-yloxy)-benzofuran-3-ylmethyl]-piperidin-4-yl}-acetamide;
N-{1-[6-(7-methyl-thiazolo[4,5-b]pyridin-2-yloxy)-benzofuran-3-ylmethyl]-piperidin-4-yl}-acetamide;
N-{1-[6-(thiazolo[4,5-b]pyrazin-2-yloxy)-benzofuran-3-ylmethyl]-piperidin-4-yl}-acetamide;
N-{1-[6-(6-chloro-thiazolo[4,5-b]pyridin-2-yloxy)-benzofuran-3-ylmethyl]-piperidin-4-yl}-acetamide;
N-{1-[6-(6-fluoro-thiazolo[4,5-b]pyridin-2-yloxy)-benzofuran-3-ylmethyl]-piperidin-4-yl}-acetamide;
2-[3-(2-morpholin-4-yl-ethyl)-benzofuran-6-yloxy]-thiazolo[4,5-b]pyridine;
1-(4-{2-[6-(thiazolo[4,5-b]pyridin-2-yloxy)-benzofuran-3-yl]-ethyl}-piperazin-1-yl)-ethanone;
(1S,4S)-1-(5-{2-[6-(thiazolo[4,5-b]pyridin-2-yloxy)-benzofuran-3-yl]-ethyl}-2,5-diaza-bicyclo[2.2.1]hept-2-yl)-ethanone;
and pharmaceutically acceptable salts and prodrugs thereof.

30. A pharmaceutical composition as in claim 28, wherein said chemical entity is selected from the group consisting of
1-{4-[5-(thiazolo[4,5-b]pyridin-2-yloxy)-benzofuran-2-ylmethyl]-piperazin-1-yl}-ethanone;
5-[6-(thiazolo[4,5-b]pyridin-2-yloxy)-benzofuran-3-ylmethyl]-hexahydro-pyrrolo[3,4-c]pyrrole-2-carboxylic acid tert-butyl ester;
(1S,4S)-5-[6-(thiazolo[4,5-b]pyridin-2-yloxy)-benzofuran-3-ylmethyl]-2,5-diaza-bicyclo[2.2.1]heptane-2-carboxylic acid tert-butyl ester;
2-[3-(hexahydro-pyrrolo[3,4-c]pyrrol-2-ylmethyl)-benzofuran-6-yloxy]-thiazolo[4,5-b]pyridine;
(1S,4S)-2-[3-(2,5-diaza-bicyclo[2.2.1]hept-2-ylmethyl)-benzofuran-6-yloxy]-thiazolo[4,5-b]pyridine;
2-[3-(2,8-diaza-spiro[4.5]dec-8-ylmethyl)-benzofuran-6-yloxy]-thiazolo[4,5-b]pyridine;
1-{8-[6-(thiazolo[4,5-b]pyridin-2-yloxy)-benzofuran-3-ylmethyl]-2,8-diaza-spiro[4.5]dec-2-yl}-ethanone;
2-[6-(thiazolo[4,5-b]pyridin-2-yloxy)-benzofuran-3-ylmethyl]-decahydro-isoquinoline;
1-[6-(thiazolo[4,5-b]pyridin-2-yloxy)-benzofuran-3-ylmethyl]-decahydro-quinoline;
1-[6-(thiazolo[4,5-b]pyridin-2-yloxy)-benzofuran-3-ylmethyl]-piperidin-4-ol;
{1-[6-(thiazolo[4,5-b]pyridin-2-yloxy)-benzofuran-3-ylmethyl]-piperidin-4-yl}-methanol;
2-[3-(4-fluoro-piperidin-1-ylmethyl)-benzofuran-6-yloxy]-thiazolo[4,5-b]pyridine;
2-[3-(4-methoxy-piperidin-1-ylmethyl)-benzofuran-6-yloxy]-thiazolo[4,5-b]pyridine;
1'-[6-(thiazolo[4,5-b]pyridin-2-yloxy)-benzofuran-3-ylmethyl]-[1,4]bipiperidinyl-2-one;
N-{1-[6-(thiazolo[4,5-b]pyridin-2-yloxy)-furo[3,2-b]pyridin-2-ylmethyl]-piperidin-4-yl}-acetamide;
(1S,4S)-1-{5-[6-(thiazolo[4,5-b]pyridin-2-yloxy)-furo[3,2-b]pyridin-2-ylmethyl]-2,5-diaza-bicyclo[2.2.1]hept-2-yl}-ethanone;
4-phenyl-1-[6-(thiazolo[4,5-b]pyridin-2-yloxy)-benzofuran-3-ylmethyl]-piperidin-4-ol;
cyclopropyl-{4-[6-(thiazolo[4,5-b]pyridin-2-yloxy)-benzofuran-3-ylmethyl]-piperazin-1-yl}-methanone;
2-[3-(4-cyclopropyl-piperazin-1-ylmethyl)-benzofuran-6-yloxy]-thiazolo[4,5-b]pyridine;
8-[6-(thiazolo[4,5-b]pyridin-2-yloxy)-benzofuran-3-ylmethyl]-2,8-diaza-spiro[4.5]decane-2-carboxylic acid tert-butyl ester;
2-[3-(4-benzyl-piperidin-1-ylmethyl)-benzofuran-6-yloxy]-thiazolo[4,5-b]pyridine;
2-[3-(4-phenyl-piperidin-1-ylmethyl)-benzofuran-6-yloxy]-thiazolo[4,5-b]pyridine;
2-[3-(3,5-dimethyl-piperidin-1-ylmethyl)-benzofuran-6-yloxy]-thiazolo[4,5-b]pyridine;
dimethyl-{1-[6-(thiazolo[4,5-b]pyridin-2-yloxy)-benzofuran-3-ylmethyl]-piperidin-4-yl}-amine;
2-[3-(4-pyrrolidin-1-yl-piperidin-1-ylmethyl)-benzofuran-6-yloxy]-thiazolo[4,5-b]pyridine;
1'-[6-(thiazolo[4,5-b]pyridin-2-yloxy)-benzofuran-3-ylmethyl]-[1,4]bipiperidinyl;
2-[3-(4-morpholin-4-yl-piperidin-1-ylmethyl)-benzofuran-6-yloxy]-thiazolo[4,5-b]pyridine;
2-[3-(4-methyl-piperidin-1-ylmethyl)-benzofuran-6-yloxy]-thiazolo[4,5-b]pyridine;
2-[3-(4-phenyl-piperazin-1-ylmethyl)-benzofuran-6-yloxy]-thiazolo[4,5-b]pyridine;
2-[3-(4-pyridin-2-yl-piperazin-1-ylmethyl)-benzofuran-6-yloxy]-thiazolo[4,5-b]pyridine;
2-[3-(4-pyridin-4-yl-piperazin-1-ylmethyl)-benzofuran-6-yloxy]-thiazolo[4,5-b]pyridine;
2-{3-[4-(4-methoxy-phenyl)-piperazin-1-ylmethyl]-benzofuran-6-yloxy}-thiazolo[4,5-b]pyridine;
2-[3-(4-phenethyl-piperazin-1-ylmethyl)-benzofuran-6-yloxy]-thiazolo[4,5-b]pyridine;
2-[3-(4-pyrimidin-2-yl-piperazin-1-ylmethyl)-benzofuran-6-yloxy]-thiazolo[4,5-b]pyridine;
2-[6-(thiazolo[4,5-b]pyridin-2-yloxy)-benzofuran-3-ylmethyl]-1,2,3,4-tetrahydro-isoquinoline;
methyl-(1-methyl-piperidin-4-yl)-[6-(thiazolo[4,5-b]pyridin-2-yloxy)-benzofuran-3-ylmethyl]-amine;
meso-1-{3-[6-(thiazolo[4,5-b]pyridin-2-yloxy)-benzofuran-3-ylmethyl]-3,8-diaza-bicyclo[3.2.1]oct-8-yl}-ethanone;
meso-endo-N-{8-[6-(thiazolo[4,5-b]pyridin-2-yloxy)-furo[3,2-b]pyridin-2-ylmethyl]-8-aza-bicyclo[3.2.1]oct-3-yl}-acetamide;
cyclopropyl-[6-(thiazolo[4,5-b]pyridin-2-yloxy)-benzofuran-3-ylmethyl]-amine;
cyclopentyl-[6-(thiazolo[4,5-b]pyridin-2-yloxy)-benzofuran-3-ylmethyl]-amine;
cyclohexyl-[6-(thiazolo[4,5-b]pyridin-2-yloxy)-benzofuran-3-ylmethyl]-amine;
[6-(thiazolo[4,5-b]pyridin-2-yloxy)-benzofuran-3-ylmethyl]-thiophen-2-ylmethyl-amine;
tert-butyl-[6-(thiazolo[4,5-b]pyridin-2-yloxy)-benzofuran-3-ylmethyl]-amine;
2-[3-(4-tert-butyl-piperidin-1-ylmethyl)-benzofuran-6-yloxy]-thiazolo[4,5-b]pyridine;
propyl-[6-(thiazolo[4,5-b]pyridin-2-yloxy)-benzofuran-3-ylmethyl]-amine;
isobutyl-[6-(thiazolo[4,5-b]pyridin-2-yloxy)-benzofuran-3-ylmethyl]-amine;
(2-piperidin-1-yl-ethyl)-[6-(thiazolo[4,5-b]pyridin-2-yloxy)-benzofuran-3-ylmethyl]-amine;
(2-morpholin-4-yl-ethyl)-[6-(thiazolo[4,5-b]pyridin-2-yloxy)-benzofuran-3-ylmethyl]-amine;
N-{1-[6-(thiazolo[4,5-b]pyridin-2-yloxy)-benzofuran-3-ylmethyl]-pyrrolidin-3-yl}-acetamide;
2-[3-(4-isobutyl-piperazin-1-ylmethyl)-benzofuran-6-yloxy]-thiazolo[4,5-b]pyridine;
N-methyl-N-{1-[6-(thiazolo[4,5-b]pyridin-2-yloxy)-benzofuran-3-ylmethyl]-pyrrolidin-3-yl}-acetamide;
(S)—N-{1-[6-(thiazolo[4,5-b]pyridin-2-yloxy)-benzofuran-3-ylmethyl]-pyrrolidin-3-yl}-acetamide;
4-(2-{[6-(benzothiazol-2-yloxy)-benzofuran-3-ylmethyl]-amino}-ethyl)-benzenesulfonamide;
(S)-{1-[6-(benzothiazol-2-yloxy)-benzofuran-3-ylmethyl]-pyrrolidin-2-yl}-methanol;
{1-[6-(benzothiazol-2-yloxy)-benzofuran-3-ylmethyl]-piperidin-4-yl}-carbamic acid tert-butyl ester;
2-[3-(3-propoxy-azetidin-1-ylmethyl)-benzofuran-6-yloxy]-thiazolo[4,5-b]pyridine;
1-[6-(thiazolo[4,5-b]pyridin-2-yloxy)-benzofuran-3-ylmethyl]-azetidin-3-ol;
2-[3-(3,3-difluoro-azetidin-1-ylmethyl)-benzofuran-6-yloxy]-thiazolo[4,5-b]pyridine;
N,N-diethyl-N'-[6-(thiazolo[4,5-b]pyridin-2-yloxy)-benzofuran-3-ylmethyl]-ethane-1,2-diamine;
cyclohexyl-ethyl-[6-(thiazolo[4,5-b]pyridin-2-yloxy)-benzofuran-3-ylmethyl]-amine;
(2-phenoxy-ethyl)-[6-(thiazolo[4,5-b]pyridin-2-yloxy)-benzofuran-3-ylmethyl]-amine;
indan-2-yl-[6-(thiazolo[4,5-b]pyridin-2-yloxy)-benzofuran-3-ylmethyl]-amine;
phenethyl-[6-(thiazolo[4,5-b]pyridin-2-yloxy)-benzofuran-3-ylmethyl]-amine;
N-cyclopropyl-N-{1-[6-(thiazolo[4,5-b]pyridin-2-yloxy)-benzofuran-3-ylmethyl]-piperidin-4-yl}-acetamide;
N-isopropyl-N-{1-[6-(thiazolo[4,5-b]pyridin-2-yloxy)-benzofuran-3-ylmethyl]-piperidin-4-yl}-acetamide;
(R)—N-{1-[6-(thiazolo[4,5-b]pyridin-2-yloxy)-benzofuran-3-ylmethyl]-pyrrolidin-3-yl}-acetamide;

2-[3-(4-thiophen-2-ylmethyl-piperazin-1-ylmethyl)-benzofuran-6-yloxy]-thiazolo[4,5-b]pyridine;
2-[3-(hexahydro-pyrrolo[1,2-a]pyrazin-2-ylmethyl)-benzofuran-6-yloxy]-thiazolo[4,5-b]pyridine;
diethyl-{1-[6-(thiazolo[4,5-b]pyridin-2-yloxy)-benzofuran-3-ylmethyl]-pyrrolidin-3-yl}-amine;
(R)-2-[3-(3-fluoro-pyrrolidin-1-ylmethyl)-benzofuran-6-yloxy]-thiazolo[4,5-b]pyridine;
diethyl-[5-(thiazolo[4,5-b]pyridin-2-yloxy)-benzofuran-2-ylmethyl]-amine;
2-[3-(5-fluoro-1,3-dihydro-isoindol-2-ylmethyl)-benzofuran-6-yloxy]-thiazolo[4,5-b]-pyridine;
2-[3-(1,3-dihydro-isoindol-2-ylmethyl)-benzofuran-6-yloxy]-thiazolo[4,5-b]pyridine;
meso-endo-1-(3-{[6-(thiazolo[4,5-b]pyridin-2-yloxy)-benzofuran-3-ylmethyl]-amino}-8-aza-bicyclo[3.2.1]oct-8-yl)-ethanone;
meso-exo-1-(3-{[6-(thiazolo[4,5-b]pyridin-2-yloxy)-benzofuran-3-ylmethyl]-amino}-8-aza-bicyclo[3.2.1]oct-8-yl)-ethanone;
3-{methyl-[6-(thiazolo[4,5-b]pyridin-2-yloxy)-benzofuran-3-ylmethyl]-amino}-propionic acid ethyl ester;
3-{methyl-[6-(thiazolo[4,5-b]pyridin-2-yloxy)-benzofuran-3-ylmethyl]-amino}-propionic acid;
meso-exo-N-{8-[6-(thiazolo[4,5-b]pyridin-2-yloxy)-furo[3,2-b]pyridin-2-ylmethyl]-8-aza-bicyclo[3.2.1]oct-3-yl}-acetamide;
(1S,4S)-5-[6-(thiazolo[4,5-b]pyridin-2-yloxy)-furo[3,2-b]pyridin-2-ylmethyl]-2,5-diaza-bicyclo[2.2.1]heptane-2-carboxylic acid amide;
meso-1-{8-[6-(thiazolo[4,5-b]pyridin-2-yloxy)-furo[3,2-b]pyridin-2-ylmethyl]-3,8-diaza-bicyclo[3.2.1]oct-3-yl}-ethanone;
(1S,4S)-1-{5-[6-(thiazolo[4,5-b]pyridin-2-yloxy)-furo[3,2-b]pyridin-2-ylmethyl]-2,5-diaza-bicyclo[2.2.2]oct-2-yl}-ethanone;
(1R,4R)-1-{5-[6-(thiazolo[4,5-b]pyridin-2-yloxy)-furo[3,2-b]pyridin-2-ylmethyl]-2,5-diaza-bicyclo[2.2.1]hept-2-yl}-ethanone;
1-{1-[6-(thiazolo[4,5-b]pyridin-2-yloxy)-furo[3,2-b]pyridin-2-ylmethyl]-piperidin-4-yl}-pyrrolidin-2-one;
4-[6-(thiazolo[4,5-b]pyridin-2-yloxy)-benzofuran-3-ylmethyl]-piperazin-2-one;
1-{4-[6-(thiazolo[4,5-b]pyridin-2-yloxy)-furo[3,2-b]pyridin-2-ylmethyl]-piperazin-1-yl}-ethanone;
benzyl-[6-(thiazolo[4,5-b]pyridin-2-yloxy)-benzofuran-3-ylmethyl]-amine;
(4-fluoro-benzyl)-[6-(thiazolo[4,5-b]pyridin-2-yloxy)-benzofuran-3-ylmethyl]-amine;
(4-methoxy-benzyl)-[6-(thiazolo[4,5-b]pyridin-2-yloxy)-benzofuran-3-ylmethyl]-amine;
4-(4-chloro-phenyl)-1-[6-(thiazolo[4,5-b]pyridin-2-yloxy)-benzofuran-3-ylmethyl]-piperidin-4-ol;
4-(4-bromo-phenyl)-1-[6-(thiazolo[4,5-b]pyridin-2-yloxy)-benzofuran-3-ylmethyl]-piperidin-4-ol;
2-[3-(2,6-dimethyl-morpholin-4-ylmethyl)-benzofuran-6-yloxy]-thiazolo[4,5-b]pyridine;
2-[3-(3-fluoro-piperidin-1-ylmethyl)-benzofuran-6-yloxy]-thiazolo[4,5-b]pyridine;
4-{1-[6-(thiazolo[4,5-b]pyridin-2-yloxy)-benzofuran-3-ylmethyl]-piperidin-4-yl}-2,4-dihydro-[1,2,4]triazol-3-one;
1-{7-[6-(thiazolo[4,5-b]pyridin-2-yloxy)-benzofuran-3-ylmethyl]-3,7-diaza-bicyclo[3.3.1]non-3-yl}-ethanone;
N-ethyl-N-{1-[6-(thiazolo[4,5-b]pyridin-2-yloxy)-benzofuran-3-ylmethyl]-piperidin-4-yl}-acetamide;
(tetrahydro-furan-3-yl)-{5-[6-(thiazolo[4,5-b]pyridin-2-yloxy)-benzofuran-3-ylmethyl]-hexahydro-pyrrolo[3,4-c]pyrrol-2-yl}-methanone;
2-hydroxy-1-{5-[6-(thiazolo[4,5-b]pyridin-2-yloxy)-benzofuran-3-ylmethyl]-hexahydro-pyrrolo[3,4-c]pyrrol-2-yl}-ethanone;
(1S,4S)-pyrazin-2-yl-{5-[6-(thiazolo[4,5-b]pyridin-2-yloxy)-benzofuran-3-ylmethyl]-2,5-diaza-bicyclo[2.2.1]hept-2-yl}-methanone;
(1S,4S)-cyclobutyl-{5-[6-(thiazolo[4,5-b]pyridin-2-yloxy)-benzofuran-3-ylmethyl]-2,5-diaza-bicyclo[2.2.1]hept-2-yl}-methanone;
(1S,4S)-isoxazol-5-yl-{5-[6-(thiazolo[4,5-b]pyridin-2-yloxy)-benzofuran-3-ylmethyl]-2,5-diaza-bicyclo[2.2.1]hept-2-yl}-methanone;
furan-3-yl-{5-[6-(thiazolo[4,5-b]pyridin-2-yloxy)-benzofuran-3-ylmethyl]-hexahydro-pyrrolo[3,4-c]pyrrol-2-yl}-methanone;
(1S,4S)-4-{5-[6-(thiazolo[4,5-b]pyridin-2-yloxy)-benzofuran-3-ylmethyl]-2,5-diaza-bicyclo[2.2.1]hept-2-ylmethyl}-benzoic acid methyl ester;
dimethyl-[6-(thiazolo[4,5-b]pyridin-2-yloxy)-benzofuran-3-ylmethyl]-amine;
(2-{1-[6-(benzothiazol-2-yloxy)-benzofuran-3-ylmethyl]-piperidin-4-yl}-ethyl)-carbamic acid tert-butyl ester;
N-{1-[6-(benzothiazol-2-yloxy)-benzofuran-3-ylmethyl]-piperidin-4-yl}-methanesulfonamide;
N-(2-{1-[6-(benzothiazol-2-yloxy)-benzofuran-3-ylmethyl]-piperidin-4-yl}-ethyl)-methanesulfonamide;
5-(thiazolo[4,5-b]pyridin-2-yloxy)-benzofuran-2-carboxylic acid benzyl-methyl-amide;
(1R,4R)-1-{5-[5-(thiazolo[4,5-b]pyridin-2-yloxy)-benzofuran-2-carbonyl]-2,5-diaza-bicyclo[2.2.1]hept-2-yl}-ethanone;
6-(thiazolo[4,5-b]pyridin-2-yloxy)-benzofuran-3-carboxylic acid methylamide;
N-{1-[6-(thiazolo[4,5-b]pyridin-2-yloxy)-benzofuran-3-carbonyl]-piperidin-4-yl}-acetamide;
meso-endo-N-{8-[6-(thiazolo[4,5-b]pyridin-2-yloxy)-benzofuran-3-carbonyl]-8-aza-bicyclo[3.2.1]oct-3-yl}-acetamide;
1-{1-[6-(thiazolo[4,5-b]pyridin-2-yloxy)-benzofuran-3-carbonyl]-piperidin-4-yl}-pyrrolidin-2-one;
(1S,4S)-1-{5-[6-(thiazolo[4,5-b]pyridin-2-yloxy)-benzofuran-3-carbonyl]-2,5-diaza-bicyclo[2.2.1]hept-2-yl}-ethanone;
1-{4-[6-(thiazolo[4,5-b]pyridin-2-yloxy)-benzofuran-3-carbonyl]-[1,4]diazepan-1-yl}-ethanone;
6-(thiazolo[4,5-b]pyridin-2-yloxy)-benzofuran-3-carboxylic acid isopropyl-methyl-amide;
meso-8-[6-(thiazolo[4,5-b]pyridin-2-yloxy)-benzofuran-3-carbonyl]-3,8-diaza-bicyclo[3.2.1]octane-3-carboxylic acid amide;
(1S,4S)-5-[6-(thiazolo[4,5-b]pyridin-2-yloxy)-benzofuran-3-carbonyl]-2,5-diaza-bicyclo[2.2.1]heptane-2-carboxylic acid amide;
(4-fluoro-piperidin-1-yl)-[6-(thiazolo[4,5-b]pyridin-2-yloxy)-benzofuran-3-yl]-methanone;
(4-phenyl-piperidin-1-yl)-[6-(thiazolo[4,5-b]pyridin-2-yloxy)-benzofuran-3-yl]-methanone;
1-[6-(thiazolo[4,5-b]pyridin-2-yloxy)-benzofuran-3-carbonyl]-piperidine-4-carboxylic acid amide;
(4-cyclohexyl-piperazin-1-yl)-[6-(thiazolo[4,5-b]pyridin-2-yloxy)-benzofuran-3-yl]-methanone;
1-{4-[6-(thiazolo[4,5-b]pyridin-2-yloxy)-benzofuran-3-carbonyl]-piperazin-1-yl}-ethanone;
6-(thiazolo[4,5-b]pyridin-2-yloxy)-benzofuran-3-carboxylic acid cyclohexyl-ethyl-amide;
[4-(pyrimidin-2-yloxy)-piperidin-1-yl]-[6-(thiazolo[4,5-b]pyridin-2-yloxy)-benzofuran-3-yl]-methanone;
piperidin-1-yl-[6-(thiazolo[4,5-b]pyridin-2-yloxy)-benzofuran-3-yl]-methanone;

[4-(piperidine-1-carbonyl)-piperidin-1-yl]-[6-(thiazolo[4,5-b]pyridin-2-yloxy)-benzofuran-3-yl]-methanone;
(octahydro-isoquinolin-2-yl)-[6-(thiazolo[4,5-b]pyridin-2-yloxy)-benzofuran-3-yl]-methanone;
(3,4-dihydro-1H-isoquinolin-2-yl)-[6-(thiazolo[4,5-b]pyridin-2-yloxy)-benzofuran-3-yl]-methanone;
(4-benzoyl-piperidin-1-yl)-[6-(thiazolo[4,5-b]pyridin-2-yloxy)-benzofuran-3-yl]-methanone;
6-(thiazolo[4,5-b]pyridin-2-yloxy)-benzofuran-3-carboxylic acid (3-dimethylamino-propyl)-methyl-amide;
endo-bicyclo[2.2.1]heptane-2-carboxylic acid [6-(thiazolo[4,5-b]pyridin-2-yloxy)-benzofuran-3-ylmethyl]-amide;
2-(4-acetyl-piperazin-1-yl)-N-[6-(thiazolo[4,5-b]pyridin-2-yloxy)-benzofuran-3-ylmethyl]-acetamide;
2-(3-methyl-isoxazol-5-yl)-N-[6-(thiazolo[4,5-b]pyridin-2-yloxy)-benzofuran-3-ylmethyl]-acetamide;
4-hydroxy-cyclohexanecarboxylic acid [6-(thiazolo[4,5-b]pyridin-2-yloxy)-benzofuran-3-ylmethyl]-amide;
N-[6-(thiazolo[4,5-b]pyridin-2-yloxy)-benzofuran-3-ylmethyl]-terephthalamic acid methyl ester;
2-(4-chloro-phenyl)-N-[6-(thiazolo[4,5-b]pyridin-2-yloxy)-benzofuran-3-ylmethyl]-acetamide;
N-[6-(thiazolo[4,5-b]pyridin-2-yloxy)-benzofuran-3-ylmethyl]-acetamide;
N-[6-(thiazolo[4,5-b]pyridin-2-yloxy)-benzofuran-3-ylmethyl]-terephthalamic acid;
1-[6-(thiazolo[4,5-b]pyridin-2-yloxy)-benzofuran-3-ylmethyl]-3,4-dihydro-1H-quinolin-2-one;
1-[6-(thiazolo[4,5-b]pyridin-2-yloxy)-benzofuran-3-ylmethyl]-6-trifluoromethyl-1,3-dihydro-indol-2-one;
1-[6-(thiazolo[4,5-b]pyridin-2-yloxy)-benzofuran-3-ylmethyl]-1,3-dihydro-indol-2-one;
1-[6-(thiazolo[4,5-b]pyridin-2-yloxy)-benzofuran-3-ylmethyl]-5-trifluoromethyl-1,3-dihydro-indol-2-one;
5-chloro-1-[6-(thiazolo[4,5-b]pyridin-2-yloxy)-benzofuran-3-ylmethyl]-1,3-dihydro-indol-2-one;
6-chloro-1-[6-(thiazolo[4,5-b]pyridin-2-yloxy)-benzofuran-3-ylmethyl]-1,3-dihydro-indol-2-one;
5-fluoro-1-[6-(thiazolo[4,5-b]pyridin-2-yloxy)-benzofuran-3-ylmethyl]-1,3-dihydro-indol-2-one;
(R)—N-(1-aza-bicyclo[2.2.2]oct-3-yl)-N-[6-(thiazolo[4,5-b]pyridin-2-yloxy)-benzofuran-3-ylmethyl]-acetamide;
2-(3-piperidin-1-ylmethyl-benzofuran-6-yloxy)-benzothiazole;
2-(2-piperidin-1-ylmethyl-benzofuran-6-yloxy)-benzothiazole;
and pharmaceutically acceptable salts and prodrugs thereof.

31. A method for inhibiting leukotriene $A_4$ hydrolase activity, comprising exposing leukotriene $A_4$ hydrolase to an effective amount of at least one chemical entity selected from the group consisting of compounds of Formula (I), pharmaceutically acceptable salts of compounds of Formula (I), and pharmaceutically acceptable prodrugs of compounds of Formula (I)

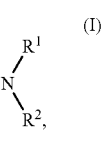

wherein
A is O, bound at site a or at site b;
Z is O or S;
$G_1$, $G_2$ and $G_3$ are each independently $CR^4$ or N;
$R^4$ is H, —$C_{1-4}$alkyl, or halo;
X is CH or N;
Y is O, S, or $NR^3$;
$R^3$ is H or —$C_{1-4}$alkyl;
when Y is O, then L is —$CH_2$—, —$CH_2CH_2$—, or —C(O)—;
when Y is S or $NR^3$, then L is —$CH_2$— or —$CH_2CH_2$—;
$R^1$ and $R^2$ are each independently H, —$C_{1-4}$alkyl, —C(O)$R^i$, —$(CH_2)_2C(O)OR^3$, —$(CH_2)_2N(CH_2CH_3)_2$, —$(CH_2)_3N(CH_3)_2$, —$C_{3-6}$cycloalkyl, —$(CH_2)_{1-4}OCH_3$, indan-2-yl,

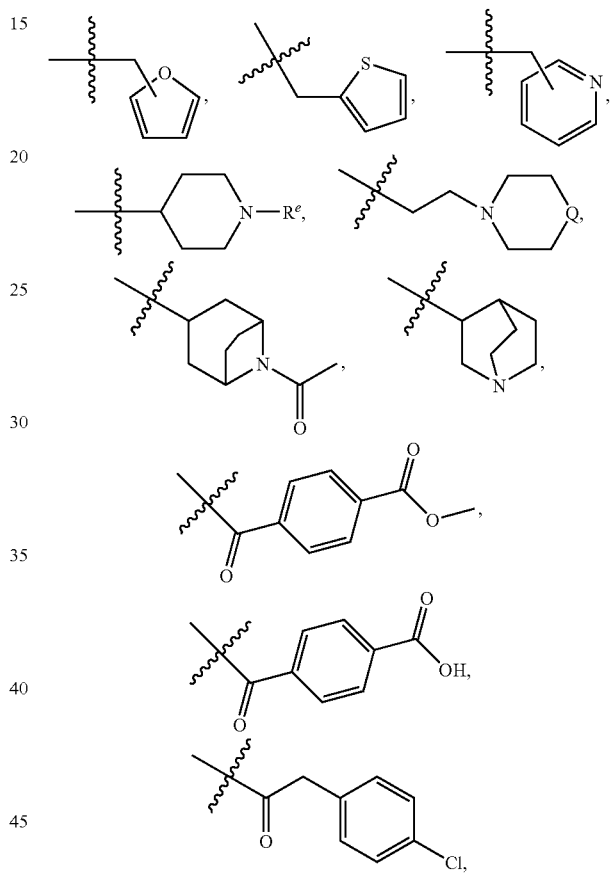

or —$(CH_2)_{0-2}$—$(O)_{0-1}$-phenyl wherein said phenyl is optionally substituted with halo, —$OCH_3$, or —$SO_2NH_2$; provided that $R^1$ and $R^2$ are not both H simultaneously;
$R^i$ is —$CH_3$, 4-acetyl-piperazin-1-ylmethyl, 3-methyl-isoxazol-5-ylmethyl, 4-hydroxy-cyclohexyl, or;

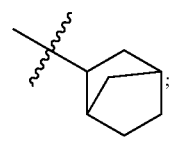 [SMILES: *C1CC2CCC1C2]

or
$R^1$ and $R^2$ are taken together as in one of the following assignments (i) and (ii);
(i) $R^1$ and $R^2$ taken together with the nitrogen member to which they are attached form an unbridged monocyclic moiety, said moiety optionally containing one additional heteroatom member selected from N, O, and S; said moiety being optionally substituted with $R^5$ and $(R^{5'})_m$;

m is 0 or 1;

when m is 1, $R^{5'}$ is —$C_{1-4}$alkyl, halo, or OH;

$R^5$ is selected from H; halo; =O; —OH; —$OR^3$; —$CF_3$; —S(O)(O)$CH_3$; —$C_{1-4}$alkyl; —$OC_{1-4}$alkyl; —$C(CH_3)_2$OH; —$(CH_2)_{0-1}C(O)OR^3$; —$N(R^3)_2$; —$CH_2$OH; —$CH_2OCH_3$; —$(CH_2)_{0-2}NR^9C(O)R^7$; —$(CH_2)_{0-2}$NHS(O)(O)$CH_3$; —$C(O)R^8$; —$C_{3-6}$cycloalkyl; pyrimidin-2-yloxy; 1-piperidinyl; 1-piperidinyl-2-one; 1-pyrrolidinyl; 4-morpholinyl; pyridinyl; pyrimidyl; thiophenylmethyl; 5-oxo-1; 5-dihydro-[1,2,4]triazol-4-yl; —$(CH_2)_{0-2}$-phenyl wherein said phenyl is optionally substituted with halo or $OCH_3$; and 1-pyrrolidinyl-2-one optionally substituted with —OH;

Q is $CH_2$ or O;

$R^7$ is —$C_{1-4}$alkyl, —$NH_2$, or —$OC_{1-4}$alkyl;

$R^8$ is —$C_{1-4}$alkyl; —$NH_2$; —$NHCH_3$; —$C_{3-6}$cycloalkyl; —$(CH_2)_{0-1}$phenyl wherein said phenyl is optionally substituted with halo or $CO_2$H; 1-pyrrolidinyl; or

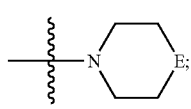

E is $CH_2$, O, or $N(CH_3)$;

$R^9$ is H, —$C_{1-4}$alkyl, or —$C_{3-6}$cycloalkyl;

(ii) $R^1$ and $R^2$ taken together with the nitrogen member to which they are attached form one of the following

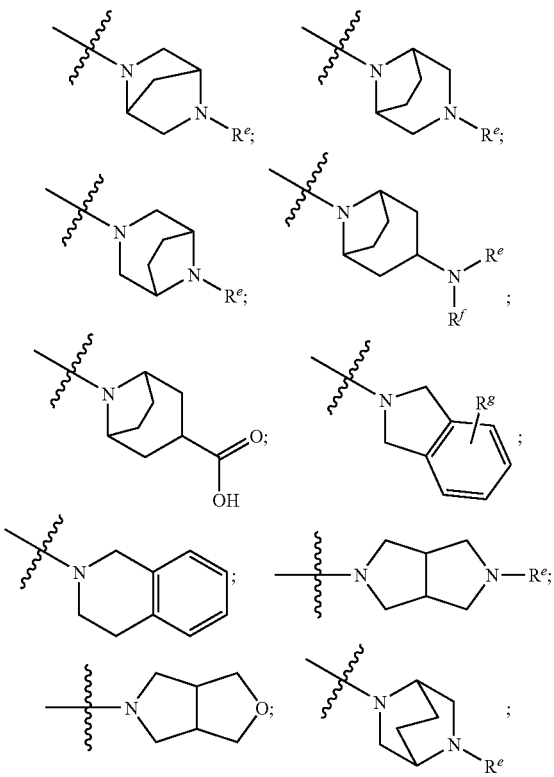

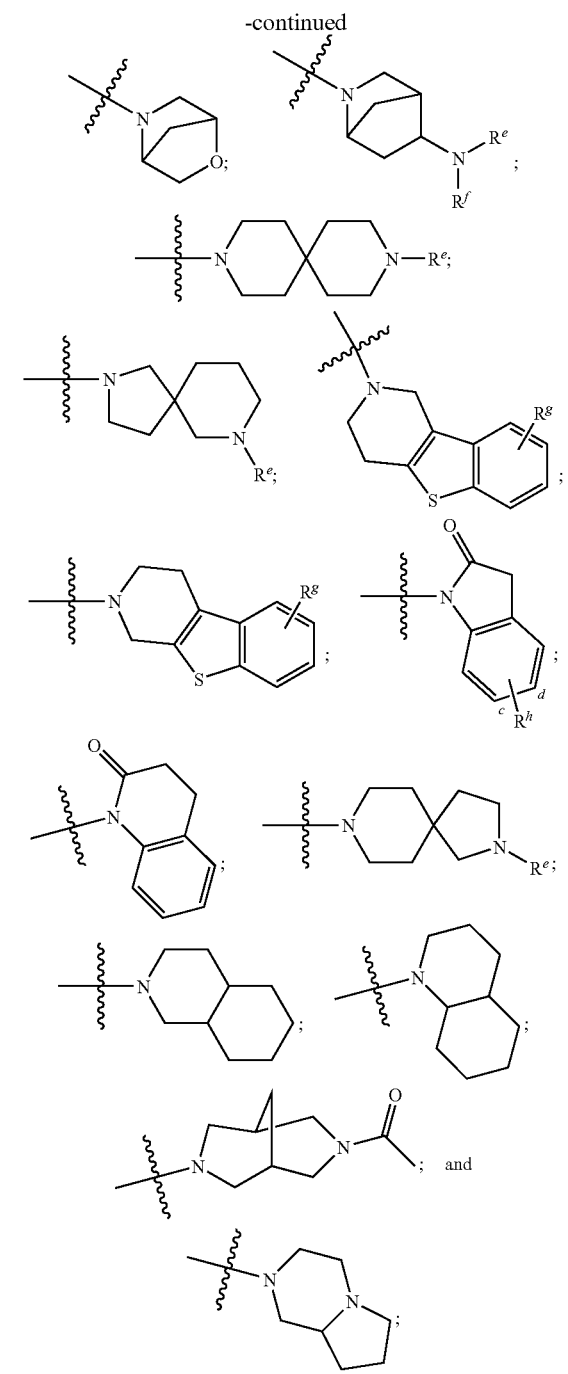

$R^e$ is H, —$C_{1-4}$alkyl, —$C(O)C_{1-4}$alkyl, —$C(O)OC_{1-4}$alkyl, —$C(O)NH_2$, —$C(O)$-tetrahydrofuranyl, —$C(O)CH_2OH$, —$C(O)$isoxazol-5-yl, —$C(O)$furan-3-yl, —$C(O)$pyrazin-2-yl, —$C(O)$cyclobutyl, —S(O)(O)$CH_3$, or 4-methoxycarbonyl-benzyl;

$R^f$ is H, —$CH_3$, or —$CH_2C(O)OR^3$;

$R^g$ is H or halo; and $R^h$ is bound at site c or d and is selected from H, $CF_3$, and halo.

32. A method as in claim 31, wherein the leukotriene $A_4$ hydrolase is in a subject with a disease, disorder, or medical condition mediated by leukotriene $A_4$ hydrolase activity.

33. A method as in claim 32, wherein the disease, disorder, or medical condition is inflammation.

34. A method as in claim 32, wherein the disease, disorder, or medical condition is selected from the group consisting of: inflammatory disorders, allergic disorders, dermatological disorders, autoimmune disease, lymphatic disorders, and immunodeficiency disorders.

35. A method as in claim 32, wherein the disease, disorder, or medical condition is selected from the group consisting of: allergy, abdominal aortic aneurysm, asthma, nasal polyps, allergic rhinitis, nasal itch, ocular inflammation, post-surgical ocular inflammation, conjunctivitis, uveitis, dry eye, psoriasis, pruritis, itch, itchy skin, atopic dermatitis, urticaria, hives, contact dermatitis, scleroderma, skin burns, acne, inflammatory bowel diseases, colitis, Crohn's disease, ulcerative colitis, chronic obstructive pulmonary disease, α1-antitrypsin (α1AT) deficiency, atherosclerosis, type II diabetes, arthritis, rheumatoid arthritis, multiple sclerosis, myocardial infarction, stroke, pain, gingivitis, bronchitis, cystic fibrosis, upper gastrointestinal cancer, sepsis, autoimmune thyroid diseases, immune-mediated diabetes mellitus, lupus, Myasthenia gravis, autoimmune neuropathies, Guillain-Barré, autoimmune uveitis, autoimmune hemolytic anemia, pernicious anemia, autoimmune thrombocytopenia, temporal arteritis, antiphospholipid syndrome, vasculitides, Wegener's granulomatosis, Behcet's disease, dermatitis herpetiformis, pemphigus vulgaris, vitiligio, primary biliary cirrhosis, autoimmune hepatitis, autoimmune oophoritis and orchitis, autoimmune disease of the adrenal gland, polymyositis, dermatomyositis, spondyloarthropathies, ankylosing spondylitis, Sjogren syndrome, and Sjogren-Larsson syndrome.

36. A method as in claim 32, wherein the disease, disorder, or medical condition is selected from the group consisting of: allergy, aortic aneurysm, asthma, autoimmune diseases, pruritis, inflammatory bowel disease, ulcerative colitis, and cardiovascular disease.

37. A method as in claim 31, wherein said at least one chemical entity is selected from the group consisting of
2-(3-pyrrolidin-1-ylmethyl-1H-indol-6-yloxy)-benzothiazole;
2-(3-piperidin-1-ylmethyl-1H-indol-6-yloxy)-benzothiazole;
2-(3-morpholin-4-ylmethyl-1H-indol-6-yloxy)-benzothiazole;
2-[3-(4-methanesulfonyl-piperidin-1-ylmethyl)-1H-indol-6-yloxy]-benzothiazole;
[6-(benzothiazol-2-yloxy)-1H-indol-3-ylmethyl]-benzyl-methyl-amine;
2-[3-(1,3-dihydro-isoindol-2-ylmethyl)-1H-indol-6-yloxy]-benzothiazole;
2-[6-(benzothiazol-2-yloxy)-1H-indol-3-ylmethyl]-1,2,3,4-tetrahydro-isoquinoline;
2-[3-(4-phenyl-piperidin-1-ylmethyl)-1H-indol-6-yloxy]-benzothiazole;
2-(3-pyrrolidin-1-ylmethyl-1H-indol-5-yloxy)-benzothiazole;
2-(3-piperidin-1-ylmethyl-1H-indol-5-yloxy)-benzothiazole;
2-(3-morpholin-4-ylmethyl-1H-indol-5-yloxy)-benzothiazole;
(1S,4S)-2-[3-(2-oxa-5-aza-bicyclo[2.2.1]hept-5-ylmethyl)-1H-indol-6-yloxy]-benzothiazole;
meso-endo-N-{8-[6-(benzothiazol-2-yloxy)-1H-indol-3-ylmethyl]-8-aza-bicyclo[3.2.1]oct-3-yl}-acetamide;
meso-endo-N-{8-[6-(4-fluoro-benzothiazol-2-yloxy)-1H-indol-3-ylmethyl]-8-aza-bicyclo[3.2.1]oct-3-yl}-acetamide;
2-(3-piperidin-1-ylmethyl-1H-indol-6-yloxy)-benzooxazole;
2-(3-piperidin-1-ylmethyl-1H-indol-6-yloxy)-thiazolo[4,5-b]pyridine;
1-[6-(thiazolo[4,5-b]pyridin-2-yloxy)-1H-indol-3-ylmethyl]-piperidine-4-carboxylic acid amide;
meso-endo-N-{8-[6-(thiazolo[4,5-b]pyridin-2-yloxy)-1H-indol-3-ylmethyl]-8-aza-bicyclo[3.2.1]oct-3-yl}-acetamide;
(1S,4S)-1-{5-[6-(thiazolo[4,5-b]pyridin-2-yloxy)-1H-indol-3-ylmethyl]-2,5-diaza-bicyclo[2.2.1]hept-2-yl}-ethanone;
1-{1-[6-(thiazolo[4,5-b]pyridin-2-yloxy)-1H-indol-3-ylmethyl]-piperidin-4-yl}-pyrrolidin-2-one;
1-[6-(benzothiazol-2-yloxy)-1H-indol-3-ylmethyl]-piperidine-4-carboxylic acid amide;
1-[6-(benzothiazol-2-yloxy)-1H-indol-3-ylmethyl]-piperidine-4-carboxylic acid methylamide;
{1-[6-(benzothiazol-2-yloxy)-1H-indol-3-ylmethyl]-piperidin-4-yl}-pyrrolidin-1-yl-methanone;
{1-[6-(benzothiazol-2-yloxy)-1H-indol-3-ylmethyl]-piperidin-4-yl}-piperidin-1-yl-methanone;
{1-[6-(benzothiazol-2-yloxy)-1H-indol-3-ylmethyl]-piperidin-4-yl}-morpholin-4-yl-methanone;
{1-[6-(benzothiazol-2-yloxy)-1H-indol-3-ylmethyl]-piperidin-4-yl}-(4-methyl-piperazin-1-yl)-methanone;
(3S)-1-[6-(benzothiazol-2-yloxy)-1H-indol-3-ylmethyl]-piperidine-3-carboxylic acid amide;
{1-[6-(benzothiazol-2-yloxy)-1H-indol-3-ylmethyl]-piperidin-4-yl}-methanol;
{1-[6-(benzothiazol-2-yloxy)-1H-indol-3-ylmethyl]-piperidin-4-yl}-carbamic acid ethyl ester;
1-{1-[6-(benzothiazol-2-yloxy)-1H-indol-3-ylmethyl]-piperidin-4-yl}-pyrrolidin-2-one;
2-(3-piperidin-1-ylmethyl-1H-pyrrolo[3,2-b]pyridin-6-yloxy)-benzothiazole;
2-(3-morpholin-4-ylmethyl-1H-pyrrolo[3,2-b]pyridin-6-yloxy)-benzothiazole;
1-[6-(benzothiazol-2-yloxy)-1H-pyrrolo[3,2-b]pyridin-3-ylmethyl]-piperidine-4-carboxylic acid amide;
2-[6-(thiazolo[4,5-b]pyridin-2-yloxy)-1H-indol-3-ylmethyl]-1,2,3,4-tetrahydro-benzo[4,5]thieno[3,2-c]pyridine;
2-[6-(thiazolo[4,5-b]pyridin-2-yloxy)-1H-indol-3-ylmethyl]-1,2,3,4-tetrahydro-benzo[4,5]thieno[2,3-c]pyridine;
8-chloro-2-[6-(thiazolo[4,5-b]pyridin-2-yloxy)-1H-indol-3-ylmethyl]-1,2,3,4-tetrahydro-benzo[4,5]thieno[3,2-c]pyridine;
6-chloro-2-[6-(thiazolo[4,5-b]pyridin-2-yloxy)-1H-indol-3-ylmethyl]-1,2,3,4-tetrahydro-benzo[4,5]thieno[2,3-c]pyridine;
8-fluoro-2-[6-(thiazolo[4,5-b]pyridin-2-yloxy)-1H-indol-3-ylmethyl]-1,2,3,4-tetrahydro-benzo[4,5]thieno[3,2-c]pyridine;
2-[6-(benzothiazol-2-yloxy)-1H-indol-3-ylmethyl]-1,2,3,4-tetrahydro-benzo[4,5]thieno[3,2-c]pyridine;
2-(3-morpholin-4-ylmethyl-1H-indol-6-yloxy)-thiazolo[4,5-b]pyridine;
(3S)-2-[3-(3-Methyl-morpholin-4-ylmethyl)-1H-indol-6-yloxy]-thiazolo[4,5-b]pyridine;
2-(3-thiomorpholin-4-ylmethyl-1H-indol-6-yloxy)-thiazolo[4,5-b]pyridine;
meso-endo-N-{8-[6-(Thiazolo[5,4-b]pyridin-2-yloxy)-1H-indol-3-ylmethyl]-8-aza-bicyclo[3.2.1]oct-3-yl}-acetamide;
(4R)-1-{1-[6-(benzothiazol-2-yloxy)-1H-indol-3-ylmethyl]-piperidin-4-yl}-4-hydroxy-pyrrolidin-2-one;
1-[6-(benzothiazol-2-yloxy)-1H-indol-3-ylmethyl]-piperidine-4-carboxylic acid;
{1-[6-(benzothiazol-2-yloxy)-1H-indol-3-ylmethyl]-piperidin-4-yl}-acetic acid;
1-[6-(benzothiazol-2-yloxy)-1H-indol-3-ylmethyl]-piperidine-3-carboxylic acid;

meso-endo-(acetyl-{8-[6-(benzothiazol-2-yloxy)-1H-indol-3-ylmethyl]-8-aza-bicyclo[3.2.1]oct-3-yl}-amino)-acetic acid;
meso-endo-(acetyl-{8-[5-(benzothiazol-2-yloxy)-1H-indol-3-ylmethyl]-8-aza-bicyclo[3.2.1]oct-3-yl}-amino)-acetic acid;
1-[6-(benzothiazol-2-yloxy)-1H-indol-3-ylmethyl]-piperidin-4-ylamine;
2-[3-(hexahydro-pyrrolo[3,4-c]pyrrol-2-ylmethyl)-1H-indol-6-yloxy]-benzothiazole;
(1S,4S)-2-[3-(2,5-diaza-bicyclo[2.2.1]hept-2-ylmethyl)-1H-indol-6-yloxy]-benzothiazole;
N-{1-[6-(benzothiazol-2-yloxy)-1H-indol-3-ylmethyl]-piperidin-4-yl}-acetamide;
1-{5-[6-(benzothiazol-2-yloxy)-1H-indol-3-ylmethyl]-hexahydro-pyrrolo[3,4-c]pyrrol-2-yl}-ethanone;
(1S,4S)-1-{5-[6-(benzothiazol-2-yloxy)-1H-indol-3-ylmethyl]-2,5-diaza-bicyclo[2.2.1]hept-2-yl}-ethanone;
2-(3-morpholin-4-ylmethyl-1H-indol-6-yloxy)-thiazolo[4,5-b]pyrazine;
7-methyl-2-(3-morpholin-4-ylmethyl-1H-indol-6-yloxy)-thiazolo[4,5-b]pyridine;
6-fluoro-2-(3-morpholin-4-ylmethyl-1H-indol-6-yloxy)-thiazolo[4,5-b]pyridine;
6-chloro-2-(3-morpholin-4-ylmethyl-1H-indol-6-yloxy)-thiazolo[4,5-b]pyridine;
6-fluoro-2-(3-morpholin-4-ylmethyl-1H-indol-6-yloxy)-thiazolo[5,4-b]pyridine;
2-(1-methyl-3-morpholin-4-ylmethyl-1H-indol-6-yloxy)-benzothiazole;
2-(1-ethyl-2-piperidin-1-ylmethyl-1H-indol-5-yloxy)-benzothiazole;
2-(1-ethyl-2-morpholin-4-ylmethyl-1H-indol-5-yloxy)-benzothiazole;
2-(1-ethyl-2-pyrrolidin-1-ylmethyl-1H-indol-5-yloxy)-benzothiazole;
2-(2-piperidin-1-ylmethyl-1H-indol-5-yloxy)-benzothiazole;
2-(2-pyrrolidin-1-ylmethyl-1H-indol-5-yloxy)-benzothiazole;
2-(2-piperidin-1-ylmethyl-1H-indol-6-yloxy)-benzothiazole;
2-(2-pyrrolidin-1-ylmethyl-1H-indol-6-yloxy)-benzothiazole;
1-[6-(benzothiazol-2-yloxy)-1H-indol-2-ylmethyl]-piperidine-4-carboxylic acid amide;
meso-endo-N-{8-[6-(benzothiazol-2-yloxy)-1H-indol-2-ylmethyl]-8-aza-bicyclo[3.2.1]oct-3-yl}-acetamide;
2-(2-piperidin-1-ylmethyl-1H-indol-6-yloxy)-thiazolo[4,5-b]pyridine;
meso-endo-N-{8-[6-(thiazolo[4,5-b]pyridin-2-yloxy)-1H-indol-2-ylmethyl]-8-aza-bicyclo[3.2.1]oct-3-yl}-acetamide;
1-{2-[5-(benzothiazol-2-yloxy)-1H-indol-3-yl]-ethyl}-piperidine-4-carboxylic acid;
2-[3-(2-piperidin-1-yl-ethyl)-1H-indol-5-yloxy]-benzothiazole;
1-{2-[5-(benzothiazol-2-yloxy)-1H-indol-3-yl]-ethyl}-piperidine-4-carboxylic acid amide;
1-[5-(benzothiazol-2-yloxy)-benzofuran-2-ylmethyl]-piperidine-4-carboxylic acid;
1-[6-(benzothiazol-2-yloxy)-benzofuran-2-ylmethyl]-piperidine-4-carboxylic acid;
{1-[6-(benzothiazol-2-yloxy)-benzofuran-2-ylmethyl]-piperidin-4-yl}-acetic acid;
{4-[6-(benzothiazol-2-yloxy)-benzofuran-2-ylmethyl]-piperazin-1-yl}-acetic acid;
1-{2-[6-(benzothiazol-2-yloxy)-benzofuran-3-yl]-ethyl}-piperidine-4-carboxylic acid;
meso-endo-{8-[6-(benzothiazol-2-yloxy)-benzofuran-2-ylmethyl]-8-aza-bicyclo[3.2.1]oct-3-ylamino}-acetic acid;
2-(2-piperidin-1-ylmethyl-benzofuran-5-yloxy)-benzothiazole;
meso-endo-N-{8-[5-(benzothiazol-2-yloxy)-benzofuran-2-ylmethyl]-8-aza-bicyclo[3.2.1]oct-3-yl}-acetamide;
4-fluoro-2-(2-piperidin-1-ylmethyl-benzofuran-5-yloxy)-benzothiazole;
meso-endo-N-{8-[5-(4-fluoro-benzothiazol-2-yloxy)-benzofuran-2-ylmethyl]-8-aza-bicyclo[3.2.1]oct-3-yl}-acetamide;
2-(2-piperidin-1-ylmethyl-benzofuran-5-yloxy)-thiazolo[4,5-b]pyridine;
meso-endo-N-{8-[5-(thiazolo[4,5-b]pyridin-2-yloxy)-benzofuran-2-ylmethyl]-8-aza-bicyclo[3.2.1]oct-3-yl}-acetamide;
1-[5-(thiazolo[4,5-b]pyridin-2-yloxy)-benzofuran-2-ylmethyl]-piperidine-4-carboxylic acid amide;
2-{2-[4-(pyrimidin-2-yloxy)-piperidin-1-ylmethyl]-benzofuran-5-yloxy}-thiazolo[4,5-b]-pyridine;
1-{5-[5-(thiazolo[4,5-b]pyridin-2-yloxy)-benzofuran-2-ylmethyl]-hexahydro-pyrrolo[3,4-c]pyrrol-2-yl}-ethanone;
5-[5-(thiazolo[4,5-b]pyridin-2-yloxy)-benzofuran-2-ylmethyl]-hexahydro-pyrrolo[3,4-c]pyrrole-2-carboxylic acid amide;
2-[2-(4-methanesulfonyl-piperidin-1-ylmethyl)-benzofuran-5-yloxy]-thiazolo[4,5-b]-pyridine;
meso-1-{8-[5-(thiazolo[4,5-b]pyridin-2-yloxy)-benzofuran-2-ylmethyl]-3,8-diaza-bicyclo[3.2.1]oct-3-yl}-ethanone;
meso-8-[5-(thiazolo[4,5-b]pyridin-2-yloxy)-benzofuran-2-ylmethyl]-3,8-diaza-bicyclo[3.2.1]octane-3-carboxylic acid amide;
(1S,4S)-1-{5-[5-(thiazolo[4,5-b]pyridin-2-yloxy)-benzofuran-2-ylmethyl]-2,5-diaza-bicyclo[2.2.1]hept-2-yl}-ethanone;
1-{1-[5-(thiazolo[4,5-b]pyridin-2-yloxy)-benzofuran-2-ylmethyl]-piperidin-4-yl}-pyrrolidin-2-one;
2-(2-morpholin-4-ylmethyl-benzofuran-5-yloxy)-thiazolo[4,5-b]pyridine;
(3S)-2-[2-(3-methyl-morpholin-4-ylmethyl)-benzofuran-5-yloxy]-thiazolo[4,5-b]pyridine;
(1S,4S)-2-[2-(2-oxa-5-aza-bicyclo[2.2.1]hept-5-ylmethyl)-benzofuran-5-yloxy]-thiazolo[4,5-b]pyridine;
(1S,4S)-5-[5-(thiazolo[4,5-b]pyridin-2-yloxy)-benzofuran-2-ylmethyl]-2,5-diaza-bicyclo[2.2.1]heptane-2-carboxylic acid amide;
(1R,4R)-5-[5-(thiazolo[4,5-b]pyridin-2-yloxy)-benzofuran-2-ylmethyl]-2,5-diaza-bicyclo[2.2.1]heptane-2-carboxylic acid amide;
(1R,4R)-1-{5-[5-(thiazolo[4,5-b]pyridin-2-yloxy)-benzofuran-2-ylmethyl]-2,5-diaza-bicyclo[2.2.1]hept-2-yl}-ethanone;
meso-endo-N-{8-[5-(thiazolo[4,5-b]pyridin-2-yloxy)-benzofuran-2-ylmethyl]-8-aza-bicyclo[3.2.1]oct-3-yl}-urea;
meso-exo-N-{8-[5-(thiazolo[4,5-b]pyridin-2-yloxy)-benzofuran-2-ylmethyl]-8-aza-bicyclo[3.2.1]oct-3-yl}-acetamide;
1-[5-(benzothiazol-2-yloxy)-benzofuran-2-ylmethyl]-piperidine-4-carboxylic acid amide;
meso-exo-N-{8-[6-(thiazolo[4,5-b]pyridin-2-yloxy)-benzofuran-2-ylmethyl]-8-aza-bicyclo[3.2.1]oct-3-yl}-acetamide;
(1R,4R)-1-{5-[6-(thiazolo[4,5-b]pyridin-2-yloxy)-benzofuran-2-ylmethyl]-2,5-diaza-bicyclo[2.2.1]hept-2-yl}-ethanone;

1-{1-[6-(thiazolo[4,5-b]pyridin-2-yloxy)-benzofuran-2-ylmethyl]-piperidin-4-yl}-pyrrolidin-2-one;
(1S,4S)-2-[2-(2-oxa-5-aza-bicyclo[2.2.1]hept-5-ylmethyl)-benzofuran-6-yloxy]-thiazolo[4,5-b]pyridine;
2-[2-(tetrahydro-furo[3,4-c]pyrrol-5-ylmethyl)-benzofuran-6-yloxy]-thiazolo[4,5-b]pyridine;
2-[2-(4-fluoro-piperidin-1-ylmethyl)-benzofuran-5-yloxy]-thiazolo[4,5-b]pyridine;
dimethyl-[5-(thiazolo[4,5-b]pyridin-2-yloxy)-benzofuran-2-ylmethyl]-amine;
2-[2-(tetrahydro-furo[3,4-c]pyrrol-5-ylmethyl)-benzofuran-5-yloxy]-thiazolo[4,5-b]pyridine;
benzyl-methyl-[5-(thiazolo[4,5-b]pyridin-2-yloxy)-benzofuran-2-ylmethyl]-amine;
2-(2-morpholin-4-ylmethyl-benzofuran-6-yloxy)-thiazolo[4,5-b]pyridine;
1-[6-(thiazolo[4,5-b]pyridin-2-yloxy)-benzofuran-2-ylmethyl]-piperidine-4-carboxylic acid amide;
(1S,4S)-5-[6-(thiazolo[4,5-b]pyridin-2-yloxy)-benzofuran-2-ylmethyl]-2,5-diaza-bicyclo[2.2.1]heptane-2-carboxylic acid amide;
meso-endo-N-{8-[6-(thiazolo[4,5-b]pyridin-2-yloxy)-benzofuran-2-ylmethyl]-8-aza-bicyclo[3.2.1]oct-3-yl}-acetamide;
meso-1-{8-[6-(thiazolo[4,5-b]pyridin-2-yloxy)-benzofuran-2-ylmethyl]-3,8-diaza-bicyclo[3.2.1]oct-3-yl}-ethanone;
N-(1-{[6-([1,3]thiazolo[4,5-b]pyridin-2-yloxy)-1-benzofuran-2-yl]methyl}pyrrolidin-3-yl)acetamide;
(1S,4S)-1-{5-[5-(thiazolo[5,4-b]pyridin-2-yloxy)-benzofuran-2-ylmethyl]-2,5-diaza-bicyclo[2.2.1]hept-2-yl}-ethanone;
(1S,4S)-1-{5-[6-(thiazolo[5,4-b]pyridin-2-yloxy)-benzofuran-2-ylmethyl]-2,5-diaza-bicyclo[2.2.1]hept-2-yl}-ethanone;
meso-1-{8-[5-(thiazolo[5,4-b]pyridin-2-yloxy)-benzofuran-2-ylmethyl]-3,8-diaza-bicyclo[3.2.1]oct-3-yl}-ethanone;
meso-1-{8-[6-(thiazolo[5,4-b]pyridin-2-yloxy)-benzofuran-2-ylmethyl]-3,8-diaza-bicyclo[3.2.1]oct-3-yl}-ethanone;
meso-endo-N-{8-[5-(thiazolo[5,4-b]pyridin-2-yloxy)-benzofuran-2-ylmethyl]-8-aza-bicyclo[3.2.1]oct-3-yl}-acetamide;
meso-endo-N-{8-[6-(thiazolo[5,4-b]pyridin-2-yloxy)-benzofuran-2-ylmethyl]-8-aza-bicyclo[3.2.1]oct-3-yl}-acetamide;
1-(1-{[6-([1,3]thiazolo[4,5-b]pyridin-2-yloxy)-1-benzofuran-2-yl]methyl}pyrrolidin-3-yl)urea;
N-(1-{[6-([1,3]thiazolo[4,5-b]pyridin-2-yloxy)-1-benzofuran-2-yl]methyl}pyrrolidin-3-yl)methanesulfonamide;
meso-endo-N-(8-{2-[6-(benzothiazol-2-yloxy)-benzofuran-3-yl]-ethyl}-8-aza-bicyclo[3.2.1]oct-3-yl)-acetamide;
meso-1-(8-{2-[6-(thiazolo[4,5-b]pyridin-2-yloxy)-benzofuran-3-yl]-ethyl}-3,8-diaza-bicyclo[3.2.1]oct-3-yl)-ethanone;
meso-endo-N-(8-{2-[6-(thiazolo[4,5-b]pyridin-2-yloxy)-benzofuran-3-yl]-ethyl}-8-aza-bicyclo[3.2.1]oct-3-yl)-acetamide;
2-(2-piperidin-1-ylmethyl-benzo[b]thiophen-6-yloxy)-benzothiazole;
(2-morpholin-4-ylmethyl-benzo[b]thiophen-6-yloxy)-benzothiazole;
meso-endo-N-{8-[6-(benzothiazol-2-yloxy)-benzo[b]thiophen-2-ylmethyl]-8-aza-bicyclo[3.2.1]oct-3-yl}-acetamide;
meso-endo-N-{8-[6-(thiazolo[4,5-b]pyridin-2-yloxy)-benzo[b]thiophen-2-ylmethyl]-8-aza-bicyclo[3.2.1]oct-3-yl}-acetamide;
2-(2-piperidin-1-ylmethyl-benzo[b]thiophen-6-yloxy)-thiazolo[4,5-b]pyridine;
2-(3-morpholin-4-ylmethyl-benzo[b]thiophen-6-yloxy)-thiazolo[4,5-b]pyridine;
1-[6-(thiazolo[4,5-b]pyridin-2-yloxy)-benzo[b]thiophen-2-ylmethyl]-piperidine-4-carboxylic acid amide;
1-[6-(benzothiazol-2-yloxy)-1H-indol-3-ylmethyl]-piperidine-4-carboxylic acid ethyl ester;
1-[6-(thiazolo[5,4-b]pyridin-2-yloxy)-1H-indol-3-ylmethyl]-piperidine-4-carboxylic acid ethyl ester;
{1-[6-(benzothiazol-2-yloxy)-1H-indol-3-ylmethyl]-piperidin-4-yl}-acetic acid methyl ester;
meso-endo-(acetyl-{8-[6-(benzothiazol-2-yloxy)-1H-indol-3-ylmethyl]-8-aza-bicyclo[3.2.1]oct-3-yl}-amino)-acetic acid ethyl ester;
meso-endo-(acetyl-{8-[5-(benzothiazol-2-yloxy)-1H-indol-3-ylmethyl]-8-aza-bicyclo[3.2.1]oct-3-yl}-amino)-acetic acid ethyl ester;
(3R)-1-[6-(benzothiazol-2-yloxy)-1H-indol-3-ylmethyl]-piperidine-3-carboxylic acid ethyl ester;
{1-[6-(benzothiazol-2-yloxy)-1H-indol-3-ylmethyl]-piperidin-4-yl}-carbamic acid tert-butyl ester;
5-[6-(benzothiazol-2-yloxy)-1H-indol-3-ylmethyl]-hexahydro-pyrrolo[3,4-c]pyrrole-2-carboxylic acid tert-butyl ester;
(1S,4S)-5-[6-(benzothiazol-2-yloxy)-1H-indol-3-ylmethyl]-2,5-diaza-bicyclo[2.2.1]heptane-2-carboxylic acid tert-butyl ester;
1-{2-[5-(benzothiazol-2-yloxy)-1H-indol-3-yl]-ethyl}-piperidine-4-carboxylic acid ethyl ester;
1-{2-[6-(benzothiazol-2-yloxy)-benzofuran-3-yl]-ethyl}-piperidine-4-carboxylic acid ethyl ester;
meso-endo-({8-[6-(benzothiazol-2-yloxy)-benzofuran-2-ylmethyl]-8-aza-bicyclo[3.2.1]oct-3-yl}-tert-butoxycarbonyl-amino)-acetic acid tert-butyl ester;
{1-[6-(thiazolo[4,5-b]pyridin-2-yloxy)-benzofuran-2-ylmethyl]-pyrrolidin-3-yl}-carbamic acid tert-butyl ester;
1-[6-(thiazolo[4,5-b]pyridin-2-yloxy)-benzofuran-2-ylmethyl]-pyrrolidin-3-ylamine;
1-{8-[6-(thiazolo[4,5-b]pyridin-2-yloxy)-benzofuran-3-ylmethyl]-3,8-diaza-bicyclo[3.2.1]oct-3-yl}-ethanone;
(1S,4S)-1-{5-[6-(thiazolo[4,5-b]pyridin-2-yloxy)-benzofuran-3-ylmethyl]-2,5-diaza-bicyclo[2.2.1]hept-2-yl}-ethanone;
meso-endo-N-{8-[6-(thiazolo[4,5-b]pyridin-2-yloxy)-benzofuran-3-ylmethyl]-8-aza-bicyclo[3.2.1]oct-3-yl}-acetamide;
2-(3-morpholin-4-ylmethyl-benzofuran-6-yloxy)-thiazolo[4,5-b]pyridine;
(1R,4R)-1-{5-[6-(thiazolo[4,5-b]pyridin-2-yloxy)-benzofuran-3-ylmethyl]-2,5-diaza-bicyclo[2.2.1]hept-2-yl}-ethanone;
(1S,4S)-2-[3-(2-oxa-5-aza-bicyclo[2.2.1]hept-5-ylmethyl)-benzofuran-6-yloxy]-thiazolo[4,5-b]pyridine;
(S)-2-[3-(3-methyl-morpholin-4-ylmethyl)-benzofuran-6-yloxy]-thiazolo[4,5-b]pyridine;
(1R,4R)-5-[6-(thiazolo[4,5-b]pyridin-2-yloxy)-benzofuran-3-ylmethyl]-2,5-diaza-bicyclo[2.2.1]heptane-2-carboxylic acid amide;
5-[6-(thiazolo[4,5-b]pyridin-2-yloxy)-benzofuran-3-ylmethyl]-hexahydro-pyrrolo[3,4-c]pyrrole-2-carboxylic acid amide;
N-{1-[6-(thiazolo[4,5-b]pyridin-2-yloxy)-benzofuran-3-ylmethyl]-piperidin-4-ylmethyl}-acetamide;
2-[3-(4-trifluoromethyl-piperidin-1-ylmethyl)-benzofuran-6-yloxy]-thiazolo[4,5-b]pyridine;

(1S,4S)-1-{5-[6-(benzothiazol-2-yloxy)-benzofuran-3-yl-methyl]-2,5-diaza-bicyclo[2.2.1]hept-2-yl}-ethanone;
2-(3-morpholin-4-ylmethyl-benzofuran-6-yloxy)-benzothiazole;
1-{2-[5-(thiazolo[4,5-b]pyridin-2-yloxy)-benzofuran-2-ylmethyl]-2,7-diaza-spiro[4.5]dec-7-yl}-ethanone;
1-{9-[5-(thiazolo[4,5-b]pyridin-2-yloxy)-benzofuran-2-ylmethyl]-3,9-diaza-spiro[5.5]undec-3-yl}-ethanone;
(1S,4S)-1-{5-[6-(thiazolo[4,5-b]pyridin-2-yloxy)-benzofuran-2-ylmethyl]-2,5-diaza-bicyclo[2.2.1]hept-2-yl}-ethanone;
meso-1-{5-[5-(thiazolo[4,5-b]pyridin-2-yloxy)-benzofuran-2-ylmethyl]-2,5-diaza-bicyclo[2.2.2]oct-2-yl}-ethanone;
meso-1-{5-[6-(thiazolo[4,5-b]pyridin-2-yloxy)-benzofuran-2-ylmethyl]-2,5-diaza-bicyclo[2.2.2]oct-2-yl}-ethanone;
1-{4-[6-(thiazolo[4,5-b]pyridin-2-yloxy)-benzofuran-2-ylmethyl]-piperazin-1-yl}-ethanone;
meso-endo-{8-[6-(thiazolo[4,5-b]pyridin-2-yloxy)-benzofuran-2-ylmethyl]-8-aza-bicyclo[3.2.1]oct-3-yl}-urea;
meso-8-[5-(benzothiazol-2-yloxy)-benzofuran-2-ylmethyl]-3,8-diaza-bicyclo[3.2.1]octane-3-carboxylic acid amide;
(1S,4S)-5-[5-(thiazolo[4,5-b]pyridin-2-yloxy)-benzofuran-2-ylmethyl]-2,5-diaza-bicyclo[2.2.1]heptane-2-carboxylic acid amide;
meso-endo-{8-[6-(thiazolo[4,5-b]pyridin-2-yloxy)-benzofuran-3-ylmethyl]-8-aza-bicyclo[3.2.1]oct-3-yl}-urea;
furan-2-ylmethyl-methyl-[6-(thiazolo[4,5-b]pyridin-2-yloxy)-benzofuran-3-ylmethyl]-amine;
methyl-pyridin-4-ylmethyl-[6-(thiazolo[4,5-b]pyridin-2-yloxy)-benzofuran-3-ylmethyl]-amine;
methyl-pyridin-3-ylmethyl-[6-(thiazolo[4,5-b]pyridin-2-yloxy)-benzofuran-3-ylmethyl]-amine;
1-{1-[6-(benzothiazol-2-yloxy)-benzofuran-3-ylmethyl]-piperidin-4-yl}-pyrrolidin-2-one;
N-{1-[6-(benzothiazol-2-yloxy)-benzofuran-3-ylmethyl]-piperidin-4-yl}-acetamide;
meso-endo-N-{8-[6-(benzothiazol-2-yloxy)-benzofuran-3-ylmethyl]-8-aza-bicyclo[3.2.1]oct-3-yl}-acetamide;
1-{4-[6-(thiazolo[4,5-b]pyridin-2-yloxy)-benzofuran-3-ylmethyl]-[1,4]diazepan-1-yl}-ethanone;
2-[3-(4-methanesulfonyl-piperidin-1-ylmethyl)-benzofuran-6-yloxy]-thiazolo[4,5-b]pyridine;
(2-methoxy-ethyl)-methyl-[6-(thiazolo[4,5-b]pyridin-2-yloxy)-benzofuran-3-ylmethyl]-amine;
2-(3-pyrrolidin-1-ylmethyl-benzofuran-6-yloxy)-thiazolo[4,5-b]pyridine;
(2S)-2-[3-(2-methoxymethyl-pyrrolidin-1-ylmethyl)-benzofuran-6-yloxy]-thiazolo[4,5-b]pyridine;
(1S,4S,5S)—N-{2-[6-(thiazolo[4,5-b]pyridin-2-yloxy)-benzofuran-3-ylmethyl]-2-aza-bicyclo[2.2.1]hept-5-yl}-acetamide;
(1S,4S,5S)—N-{2-[5-(thiazolo[4,5-b]pyridin-2-yloxy)-benzofuran-2-ylmethyl]-2-aza-bicyclo[2.2.1]hept-5-yl}-acetamide;
(1S,4S,5S)—N-{2-[6-(thiazolo[4,5-b]pyridin-2-yloxy)-benzofuran-2-ylmethyl]-2-aza-bicyclo[2.2.1]hept-5-yl}-acetamide;
2-[2-(4-fluoro-piperidin-1-ylmethyl)-benzofuran-6-yloxy]-thiazolo[4,5-b]pyridine;
2-[2-(4-trifluoromethyl-piperidin-1-ylmethyl)-benzofuran-6-yloxy]-thiazolo[4,5-b]pyridine;
2-(2-piperidin-1-ylmethyl-benzofuran-6-yloxy)-thiazolo[4,5-b]pyridine;
(1R,4R)-5-[6-(thiazolo[4,5-b]pyridin-2-yloxy)-benzofuran-2ylmethyl]-2,5-diaza-bicyclo[2.2.1]heptane-2-carboxylic acid amide;
5-[6-(thiazolo[4,5-b]pyridin-2-yloxy)-benzofuran-2-ylmethyl]-hexahydro-pyrrolo[3,4-c]pyrrole-2-carboxylic acid amide;
1-{5-[6-(thiazolo[4,5-b]pyridin-2-yloxy)-benzofuran-2-ylmethyl]-hexahydro-pyrrolo[3,4-c]pyrrol-2-yl}-ethanone;
1-{4-[6-(thiazolo[4,5-b]pyridin-2-yloxy)-benzofuran-3-ylmethyl]-piperazin-1-yl}-ethanone;
N-{1-[6-(thiazolo[4,5-b]pyridin-2-yloxy)-benzofuran-3-ylmethyl]-piperidin-4-yl}-acetamide;
diethyl-[6-(thiazolo[4,5-b]pyridin-2-yloxy)-benzofuran-2-ylmethyl]-amine;
(1S,4S)-1-{5-[5-(thiazolo[4,5-c]pyridin-2-yloxy)-benzofuran-2-ylmethyl]-2,5-diaza-bicyclo[2.2.1]hept-2-yl}-ethanone;
meso-endo-N-{8-[5-(thiazolo[4,5-c]pyridin-2-yloxy)-benzofuran-2-ylmethyl]-8-aza-bicyclo[3.2.1]oct-3-yl}-acetamide;
meso-endo-N-{8-[6-(thiazolo[4,5-c]pyridin-2-yloxy)-benzofuran-2-ylmethyl]-8-aza-bicyclo[3.2.1]oct-3-yl}-acetamide;
meso-1-{8-[6-(thiazolo[4,5-c]pyridin-2-yloxy)-benzofuran-2-ylmethyl]-3,8-diaza-bicyclo[3.2.1]oct-3-yl}-ethanone;
(1S,4S)-1-{5-[6-(thiazolo[4,5-c]pyridin-2-yloxy)-benzofuran-2-ylmethyl]-2,5-diaza-bicyclo[2.2.1]hept-2-yl}-ethanone;
1-[6-(thiazolo[4,5-b]pyridin-2-yloxy)-benzofuran-2-ylmethyl]-piperidine-4-carboxylic acid methylamide;
pyrrolidin-1-yl-{1-[6-(thiazolo[4,5-b]pyridin-2-yloxy)-benzofuran-2-ylmethyl]-piperidin-4-yl}-methanone;
meso-1-{8-[5-(thiazolo[4,5-c]pyridin-2-yloxy)-benzofuran-2-ylmethyl]-3,8-diaza-bicyclo[3.2.1]oct-3-yl}-ethanone;
meso-exo-{8-[6-(thiazolo[4,5-b]pyridin-2-yloxy)-benzofuran-3-ylmethyl]-8-aza-bicyclo[3.2.1]oct-3-yl}-urea;
meso-exo-N-{8-[6-(thiazolo[4,5-b]pyridin-2-yloxy)-benzofuran-3-ylmethyl]-8-aza-bicyclo[3.2.1]oct-3-yl}-acetamide;
(1S,4S)-5-[6-(thiazolo[4,5-b]pyridin-2-yloxy)-benzofuran-3-ylmethyl]-2,5-diaza-bicyclo[2.2.1]heptane-2-carboxylic acid amide;
meso-8-[6-(thiazolo[4,5-b]pyridin-2-yloxy)-benzofuran-3-ylmethyl]-3,8-diaza-bicyclo[3.2.1]octane-3-carboxylic acid amide;
meso-1-{5-[6-(thiazolo[4,5-b]pyridin-2-yloxy)-benzofuran-3-ylmethyl]-hexahydro-pyrrolo[3,4-c]pyrrol-2-yl}-ethanone;
2-(3-piperidin-1-ylmethyl-benzofuran-6-yloxy)-thiazolo[4,5-b]pyridine;
1-[6-(thiazolo[4,5-b]pyridin-2-yloxy)-benzofuran-3-ylmethyl]-piperidine-4-carboxylic acid amide;
1-[6-(thiazolo[4,5-b]pyridin-2-yloxy)-benzofuran-3-ylmethyl]-piperidine-4-carboxylic acid methylamide;
1-{1-[6-(thiazolo[4,5-b]pyridin-2-yloxy)-benzofuran-3-ylmethyl]-piperidin-4-yl}-pyrrolidin-2-one;
(3-S)-1-[6-(thiazolo[4,5-b]pyridin-2-yloxy)-benzofuran-3-ylmethyl]-piperidine-3-carboxylic acid amide;
2-{3-[4-(pyrimidin-2-yloxy)-piperidin-1-ylmethyl]-benzofuran-6-yloxy}-thiazolo[4,5-b]pyridine;
2-{1-[6-(thiazolo[4,5-b]pyridin-2-yloxy)-benzofuran-3-ylmethyl]-piperidin-4-yl}-propan-2-ol;
diethyl-[6-(thiazolo[4,5-b]pyridin-2-yloxy)-benzofuran-3-ylmethyl]-amine;
1-[6-(thiazolo[4,5-b]pyridin-2-yloxy)-benzofuran-3-ylmethyl]-1,2,3,4,5,6-hexahydro-[4,4']bipyridinyl;

(1S,4S)-1-{5-[6-(thiazolo[5,4-b]pyridin-2-yloxy)-benzofuran-3-ylmethyl]-2,5-diaza-bicyclo[2.2.1]hept-2-yl}-ethanone;
(1S,4S)-1-{5-[6-(thiazolo[4,5-c]pyridin-2-yloxy)-benzofuran-3-ylmethyl]-2,5-diaza-bicyclo[2.2.1]hept-2-yl}-ethanone;
1-[6-(benzothiazol-2-yloxy)-benzofuran-3-ylmethyl]-piperidine-4-carboxylic acid ethyl ester;
1-[6-(thiazolo[4,5-b]pyridin-2-yloxy)-benzofuran-3-ylmethyl]-piperidine-4-carboxylic acid ethyl ester;
1-[6-(thiazolo[4,5-b]pyridin-2-yloxy)-benzofuran-2-ylmethyl]-piperidine-4-carboxylic acid tert-butyl ester;
4-[6-(thiazolo[4,5-b]pyridin-2-yloxy)-benzofuran-3-ylmethyl]-piperazine-1-carboxylic acid tert-butyl ester;
{1-[6-(thiazolo[4,5-b]pyridin-2-yloxy)-benzofuran-3-ylmethyl]-piperidin-4-yl}-carbamic acid tert-butyl ester;
4-[6-(thiazolo[4,5-b]pyridin-2-yloxy)-benzofuran-3-ylmethyl]-[1,4]diazepane-1-carboxylic acid tert-butyl ester;
(1S,4S)-5-[6-(thiazolo[4,5-b]pyridin-2-yloxy)-benzofuran-3-ylmethyl]-2,5-diaza-bicyclo[2.2.2]octane-2-carboxylic acid tert-butyl ester;
4-{cyclopropyl-[6-(thiazolo[4,5-b]pyridin-2-yloxy)-benzofuran-3-ylmethyl]-amino}-piperidine-1-carboxylic acid tert-butyl ester;
2-(3-piperazin-1-ylmethyl-benzofuran-6-yloxy)-thiazolo[4,5-b]pyridine;
1-[6-(thiazolo[4,5-b]pyridin-2-yloxy)-benzofuran-3-ylmethyl]-piperidin-4-ylamine;
2-(3-[1,4]diazepan-1-ylmethyl-benzofuran-6-yloxy)-thiazolo[4,5-b]pyridine;
(1S,4S)-2-[6-(thiazolo[4,5-b]pyridin-2-yloxy)-benzofuran-3-ylmethyl]-2,5-diaza-bicyclo[2.2.2]octane;
cyclopropyl-piperidin-4-yl-[6-(thiazolo[4,5-b]pyridin-2-yloxy)-benzofuran-3-ylmethyl]-amine;
2,2-dimethyl-N-{1-[6-(thiazolo[4,5-b]pyridin-2-yloxy)-benzofuran-2-ylmethyl-pyrrolidin-3-yl]-propionamide;
(1S,4S)1-{5-[6-(thiazolo[4,5-b]pyridin-2-yloxy)-benzofuran-3-ylmethyl]-2,5-diaza-bicyclo[2.2.2]oct-2-yl}-ethanone;
1-(4-{cyclopropyl-[6-(thiazolo[4,5-b]pyridin-2-yloxy)-benzofuran-3-ylmethyl]-amino}-piperidin-1-yl)-ethanone;
4-[6-(thiazolo[4,5-b]pyridin-2-yloxy)-benzofuran-3-ylmethyl]-piperazine-1-carboxylic acid amide;
{1-[6-(thiazolo[4,5-b]pyridin-2-yloxy)-benzofuran-3-ylmethyl]-piperidin-4-yl}-urea;
(1S,4S)-5-[6-(thiazolo[4,5-b]pyridin-2-yloxy)-benzofuran-3-ylmethyl]-2,5-diaza-bicyclo[2.2.2]octane-2-carboxylic acid amide;
4-{cyclopropyl-[6-(thiazolo[4,5-b]pyridin-2-yloxy)-benzofuran-3-ylmethyl]-amino}-piperidine-1-carboxylic acid amide;
2-[3-(4-methanesulfonyl-piperazin-1-ylmethyl)-benzofuran-6-yloxy]-thiazolo[4,5-b]pyridine;
N-{1-[6-(thiazolo[4,5-b]pyridin-2-yloxy)-benzofuran-3-ylmethyl]-piperidin-4-yl}-methanesulfonamide;
(1S,4S)-2-methanesulfonyl-5-[6-(thiazolo[4,5-b]pyridin-2-yloxy)-benzofuran-3-ylmethyl]-2,5-diaza-bicyclo[2.2.2]octane;
cyclopropyl-(1-methanesulfonyl-piperidin-4-yl)-[6-(thiazolo[4,5-b]pyridin-2-yloxy)-benzofuran-3-ylmethyl]-amine;
2-[3-(4-methanesulfonyl-[1,4]diazepan-1-ylmethyl)-benzofuran-6-yloxy]-thiazolo[4,5-b]pyridine;
1-[6-(benzothiazol-2-yloxy)-benzofuran-3-ylmethyl]-piperidine-4-carboxylic acid;
1-[6-(thiazolo[4,5-b]pyridin-2-yloxy)-benzofuran-3-ylmethyl]-piperidine-4-carboxylic acid;
N-{1-[6-(5-methyl-thiazolo[4,5-b]pyridin-2-yloxy)-benzofuran-3-ylmethyl]-piperidin-4-yl}-acetamide;
N-{1-[6-(6-methyl-thiazolo[4,5-b]pyridin-2-yloxy)-benzofuran-3-ylmethyl]-piperidin-4-yl}-acetamide;
N-{1-[6-(7-methyl-thiazolo[4,5-b]pyridin-2-yloxy)-benzofuran-3-ylmethyl]-piperidin-4-yl}-acetamide;
N-{1-[6-(thiazolo[4,5-b]pyrazin-2-yloxy)-benzofuran-3-ylmethyl]-piperidin-4-yl}-acetamide;
N-{1-[6-(6-chloro-thiazolo[4,5-b]pyridin-2-yloxy)-benzofuran-3-ylmethyl]-piperidin-4-yl}-acetamide;
N-{1-[6-(6-fluoro-thiazolo[4,5-b]pyridin-2-yloxy)-benzofuran-3-ylmethyl]-piperidin-4-yl}-acetamide;
2-[3-(2-morpholin-4-yl-ethyl)-benzofuran-6-yloxy]-thiazolo[4,5-b]pyridine;
1-(4-{2-[6-(thiazolo[4,5-b]pyridin-2-yloxy)-benzofuran-3-yl]-ethyl}-piperazin-1-yl)-ethanone;
(1S,4S)-1-(5-{2-[6-(thiazolo[4,5-b]pyridin-2-yloxy)-benzofuran-3-yl]-ethyl}-2,5-diaza-bicyclo[2.2.1]hept-2-yl)-ethanone;
and pharmaceutically acceptable salts and prodrugs thereof.

38. A method as in claim 31, wherein said at least one chemical entity is selected from the group consisting of
1-{4-[5-(thiazolo[4,5-b]pyridin-2-yloxy)-benzofuran-2-ylmethyl]-piperazin-1-yl}-ethanone;
5-[6-(thiazolo[4,5-b]pyridin-2-yloxy)-benzofuran-3-ylmethyl]-hexahydro-pyrrolo[3,4-c]pyrrole-2-carboxylic acid tert-butyl ester;
(1S,4S)-5-[6-(thiazolo[4,5-b]pyridin-2-yloxy)-benzofuran-3-ylmethyl]-2,5-diaza-bicyclo[2.2.1]heptane-2-carboxylic acid tert-butyl ester;
2-[3-(hexahydro-pyrrolo[3,4-c]pyrrol-2-ylmethyl)-benzofuran-6-yloxy]-thiazolo[4,5-b]pyridine;
(1S,4S)-2-[3-(2,5-diaza-bicyclo[2.2.1]hept-2-ylmethyl)-benzofuran-6-yloxy]-thiazolo[4,5-b]pyridine;
2-[3-(2,8-diaza-spiro[4.5]dec-8-ylmethyl)-benzofuran-6-yloxy]-thiazolo[4,5-b]pyridine;
1-{8-[6-(thiazolo[4,5-b]pyridin-2-yloxy)-benzofuran-3-ylmethyl]-2,8-diaza-spiro[4.5]dec-2-yl}-ethanone;
2-[6-(thiazolo[4,5-b]pyridin-2-yloxy)-benzofuran-3-ylmethyl]-decahydro-isoquinoline;
1-[6-(thiazolo[4,5-b]pyridin-2-yloxy)-benzofuran-3-ylmethyl]-decahydro-quinoline;
1-[6-(thiazolo[4,5-b]pyridin-2-yloxy)-benzofuran-3-ylmethyl]-piperidin-4-ol;
{1-[6-(thiazolo[4,5-b]pyridin-2-yloxy)-benzofuran-3-ylmethyl]-piperidin-4-yl}-methanol;
2-[3-(4-fluoro-piperidin-1-ylmethyl)-benzofuran-6-yloxy]-thiazolo[4,5-b]pyridine;
2-[3-(4-methoxy-piperidin-1-ylmethyl)-benzofuran-6-yloxy]-thiazolo[4,5-b]pyridine;
1'-[6-(thiazolo[4,5-b]pyridin-2-yloxy)-benzofuran-3-ylmethyl]-[1,4]bipiperidinyl-2-one;
N-{1-[6-(thiazolo[4,5-b]pyridin-2-yloxy)-furo[3,2-b]pyridin-2-ylmethyl]-piperidin-4-yl}-acetamide;
(1S,4S)-1-{5-[6-(thiazolo[4,5-b]pyridin-2-yloxy)-furo[3,2-b]pyridin-2-ylmethyl]-2,5-diaza-bicyclo[2.2.1]hept-2-yl}-ethanone;
4-phenyl-1-[6-(thiazolo[4,5-b]pyridin-2-yloxy)-benzofuran-3-ylmethyl]-piperidin-4-ol,
cyclopropyl-{4-[6-(thiazolo[4,5-b]pyridin-2-yloxy)-benzofuran-3-ylmethyl]-piperazin-1-yl}-methanone;
2-[3-(4-cyclopropyl-piperazin-1-ylmethyl)-benzofuran-6-yloxy]-thiazolo[4,5-b]pyridine;
8-[6-(thiazolo[4,5-b]pyridin-2-yloxy)-benzofuran-3-ylmethyl]-2,8-diaza-spiro[4.5]decane-2-carboxylic acid tert-butyl ester;
2-[3-(4-benzyl-piperidin-1-ylmethyl)-benzofuran-6-yloxy]-thiazolo[4,5-b]pyridine;

2-[3-(4-phenyl-piperidin-1-ylmethyl)-benzofuran-6-yloxy]-thiazolo[4,5-b]pyridine;
2-[3-(3,5-dimethyl-piperidin-1-ylmethyl)-benzofuran-6-yloxy]-thiazolo[4,5-b]pyridine;
dimethyl-{1-[6-(thiazolo[4,5-b]pyridin-2-yloxy)-benzofuran-3-ylmethyl]-piperidin-4-yl}-amine;
2-[3-(4-pyrrolidin-1-yl-piperidin-1-ylmethyl)-benzofuran-6-yloxy]-thiazolo[4,5-b]pyridine;
1'-[6-(thiazolo[4,5-b]pyridin-2-yloxy)-benzofuran-3-ylmethyl]-[1,4]bipiperidinyl;
2-[3-(4-morpholin-4-yl-piperidin-1-ylmethyl)-benzofuran-6-yloxy]-thiazolo[4,5-b]pyridine;
2-[3-(4-methyl-piperidin-1-ylmethyl)-benzofuran-6-yloxy]-thiazolo[4,5-b]pyridine;
2-[3-(4-phenyl-piperazin-1-ylmethyl)-benzofuran-6-yloxy]-thiazolo[4,5-b]pyridine;
2-[3-(4-pyridin-2-yl-piperazin-1-ylmethyl)-benzofuran-6-yloxy]-thiazolo[4,5-b]pyridine;
2-[3-(4-pyridin-4-yl-piperazin-1-ylmethyl)-benzofuran-6-yloxy]-thiazolo[4,5-b]pyridine;
2-{3-[4-(4-methoxy-phenyl)-piperazin-1-ylmethyl]-benzofuran-6-yloxy}-thiazolo[4,5-b]pyridine;
2-[3-(4-phenethyl-piperazin-1-ylmethyl)-benzofuran-6-yloxy]-thiazolo[4,5-b]pyridine;
2-[3-(4-pyrimidin-2-yl-piperazin-1-ylmethyl)-benzofuran-6-yloxy]-thiazolo[4,5-b]pyridine;
2-[6-(thiazolo[4,5-b]pyridin-2-yloxy)-benzofuran-3-ylmethyl]-1,2,3,4-tetrahydro-isoquinoline;
methyl-(1-methyl-piperidin-4-yl)-[6-(thiazolo[4,5-b]pyridin-2-yloxy)-benzofuran-3-ylmethyl]-amine;
meso-1-{3-[6-(thiazolo[4,5-b]pyridin-2-yloxy)-benzofuran-3-ylmethyl]-3,8-diaza-bicyclo[3.2.1]oct-8-yl}-ethanone;
meso-endo-N-{8-[6-(thiazolo[4,5-b]pyridin-2-yloxy)-furo[3,2-b]pyridin-2-ylmethyl]-8-aza-bicyclo[3.2.1]oct-3-yl}-acetamide;
cyclopropyl-[6-(thiazolo[4,5-b]pyridin-2-yloxy)-benzofuran-3-ylmethyl]-amine;
cyclopentyl-[6-(thiazolo[4,5-b]pyridin-2-yloxy)-benzofuran-3-ylmethyl]-amine;
cyclohexyl-[6-(thiazolo[4,5-b]pyridin-2-yloxy)-benzofuran-3-ylmethyl]-amine;
[6-(thiazolo[4,5-b]pyridin-2-yloxy)-benzofuran-3-ylmethyl]-thiophen-2-ylmethyl-amine;
tert-butyl-[6-(thiazolo[4,5-b]pyridin-2-yloxy)-benzofuran-3-ylmethyl]-amine;
2-[3-(4-tert-butyl-piperidin-1-ylmethyl)-benzofuran-6-yloxy]-thiazolo[4,5-b]pyridine;
propyl-[6-(thiazolo[4,5-b]pyridin-2-yloxy)-benzofuran-3-ylmethyl]-amine;
isobutyl-[6-(thiazolo[4,5-b]pyridin-2-yloxy)-benzofuran-3-ylmethyl]-amine;
(2-piperidin-1-yl-ethyl)-[6-(thiazolo[4,5-b]pyridin-2-yloxy)-benzofuran-3-ylmethyl]-amine;
(2-morpholin-4-yl-ethyl)-[6-(thiazolo[4,5-b]pyridin-2-yloxy)-benzofuran-3-ylmethyl]-amine;
N-{1-[6-(thiazolo[4,5-b]pyridin-2-yloxy)-benzofuran-3-ylmethyl]-pyrrolidin-3-yl}-acetamide;
2-[3-(4-isobutyl-piperazin-1-ylmethyl)-benzofuran-6-yloxy]-thiazolo[4,5-b]pyridine;
N-methyl-N-{1-[6-(thiazolo[4,5-b]pyridin-2-yloxy)-benzofuran-3-ylmethyl]-pyrrolidin-3-yl}-acetamide;
(S)—N-{1-[6-(thiazolo[4,5-b]pyridin-2-yloxy)-benzofuran-3-ylmethyl]-pyrrolidin-3-yl}-acetamide;
4-(2-{[6-(benzothiazol-2-yloxy)-benzofuran-3-ylmethyl]-amino}-ethyl)-benzenesulfonamide;
(S)-{1-[6-(benzothiazol-2-yloxy)-benzofuran-3-ylmethyl]-pyrrolidin-2-yl}-methanol;
{1-[6-(benzothiazol-2-yloxy)-benzofuran-3-ylmethyl]-piperidin-4-yl}-carbamic acid tert-butyl ester;
2-[3-(3-propoxy-azetidin-1-ylmethyl)-benzofuran-6-yloxy]-thiazolo[4,5-b]pyridine;
1-[6-(thiazolo[4,5-b]pyridin-2-yloxy)-benzofuran-3-ylmethyl]-azetidin-3-ol;
2-[3-(3,3-difluoro-azetidin-1-ylmethyl)-benzofuran-6-yloxy]-thiazolo[4,5-b]pyridine;
N,N-diethyl-N'-[6-(thiazolo[4,5-b]pyridin-2-yloxy)-benzofuran-3-ylmethyl]-ethane-1,2-diamine;
cyclohexyl-ethyl-[6-(thiazolo[4,5-b]pyridin-2-yloxy)-benzofuran-3-ylmethyl]-amine;
(2-phenoxy-ethyl)-[6-(thiazolo[4,5-b]pyridin-2-yloxy)-benzofuran-3-ylmethyl]-amine;
indan-2-yl-[6-(thiazolo[4,5-b]pyridin-2-yloxy)-benzofuran-3-ylmethyl]-amine;
phenethyl-[6-(thiazolo[4,5-b]pyridin-2-yloxy)-benzofuran-3-ylmethyl]-amine;
N-cyclopropyl-N-{1-[6-(thiazolo[4,5-b]pyridin-2-yloxy)-benzofuran-3-ylmethyl]-piperidin-4-yl}-acetamide;
N-isopropyl-N-{1-[6-(thiazolo[4,5-b]pyridin-2-yloxy)-benzofuran-3-ylmethyl]-piperidin-4-yl}-acetamide;
(R)—N-{1-[6-(thiazolo[4,5-b]pyridin-2-yloxy)-benzofuran-3-ylmethyl]-pyrrolidin-3-yl}-acetamide;
2-[3-(4-thiophen-2-ylmethyl-piperazin-1-ylmethyl)-benzofuran-6-yloxy]thiazolo[4,5-b]pyridine;
2-[3-(hexahydro-pyrrolo[1,2-a]pyrazin-2-ylmethyl)-benzofuran-6-yloxy]-thiazolo[4,5-b]pyridine;
diethyl-{1-[6-(thiazolo[4,5-b]pyridin-2-yloxy)-benzofuran-3-ylmethyl]-pyrrolidin-3-yl}-amine;
(R)-2-[3-(3-fluoro-pyrrolidin-1-ylmethyl)-benzofuran-6-yloxy]-thiazolo[4,5-b]pyridine;
diethyl-[5-(thiazolo[4,5-b]pyridin-2-yloxy)-benzofuran-2-ylmethyl]-amine;
2-[3-(5-fluoro-1,3-dihydro-isoindol-2-ylmethyl)-benzofuran-6-yloxy]-thiazolo[4,5-b]-pyridine;
2-[3-(1,3-dihydro-isoindol-2-ylmethyl)-benzofuran-6-yloxy]-thiazolo[4,5-b]pyridine;
meso-endo-1-(3-{[6-(thiazolo[4,5-b]pyridin-2-yloxy)-benzofuran-3-ylmethyl]-amino}-8-aza-bicyclo[3.2.1]oct-8-yl)-ethanone;
meso-exo-1-(3-{[6-(thiazolo[4,5-b]pyridin-2-yloxy)-benzofuran-3-ylmethyl]-amino}-8-aza-bicyclo[3.2.1]oct-8-yl)-ethanone;
3-{methyl-[6-(thiazolo[4,5-b]pyridin-2-yloxy)-benzofuran-3-ylmethyl]-amino}-propionic acid ethyl ester;
3-{methyl-[6-(thiazolo[4,5-b]pyridin-2-yloxy)-benzofuran-3-ylmethyl]-amino}-propionic acid;
meso-exo-N-{8-[6-(thiazolo[4,5-b]pyridin-2-yloxy)-furo[3,2-b]pyridin-2-ylmethyl]-8-aza-bicyclo[3.2.1]oct-3-yl}-acetamide;
(1S,4S)-5-[6-(thiazolo[4,5-b]pyridin-2-yloxy)-furo[3,2-b]pyridin-2-ylmethyl]-2,5-diaza-bicyclo[2.2.1]heptane-2-carboxylic acid amide;
meso-1-{8-[6-(thiazolo[4,5-b]pyridin-2-yloxy)-furo[3,2-b]pyridin-2-ylmethyl]-3,8-diaza-bicyclo[3.2.1]oct-3-yl}-ethanone;
(1S,4S)-1-{5-[6-(thiazolo[4,5-b]pyridin-2-yloxy)-furo[3,2-b]pyridin-2-ylmethyl]-2,5-diaza-bicyclo[2.2.2]oct-2-yl}-ethanone;
(1R,4R)-1-{5-[6-(thiazolo[4,5-b]pyridin-2-yloxy)-furo[3,2-b]pyridin-2-ylmethyl]-2,5-diaza-bicyclo[2.2.1]hept-2-yl}-ethanone;
1-{1-[6-(thiazolo[4,5-b]pyridin-2-yloxy)-furo[3,2-b]pyridin-2-ylmethyl]-piperidin-4-yl}-pyrrolidin-2-one;
4-[6-(thiazolo[4,5-b]pyridin-2-yloxy)-benzofuran-3-ylmethyl]-piperazin-2-one;
1-{4-[6-(thiazolo[4,5-b]pyridin-2-yloxy)-furo[3,2-b]pyridin-2-ylmethyl]-piperazin-1-yl}-ethanone;
benzyl-[6-(thiazolo[4,5-b]pyridin-2-yloxy)-benzofuran-3-ylmethyl]-amine;

(4-fluoro-benzyl)-[6-(thiazolo[4,5-b]pyridin-2-yloxy)-benzofuran-3-ylmethyl]-amine;
(4-methoxy-benzyl)-[6-(thiazolo[4,5-b]pyridin-2-yloxy)-benzofuran-3-ylmethyl]-amine;
4-(4-chloro-phenyl)-1-[6-(thiazolo[4,5-b]pyridin-2-yloxy)-benzofuran-3-ylmethyl]-piperidin-4-ol;
4-(4-bromo-phenyl)-1-[6-(thiazolo[4,5-b]pyridin-2-yloxy)-benzofuran-3-ylmethyl]-piperidin-4-ol;
2-[3-(2,6-dimethyl-morpholin-4-ylmethyl)-benzofuran-6-yloxy]-thiazolo[4,5-b]pyridine;
2-[3-(3-fluoro-piperidin-1-ylmethyl)-benzofuran-6-yloxy]-thiazolo[4,5-b]pyridine;
4-{1-[6-(thiazolo[4,5-b]pyridin-2-yloxy)-benzofuran-3-ylmethyl]-piperidin-4-yl}-2,4-dihydro-[1,2,4]triazol-3-one;
1-{7-[6-(thiazolo[4,5-b]pyridin-2-yloxy)-benzofuran-3-ylmethyl]-3,7-diaza-bicyclo[3.3.1]non-3-yl}-ethanone;
N-ethyl-N-{1-[6-(thiazolo[4,5-b]pyridin-2-yloxy)-benzofuran-3-ylmethyl]-piperidin-4-yl}-acetamide;
(tetrahydro-furan-3-yl)-{5-[6-(thiazolo[4,5-b]pyridin-2-yloxy)-benzofuran-3-ylmethyl]-hexahydro-pyrrolo[3,4-c]pyrrol-2-yl}-methanone;
2-hydroxy-1-{5-[6-(thiazolo[4,5-b]pyridin-2-yloxy)-benzofuran-3-ylmethyl]-hexahydro-pyrrolo[3,4-c]pyrrol-2-yl}-ethanone;
(1S,4S)-pyrazin-2-yl-{5-[6-(thiazolo[4,5-b]pyridin-2-yloxy)-benzofuran-3-ylmethyl]-2,5-diaza-bicyclo[2.2.1]hept-2-yl}-methanone;
(1S,4S)-cyclobutyl-{5-[6-(thiazolo[4,5-b]pyridin-2-yloxy)-benzofuran-3-ylmethyl]-2,5-diaza-bicyclo[2.2.1]hept-2-yl}-methanone;
(1S,4S)-isoxazol-5-yl-{5-[6-(thiazolo[4,5-b]pyridin-2-yloxy)-benzofuran-3-ylmethyl]-2,5-diaza-bicyclo[2.2.1]hept-2-yl}-methanone;
furan-3-yl-{5-[6-(thiazolo[4,5-b]pyridin-2-yloxy)-benzofuran-3-ylmethyl]-hexahydro-pyrrolo[3,4-c]pyrrol-2-yl}-methanone;
(1S,4S)-4-{5-[6-(thiazolo[4,5-b]pyridin-2-yloxy)-benzofuran-3-ylmethyl]-2,5-diaza-bicyclo[2.2.1]hept-2-ylmethyl}-benzoic acid methyl ester;
dimethyl-[6-(thiazolo[4,5-b]pyridin-2-yloxy)-benzofuran-3-ylmethyl]-amine;
(2-{1-[6-(benzothiazol-2-yloxy)-benzofuran-3-ylmethyl]-piperidin-4-yl}-ethyl)-carbamic acid tert-butyl ester;
N-{1-[6-(benzothiazol-2-yloxy)-benzofuran-3-ylmethyl]-piperidin-4-yl}-methanesulfonamide;
N-(2-{1-[6-(benzothiazol-2-yloxy)-benzofuran-3-ylmethyl]-piperidin-4-yl}-ethyl)-methanesulfonamide;
5-(thiazolo[4,5-b]pyridin-2-yloxy)-benzofuran-2-carboxylic acid benzyl-methyl-amide;
(1R,4R)-1-{5-[5-(thiazolo[4,5-b]pyridin-2-yloxy)-benzofuran-2-carbonyl]-2,5-diaza-bicyclo[2.2.1]hept-2-yl}-ethanone;
6-(thiazolo[4,5-b]pyridin-2-yloxy)-benzofuran-3-carboxylic acid methylamide;
N-{1-[6-(thiazolo[4,5-b]pyridin-2-yloxy)-benzofuran-3-carbonyl]-piperidin-4-yl}-acetamide;
meso-endo-N-{8-[6-(thiazolo[4,5-b]pyridin-2-yloxy)-benzofuran-3-carbonyl]-8-aza-bicyclo[3.2.1]oct-3-yl}-acetamide;
1-{1-[6-(thiazolo[4,5-b]pyridin-2-yloxy)-benzofuran-3-carbonyl]-piperidin-4-yl}-pyrrolidin-2-one;
(1S,4S)-1-{5-[6-(thiazolo[4,5-b]pyridin-2-yloxy)-benzofuran-3-carbonyl]-2,5-diaza-bicyclo[2.2.1]hept-2-yl}-ethanone;
1-{4-[6-(thiazolo[4,5-b]pyridin-2-yloxy)-benzofuran-3-carbonyl]-[1,4]diazepan-1-yl}-ethanone;
6-(thiazolo[4,5-b]pyridin-2-yloxy)-benzofuran-3-carboxylic acid isopropyl-methyl-amide;
meso-8-[6-(thiazolo[4,5-b]pyridin-2-yloxy)-benzofuran-3-carbonyl]-3,8-diaza-bicyclo[3.2.1]octane-3-carboxylic acid amide;
(1S,4S)-5-[6-(thiazolo[4,5-b]pyridin-2-yloxy)-benzofuran-3-carbonyl]-2,5-diaza-bicyclo[2.2.1]heptane-2-carboxylic acid amide;
(4-fluoro-piperidin-1-yl)-[6-(thiazolo[4,5-b]pyridin-2-yloxy)-benzofuran-3-yl]-methanone;
(4-phenyl-piperidin-1-yl)-[6-(thiazolo[4,5-b]pyridin-2-yloxy)-benzofuran-3-yl]-methanone;
1-[6-(thiazolo[4,5-b]pyridin-2-yloxy)-benzofuran-3-carbonyl]-piperidine-4-carboxylic acid amide;
(4-cyclohexyl-piperazin-1-yl)-[6-(thiazolo[4,5-b]pyridin-2-yloxy)-benzofuran-3-yl]-methanone;
1-{4-[6-(thiazolo[4,5-b]pyridin-2-yloxy)-benzofuran-3-carbonyl]-piperazin-1-yl}-ethanone;
6-(thiazolo[4,5-b]pyridin-2-yloxy)-benzofuran-3-carboxylic acid cyclohexyl-ethyl-amide;
[4-(pyrimidin-2-yloxy)-piperidin-1-yl]-[6-(thiazolo[4,5-b]pyridin-2-yloxy)-benzofuran-3-yl]-methanone;
piperidin-1-yl-[6-(thiazolo[4,5-b]pyridin-2-yloxy)-benzofuran-3-yl]-methanone;
[4-(piperidine-1-carbonyl)-piperidin-1-yl]-[6-(thiazolo[4,5-b]pyridin-2-yloxy)-benzofuran-3-yl]-methanone;
(octahydro-isoquinolin-2-yl)-[6-(thiazolo[4,5-b]pyridin-2-yloxy)-benzofuran-3-yl]-methanone;
(3,4-dihydro-1H-isoquinolin-2-yl)-[6-(thiazolo[4,5-b]pyridin-2-yloxy)-benzofuran-3-yl]-methanone;
(4-benzoyl-piperidin-1-yl)-[6-(thiazolo[4,5-b]pyridin-2-yloxy)-benzofuran-3-yl]methanone;
6-(thiazolo[4,5-b]pyridin-2-yloxy)-benzofuran-3-carboxylic acid (3-dimethylamino-propyl)-methyl-amide;
endo-bicyclo[2.2.1]heptane-2-carboxylic acid [6-(thiazolo[4,5-b]pyridin-2-yloxy)-benzofuran-3-ylmethyl]-amide;
2-(4-acetyl-piperazin-1-yl)-N-[6-(thiazolo[4,5-b]pyridin-2-yloxy)-benzofuran-3-ylmethyl]-acetamide;
2-(3-methyl-isoxazol-5-yl)-N-[6-(thiazolo[4,5-b]pyridin-2-yloxy)-benzofuran-3-ylmethyl]-acetamide;
4-hydroxy-cyclohexa necarboxylic acid [6-(thiazolo[4,5-b]pyridin-2-yloxy)-benzofuran-3-ylmethyl]-amide;
N-[6-(thiazolo[4,5-b]pyridin-2-yloxy)-benzofuran-3-ylmethyl]-terephthalamic acid methyl ester;
2-(4-chloro-phenyl)-N-[6-(thiazolo[4,5-b]pyridin-2-yloxy)-benzofuran-3-ylmethyl]-acetamide;
N-[6-(thiazolo[4,5-b]pyridin-2-yloxy)-benzofuran-3-ylmethyl]-acetamide;
N-[6-(thiazolo[4,5-b]pyridin-2-yloxy)-benzofuran-3-ylmethyl]-terephthalamic acid;
1-[6-(thiazolo[4,5-b]pyridin-2-yloxy)-benzofuran-3-ylmethyl]-3,4-dihydro-1H-quinolin-2-one;
1-[6-(thiazolo[4,5-b]pyridin-2-yloxy)-benzofuran-3-ylmethyl]-6-trifluoromethyl-1,3-dihydro-indol-2-one;
1-[6-(thiazolo[4,5-b]pyridin-2-yloxy)-benzofuran-3-ylmethyl]-1,3-d i hydro-indol-2-one;
1-[6-(thiazolo[4,5-b]pyridin-2-yloxy)-benzofuran-3-ylmethyl]-5-trifluoromethyl-1,3-dihydro-indol-2-one;
5-chloro-1-[6-(thiazolo[4,5-b]pyridin-2-yloxy)-benzofuran-3-ylmethyl]-1,3-dihydro-indol-2-one;
6-chloro-1-[6-(thiazolo[4,5-b]pyridin-2-yloxy)-benzofuran-3-ylmethyl]-1,3-dihydro-indol-2-one;
5-fluoro-1-[6-(thiazolo[4,5-b]pyridin-2-yloxy)-benzofuran-3-ylmethyl]-1,3-dihydro-indol-2-one;
(R)—N-(1-aza-bicyclo[2.2.2]oct-3-yl)-N-[6-(thiazolo[4,5-b]pyridin-2-yloxy)-benzofuran-3-ylmethyl]-acetamide;
2-(3-piperidin-1-ylmethyl-benzofuran-6-yloxy)-benzothiazole;
2-(2-piperidin-1-ylmethyl-benzofuran-6-yloxy)-benzothiazole;

and pharmaceutically acceptable salts and prodrugs thereof.

39. A method of treating a subject suffering from or diagnosed with a disease, disorder, or medical condition mediated by leukotriene $A_4$ hydrolase activity, comprising administering to a subject in need of such treatment an effective amount of at least one chemical entity selected from the group consisting of compounds of Formula (I), pharmaceutically acceptable salts of compounds of Formula (I), and pharmaceutically acceptable prodrugs of compounds of Formula (I)

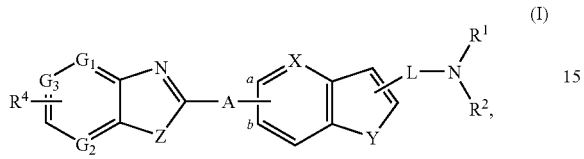
(I)

wherein

A is O, bound at site a or at site b;

Z is O or S;

$G_1$, $G_2$ and $G_3$ are each independently $CR^4$ or N;

$R^4$ is H, —$C_{1-4}$alkyl, or halo;

X is CH or N;

Y is O, S, or $NR^3$;

$R^3$ is H or —$C_{1-4}$alkyl;

when Y is O, then L is —$CH_2$—, —$CH_2CH_2$—, or —C(O)—;

when Y is S or $NR^3$, then L is —$CH_2$— or —$CH_2CH_2$—;

$R^1$ and $R^2$ are each independently H, —$C_{1-4}$alkyl, —C(O)$R^i$, —$(CH_2)_2$C(O)$OR^3$, —$(CH_2)_2$N$(CH_2CH_3)_2$, —$(CH_2)_3$N$(CH_3)_2$, —$C_{3-6}$cycloalkyl, —$(CH_2)_{1-4}$OCH$_3$, indan-2-yl,

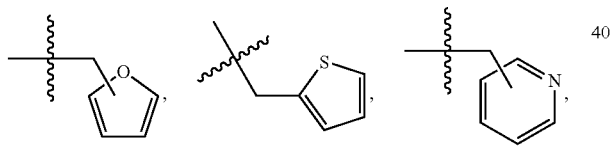

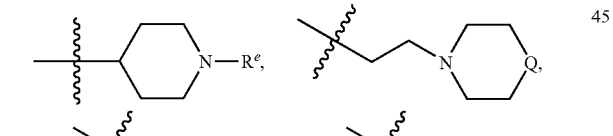

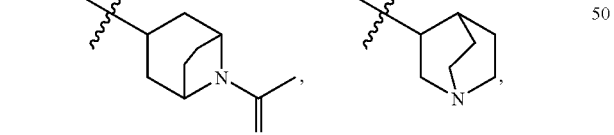

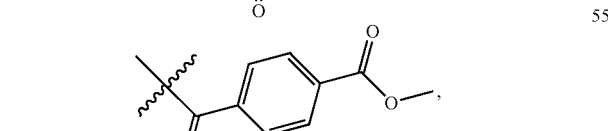

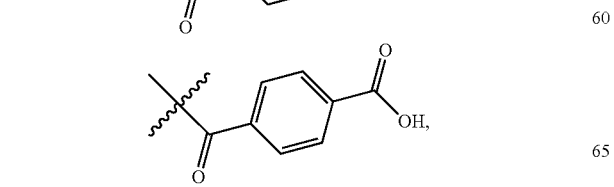

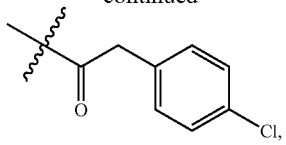

or —$(CH_2)_{0-2}$—(O)$_{0-1}$-phenyl
wherein said phenyl is optionally substituted with halo, —OCH$_3$, or —SO$_2$NH$_2$; provided that $R^1$ and $R^2$ are not both H simultaneously;

$R^i$ is —CH$_3$, 4-acetyl-piperazin-1-ylmethyl, 3-methyl-isoxazol-5-ylmethyl, 4-hydroxy-cyclohexyl, or

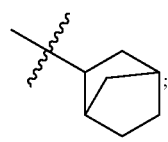 [SMILES: *C1CC2CCC1C2]

or
$R^1$ and $R^2$ are taken together as in one of the following assignments (i) and (ii);
(i) $R^1$ and $R^2$ taken together with the nitrogen member to which they are attached form an unbridged monocyclic moiety, said moiety optionally containing one additional heteroatom member selected from N, O, and S; said moiety being optionally substituted with $R^5$ and $(R^{5'})_m$;
m is 0 or 1;
when m is 1, $R^{5'}$ is —$C_{1-4}$alkyl, halo, or OH;
$R^5$ is selected from H; halo; =O; —OH; —OR$^3$; —CF$_3$; —S(O)(O)CH$_3$; —$C_{1-4}$alkyl; —OC$_{1-4}$alkyl; —C(CH$_3$)$_2$OH; —(CH$_2$)$_{0-1}$C(O)OR$^3$; —N(R$^3$)$_2$; —CH$_2$OH; —CH$_2$OCH$_3$; —(CH$_2$)$_{0-2}$NR$^9$C(O)R$^7$; —(CH$_2$)$_{0-2}$NHS(O)(O)CH$_3$; —C(O)R$^8$; —$C_{3-6}$cycloalkyl; pyrimidin-2-yloxy; 1-piperidinyl; 1-piperidinyl-2-one; 1-pyrrolidinyl; 4-morpholinyl; pyridinyl; pyrimidyl; thiophenylmethyl; 5-oxo-1; 5-dihydro-[1,2,4]triazol-4-yl; —(CH$_2$)$_{0-2}$-phenyl wherein said phenyl is optionally substituted with halo or OCH$_3$; and 1-pyrrolidinyl-2-one optionally substituted with —OH;
Q is CH$_2$ or O;
$R^7$ is —$C_{1-4}$alkyl, —NH$_2$, or —OC$_{1-4}$alkyl;
$R^8$ is —$C_{1-4}$alkyl; —NH$_2$; —NHCH$_3$; —$C_{3-6}$cycloalkyl; —(CH$_2$)$_{0-1}$phenyl wherein said phenyl is optionally substituted with halo or CO$_2$H; 1-pyrrolidinyl; or

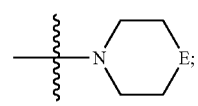

E is CH$_2$, O, or N(CH$_3$);
$R^9$ is H, —$C_{1-4}$alkyl, or —$C_{3-6}$cycloalkyl;
(ii) $R^1$ and $R^2$ taken together with the nitrogen member to which they are attached form one of the following

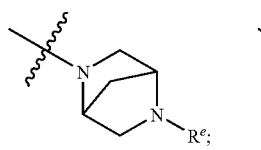 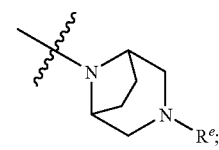

-continued

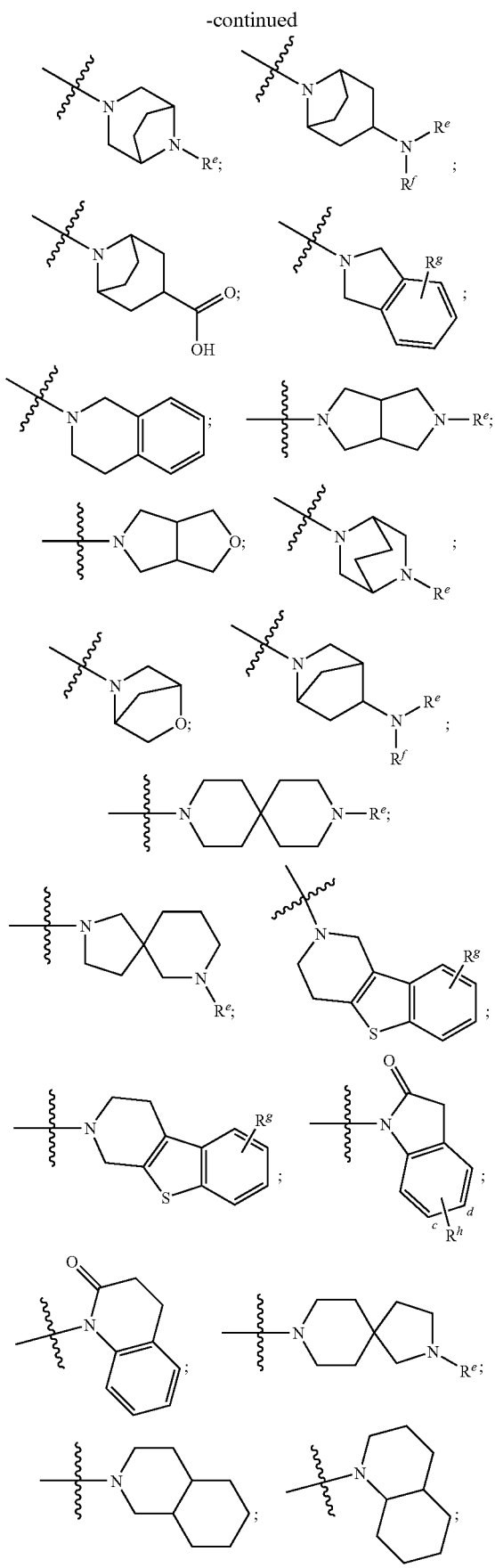

-continued

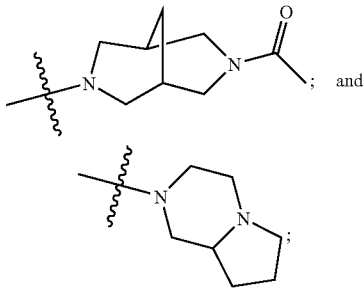

$R^e$ is H, —$C_{1-4}$alkyl, —C(O)$C_{1-4}$alkyl, —C(O)O$C_{1-4}$alkyl, —C(O)NH$_2$, —C(O)-tetrahydrofuranyl, —C(O)CH$_2$OH, —C(O)isoxazol-5-yl, —C(O)furan-3-yl, —C(O)pyrazin-2-yl, —C(O)cyclobutyl, —S(O)(O)CH$_3$, or 4-methoxycarbonyl-benzyl;

$R^f$ is H, —CH$_3$, or —CH$_2$C(O)O$R^3$;

$R^g$ is H or halo; and $R^h$ is bound at site c or d and is selected from H, CF$_3$, and halo.

40. A method as in claim 39, wherein the disease, disorder, or medical condition is inflammation.

41. A method as in claim 39, wherein the disease, disorder, or medical condition is selected from the group consisting of: inflammatory disorders, allergic disorders, dermatological disorders, autoimmune disease, lymphatic disorders, and immunodeficiency disorders.

42. A method as in claim 39, wherein the disease, disorder, or medical condition is selected from the group consisting of: allergy, abdominal aortic aneurysm, asthma, nasal polyps, allergic rhinitis, nasal itch, ocular inflammation, post-surgical ocular inflammation, conjunctivitis, uveitis, dry eye, psoriasis, pruritis, itch, itchy skin, atopic dermatitis, urticaria, hives, contact dermatitis, scleroderma, skin burns, acne, inflammatory bowel diseases, colitis, Crohn's disease, ulcerative colitis, chronic obstructive pulmonary disease, α1-antitrypsin (α1AT) deficiency, atherosclerosis, type II diabetes, arthritis, rheumatoid arthritis, multiple sclerosis, myocardial infarction, stroke, pain, gingivitis, bronchitis, cystic fibrosis, upper gastrointestinal cancer, sepsis, autoimmune thyroid diseases, immune-mediated diabetes mellitus, lupus, Myasthenia gravis, autoimmune neuropathies, Guillain-Barré, autoimmune uveitis, autoimmune hemolytic anemia, pernicious anemia, autoimmune thrombocytopenia, temporal arteritis, anti-phospholipid syndrome, vasculitides, Wegener's granulomatosis, Behcet's disease, dermatitis herpetiformis, pemphigus vulgaris, vitiligio, primary biliary cirrhosis, autoimmune hepatitis, autoimmune oophoritis and orchitis, autoimmune disease of the adrenal gland, polymyositis, dermatomyositis, spondyloarthropathies, ankylosing spondylitis, Sjogren syndrome, and Sjogren-Larsson syndrome.

43. A method as in claim 39, wherein the disease, disorder, or medical condition is selected from the group consisting of: allergy, aortic aneurysm, asthma, autoimmune diseases, pruritis, inflammatory bowel disease, ulcerative colitis, and cardiovascular disease.

44. A method as in claim 39, wherein said at least one chemical entity is selected from the group consisting of
2-(3-pyrrolidin-1-ylmethyl-1H-indol-6-yloxy)-benzothiazole;
2-(3-piperidin-1-ylmethyl-1H-indol-6-yloxy)-benzothiazole;
2-(3-morpholin-4-ylmethyl-1H-indol-6-yloxy)-benzothiazole;
2-[3-(4-methanesulfonyl-piperidin-1-ylmethyl)-1H-indol-6-yloxy]-benzothiazole;

[6-(benzothiazol-2-yloxy)-1H-indol-3-ylmethyl]-benzyl-methyl-amine;
2-[3-(1,3-dihydro-isoindol-2-ylmethyl)-1H-indol-6-yloxy]-benzothiazole;
2-[6-(benzothiazol-2-yloxy)-1H-indol-3-ylmethyl]-1,2,3,4-tetrahydro-isoquinoline;
2-[3-(4-phenyl-piperidin-1-ylmethyl)-1H-indol-6-yloxy]-benzothiazole;
2-(3-pyrrolidin-1-ylmethyl-1H-indol-5-yloxy)-benzothiazole;
2-(3-piperidin-1-ylmethyl-1H-indol-5-yloxy)-benzothiazole;
2-(3-morpholin-4-ylmethyl-1H-indol-5-yloxy)-benzothiazole;
(1S,4S)-2-[3-(2-oxa-5-aza-bicyclo[2.2.1]hept-5-ylmethyl)-1H-indol-6-yloxy]-benzothiazole;
meso-endo-N-{8-[6-(benzothiazol-2-yloxy)-1H-indol-3-ylmethyl]-8-aza-bicyclo[3.2.1]oct-3-yl}-acetamide;
meso-endo-N-{8-[6-(4-fluoro-benzothiazol-2-yloxy)-1H-indol-3-ylmethyl]-8-aza-bicyclo[3.2.1]oct-3-yl}-acetamide;
2-(3-piperidin-1-ylmethyl-1H-indol-6-yloxy)-benzooxazole;
2-(3-piperidin-1-ylmethyl-1H-indol-6-yloxy)-thiazolo[4,5-b]pyridine;
1-[6-(thiazolo[4,5-b]pyridin-2-yloxy)-1H-indol-3-ylmethyl]-piperidine-4-carboxylic acid amide;
meso-endo-N-{8-[6-(thiazolo[4,5-b]pyridin-2-yloxy)-1H-indol-3-ylmethyl]-8-aza-bicyclo[3.2.1]oct-3-yl}-acetamide;
(1S,4S)-1-{5-[6-(thiazolo[4,5-b]pyridin-2-yloxy)-1H-indol-3-ylmethyl]-2,5-diaza-bicyclo[2.2.1]hept-2-yl}-ethanone;
1-{1-[6-(thiazolo[4,5-b]pyridin-2-yloxy)-1H-indol-3-ylmethyl]-piperidin-4-yl}-pyrrolidin-2-one;
1-[6-(benzothiazol-2-yloxy)-1H-indol-3-ylmethyl]-piperidine-4-carboxylic acid amide;
1-[6-(benzothiazol-2-yloxy)-1H-indol-3-ylmethyl]-piperidine-4-carboxylic acid methylamide;
{1-[6-(benzothiazol-2-yloxy)-1H-indol-3-ylmethyl]-piperidin-4-yl}-pyrrolidin-1-yl-methanone;
{1-[6-(benzothiazol-2-yloxy)-1H-indol-3-ylmethyl]-piperidin-4-yl}-piperidin-1-yl-methanone;
{1-[6-(benzothiazol-2-yloxy)-1H-indol-3-ylmethyl]-piperidin-4-yl}-morpholin-4-yl-methanone;
{1-[6-(benzothiazol-2-yloxy)-1H-indol-3-ylmethyl]-piperidin-4-yl}-(4-methyl-piperazin-1-yl)-methanone;
(3S)-1-[6-(benzothiazol-2-yloxy)-1H-indol-3-ylmethyl]-piperidine-3-carboxylic acid amide;
{1-[6-(benzothiazol-2-yloxy)-1H-indol-3-ylmethyl]-piperidin-4-yl}-methanol;
{1-[6-(benzothiazol-2-yloxy)-1H-indol-3-ylmethyl]-piperidin-4-yl}-carbamic acid ethyl ester;
1-{1-[6-(benzothiazol-2-yloxy)-1H-indol-3-ylmethyl]-piperidin-4-yl}-pyrrolidin-2-one;
2-(3-piperidin-1-ylmethyl-1H-pyrrolo[3,2-b]pyridin-6-yloxy)-benzothiazole;
2-(3-morpholin-4-ylmethyl-1H-pyrrolo[3,2-b]pyridin-6-yloxy)-benzothiazole;
1-[6-(benzothiazol-2-yloxy)-1H-pyrrolo[3,2-b]pyridin-3-ylmethyl]-piperidine-4-carboxylic acid amide;
2-[6-(thiazolo[4,5-b]pyridin-2-yloxy)-1H-indol-3-ylmethyl]-1,2,3,4-tetrahydro-benzo[4,5]thieno[3,2-c]pyridine;
2-[6-(thiazolo[4,5-b]pyridin-2-yloxy)-1H-indol-3-ylmethyl]-1,2,3,4-tetrahydro-benzo[4,5]thieno[2,3-c]pyridine;
8-chloro-2-[6-(thiazolo[4,5-b]pyridin-2-yloxy)-1H-indol-3-ylmethyl]-1,2,3,4-tetrahydro-benzo[4,5]thieno[3,2-c]pyridine;
6-chloro-2-[6-(thiazolo[4,5-b]pyridin-2-yloxy)-1H-indol-3-ylmethyl]-1,2,3,4-tetrahydro-benzo[4,5]thieno[2,3-c]pyridine;
8-fluoro-2-[6-(thiazolo[4,5-b]pyridin-2-yloxy)-1H-indol-3-ylmethyl]-1,2,3,4-tetrahydro-benzo[4,5]thieno[3,2-c]pyridine;
2-[6-(benzothiazol-2-yloxy)-1H-indol-3-ylmethyl]-1,2,3,4-tetrahydro-benzo[4,5]thieno[3,2-c]pyridine;
2-(3-morpholin-4-ylmethyl-1H-indol-6-yloxy)-thiazolo[4,5-b]pyridine;
(3S)-2-[3-(3-Methyl-morpholin-4-ylmethyl)-1H-indol-6-yloxy]-thiazolo[4,5-b]pyridine;
2-(3-thiomorpholin-4-ylmethyl-1H-indol-6-yloxy)-thiazolo[4,5-b]pyridine;
meso-endo-N-{8-[6-(Thiazolo[5,4-b]pyridin-2-yloxy)-1H-indol-3-ylmethyl]-8-aza-bicyclo[3.2.1]oct-3-yl}-acetamide;
(4R)-1-{1-[6-(benzothiazol-2-yloxy)-1H-indol-3-ylmethyl]-piperidin-4-yl}-4-hydroxy-pyrrolidin-2-one;
1-[6-(benzothiazol-2-yloxy)-1H-indol-3-ylmethyl]-piperidine-4-carboxylic acid;
{1-[6-(benzothiazol-2-yloxy)-1H-indol-3-ylmethyl]-piperidin-4-yl}-acetic acid;
1-[6-(benzothiazol-2-yloxy)-1H-indol-3-ylmethyl]-piperidine-3-carboxylic acid;
meso-endo-(acetyl-{8-[6-(benzothiazol-2-yloxy)-1H-indol-3-ylmethyl]-8-aza-bicyclo[3.2.1]oct-3-yl}-amino)-acetic acid;
meso-endo-(acetyl-{8-[5-(benzothiazol-2-yloxy)-1H-indol-3-ylmethyl]-8-aza-bicyclo[3.2.1]oct-3-yl}-amino)-acetic acid;
1-[6-(benzothiazol-2-yloxy)-1H-indol-3-ylmethyl]-piperidin-4-ylamine;
2-[3-(hexahydro-pyrrolo[3,4-c]pyrrol-2-ylmethyl)-1H-indol-6-yloxy]-benzothiazole;
(1S,4S)-2-[3-(2,5-diaza-bicyclo[2.2.1]hept-2-ylmethyl)-1H-indol-6-yloxy]-benzothiazole;
N-{1-[6-(benzothiazol-2-yloxy)-1H-indol-3-ylmethyl]-piperidin-4-yl}-acetamide;
1-{5-[6-(benzothiazol-2-yloxy)-1H-indol-3-ylmethyl]-hexahydro-pyrrolo[3,4-c]pyrrol-2-yl}-ethanone;
(1S,4S)-1-{5-[6-(benzothiazol-2-yloxy)-1H-indol-3-ylmethyl]-2,5-diaza-bicyclo[2.2.1]hept-2-yl}-ethanone;
2-(3-morpholin-4-ylmethyl-1H-indol-6-yloxy)-thiazolo[4,5-b]pyrazine;
7-methyl-2-(3-morpholin-4-ylmethyl-1H-indol-6-yloxy)-thiazolo[4,5-b]pyridine;
6-fluoro-2-(3-morpholin-4-ylmethyl-1H-indol-6-yloxy)-thiazolo[4,5-b]pyridine;
6-chloro-2-(3-morpholin-4-ylmethyl-1H-indol-6-yloxy)-thiazolo[4,5-b]pyridine;
6-fluoro-2-(3-morpholin-4-ylmethyl-1H-indol-6-yloxy)-thiazolo[5,4-b]pyridine;
2-(1-methyl-3-morpholin-4-ylmethyl-1H-indol-6-yloxy)-benzothiazole;
2-(1-ethyl-2-piperidin-1-ylmethyl-1H-indol-5-yloxy)-benzothiazole;
2-(1-ethyl-2-morpholin-4-ylmethyl-1H-indol-5-yloxy)-benzothiazole;
2-(1-ethyl-2-pyrrolidin-1-ylmethyl-1H-indol-5-yloxy)-benzothiazole;
2-(2-piperidin-1-ylmethyl-1H-indol-5-yloxy)-benzothiazole;
2-(2-pyrrolidin-1-ylmethyl-1H-indol-5-yloxy)-benzothiazole;
2-(2-piperidin-1-ylmethyl-1H-indol-6-yloxy)-benzothiazole;
2-(2-pyrrolidin-1-ylmethyl-1H-indol-6-yloxy)-benzothiazole;

1-[6-(benzothiazol-2-yloxy)-1H-indol-2-ylmethyl]-piperidine-4-carboxylic acid amide;
meso-endo-N-{8-[6-(benzothiazol-2-yloxy)-1H-indol-2-ylmethyl]-8-aza-bicyclo[3.2.1]oct-3-yl}-acetamide;
2-(2-piperidin-1-ylmethyl-1H-indol-6-yloxy)-thiazolo[4,5-b]pyridine;
meso-endo-N-{8-[6-(thiazolo[4,5-b]pyridin-2-yloxy)-1H-indol-2-ylmethyl]-8-aza-bicyclo[3.2.1]oct-3-yl}-acetamide;
1-{2-[5-(benzothiazol-2-yloxy)-1H-indol-3-yl]-ethyl}-piperidine-4-carboxylic acid;
2-[3-(2-piperidin-1-yl-ethyl)-1H-indol-5-yloxy]-benzothiazole;
1-{2-[5-(benzothiazol-2-yloxy)-1H-indol-3-yl]-ethyl}-piperidine-4-carboxylic acid amide;
1-[5-(benzothiazol-2-yloxy)-benzofuran-2-ylmethyl]-piperidine-4-carboxylic acid;
1-[6-(benzothiazol-2-yloxy)-benzofuran-2-ylmethyl]-piperidine-4-carboxylic acid;
{1-[6-(benzothiazol-2-yloxy)-benzofuran-2-ylmethyl]-piperidin-4-yl}-acetic acid;
{4-[6-(benzothiazol-2-yloxy)-benzofuran-2-ylmethyl]-piperazin-1-yl}-acetic acid;
1-{2-[6-(benzothiazol-2-yloxy)-benzofuran-3-yl]-ethyl}-piperidine-4-carboxylic acid;
meso-endo-{8-[6-(benzothiazol-2-yloxy)-benzofuran-2-ylmethyl]-8-aza-bicyclo[3.2.1]oct-3-ylamino}-acetic acid;
2-(2-piperidin-1-ylmethyl-benzofuran-5-yloxy)-benzothiazole;
meso-endo-N-{8-[5-(benzothiazol-2-yloxy)-benzofuran-2-ylmethyl]-8-aza-bicyclo[3.2.1]oct-3-yl}-acetamide;
4-fluoro-2-(2-piperidin-1-ylmethyl-benzofuran-5-yloxy)-benzothiazole;
meso-endo-N-{8-[5-(4-fluoro-benzothiazol-2-yloxy)-benzofuran-2-ylmethyl]-8-aza-bicyclo[3.2.1]oct-3-yl}-acetamide;
2-(2-piperidin-1-ylmethyl-benzofuran-5-yloxy)-thiazolo[4,5-b]pyridine;
meso-endo-N-{8-[5-(thiazolo[4,5-b]pyridin-2-yloxy)-benzofuran-2-ylmethyl]-8-aza-bicyclo[3.2.1]oct-3-yl}-acetamide;
1-[5-(thiazolo[4,5-b]pyridin-2-yloxy)-benzofuran-2-ylmethyl]-piperidine-4-carboxylic acid amide;
2-{2-[4-(pyrimidin-2-yloxy)-piperidin-1-ylmethyl]-benzofuran-5-yloxy}-thiazolo[4,5-b]-pyridine;
1-{5-[5-(thiazolo[4,5-b]pyridin-2-yloxy)-benzofuran-2-ylmethyl]-hexahydro-pyrrolo[3,4-c]pyrrol-2-yl}-ethanone;
5-[5-(thiazolo[4,5-b]pyridin-2-yloxy)-benzofuran-2-ylmethyl]-hexahydro-pyrrolo[3,4-c]pyrrole-2-carboxylic acid amide;
2-[2-(4-methanesulfonyl-piperidin-1-ylmethyl)-benzofuran-5-yloxy]-thiazolo[4,5-b]-pyridine;
meso-1-{8-[5-(thiazolo[4,5-b]pyridin-2-yloxy)-benzofuran-2-ylmethyl]-3,8-diaza-bicyclo[3.2.1]oct-3-yl}-ethanone;
meso-8-[5-(thiazolo[4,5-b]pyridin-2-yloxy)-benzofuran-2-ylmethyl]-3,8-diaza-bicyclo[3.2.1]octane-3-carboxylic acid amide;
(1S,4S)-1-{5-[5-(thiazolo[4,5-b]pyridin-2-yloxy)-benzofuran-2-ylmethyl]-2,5-diaza-bicyclo[2.2.1]hept-2-yl}-ethanone;
1-{1-[5-(thiazolo[4,5-b]pyridin-2-yloxy)-benzofuran-2-ylmethyl]-piperidin-4-yl}-pyrrolidin-2-one;
2-(2-morpholin-4-ylmethyl-benzofuran-5-yloxy)-thiazolo[4,5-b]pyridine;
(3S)-2-[2-(3-methyl-morpholin-4-ylmethyl)-benzofuran-5-yloxy]-thiazolo[4,5-b]pyridine;
(1S,4S)-2-[2-(2-oxa-5-aza-bicyclo[2.2.1]hept-5-ylmethyl)-benzofuran-5-yloxy]-thiazolo[4,5-b]pyridine;
(1S,4S)-5-[5-(thiazolo[4,5-b]pyridin-2-yloxy)-benzofuran-2-ylmethyl]-2,5-diaza-bicyclo[2.2.1]heptane-2-carboxylic acid amide;
(1R,4R)-5-[5-(thiazolo[4,5-b]pyridin-2-yloxy)-benzofuran-2-ylmethyl]-2,5-diaza-bicyclo[2.2.1]heptane-2-carboxylic acid amide;
(1R,4R)-1-{5-[5-(thiazolo[4,5-b]pyridin-2-yloxy)-benzofuran-2-ylmethyl]-2,5-diaza-bicyclo[2.2.1]hept-2-yl}-ethanone;
meso-endo-N-{8-[5-(thiazolo[4,5-b]pyridin-2-yloxy)-benzofuran-2-ylmethyl]-8-aza-bicyclo[3.2.1]oct-3-yl}-urea;
meso-exo-N-{8-[5-(thiazolo[4,5-b]pyridin-2-yloxy)-benzofuran-2-ylmethyl]-8-aza-bicyclo[3.2.1]oct-3-yl}-acetamide;
1-[5-(benzothiazol-2-yloxy)-benzofuran-2-ylmethyl]-piperidine-4-carboxylic acid amide;
meso-exo-N-{8-[6-(thiazolo[4,5-b]pyridin-2-yloxy)-benzofuran-2-ylmethyl]-8-aza-bicyclo[3.2.1]oct-3-yl}-acetamide;
(1R,4R)-1-{5-[6-(thiazolo[4,5-b]pyridin-2-yloxy)-benzofuran-2-ylmethyl]-2,5-diaza-bicyclo[2.2.1]hept-2-yl}-ethanone;
1-{1-[6-(thiazolo[4,5-b]pyridin-2-yloxy)-benzofuran-2-ylmethyl]-piperidin-4-yl}-pyrrolidin-2-one;
(1S,4S)-2-[2-(2-oxa-5-aza-bicyclo[2.2.1]hept-5-ylmethyl)-benzofuran-6-yloxy]-thiazolo[4,5-b]pyridine;
2-[2-(tetrahydro-furo[3,4-c]pyrrol-5-ylmethyl)-benzofuran-6-yloxy]-thiazolo[4,5-b]pyridine;
2-[2-(4-fluoro-piperidin-1-ylmethyl)-benzofuran-5-yloxy]-thiazolo[4,5-b]pyridine;
dimethyl-[5-(thiazolo[4,5-b]pyridin-2-yloxy)-benzofuran-2-ylmethyl]-amine;
2-[2-(tetrahydro-furo[3,4-c]pyrrol-5-ylmethyl)-benzofuran-5-yloxy]-thiazolo[4,5-b]pyridine;
benzyl-methyl-[5-(thiazolo[4,5-b]pyridin-2-yloxy)-benzofuran-2-ylmethyl]-amine;
2-(2-morpholin-4-ylmethyl-benzofuran-6-yloxy)-thiazolo[4,5-b]pyridine;
1-[6-(thiazolo[4,5-b]pyridin-2-yloxy)-benzofuran-2-ylmethyl]-piperidine-4-carboxylic acid amide;
(1S,4S)-5-[6-(thiazolo[4,5-b]pyridin-2-yloxy)-benzofuran-2-ylmethyl]-2,5-diaza-bicyclo[2.2.1]heptane-2-carboxylic acid amide;
meso-endo-N-{8-[6-(thiazolo[4,5-b]pyridin-2-yloxy)-benzofuran-2-ylmethyl]-8-aza-bicyclo[3.2.1]oct-3-yl}-acetamide;
meso-1-{8-[6-(thiazolo[4,5-b]pyridin-2-yloxy)-benzofuran-2-ylmethyl]-3,8-diaza-bicyclo[3.2.1]oct-3-yl}-ethanone;
N-(1-{[6-([1,3]thiazolo[4,5-b]pyridin-2-yloxy)-1-benzofuran-2-yl]methyl}pyrrolidin-3-yl)acetamide;
(1S,4S)-1-{5-[5-(thiazolo[5,4-b]pyridin-2-yloxy)-benzofuran-2-ylmethyl]-2,5-diaza-bicyclo[2.2.1]hept-2-yl}-ethanone;
(1S,4S)-1-{5-[6-(thiazolo[5,4-b]pyridin-2-yloxy)-benzofuran-2-ylmethyl]-2,5-diaza-bicyclo[2.2.1]hept-2-yl}-ethanone;
meso-1-{8-[5-(thiazolo[5,4-b]pyridin-2-yloxy)-benzofuran-2-ylmethyl]-3,8-diaza-bicyclo[3.2.1]oct-3-yl}-ethanone;
meso-1-{8-[6-(thiazolo[5,4-b]pyridin-2-yloxy)-benzofuran-2-ylmethyl]-3,8-diaza-bicyclo[3.2.1]oct-3-yl}-ethanone;
meso-endo-N-{8-[5-(thiazolo[5,4-b]pyridin-2-yloxy)-benzofuran-2-ylmethyl]-8-aza-bicyclo[3.2.1]oct-3-yl}-acetamide;

meso-endo-N-{8-[6-(thiazolo[5,4-b]pyridin-2-yloxy)-benzofuran-2-ylmethyl]-8-aza-bicyclo[3.2.1]oct-3-yl}-acetamide;
1-(1-{[6-([1,3]thiazolo[4,5-b]pyridin-2-yloxy)-1-benzofuran-2-yl]methyl}pyrrolidin-3-yl)urea;
N-(1-{[6-([1,3]thiazolo[4,5-b]pyridin-2-yloxy)-1-benzofuran-2-yl]methyl}pyrrolidin-3-yl)methanesulfonamide;
meso-endo-N-(8-{2-[6-(benzothiazol-2-yloxy)-benzofuran-3-yl]-ethyl}-8-aza-bicyclo[3.2.1]oct-3-yl)-acetamide;
meso-1-(8-{2-[6-(thiazolo[4,5-b]pyridin-2-yloxy)-benzofuran-3-yl]-ethyl}-3,8-diaza-bicyclo[3.2.1]oct-3-yl)-ethanone;
meso-endo-N-(8-{2-[6-(thiazolo[4,5-b]pyridin-2-yloxy)-benzofuran-3-yl]-ethyl}-8-aza-bicyclo[3.2.1]oct-3-yl)-acetamide;
2-(2-piperidin-1-ylmethyl-benzo[b]thiophen-6-yloxy)-benzothiazole;
(2-morpholin-4-ylmethyl-benzo[b]thiophen-6-yloxy)-benzothiazole;
meso-endo-N-{8-[6-(benzothiazol-2-yloxy)-benzo[b]thiophen-2-ylmethyl]-8-aza-bicyclo[3.2.1]oct-3-yl}-acetamide;
meso-endo-N-{8-[6-(thiazolo[4,5-b]pyridin-2-yloxy)-benzo[b]thiophen-2-ylmethyl]-8-aza-bicyclo[3.2.1]oct-3-yl}-acetamide;
2-(2-piperidin-1-ylmethyl-benzo[b]thiophen-6-yloxy)-thiazolo[4,5-b]pyridine;
2-(3-morpholin-4-ylmethyl-benzo[b]thiophen-6-yloxy)-thiazolo[4,5-b]pyridine;
1-[6-(thiazolo[4,5-b]pyridin-2-yloxy)-benzo[b]thiophen-2-ylmethyl]-piperidine-4-carboxylic acid amide;
1-[6-(benzothiazol-2-yloxy)-1H-indol-3-ylmethyl]-piperidine-4-carboxylic acid ethyl ester;
1-[6-(thiazolo[5,4-b]pyridin-2-yloxy)-1H-indol-3-ylmethyl]-piperidine-4-carboxylic acid ethyl ester;
{1-[6-(benzothiazol-2-yloxy)-1H-indol-3-ylmethyl]-piperidin-4-yl}-acetic acid methyl ester;
meso-endo-(acetyl-{8-[6-(benzothiazol-2-yloxy)-1H-indol-3-ylmethyl]-8-aza-bicyclo[3.2.1]oct-3-yl}-amino)-acetic acid ethyl ester;
meso-endo-(acetyl-{8-[5-(benzothiazol-2-yloxy)-1H-indol-3-ylmethyl]-8-aza-bicyclo[3.2.1]oct-3-yl}-amino)-acetic acid ethyl ester;
(3R)-[6-(benzothiazol-2-yloxy)-1H-indol-3-ylmethyl]-piperidine-3-carboxylic acid ethyl ester;
{1-[6-(benzothiazol-2-yloxy)-1H-indol-3-ylmethyl]-piperidin-4-yl}-carbamic acid tert-butyl ester;
5-[6-(benzothiazol-2-yloxy)-1H-indol-3-ylmethyl]-hexahydro-pyrrolo[3,4-c]pyrrole-2-carboxylic acid tert-butyl ester;
(1S,4S)-5-[6-(benzothiazol-2-yloxy)-1H-indol-3-ylmethyl]-2,5-diaza-bicyclo[2.2.1]heptane-2-carboxylic acid tert-butyl ester;
1-{2-[5-(benzothiazol-2-yloxy)-1H-indol-3-yl]-ethyl}-piperidine-4-carboxylic acid ethyl ester;
1-{2-[6-(benzothiazol-2-yloxy)-benzofuran-3-yl]-ethyl}-piperidine-4-carboxylic acid ethyl ester;
meso-endo-({8-[6-(benzothiazol-2-yloxy)-benzofuran-2-ylmethyl]-8-aza-bicyclo[3.2.1]oct-3-yl}-tert-butoxy-carbonyl-amino)-acetic acid tert-butyl ester;
{1-[6-(thiazolo[4,5-b]pyridin-2-yloxy)-benzofuran-2-ylmethyl]-pyrrolidin-3-yl}-carbamic acid tert-butyl ester;
1-[6-(thiazolo[4,5-b]pyridin-2-yloxy)-benzofuran-2-ylmethyl]-pyrrolidin-3-ylamine;
1-{8-[6-(thiazolo[4,5-b]pyridin-2-yloxy)-benzofuran-2-ylmethyl]-3,8-diaza-bicyclo[3.2.1]oct-3-yl}-ethanone;
(1S,4S)-1-{5-[6-(thiazolo[4,5-b]pyridin-2-yloxy)-benzofuran-3-ylmethyl]-2,5-diaza-bicyclo[2.2.1]hept-2-yl}-ethanone;
meso-endo-N-{8-[6-(thiazolo[4,5-b]pyridin-2-yloxy)-benzofuran-3-ylmethyl]-8-aza-bicyclo[3.2.1]oct-3-yl}-acetamide;
2-(3-morpholin-4-ylmethyl-benzofuran-6-yloxy)-thiazolo[4,5-b]pyridine;
(1R,4R)-1-{5-[6-(thiazolo[4,5-b]pyridin-2-yloxy)-benzofuran-3-ylmethyl]-2,5-diaza-bicyclo[2.2.1]hept-2-yl}-ethanone;
(1S,4S)-2-[3-(2-oxa-5-aza-bicyclo[2.2.1]hept-5-ylmethyl)-benzofuran-6-yloxy]-thiazolo[4,5-b]pyridine;
(S)-2-[3-(3-methyl-morpholin-4-ylmethyl)-benzofuran-6-yloxy]-thiazolo[4,5-b]pyridine;
(1R,4R)-5-[6-(thiazolo[4,5-b]pyridin-2-yloxy)-benzofuran-3-ylmethyl]-2,5-diaza-bicyclo[2.2.1]heptane-2-carboxylic acid amide;
5-[6-(thiazolo[4,5-b]pyridin-2-yloxy)-benzofuran-3-ylmethyl]-hexahydro-pyrrolo[3,4-c]pyrrole-2-carboxylic acid amide;
N-{1-[6-(thiazolo[4,5-b]pyridin-2-yloxy)-benzofuran-3-ylmethyl]-piperidin-4-ylmethyl}-acetamide;
2-[3-(4-trifluoromethyl-piperidin-1-ylmethyl)-benzofuran-6-yloxy]-thiazolo[4,5-b]pyridine;
(1S,4S)-1-{5-[6-(benzothiazol-2-yloxy)-benzofuran-3-ylmethyl]-2,5-diaza-bicyclo[2.2.1]hept-2-yl}-ethanone;
2-(3-morpholin-4-ylmethyl-benzofuran-6-yloxy)-benzothiazole;
1-{2-[5-(thiazolo[4,5-b]pyridin-2-yloxy)-benzofuran-2-ylmethyl]-2,7-diaza-spiro[4.5]dec-7-yl}-ethanone;
1-{9-[5-(thiazolo[4,5-b]pyridin-2-yloxy)-benzofuran-2-ylmethyl]-3,9-diaza-spiro[5.5]undec-3-yl}-ethanone;
(1S,4S)-1-{5-[6-(thiazolo[4,5-b]pyridin-2-yloxy)-benzofuran-2-ylmethyl]-2,5-diaza-bicyclo[2.2.1]hept-2-yl}-ethanone;
meso-1-{5-[5-(thiazolo[4,5-b]pyridin-2-yloxy)-benzofuran-2-ylmethyl]-2,5-diaza-bicyclo[2.2.2]oct-2-yl}-ethanone;
meso-1-{5-[6-(thiazolo[4,5-b]pyridin-2-yloxy)-benzofuran-2-ylmethyl]-2,5-diaza-bicyclo[2.2.2]oct-2-yl}-ethanone;
1-{4-[6-(thiazolo[4,5-b]pyridin-2-yloxy)-benzofuran-2-ylmethyl]-piperazin-1-yl}-ethanone;
meso-endo-{8-[6-(thiazolo[4,5-b]pyridin-2-yloxy)-benzofuran-2-ylmethyl]-8-aza-bicyclo[3.2.1]oct-3-yl}-urea;
meso-8-[5-(benzothiazol-2-yloxy)-benzofuran-2-ylmethyl]-3,8-diaza-bicyclo[3.2.1]octane-3-carboxylic acid amide;
(1S,4S)-5-[5-(thiazolo[4,5-b]pyridin-2-yloxy)-benzofuran-2-ylmethyl]-2,5-diaza-bicyclo[2.2.1]heptane-2-carboxylic acid amide;
meso-endo-{8-[6-(thiazolo[4,5-b]pyridin-2-yloxy)-benzofuran-3-ylmethyl]-8-aza-bicyclo[3.2.1]oct-3-yl}-urea;
furan-2-ylmethyl-methyl-[6-(thiazolo[4,5-b]pyridin-2-yloxy)-benzofuran-3-ylmethyl]-amine;
methyl-pyridin-4-ylmethyl-[6-(thiazolo[4,5-b]pyridin-2-yloxy)-benzofuran-3-ylmethyl]-amine;
methyl-pyridin-3-ylmethyl-[6-(thiazolo[4,5-b]pyridin-2-yloxy)-benzofuran-3-ylmethyl]-amine;
1-{1-[6-(benzothiazol-2-yloxy)-benzofuran-3-ylmethyl]-piperidin-4-yl}-pyrrolidin-2-one;
N-{1-[6-(benzothiazol-2-yloxy)-benzofuran-3-ylmethyl]-piperidin-4-yl}-acetamide;
meso-endo-N-{8-[6-(benzothiazol-2-yloxy)-benzofuran-3-ylmethyl]-8-aza-bicyclo[3.2.1]oct-3-yl}-acetamide;
1-{4-[6-(thiazolo[4,5-b]pyridin-2-yloxy)-benzofuran-3-ylmethyl]-[1,4]diazepan-1-yl}-ethanone;

2-[3-(4-methanesulfonyl-piperidin-1-ylmethyl)-benzofuran-6-yloxy]-thiazolo[4,5-b]pyridine;
(2-methoxy-ethyl)-methyl-[6-(thiazolo[4,5-b]pyridin-2-yloxy)-benzofuran-3-ylmethyl]-amine;
2-(3-pyrrolidin-1-ylmethyl-benzofuran-6-yloxy)-thiazolo[4,5-b]pyridine;
(2S)-2-[3-(2-methoxymethyl-pyrrolidin-1-ylmethyl)-benzofuran-6-yloxy]-thiazolo[4,5-b]pyridine;
(1S,4S,5S)—N-{2-[6-(thiazolo[4,5-b]pyridin-2-yloxy)-benzofuran-3-ylmethyl]-2-aza-bicyclo[2.2.1]hept-5-yl}-acetamide;
(1S,4S,5S)—N-{2-[5-(thiazolo[4,5-b]pyridin-2-yloxy)-benzofuran-2-ylmethyl]-2-aza-bicyclo[2.2.1]hept-5-yl}-acetamide;
(1S,4S,5S)—N-{2-[6-(thiazolo[4,5-b]pyridin-2-yloxy)-benzofuran-2-ylmethyl]-2-aza-bicyclo[2.2.1]hept-5-yl}-acetamide;
2-[2-(4-fluoro-piperidin-1-ylmethyl)-benzofuran-6-yloxy]-thiazolo[4,5-b]pyridine;
2-[2-(4-trifluoromethyl-piperidin-1-ylmethyl)-benzofuran-6-yloxy]-thiazolo[4,5-b]pyridine;
2-(2-piperidin-1-ylmethyl-benzofuran-6-yloxy)-thiazolo[4,5-b]pyridine;
(1R,4R)-5-[6-(thiazolo[4,5-b]pyridin-2-yloxy)-benzofuran-2ylmethyl]-2,5-diaza-bicyclo[2.2.1]heptane-2-carboxylic acid amide;
5-[6-(thiazolo[4,5-b]pyridin-2-yloxy)-benzofuran-2-ylmethyl]-hexahydro-pyrrolo[3,4-c]pyrrole-2-carboxylic acid amide;
1-{5-[6-(thiazolo[4,5-b]pyridin-2-yloxy)-benzofuran-2-ylmethyl]-hexahydro-pyrrolo[3,4-c]pyrrol-2-yl}-ethanone;
1-{4-[6-(thiazolo[4,5-b]pyridin-2-yloxy)-benzofuran-3-ylmethyl]-piperazin-1-yl}-ethanone;
N-{1-[6-(thiazolo[4,5-b]pyridin-2-yloxy)-benzofuran-3-ylmethyl]-piperidin-4-yl}-acetamide;
diethyl-[6-(thiazolo[4,5-b]pyridin-2-yloxy)-benzofuran-2-ylmethyl]-amine;
(1S,4S)-1-{5-[5-(thiazolo[4,5-c]pyridin-2-yloxy)-benzofuran-2-ylmethyl]-2,5-diaza-bicyclo[2.2.1]hept-2-yl}-ethanone;
meso-endo-N-{8-[5-(thiazolo[4,5-c]pyridin-2-yloxy)-benzofuran-2-ylmethyl]-8-aza-bicyclo[3.2.1]oct-3-yl}-acetamide;
meso-endo-N-{8-[6-(thiazolo[4,5-c]pyridin-2-yloxy)-benzofuran-2-ylmethyl]-8-aza-bicyclo[3.2.1]oct-3-yl}-acetamide;
meso-1-{8-[6-(thiazolo[4,5-c]pyridin-2-yloxy)-benzofuran-2-ylmethyl]-3,8-diaza-bicyclo[3.2.1]oct-3-yl}-ethanone;
(1S,4S)-1-{5-[6-(thiazolo[4,5-c]pyridin-2-yloxy)-benzofuran-2-ylmethyl]-2,5-diaza-bicyclo[2.2.1]hept-2-yl}-ethanone;
1-[6-(thiazolo[4,5-b]pyridin-2-yloxy)-benzofuran-2-ylmethyl]-piperidine-4-carboxylic acid methylamide;
pyrrolidin-1-yl-{1-[6-(thiazolo[4,5-b]pyridin-2-yloxy)-benzofuran-3-ylmethyl]-piperidin-4-yl}-methanone;
meso-1-{8-[5-(thiazolo[4,5-c]pyridin-2-yloxy)-benzofuran-2-ylmethyl]-3,8-diaza-bicyclo[3.2.1]oct-3-yl}-ethanone;
meso-exo-{8-[6-(thiazolo[4,5-b]pyridin-2-yloxy)-benzofuran-3-ylmethyl]-8-aza-bicyclo[3.2.1]oct-3-yl}-urea;
meso-exo-N-{8-[6-(thiazolo[4,5-b]pyridin-2-yloxy)-benzofuran-3-ylmethyl]-8-aza-bicyclo[3.2.1]oct-3-yl}-acetamide;
(1S,4S)-5-[6-(thiazolo[4,5-b]pyridin-2-yloxy)-benzofuran-3-ylmethyl]-2,5-diaza-bicyclo[2.2.1]heptane-2-carboxylic acid amide;
meso-8-[6-(thiazolo[4,5-b]pyridin-2-yloxy)-benzofuran-3-ylmethyl]-3,8-diaza-bicyclo[3.2.1]octane-3-carboxylic acid amide;
meso-1-{5-[6-(thiazolo[4,5-b]pyridin-2-yloxy)-benzofuran-3-ylmethyl]-hexahydro-pyrrolo[3,4-c]pyrrol-2-yl}-ethanone;
2-(3-piperidin-1-ylmethyl-benzofuran-6-yloxy)-thiazolo[4,5-b]pyridine;
1-[6-(thiazolo[4,5-b]pyridin-2-yloxy)-benzofuran-3-ylmethyl]-piperidine-4-carboxylic acid amide;
1-[6-(thiazolo[4,5-b]pyridin-2-yloxy)-benzofuran-3-ylmethyl]-piperidine-4-carboxylic acid methylamide;
1-{1-[6-(thiazolo[4,5-b]pyridin-2-yloxy)-benzofuran-3-ylmethyl]-piperidin-4-yl}-pyrrolidin-2-one;
(3-S)-1-[6-(thiazolo[4,5-b]pyridin-2-yloxy)-benzofuran-3-ylmethyl]-piperidine-3-carboxylic acid amide;
2-{3-[4-(pyridin-2-yloxy)-piperidin-1-ylmethyl]-benzofuran-6-yloxy}-thiazolo[4,5-b]pyridine;
2-{1-[6-(thiazolo[4,5-b]pyridin-2-yloxy)-benzofuran-3-ylmethyl]-piperidin-4-yl}-propan-2-ol;
diethyl-[6-(thiazolo[4,5-b]pyridin-2-yloxy)-benzofuran-3-ylmethyl]-amine;
1-[6-(thiazolo[4,5-b]pyridin-2-yloxy)-benzofuran-3-ylmethyl]-1,2,3,4,5,6-hexahydro-[4,4']bipyridinyl;
(1S,4S)-1-{5-[6-(thiazolo[5,4-b]pyridin-2-yloxy)-benzofuran-3-ylmethyl]-2,5-diaza-bicyclo[2.2.1]hept-2-yl}-ethanone;
(1S,4S)-1-{5-[6-(thiazolo[4,5-c]pyridin-2-yloxy)-benzofuran-3-ylmethyl]-2,5-diaza-bicyclo[2.2.1]hept-2-yl}-ethanone;
1-[6-(benzothiazol-2-yloxy)-benzofuran-3-ylmethyl]-piperidine-4-carboxylic acid ethyl ester;
1-[6-(thiazolo[4,5-b]pyridin-2-yloxy)-benzofuran-3-ylmethyl]-piperidine-4-carboxylic acid ethyl ester;
1-[6-(thiazolo[4,5-b]pyridin-2-yloxy)-benzofuran-2-ylmethyl]-piperidine-4-carboxylic acid tert-butyl ester;
4-[6-(thiazolo[4,5-b]pyridin-2-yloxy)-benzofuran-2-ylmethyl]-piperazine-1-carboxylic acid tert-butyl ester;
{1-[6-(thiazolo[4,5-b]pyridin-2-yloxy)-benzofuran-3-ylmethyl]-piperidin-4-yl}-carbamic acid tert-butyl ester;
4-[6-(thiazolo[4,5-b]pyridin-2-yloxy)-benzofuran-3-ylmethyl]-[1,4]diazepane-1-carboxylic acid tert-butyl ester;
(1S,4S)-5-[6-(thiazolo[4,5-b]pyridin-2-yloxy)-benzofuran-3-ylmethyl]-2,5-diaza-bicyclo[2.2.2]octane-2-carboxylic acid tert-butyl ester;
4-{cyclopropyl-[6-(thiazolo[4,5-b]pyridin-2-yloxy)-benzofuran-3-ylmethyl]-amino}-piperidine-1-carboxylic acid tert-butyl ester;
2-(3-piperazin-1-ylmethyl-benzofuran-6-yloxy)-thiazolo[4,5-b]pyridine;
1-[6-(thiazolo[4,5-b]pyridin-2-yloxy)-benzofuran-3-ylmethyl]-piperidin-4-ylamine;
2-(3-[1,4]diazepan-1-ylmethyl-benzofuran-6-yloxy)-thiazolo[4,5-b]pyridine;
(1S,4S)-2-[6-(thiazolo[4,5-b]pyridin-2-yloxy)-benzofuran-3-ylmethyl]-2,5-diaza-bicyclo[2.2.2]octane;
cyclopropyl-piperidin-4-yl-[6-(thiazolo[4,5-b]pyridin-2-yloxy)-benzofuran-3-ylmethyl]-amine;
2,2-dimethyl-N-{1-[6-(thiazolo[4,5-b]pyridin-2-yloxy)-benzofuran-2-ylmethyl]-pyrrolidin-3-yl}-propionamide;
(1S,4S)1-{5-[6-(thiazolo[4,5-b]pyridin-2-yloxy)-benzofuran-3-ylmethyl]-2,5-diaza-bicyclo[2.2.2]oct-2-yl}-ethanone;
1-(4-{cyclopropyl-[6-(thiazolo[4,5-b]pyridin-2-yloxy)-benzofuran-3-ylmethyl]-amino}-piperidin-1-yl)-ethanone;
4-[6-(thiazolo[4,5-b]pyridin-2-yloxy)-benzofuran-3-ylmethyl]-piperazine-1-carboxylic acid amide;

{1-[6-(thiazolo[4,5-b]pyridin-2-yloxy)-benzofuran-3-yl-methyl]-piperidin-4-yl}-urea;
(1S,4S)-5-[6-(thiazolo[4,5-b]pyridin-2-yloxy)-benzofuran-3-ylmethyl]-2,5-diaza-bicyclo[2.2.2]octane-2-carboxylic acid amide;
4-{cyclopropyl-[6-(thiazolo[4,5-b]pyridin-2-yloxy)-benzofuran-3-ylmethyl]-amino}-piperidine-1-carboxylic acid amide;
2-[3-(4-methanesulfonyl-piperazin-1-ylmethyl)-benzofuran-6-yloxy]-thiazolo[4,5-b]pyridine;
N-{1-[6-(thiazolo[4,5-b]pyridin-2-yloxy)-benzofuran-3-ylmethyl]-piperidin-4-yl}-methanesulfonamide;
(1S,4S)-2-methanesulfonyl-5-[6-(thiazolo[4,5-b]pyridin-2-yloxy)-benzofuran-3-ylmethyl]-2,5-diaza-bicyclo[2.2.2]octane;
cyclopropyl-(1-methanesulfonyl-piperidin-4-yl)-[6-(thiazolo[4,5-b]pyridin-2-yloxy)-benzofuran-3-ylmethyl]-amine;
2-[3-(4-methanesulfonyl-[1,4]diazepan-1-ylmethyl)-benzofuran-6-yloxy]-thiazolo[4,5-b]pyridine;
1-[6-(benzothiazol-2-yloxy)-benzofuran-3-ylmethyl]-piperidine-4-carboxylic acid;
1-[6-(thiazolo[4,5-b]pyridin-2-yloxy)-benzofuran-3-ylmethyl]-piperidine-4-carboxylic acid;
N-{1-[6-(5-methyl-thiazolo[4,5-b]pyridin-2-yloxy)-benzofuran-3-ylmethyl]-piperidin-4-yl}-acetamide;
N-{1-[6-(6-methyl-thiazolo[4,5-b]pyridin-2-yloxy)-benzofuran-3-ylmethyl]-piperidin-4-yl}-acetamide;
N-{1-[6-(7-methyl-thiazolo[4,5-b]pyridin-2-yloxy)-benzofuran-3-ylmethyl]-piperidin-4-yl}-acetamide;
N-{1-[6-(thiazolo[4,5-b]pyrazin-2-yloxy)-benzofuran-3-ylmethyl]-piperidin-4-yl}-acetamide;
N-{1-[6-(6-chloro-thiazolo[4,5-b]pyridin-2-yloxy)-benzofuran-3-ylmethyl]-piperidin-4-yl}-acetamide;
N-{1-[6-(6-fluoro-thiazolo[4,5-b]pyridin-2-yloxy)-benzofuran-3-ylmethyl]-piperidin-4-yl}-acetamide;
2-[3-(2-morpholin-4-yl-ethyl)-benzofuran-6-yloxy]-thiazolo[4,5-b]pyridine;
1-(4-{2-[6-(thiazolo[4,5-b]pyridin-2-yloxy)-benzofuran-3-yl]-ethyl}-piperazin-1-yl)-ethanone;
(1S,4S)-1-(5-{2-[6-(thiazolo[4,5-b]pyridin-2-yloxy)-benzofuran-3-yl]-ethyl}-2,5-diaza-bicyclo[2.2.1]hept-2-yl)-ethanone;
and pharmaceutically acceptable salts and prodrugs thereof.

45. A method as in claim 39, wherein said at least one chemical entity is selected from the group consisting of
1-{4-[5-(thiazolo[4,5-b]pyridin-2-yloxy)-benzofuran-2-ylmethyl]-piperazin-1-yl}-ethanone;
5-[6-(thiazolo[4,5-b]pyridin-2-yloxy)-benzofuran-3-ylmethyl]-hexahydro-pyrrolo[3,4-c]pyrrole-2-carboxylic acid tert-butyl ester;
(1S,4S)-5-[6-(thiazolo[4,5-b]pyridin-2-yloxy)-benzofuran-3-ylmethyl]-2,5-diaza-bicyclo[2.2.1]heptane-2-carboxylic acid tert-butyl ester;
2-[3-(hexahydro-pyrrolo[3,4-c]pyrrol-2-ylmethyl)-benzofuran-6-yloxy]-thiazolo[4,5-b]pyridine;
(1S,4S)-2-[3-(2,5-diaza-bicyclo[2.2.1]hept-2-ylmethyl)-benzofuran-6-yloxy]-thiazolo[4,5-b]pyridine;
2-[3-(2,8-diaza-spiro[4.5]dec-8-ylmethyl)-benzofuran-6-yloxy]-thiazolo[4,5-b]pyridine;
1-{8-[6-(thiazolo[4,5-b]pyridin-2-yloxy)-benzofuran-3-ylmethyl]-2,8-diaza-spiro[4.5]dec-2-yl}-ethanone;
2-[6-(thiazolo[4,5-b]pyridin-2-yloxy)-benzofuran-3-ylmethyl]-decahydro-isoquinoline;
1-[6-(thiazolo[4,5-b]pyridin-2-yloxy)-benzofuran-3-ylmethyl]-decahydro-quinoline;
1-[6-(thiazolo[4,5-b]pyridin-2-yloxy)-benzofuran-3-ylmethyl]-piperidin-4-ol;
{1-[6-(thiazolo[4,5-b]pyridin-2-yloxy)-benzofuran-3-ylmethyl]-piperidin-4-yl}-methanol;
2-[3-(4-fluoro-piperidin-1-ylmethyl)-benzofuran-6-yloxy]-thiazolo[4,5-b]pyridine;
2-[3-(4-methoxy-piperidin-1-ylmethyl)-benzofuran-6-yloxy]-thiazolo[4,5-b]pyridine;
1'-[6-(thiazolo[4,5-b]pyridin-2-yloxy)-benzofuran-3-ylmethyl]-[1,4]bipiperidinyl-2-one;
N-{1-[6-(thiazolo[4,5-b]pyridin-2-yloxy)-furo[3,2-b]pyridin-2-ylmethyl]-piperidin-4-yl}-acetamide;
(1S,4S)-1-{5-[6-(thiazolo[4,5-b]pyridin-2-yloxy)-furo[3,2-b]pyridin-2-ylmethyl]-2,5-diaza-bicyclo[2.2.1]hept-2-yl}-ethanone;
4-phenyl-1-[6-(thiazolo[4,5-b]pyridin-2-yloxy)-benzofuran-3-ylmethyl]-piperidin-4-ol,
cyclopropyl-{4-[6-(thiazolo[4,5-b]pyridin-2-yloxy)-benzofuran-3-ylmethyl]-piperazin-1-yl}-methanone;
2-[3-(4-cyclopropyl-piperazin-1-ylmethyl)-benzofuran-6-yloxy]-thiazolo[4,5-b]pyridine;
8-[6-(thiazolo[4,5-b]pyridin-2-yloxy)-benzofuran-3-ylmethyl]-2,8-diaza-spiro[4.5]decane-2-carboxylic acid tert-butyl ester;
2-[3-(4-benzyl-piperidin-1-ylmethyl)-benzofuran-6-yloxy]-thiazolo[4,5-b]pyridine;
2-[3-(4-phenyl-piperidin-1-ylmethyl)-benzofuran-6-yloxy]-thiazolo[4,5-b]pyridine;
2-[3-(3,5-dimethyl-piperidin-1-ylmethyl)-benzofuran-6-yloxy]-thiazolo[4,5-b]pyridine;
dimethyl-{1-[6-(thiazolo[4,5-b]pyridin-2-yloxy)-benzofuran-3-ylmethyl]-piperidin-4-yl}-amine;
2-[3-(4-pyrrolidin-1-yl-piperidin-1-ylmethyl)-benzofuran-6-yloxy]-thiazolo[4,5-b]pyridine;
1'-[6-(thiazolo[4,5-b]pyridin-2-yloxy)-benzofuran-3-ylmethyl]-[1,4]bipiperidinyl;
2-[3-(4-morpholin-4-yl-piperidin-1-ylmethyl)-benzofuran-6-yloxy]-thiazolo[4,5-b]pyridine;
2-[3-(4-methyl-piperidin-1-ylmethyl)-benzofuran-6-yloxy]-thiazolo[4,5-b]pyridine;
2-[3-(4-phenyl-piperazin-1-ylmethyl)-benzofuran-6-yloxy]-thiazolo[4,5-b]pyridine;
2-[3-(4-pyridin-2-yl-piperazin-1-ylmethyl)-benzofuran-6-yloxy]-thiazolo[4,5-b]pyridine;
2-[3-(4-pyridin-4-yl-piperazin-1-ylmethyl)-benzofuran-6-yloxy]-thiazolo[4,5-b]pyridine;
2-{3-[4-(4-methoxy-phenyl)-piperazin-1-ylmethyl]-benzofuran-6-yloxy}-thiazolo[4,5-b]pyridine;
2-[3-(4-phenethyl-piperazin-1-ylmethyl)-benzofuran-6-yloxy]-thiazolo[4,5-b]pyridine;
2-[3-(4-pyrimidin-2-yl-piperazin-1-ylmethyl)-benzofuran-6-yloxy]-thiazolo[4,5-b]pyridine;
2-[6-(thiazolo[4,5-b]pyridin-2-yloxy)-benzofuran-3-ylmethyl]-1,2,3,4-tetrahydro-isoquinoline;
methyl-(1-methyl-piperidin-4-yl)-[6-(thiazolo[4,5-b]pyridin-2-yloxy)-benzofuran-3-ylmethyl]-amine;
meso-1-{3-[6-(thiazolo[4,5-b]pyridin-2-yloxy)-benzofuran-3-ylmethyl]-3,8-diaza-bicyclo[3.2.1]oct-8-yl}-ethanone;
meso-endo-N-{8-[6-(thiazolo[4,5-b]pyridin-2-yloxy)-furo[3,2-b]pyridin-2-ylmethyl]-8-aza-bicyclo[3.2.1]oct-3-yl}-acetamide;
cyclopropyl-[6-(thiazolo[4,5-b]pyridin-2-yloxy)-benzofuran-3-ylmethyl]-amine;
cyclopentyl-[6-(thiazolo[4,5-b]pyridin-2-yloxy)-benzofuran-3-ylmethyl]-amine;
cyclohexyl-[6-(thiazolo[4,5-b]pyridin-2-yloxy)-benzofuran-3-ylmethyl]-amine;
[6-(thiazolo[4,5-b]pyridin-2-yloxy)-benzofuran-3-ylmethyl]-thiophen-2-ylmethyl-amine;
tert-butyl-[6-(thiazolo[4,5-b]pyridin-2-yloxy)-benzofuran-3-ylmethyl]-amine;

2-[3-(4-tert-butyl-piperidin-1-ylmethyl)-benzofuran-6-yloxy]-thiazolo[4,5-b]pyridine;
propyl-[6-(thiazolo[4,5-b]pyridin-2-yloxy)-benzofuran-3-ylmethyl]-amine;
isobutyl-[6-(thiazolo[4,5-b]pyridin-2-yloxy)-benzofuran-3-ylmethyl]-amine;
(2-piperidin-1-yl-ethyl)-[6-(thiazolo[4,5-b]pyridin-2-yloxy)-benzofuran-3-ylmethyl]-amine;
(2-morpholin-4-yl-ethyl)-[6-(thiazolo[4,5-b]pyridin-2-yloxy)-benzofuran-3-ylmethyl]-amine;
N-{1-[6-(thiazolo[4,5-b]pyridin-2-yloxy)-benzofuran-3-ylmethyl]-pyrrolidin-3-yl}-acetamide;
2-[3-(4-isobutyl-piperazin-1-ylmethyl)-benzofuran-6-yloxy]-thiazolo[4,5-b]pyridine;
N-methyl-N-{1-[6-(thiazolo[4,5-b]pyridin-2-yloxy)-benzofuran-3-ylmethyl]pyrrolidin-3-yl}-acetamide;
(S)—N-{1-[6-(thiazolo[4,5-b]pyridin-2-yloxy)-benzofuran-3-ylmethyl]-pyrrolidin-3-yl}-acetamide;
4-(2-{[6-(benzothiazol-2-yloxy)-benzofuran-3-ylmethyl]-amino}-ethyl)-benzenesulfonamide;
(S)-{1-[6-(benzothiazol-2-yloxy)-benzofuran-3-ylmethyl]-pyrrolidin-2-yl}-methanol;
{1-[6-(benzothiazol-2-yloxy)-benzofuran-3-ylmethyl]-piperidin-4-yl}-carbamic acid tert-butyl ester;
2-[3-(3-propoxy-azetidin-1-ylmethyl)-benzofuran-6-yloxy]-thiazolo[4,5-b]pyridine;
1-[6-(thiazolo[4,5-b]pyridin-2-yloxy)-benzofuran-3-ylmethyl]-azetidin-3-ol;
2-[3-(3,3-difluoro-azetidin-1-ylmethyl)-benzofuran-6-yloxy]-thiazolo[4,5-b]pyridine;
N,N-diethyl-N'-[6-(thiazolo[4,5-b]pyridin-2-yloxy)-benzofuran-3-ylmethyl]-ethane-1,2-diamine;
cyclohexyl-ethyl-[6-(thiazolo[4,5-b]pyridin-2-yloxy)-benzofuran-3-ylmethyl]-amine;
(2-phenoxy-ethyl)-[6-(thiazolo[4,5-b]pyridin-2-yloxy)-benzofuran-3-ylmethyl]-amine;
indan-2-yl-[6-(thiazolo[4,5-b]pyridin-2-yloxy)-benzofuran-3-ylmethyl]-amine;
phenethyl-[6-(thiazolo[4,5-b]pyridin-2-yloxy)-benzofuran-3-ylmethyl]-amine;
N-cyclopropyl-N-{1-[6-(thiazolo[4,5-b]pyridin-2-yloxy)-benzofuran-3-ylmethyl]-piperidin-4-yl}-acetamide;
N-isopropyl-N-{1-[6-(thiazolo[4,5-b]pyridin-2-yloxy)-benzofuran-3-ylmethyl]-piperidin-4-yl}-acetamide;
(R)—N-{1-[6-(thiazolo[4,5-b]pyridin-2-yloxy)-benzofuran-3-ylmethyl]-pyrrolidin-3-yl}-acetamide;
2-[3-(4-thiophen-2-ylmethyl-piperazin-1-ylmethyl)-benzofuran-6-yloxy]-thiazolo[4,5-b]pyridine;
2-[3-(hexahydro-pyrrolo[1,2-a]pyrazin-2-ylmethyl)-benzofuran-6-yloxy]-thiazolo[4,5-b]pyridine;
diethyl-{1-[6-(thiazolo[4,5-b]pyridin-2-yloxy)-benzofuran-3-ylmethyl]-pyrrolidin-3-yl}-amine;
(R)-2-[3-(3-fluoro-pyrrolidin-1-ylmethyl)-benzofuran-6-yloxy]-thiazolo[4,5-b]pyridine;
diethyl-[5-(thiazolo[4,5-b]pyridin-2-yloxy)-benzofuran-2-ylmethyl]-amine;
2-[3-(5-fluoro-1,3-dihydro-isoindol-2-ylmethyl)-benzofuran-6-yloxy]-thiazolo[4,5-b]-pyridine;
2-[3-(1,3-dihydro-isoindol-2-ylmethyl)-benzofuran-6-yloxy]-thiazolo[4,5-b]pyridine;
meso-endo-1-(3-{[6-(thiazolo[4,5-b]pyridin-2-yloxy)-benzofuran-3-ylmethyl]-amino}-8-aza-bicyclo[3.2.1]oct-8-yl)-ethanone;
meso-exo-1-(3-{[6-(thiazolo[4,5-b]pyridin-2-yloxy)-benzofuran-3-ylmethyl]-amino}-8-aza-bicyclo[3.2.1]oct-8-yl)-ethanone;
3-{methyl-[6-(thiazolo[4,5-b]pyridin-2-yloxy)-benzofuran-3-ylmethyl]-amino}-propionic acid ethyl ester;
3-{methyl-[6-(thiazolo[4,5-b]pyridin-2-yloxy)-benzofuran-3-ylmethyl]-amino}-propionic acid;
meso-exo-N-{8-[6-(thiazolo[4,5-b]pyridin-2-yloxy)-furo[3,2-b]pyridin-2-ylmethyl]-8-aza-bicyclo[3.2.1]oct-3-yl}-acetamide;
(1S,4S)-5-[6-(thiazolo[4,5-b]pyridin-2-yloxy)-furo[3,2-b]pyridin-2-ylmethyl]-2,5-diaza-bicyclo[2.2.1]heptane-2-carboxylic acid amide;
meso-1-{8-[6-(thiazolo[4,5-b]pyridin-2-yloxy)-furo[3,2-b]pyridin-2-ylmethyl]-3,8-diaza-bicyclo[3.2.1]oct-3-yl}-ethanone;
(1S,4S)-1-{5-[6-(thiazolo[4,5-b]pyridin-2-yloxy)-furo[3,2-b]pyridin-2-ylmethyl]-2,5-diaza-bicyclo[2.2.2]oct-2-yl}-ethanone;
(1R,4R)-1-{5-[6-(thiazolo[4,5-b]pyridin-2-yloxy)-furo[3,2-b]pyridin-2-ylmethyl]-2,5-diaza-bicyclo[2.2.1]hept-2-yl}-ethanone;
1-{1-[6-(thiazolo[4,5-b]pyridin-2-yloxy)-furo[3,2-b]pyridin-2-ylmethyl]-piperidin-4-yl}-pyrrolidin-2-one;
4-[6-(thiazolo[4,5-b]pyridin-2-yloxy)-benzofuran-3-ylmethyl]-piperazin-2-one;
1-{4-[6-(thiazolo[4,5-b]pyridin-2-yloxy)-furo[3,2-b]pyridin-2-ylmethyl]-piperazin-1-yl}-ethanone;
benzyl-[6-(thiazolo[4,5-b]pyridin-2-yloxy)-benzofuran-3-ylmethyl]-amine;
(4-fluoro-benzyl)-[6-(thiazolo[4,5-b]pyridin-2-yloxy)-benzofuran-3-ylmethyl]-amine;
(4-methoxy-benzyl)-[6-(thiazolo[4,5-b]pyridin-2-yloxy)-benzofuran-3-ylmethyl]-amine;
4-(4-chloro-phenyl)-1-[6-(thiazolo[4,5-b]pyridin-2-yloxy)-benzofuran-3-ylmethyl]-piperidin-4-ol;
4-(4-bromo-phenyl)-1-[6-(thiazolo[4,5-b]pyridin-2-yloxy)-benzofuran-3-ylmethyl]-piperidin-4-ol;
2-[3-(2,6-dimethyl-morpholin-4-ylmethyl)-benzofuran-6-yloxy]-thiazolo[4,5-b]pyridine;
2-[3-(3-fluoro-piperidin-1-ylmethyl)-benzofuran-6-yloxy]-thiazolo[4,5-b]pyridine;
4-{1-[6-(thiazolo[4,5-b]pyridin-2-yloxy)-benzofuran-3-ylmethyl]-piperidin-4-yl}-2,4-dihydro-[1,2,4]triazol-3-one;
1-{7-[6-(thiazolo[4,5-b]pyridin-2-yloxy)-benzofuran-3-ylmethyl]-3,7-diaza-bicyclo[3.3.1]non-3-yl}-ethanone;
N-ethyl-N-{1-[6-(thiazolo[4,5-b]pyridin-2-yloxy)-benzofuran-3-ylmethyl]-piperidin-4-yl}-acetamide;
(tetrahydro-furan-3-yl)-{5-[6-(thiazolo[4,5-b]pyridin-2-yloxy)-benzofuran-3-ylmethyl]-hexahydro-pyrrolo[3,4-c]pyrrol-2-yl}-methanone;
2-hydroxy-1-{5-[6-(thiazolo[4,5-b]pyridin-2-yloxy)-benzofuran-3-ylmethyl]-hexahydro-pyrrolo[3,4-c]pyrrol-2-yl}-ethanone;
(1S,4S)-pyrazin-2-yl-{5-[6-(thiazolo[4,5-b]pyridin-2-yloxy)-benzofuran-3-ylmethyl]-2,5-diaza-bicyclo[2.2.1]hept-2-yl}-methanone;
(1S,4S)-cyclobutyl-{5-[6-(thiazolo[4,5-b]pyridin-2-yloxy)-benzofuran-3-ylmethyl]-2,5-diaza-bicyclo[2.2.1]hept-2-yl}-methanone;
(1S,4S)-isoxazol-5-yl-{5-[6-(thiazolo[4,5-b]pyridin-2-yloxy)-benzofuran-3-ylmethyl]-2,5-diaza-bicyclo[2.2.1]hept-2-yl}-methanone;
furan-3-yl-{5-[6-(thiazolo[4,5-b]pyridin-2-yloxy)-benzofuran-3-ylmethyl]-hexahydro-pyrrolo[3,4-c]pyrrol-2-yl}-methanone;
(1S,4S)-4-{5-[6-(thiazolo[4,5-b]pyridin-2-yloxy)-benzofuran-3-ylmethyl]-2,5-diaza-bicyclo[2.2.1]hept-2-ylmethyl}-benzoic acid methyl ester;
dimethyl-[6-(thiazolo[4,5-b]pyridin-2-yloxy)-benzofuran-3-ylmethyl]-amine;
(2-{1-[6-(benzothiazol-2-yloxy)-benzofuran-3-ylmethyl]-piperidin-4-yl}-ethyl)-carbamic acid tert-butyl ester;
N-{1-[6-(benzothiazol-2-yloxy)-benzofuran-3-ylmethyl]-piperidin-4-yl}-methanesulfonamide;

N-(2-{1-[6-(benzothiazol-2-yloxy)-benzofuran-3-ylmethyl]-piperidin-4-yl}-ethyl)-methanesulfonamide;
5-(thiazolo[4,5-b]pyridin-2-yloxy)-benzofuran-2-carboxylic acid benzyl-methyl-amide;
(1R,4R)-1-{5-[5-(thiazolo[4,5-b]pyridin-2-yloxy)-benzofuran-2-carbonyl]-2,5-diaza-bicyclo[2.2.1]hept-2-yl}-ethanone;
6-(thiazolo[4,5-b]pyridin-2-yloxy)-benzofuran-3-carboxylic acid methylamide;
N-{1-[6-(thiazolo[4,5-b]pyridin-2-yloxy)-benzofuran-3-carbonyl]-piperidin-4-yl}-acetamide;
meso-endo-N-{8-[6-(thiazolo[4,5-b]pyridin-2-yloxy)-benzofuran-3-carbonyl]-8-aza-bicyclo[3.2.1]oct-3-yl}-acetamide;
1-{1-[6-(thiazolo[4,5-b]pyridin-2-yloxy)-benzofuran-3-carbonyl]-piperidin-4-yl}-pyrrolidin-2-one;
(1S,4S)-1-{5-[6-(thiazolo[4,5-b]pyridin-2-yloxy)-benzofuran-3-carbonyl]-2,5-diaza-bicyclo[2.2.1]hept-2-yl}-ethanone;
1-{4-[6-(thiazolo[4,5-b]pyridin-2-yloxy)-benzofuran-3-carbonyl]-[1,4]diazepan-1-yl}-ethanone;
6-(thiazolo[4,5-b]pyridin-2-yloxy)-benzofuran-3-carboxylic acid isopropyl-methyl-amide;
meso-8-[6-(thiazolo[4,5-b]pyridin-2-yloxy)-benzofuran-3-carbonyl]-3,8-diaza-bicyclo[3.2.1]octane-3-carboxylic acid amide;
(1S,4S)-5-[6-(thiazolo[4,5-b]pyridin-2-yloxy)-benzofuran-3-carbonyl]-2,5-diaza-bicyclo[2.2.1]heptane-2-carboxylic acid amide;
(4-fluoro-piperidin-1-yl)-[6-(thiazolo[4,5-b]pyridin-2-yloxy)-benzofuran-3-yl]-methanone;
(4-phenyl-piperidin-1-yl)-[6-(thiazolo[4,5-b]pyridin-2-yloxy)-benzofuran-3-yl]-methanone;
1-[6-(thiazolo[4,5-b]pyridin-2-yloxy)-benzofuran-3-carbonyl]-piperidine-4-carboxylic acid amide;
(4-cyclohexyl-piperazin-1-yl)-[6-(thiazolo[4,5-b]pyridin-2-yloxy)-benzofuran-3-yl]-methanone;
1-{4-[6-(thiazolo[4,5-b]pyridin-2-yloxy)-benzofuran-3-carbonyl]-piperazin-1-yl}-ethanone;
6-(thiazolo[4,5-b]pyridin-2-yloxy)-benzofuran-3-carboxylic acid cyclohexyl-ethyl-amide;
[4-(pyrimidin-2-yloxy)-piperidin-1-yl]-[6-(thiazolo[4,5-b]pyridin-2-yloxy)-benzofuran-3-yl]-methanone;
piperidin-1-yl-[6-(thiazolo[4,5-b]pyridin-2-yloxy)-benzofuran-3-yl]-methanone;
[4-(piperidine-1-carbonyl)-piperidin-1-yl]-[6-(thiazolo[4,5-b]pyridin-2-yloxy)-benzofuran-3-yl]-methanone;
(octahydro-isoquinolin-2-yl)-[6-(thiazolo[4,5-b]pyridin-2-yloxy)-benzofuran-3-yl]-methanone;
(3,4-dihydro-1H-isoquinolin-2-yl)-[6-(thiazolo[4,5-b]pyridin-2-yloxy)-benzofuran-3-yl]-methanone;
(4-benzoyl-piperidin-1-yl)-[6-(thiazolo[4,5-b]pyridin-2-yloxy)-benzofuran-3-yl]-methanone;
6-(thiazolo[4,5-b]pyridin-2-yloxy)-benzofuran-3-carboxylic acid (3-dimethylamino-propyl)-methyl-amide;
endo-bicyclo[2.2.1]heptane-2-carboxylic acid [6-(thiazolo[4,5-b]pyridin-2-yloxy)-benzofuran-3-ylmethyl]-amide;
2-(4-acetyl-piperazin-1-yl)-N-[6-(thiazolo[4,5-b]pyridin-2-yloxy)-benzofuran-3-ylmethyl]-acetamide;
2-(3-methyl-isoxazol-5-yl)-N-[6-(thiazolo[4,5-b]pyridin-2-yloxy)-benzofuran-3-ylmethyl]-acetamide;
4-hydroxy-cyclohexanecarboxylic acid [6-(thiazolo[4,5-b]pyridin-2-yloxy)-benzofuran-3-ylmethyl]-amide;
N-[6-(thiazolo[4,5-b]pyridin-2-yloxy)-benzofuran-3-ylmethyl]-terephthalamic acid methyl ester;
2-(4-chloro-phenyl)-N-[6-(thiazolo[4,5-b]pyridin-2-yloxy)-benzofuran-3-ylmethyl]-acetamide;
N-[6-(thiazolo[4,5-b]pyridin-2-yloxy)-benzofuran-3-ylmethyl]-acetamide;
N-[6-(thiazolo[4,5-b]pyridin-2-yloxy)-benzofuran-3-ylmethyl]-terephthalamic acid;
1-[6-(thiazolo[4,5-b]pyridin-2-yloxy)-benzofuran-3-ylmethyl]-3,4-dihydro-1H-quinolin-2-one;
1-[6-(thiazolo[4,5-b]pyridin-2-yloxy)-benzofuran-3-ylmethyl]-6-trifluoromethyl-1,3-dihydro-indol-2-one;
1-[6-(thiazolo[4,5-b]pyridin-2-yloxy)-benzofuran-3-ylmethyl]-1,3-dihydro-indol-2-one;
1-[6-(thiazolo[4,5-b]pyridin-2-yloxy)-benzofuran-3-ylmethyl]-5-trifluoromethyl-1,3-dihydro-indol-2-one;
5-chloro-1-[6-(thiazolo[4,5-b]pyridin-2-yloxy)-benzofuran-3-ylmethyl]-1,3-dihydro-indol-2-one;
6-chloro-1-[6-(thiazolo[4,5-b]pyridin-2-yloxy)-benzofuran-3-ylmethyl]-1,3-dihydro-indol-2-one;
5-fluoro-1-[6-(thiazolo[4,5-b]pyridin-2-yloxy)-benzofuran-3-ylmethyl]-1,3-dihydro-indol-2-one;
(R)—N-(1-aza-bicyclo[2.2.2]oct-3-yl)-N-[6-(thiazolo[4,5-b]pyridin-2-yloxy)-benzofuran-3-ylmethyl]-acetamide;
2-(3-piperidin-1-ylmethyl-benzofuran-6-yloxy)-benzothiazole;
2-(2-piperidin-1-ylmethyl-benzofuran-6-yloxy)-benzothiazole;

and pharmaceutically acceptable salts and prodrugs thereof.

46. A method as in claim 39, further comprising administering to the subject in need of such treatment an effective amount of at least one of CysLT receptor antagonist and LTC$_4$ synthase inhibitor.

47. A method as in claim 40, further comprising administering to the subject in need of such treatment an effective amount of at least one of CysLT receptor antagonist and LTC$_4$ synthase inhibitor.

48. A method as in claim 41, further comprising administering to the subject in need of such treatment an effective amount of at least one of CysLT receptor antagonist and LTC$_4$ synthase inhibitor.

49. A method as in claim 42, further comprising administering to the subject in need of such treatment an effective amount of at least one of CysLT receptor antagonist and LTC$_4$synthase inhibitor.

50. A method as in claim 43, further comprising administering to the subject in need of such treatment an effective amount of at least one of CysLT receptor antagonist and LTC$_4$ synthase inhibitor.

51. A method as in claim 44, further comprising administering to the subject in need of such treatment an effective amount of at least one of CysLT receptor antagonist and LTC$_4$ synthase inhibitor.

52. A method as in claim 44, wherein the disease, disorder, or medical condition is selected from the group consisting of: allergy, abdominal aortic aneurysm, asthma, nasal polyps, allergic rhinitis, nasal itch, ocular inflammation, post-surgical ocular inflammation, conjunctivitis, uveitis, dry eye, psoriasis, pruritis, itch, itchy skin, atopic dermatitis, urticaria, hives, contact dermatitis, scleroderma, skin burns, acne, inflammatory bowel diseases, colitis, Crohn's disease, ulcerative colitis, chronic obstructive pulmonary disease, α1-antitrypsin (α1AT) deficiency, atherosclerosis, type II diabetes, arthritis, rheumatoid arthritis, multiple sclerosis, myocardial infarction, stroke, pain, gingivitis, bronchitis, cystic fibrosis, upper gastrointestinal cancer, sepsis, autoimmune thyroid diseases, immune-mediated diabetes mellitus, lupus, Myasthenia gravis, autoimmune neuropathies, Guillain-Barré, autoimmune uveitis, autoimmune hemolytic anemia, pernicious anemia, autoimmune thrombocytopenia, temporal arteritis, anti-phospholipid syndrome, vasculitides, Wegener's granulomatosis, Behcet's disease, dermatitis herpetiformis, pemphigus vulgaris, vitiligio, primary biliary cirrhosis, autoimmune hepatitis, autoimmune oophoritis and orchitis, autoimmune disease of the adrenal gland, polymyositis, dermatomyositis, spondyloarthropathies, ankylosing spondylitis, Sjogren syndrome, and Sjogren-Larsson syndrome.

53. A method as in claim 45, further comprising administering to the subject in need of such treatment an effective amount of at least one of CysLT receptor antagonist and $LTC_4$ synthase inhibitor.

54. A method as in claim 45, wherein the disease, disorder, or medical condition is selected from the group consisting of: allergy, abdominal aortic aneurysm, asthma, nasal polyps, allergic rhinitis, nasal itch, ocular inflammation, post-surgical ocular inflammation, conjunctivitis, uveitis, dry eye, psoriasis, pruritis, itch, itchy skin, atopic dermatitis, urticaria, hives, contact dermatitis, scleroderma, skin burns, acne, inflammatory bowel diseases, colitis, Crohn's disease, ulcerative colitis, chronic obstructive pulmonary disease, α1-antitrypsin (α1AT) deficiency, atherosclerosis, type II diabetes, arthritis, rheumatoid arthritis, multiple sclerosis, myocardial infarction, stroke, pain, gingivitis, bronchitis, cystic fibrosis, upper gastrointestinal cancer, sepsis, autoimmune thyroid diseases, immune-mediated diabetes mellitus, lupus, Myasthenia gravis, autoimmune neuropathies, Guillain-Barré, autoimmune uveitis, autoimmune hemolytic anemia, pernicious anemia, autoimmune thrombocytopenia, temporal arteritis, anti-phospholipid syndrome, vasculitides, Wegener's granulomatosis, Behcet's disease, dermatitis herpetiformis, pemphigus vulgaris, vitiligio, primary biliary cirrhosis, autoimmune hepatitis, autoimmune oophoritis and orchitis, autoimmune disease of the adrenal gland, polymyositis, dermatomyositis, spondyloarthropathies, ankylosing spondylitis, Sjogren syndrome, and Sjogren-Larsson syndrome.

\* \* \* \* \*